US007265130B2

(12) United States Patent
Kawanishi et al.

(10) Patent No.: US 7,265,130 B2
(45) Date of Patent: Sep. 4, 2007

(54) NPY Y5 ANTAGONIST

(75) Inventors: Yasuyuki Kawanishi, Osaka (JP); Hideyuki Takenaka, Koka-cho (JP); Kohji Hanasaki, Osaka (JP); Tetsuo Okada, Sakai (JP)

(73) Assignee: Shionogi & Co., Ltd., Osaka (JP)

(*) Notice: Subject to any disclaimer, the term of this patent is extended or adjusted under 35 U.S.C. 154(b) by 277 days.

(21) Appl. No.: 10/747,359

(22) Filed: Dec. 30, 2003

(65) Prior Publication Data

US 2004/0180964 A1 Sep. 16, 2004

Related U.S. Application Data

(62) Division of application No. 10/111,981, filed as application No. PCT/JP00/08197 on Nov. 21, 2000, now Pat. No. 6,699,891.

(30) Foreign Application Priority Data

Nov. 26, 1999 (JP) ................................ 11-336469
Dec. 14, 1999 (JP) ................................ 11-353786

(51) Int. Cl.
*A61K 31/47* (2006.01)
*A61K 31/165* (2006.01)

(52) U.S. Cl. ...................... 514/307; 514/309; 514/313; 514/367; 514/377; 514/403; 514/415; 514/443; 514/452; 514/456; 514/464; 514/529; 514/602; 514/603; 546/159; 546/141; 546/143; 548/162; 548/222; 548/365.5; 548/483; 549/57; 549/362; 549/398; 549/434; 564/80; 564/82; 564/90; 564/92; 560/125

(58) Field of Classification Search ................ 514/529, 514/602, 603, 307, 309, 313, 367, 377, 403, 514/415, 443, 452, 456, 464; 564/80, 82, 564/90, 92; 560/125; 544/3; 546/159, 141, 546/143; 548/162, 222, 365.5, 483; 549/57, 549/362, 398, 434
See application file for complete search history.

(56) References Cited

U.S. PATENT DOCUMENTS

| | | | | |
|---|---|---|---|---|
| 3,704,290 | A | 11/1972 | Hou et al. | |
| 4,948,809 | A | 8/1990 | Witte et al. | |
| 4,981,873 | A | 1/1991 | Witte et al. | |
| 5,817,677 | A | 10/1998 | Linz et al. | |
| 6,124,331 | A | 9/2000 | Marzabadi | |
| 6,140,354 | A | 10/2000 | Dax | |
| 6,172,108 | B1 | 1/2001 | Vega et al. | |
| 6,335,334 | B1 * | 1/2002 | Schindler et al. | 514/231.5 |
| 6,380,224 | B1 | 4/2002 | Dax | |
| 6,503,901 | B1 | 1/2003 | Thompson et al. | |
| 2005/0222255 | A1 | 10/2005 | Kawanishi et al. | |

FOREIGN PATENT DOCUMENTS

| | | | | |
|---|---|---|---|---|
| EP | 0 148 725 | A1 | | 7/1985 |
| EP | 0 226 346 | A1 | | 6/1987 |
| EP | 0 837 052 | A1 | | 4/1996 |
| EP | 0 757 037 A2 | A2 | | 2/1997 |
| EP | 0 915 086 A1 | A1 | | 5/1999 |
| EP | 0 950 656 | A1 | | 10/1999 |
| EP | 1 010 691 | A2 | | 6/2000 |
| EP | 1 184 373 A1 | A1 | | 3/2002 |
| JP | 59-16871 | A | | 1/1984 |
| JP | 2-180862 A | A | | 7/1990 |
| JP | 4-364158 A | A | | 12/1992 |
| JP | 5-194370 A | A | | 8/1993 |
| JP | 5-262643 A | A | | 10/1993 |
| JP | 8-92249 A | A | | 4/1996 |
| JP | 2001-122865 | A | | 5/2001 |
| JP | 2001-172257 | A | | 6/2001 |
| WO | WO95/35276 A1 | A1 | | 12/1995 |
| WO | WO96/00214 A1 | A1 | | 1/1996 |
| WO | WO97/15567 | | | 5/1997 |
| WO | WO-97/19682 | A1 | | 6/1997 |
| WO | WO97/20820 | A1 | | 6/1997 |

(Continued)

OTHER PUBLICATIONS

Gera et al. "Stereochemical studies . . . " CA 91:557328 (1979).*

(Continued)

*Primary Examiner*—Celia Chang
(74) *Attorney, Agent, or Firm*—Birch, Stewart, Kolasch & Birch, LLP

(57) ABSTRACT

The present invention provides a pharmaceutical composition for use as an NPY Y5 receptor antagonist comprising a compound of the formula (I):

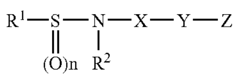

(I)

wherein $R^1$ is lower alkyl, cycloalkyl or the like,
$R^2$ is hydrogen, lower alkyl or the like,
n is 1 or 2,
X is lower alkylene, lower alkenylene, arylene, cycloalkylene or the like,
Y is $CONR^7$, $CSNR^7$, $NR^7CO$, $NR^7CS$ or the like,
Z is lower alkyl, optionally substituted carbocyclyl, optionally substituted heterocyclyl or the like and $R^7$ is hydrogen or lower alkyl,
prodrug, pharmaceutically acceptable salt or solvate thereof.

17 Claims, No Drawings

FOREIGN PATENT DOCUMENTS

| | | | |
|---|---|---|---|
| WO | WO97/20821 | A1 | 6/1997 |
| WO | WO97/20823 | A1 | 6/1997 |
| WO | WO97/28137 A1 | A1 | 8/1997 |
| WO | WO97/44315 A1 | A1 | 11/1997 |
| WO | WO99/32466 | A1 | 7/1999 |
| WO | WO99/64394 | A1 | 12/1999 |
| WO | WO 01/07409 | A1 | 7/2000 |
| WO | WO 00/63171 | A1 | 10/2000 |
| WO | WO 00/64880 | A1 | 11/2000 |
| WO | WO 00/68197 | A1 | 11/2000 |
| WO | WO 01/02379 | A1 | 1/2001 |
| WO | WO 01/09120 | A1 | 2/2001 |

OTHER PUBLICATIONS

Carini et al. "Preparation of angiotensin . . . " CA 109:529008 (1988).*

Taniguchi et al. Preparation of acylamino . . . CA 129:40984 (1998).*

Dax et al. preparation of N-substituted . . . CA 131:310453 (1999).*

Schindler et al. "preparation of arylsulfonyl . . . " CA 132:93102 (2000).*

McNally et al., Biorganic & Medical Chemistry Letters, vol. 10, pp. 213-216 (2000).

Youngman et al., J. Med. Chem., vol. 43, pp. 346-350 (2000).

Shionogi et al., "Sulfonamide type benzamides" CA 100:209423 (1984).

Linz et al., "Five membered heterocycles . . . " CA 127:17681 (1997).

Taniguchi et al., "Preparation of acylamino substituted . . " CA 129:40984 (1998).

Rubini et al., "Synthesis of isosteric methylene-oxy . . . " Tetrahedron V.42, p. 6039-54 (1996).

* cited by examiner

NPY Y5 ANTAGONIST

This application is a Divisional of application Ser. No. 10/111,981 filed on May 1, 2002, now U.S. Pat. No. 6,699,891, and for which priority is claimed under 35 U.S.C. § 120. Application Ser. No. 10/111,981 is the national phase of PCT International Application No. PCT/JP00/08197 filed on Nov. 21, 2000 under 35 U.S.C. § 371. The entire contents of each of the above-identified applications are hereby incorporated by reference. This application also claims priority of Application Nos. 11-336469 and 11-353786 filed in Japan on Nov. 26, 1999 and Dec. 14, 1999, respectively under 35 U.S.C. § 119.

TECHNICAL FIELD

The present invention relates to a pharmaceutical composition for use as an NPY Y5 receptor antagonist, specifically, anti-obestic agent and novel compounds having an anti-obestic activity.

BACKGROUND ART

Neuropeptide Y (hereinafter referred to as NPY) is a peptide which consists of 36 amino acid residues and was isolated from porcine brain in 1982. NPY is widely distributed in the central nervous system and peripheral tissues of humans and animals.

It has been reported that NPY possesses a stimulating activity of food intake, an anti-seizure activity, a learning-promoting activity, an anti-anxiety activity, an anti-stress activity etc., in central nervous system, and it may be pivotally involved in the central nervous system diseases such as depression, Alzheimer's disease and Parkinson's disease. NPY is thought to be associated with the cardiovascular diseases, since it induces a contraction of smooth muscles such as blood vessels or cardiac muscles in the peripheral tissues. Furthermore, NPY is also known to be involved in the metabolic diseases such as obesity, diabetes, and hormone abnormalities (Trends in Pharmacological Sciences, Vol. 15, and 153 (1994)). Therefore, an NPY receptor antagonist is expected as a medicine for preventing or treating various diseases involved in the NPY receptor.

Subtypes of Y1, Y2, Y3, Y4, Y5, and Y6 have now been identified as the NPY receptor (Trends in Pharmacological Sciences, Vol. 18, and 372 (1997)). It has been suggested that the Y5 receptor is at least involved in the feeding behavior and its antagonist is expected as an anti-obestic agent (Peptides, Vol. 18, and 445 (1997)).

Quinazoline compounds having similar structures to those of the compounds of the present invention and exhibiting an NPY receptor antagonistic activity are described in WO97/20820, WO97/20821, WO97/20823 and the like. In addition, it is described that urea derivatives having a sulfonamide group and amide derivatives having a sulfonyl group in WO99/64349 and benzyl sulfonamide derivatives in EP1010691-A, have an NPY antagonistic activity.

Compounds having similar structures to those of the compounds of the present invention are described in JP59-16871-A and WO97/15567. Their activities are quite different from that of the present invention and these documents do not suggest the present invention.

DISCLOSURE OF INVENTION

The object of the present invention is to provide a superior pharmaceutical composition for use as an NPY Y5 receptor antagonist and novel compounds having the activity.

The present invention provides

[1]A pharmaceutical composition for use as an NPY Y5 receptor antagonist comprising a compound of the formula (I):

(I)

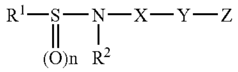

wherein $R^1$ is optionally substituted lower alkyl, optionally substituted cycloalkyl or optionally substituted aryl, $R^2$ is hydrogen or lower alkyl, and $R^1$ and $R^2$ taken together may form lower alkylene, n is 1 or 2, X is optionally substituted lower alkylene, optionally substituted lower alkenylene, optionally substituted —CO-lower alkylene, optionally substituted —CO-lower alkenylene or

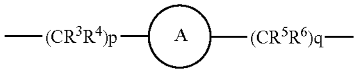

wherein $R^3$, $R^4$, $R^5$ and $R^6$ are each independently hydrogen or lower alkyl

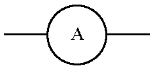

is optionally substituted cycloalkylene, optionally substituted cycloalkenylene, optionally substituted bicycloalkylene, optionally substituted arylene or optionally substituted heterocyclediyl and p and q are each independently 0 or 1, —$NR^2$—X— may be

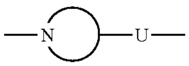

wherein

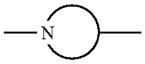

is piperidinediyl, piperazinediyl, pyridinediyl, pyrazinediyl, pyrrolidinediyl or pyrrolediyl and U is single bond, lower alkylene or lower alkenylene, Y is $OCONR^7$, $CONR^7$, $CSNR^7$, $NR^7CO$ or $NR^7CS$, $R^7$ is hydrogen or lower alkyl, and Z is optionally substituted lower alkyl, optionally substituted lower alkenyl, optionally substituted amino, optionally substituted lower alkoxy, optionally substituted carbocyclyle or optionally substituted heterocyclyl, prodrug, pharmaceutically acceptable salt or solvate thereof,

[2] The pharmaceutical composition for use as an NPY Y5 receptor antagonist described in [1] wherein $R^2$ is hydrogen or lower alkyl and Z is optionally substituted lower alkyl, optionally substituted lower alkenyl, optionally substituted lower alkoxy, optionally substituted carbocyclyl, optionally substituted heterocyclyl or optionally substituted amino, provided that $R^1$ is optionally substituted C3 to C10 alkyl when Z is optionally substituted amino,

[3] The pharmaceutical composition for use as an NPY Y5 receptor antagonist described in [1] wherein $R^1$ is optionally substituted lower alkyl or optionally substituted cycloalkyl, X is optionally substituted lower alkylene optionally substituted lower alkenylene or

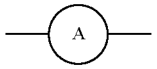

wherein

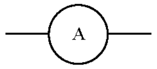

is the same as defined in [1], and

Z is optionally substituted lower alkyl, optionally substituted carbocyclyl or optionally substituted heterocyclyl,

[4] The pharmaceutical composition for use as an NPY Y5 receptor antagonist described in any one of [1] to [3] wherein $R^1$ is optionally substituted C3 to C10 alkyl,

[5] The pharmaceutical composition for use as an NPY Y5 receptor antagonist described in any one of [1] to [4] which is an anti-obestic agent,

[6] The pharmaceutical composition for use as an NPY Y5 receptor antagonist described in any one of [1] to [4] which is an anorectic agent,

[7] A method for treating and/or preventing obesity comprising administering an effective dose of an NPY Y5 receptor antagonist described in any one of [1] to [4],

[8] A method for suppressing food intake comprising administering an effective dose of an NPY Y5 receptor antagonist described in any one of [1] to [4],

[9] Use of an NPY Y5 receptor antagonist described in any one of [1] to [4] for manufacturing a medicine for treating and/or preventing obesity,

[10] Use of an NPY Y5 receptor antagonist described in any one of [1] to [4] for manufacturing a medicine for suppressing food intake,

[11] A compound of the formula (I):

(I)

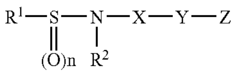

wherein X is C2 to C6 alkylene or C3 to C6 alkenylene, $R^1$ is optionally substituted C3 to C10 alkyl or optionally substituted C5 to C6 cycloalkyl and the other symbols are the same as defined in [1], provided that Z is not lower alkylphenylamino, hydroxy(lower)alkylphenylamino and acylphenylamino when Y is $NR^7CO$, prodrug, pharmaceutically acceptable salt or solvate thereof,

[12] The compound described in [11] wherein Z is optionally substituted lower alkyl or optionally substituted phenyl, prodrug, pharmaceutically acceptable salt or solvate thereof,

[13] A compound of the formula (I):

(I)

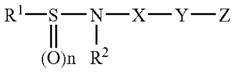

wherein X is

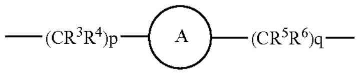

,

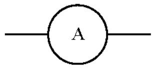

is optionally substituted cycloalkylene, optionally substituted cycloalkenylene, optionally substituted bicycloalkylene or optionally substituted piperidinylene, $R^1$ is optionally substituted C3 to C10 alkyl or optionally substituted C5 to C6 cycloalkyl and the other symbols are the same as defined in [1], prodrug, pharmaceutically acceptable salt or solvate thereof,

[14] The compound described in [13] wherein is optionally substituted cyclohexylene or optionally substituted piperidinylene and p and q are simultaneously 0, prodrug, pharmaceutically acceptable salt or solvate thereof,

[15] The compound described in [13] or [14] wherein Y is CONH, prodrug, pharmaceutically acceptable salt or solvate thereof,

[16] The compound described in any one of [13] to [15] wherein Z is optionally substituted lower alkyl, optionally substituted phenyl, optionally substituted pyridyl or optionally substituted benzopyranyl, prodrug, pharmaceutically acceptable salt or solvate thereof,

[17] A compound of the formula (I):

(I)

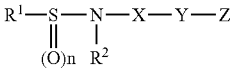

wherein X is

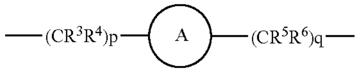

, $R^1$ is optionally substituted C3 to C10 alkyl or optionally substituted C5 to C6 cycloalkyl, Z is p-(lower)alkylphenyl and the other symbols are the same as defined in [1], provided—that Z is not p-n-butylphenyl when $R^1$ is isopropyl, prodrug, pharmaceutically acceptable salt or solvate thereof,

[18] A compound of the formula (I):

(I)

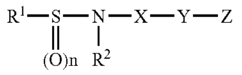

wherein X is

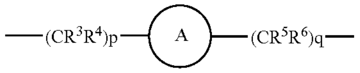 ,

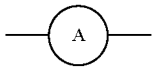

is heteroarylene, $R^1$ is optionally substituted C3 to C10 alkyl or optionally substituted C5 to C6 cycloalkyl and the other symbols are the same as defined in [1], prodrug, pharmaceutically acceptable salt or solvate thereof,

[19] The compound described in [18] wherein

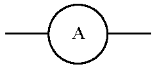

is thiophenediyl or furandiyl, prodrug, pharmaceutically acceptable salt or solvate thereof and

[20] A pharmaceutical composition comprising the compound described in any one of [11] to [19], prodrug, pharmaceutically acceptable salt or solvate thereof.

BEST MODE FOR CARRYING OUT THE INVENTION

In the present specification, the term "halogen" includes fluorine, chlorine, bromine and iodine. Fluorine or chlorine is preferable.

The term "protective group" in "optionally protected hydroxy" and "optionally protected hydroxy(lower)alkyl" includes all of hydroxy protecting groups usually used. For example, acyl such as acetyl, trichloroacetyl and benzoyl, lower alkoxycarbonyl such as t-butoxycarbonyl, lower alkylsulfonyl such as methane sulfonyl, lower alkoxy(lower) alkyl such as methoxymethyl, trialkylsilyl such as t-butyldimethylsilyl are included.

The term "lower alkyl" includes C1 to C10 straight or branched alkyl. The examples of "lower alkyl" are methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl and n-decyl.

"Lower alkyl" represented by $R^1$ is preferably C3 to C10 alkyl, more preferably C3 to C6 alkyl and most preferably isopropyl or t-butyl.

"Lower alkyl" in other cases is preferably C1 to C6 alkyl and more preferably C1 to C4 alkyl.

The examples of substituents of "optionally substituted lower alkyl" represented by Z are, (1) halogen; (2) cyano;

(3) the following groups (i) to (xvi), which are optionally substituted with one or more substituents selected from "a substituents group β" defined below,
   (i) hydroxy, (ii) lower alkoxy, (iii) mercapto, (iv) lower alkylthio, (v) acyl, (vi) acyloxy, (vii) carboxy, (viii) lower alkoxycarbonyl, (ix) imino, (x) carbamoyl, (xi) thiocarbamoyl, (xii) lower alkylcarbamoyl, (xiii) lower alkylthiocarbamoyl, (xiv) amino, (xv) lower alkylamino or (xvi) heterocyclylcarbonyl; or (4) a group of the formula:

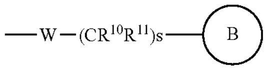

wherein $R^{10}$ and $R^{11}$ are each independently hydrogen or lower alkyl and when this group has two or more of $R^{10}$ and/or two or more of $R^{11}$, each $R^{10}$ and/or each $R^{11}$ may be different, W is single bond, O, S or $NR^{12}$, $R^{12}$ is hydrogen, lower alkyl or phenyl,

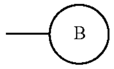

is cycloalkyl, bicycloalkyl, cycloalkenyl, aryl or heterocyclyl, each of which is optionally substituted with one or more of substituents selected from "a substituents group α" defined below and s is an integer of 0 to 4.

In the present specification, "a substituents group α" is a group constituting of (1) halogen; (2) oxo; (3) cyano; (4) nitro; (5) imino optionally substituted with lower alkyl or hydroxy;

(6) the following groups (i) to (xxi), which are optionally substituted with one or more of groups selected from the substituents group β,
   (i) hydroxy, (ii) lower alkyl, (iii) lower alkenyl, (iv) lower alkoxy, (v) carboxy, (vi) lower alkoxycarbonyl, (vii) acyl, (viii) acyloxy, (ix) imino, (x) mercapto, (xi) lower alkylthio, (xii) carbamoyl, (xiii) lower alkylcarbamoyl, (xiv) cycloalkylcarbamoyl, (xv) thiocarbamoyl, (xvi) lower alkylthiocarbamoyl, (xvii) lower alkylsulfinyl, (xviii) lower alkylsulfonyl, (xix) sulfamoyl, (xx) lower alkylsulfamoyl and (xxi) cycloalkylsulfamoyl;

(7) the following groups (i) to (v), which are optionally substituted with the substituents group β, lower alkyl, lower alkoxy(lower)alkyl, optionally protected hydroxy (lower)alkyl, halogeno(lower)alkyl, lower alkylsulfonyl and/or arylsulfonyl,
   (i) cycloalkyl, (ii) cycloalkenyl, (iii)cycloalkyloxy, (iv) amino and (v) alkylenedioxy; and (8) the following groups (i) to (xii), which are optionally substituted with the substituents group β, lower alkyl, halogeno(lower)alkyl and/or oxo,
   (i) phenyl, (ii) naphthyl, (iii) phenoxy, (iv) phenyl(lower) alkoxy, (v) phenylthio, (vi) phenyl(lower)alkylthio, (vii) phenylazo, (viii) heterocyclyl, (ix) heterocyclyloxy, (x) heterocyclylthio, (xi) heterocyclylcarbonyl and (xii) heterocyclylsulfonyl.

The preferable examples of the substituents group α as substituents for B ring are halogen; nitro; hydroxy;

optionally substituted lower alkyl wherein the substituents is halogen, cyano, phenyl, carboxy and/or lower alkoxycarbonyl;

lower alkenyl; lower alkoxycarbonyl(lower)alkenyl;

optionally substituted lower alkoxy wherein the substituents is halogen, hydroxy, lower alkoxy, carboxy, lower alkoxycarbonyl, lower alkylamino and/or cyano;

acyl; hydroxyimino; lower alkylthio; lower alkylsulfinyl; sulfamoyl;

optionally substituted amino wherein the substituents is lower alkyl, optionally protected hydroxy(lower)alkyl, phenyl and/or acyl;

alkylenedioxy; cyanophenyl; heterocyclylphenyl; biphenylyl; phenoxy; phenylazo optionally substituted with lower alkyl; or optionally substituted heterocyclyl wherein the substituents is optionally protected hydroxy, mercapto, halogen, lower alkyl, cycloalkyl, lower alkoxycarbonyl, amino, lower alkoxycarbonyl amino, carbamoyl, oxo, phenyl, lower alkoxyphenyl or heterocyclyl.

More preferable examples are halogen; lower alkyl optionally substituted with halogen; or lower alkoxy optionally substituted with halogen.

"A substituents group β" is a group consisting of halogen, optionally protected hydroxy, mercapto, lower alkoxy, lower alkenyl, amino, lower alkylamino, lower alkoxycarbonylamino, lower alkylthio, acyl, carboxy, lower alkoxycarbonyl, carbamoyl, cyano, cycloalkyl, phenyl, phenoxy, lower alkylphenyl, lower alkoxyphenyl, halogenophenyl, naphthyl and heterocyclyl.

Examples of the substituents for "optionally substituted lower alkyl" represented by any other than Z (e.g., $R^1$) are one or more substituents selected from the substituents group β. The lower alkyl may be substituted with these substituents at any possible positions.

The lower alkyl part in "lower alkoxy", "lower alkoxycarbonyl", "lower alkoxycarbonyl(lower)alkyl", "lower alkylphenyl", "lower alkoxyphenyl", "lower alkylcarbamoyl", "lower alkylthiocarbamoyl", "lower alkylamino", "halogeno(lower)alkyl", "hydroxy(lower)alkyl", "phenyl (lower)alkoxy", "lower alkylthio", "phenyl(lower)alkylthio", "lower alkoxycarbonylamino", "lower alkoxycarbonyl(lower)alkenyl", "lower alkylsulfinyl", "lower alkylsulfonyl", "aryl(lower)alkoxycarbonyl", "lower alkylbenzoyl" and "lower alkoxybenzoyl" is the same as defined in the above "lower alkyl".

Examples of substituents for "optionally substituted lower alkoxy" are one or more substituents selected from the substituents group β. Preferable examples are phenyl, lower alkylphenyl, lower alkoxyphenyl, naphthyl and heterocyclyl.

The term "cycloalkyl" includes C3 to C8 cyclic alkyl and preferably C5 to C6 cyclic alkyl. Examples are cyclopropyl, cyclobutyl, cyclopentyl, cyclohexyl, cycloheptyl and cyclooctyl.

Examples of substituents for "optionally substituted cycloalkyl" are one or more substituents selected from the substituents group α and the cycloalkyl may be substituted with these substituents at any possible positions.

The term "bicycloalkyl" includes a group which is formed by excluding one hydrogen from a C5 to C8 aliphatic cycle containing two rings which possess two or more of atoms in common. Examples are bicyclo[2.1.0]pentyl, bicyclo[2.2.1]heptyl, bicyclo[2.2.2]octyl and bicyclo[3.2.1]octyl.

The term "lower alkenyl" includes C2 to C10, preferably C2 to C8 and more preferably C3 to C6 straight or branched alkenyl having one or more double bonds at any possible positions. Examples are vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl and decenyl.

The "lower alkenyl" part in "lower alkoxycarbonyl(lower)alkenyl" is the same as the above "lower alkenyl".

Examples of the substituents for "optionally substituted lower alkenyl" are halogen, lower alkoxy, lower alkenyl, amino, lower alkylamino, lower alkoxycarbonylamino, lower alkylthio, acyl, carboxy, lower alkoxycarbonyl, carbamoyl, cyano, cycloalkyl, phenyl, lower alkylphenyl, lower alkoxyphenyl, naphthyl and/or heterocyclyl.

The term "acyl" includes (1) C1 to C10, preferably C1 to C6 and more preferably C1 to C4 straight or branched alkylcarbonyl or alkenylcarbonyl, (2) C4 to C9 and preferably C4 to C7 cycloalkylcarbonyl and (3) C7 to C11 arylcarbonyl. Examples are formyl, acetyl, propionyl, butyryl, isobutyryl, valeryl, pivaloyl, hexanoyl, acryloyl, propioloyl, methacryloyl, crotonoyl, cyclopropylcarbonyl, cyclohexylcarbonyl, cyclooctylcarbonyl and benzoyl.

The "acyl" part in "acyloxy" is the same as the above.

The term "cycloalkenyl" includes a group having at least one double bond at any possible positions in the above cycloalkyl. Examples are cyclopropenyl, cyclobutenyl, cyclopentenyl, cyclohexenyl and cyclohexadienyl.

Examples of substituents for "optionally substituted cycloalkenyl" are one or more substituents selected from the substituents group β.

Examples of substituents for "optionally substituted amino" are the substituents group β, optionally substituted benzoyl and/or optionally substituted heterocyclylcarbonyl wherein the substituents is hydroxy, lower alkyl, lower alkoxy and/or lower alkylthio.

The term "aryl" includes a monocyclic of polycyclic aromatic carbocyclyl group and examples are phenyl, naphthyl, anthryl and phenanthryl. "Aryl" includes aryl fused with other a non-aromatic carbocyclyl group, for example, indanyl, indenyl, biphenylyl, acenaphthyl, tetrahydronaphthyl and fluorenyl. Phenyl is preferable.

The aryl part in "aryl lower alkoxycarbonyl" is the same as the above.

The term "optionally substituted aryl" and "optionally substituted phenyl" represented by Z include the above "aryl" and "phenyl" respectively, which may be substituted with the substituents group α or lower alkyl which may be substituted with one or more group selected from the substituents group α.

Examples of the substituents for "optionally substituted aryl" and "optionally substituted phenyl" represented by any other than Z are one or more groups selected from the substituents group β.

The term "carbocyclyl" includes the above "cycloalkyl", "cycloalkenyl", "bicycloalkyl" and "aryl".

The term "non-aromatic carbocyclyl" includes the above "cycloalkyl", "cycloalkenyl" and "bicycloalkyl".

The term "optionally substituted carbocyclyl" includes the above "optionally substituted cycloalkyl", "optionally substituted cycloalkenyl", "optionally substituted bicycloalkyl" and "optionally substituted aryl".

The term "heterocyclyl" includes a heterocyclic group containing at least one heteroatom arbitrarily selected from O, S and N. For example, 5- or 6-membered heteroaryl such as pyrrolyl, imidazolyl, pyrazolyl, pyridyl, pyridazinyl, pyrimidinyl, oxazolyl, oxadiazolyl, isothiazolyl, thiazolyl, thiadiazolyl, furyl and thienyl; fused heterocyclyl consisting of two rings such as indolyl, isoindolyl, inclazolyl, indolizinyl, indolinyl, isoindolinyl, quinolyl, isoquinolyl, cinnolinyl, phthalazinyl, quinazolinyl, naphthyridinyl, quinoxalinyl, plurinyl, pteridinyl, benzopyranyl, benzimidazolyl, benzisoxazolyl, benzoxazolyl, benbzoxadiazolyl, benzisothiazolyl, benzothiazolyl, benzothiadiazolyl, benzofuryl, isobenzofuryl, benzothienyl, benzotriazolyl, imidazopyridyl, triazoropyridyl, imidazothiazolyl, pyrazinopyridazinyl, quinazolinyl, quinolyl, isoquinolyl, naphthyridinyl, dihydropyridyl, tetrahydroquinolyl and tetrahydrobenzothienyl; fused heterocyclyl consisting of three rings such as carbazolyl, acridinyl xanthenyl, phenothiazinyl, phenoxathiinyl, phenoxazinyl and dibenzofuryl; and non-aromatic heterocyclyl such as dioxanyl, thiiranyl, oxiranyl, oxathiolanyl, azetidinyl, thianyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydrofuryl, tetrahydropyranyl, tetrahydrothiazolyl and tetrahydroisothiazolyl.

"Fused heterocyclyl" fused with a ring other than a heterocycle (e.g., benzothiazolyl), may connect at any possible position.

Substituents for "optionally substituted heterocyclyl" are the same as those for the above "optionally substituted aryl".

Heterocyclyl parts in "heterocycylcarbonyl", "heterocyclyloxy", "heterocyclylthio" and "heterocyclyl substituted phenyl" are the same as the above "heterocyclyl".

The term "lower alkylene" includes a bivalent group comprising 1 to 6 of methylene, preferably 2 to 6 of methylene and more preferably 3 to 6 of methylene. For example, methylene, ethylene, trimethylene, tetramethylene, pentamethylene and hexamethylene are included. Tetramethylene is preferable.

"$R^1$ and $R^2$ taken together may form lower alkylene" includes the case

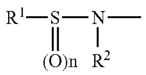 is 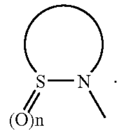 .

Preferable examples are

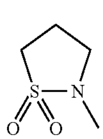 and 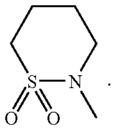 .

Lower alkylene part in "lower alkylenedioxy" is the same as the above "lower alkylene". Methylenedioxy or ethylenedioxy is preferable.

The term "lower alkenylene" includes a bivalent group comprising 2 to 6 of methylene, preferably 3 to 6 of methylene and more preferably 4 to 5 of methylene and including at least one double bond.

The term "cycloalkylene" includes a bivalent group which is formed by excluding one hydrogen from the above "cycloalkyl". A preferable example of cycloalkylene represented by X is 1,4-cyclohexanediyl.

The term "cycloalkenylene" includes a group containing at least one double bonds in the above cycloalkylene.

The term "bicycloalkylene" includes a group which is formed by excluding one hydrogen from the above "bicycloalkyl". Examples are bicyclo[2.1.0]pentylene, bicyclo [2.2.1]heptylene, bicyclo[2.2.2]octylene, and bicyclo[3.2.1] octylene.

The term "heterocyclediyl" includes a bivalent group which is formed by excluding one hydrogen from the above "heterocyclyl". Piperilinediyl, piperazinediyl, pyridinediyl, pyrimidinediyl, pyrazinediyl, pyrrolidinediyl or pyrrolediyl is preferable and piperidindiyl is more preferable.

The term "arylene" includes a bivalent group which is formed by excluding one hydrogen from the above "aryl". Phenylene is preferable.

The term "heteroarylene" includes aromatic groups in the above "heterocyclediyl". Examples are pyrrolediyl, imidazolediyl, pyrazolediyl, pyridinediyl, pyridazinediyl, pyrimidinediyl, pyrazinediyl, triazolediyl, triazinediyl, isoxazolediyl, oxazolediyl, oxadiazolediyl, isothiazolediyl, thiazolediyl, thiadiazolediyl, furandiyl and thiophenediyl.

One or more groups selected from the substituents group β are examples of substituents for "optionally substituted lower alkylene", "optionally substituted lower alkenylene", "optionally substituted cycloalkylene", "optionally substituted cyclohexylene", "optionally substituted bicycloalkylene", "optionally substituted cycloalkenylene", "optionally substituted phenylene", "optionally substituted heterocyclecdyl" and "optionally substituted piperidinylene". Halogen, hydroxy, lower alkyl, halogeno(lower)alkyl, lower alkoxy, amino, lower alkylamino, acyl, carboxy or lower alkoxycarbonyl is preferable. These substituents may attach to any possible positions.

When —$NR^2$—X— is

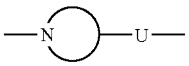 ,

U is preferably single bond or methylene. More preferably,

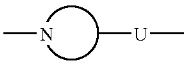

is

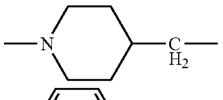 , 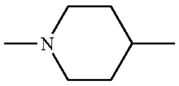 ,

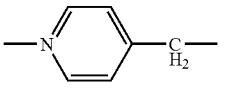 or 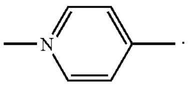 .

The compounds of the present invention include any formable and pharmaceutically acceptable salts thereof. Examples of "the pharmaceutically acceptable salt" are salts with mineral acids such as hydrochloric acid, sulfuric acid, nitric acid and phosphoric acid; salts with organic acids such as para-toluenesulfonic acid, methanesulfonic acid, oxalic acid and citric acid; salts with organic bases such as ammonium, trimethylammonium and triethylammonium; salts with alkaline metals such as sodium and potassium; and salts with alkaline earth metals such as calcium and magnesium.

The compounds of the present invention include solvates thereof. Hydrate is preferable and arbitrary numbers of water molecules may coordinate to the compound of the present invention.

The compounds of the present invention include prodrugs thereof. Prodrug includes derivatives of the compounds of the present invention which have a chemically or metabolically decomposable group and can be converted into pharmaceutically active compounds of the present invention in vivo by solvolysis or under the physiological conditions. The methods for selecting and producing suitable prodrugs are described in Design of Prodrugs, Elsevier, Amsterdam 1985.

When a compound (I) of the present invention has carboxy, examples of prodrugs are an ester derivative and an amide derivative, which can be produced by reacting a compound (I) having carboxy with a suitable alcohol or a suitable amine, respectively.

When a compound (I) of the present invention has hydroxy, an example of prodrugs is an acyloxy derivative, which can be synthesized by reacting a compound (I) having hydroxy with a suitable acyl halide or a suitable acid anhydride.

When a compound (I) of the present invention has amino, an example of prodrugs is an amide derivative, which can be synthesized by reacting a compound (I) having amino with a suitable acid halide or a suitable mixed acid anhydride.

When the compound (I) of the present invention has an asymmetric carbon atom, it includes racemates, all of enantiomers and all of stereoisomers such as diastereomer, epimer and enantiomer thereof.

When the compound (I) of the present invention having one or more double bonds forms an E isomer or Z isomer, the compound (I) includes both isomers. When X is cycloalkylene, the compound (I) includes both of cis isomer and trans isomer.

For example, the compound (I) of the present invention can be synthesized by the following methods.

(Compounds wherein Y=$CONR^7$)

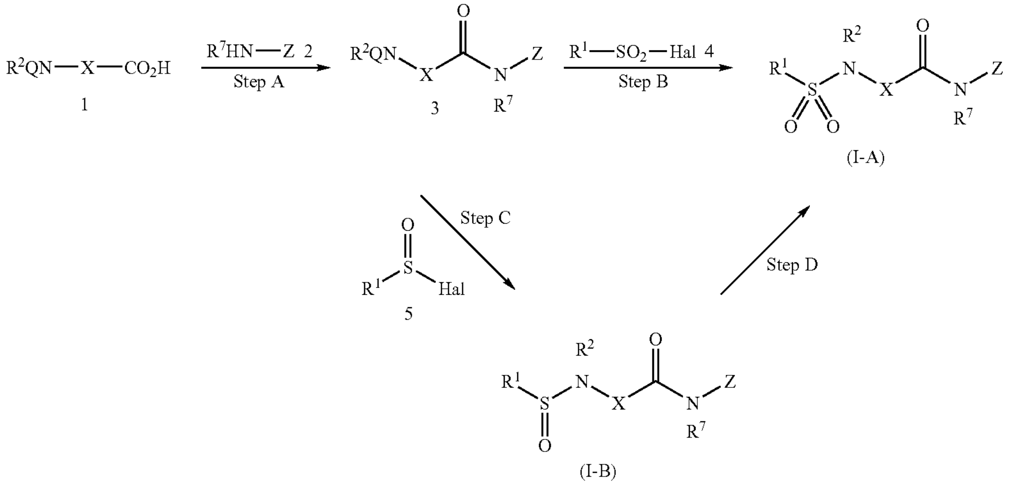

wherein Hal is halogen, Q is an amino protecting group and the other symbols are the same as the above.

Step A

Compound 1 is reacted with Amino Compound 2 having the desired substituent Z and $R^7$ in a suitable solvent at 0° C. to 50° C. for several minutes to several hours. As solvents, tetrahydrofuran, dimenthylformamide, diethyl ether, dichloromethane, toluene, benzene, xylene, cyclohexane, hexane, chloroform, ethyl acetate, butyl acetate, pentane, heptane, dioxane, acetone, acetonitrile, water, a mixture thereof etc. can be used. An activator such as thionyl chloride, acid halide, acid anhydride and activated ester can be used, if necessary.

Step B

Compound 3 is deprotected by the usual method and reacted with Sulfonyl Halide 4 having the desired substituent $R^1$ in a suitable solvent at 0° C. to 50° C. for several minutes to several hours to give Compound (I-A) wherein n is 2. Tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water and the mixture thereof etc. can be used as a solvent.

Step C

Compound (I-B) wherein n is 1 can be synthesized by reacting Compound 3 with Sulfinyl Halide 5 having substituent $R^1$. The conditions for the reaction are the same as those of the above Step B.

Step D

Compound (I-B) obtained in Step C is oxidized by the usual method to give Compound (I-A) wherein n is 2. m-Chloroperbenzoic acid, peracetic acid, hydrogen peroxide, trifluoroperacetic acid, sodium periodate, sodium hypochlorite, potassium permanganate etc. can be used as an oxidizer and the reaction may be carried out at 0° C. to 50°

C. Examples of solvents are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water, methanol, ethanol, isopropanol and mixture thereof.

In case X is heterocyclediyl containing at least one N atom and the N atom connects to $CON^7$-Z in the compound (I), the following reaction may be employed to obtain Compound (I-A') or (I-B'). Step D may be carried out just after Step C or Step E.

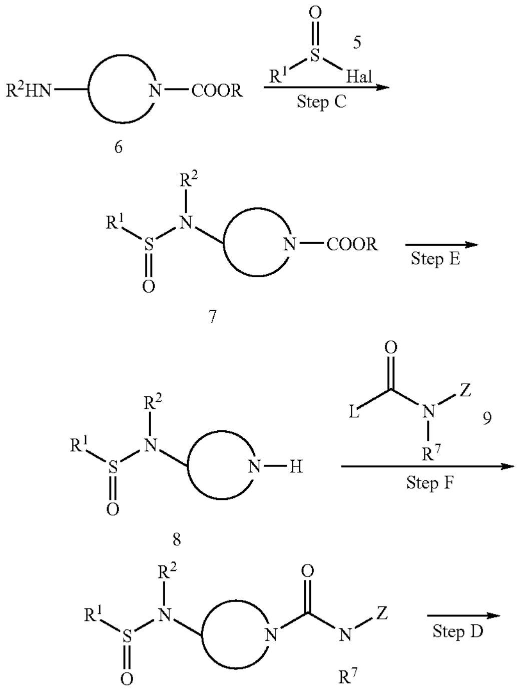

-continued

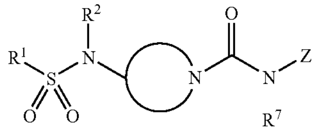

(I-A')

wherein R is lower alkyl or aryl and L is a leaving group.

Step C

Compound 5 is reacted with Compound 6 in a similar manner to the above Step C to give Compound 7.

Step E

Thus obtained Compound 7 is treated with a base in a suitable solvent to give Compound 8. For example, barium hydroxide, sodium hydroxide, potassium hydroxide, hydrazine or lithium propanethiolatecan be used as a base. As a solvent, tetrahydrofuran, dimethylformamide, dioxane, acetone, acetonitrile, methanol, ethanol, propanol, water, the mixture thereof or the like can be used. The reaction can be carried out at 0° C. to 100° C. for several minutes to several tens hours.

Step F

Compound 8 is reacted with Compound 9 having a leaving group and a desired substituent in a suitable solvent in the presence or absence of a base at 0° C. to 100° C. for several minutes to several days to give Compound (I-B'). Examples of the leaving group are phenoxy, chloro and trichloromethyl. Examples of the base are triethylamine, pyridine, diisopropylethylamine, sodium hydroxide, potassium carbonate and sodium hydrogencarbonate. Examples of the solvent are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, methanol, ethanol and the mixture thereof.

Step D

Compound (I-B') is reacted in a similar manner to the above Step D to give Compound (I-A').

(Compound wherein Y=$NR^7$CO)

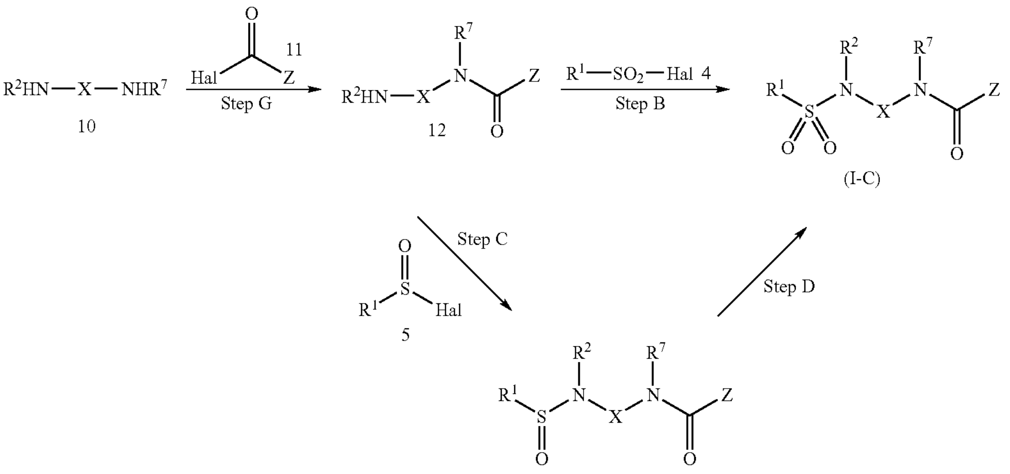

(I-D)

wherein each of the symbols is the same as the above.

Step G and Step B

Compound 10 is reacted with Compound 11 under the same reaction condition as that in Step B. Thus obtained Compound 12 is reacted in a similar manner to the above Step B to rive Compound (I-C) wherein n=2.

Step C and Step D

To synthesize Compound (I-D), Compound 12 obtained in Step G may be reacted in similar manners to the above Step C and Step D.

(Compound wherein Y=OCONR$^7$)

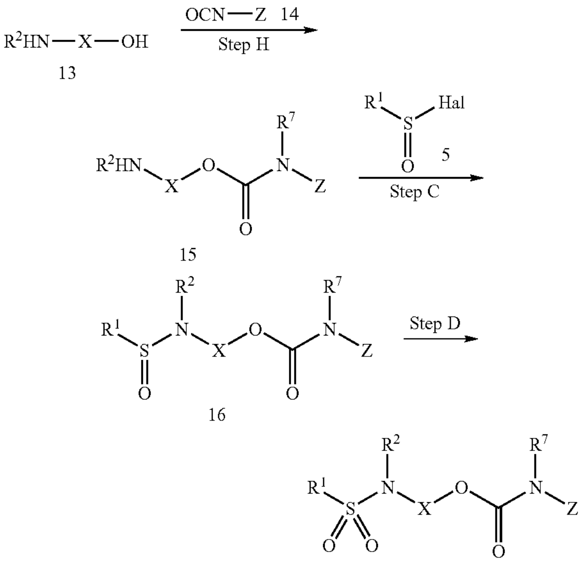

13
15
16
(I-E)

wherein each of symbols is the same as the above.

Step H

Compound 13 is reacted with isocyanate Compound 14 having a substituent Z in a suitable solvent in the presence or absence of a suitable catalyst at 0° C. to 100° C. for several minutes to several days to give Compound 15. Examples of the solvent are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile and the mixture thereof.

Step C and Step D

Thus obtained Compound 15 is reacted in similar manners to Step C and Step D to give Compound (I-E) of the present invention.

(Compound wherein Y=CSNR$^7$ or NR$^7$CS)

Compound (I) wherein Y is CSNR$^7$ or NR$^7$CS can be synthesized by reacting Compound (I) wherein Y is CONR$^7$ or NR$^7$CO synthesized in any one of the above methods with the Lawesson's reagent or phosphorus pentasulfide in a suitable solvent at 30° C. to 100° C. for several minutes to several hours. Examples of the solvent are tetrahydrofuran, dimethylformamide, diethyl ether, dichloromethane toluene, benzene, xylene, cyclohexane, hexane, chloroform, ethyl acetate, butyl acetate, pentane, heptane, dioxane, acetone, acetonitrile and the mixture thereof.

Amino groups may be protected with a suitable protecting group in the usual manner at a suitable step. For example, phthalimide, lower alkoxycarbonyl, lower alkenyloxycarbonyl, halogenoalkoxycarbonyl, aryl(lower)alkoxycarbonyl, trialkylsilyl, lower alkylsulfonyl, halogeno(lower)alkylsulfonyl, arylsulfonyl, lower alkylcarbonyl and arylcarbonyl can be used as the protecting group.

After protection of the amino group, the compound is subjected to the above-mentioned reactions and the obtained compound is deprotected by treatment of an acid or a base in a suitable solvent at a suitable stage. Examples of a solvent is tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile and the mixture thereof. Examples of a base are hydrazine, pyridine, sodium hydroxide and potassium hydroxide and examples of an acid are hydrochloric acid, trifluoroacetic acid and hydrofluoric acid.

All of the compounds of the present invention have an NPY Y5 antagonistic activity and the following compounds are specifically preferable.

In the formula (I), a compound wherein R$^1$ is optionally substituted lower alkyl or optionally substituted cycloalkyl (hereinafter referred to as "R$^1$ is R1-1"), a compound wherein R$^1$ is C3 to C10 alkyl or C5 to C6 cycloalkyl, each of which is optionally substituted with halogen (hereinafter referred to as "R$^1$ is R1-2"), a compound wherein R$^1$ is C3 to C10 alkyl optionally substituted with halogen (hereinafter referred to as "R$^1$ is R1-3"), a compound wherein R$^1$ is isopropyl or t-butyl (hereinafter referred to as "R$^1$ is R1-4"), a compound wherein R$^2$ is hydrogen or C1 to C3 alkyl (hereinafter referred to as "R$^2$ is R2-1"), a compound wherein R$^2$ is hydrogen (hereinafter referred to as "R$^2$ is R2-2"), a compound wherein X is optionally substituted lower alkylene, optionally substituted lower alkenylene or

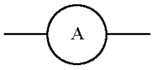

wherein

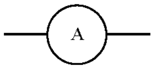

is optionally substituted cycloalkylene, optionally substituted cycloalkenylene, optionally substituted bicycloalkylene, optionally substituted phenylene or optionally substituted heterocyclediyl (hereinafter referred to as "X is X-1").

a compound wherein X is C2 to C6 alkylene, C3 to C6 alkenylene or

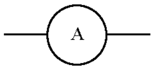

wherein

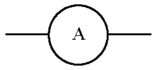

is optionally substituted cycloalkylene, optionally substituted cycloalkenylene, optionally substituted bicycloalkylene, optionally substituted phenylene, optionally substituted piperidinylene, optionally substituted thiophenediyl or optionally substituted furandiyl (hereinafter referred to as "X is X-2"), a compound wherein X is C2 to C6 alkylene or

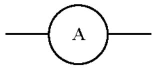

wherein is optionally substituted cycloalkylene, optionally substituted phenylene, optionally substituted piperidinylene, optionally substituted thiophenediyl or optionally substituted furandiyl (hereinafter referred to as "X is X-3"), a compound wherein X is (i) C2 to C6 alkylene or (ii) cycloalkylene or phenylene, each of which is optionally substituted with halogen, hydroxy, lower alkyl or halogeno(lower)alkyl (hereinafter referred to as "X is X-4"), a compound wherein X is C2 to C6 alkylene or to C5 to C6 cycloalkylene (hereinafter referred to as "X is X-5"), a compound wherein X is C3 to C6 alkylene or 1,4-cyclohexylene (hereinafter referred to as "X is X-6"), a compound wherein Y is $CONR^7$, $CSNR^7$, $NR^7CO$ or $NR^7CS$ and $R^7$ is hydrogen or C1 to C3 alkyl (hereinafter referred to as "Y is Y-1"), a compound wherein Y is CONH, CSNH or NHCO (hereinafter referred to as "Y is Y-2"), a compound wherein Y is CONH (hereinafter referred to as "Y is Y-3"), a compound wherein Z is optionally substituted lower alkyl, optionally substituted carbocyclyl or optionally substituted heterocyclyl (hereinafter referred to as "Z is Z-1"), a compound wherein Z is $-(CR^8R^9)r-W-(CR^{10}R^{11})s-V$ wherein $R^8$, $R^9$, $R^{10}$ and $R^{11}$ are each independently hydrogen or lower alkyl and when Z has two or more of $R^8$, two or more of $R^9$, two or more of $R^{10}$ and/or two or more of $R^{11}$, each of $R^8$, $R^9$, $R^{10}$ and $R^{11}$ may be different, W is single bond, O, S or $NR^{12}$, $R^{12}$ is hydrogen, lower alkyl or phenyl, V is hydrogen, optionally substituted cycloalkyl, optionally substituted bicycloalkyl, optionally substituted aryl or optionally substituted heterocyclyl, r is an integer of 1 to 4 and s is an integer of 0 to 4

(hereinafter referred to as "Z is Z-2"), a compound wherein Z is $-(CH_2)r-W-(CH_2)s-V$ wherein W is single bond, O, S or $NR^{12}$, $R^{12}$ is hydrogen or lower alkyl, V is optionally substituted aryl or optionally substituted heterocyclyl wherein the substituents is halogen, hydroxy, lower alkyl, halogen (lower)alkyl, lower alkoxy, tower alkenyl, amino, lower alkylamino, acyl, carboxy, lower alkoxycarbonyl, phenyl or monocyclic heteroaryl, r is an integer of 1 to 4 and s is an integer of 0 to 4

(hereinafter referred to as "Z is Z-3), a compound wherein Z is $-(CH_2)r-W-(CH_2)s-V$ wherein W is single bond, O, S, NH or NMe, V is optionally substituted phenyl or optionally substituted heteroaryl wherein the substituents is halogen, lower alkyl, halogeno(lower)alkyl, lower alkoxy, amino or lower alkylamino, r is an integer of 1 to 3 and s is an integer of 0 or 1

(hereinafter referred to as "Z is Z-4"), a compound wherein Z is optionally substituted carbocyclyl, wherein the substituent is halogen; hydroxy;

optionally substituted lower alkyl wherein the substituents is halogen, hydroxy, carboxy, lower alkoxycarbonyl, cyano and/or phenyl;

lower alkenyl optionally substituted with lower alkoxycarbonyl;

optionally substituted lower alkoxy wherein the substituents is halogen, hydroxy, lower alkoxy, carboxy, lower alkoxycarbonyl, lower alkylamino, cycloalkyl, cyano and/or heterocyclyl;

cycloalkyl; cycloalkyloxy; acyl; lower alkylthio; carbamoyl; lower alkylcarbamoyl; cycloalkylcarbamoyl; hydroxy imino;

optionally substituted amino wherein the substituents is lower alkyl, optionally protected hydroxy(lower)alkyl, lower alkoxy(lower)alkyl, acyl, lower alkylsulfonyl, arylsulfonyl and/or phenyl;

phenyl optionally substituted with halogen, cyano, phenyl and/or heterocyclyl; lower alkylsulfinyl; lower alkylsulfamoyl; cycloalkylsulfamoyl;

nitro; cyano; alkylenedioxy; phenylazo optionally substituted with lower alkyl; phenoxy; oxo;

optionally substituted heterocyclyl wherein the substituents is optionally protected hydroxy, mercapto, halogen, lower alkyl, cycloalkyl, lower alkoxycarbonyl, acyl, amino, lower alkoxycarbonylamino, carbamoyl, oxo, phenyl, lower alkoxyphenyl, halogenophenyl, heterocyclyl and/or oxo;

heterocyclylsulfonyl optionally substituted with lower alkyl; heterocyclyloxy;

heterocyclylcarbonyl optionally substituted with lower alkyl (hereinafter referred to as "Z is Z-5).

a compound wherein Z is optionally substituted phenyl wherein the substituents is halogen; hydroxy; lower alkyl optionally substituted with halogen, hydroxy, lower alkoxycarbonyl, cyano and/or phenyl; lower alkoxycarbonyl(lower)alkenyl; lower alkoxy optionally substituted with halogen, lower alkoxy, lower alkoxycarbonyl, cycloalkyl and/or heterocyclyl; cycloalkyl; cycloalkyloxy; acyl; lower alkylthio; carbamoyl; lower alkycarbamoyl; amino optionally substituted with lower alkyl, hydroxy(lower)alkyl, acyl, lower alkylsulfonyl and/or phenyl; phenyl optionally substituted with halogen, cyano, phenyl and/or heterocyclyl;

lower alkyl sulfamoyl; cycloalkylsulfamoyl; nitro; alkylenedioxy; phenylazo optionally substituted with lower alkyl; phenoxy; oxo;

heterocyclyl optionally substituted with hydroxy, halogen, lower alkyl, lower alkoxycarbonyl, amino, carbamoyl, phenyl, halogenophenyl, heterocyclyl and/or oxo;

heterocyclyloxy; and/or heterocyclylsulfonyl optionally substituted with lower alkyl (hereinafter referred to as "Z is Z-6"), a compound wherein Z is optionally substituted phenyl wherein the substituents is halogen; lower alkyl optionally substituted with halogen, hydroxy, lower alkoxycarbonyl and/or phenyl; lower alkoxy optionally substituted with halogen and/or cycloalkyl; cycloalkyl; cycloalkyloxy; acyl; lower alkylthio; lower alkylcarbamoyl; amino optionally substituted with lower alkyl, hydroxy (lower)alkyl, acyl and/or phenyl; phenyl optionally substituted with piperidyl; cycloalkylsulfamoyl alkylenedioxy; phenoxy;

morpholinyl or morpholino, each of which is optionally substituted with lower alkyl; piperidyl optionally substituted with hydroxy, lower alkyl, lower alkoxycarbonyl, phenyl, halogenophenyl and/or oxo; pyrrolidinyl optionally substituted with hydroxy, carbamoyl and/or oxo;

piperazinyl optionally substituted with phenyl or pyrimidinyl; dihydropyridyl; pyrrolyl; pyrrolinyl; imidazolyl optionally substituted with halogen and/or lower alkyl; pyrazolyl; thienyl; thiadiazolyl; furyl; oxazolyl; isoxazolyl; tetrazolyl optionally substituted with lower alkyl and/or phenyl; indolinyl; indolyl; tetrahydroquinolyl; benzothiazolyl optionally substituted with lower alkyl; tetrahydroisothiazolyl optionally substituted with oxo; benzopyranyl optionally substituted with oxo; tetrahydropyranyloxy; tetrahydrofuryloxy; morpholinosulfonyl optionally substituted with lower alkyl; and/or piperidylsulfonyl optionally substituted with lower alkyl (hereinafter referred to as "Z is Z-7"), a compound wherein Z is optionally substituted phenyl wherein the substituents is halogen, lower alkyl, halogeno (lower)alkyl, lower alkoxy, cycloalkyloxy, lower alkylcarbamoyl, phenyl, lower alkyl morpholino and/or tetrahydropyranyloxy (hereinafter referred to as "Z is Z-8"), a compound wherein Z is optionally substituted heterocyclyl wherein the substituents is halogen, hydroxy, lower alkyl, halogeno(lower)alkyl, lower alkoxy, mercapto, lower alkylthio, acyl, carboxy, lower alkoxycarbonyl, amino, lower alkylamino, phenyl, naphthyl, phenylthio optionally substituted with halogen, phenoxy optionally substituted with halogen, oxo, and/or heterocyclyl optionally substituted with lower alkyl (hereinafter referred to as "Z is Z-9"), compound wherein Z is thienyl, pyrazolyl, thiazolyl, thiadiazolyl, pyridyl, pyrimidinyl, pyrazinyl, triazinyl, indolyl, isoindolyl, indolinyl, isoindolinyl, indazolyl, benzopyranyl, benzoxazolyl, benzothienyl, benzothiazolyl, benzothiazolinyl, benzothiadiazolyl, quinolyl, isoquinolyl, dihydrobenzofuryl, carbazolyl, acridinyl or dibenzofuryl, each of which is optionally substituted with substituents selected from the group of lower alkyl; halogeno(lower)alkyl; lower alkoxy; lower alkoxycarbonyl, acyl; lower alkoxycarbonyl(lower)alkyl, mercapto; phenyl, naphthyl, phenylthio or phenoxy, each of which is optionally substituted with halogen; furyl; nitro; oxo; and morpholino optionally substituted with lower alkyl) (hereinafter referred to as "Z is Z-10"), a compound wherein Z is thienyl, thiazolyl, thiadiazolyl, pyridyl, pyrazinyl, indolyl, isoindolinyl, benzopyranyl, quinolyl, carbazolyl, dibenzofuryl, benzopyranyl, benzothienyl or benzothiazolyl, each of which is optionally substituted with one or more substituents selected from the group of lower alkyl, halogeno(lower)alkyl, lower alkoxy, lower alkoxycarbonyl, acyl, phenyl, naphthyl, phenylthio, lower alkyl morpholino and oxo) (hereinafter referred to as "Z is Z-11), a compound wherein $R^1$ is R1-2, $R^2$ is R2-2, n is 2 and a combination of X, Y and Z, i.e., (X, Y, Z), is any one of the followings.

(X, Y, Z)=(X-3, Y-2, Z-1), (X-3, Y-2, Z-2), (X-3, Y-2, Z-3), (X-3, Y-2, Z-4), (X-3, Y-2, Z-5), (X-3, Y-2, Z-6), (X-3, Y-2, Z-7), (X-3, Y-2, Z-8), (X-3, Y-2, Z-9), (X-3, Y-2, Z-10), (X-3, Y-2, Z-11), (X-3, Y-3, Z-1), (X-3, Y-3, Z-2), (X-3, Y-3, Z-3), (X3, Y-3, Z-4), (X-3, Y-3, Z-5), (X-3, Y-3, Z-6), (X3, Y-3, Z-7), (X-3, Y-3, Z-8), (X-3, Y-3, Z-9), (X-3, Y-3, Z-10), (X-3, Y-3, Z-11), (X-4, Y-2, Z-1), (X-4, Y-2, Z-2), (X-4, Y-2, Z-3), (X-4, Y-2, Z-4), (X-4, Y-2, Z-5), (X-4, Y-2, Z-6), (X-4, Y-2, Z-7), (X-4, Y-2, Z-8), (X-4, Y-2, Z-9), (X-4, Y-2, Z-10), (X-4, Y-2, Z-11), (X-4, Y-3, Z-1), (X-4, Y-3, Z-2), (X-4, Y-3, Z-3), (X-4, Y-3, Z-4), (X-4, Y-3, Z-5), (X-4, Y-3, Z-6), (X-4, Y-3, Z-7), (X-4, Y-3, Z-8), (X-4, Y-3, Z-9), (X-4, Y-3, Z-10), (X-4, Y-3, Z-11), (X-5, Y-2, Z-1), (X-5, Y-2, Z-2), (X-5, Y-2, Z-3), (X-5, Y-2, Z-4), (X-5, Y-2, Z-5), (X-5, Y-2, Z-6), (X5, Y2, Z7), (X5, Y2, Z 8), (X5, Y-2, Z-9), (X-5, Y-2, Z-10), (X-5, Y-2, Z-11), (X-5, Y-3, Z-1) ((X-5, Y-3, Z-2), (X-5, Y-3, Z-3), (X-5, Y-3, Z-4), (X-5, Y-3, Z-5), (X-5, Y3Z-6), (X-5, Y-3, Z-7), (X-5, Y-3, Z-8), (X-5, Y-3, Z-9), (X-5, Y-3, Z-10) or (X-5, Y-3, Z-11), the pharmaceutically acceptable salt, solvate or prodrug thereof.

The NPY Y5 receptor antagonist of the present invention is effective for all of the diseases in which NPY Y5 is involved and it is especially useful for preventing and/or treating obesity and suppressing food intake. Moreover, the antagonist is effective for preventing and/or treating the diseases in which obesity acts as a risk factor, for example, diabetes, hypertension, hyperlipemia, atherosclerosis and acute coronary syndrome.

In addition, the NPY Y5 receptor antagonist of the present invention has a low affinity for NPY Y1 and Y2 receptors, and has a high selectivity for NPY Y5 receptor. NPY causes a sustained vasoconstrictive action in the periphery and this action is mainly via Y1 receptor. Since Y5 receptor is not involved in this action at all, the NPY Y5 receptor antagonist has a low risk of inducing side effects based on the peripheral vasoconstriction, and is expected to be suitably used as a safe medicine.

The NPY Y5 receptor antagonist shows an anti-obestic effect by suppressing food intake. Therefore, it is one of the features that this antagonist does not induce side effects, e.g., an indigestion caused by an anti-obestic agent which inhibits digestion and absorption, and a central side effect such as anti-depression caused by a serotonin transporter inhibitor showing an anti-obesity effect.

A compound of the present invention can be administered orally or parenterally as an anti-obestic agent or anorectic agent. In the case of oral administration, it may be in any usual form such as tablets, granules, powders, capsules, pills, solutions, syrups, buccal tablets and sublingual tablets. When the compound is parenterally administered, any usual form is preferable, for example, injections (e.g., intravenous, intramuscular), suppositories, endermic agents and vapors.

Oral administration is particularly preferable because the compounds of the present invention show a high oral absorbability.

A pharmaceutical composition may be manufactured by mixing an effective amount of a compound of the present invention with various pharmaceutical additives suitable for the administration form, such as excipients, binders, moistening agents, disintegrators, lubricants and diluents. When the composition is of an injection, an active ingredient together with a suitable carrier can be sterilized to give a pharmaceutical composition.

Examples of the excipients include lactose, saccharose, glucose, starch, calcium carbonate and crystalline cellulose. Examples of the binders include methylcellulose, carboxymethylcellulose, hydroxypropylcellulose, gelatin and polyvinylpyrrolidone. Examples of the disintegrators include carboxymethylcellulose, sodium carboxymethylcellulose, starch, sodium alginate, agar and sodium lauryl sulfate. Examples of the lubricants include talc, magnesium stearate and macrogol. Cacao oil, macrogol, methylcellulose etc. may be used as base materials of suppositories. When the composition is manufactured as solutions, emulsified injections or suspended injections, dissolving accelerators, suspending agents, emulsifiers, stabilizers, preservatives, isotonic agents and the like may be added. For oral administration, sweetening agents, flavors and the like may be added.

Although the dosage of a compound of the present invention as an anti-obestic agent or anorectic agent should be determined in consideration of the patient's age and body weight, the type and degree of diseases, the administration route etc., a usual oral dosage for an adult is 0.05 to 100 mg/kg/day and preferable is 0.1 to 10 mg/kg/day. For parenteral administration, although the dosage highly varies with administration routes, a usual dosage is 0.005 to 10 mg/kg/day, preferably, 0.01 to 1 mg/kg/day. The dosage may be administered in one to several divisions per day.

The present invention is further explained by the following Examples and Experiments, which are not intended to limit the scope of the present invention.

EXAMPLES

Example 1

Synthesis of Compound (I-7)

Step 1

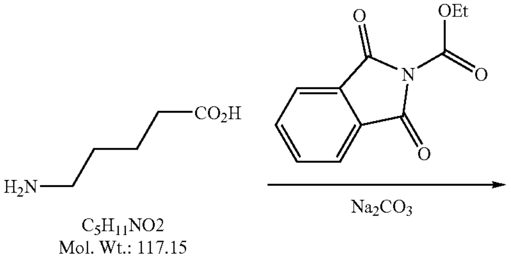

$C_5H_{11}NO2$
Mol. Wt.: 117.15

-continued

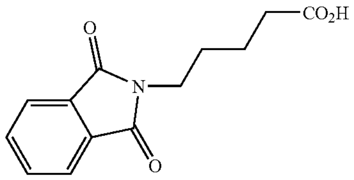

$C_{13}H_{13}NO4$
Mol. Wt.: 247.25

Sodium carbonate (995 mg, 9.38 mmol) was dissolved in 30 ml of water and starting material amino acid (1.0 g, 8.53 mmol) and N-carbethoxyphthalimide (2.49 g, 11.4 mmol) were added thereto. The mixture was stirred at room temperature overnight. The pH of the mixture was adjusted to 1 by adding conc. hydrochloric acid. Precipitated crystals were washed with water and dried to give the desired compound (1.72 g, 82% yield).

$^1$H-NMR ($CD_3OD$) δ ppm: 1.59-1.77 (m, 4H), 2.34 (t, 2H, J=6.3 Hz), 3.69 (t, 2H, J=6.6 Hz), 7.78-7.87 (m, 4H).

Step 2

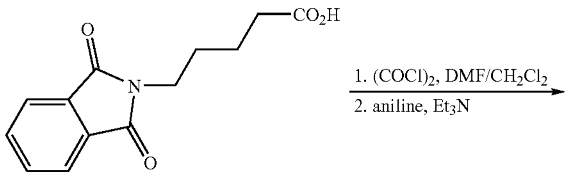

$C_{13}H_{13}NO4$
Mol. Wt.: 247.25

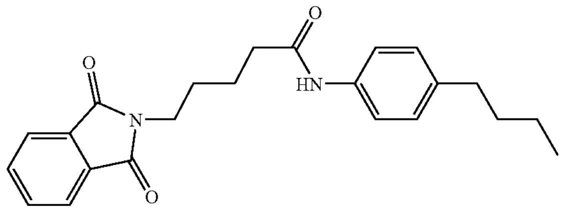

$C_{23}H_{26}N_2O3$
Mol. Wt.: 378.46

The compound obtained in Step 1 (1.0 g, 4.0 mmol) was dissolved in 5 ml of dichloromethane at room temperature. Oxalyl chloride (0.459 ml, 5.2 mmol) and trace amounts of DMF were added to the mixture under ice-cooling and the mixture was reacted under ice-cooling and at room temperature, each for 30 min. After the solvent was removed under reduced pressure, 5 ml of dichloromethane was added. Under ice-cooling, 4-butylaniline (664 mg, 4.4 mmol) and triethylamine (0.564 ml, 4.4 mmol) were added thereto and the mixture was reacted for 30 min. at room temperature. The reactant was poured into water and extracted with chloroform. The organic layer was washed with water and dried over magnesium sulfate anhydride. The solvent was removed under reduced pressure and the residue was purified by silica gel chromatography to give the desired compound (1.49 g, 97% yield).

$^1$H-NMR ($CDCl_3$) δ ppm: 0.91 (t, 3H, J=7.5 Hz), 1.27-1.39 (m, 2H), 1.51-1.62 (m, 2H), 1.72-1.84 (m, 4H), 2.40-2.46 (m, 2H), 2.56 (t, 2H, J=7.5 Hz), 3.76 (t, 1H, J=5.7 Hz), 7.12 (d, 2H, J=7.8 Hz), 7.33 (s, 1H), 7.42 (d, 2H, J=8.1 Hz), 7.71-7.73 (m, 2H), 7.83-7.86 (m, 2H).

Step 3

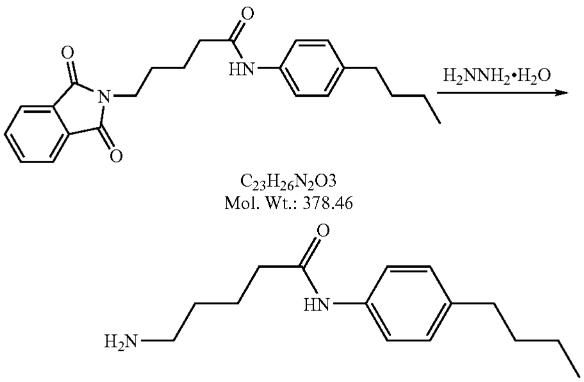

$C_{23}H_{26}N_2O3$
Mol. Wt.: 378.46

$C_{15}H_{24}N_2O$
Mol. Wt.: 248.36

After the compound obtained in Step 2 (1.49 g, 3.9 mmol) was dissolved in 30 ml of ethanol, hydrazine monohydrate (0.591 mg, 11.8 mmol) was added and the mixture was reacted at 50° C. for 3 hours. The solvent was removed, 1 mol/l aqueous NaOH was added and the solution was extracted with ethyl acetate. The organic layer was washed with water and dried over magnesium sulfate anhydride. The solvent was removed under reduced pressure to give the desired compound (808 mg, 83% yield)

$^1$H-NMR ($CD_3OD$) δ ppm: 0.93 (t, 3H, J=7.2 Hz), 1.28-1.40 (m, 2H), 1.50-1.62 (m, 4H), 1.67-1.77 (m, 2H), 2.37 (t, 2H, J=7.5 Hz), 2.56 (t, 2H, J=7.8 Hz), 2.68 (t, 2H, J=7.2 Hz), 7.11 (d, 2H, J=8.1 Hz), 7.42 (d, 2H, J=8.4 Hz).

Step 4

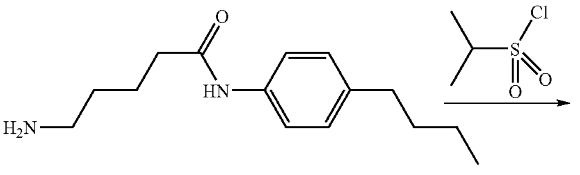

$C_{15}H_{24}N_2O$
Mol. Wt.: 248.36

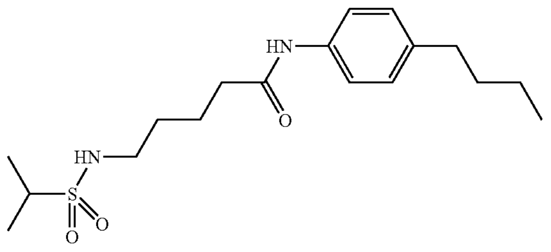

The compound obtained in Step 3 (808 mg, 3.25 mmol) was suspended in 5 ml of dichloromethane under ice-cooling and isopropylsulfonyl chloride (696 mg, 4.9 mmol) and triethylamine (494 mg, 4.9 mmol) were added. After the mixture was reacted under ice-cooling for an hour, the reactant was poured into water and extracted with chloroform. The organic layer was washed with water and dried over magnesium sulfate anhydride. The solvent was removed under reduced pressure and the residue was purified by silica gel chromatography to give the desired compound quantitatively.

$^1$H-NMR ($CDCl_3$) δ ppm: 0.91 (t, 3H, J=7.2 Hz), 1.27-1.40 (m, 2H), 1.36 (d, 6H, J=6.6 Hz), 1.51-1.69 (m, 4H), 1.77-1.86 (m, 2H), 2.38 (t, 2H, J=7.2 Hz), 2.56 (t, 2H, J=7.5 Hz), 3.12-3.21 (m, 3H), 4.38 (t, 1H, J=5.7 Hz), 7.11 (d, 2H, J=8.4 Hz), 7.36-7.41 (m, 3H).

Example 2

Synthesis of Compound (I-10)

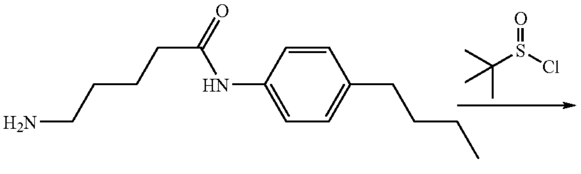

$C_{15}H_{24}N_2O$
Mol. Wt.: 248.36

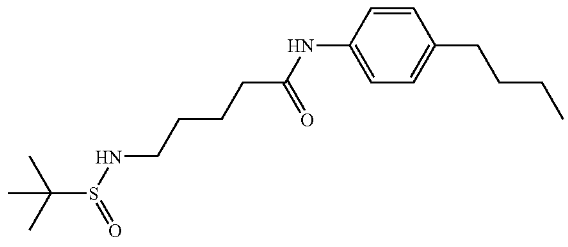

$C_{19}H_{32}N_2O_2S$
Mol. Wt.: 352.54

The desired compound was synthesized in a similar manner to Step 4 in Example 1 except that tert-butylsulfinyl chloride (689 mg, 4.9 mmol) and triethylamine (494 mg, 4.9 mmol) were added to the compound obtained in Step 3 in Example 1.

$^1$H-NMR ($CDCl_3$) δ ppm: 0.91 (t, 3H, J=7.5 Hz), 1.22 (s, 9H), 1.30-1.37 (m, 2H), 1.51-1.68 (m, 4H), 1.76-1.86 (m, 2H), 2.31-2.40 (m, 2H), 2.56 (t, 2H, J=7.5 Hz), 3.15-3.26 (m, 3H), 7.11 (t, 2H, J=8.7 Hz), 7.42 (d, 2H, J=8.1 Hz), 7.54 (s, 1H).

Example 3

Synthesis of Compound (I-11)

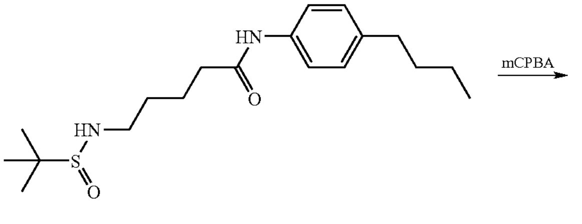

$C_{19}H_{32}N_2O_2S$
Mol. Wt.: 352.54

-continued

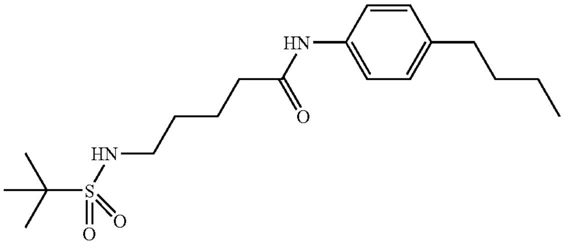

$C_{19}H_{32}N_2O_3S$
Mol. Wt.: 368.54

The compound obtained in Example 2 (352 mg, 1.0 mmol) was dissolved in 5 ml of dichloromethane under ice-cooling and mCPBA (259 mg, 1.5 mmol) was added to the solution. The solution was reacted at room temperature for an hour and the insoluble material was filtered off. The filtrate was washed with 1 mol/l NaOH, $Na_2S_2O_5$ and water, successively, and dried over magnesium sulfate anhydride. The solvent was removed under reduced pressure and the residue was purified by silica gel chromatography to give the desired compound (338 mg, 92% yield).

$^1$H-NMR ($CDCl_3$) δ ppm: 0.91 (t, 3H, J=7.5 Hz), 1.29-1.39 (m, 2H), 1.39 (s, 9H), 1.51-1.68 (m, 4H), 1.76-1.84 (m, 2H), 2.37 (t, 2H, J=7.5 Hz), 2.56 (t, 2H, J=7.8 Hz), 3.19-3.26 (m, 2H), 4.20 (t, 1H, J=5.7 Hz), 7.11 (t, 2H, J=8.1 Hz), 7.42 (d, 2H, J=8.7 Hz), 7.46 (s, 1H).

Example 4

Synthesis of Compound (I-72)

Step 1

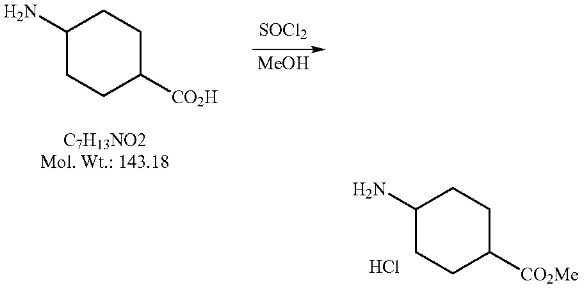

$C_7H_{13}NO2$
Mol. Wt.: 143.18

$C_8H_{16}ClNO2$
Mol. Wt.: 193.67

Starting material amino acid (a mixture of cis isomer and trans isomer) (1.0 g, 8.53 mmol) was dissolved in 7.5 ml of methanol. Thionyl chloride (1.0 ml, 13.7 mmol) was added to the mixture under ice-cooling and the mixture was stirred at room temperature overnight. Alter the mixture was concentrated under reduced pressure, diethylether was added and precipitated crystals were obtained by filtration. The crystals were washed with diethylether and dried to give the desired compound (1.25 g, 93% yield).

$^1$H-NMR ($CDCl_3$) δ ppm: 1.50-2.60 (m, 9H), 3.08-3.36 (m, 1H), 3.67 (s, 3H, $CO_2$Me of cis isomer), 3.71 (s, 3H, $CO_2$Me of trans isomer), 8.15-8.55 (m, 3H).

Step 2

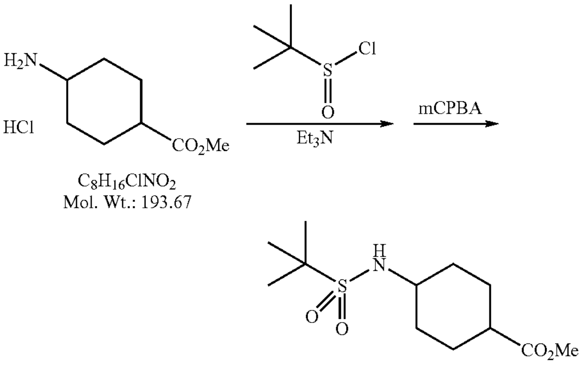

$C_8H_{16}ClNO_2$
Mol. Wt.: 193.67

$C_{12}H_{23}NO_4S$
Mol. Wt.: 277.38

The desired sulfonamide (a mixture of cis isomer and trans isomer) was synthesized from starting material methyl ester in similar manners to Step 3 in Example 1 and Example 2.

Cis Isomer $^1$H-NMR ($CDCl_3$) δ ppm: 1.39 (s, 9H), 1.52-1.99 (m, 8H), 2.43-2.53 (m, 1H), 3.42-3.55 (m, 1H), 3.69 (s, 3H), 3.85 (d, 1H, J=9.0 Hz).

Step 3

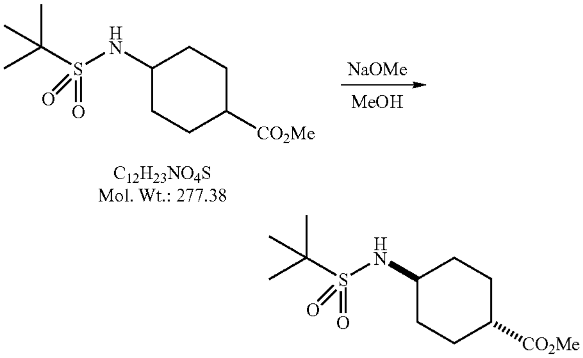

$C_{12}H_{23}NO_4S$
Mol. Wt.: 277.38

$C_{12}H_{23}NO_4S$
Mol. Wt.: 277.38

Starting material sulfonamide (19.4 g, 70.0 mmol, a mixture of cis isomer and trans isomer) was dissolved in 30 ml of methanol. To the mixture, 28% sodium methoxide (284 ml, 140.0 mmol) was added and refluxed with stirring under ice-cooling. After the solvent was removed, the residue was diluted with chloroform, and 1 mol/l HCl was added with stirring under ice-cooling until pH of an aqueous layer reached 3. The aqueous layer was extracted with chloroform and the organic layer was washed with water and dried over magnesium sulfate anhydride. The obtained crude crystals were recrystallized from hexane-ethyl acetate to give the desired sulfonamide (trans isomer, 7.75 g, 40% yield).

Trans Isomer $^1$H-NMR ($CD_3OD$) δ ppm: 1.16-1.32 (m, 2H), 1.39 (s, 9H), 1.44-1.52 (m, 2H), 1.98-2.09 (m, 2H), 2.14-2.29 (m, 3H), 3.18-3.37 (m, 1H), 3.63 (d, 1H, J=9.0 Hz) 3.67 (s, 3H).

Step 4

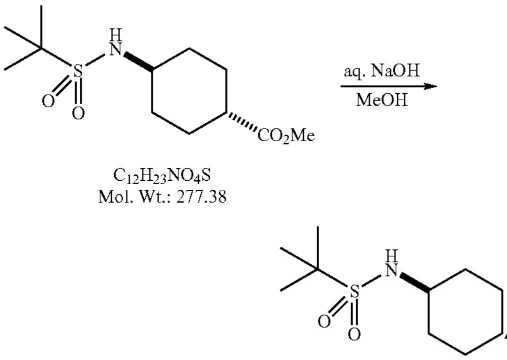

$C_{12}H_{23}NO_4S$
Mol. Wt.: 277.38

$C_{11}H_{21}NO_4S$
Mol. Wt.: 263.35

Starting material methyl ester (4.77 g, 17.2 mmol) was dissolved in 95 ml of methanol and 1 mol/l NaOH (43 ml, 43.0 mmol) was added with stirring under ice-cooling. The mixture was stirred at room temperature overnight and concentrated under reduced pressure. After 1 mol/l HCl was added with stirring until pH of the mixture reached 3 under ice-cooling, the precipitated crystals were collected by filtration, washed with water and dried. The obtained crude crystals were recrystallized from hexane-ethylacetate to give the desired carboxylic acid (4.20 g, 93% yield).

$^1$H-NMR ($CDCl_3$) δ ppm: 1.18-1.35 (m, 2H), 1.39 (s, 9H), 1.46-1.63 (m, 2H), 2.01-2.14 (m, 2H), 2.14-2.32 (m, 3H), 3.18-3.35 (m, 1H), 3.80 (d, 1H, J=9.6 Hz).

Step 5

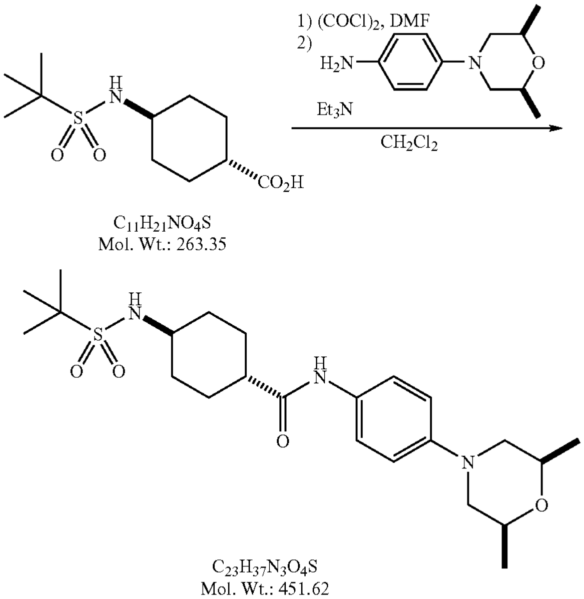

$C_{11}H_{21}NO_4S$
Mol. Wt.: 263.35

$C_{23}H_{37}N_3O_4S$
Mol. Wt.: 451.62

A starting material carboxylic acid (5.86 g, 22.3 mmol) was dissolved in 88 ml of dichloromethane at room temperature. To the mixture, oxalyl chloride (2.34 ml, 26.7 mmol) and catalytic amount of DMF were added under ice-cooling and stirred at room temperature for an hour. After the solvent was removed under reduced pressure, dichloromethane (115 ml), substituted aniline (5.05 g, 24.5 mmol) and triethylamine (4.65 ml, 33.4 mmol) were added. The mixture was stirred at room temperature for 2.5 hours, the ice-cooling water was poured thereto, and the mixture was extracted with chloroform. An organic layer was washed with water and dried over magnesium sulfate anhydride. The solvent was removed under reduced pressure and ethyl acetate and hexane were added to the residue. The precipitated crystals were collected with filtration to give the desired amide (7.00 g, 70% yield).

$^1$H-NMR ($CDCl_3$) δ ppm: 1.25 (d, 6H, J=6.3 Hz), 1.17-1.42 (m, 2H), 1.40 (s, 9H), 1.60-1.78 (m, 2H), 1.98-2.43 (m, 7H), 3.20-3.43 (m, 3H), 3.67 (d, 1H, J=9.6 Hz), 3.74-3.86 (m, 2H), 6.86 (d, 2H, J=9.0 Hz), 7.04 (s, 1H), 7.38 (d, 2H, J=9.0 Hz).

Example 5

Synthesis of Compound (I-2)

Step 1

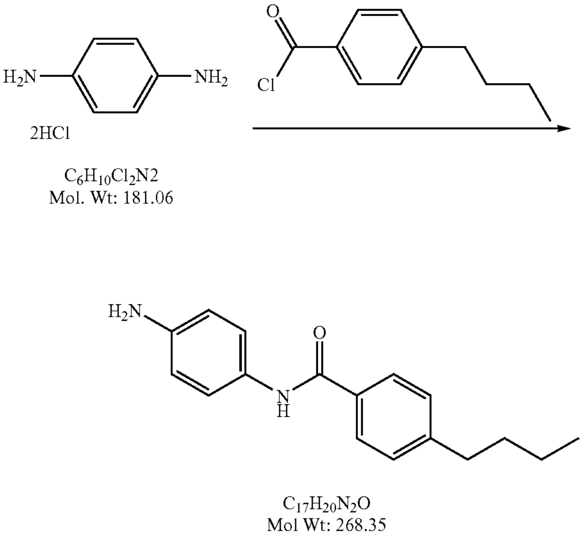

2HCl $C_6H_{10}Cl_2N2$
Mol. Wt: 181.06

$C_{17}H_{20}N_2O$
Mol Wt: 268.35

After starting material diamine (461 mg, 2.5 mmol) was suspended in dichloromethane under ice-cooling, an acid chloride (500 mg, 2.5 mmol) and triethylamine (773 mg, 7.5 mmol) were added and the mixture was reacted for 30 min. Water and dichloromethane were added to the reactant and insoluble materials were filtered off. The organic layer was washed with water and dried over magnesium sulfate anhydride. The solvent was removed under reduced pressure to give the desired compound as a residue (100 mg, 15% yield).

$^1$H-NMR ($CDCl_3$) δ ppm: 0.93 (t, 3H, J=7.2 Hz), 1.30-1.42 (m, 2H), 1.57-1.67 (m, 2H), 2.66 (t, 2H, J=7.8 Hz), 3.50 (brs, 1H), 6.57 (S, 1H), 6.68 (d, 2H, J=8.7 Hz), 7.26 (d, 2H, J=8.4 Hz), 7.39 (d, 2H, J=8.7 Hz), 7.68 (s, 1H), 7.75 (d, 2H, J=8.1 Hz), Step 2

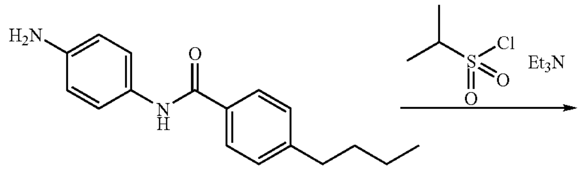

$C_{17}H_{20}N_2O$
Mol Wt.: 268.35

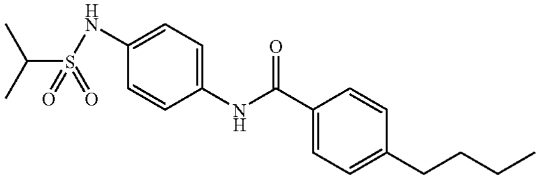

$C_{20}H_{26}N_2O_3S$
Mol Wt.: 374.50

The desired compound was synthesized in a similar manner to Step 4 in Example 1.

$^1$H-NMR ($CDCl_3$) δ ppm: 0.94 (t, 3H, J=7.5 Hz), 1.34-1.44 (m, 2H), 1.40 (d, 6H, J=6.6 Hz), 1.59-1.68 (m, 2H), 2.69 (t, 2H, J=7.8 Hz), 3.24-3.35 (m, 1H), 6.49 (s, 1H), 7.23-7.32 (m, 4H), 7.6 (d, 2H, J=8.7 Hz), 7.79 (d, 2H, J=8.1 Hz), 7.85 (s, 1H).

Example 6

Synthesis of Compound (I-31)

Step 1

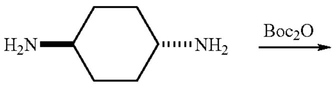

$C_6H_{14}N2$
Mol. Wt.: 114.19

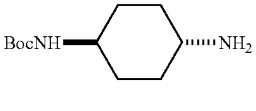

$C_{11}H_{22}N_2O2$
Mol. Wt.: 214.30

A starting material diamine (8.37 g, 73.3 mmol) was dissolved in 30 ml of dioxane at room temperature and a solution of $Boc_2O$ (2 g, 9.2 mmol) in dioxane (30 ml) was added. The mixture was reacted at room temperature for 3 days and the solvent was removed. Water was added to the residue and the mixture was extracted with chloroform. The organic layer was washed with water and dried over magnesium sulfate anhydride. The solvent was removed under reduced pressure to give the desired compound as a residue (1.8 g, 92% yield based on $Boc_2O$)

$^1$H-NMR ($CDCl_3$) δ ppm: 1.07-1.26 (m, 6H), 1.44 (s, 9H), 1.84-2.00 (m, 4H), 2.58-2.67 (m, 1H), 3.37 (brs, 1H), 4.43 (brs, 1H).

Step 2

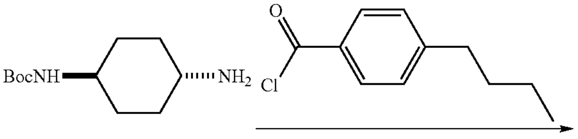

$C_{11}H_{22}N_2O2$
Mol. Wt.: 214.30

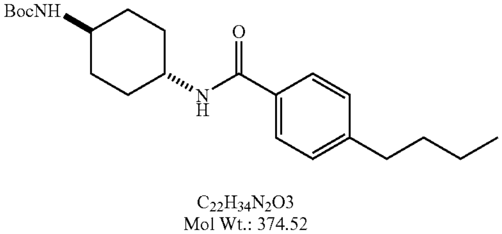

$C_{22}H_{34}N_2O3$
Mol Wt.: 374.52

The desired compound was synthesized in a similar manner to Step 1 in Example 5.

$^1$H-NMR ($CDCl_3$) δ ppm: 0.92 (t, 3H, J=7.2 Hz), 1.26-1.42 (m, 6H), 1.45 (s, 9H), 1.54-1.68 (m, 2H), 1.99-2.12 (m, 4H), 2.64 (t, 2H, J=7.8 Hz), 3.43 (brs, 1H), 3.90-4.00 (m, 1H), 4.48 (d, 1H, J=5.7 Hz), 5.95 (d, 1H, J=8.4 Hz), 7.21 (d, 2H, J=8.4 Hz), 7.65 (d, 2H, J=8.4 Hz).

Step 3

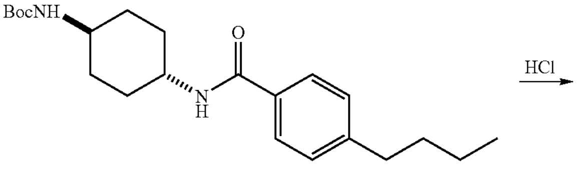

$C_{22}H_{34}N_2O3$
Mol Wt.: 374.52

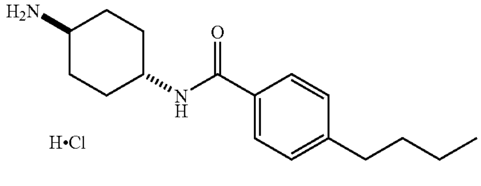

$C_{17}H_{27}ClN_2O$
Mol Wt.: 310.86

A starting material Boc compound (2.08 g, 5.55 mmol) was dissolved in 20 ml of ethyl acetate under ice-cooling and 20 ml of 4 mol/l HCl/AcOEt was added. The mixture was reacted at room temperature for an hour and the solvent was removed under reduced pressure to give the desired compound as a residue (1.7 g, 98% yield).

$^1$H-NMR ($CD_3OD$) δ ppm: 0.93 (t, 3H, J=7.2 Hz), 1.29-1.41 (m, 2H), 1.50-1.66 (m, 6H). 2.02-2.18 (m, 4H), 2.66 (t, 2H, J=7.8 Hz), 3.13 (brs, 1H), 3.82-3.94 (m, 1H), 7.26 (d, 2H, J=8.7 Hz), 7.72 (d, 2H, J=8.4 Hz).

Step 4

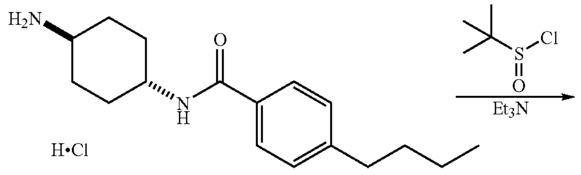

$C_{17}H_{27}ClN_2O$
Mol Wt.: 310.86

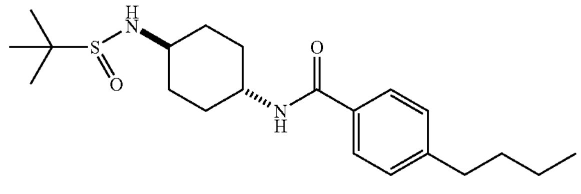

$C_{21}H_{34}N_2O_2S$
Mol Wt.: 378.57

The desired compound was synthesized in a similar manner to Step 4 in Example 1.

$^1$H-NMR ($CDCl_3$) δ ppm: 0.92 (t, 3H, J=7.5 Hz), 1.21 (s, 9H), 1.28-1.62 (m, 8H), 2.07-2.14 (m, 4H), 2.64 (t, 2H, J=7.8 Hz), 3.11 (d, 1H, J=5.1 Hz), 3.20 (brs, 1H), 3.90-4.04 (m, 1H), 6.06-6.14 (m, 1H), 7.21 (t, 2H, J=8.1 Hz), 7.67 (t, 2H, J=8.4 Hz).

Example 7

Synthesis of Compound (I-32)

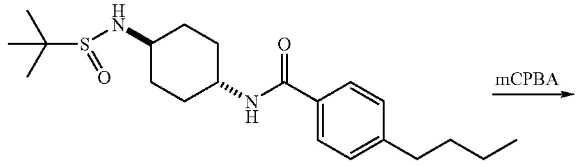

$C_{21}H_{34}N_2O_2S$
Mol Wt.: 378.57

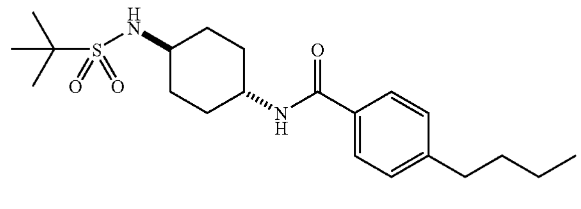

$C_{21}H_{34}N_2O_3S$
Mol Wt.: 394.57

The desired compound was synthesized from the compound obtained in Example 6 in a similar manner to Example 3.

$^1$H-NMR ($CDCl_3$) δ ppm: 0.92 (t, 3H, J=7.2 Hz), 1.27-1.65 (m, 8H), 1.40 (s, 9H), 2.10-2.23 (m, 4H), 2.65 (t, 2H, J=7.5 Hz), 3.23-3.35 (m, 1H), 3.49 (s, 1H), 3.88-4.02 (m, 1H), 5.84-5.92 (m, 1H), 7.13 (t, 2H, J=8.4 Hz), 7.65 (d, 2H, J=8.1 Hz).

Example 8

Synthesis of Compound (I-5)

Step 1

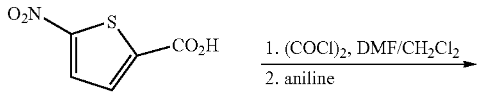

$C_5H_3NO_4S$
Mol. Wt.: 173.15

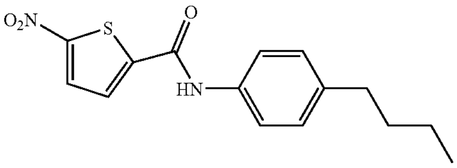

$C_{15}H_{16}N_2O_3S$
Mol. Wt: 304.37

The desired compound was synthesized in a similar manner to Step 2 in Example 1.

$^1$H-NMR ($CDCl_3$) δ ppm: 0.94 (t, 3H, J=7.5 Hz), 1.30-1.42 (m, 2H), 1.50-1.65 (m, 2H), 2.61 (t, 2H, J=7.8 Hz), 7.20 (d, 2H, J=7.2 Hz), 7.48-7.51 (m, 3H), 7.72 (s, 1H), 7.88-7.90 (m, 1H).

Step 2

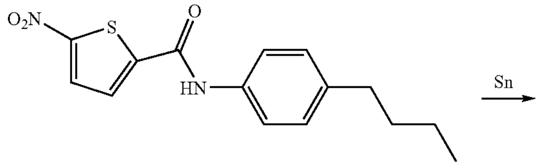

$C_{15}H_{16}N_2O_3S$
Mol. Wt: 304.37

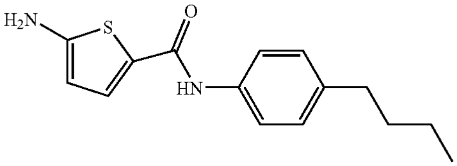

$C_{15}H_{18}N_2OS$
Mol. Wt: 274.38

To a mixture of a starting material nitro compound (593 mg, 1.95 mmol) and tin (358 mg, 3.0 mmol), 30 ml of 6 mol/l HCl and 6 ml of THF were added and reacted at 50° C. for 3 hours. After cooling, the solvent was removed and the residue was neutralized 10% with NaOH and extracted with chloroform. The organic layer was washed with water and dried over magnesium sulfate anhydride. The solvent was removed under reduced pressure and the residue was purified by silica gel chromatography to give the desired compound (110 mg, 21% yield).

$^1$H-NMR ($CDCl_3$) δ ppm: 0.91 (t, 3H, J=7.2 Hz), 1.26-1.39 (m, 2H), 1.49-1.59 (m, 2H), 2.50 (t, 2H, J=7.8 Hz), 4.37

(s, 1H), 6.65 (d, 2H, J=8.4 Hz), 6.97 (d, 2H, J=8.4 Hz), 7.14 (d, 1H, J=8.4 Hz), 7.43 (d, 1H, J=8.7 Hz).

Step 3

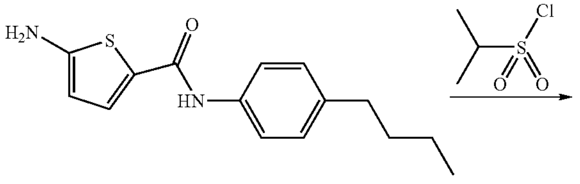

$C_{15}H_{18}N_2OS$
Mol. Wt: 274.38

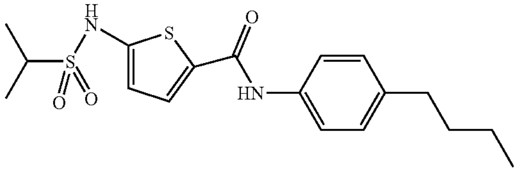

$C_{18}H_{24}N_2O_3S2$
Mol. Wt.: 380.53

The desired compound was synthesized in a similar manner to Step 4 in Example 1.

$^1$H-NMR ($CDCl_3$) δ ppm: 0.92 (t, 3H, J=7.2 Hz), 1.28-1.41 (m, 2H), 1.46 (d, 6H, J=6.9 Hz), 1.53-1.63 (m, 2H), 2.59 (t, 2H, J=7.8 Hz), 3.35-3.44 (m, 1H), 7.15 (d, 2H, J=8.7 Hz), 7.38 (s, 1H), 7.45 (d, 2H, J=8.7 Hz), 7.57 (s, 1H).

Example 9

Synthesis of Compound (I-4)

Step 1

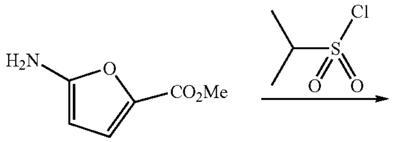

$C_6H_7NO3$
Mol. Wt.: 141.12

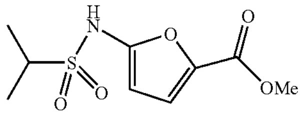

$C_9H_{13}NO_5S$
Mol. Wt.: 247.27

The desired compound was synthesized in a similar manner to Step 4 in Example 1.

$^1$H-NMR ($CDCl_3$) δ ppm: 1.44 (d, 6H, J=6.9 Hz), 3.33-3.43 (m, 1H), 3.88 (s, 9H), 6.24-6.26 (m, 1H), 7.11-7.14 (m, 2H).

Step 2

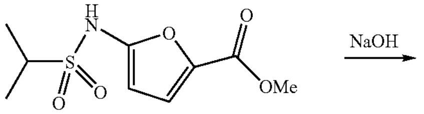

$C_9H_{13}NO_5S$
Mol. Wt.: 247.27

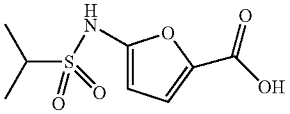

$C_8H_{11}NO_5S$
Mol. Wt.: 233.24

The desired compound was synthesized in a similar manner to Step 4 in Example 4.

$^1$H-NMR ($CDCl_3$) δ ppm: 1.44 (d, 6H, J=6.3 Hz), 3.33-3.45 (m, 1H), 6.25-6.28 (m, 1H), 7.27-7.28 (m, 1H), 7.51 (s, 1H).

Step 3

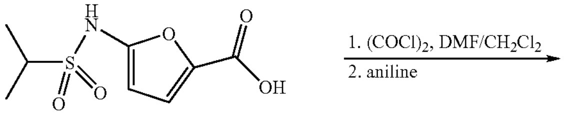

$C_8H_{11}NO_5S$
Mol. Wt.: 233.24

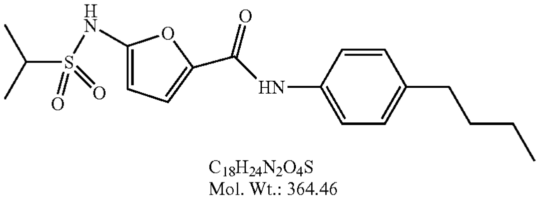

$C_{18}H_{24}N_2O_4S$
Mol. Wt.: 364.46

The desired compound was synthesized in a similar manner to Step 2 in Example 1.

$^1$H-NMR ($CD_3OD$) δ ppm: 0.92 (t, 3H, J=6.9 Hz), 1.28-1.41 (m, 2H), 1.46 (d, 6H, J=6.3 Hz), 1.53-1.63 (m, 2H), 2.58 (t, 2H, J=7.8 Hz), 3.33-3.43 (m, 1H), 6.27-6.29 (m, 1H), 7.14-7.16 (m, 3H), 7.50 (d, 2H, J=8.4 Hz), 7.90 (s, 1H).

Example 10

Synthesis of Compound (I-28)

Step 1

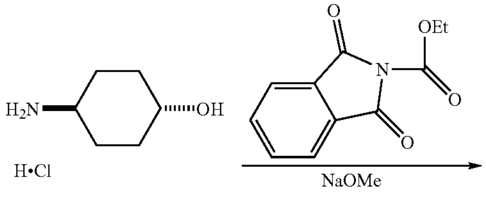

$C_6H_{14}ClNO$
Mol. Wt.: 151.63

-continued

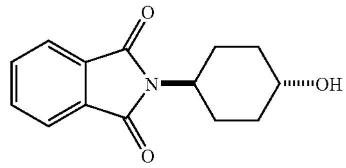

$C_{14}H_{15}NO3$
Mol. Wt.: 245.27

The desired compound was synthesized in a similar manner to Step 1 in Example 1.

$^1$H-NMR ($CDCl_3$) δ ppm: 1.37-1.52 (m, 3H), 1.74-1.79 (m, 2H), 2.07-2.13 (m, 2H), 2.28-2.42 (m, 2H), 3.72-3.81 (m, 1H), 4.09-4.20 (m, 1H), 7.68-7.73 (m, 2H), 7.81-7.85 (m, 2H).

Step 2

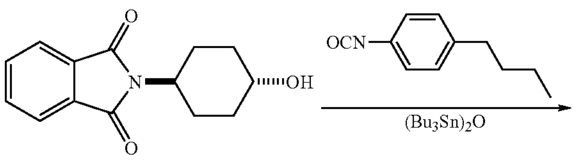

$C_{14}H_{15}NO3$
Mol. Wt.: 245.27

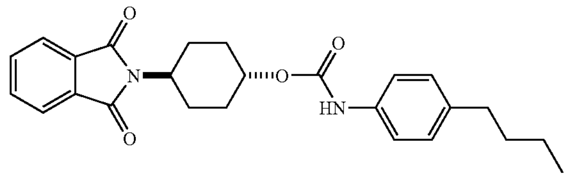

$C_{25}H_{28}N_2O4$
Mol. Wt.: 420.50

4-butylphenyl isocyanate (2.85 g, 16.3 mmol) was dissolved in 30 ml of THF, and a starting material alcohol (1.0 g, 4.08 mmol) and bis(tributyltin)oxide (972 mg, 1.63 mmol) were added. After the mixture was stirred overnight, the solvent was removed, water was added and the solution was extracted with chloroform. The organic layer was washed with water and dried over magnesium sulfate anhydride. The solvent was removed under reduced pressure and the residue was purified by silica gel chromatography to give the desired compound (332 mg, 19% yield).

$^1$H-NMR ($CDCl_3$) δ ppm: 0.92 (t, 3H, J=6.9 Hz), 1.30-1.40 (m, 2H), 1.48-1.62 (m, 4H), 1.79-1.83 (m, 2H), 2.21-2.25 (m, 2H), 2.37-2.50 (m, 2H), 2.57 (t, 2H, J=7.8 Hz), 4.11-4.22 (m, 1H), 4.77-4.87 (m, 1H), 6.49 (s, 1H), 7.11 (d, 2H, J=8.7 Hz) 7.29 (d, 2H, J=8.7 Hz), 7.69-7.73 (m, 2H), 7.80-7.84 (m, 2H).

Step 3

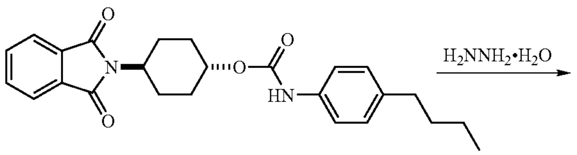

$C_{25}H_{28}N_2O4$
Mol. Wt.: 420.50

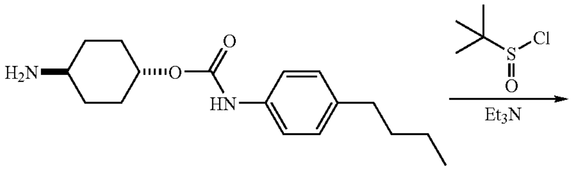

$C_{17}H_{26}N_2O2$
Mol. Wt.: 290.40

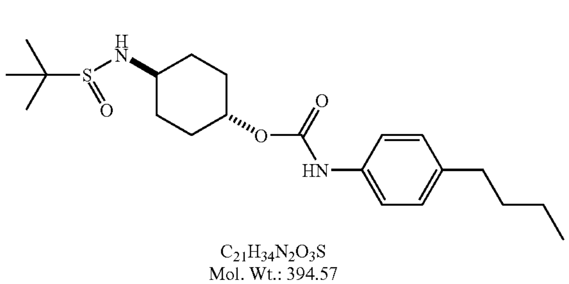

$C_{21}H_{34}N_2O_3S$
Mol. Wt.: 394.57

The desired compound was synthesized in similar manners to Step 3 in Example 1 and Example 2.

$^1$H-NMR ($CDCl_3$) δ ppm: 0.91 (t, 3H, J=7.2 Hz), 1.21 (s, 9H), 1.30-1.62 (m, 8H), 2.08 (d, 4H, J=11.1 Hz), 2.56 (t, 2H, J=7.8 Hz), 3.04 (d, 1H, J=4.8 Hz), 3.20-3.30 (m, 1H), 4.65-4.76 (m, 1H), 6.57 (s, 1H), 7.10 (d, 2H, J=8.7 Hz), 7.26 (d, 2H, J=8.1 Hz).

Example 11

Synthesis of Compound (I-29)

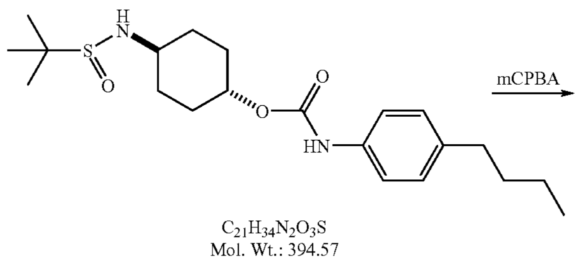

$C_{21}H_{34}N_2O_3S$
Mol. Wt.: 394.57

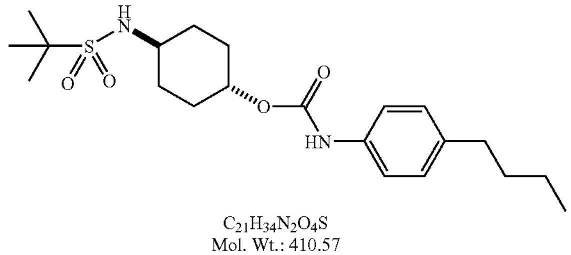

$C_{21}H_{34}N_2O_4S$
Mol. Wt.: 410.57

The desired compound was synthesized in a similar manner to Example 3.

$^1$H-NMR ($CDCl_3$) δ ppm: 0.91 (t, 3H, J=7.2 Hz), 1.23-1.62 (m, 8H), 1.40 (s, 9H), 2.12 (d, 4H, J=14.4 Hz), 2.56 (t, 2H, J=7.8 Hz), 3.28-3.40 (m, 1H), 3.90 (s, 1H), 4.60-4.73 (m, 1H), 6.57 (s, 1H), 7.10 (d, 2H, J=8.4 Hz), 7.25 (d, 2H, J=8.4 Hz).

Example 12

Synthesis of Compound (I-114)

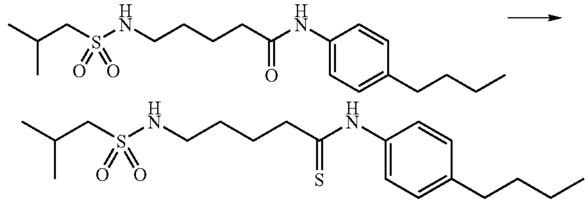

Lawesson's reagent [2,4-bis(4-methoxyphenyl)-1,3-dithia-2,4-diphosphetane-2,4-disulfide] (132 mg) was added to a solution of 100 mg of Compound (I-110) synthesized in a similar manner to Example 1 in toluene (2.7 ml) and the mixture was stirred at 80° C. for 3 hours. The reactant was concentrated under reduced pressure and the residue was purified by silica gel chromatography (ethyl acetate:n-hexane=1:1) to give pale yellow crystals (82.3 mg, 79%). The crystals were recrystallized from methylene chloride-diisopropyl ether to give the desired compound as colorless needles (50.5 mg, 48%).

Example 13

Synthesis of Compound (I-120)

Step 1

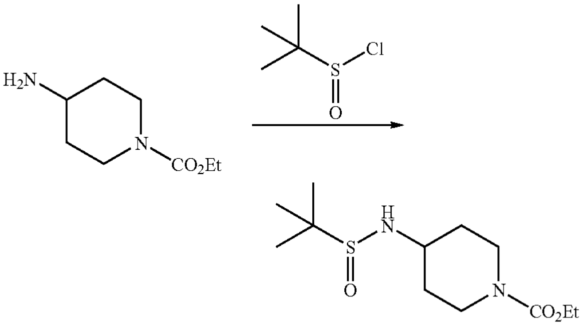

Ethyl 4-amino-1-piperidinecarboxylate (300 mg) and triethylamine (258 mg) were dissolved in 5 ml of dichloromethane. To the mixture, 2 ml of solution of t-butylsulfinyl chloride (222 mg) in dichloromethane was added and the mixture was stirred at room temperature for 4 hours. The solution was partitioned into an aqueous solution of potassium hydrogen sulfate and ethyl acetate. The organic layer was washed with brine and dried over magnesium sulfate anhydride. The solvent was removed under reduced pressure and the residue was purified by silica gel chromatography to give 378 mg of 4-t-butylsulfinylamino-1-ethoxycarbonyl piperidine.

Step 2

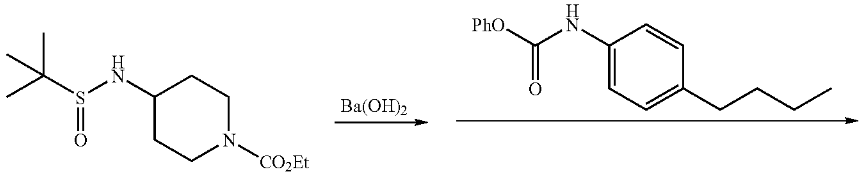

-continued

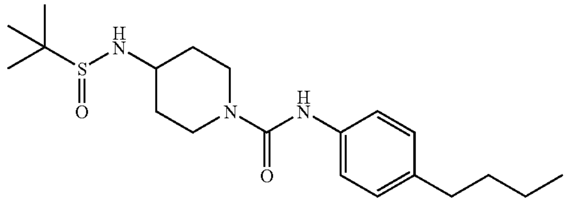

In a mixture of 5 ml of 2-propanol and 5 ml of water, 378 mg of 4-t-butylsulfinylamino-1-ethoxycarbonyl piperidine was suspended and 1.77 g of barium hydroxide was added. The mixture was refluxed with stirring and heating for 4 hours. The mixture was diluted with methanol and the insoluble material was filtered off. The solvent was removed under reduced pressure to give 4-t-butylsulfinylaminopiperidine. Without purification, the obtained material was dissolved in 5 ml of THF, and 984 mg of N-phenoxycarbonyl-4-butyl aniline and 236 mg of diisopropyl ethylamine were added, followed by stirring at room temperature overnight. An aqueous solution of potassium hydrogen sulfate was added to the mixture and the mixture was extracted with ethyl acetate. The organic layer was washed with brine and dried over magnesium sulfate anhydride. The solvent was removed under reduced pressure and the residue was purified by silica gel chromatography to give 291 mg of 4-t-butylsulfinylaminopiperidine-1-carboxylic acid(4-t-butylphenyl)amide.

$^1$H-NMR ($CDCl_3$) δ ppm: 0.89 (t, 3H, J=7.3 Hz), 1.19 (s, 9H), 1.25-1.38 (m, 4H), 1.40-1.60 (m, 4H), 1.89-2.03 (m, 3H), 2.52 (t, 2H, J=7.7 Hz), 2.89-3.04 (m, 2H), 3.14 (d, 1H, J=5.2 Hz), 3.37 (m, 1H), 3.96 (m, 2H), 6.67 (s, 1H), 7.05 (d, 2H, J=8.5 Hz), 7.22 (d, 2H, J=8.5 Hz).

Step 3

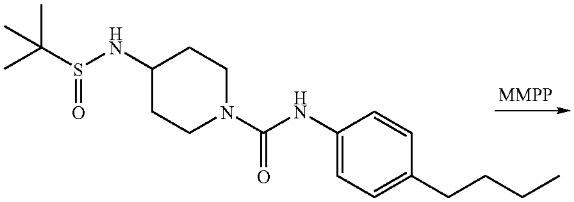

-continued

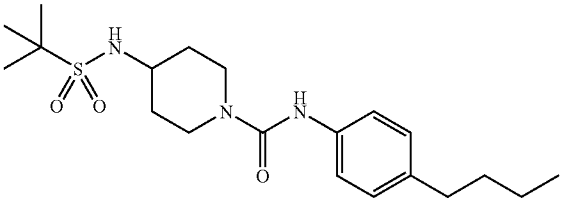

In a mixture of 2 ml of methanol and 2 ml of methylene chloride, 291 mg of 4-t-butylsulfinyl aminopiperidine-1-carboxylic acid(4-t-butylphenyl)amide was dissolved. To the mixture, 570 mg of 80%-MMPP (magnesium monoperoxyphthalate hexahydrate) was added and the mixture was stirred at room temperature for 2 hours. The solution was diluted with water and extracted with ethyl acetate. The organic layer was washed with brine and dried over magnesium sulfate anhydride. The solvent was removed under reduced pressure and the residue was purified by silica gel chromatography to give 130 mg of 4-t-butylsulfonylaminopiperidine-1-carboxylic acid(4-butylphenyl)amide (I-120).

Other Compounds (I) are synthesized by the similar methods. The structures and physical properties are shown below.

I-1

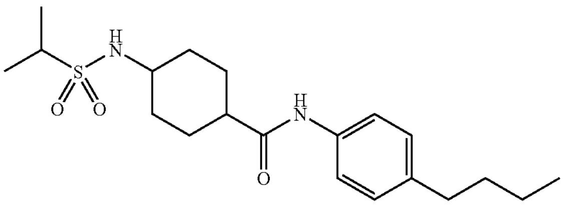

I-2

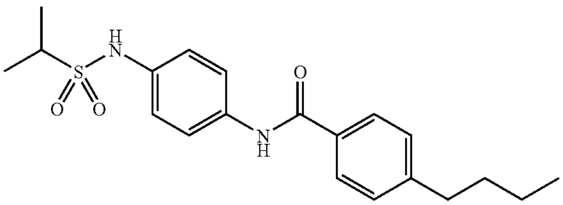

-continued
I-3
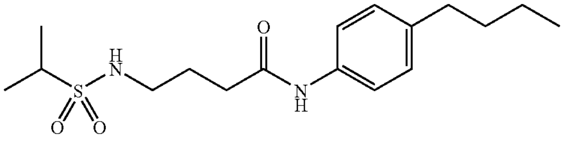
I-4
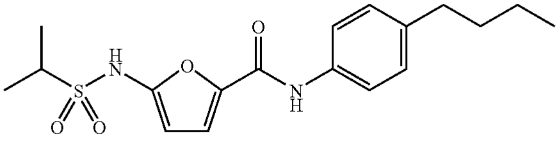
I-5
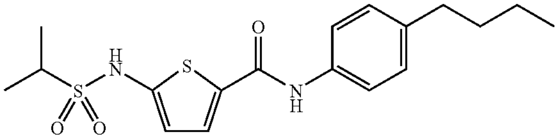
I-6
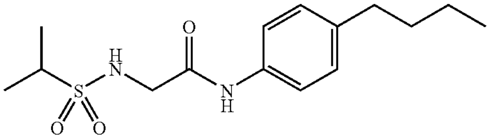
I-7
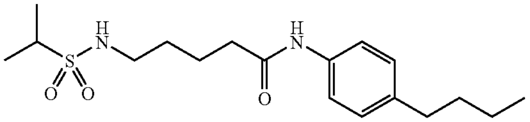
I-8
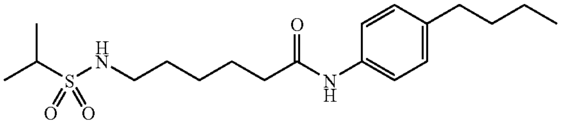
I-9
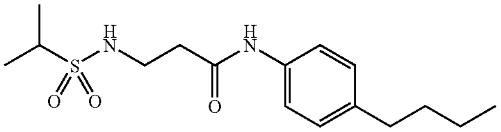
I-10
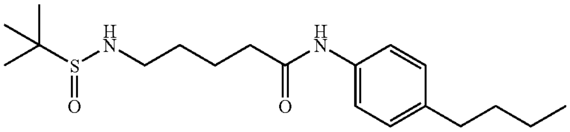
I-11
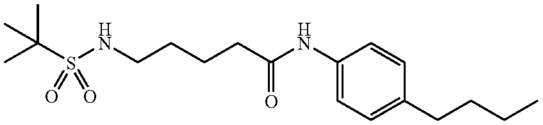
I-12
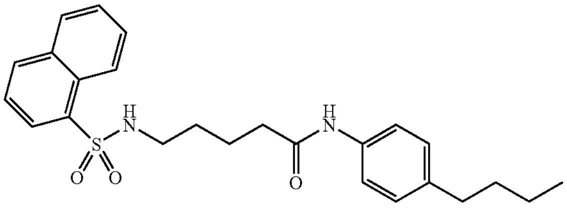
I-13
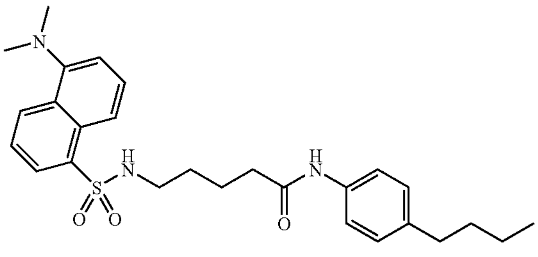
I-14
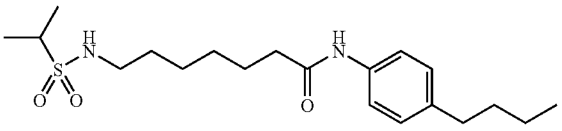
I-15
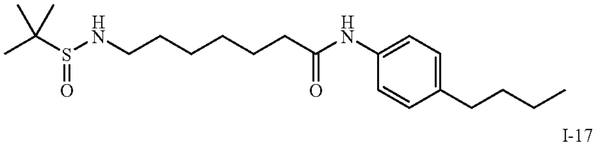
I-16
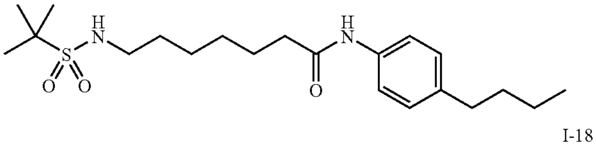
I-17
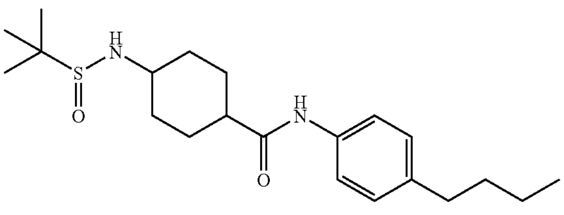
I-18
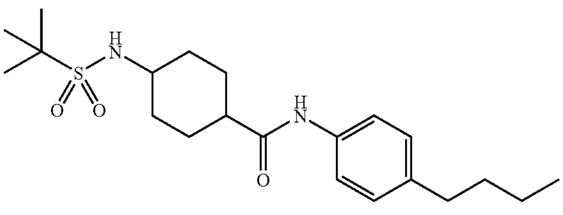

-continued
I-19
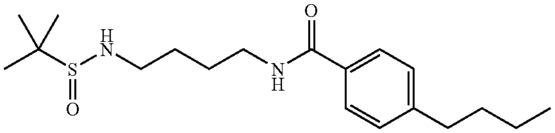
I-20
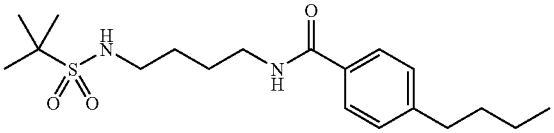
I-21
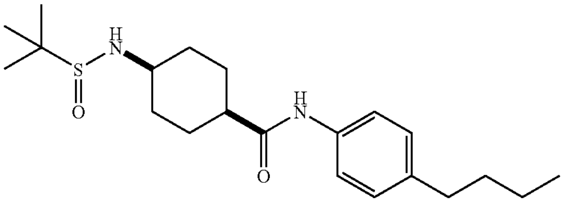
I-22
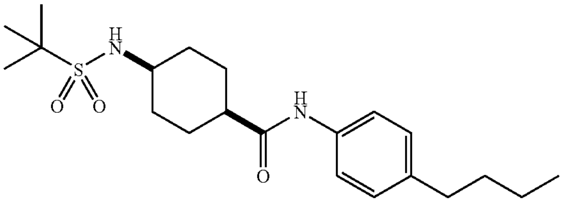
I-23
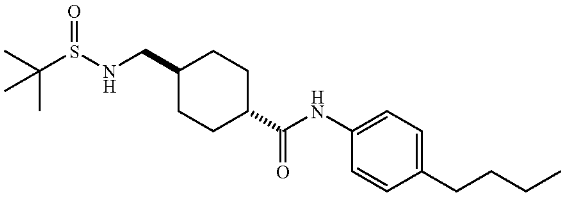
I-24
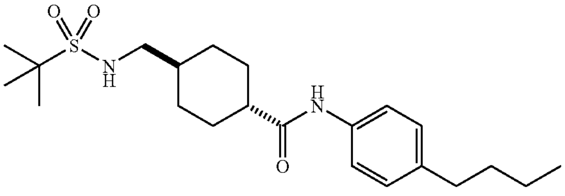
I-25
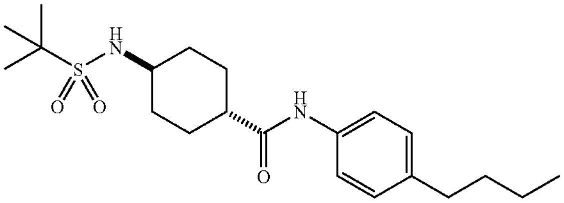
I-26
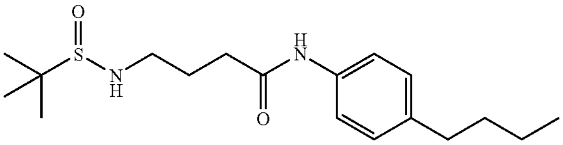
I-27
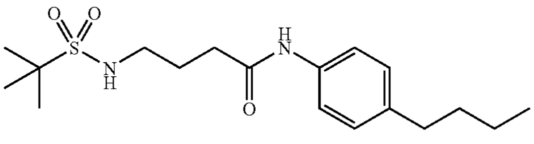
I-28
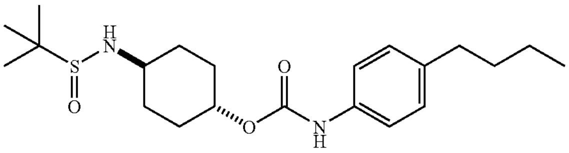
I-29
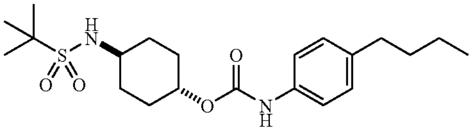
I-30
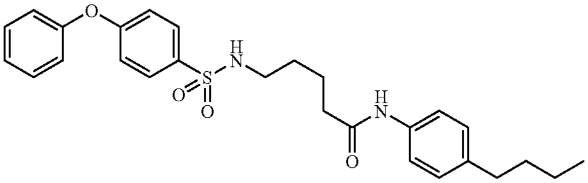
I-31
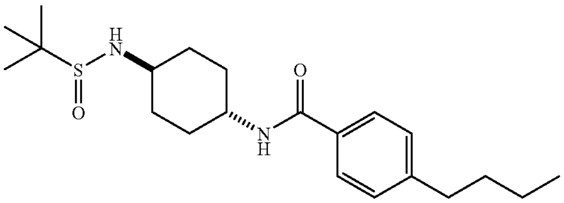
I-32
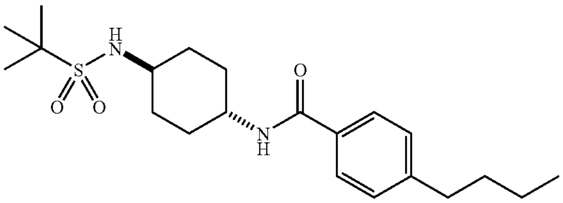

-continued
I-33
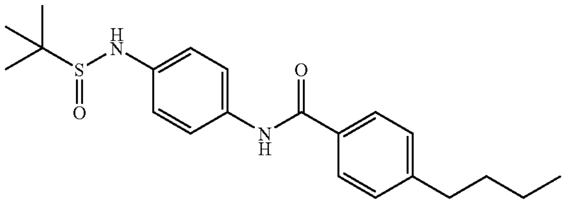
I-34
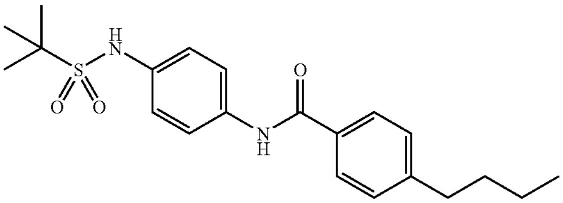
I-35
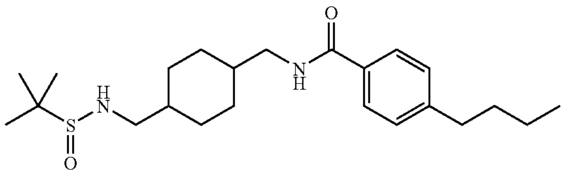
I-36
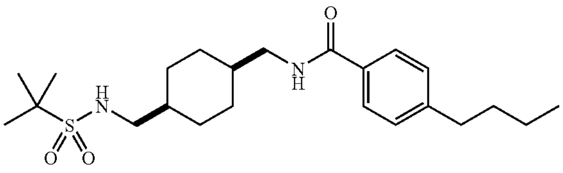
I-37
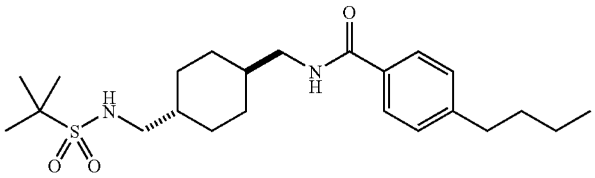
I-38
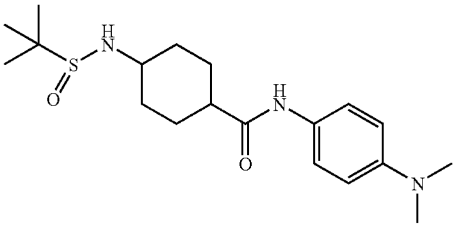
I-39
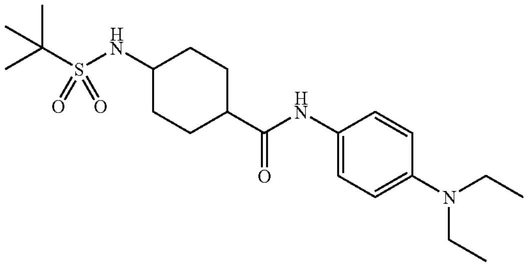
I-40
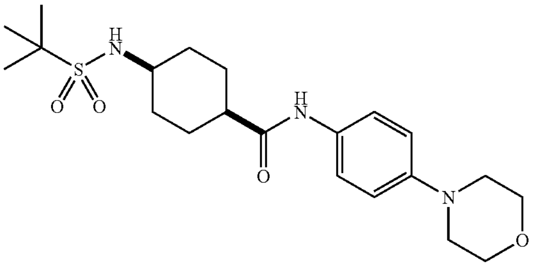
I-41
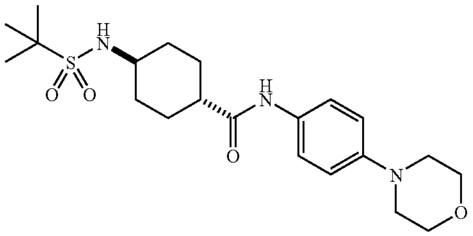
I-42
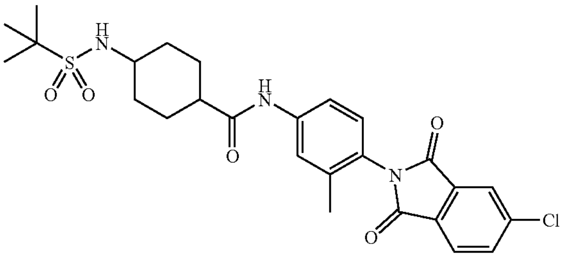
I-43
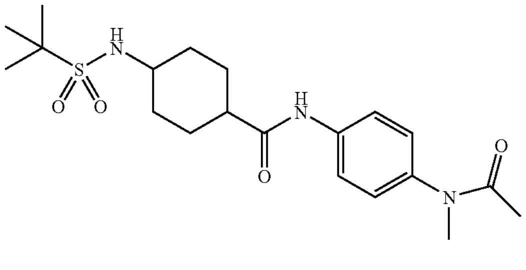
I-44
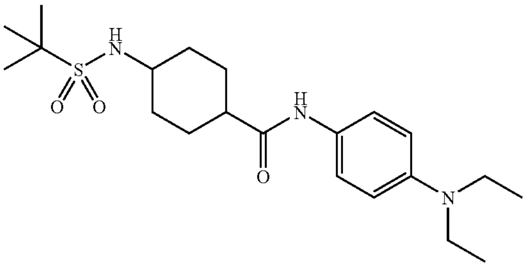

-continued
I-45
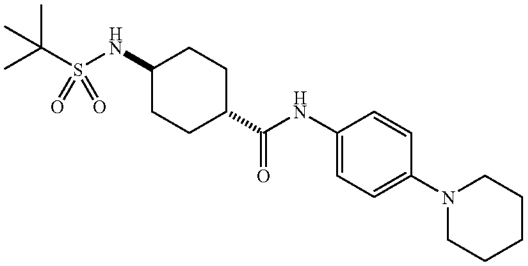
I-46
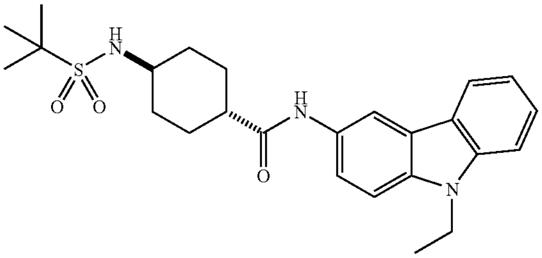
I-47
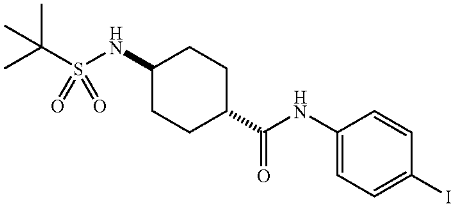
I-48
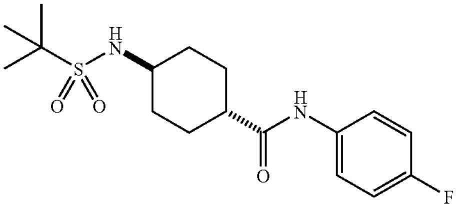
I-49
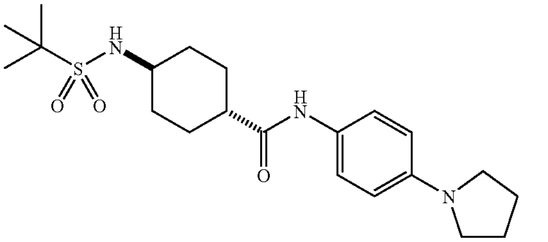
I-50
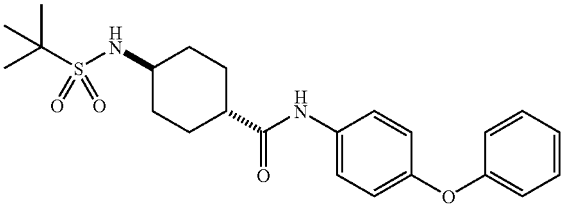
I-51
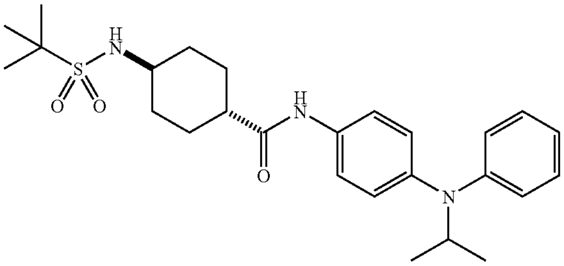
I-52
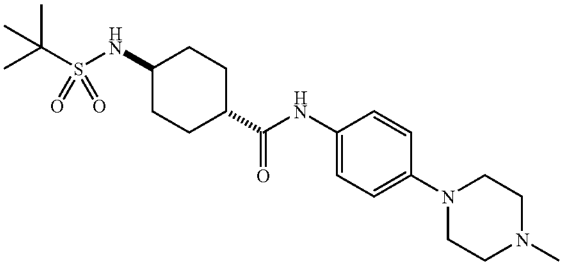
I-53
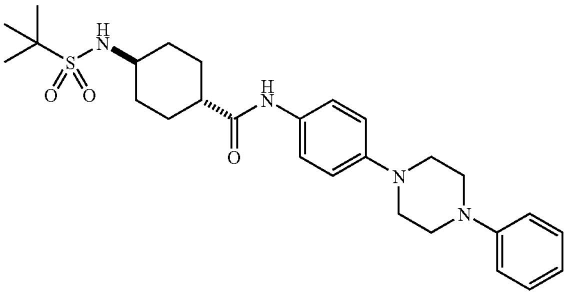
I-54
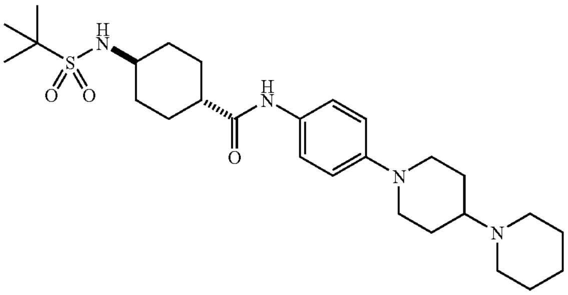

-continued
I-55
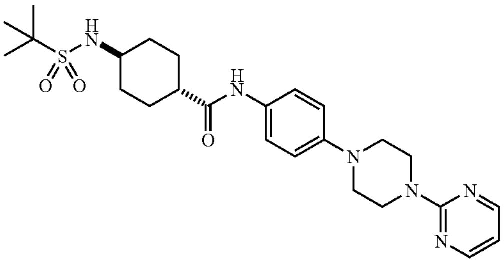
I-56
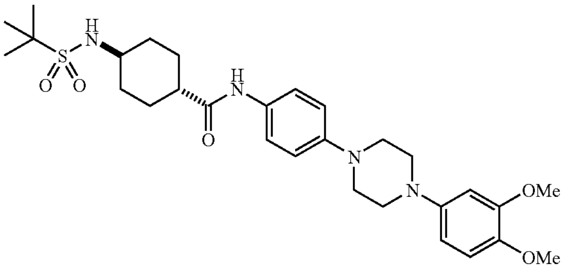
I-57
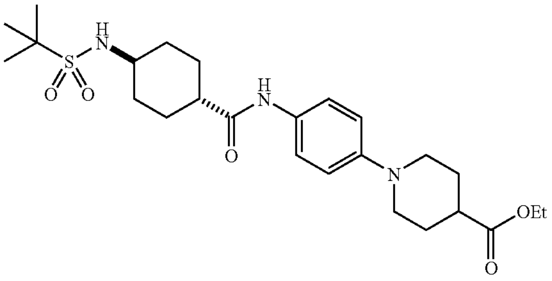
I-58
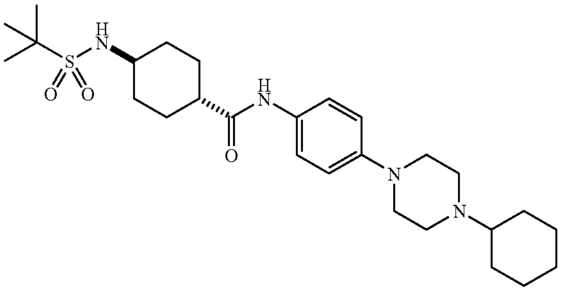
I-59
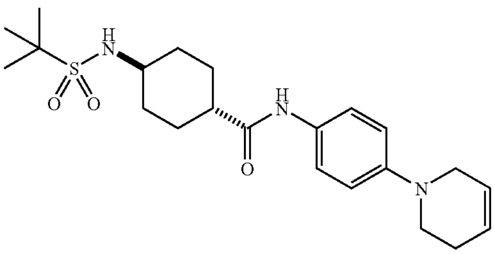
I-60
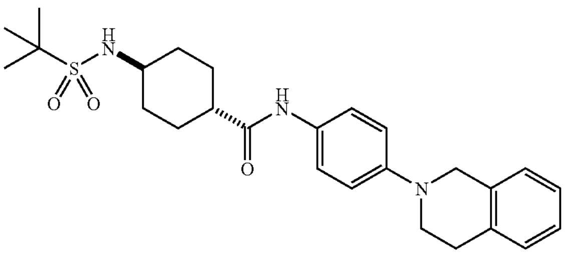
I-61
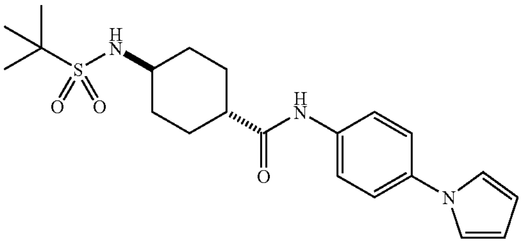
I-62
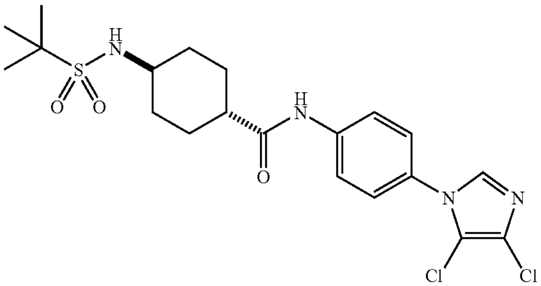
I-63
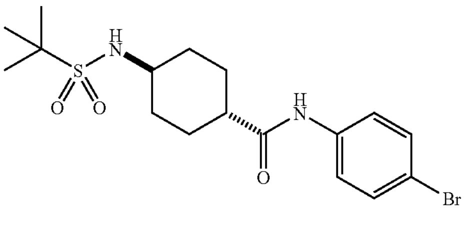
I-64
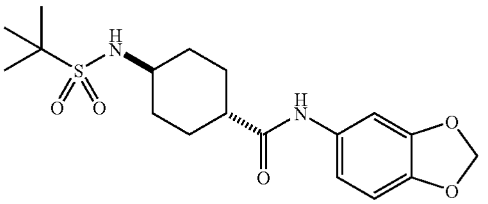

-continued
I-65
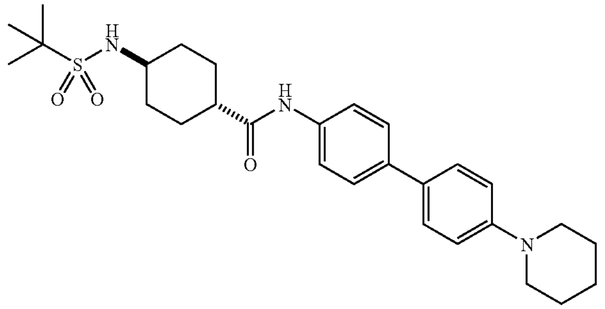
I-66
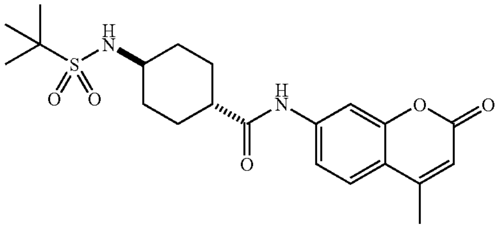
I-67
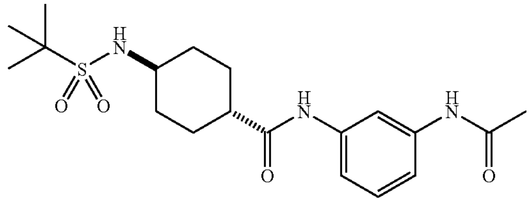
I-68
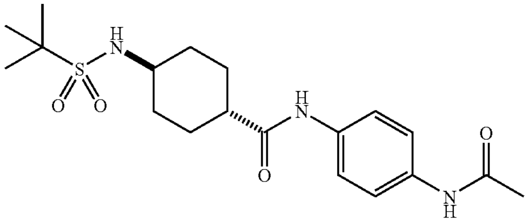
I-69
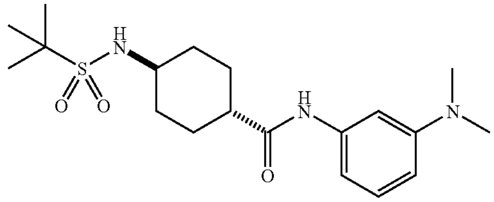
I-70
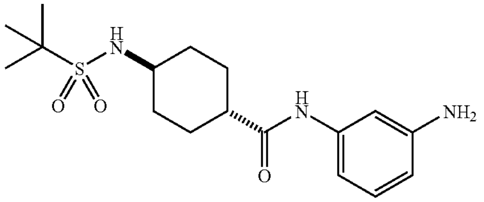
I-71
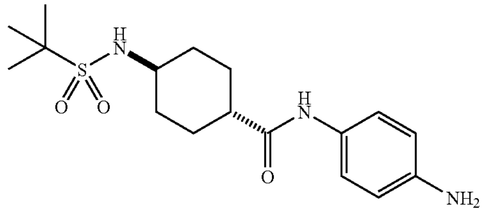
I-72
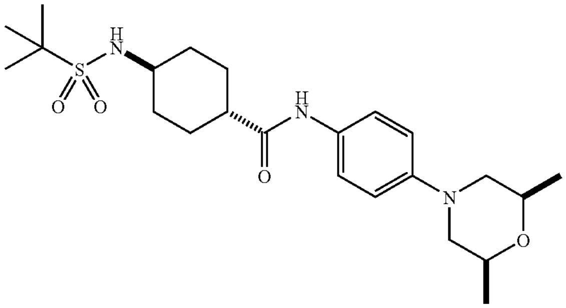
I-73
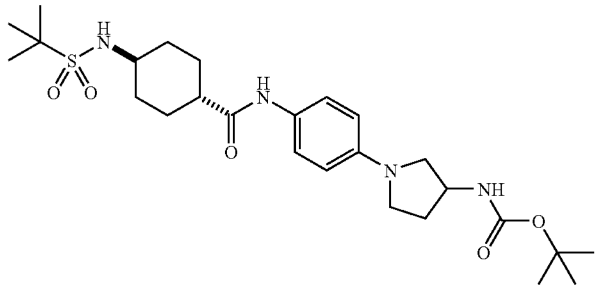
I-74
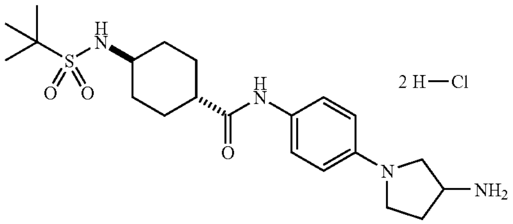

-continued
I-75
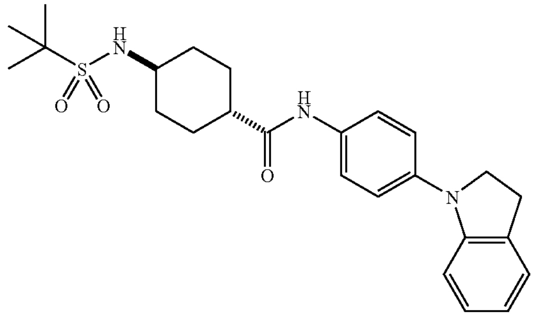
I-76
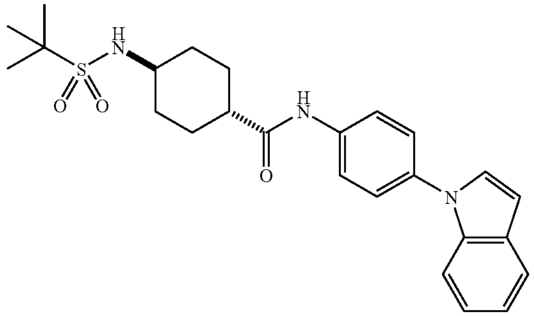
I-77
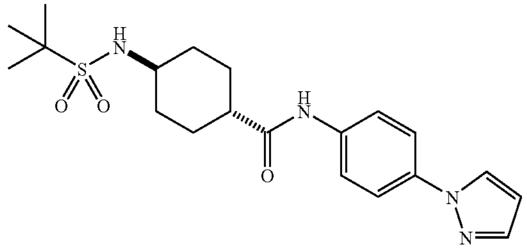
I-78
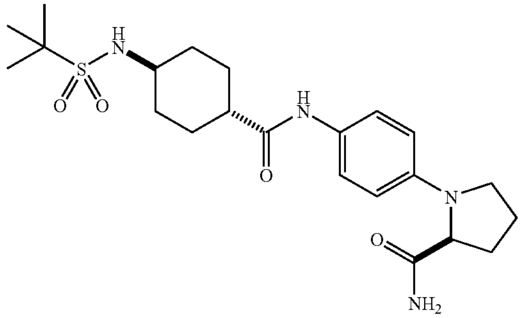
I-79
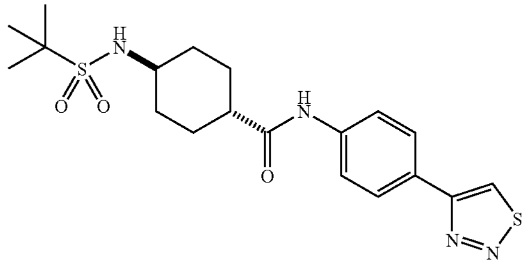
I-80
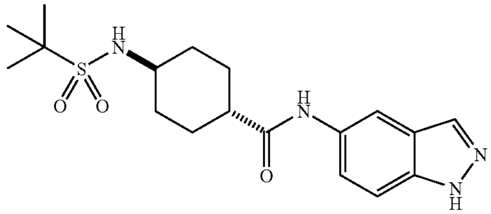
I-81
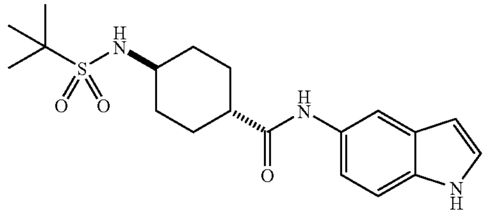
I-82
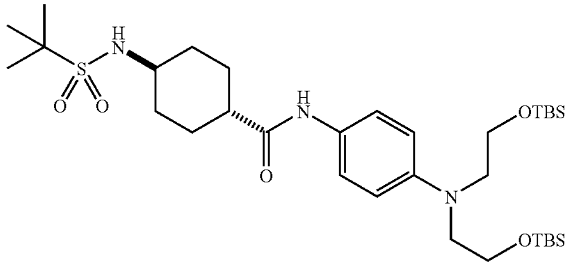
I-83
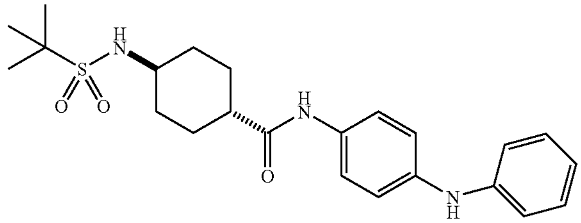
I-84
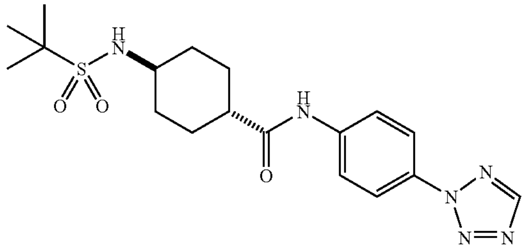

-continued
I-85
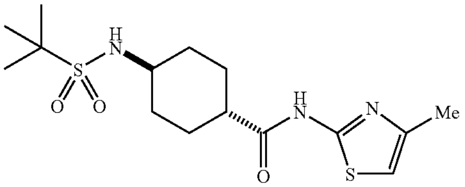
I-86
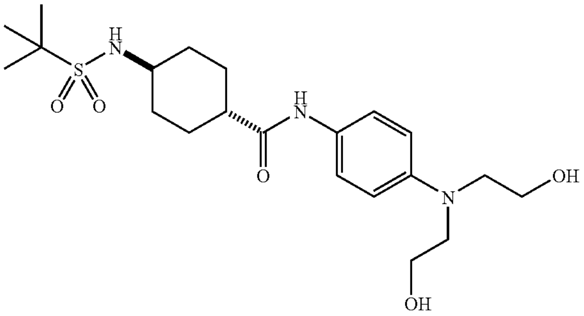
I-87
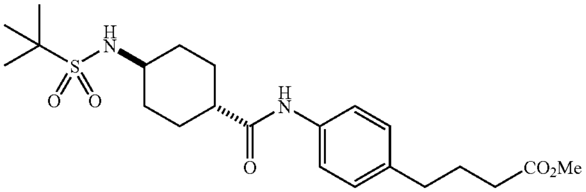
I-88
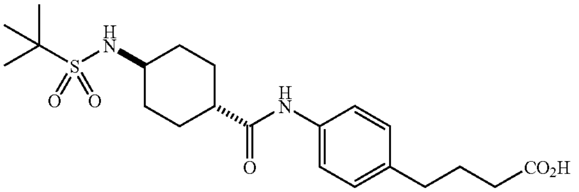
I-89
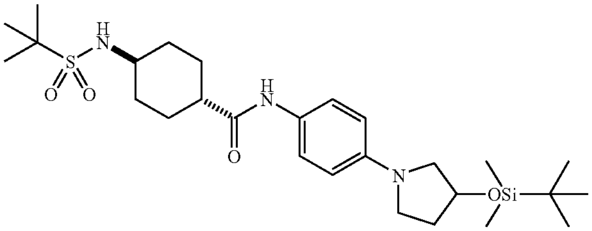
I-90
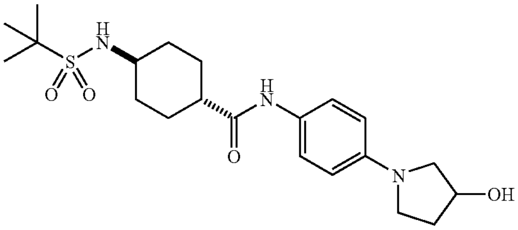
I-91
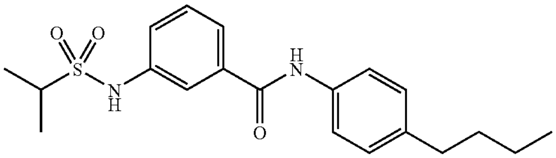
I-92
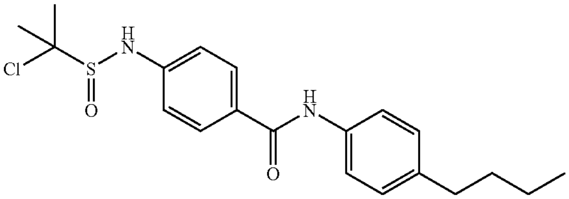
I-93
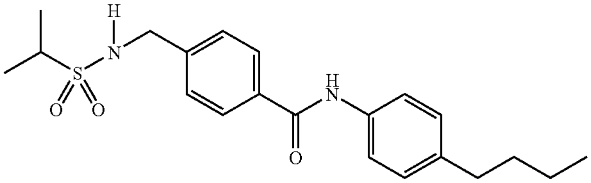
I-94
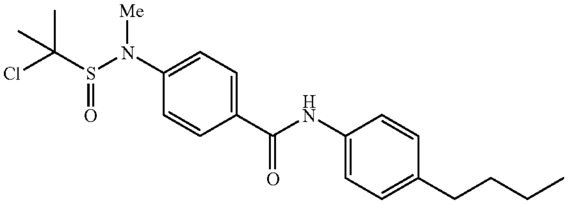
I-95
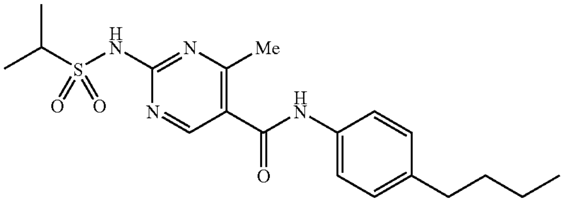
I-96
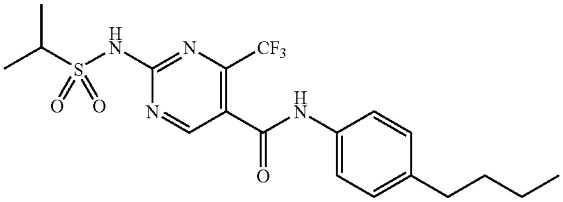

-continued
I-97
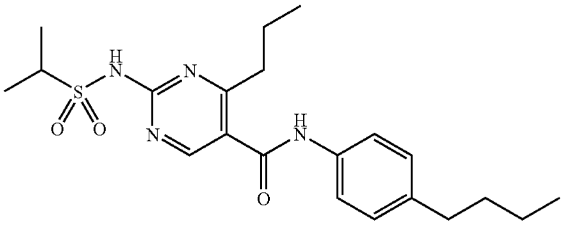
I-98
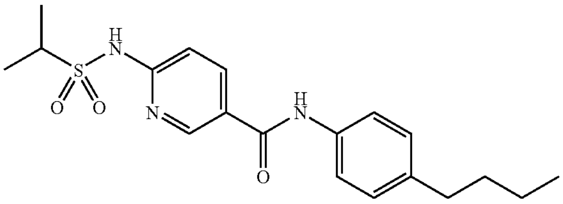
I-99
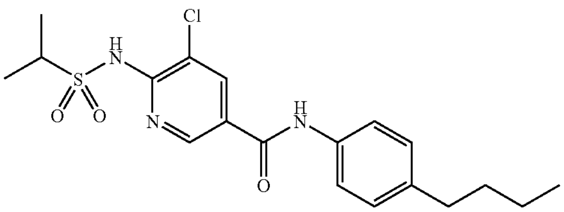
I-100
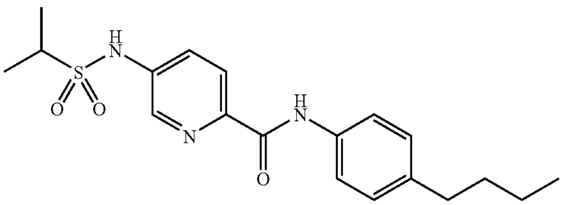
I-101
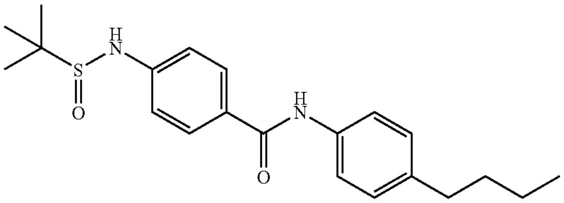
I-102
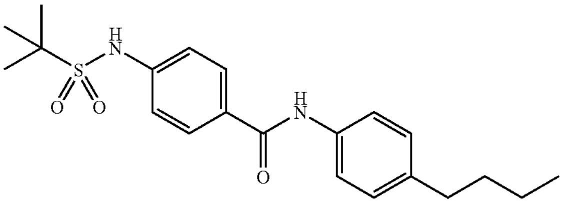
I-103
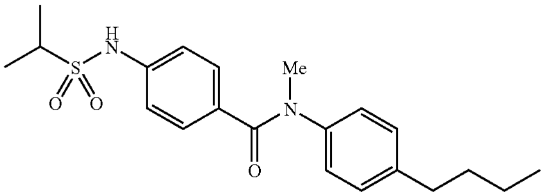
I-104
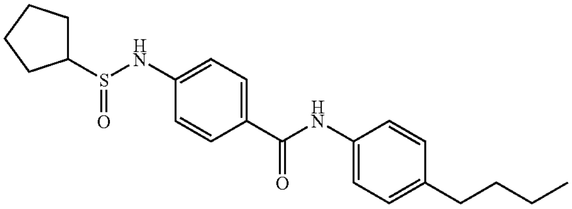
I-105
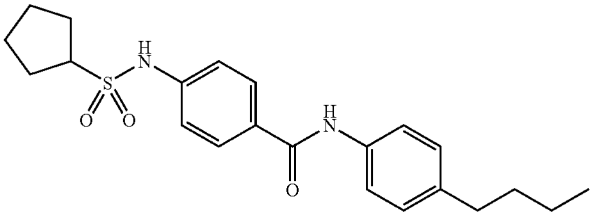
I-106
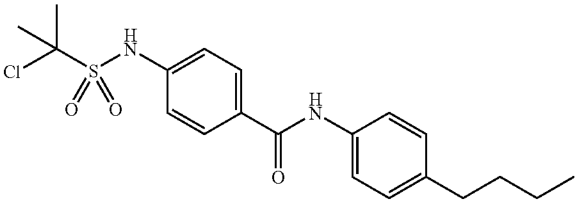
I-107
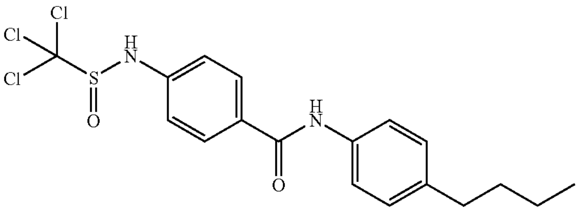
I-108
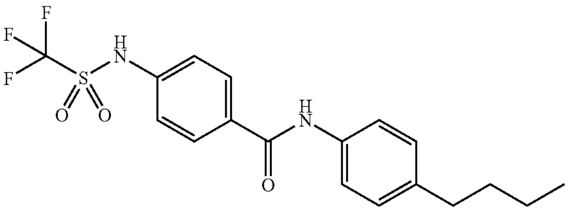
I-109
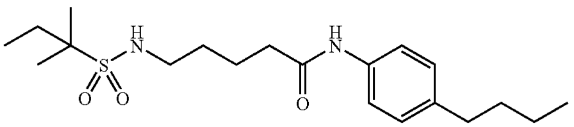
I-110
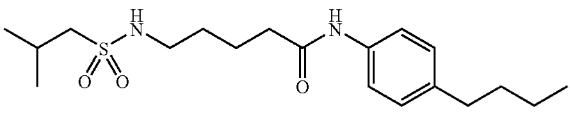

-continued
I-111
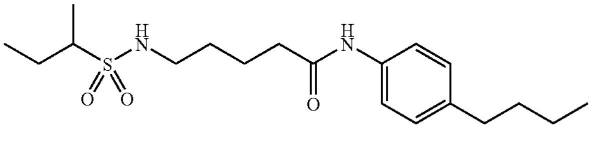
I-112
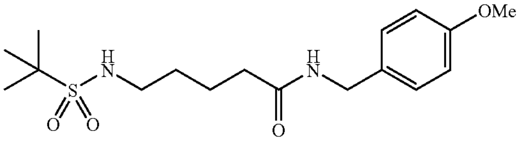
I-113
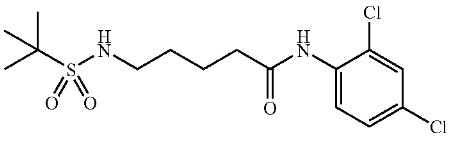
I-114
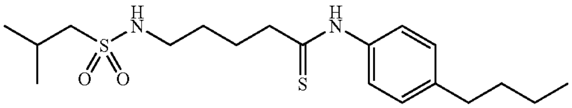
I-115
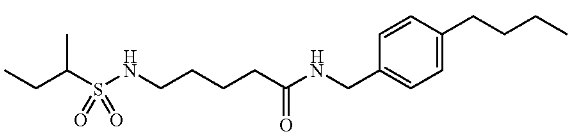
I-116
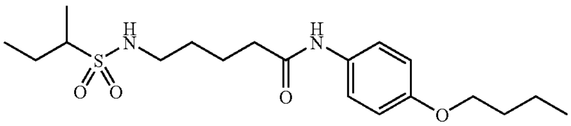
I-117
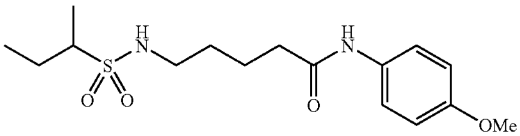
I-118
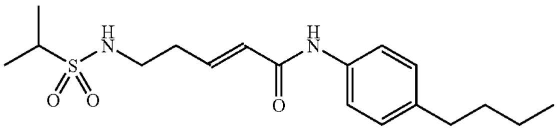
I-119
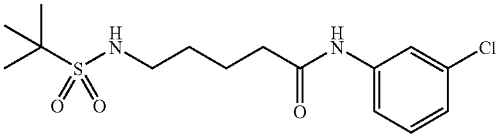
I-120
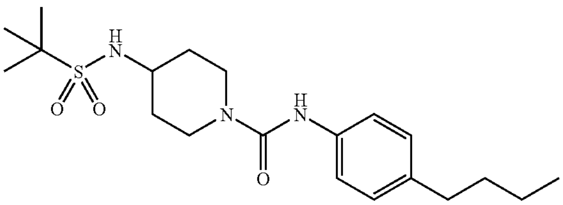
I-121
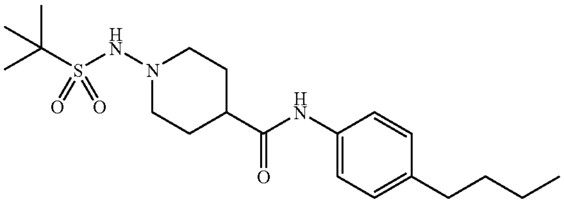
I-122
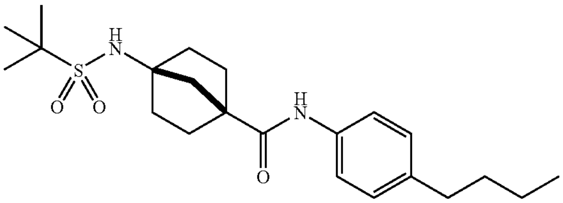
I-123
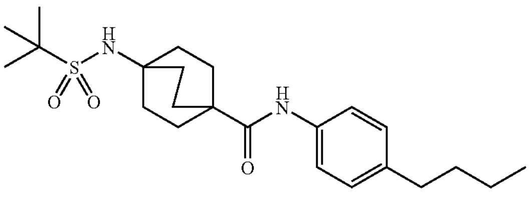
I-124
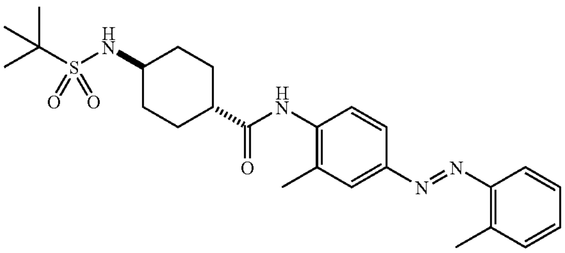

-continued
I-125
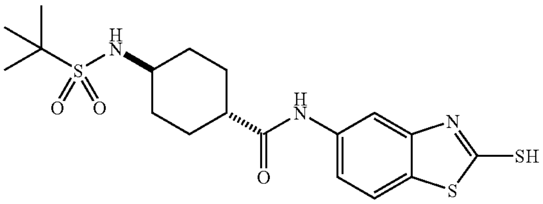
I-126
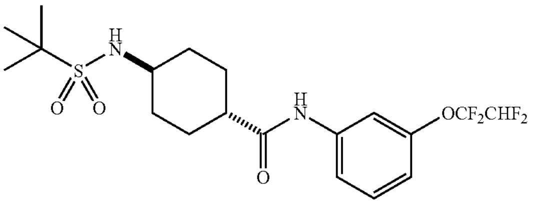
I-127
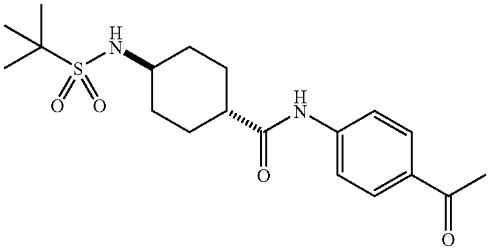
I-128
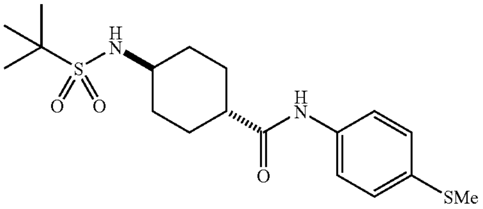
I-129
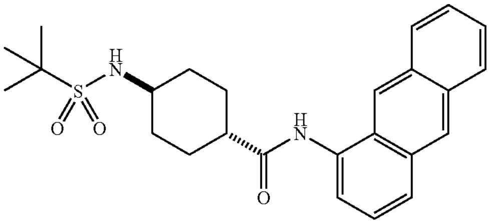
I-130
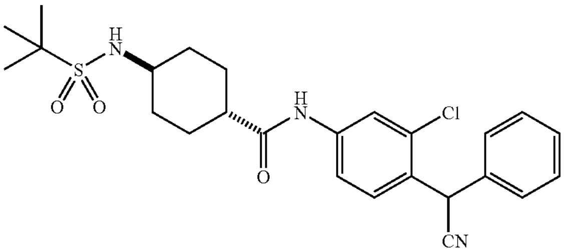
I-131
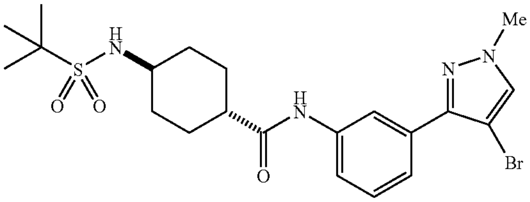
I-132
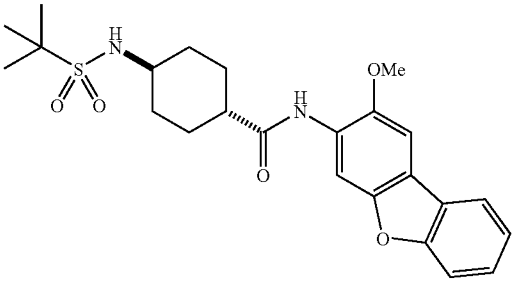
I-133
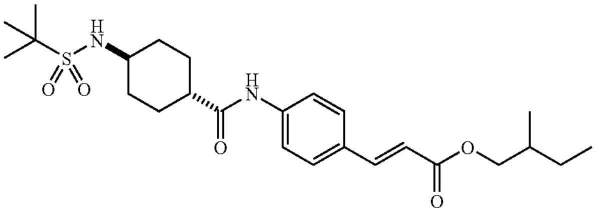
I-134
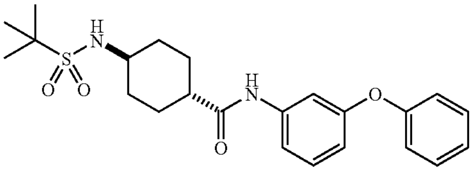
I-135
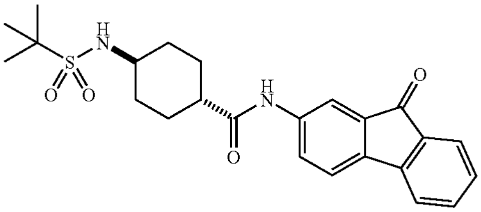
I-136
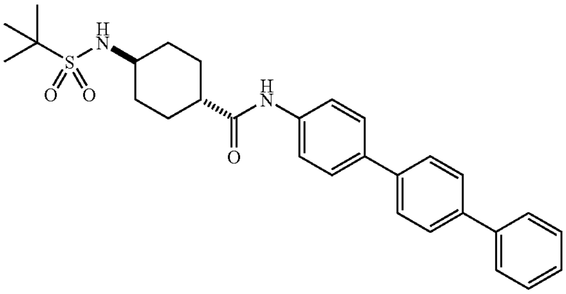

-continued
I-137
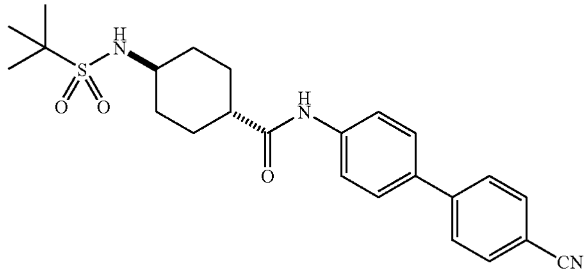
I-138
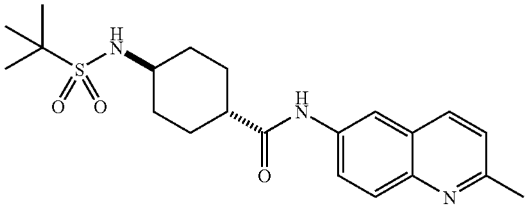
I-139
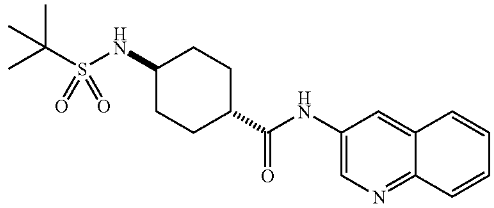
I-140
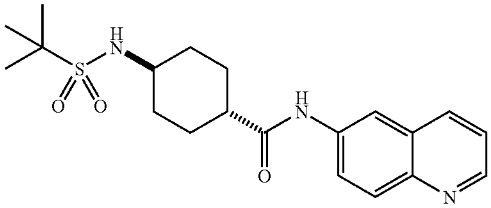
I-141
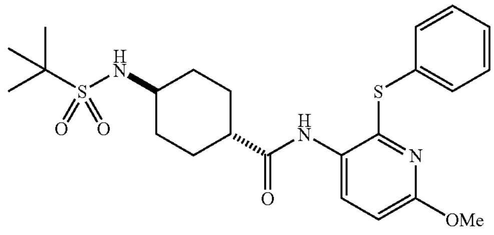
I-142
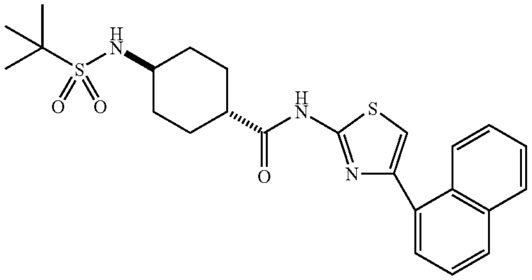
I-143
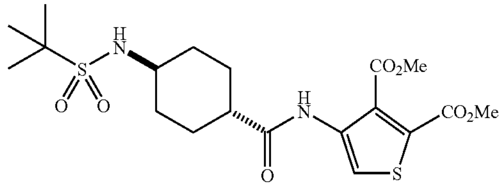
I-144
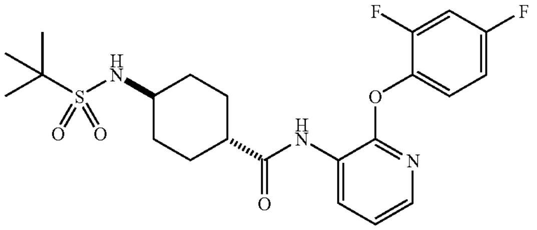
I-145
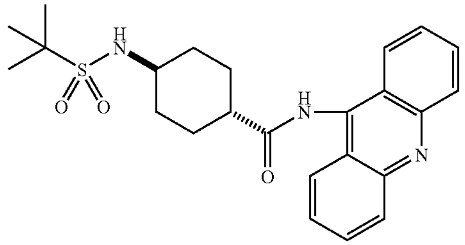
I-146
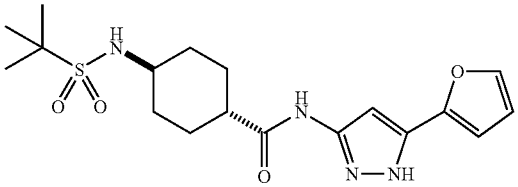
I-147
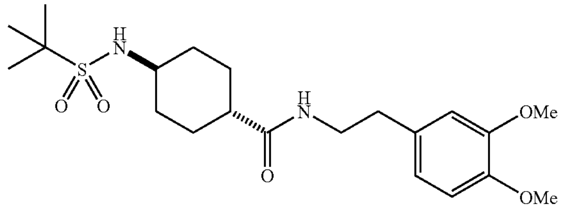
I-148
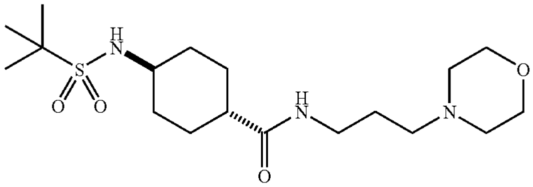

-continued
I-149
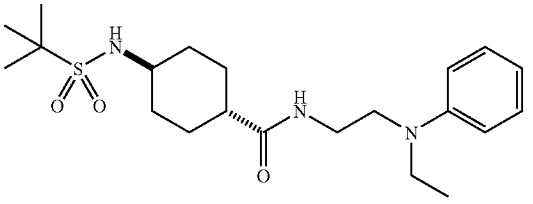
I-150
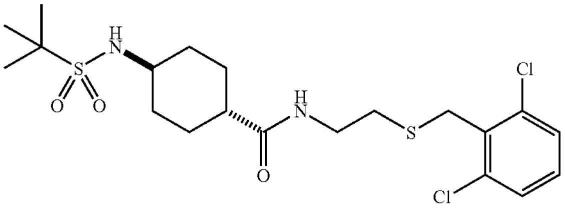
I-151
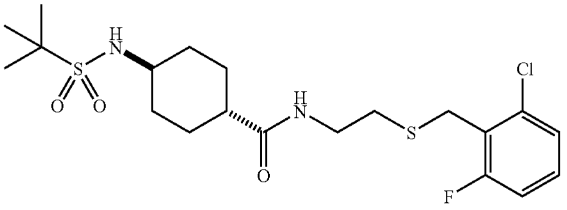
I-152
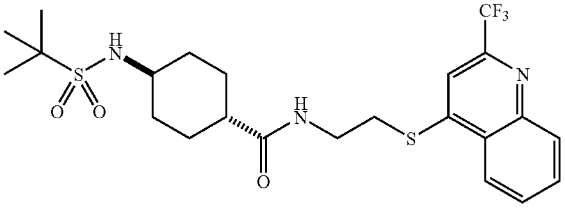
I-153
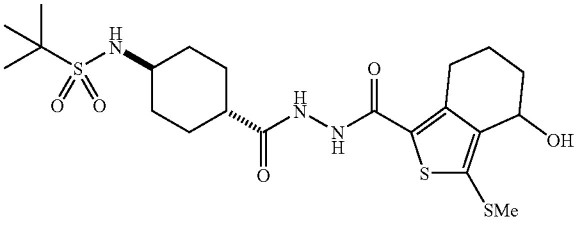
I-154
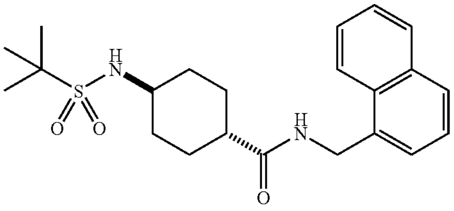
I-155
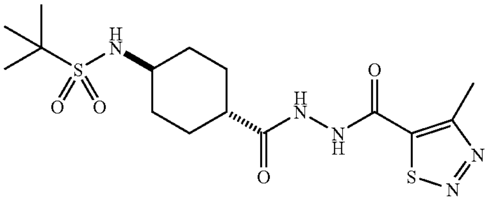
I-156
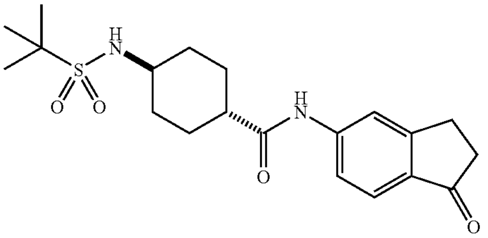
I-157
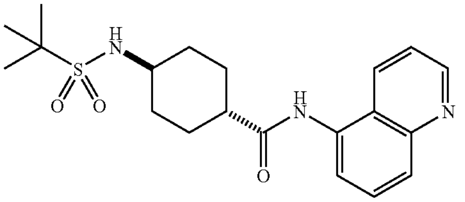
I-158
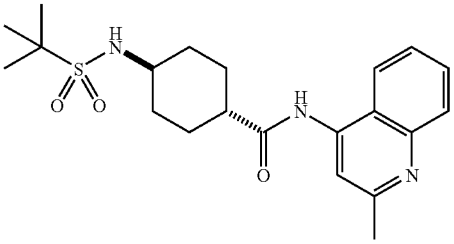
I-159
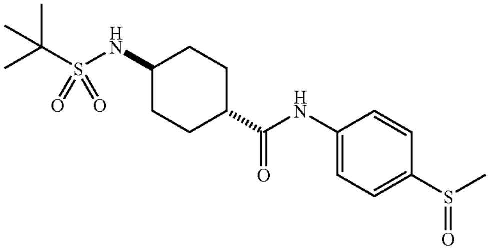
I-160
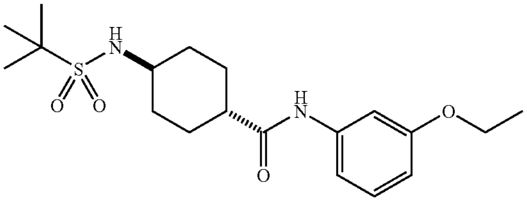

-continued
I-161
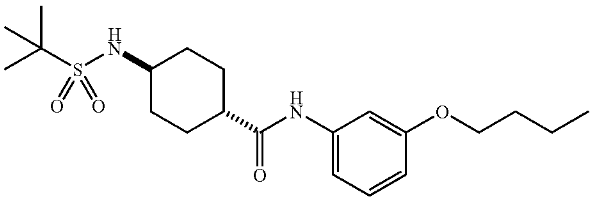
I-162
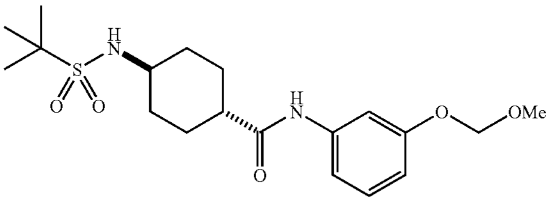
I-163
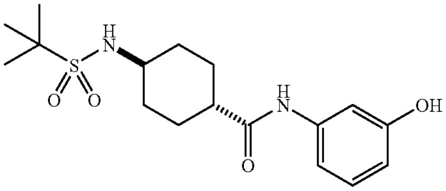
I-164
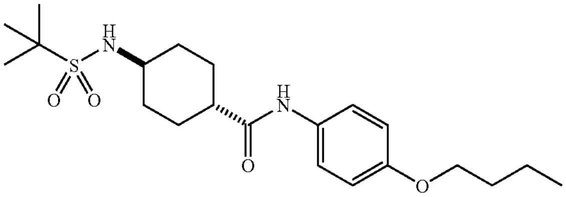
I-165
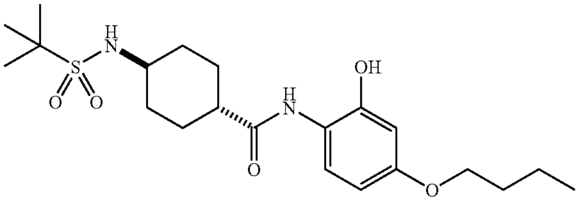
I-166
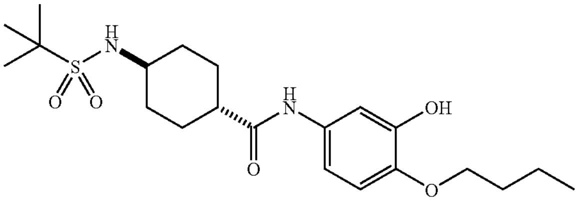
I-167
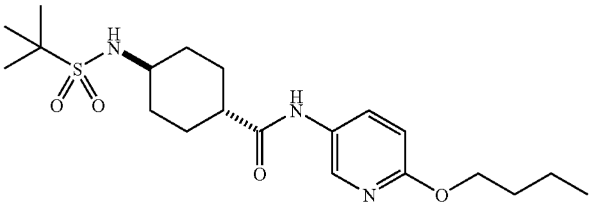
I-168
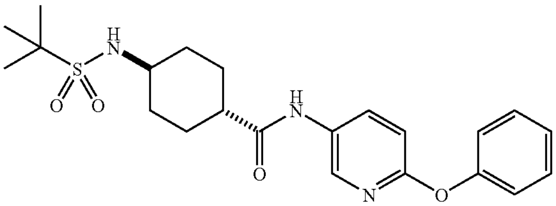
I-169
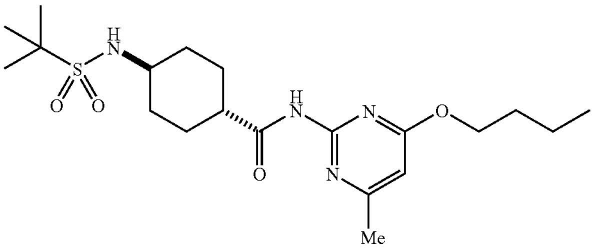
I-170
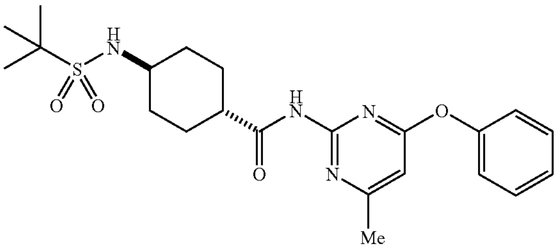
I-171
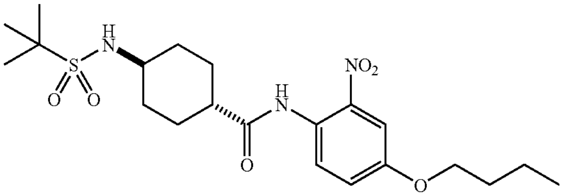
I-172
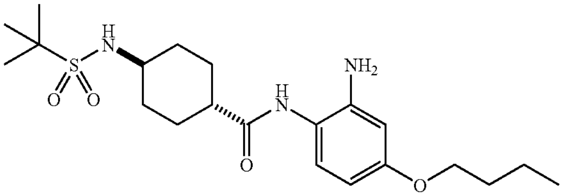

-continued
I-173
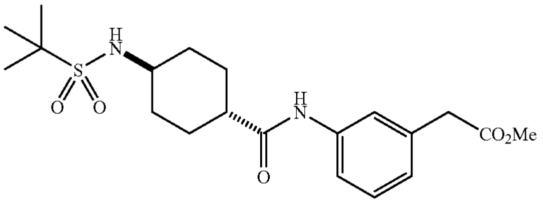
I-174
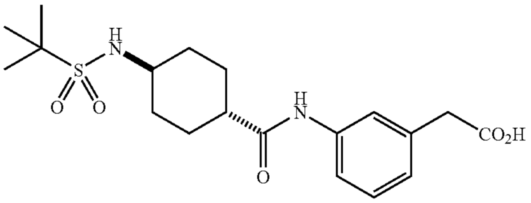
I-175
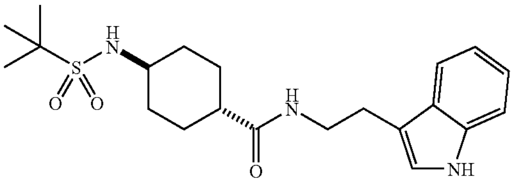
I-176
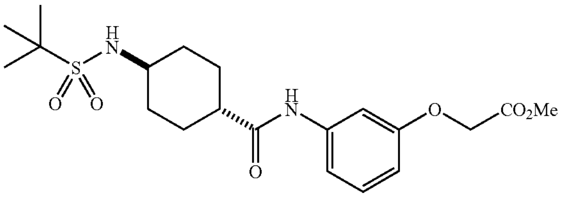
I-177
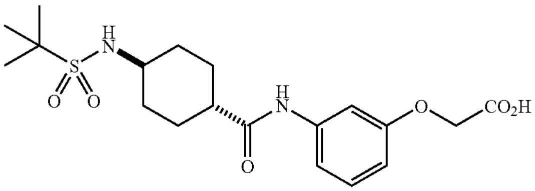
I-178
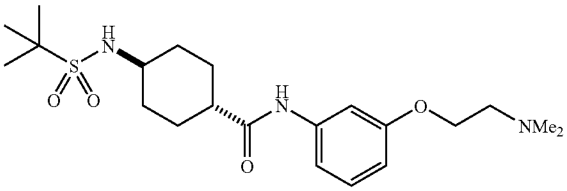
I-179
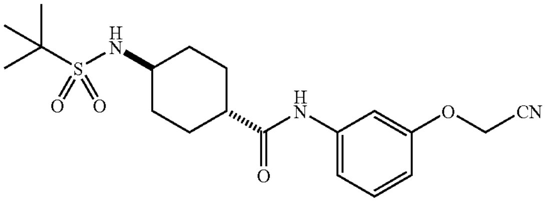
I-180
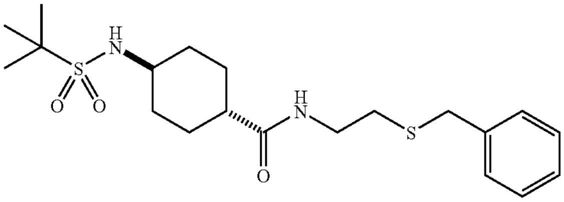
I-181
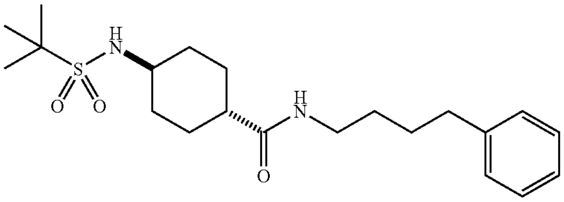
I-182
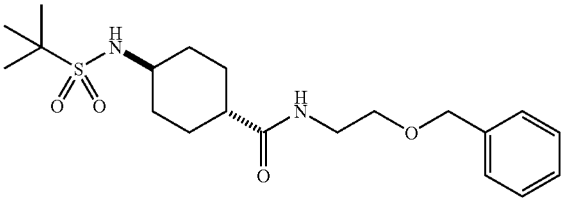
I-183
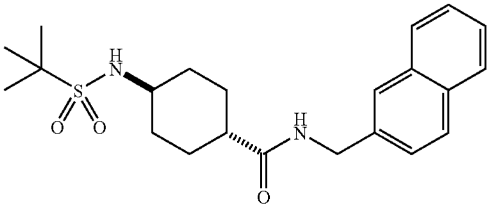
I-184
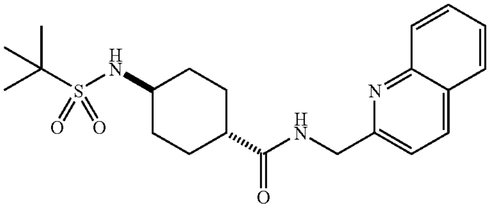
I-185
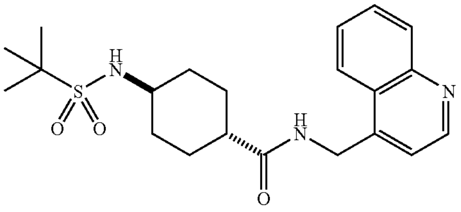
I-186
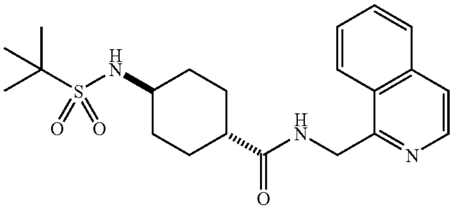

-continued
I-187
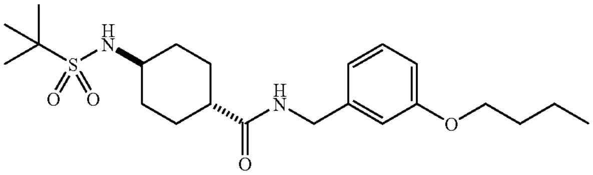
I-188
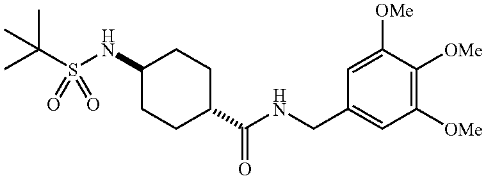
I-189
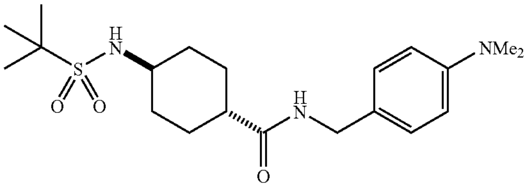
I-190
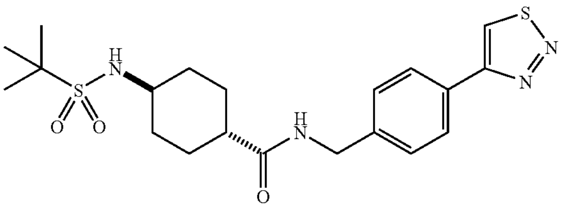
I-191
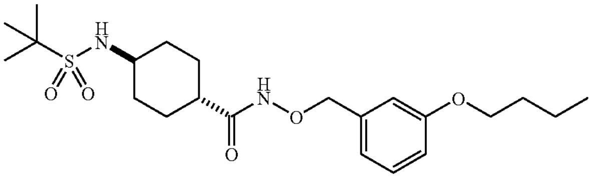
I-192
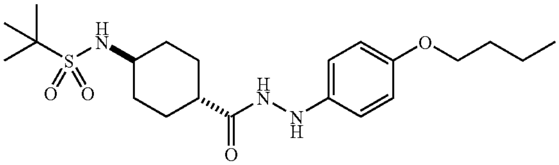
I-193
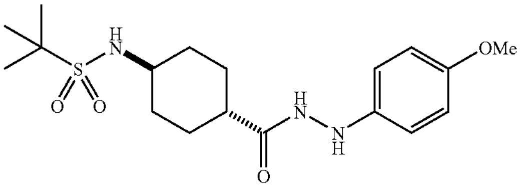
I-194
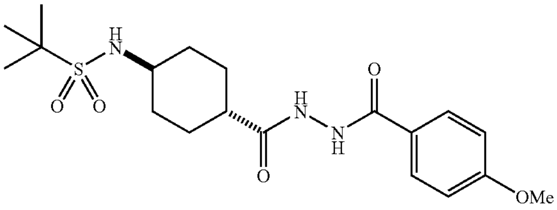
I-195
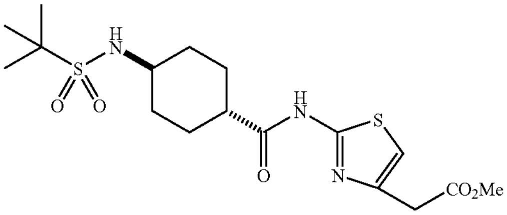
I-196
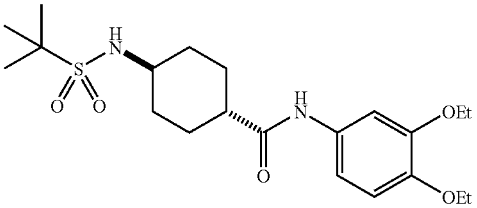
I-197
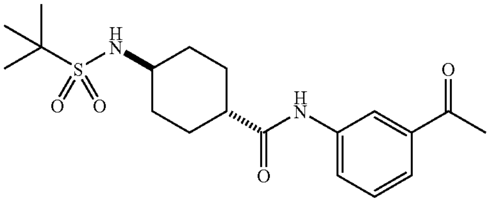
I-198
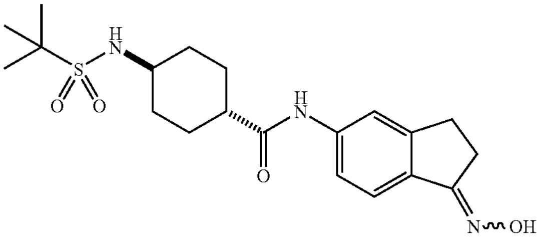
I-199
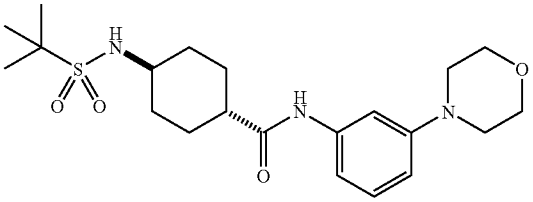
I-200
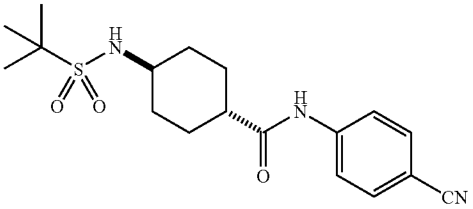

-continued
I-201
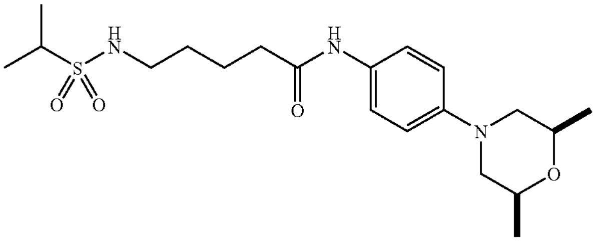
I-202
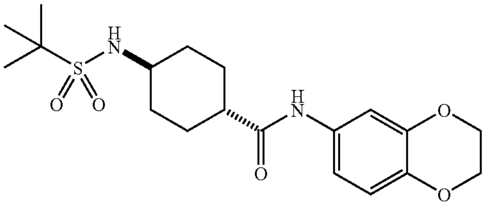
I-203
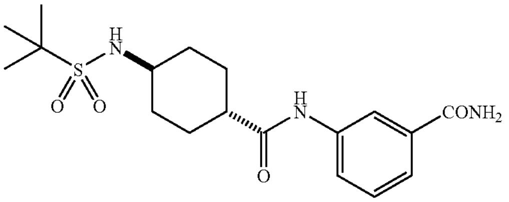
I-204
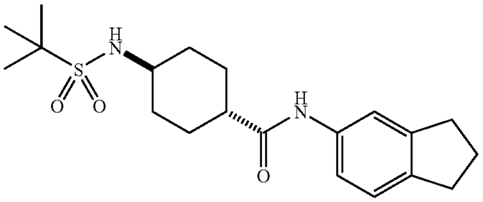
I-205
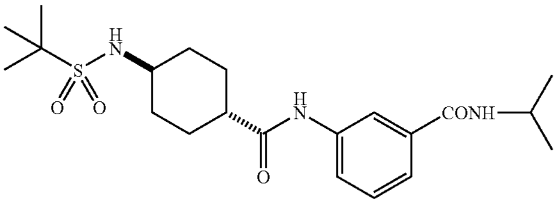
I-206
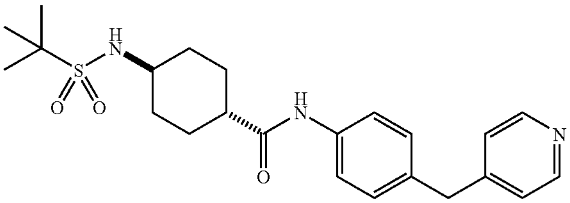
I-207
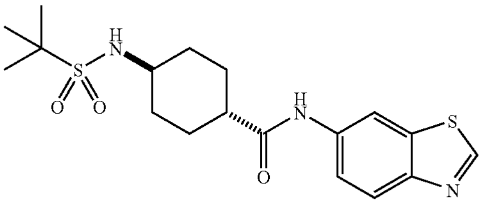
I-208
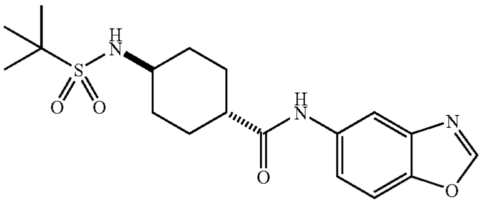
I-209
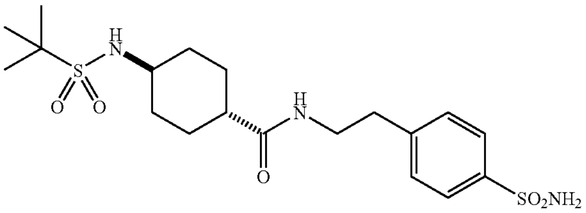
I-210
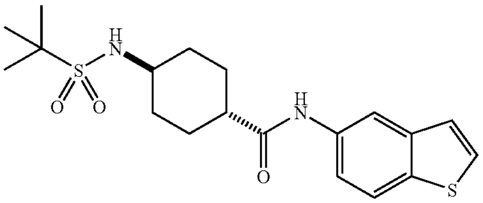
I-211
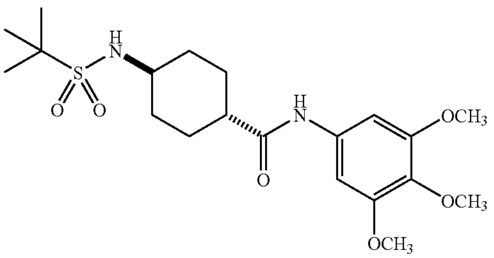
I-212
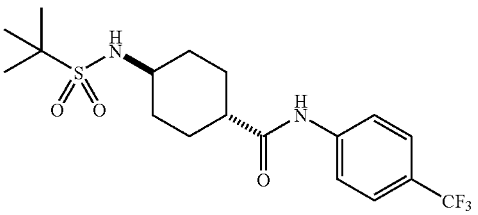

-continued
I-213
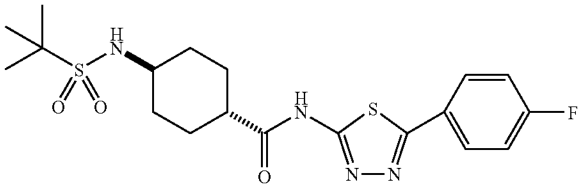
I-214
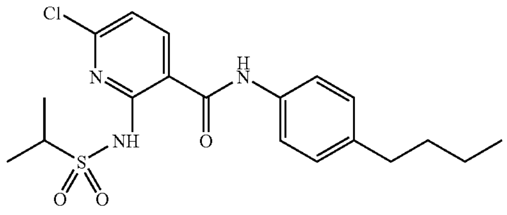
I-215
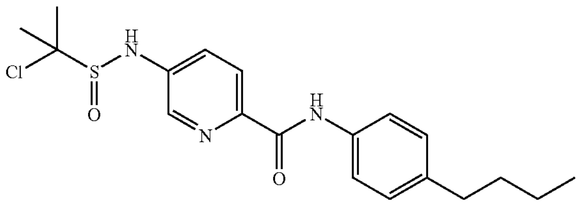
I-216
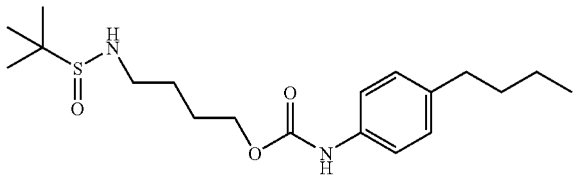
I-217
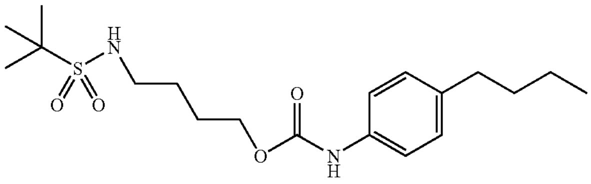
I-218
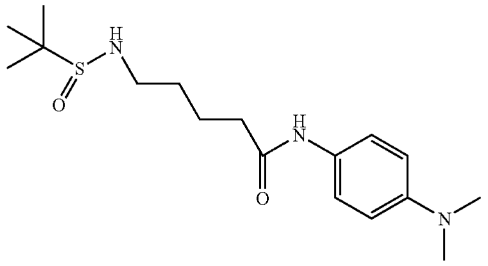
I-219
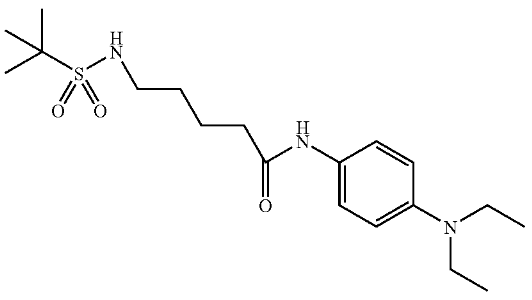
I-220
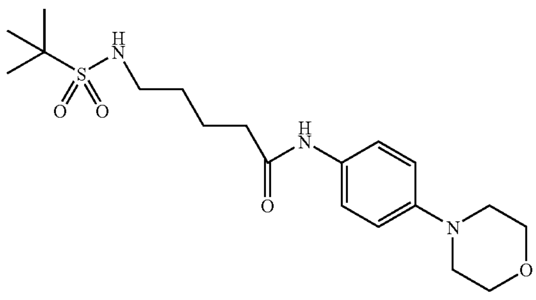
I-221
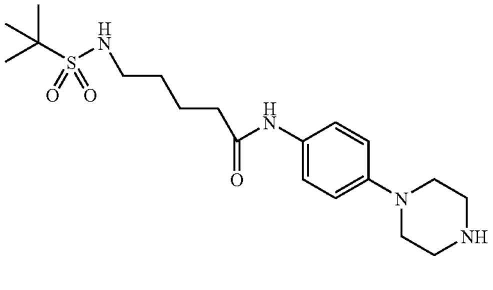
I-222
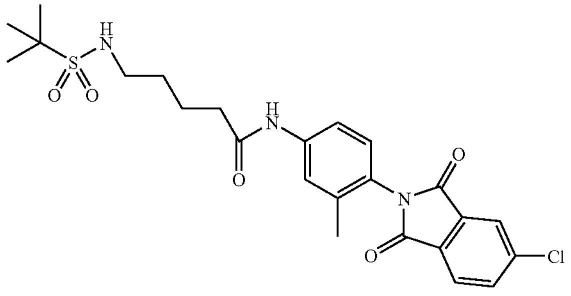

-continued
I-223
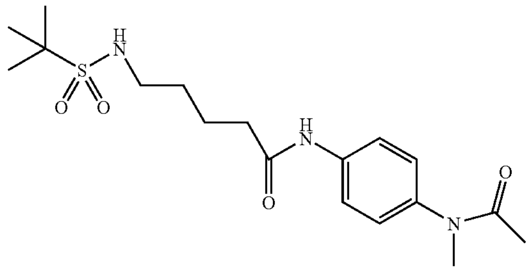
I-224
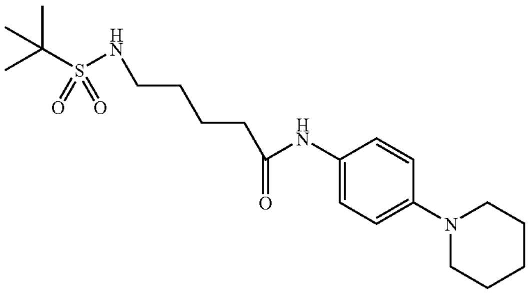
I-225
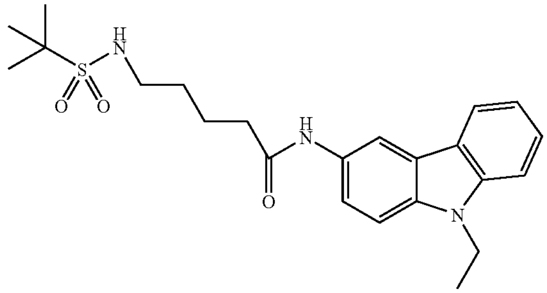
I-226
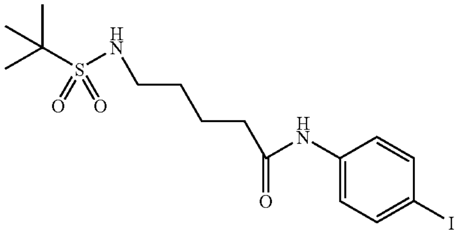
I-227
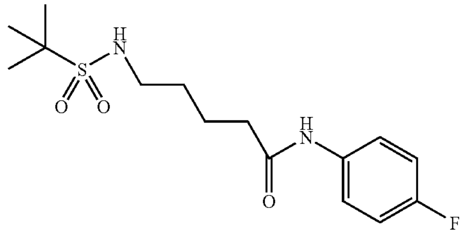
I-228
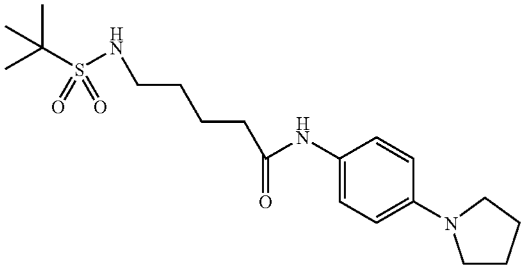
I-229
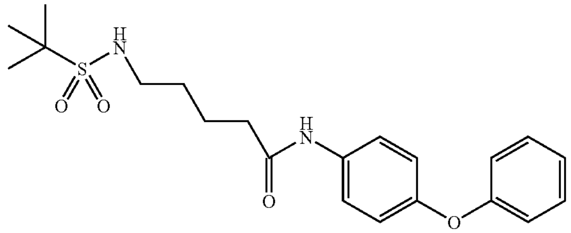
I-230
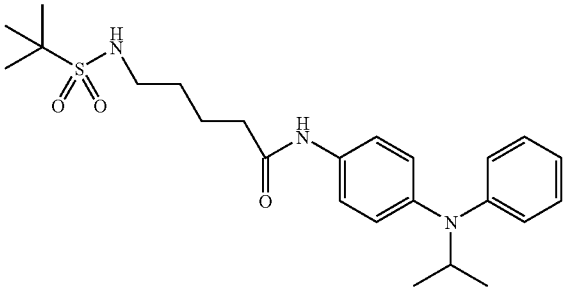
I-231
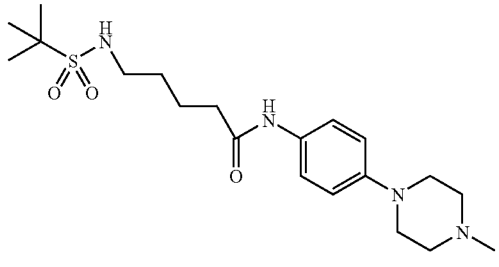
I-232
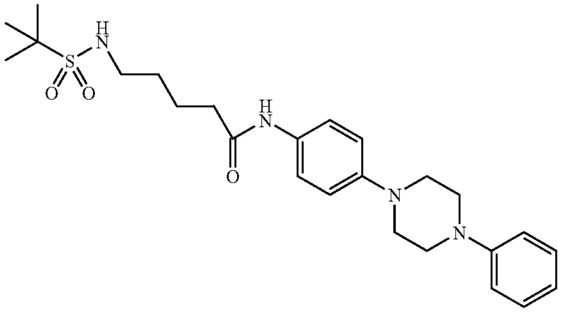

-continued
I-233
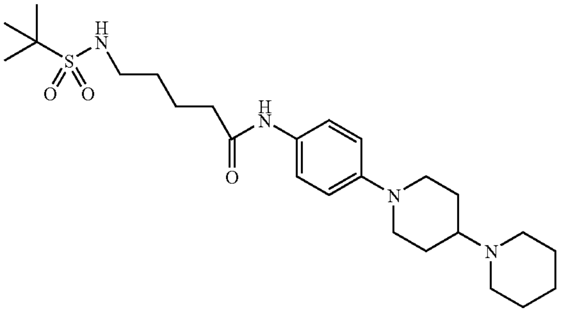
I-234
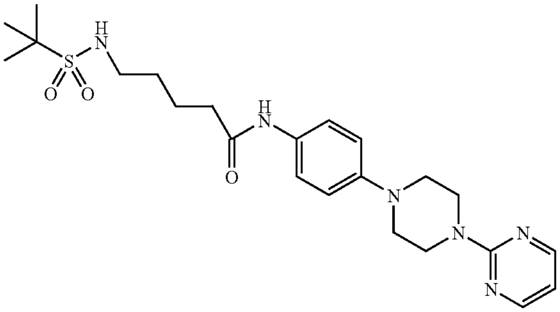
I-235
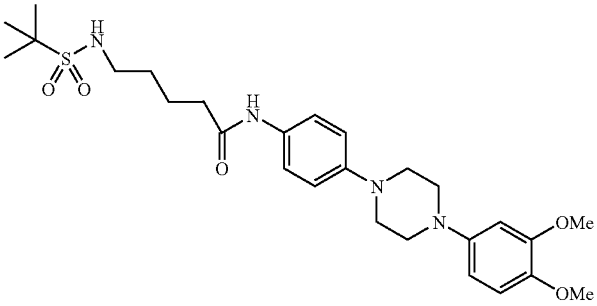
I-236
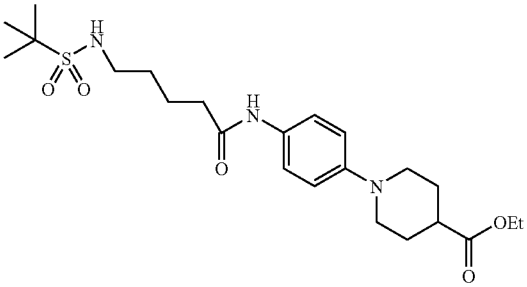
I-237
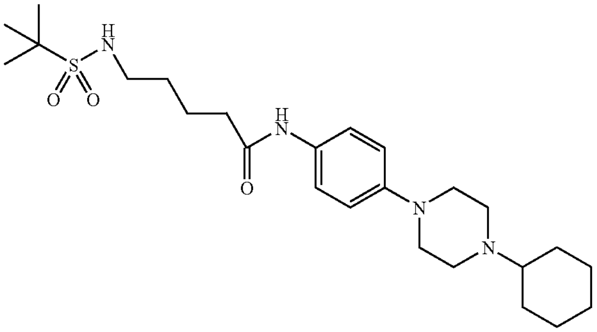
I-238
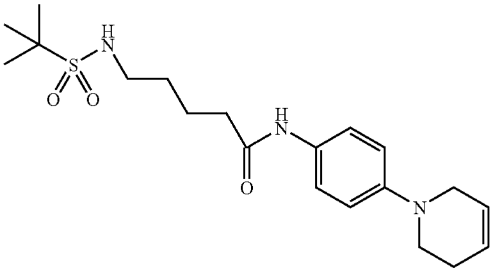
I-239
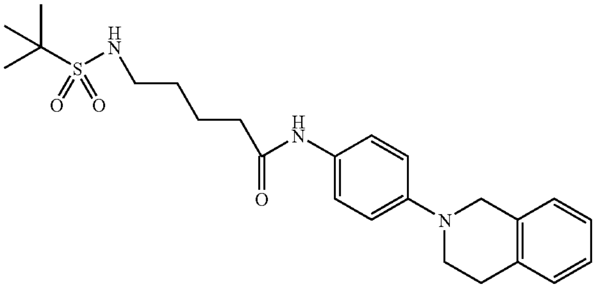
I-240
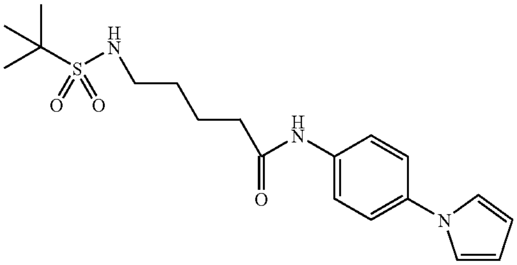

-continued
I-241
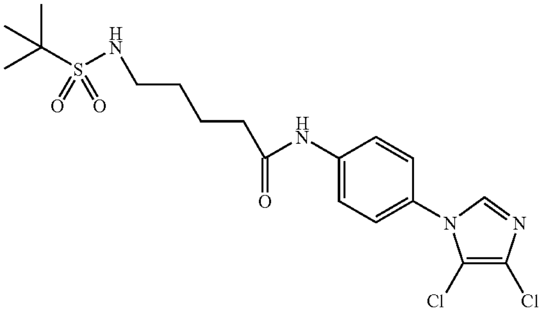
I-242
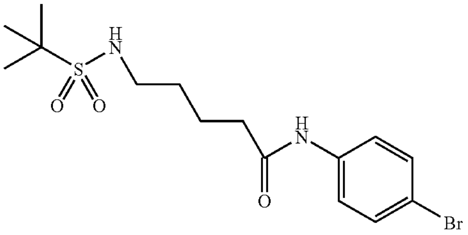
I-243
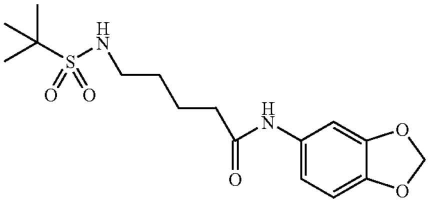
I-244
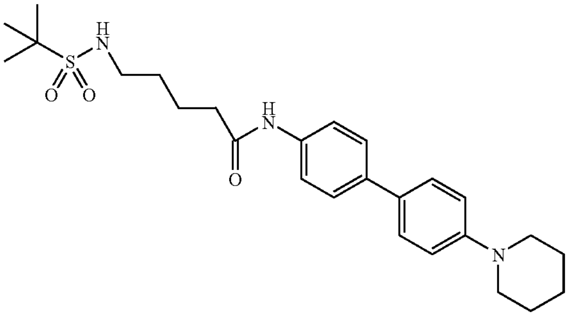
I-245
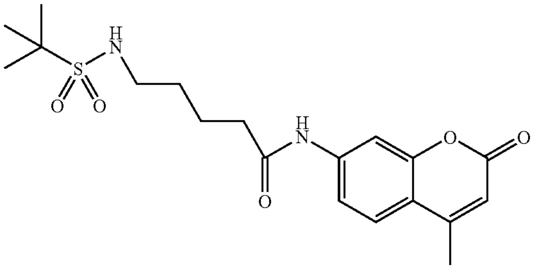
I-246
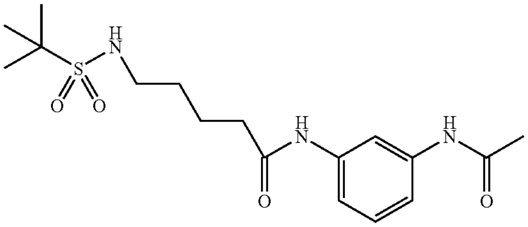
I-247
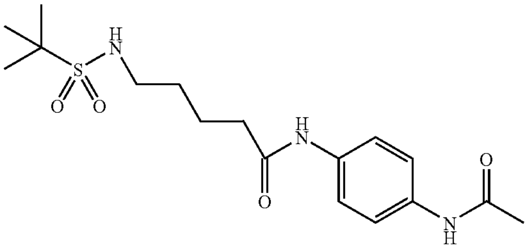
I-248
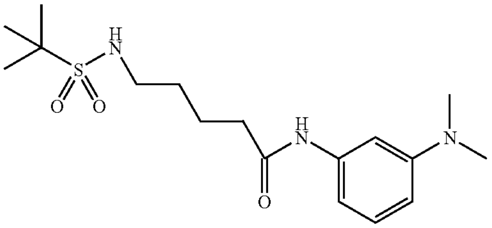
I-249
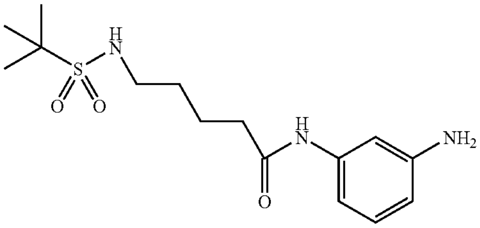
I-250
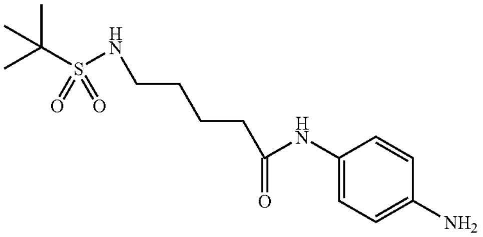

-continued
I-251
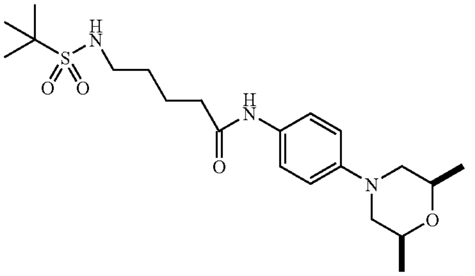
I-252
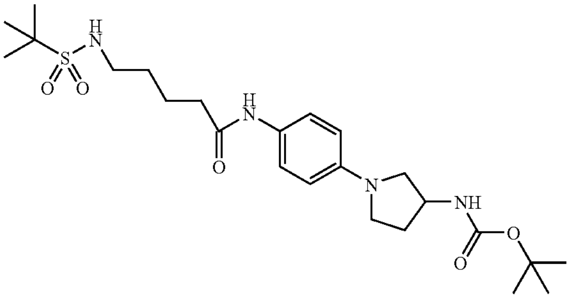
I-253
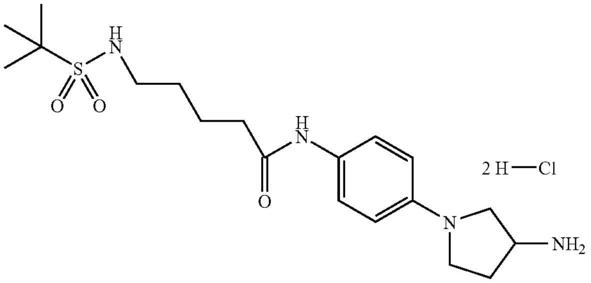
I-254
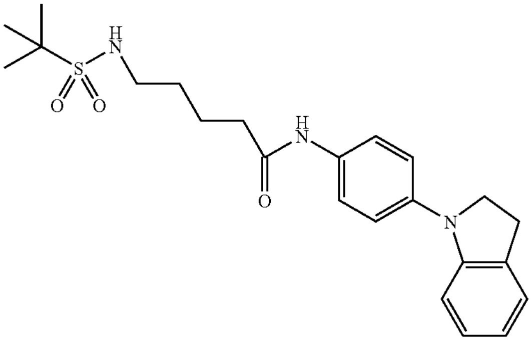
I-25
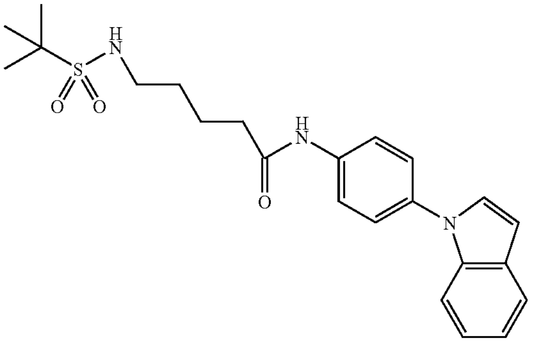
I-256
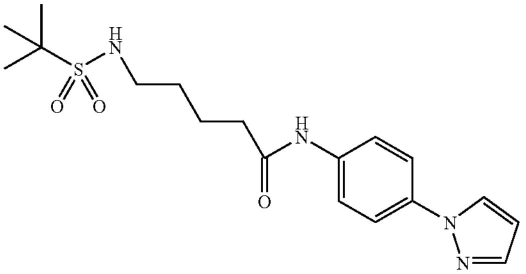
I-257
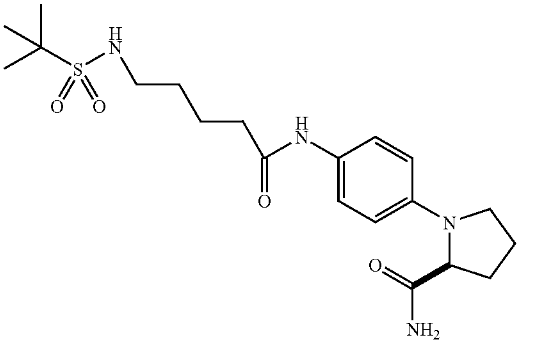
I-258
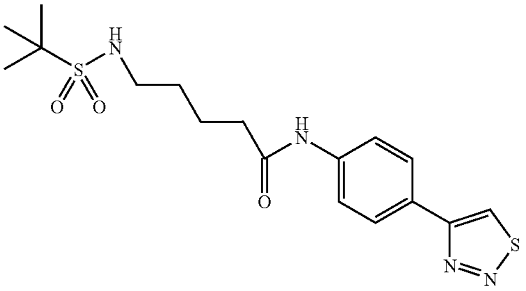
I-259
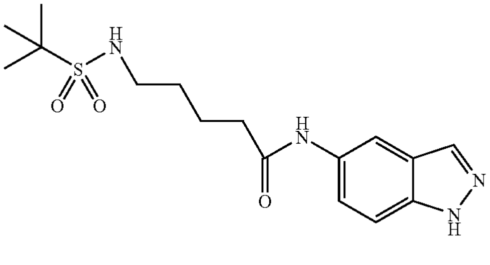
I-260
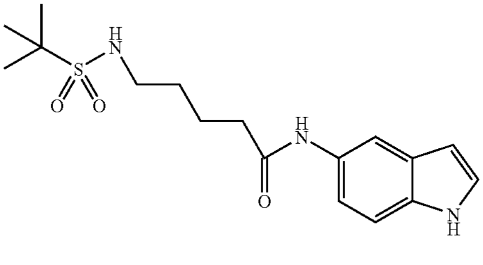

-continued
I-261
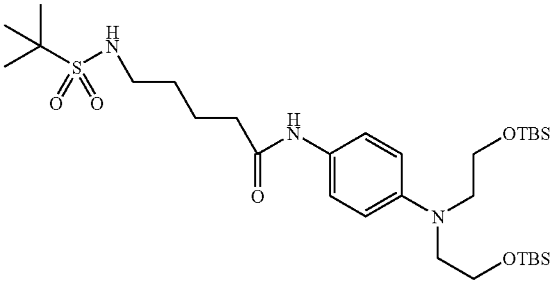
I-262
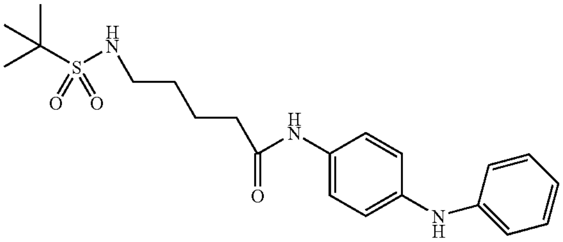
I-263
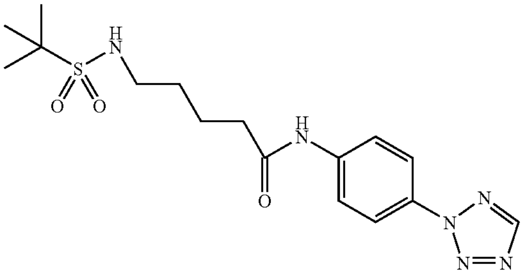
I-264
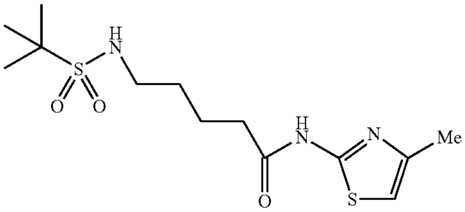
I-265
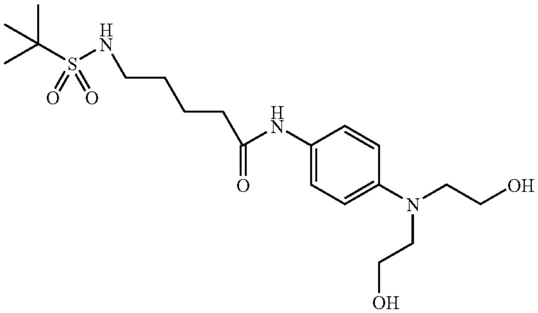
I-266
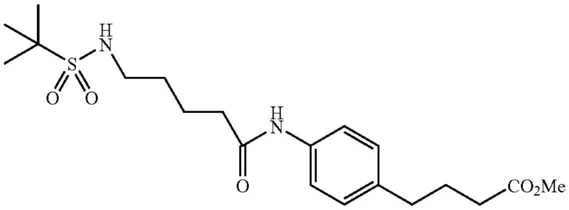
I-267
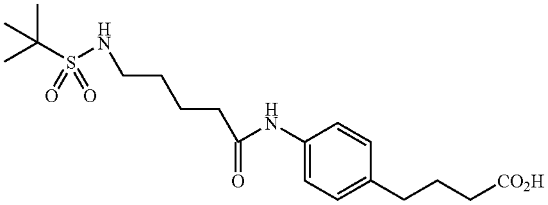
I-268
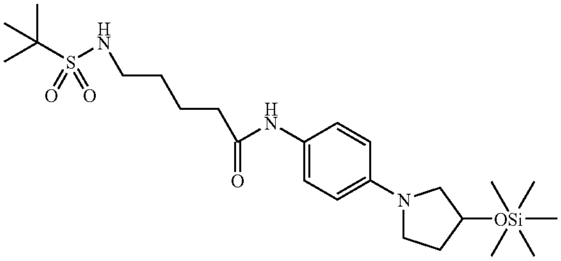
I-269
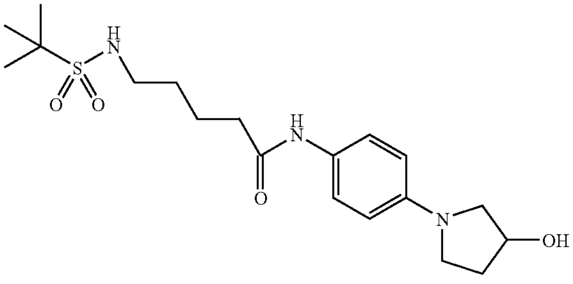
I-270
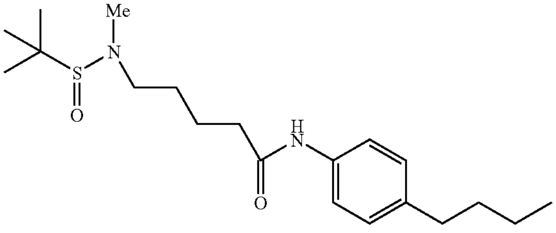

-continued
I-271
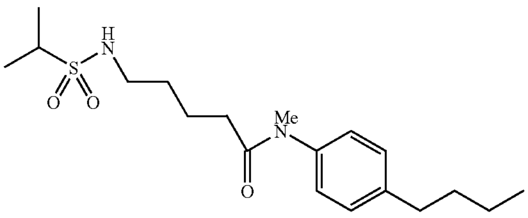
I-272
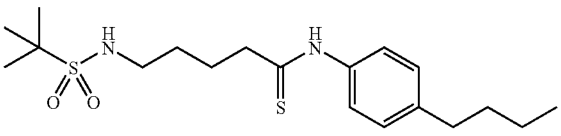
I-273
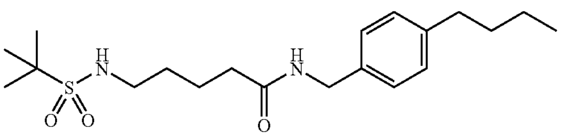
I-274
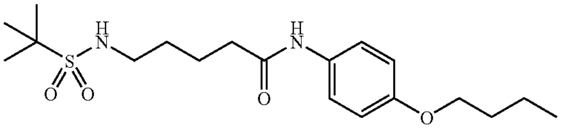
I-275
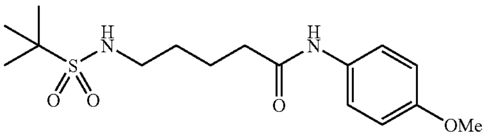
I-276
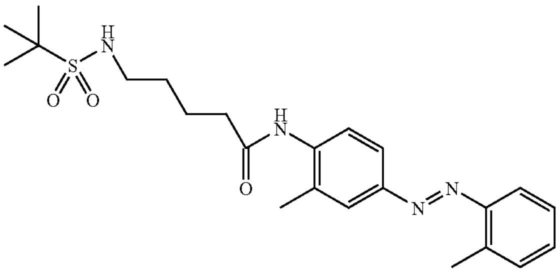
I-277
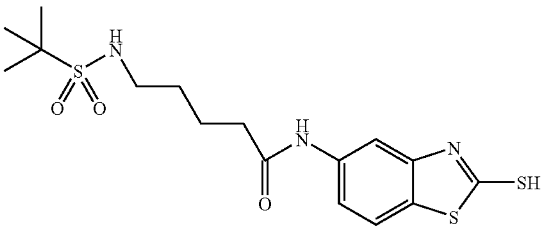
I-278
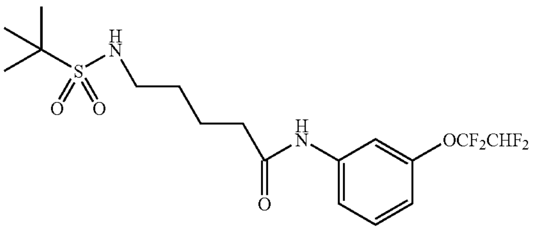
I-279
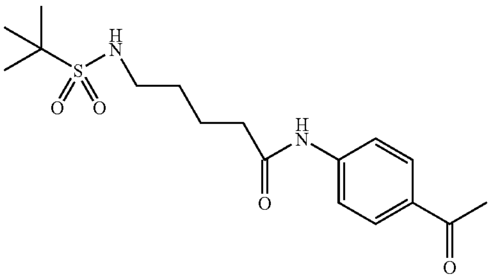
I-280
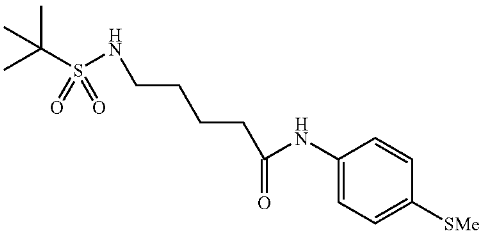
I-281
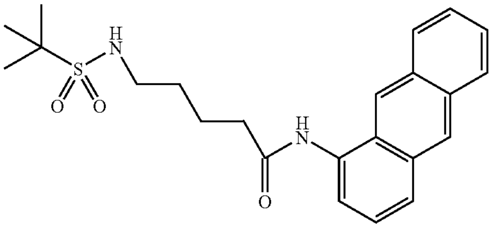
I-282
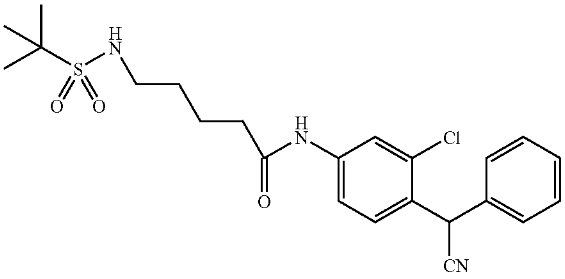

-continued
I-283
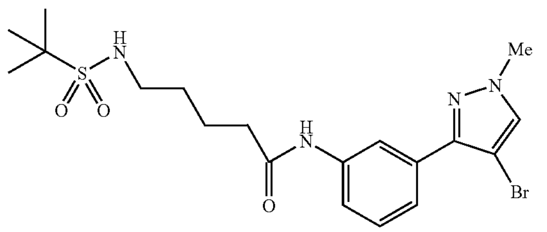
I-284
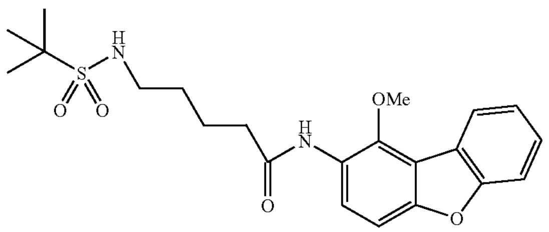
I-285
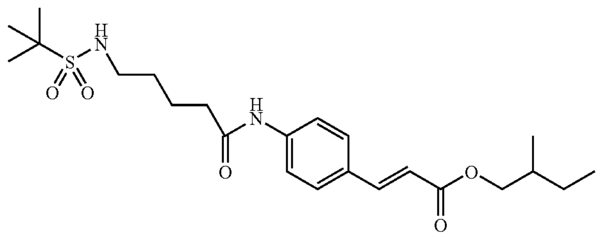
I-286
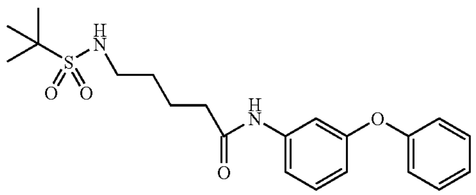
I-287
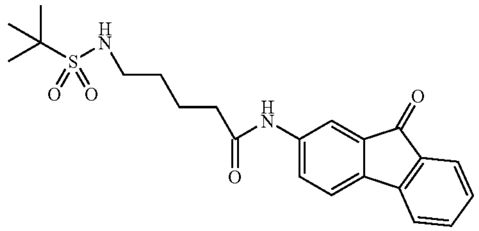
I-288
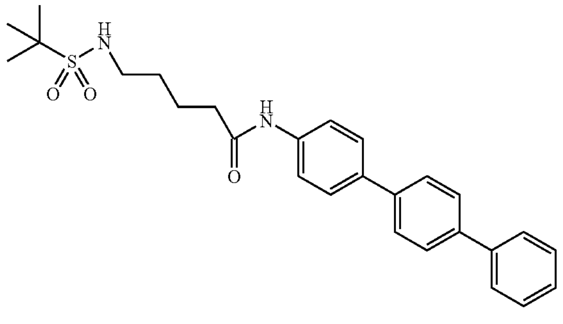
I-289
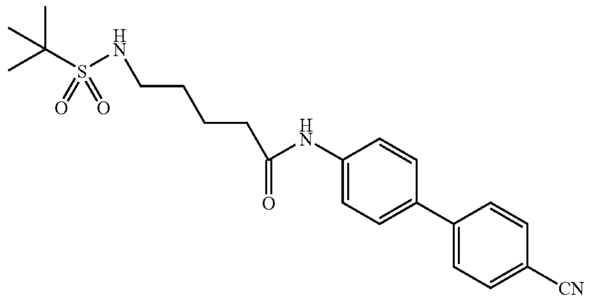
I-290
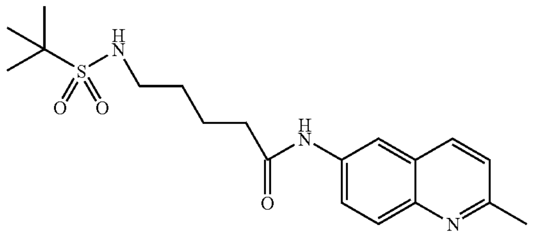
I-291
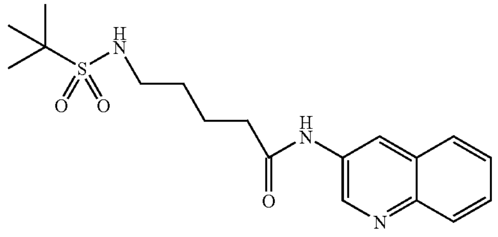
I-292
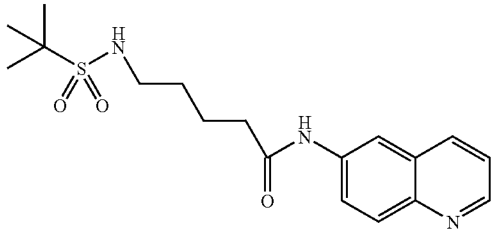

-continued
I-293
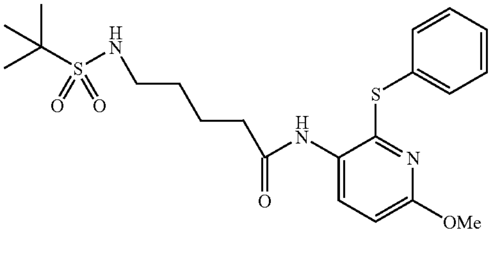
I-294
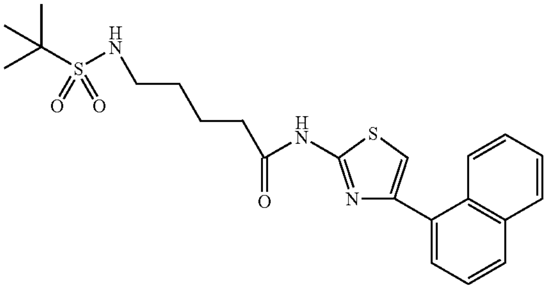
I-295
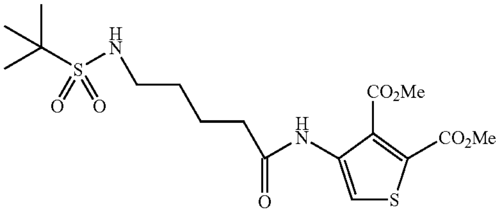
I-296
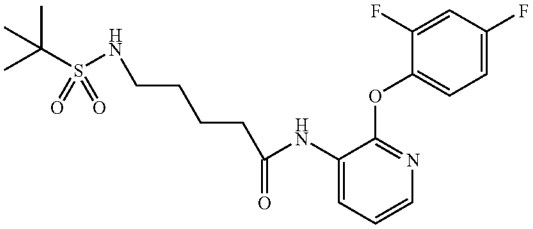
I-297
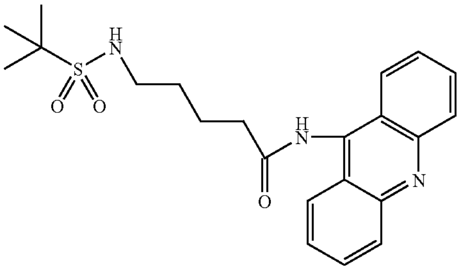
I-298
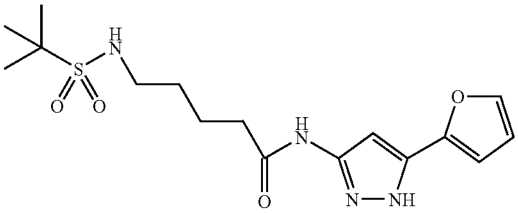
I-299
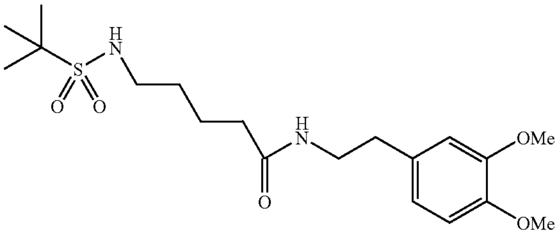
I-300
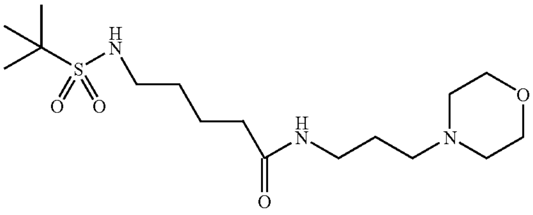
I-301
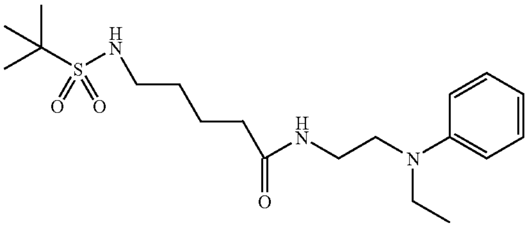
I-302
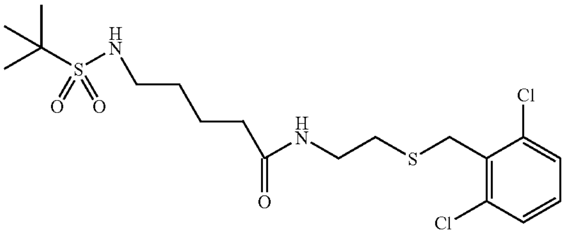
I-303
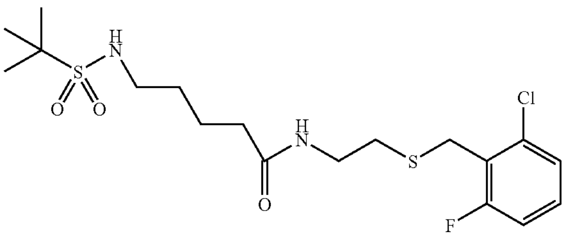
I-304
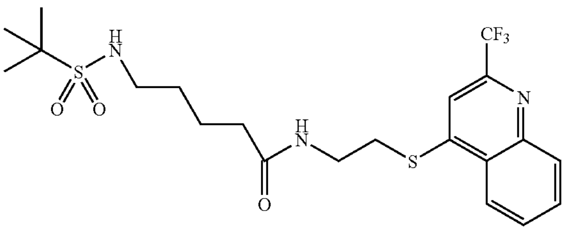

-continued
I-305
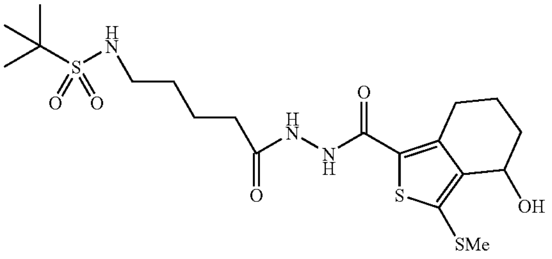
I-306
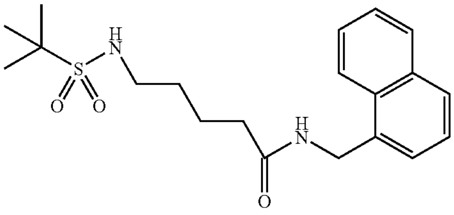
I-307
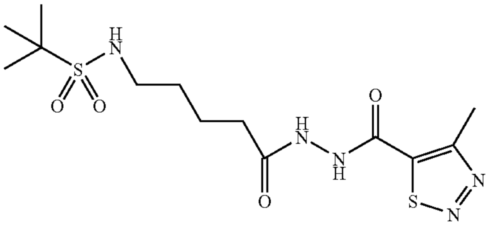
I-308
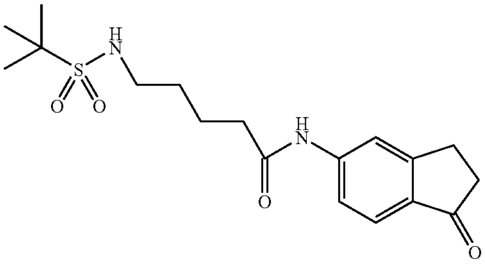
I-309
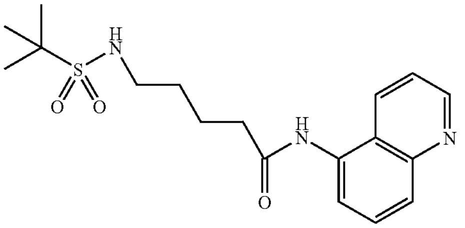
I-310
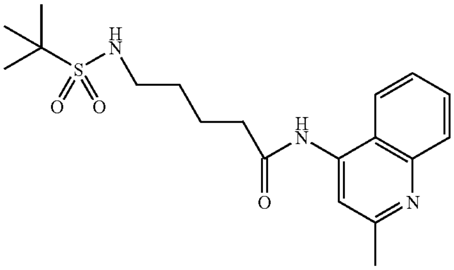
I-311
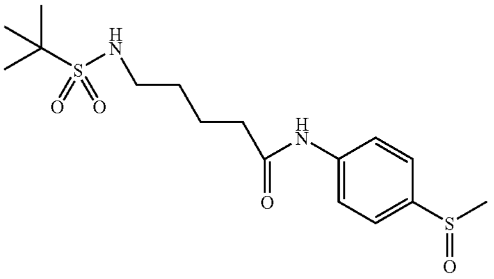
I-312
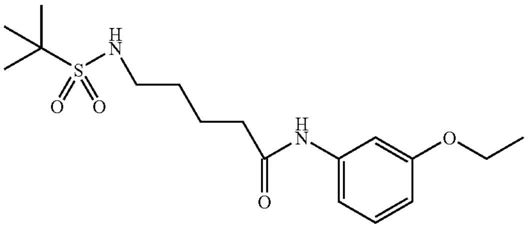
I-313
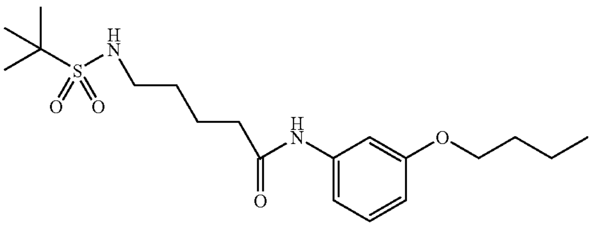
I-314
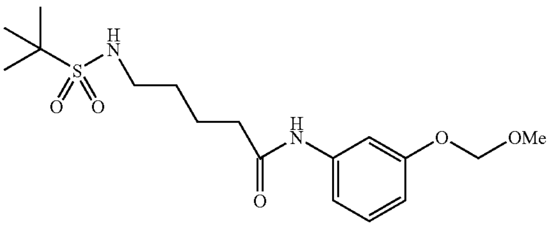
I-315
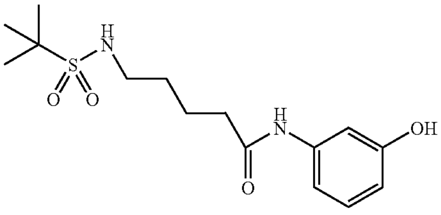
I-316
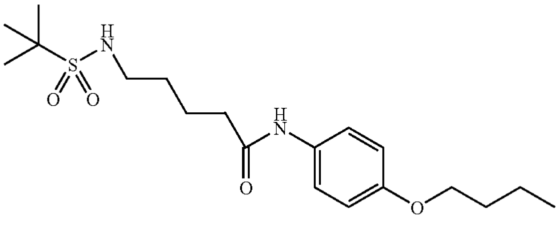

-continued
I-317
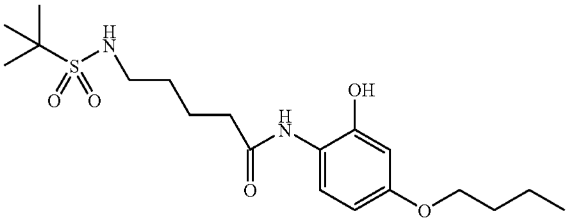
I-318
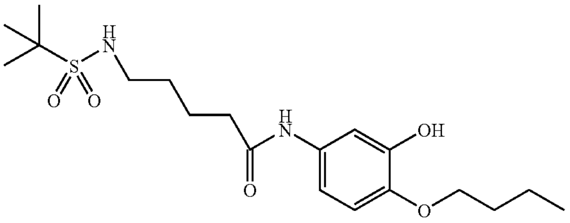
I-319
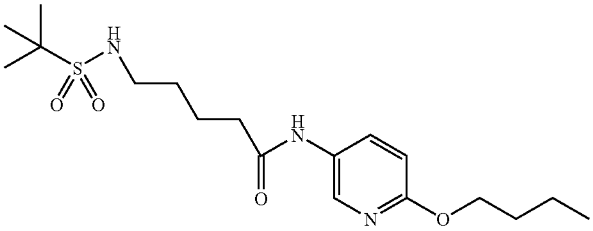
I-320
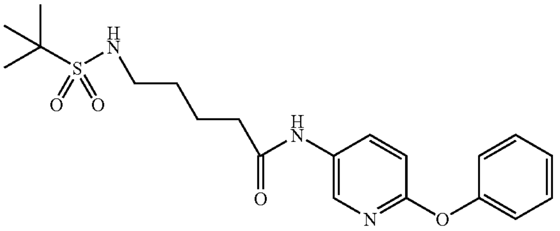
I-321
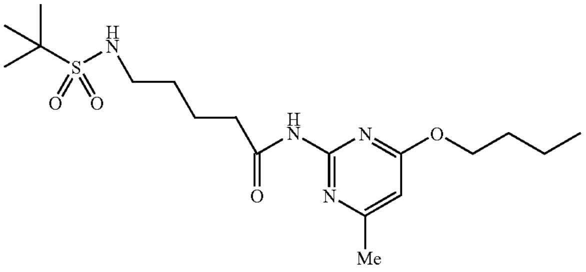
I-322
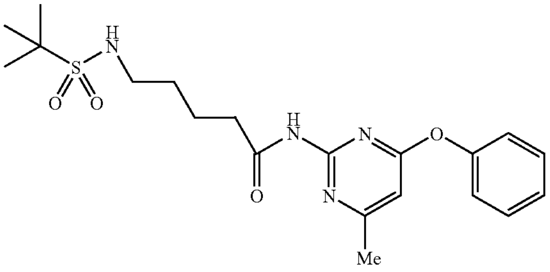
I-323
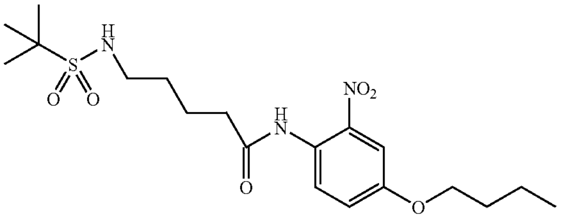
I-324
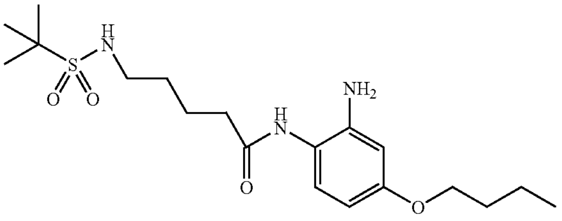
I-325
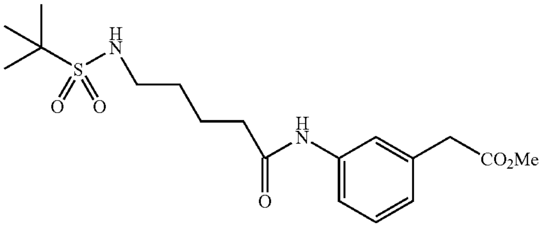
I-326
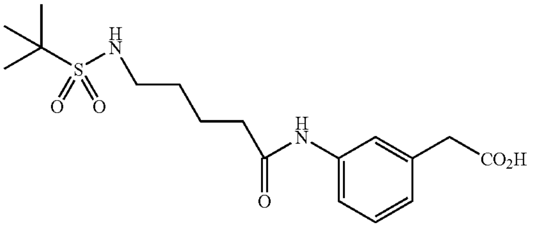
I-327
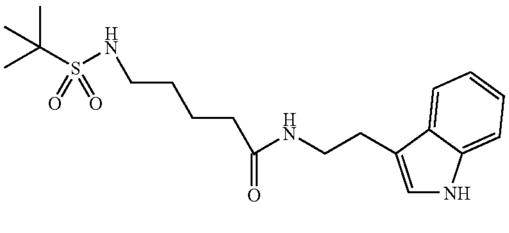
I-38
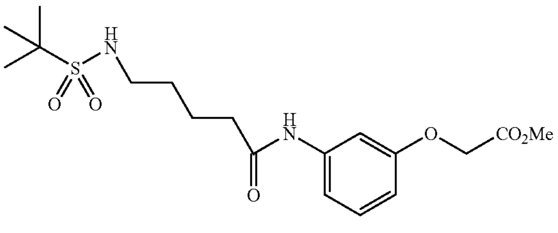

-continued
I-329
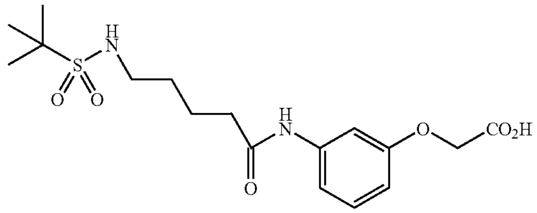
I-330
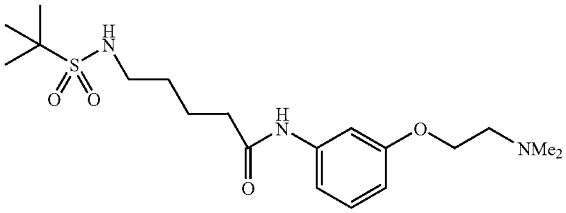
I-331
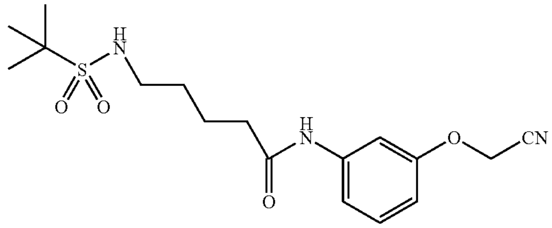
I-332
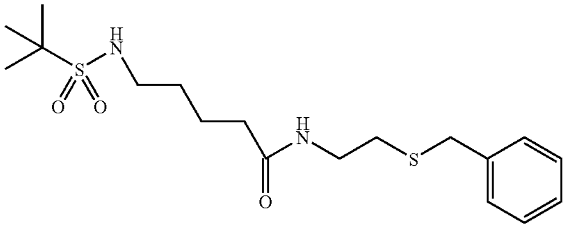
I-333
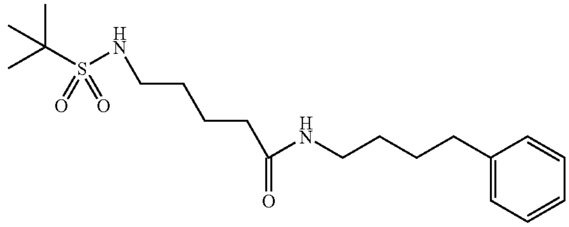
I-334
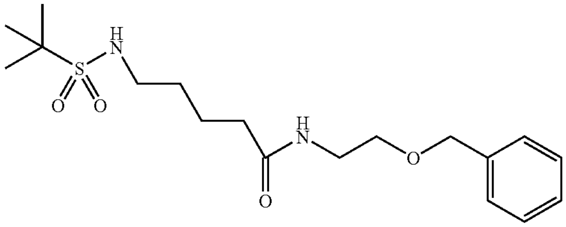
I-335
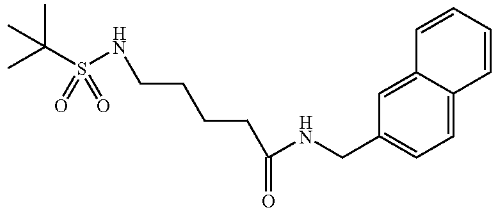
I-336
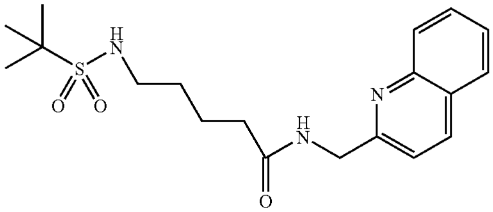
I-337
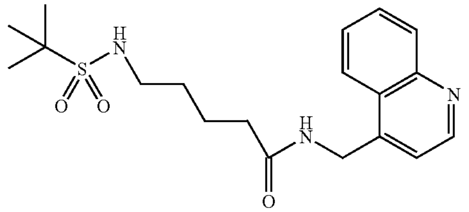
I-338
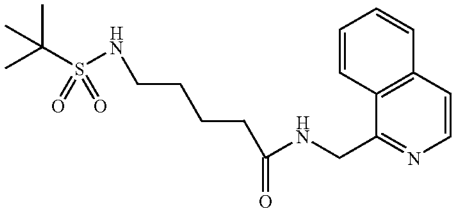
I-339
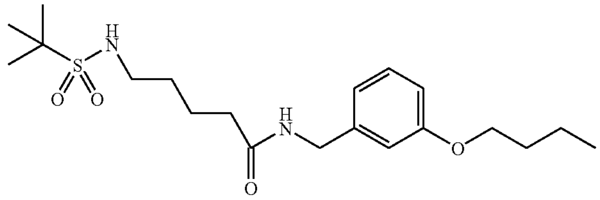
I-340
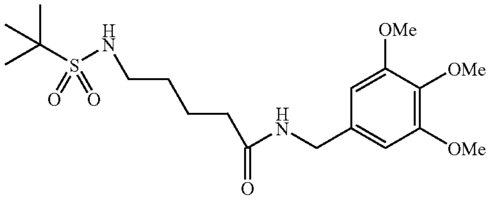

-continued
I-341
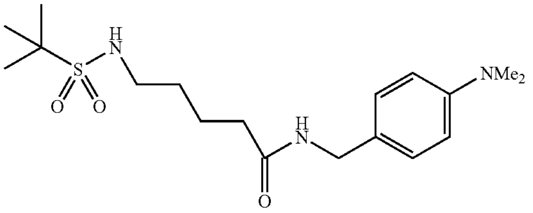
I-342
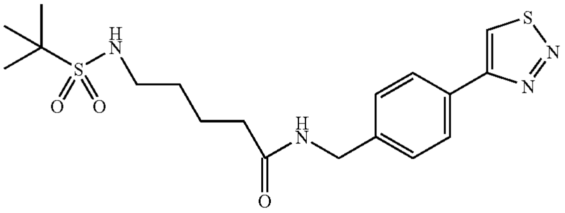
I-343
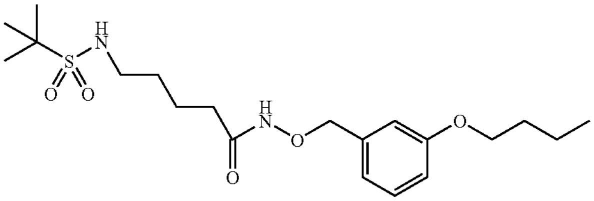
I-344
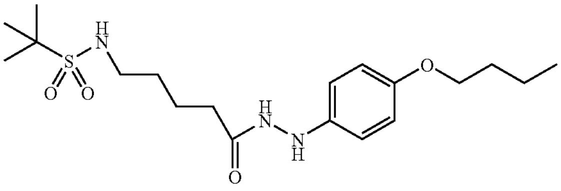
I-345
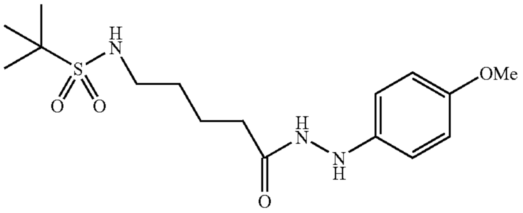
I-346
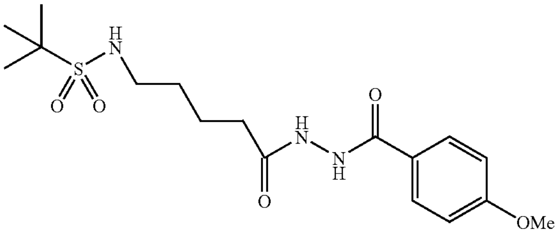
I-347
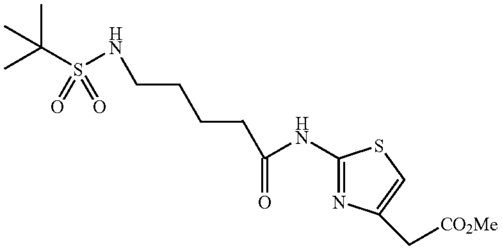
I-348
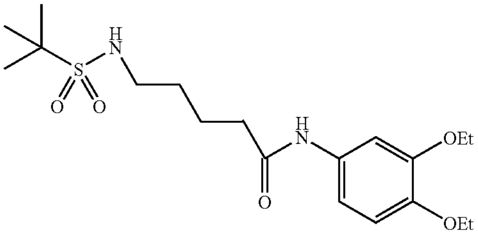
I-349
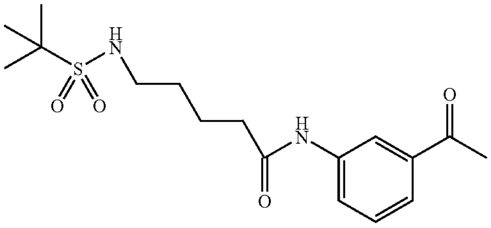
I-350
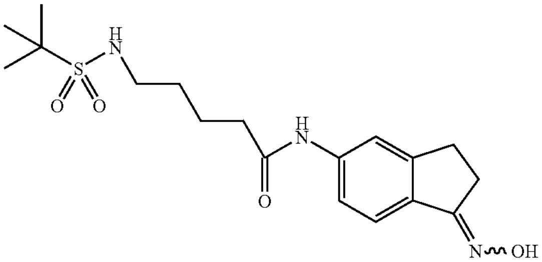
I-351
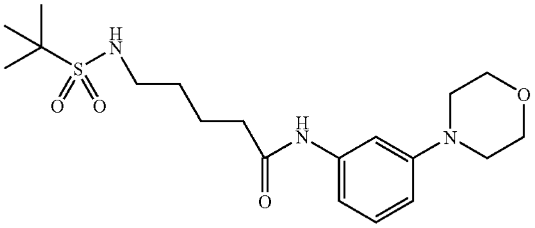
I-352
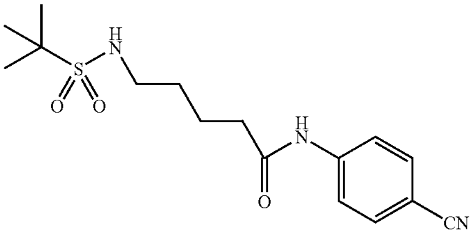

-continued
I-353
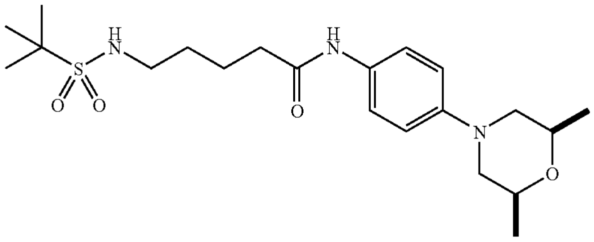
I-354
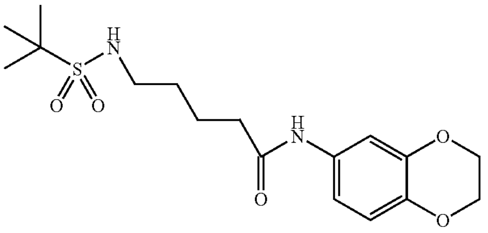
I-355
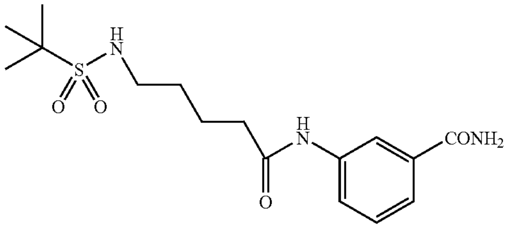
I-356
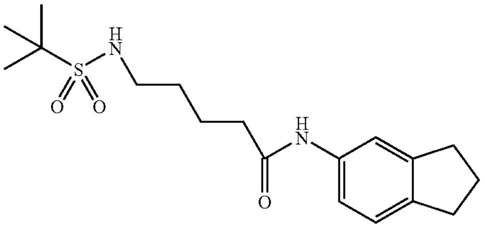
I-357
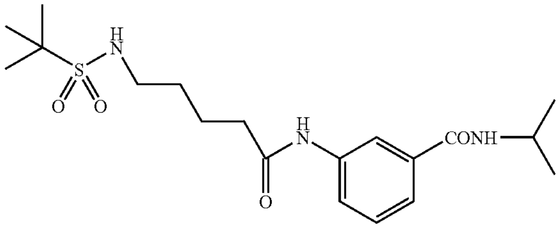
I-358
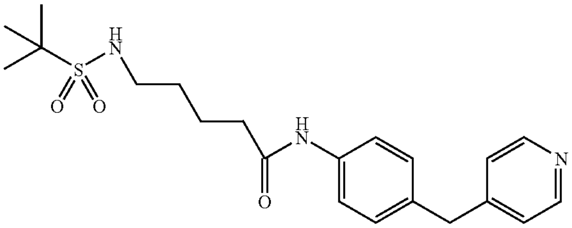
I-359
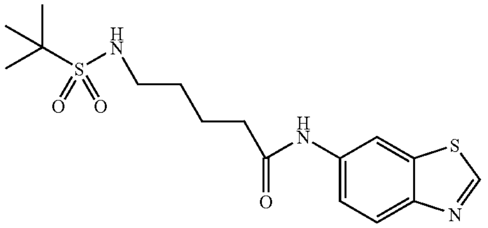
I-360
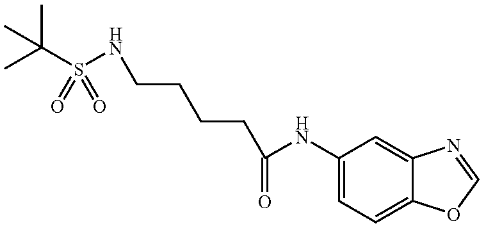
I-361
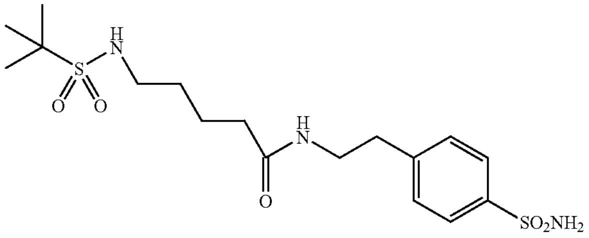
I-362
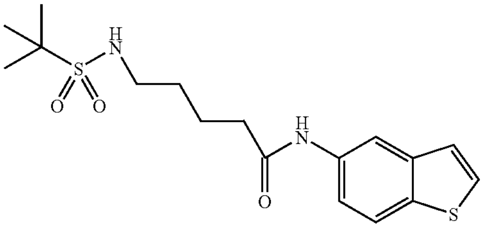
I-363
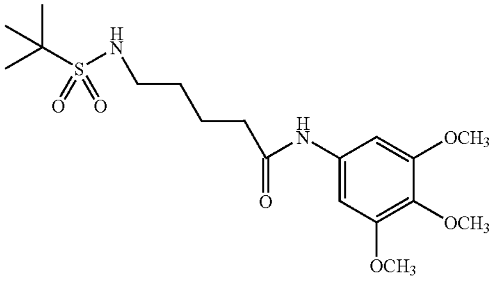
I-364
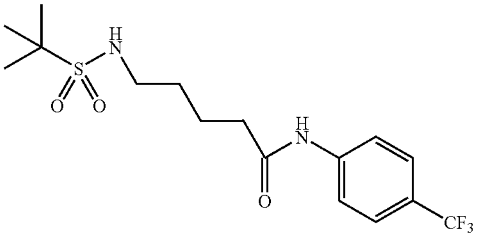

-continued
I-365
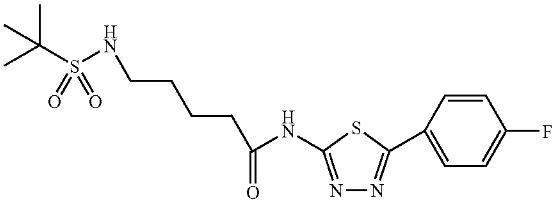
I-366
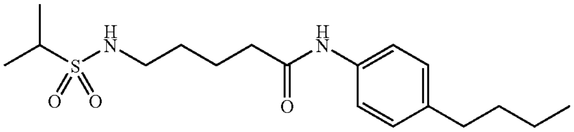
I-367
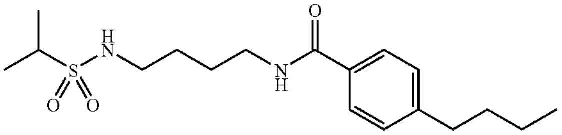
I-368
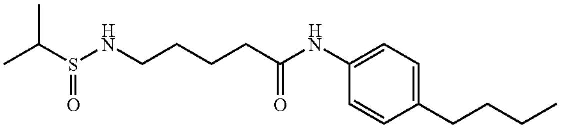
I-369
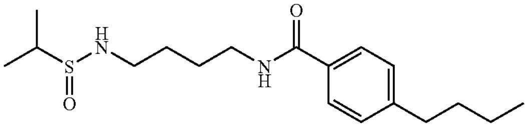
I-370
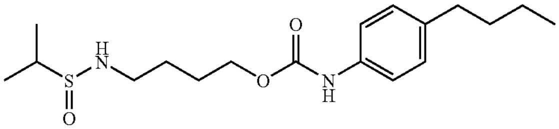
I-371
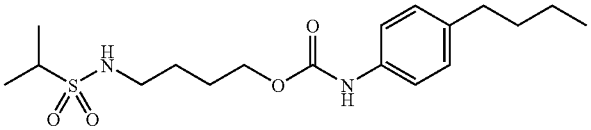
I-372
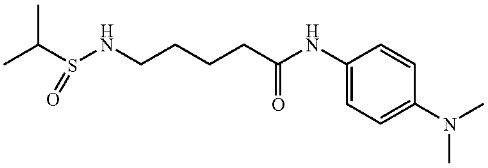
I-373
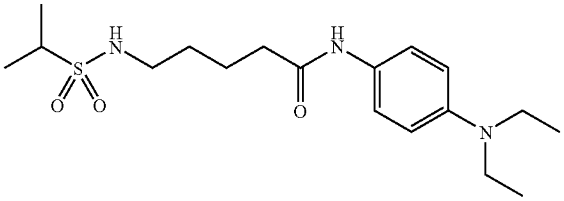
I-374
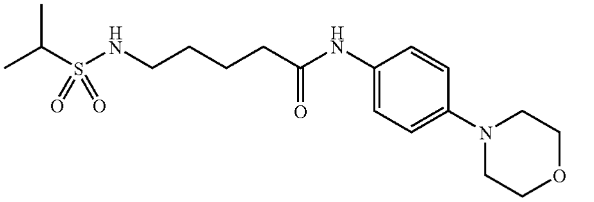
I-375
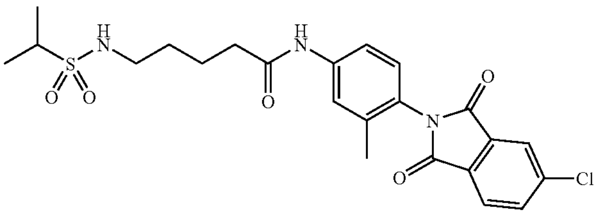
I-376
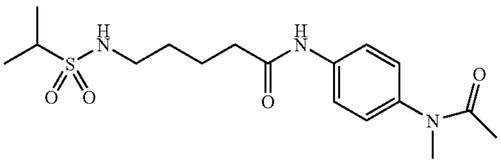
I-377
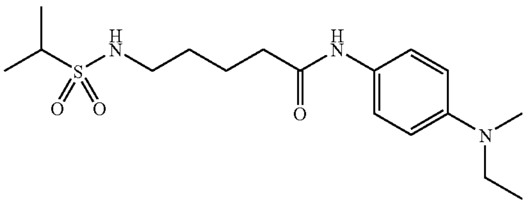
I-378
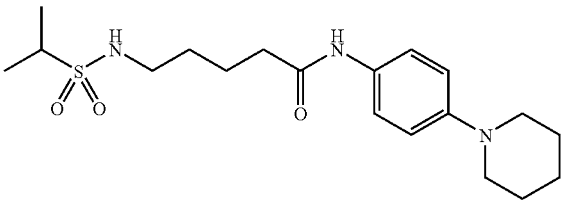

-continued
I-379
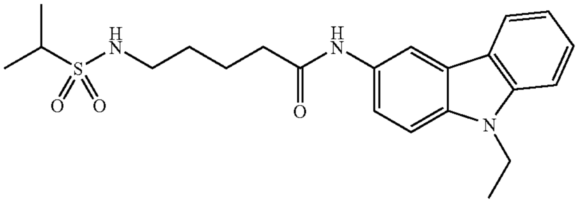
I-380
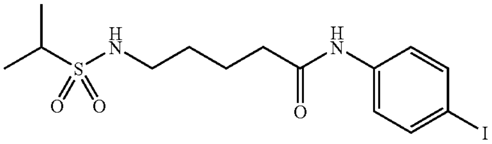
I-381
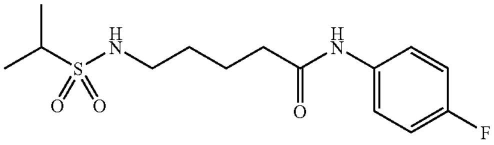
I-382
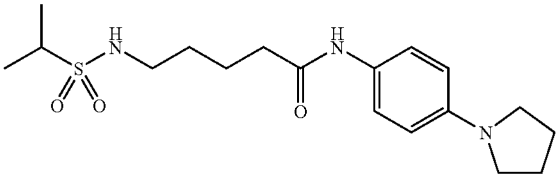
I-383
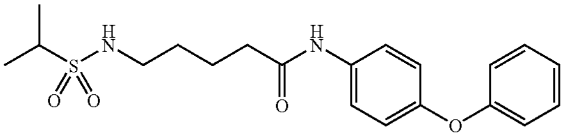
I-384
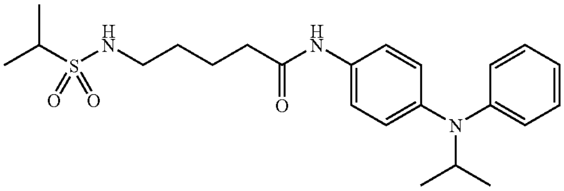
I-385
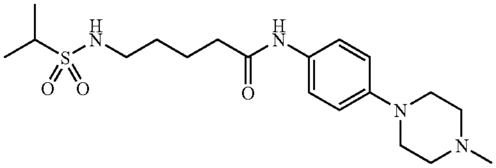
I-386
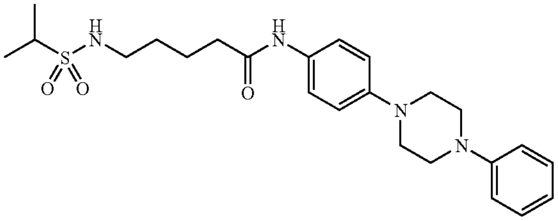
I-387
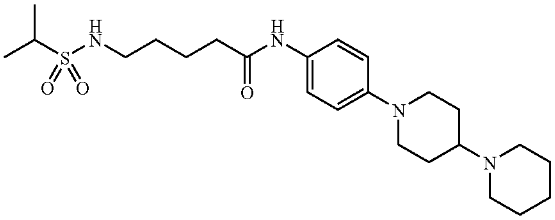
I-388
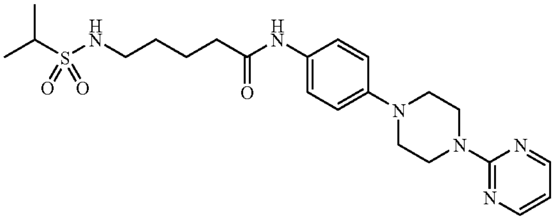
I-389
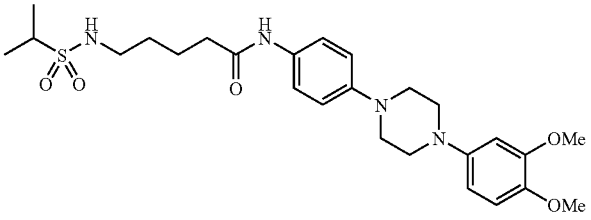
I-390
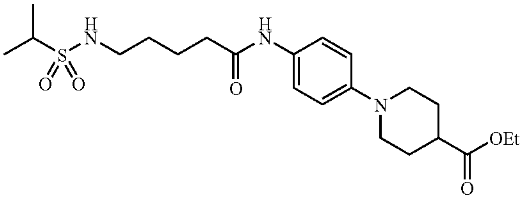

-continued
I-391
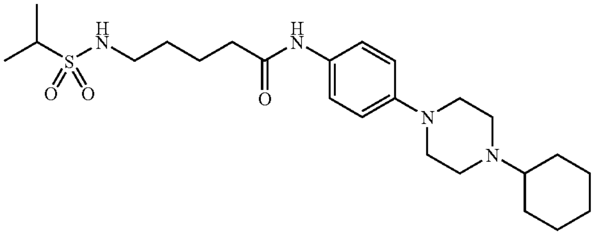
I-392
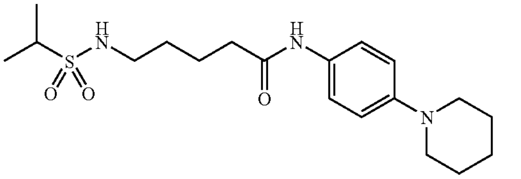
I-393
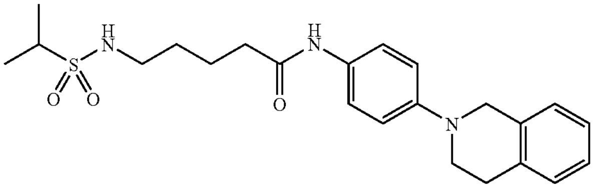
I-394
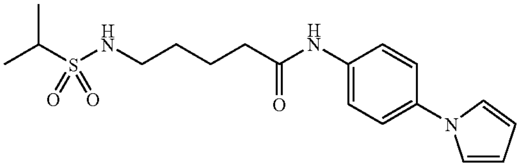
I-395
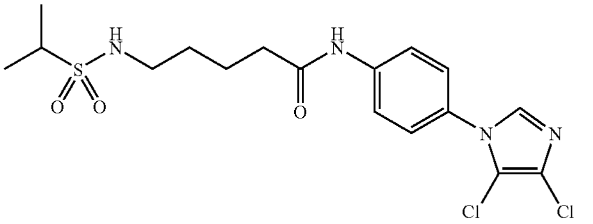
I-396
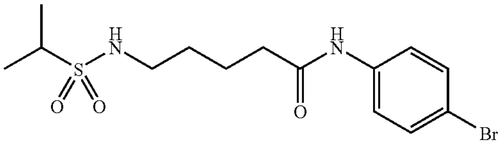
I-397
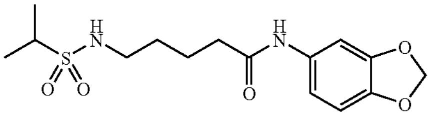
I-398
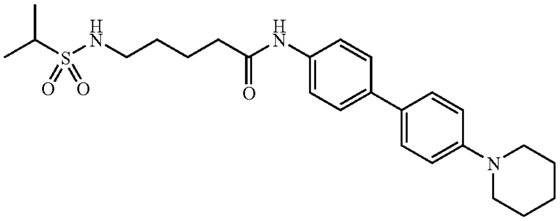
I-399
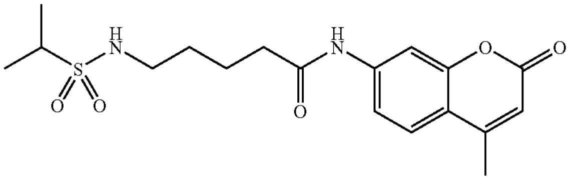
I-400
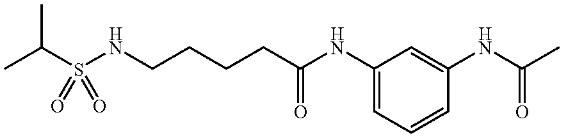
I-401
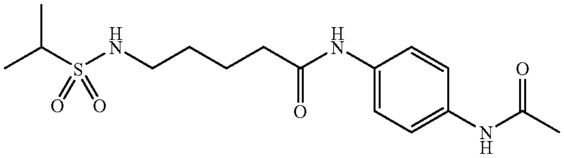
I-402
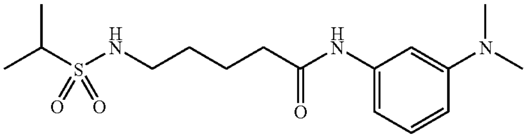
I-403
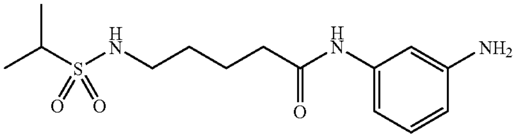
I-404
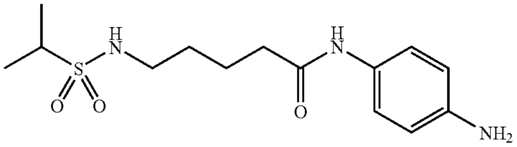

-continued
I-405
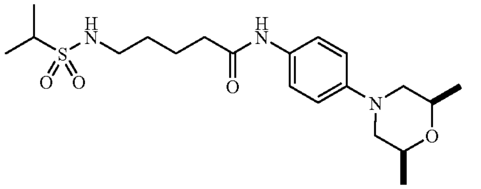
I-406
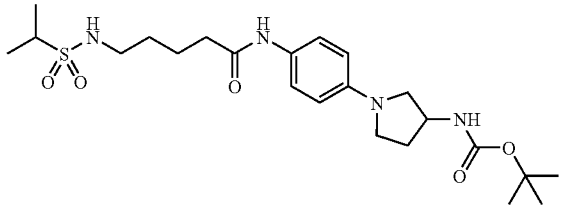
I-407
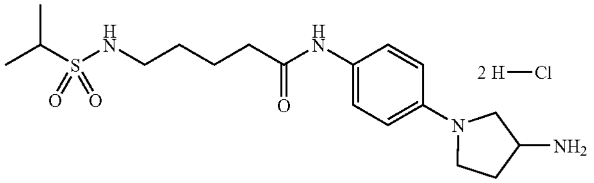
I-408
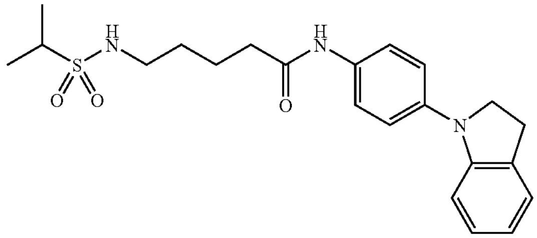
I-409
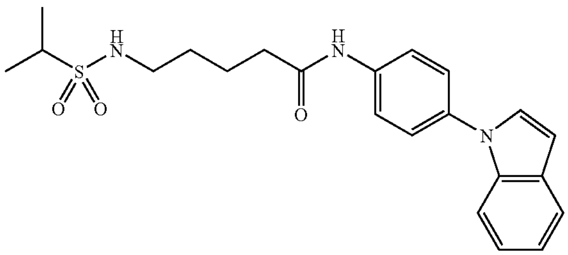
I-410
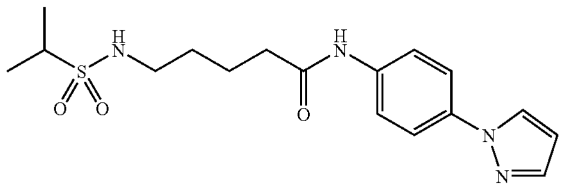
I-411
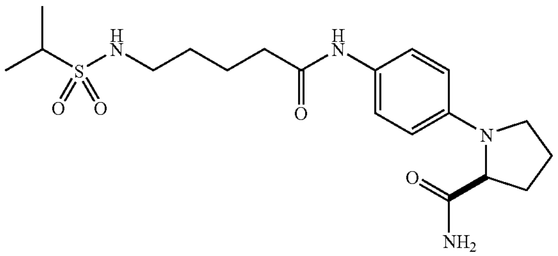
I-412
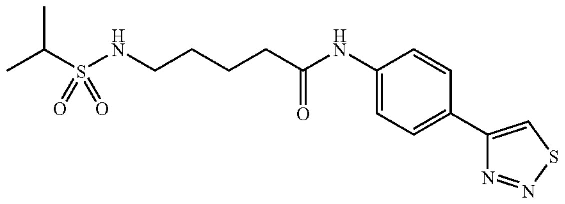
I-413
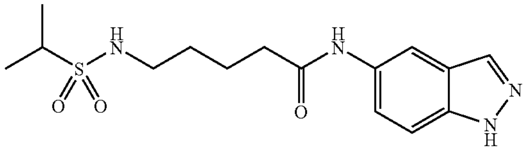
I-414
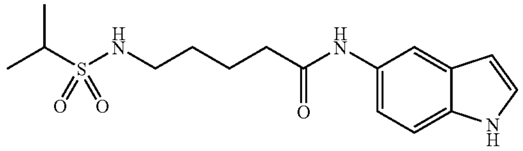
I-415
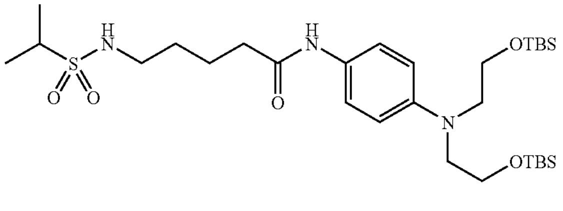
I-416
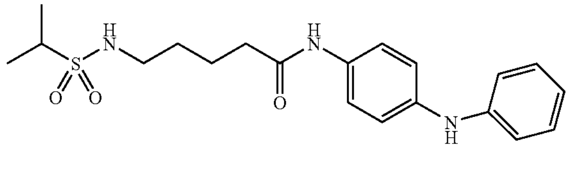

-continued
I-417
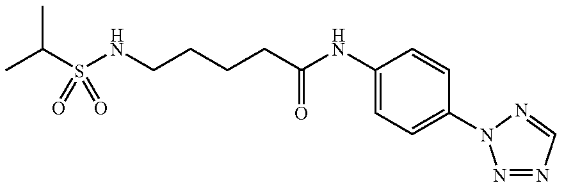
I-418
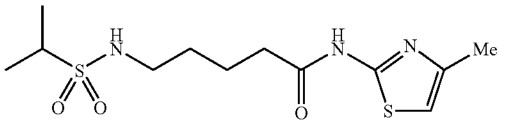
I-419
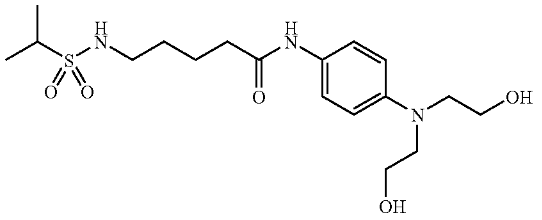
I-420
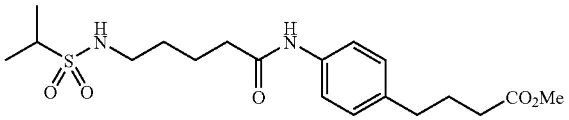
I-421
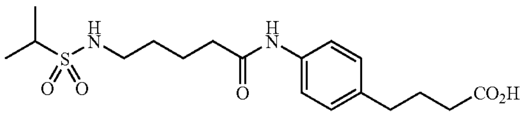
I-422
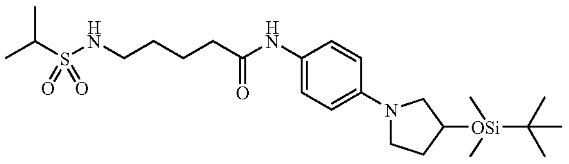
I-423
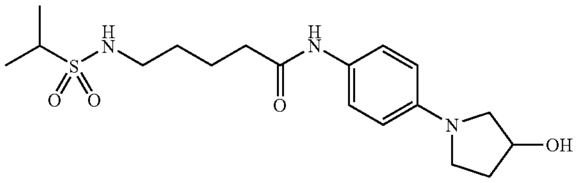
I-424
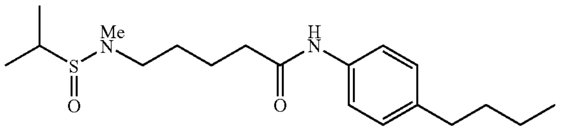
I-425
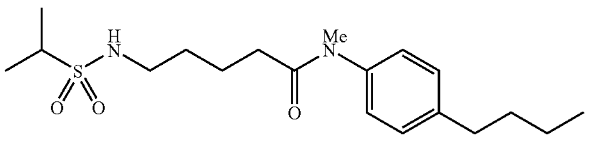
I-426
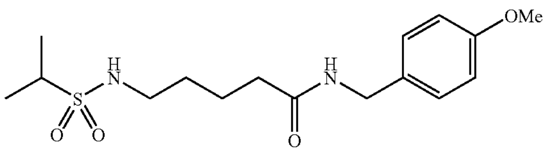
I-427
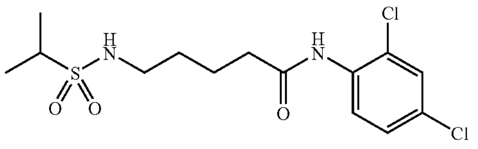
I-428
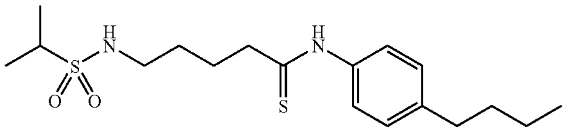
I-429
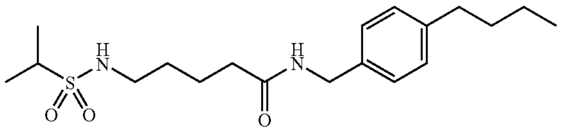
I-430
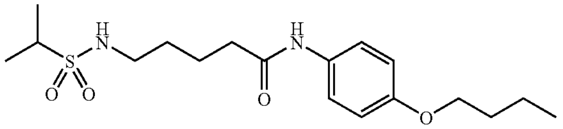
I-431
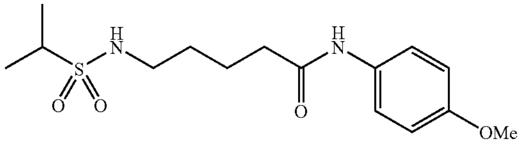
I-432
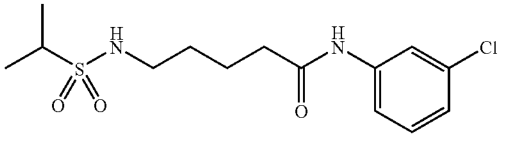

-continued
I-433
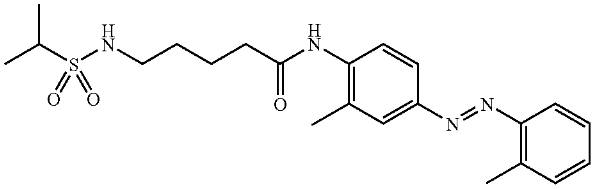
I-434
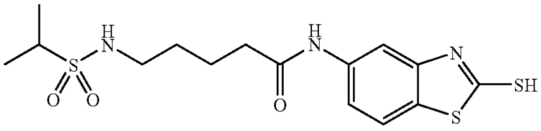
I-435
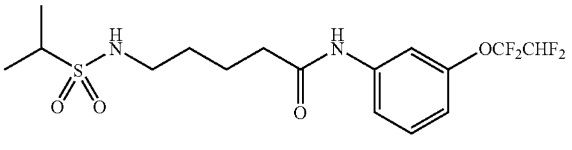
I-436
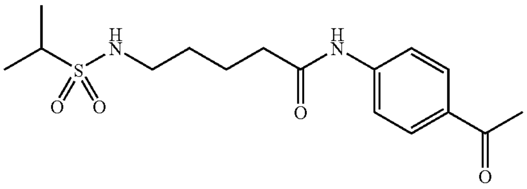
I-437
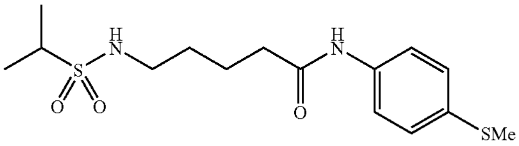
I-438
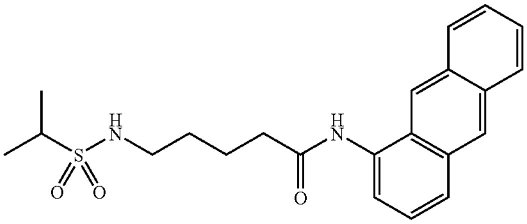
I-439
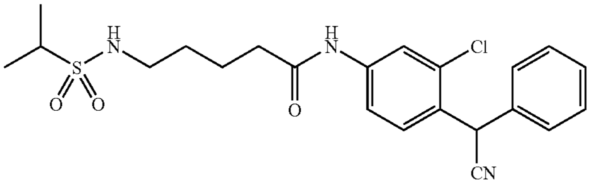
I-440
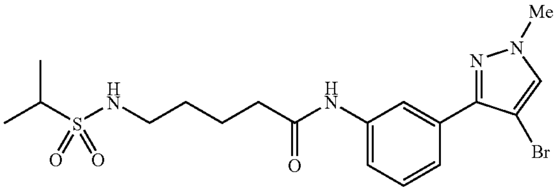
I-441
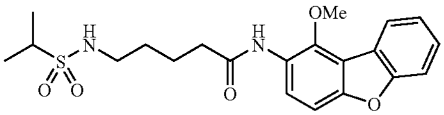
I-442
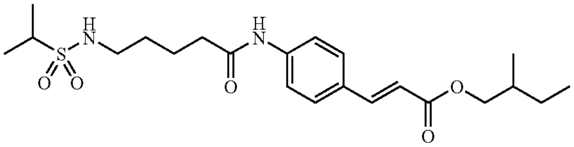
I-443
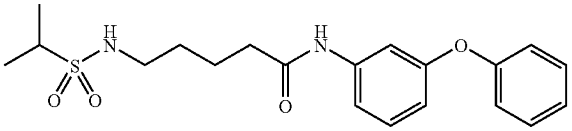
I-444
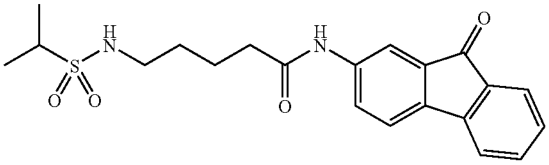
I-445
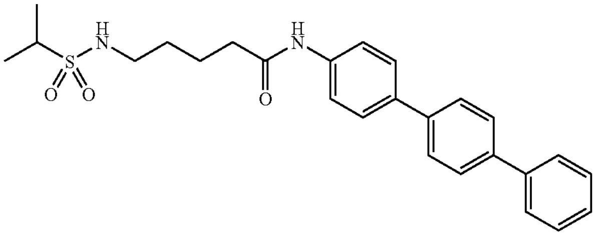
I-446
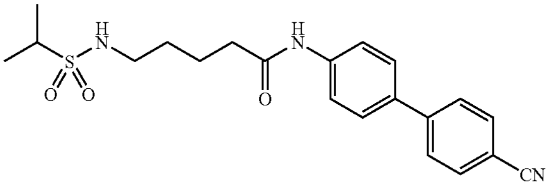

-continued
I-447
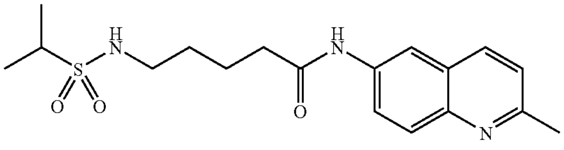
I-448
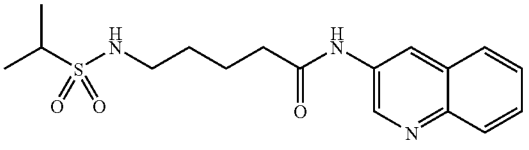
I-449
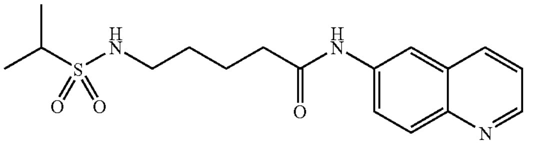
I-450
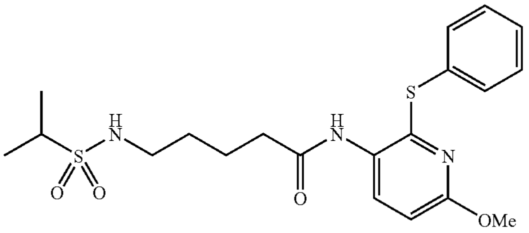
I-451
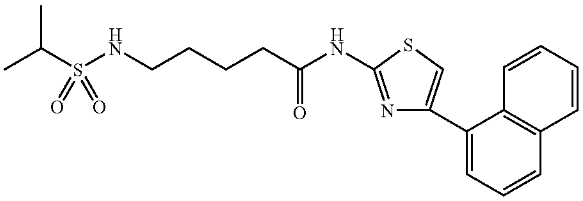
I-452
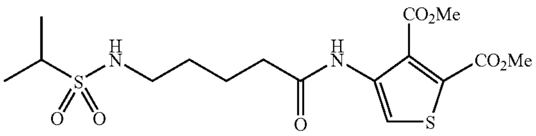
I-453
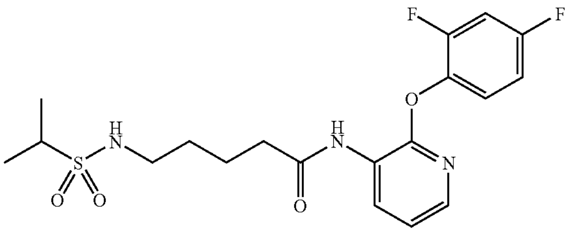
I-454
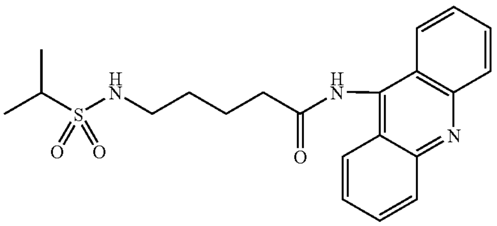
I-455
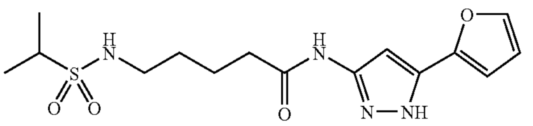
I-456
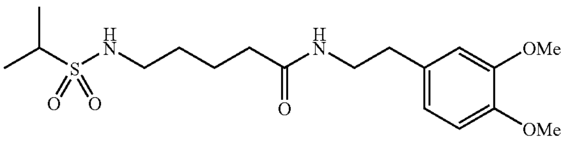
I-457
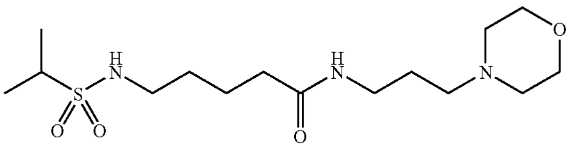
I-458
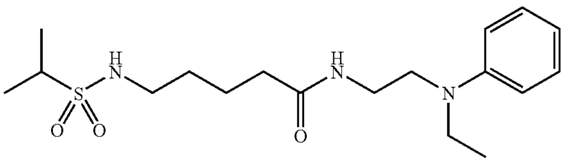
I-459
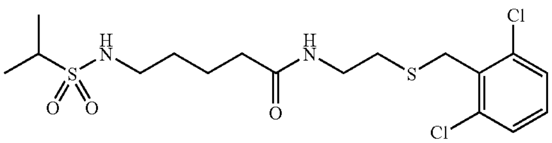
I-460
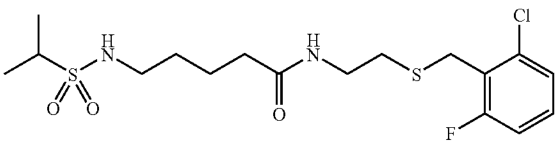

-continued
I-461
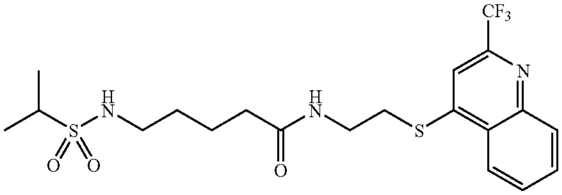
I-462
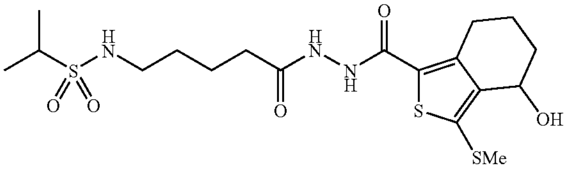
I-463
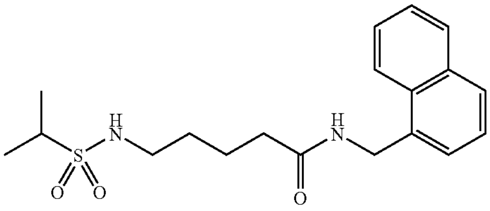
I-464
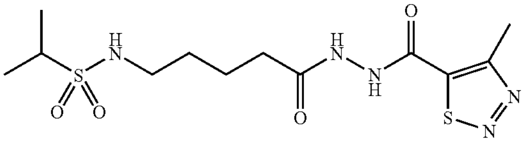
I-465
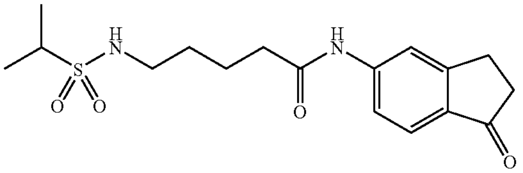
I-466
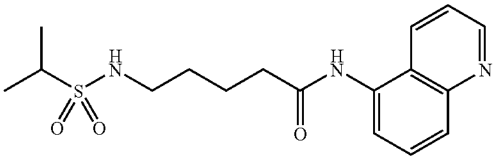
I-467
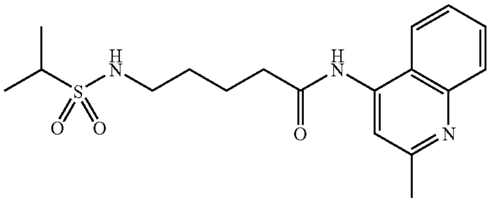
I-468
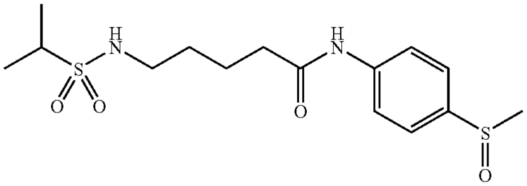
I-469
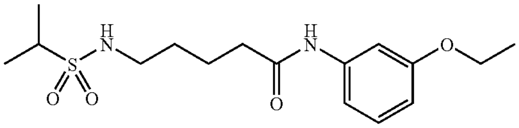
I-470
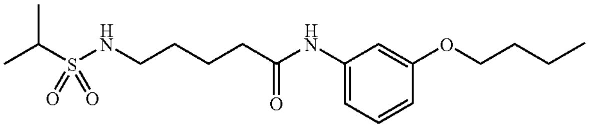
I-471
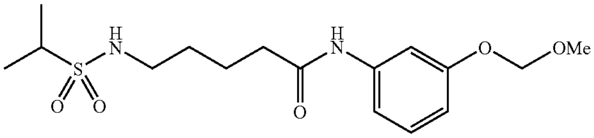
I-472
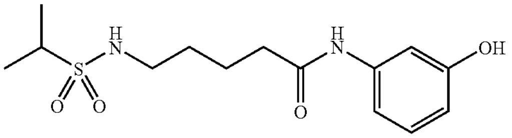
I-473
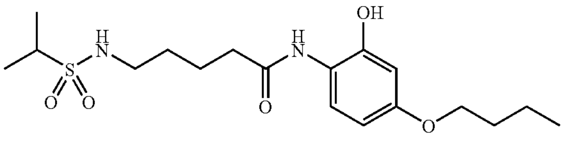
I-474
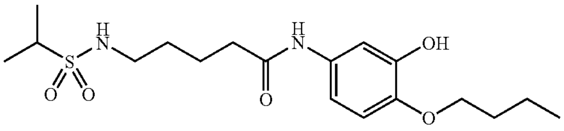
I-475
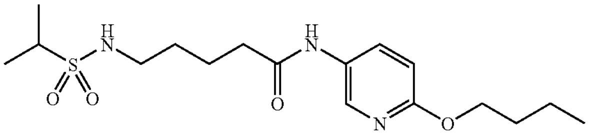
I-476
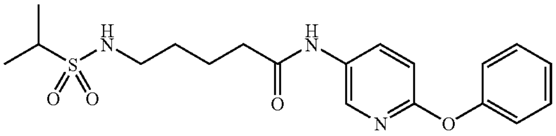

-continued
I-477
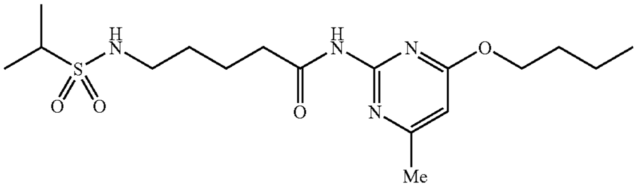
I-478
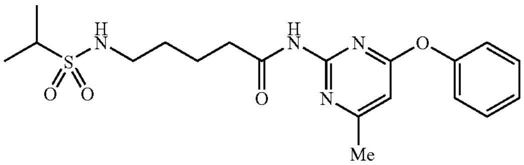
I-479
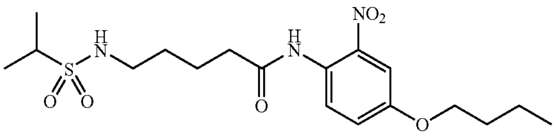
I-480
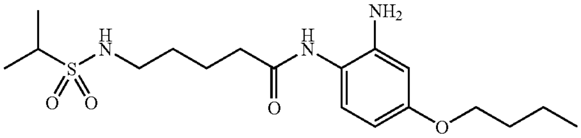
I-481
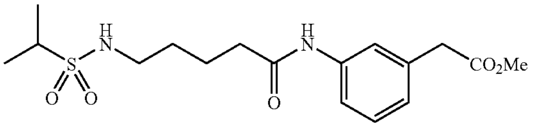
I-482
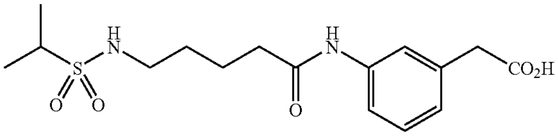
I-483
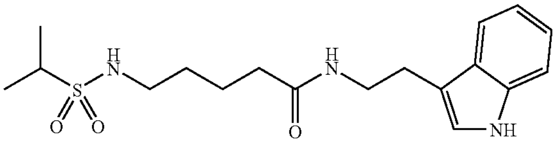
I-484
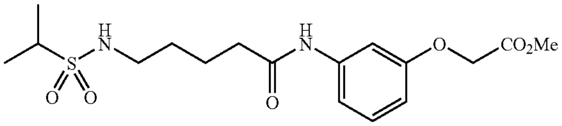
I-485
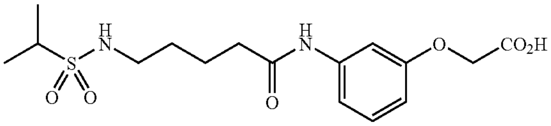
I-486
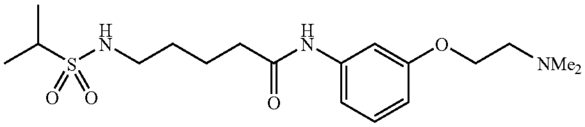
I-487
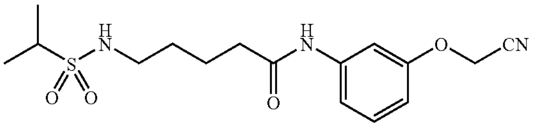
I-488
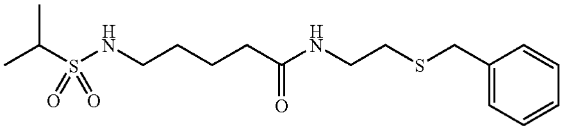
I-489
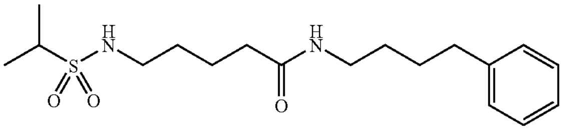
I-490
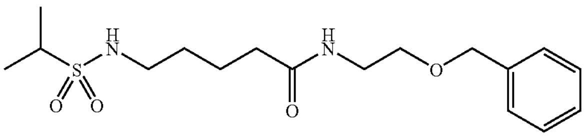
I-491
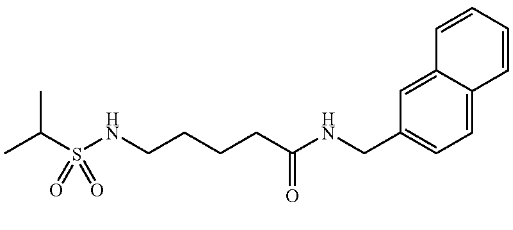

-continued
I-492
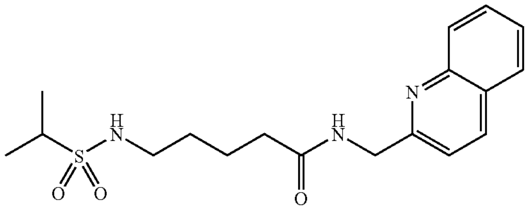
I-493
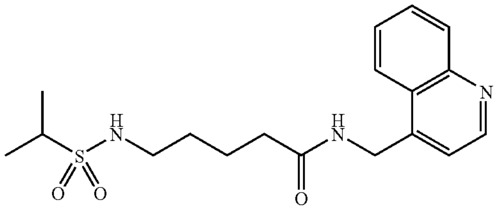
I-494
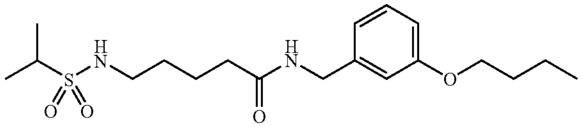
I-495
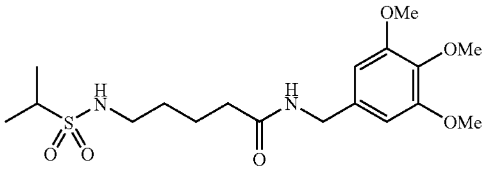
I-496
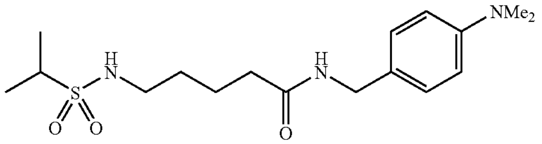
I-497
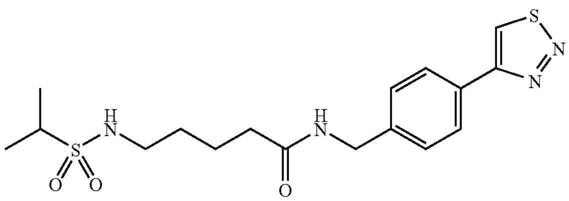
I-498
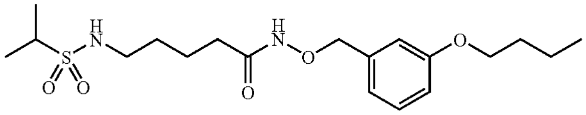
I-499
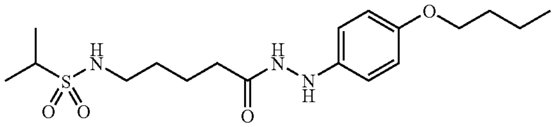
I-500
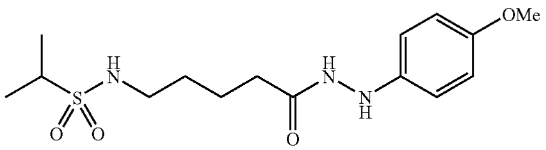
I-501
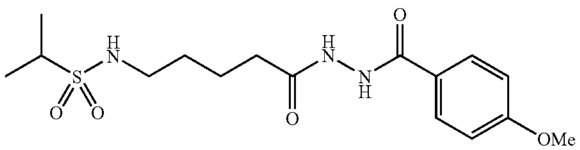
I-502
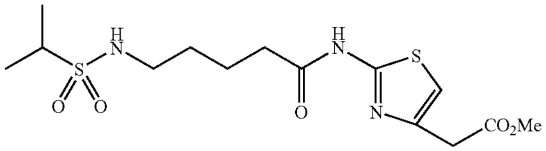
I-503
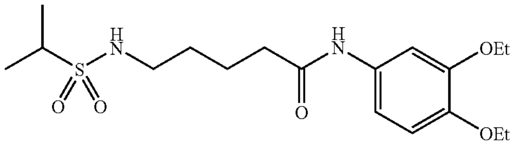
I-504
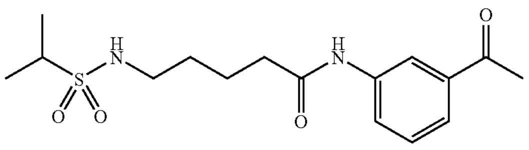
I-505
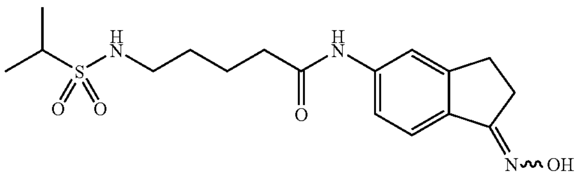
I-506
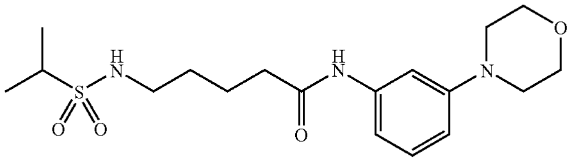
I-507
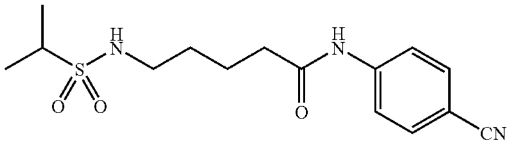

-continued
I-508
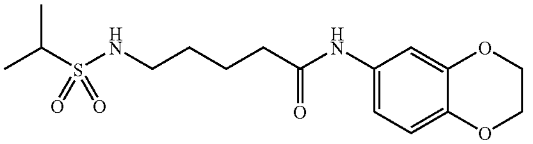
I-509
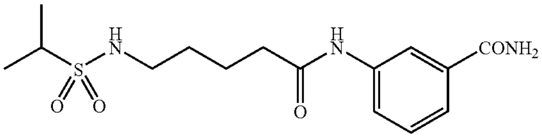
I-510
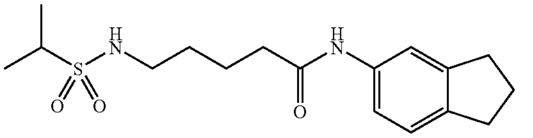
I-511
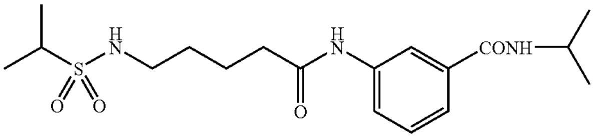
I-512
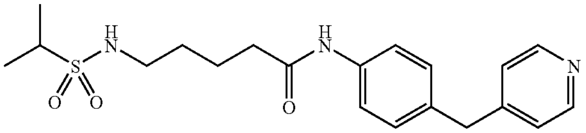
I-513
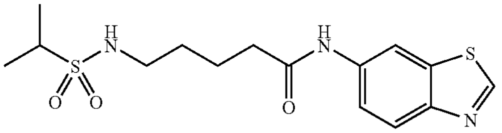
I-514
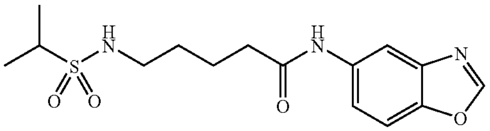
I-515
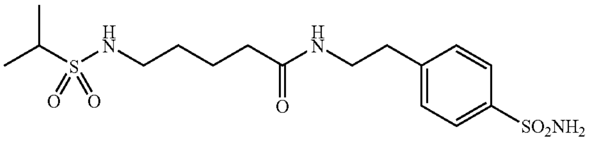
I-516
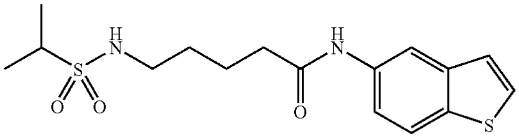
I-517
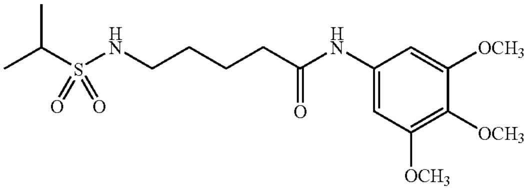
I-518
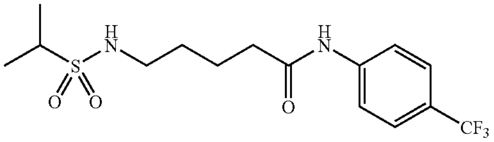
I-519
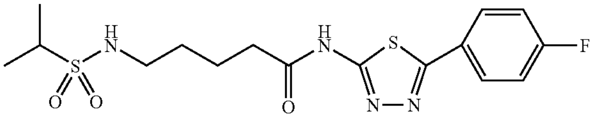
I-520
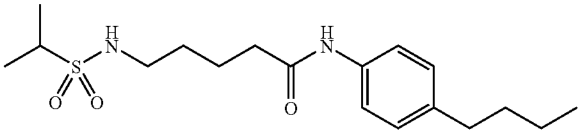
I-521
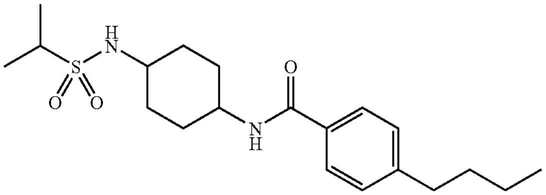
I-522
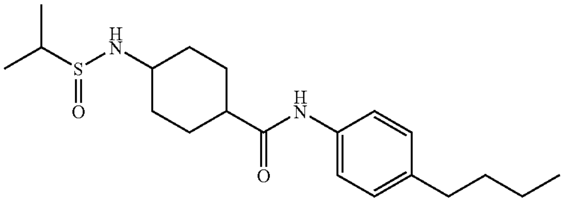
I-523
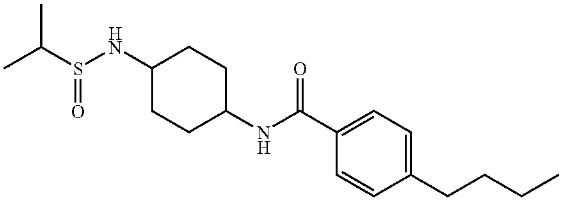

-continued
I-524
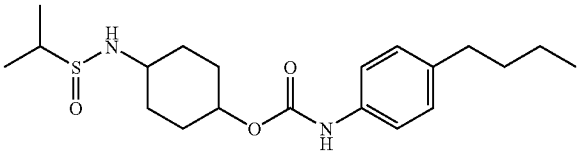
I-525
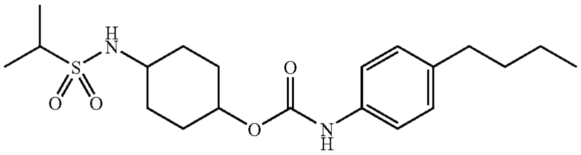
I-526
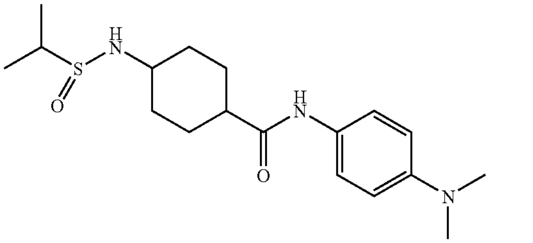
I-527
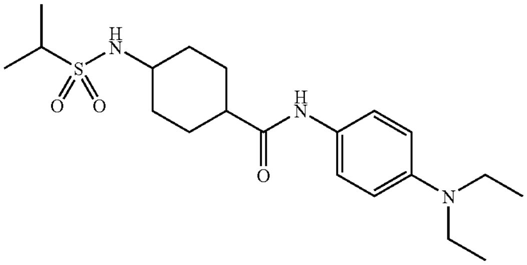
I-528
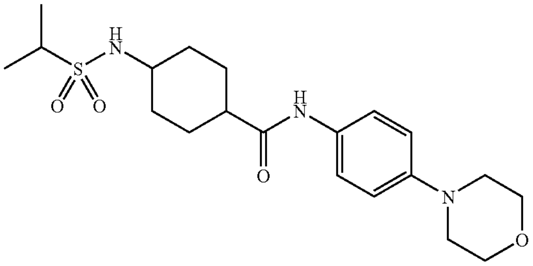
I-529
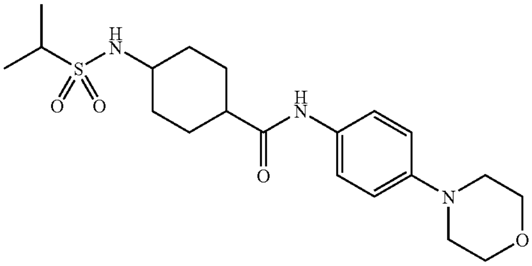
I-530
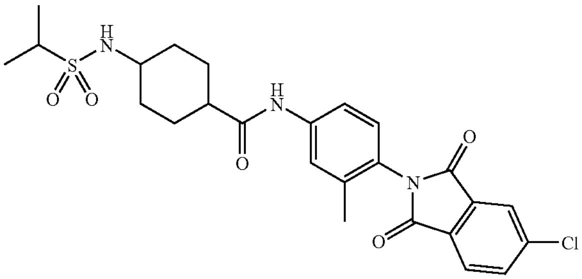
I-531
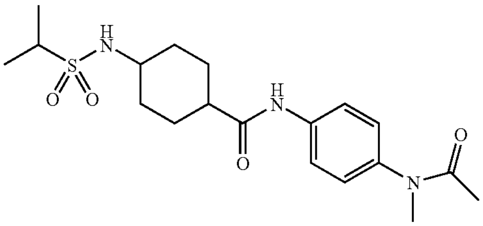
I-532
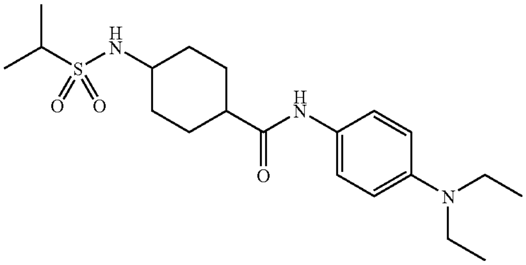
I-533
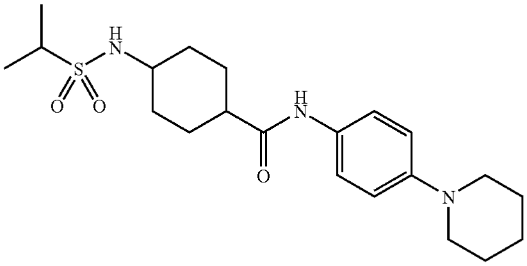
I-534
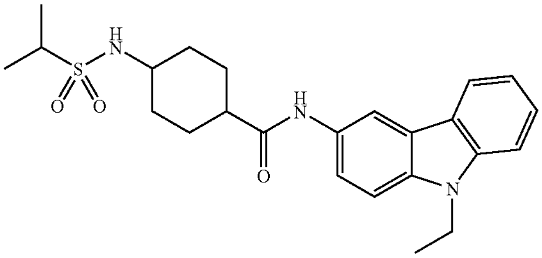
I-535
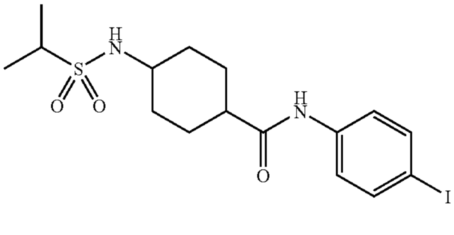

-continued
I-536
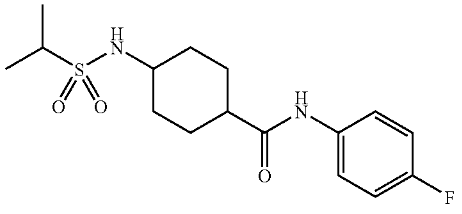
I-537
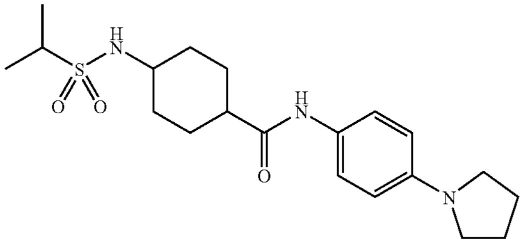
I-538
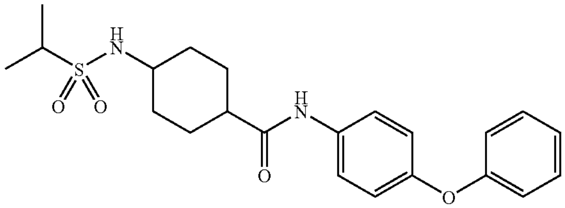
I-539
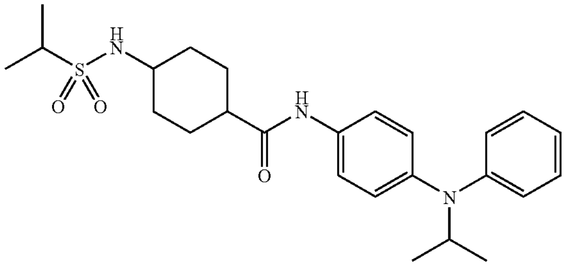
I-540
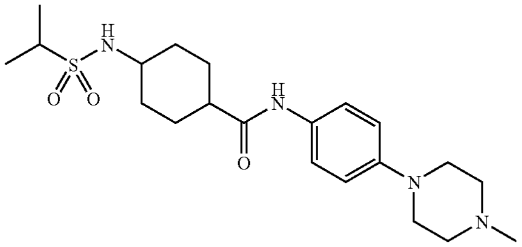
I-541
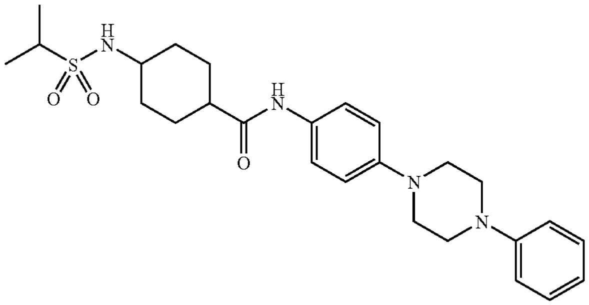
I-542
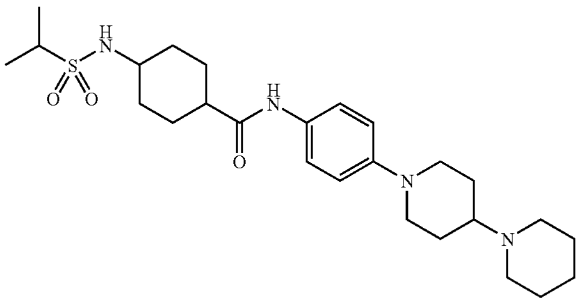
I-543
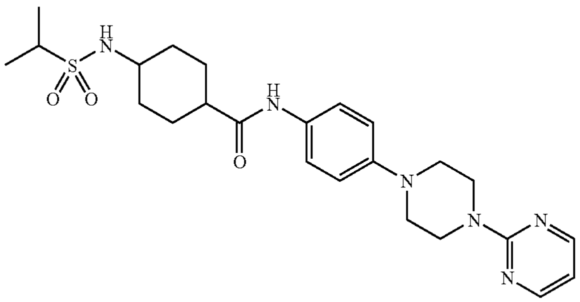
I-544
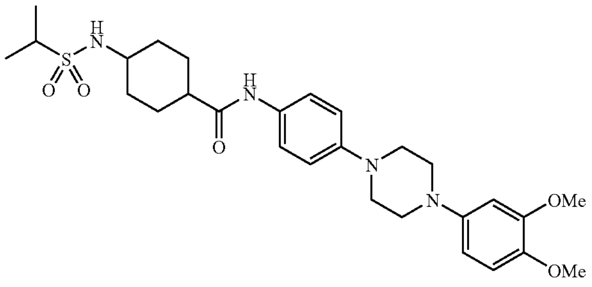
I-545
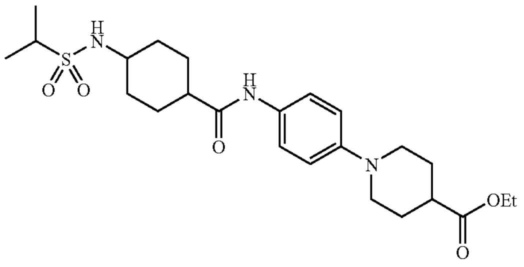

-continued
I-546
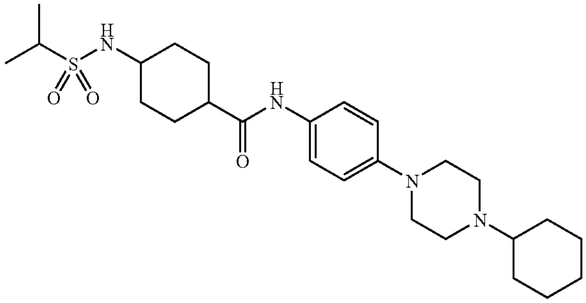
I-547
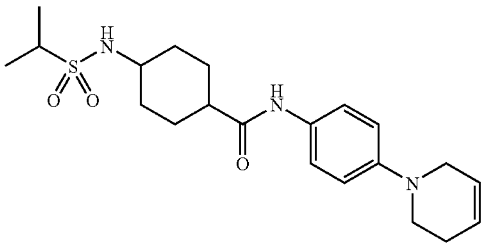
I-548
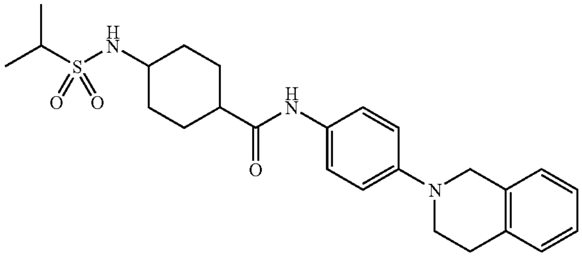
I-549
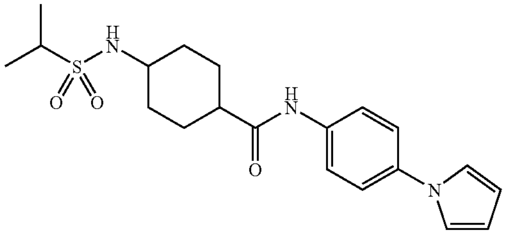
I-550
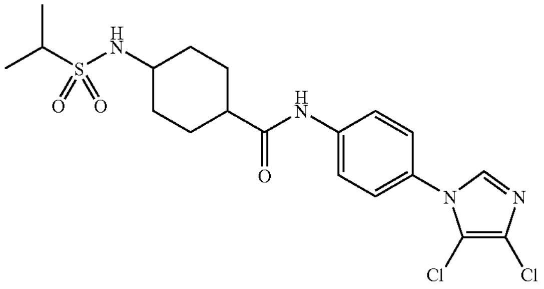
I-551
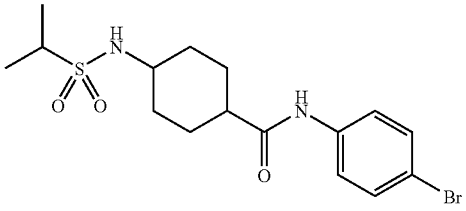
I-552
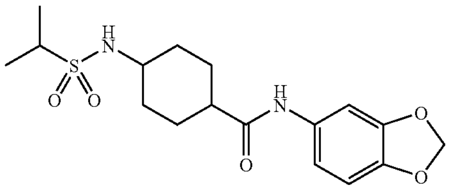
I-553
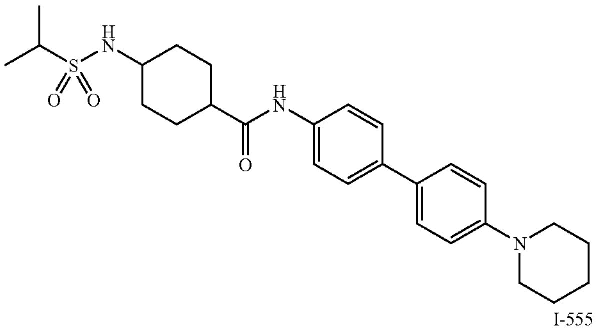
I-554
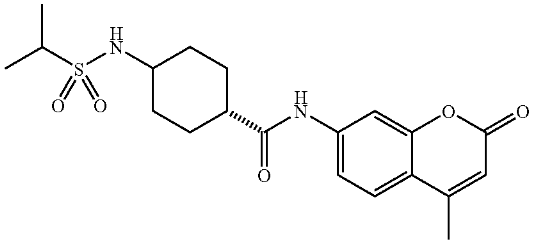
I-555
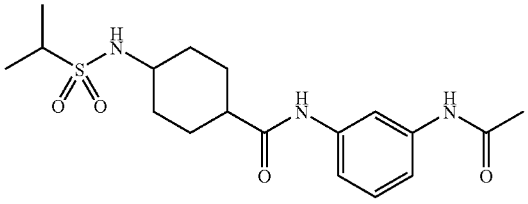

-continued
I-556
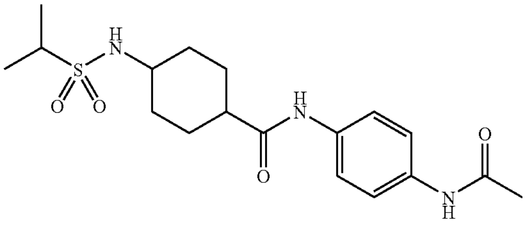
I-557
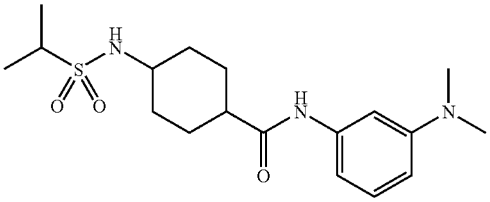
I-558
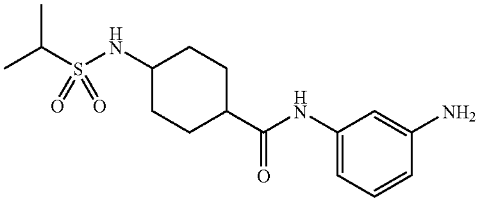
I-559
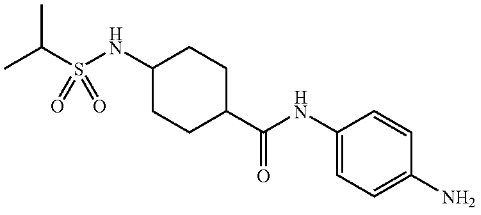
I-560
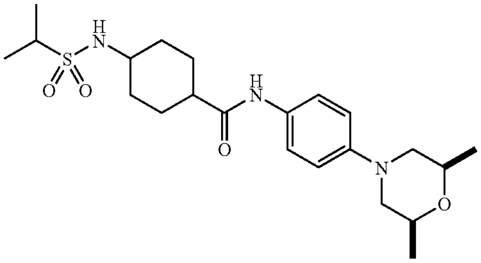
I-561
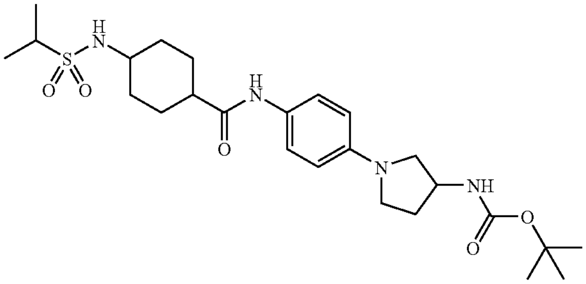
I-562
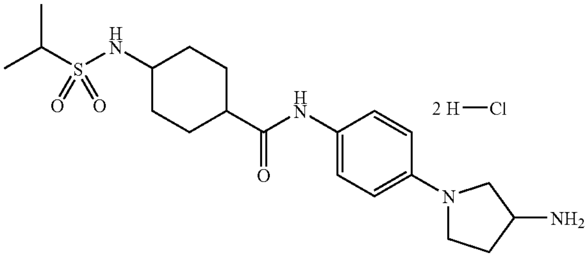
I-563
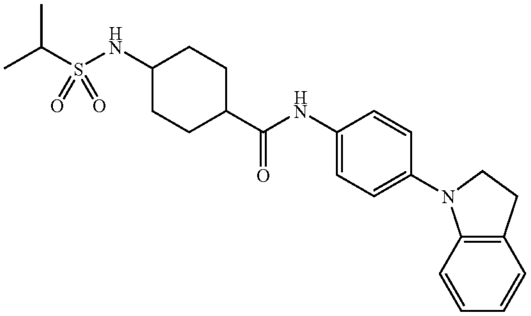
I-564
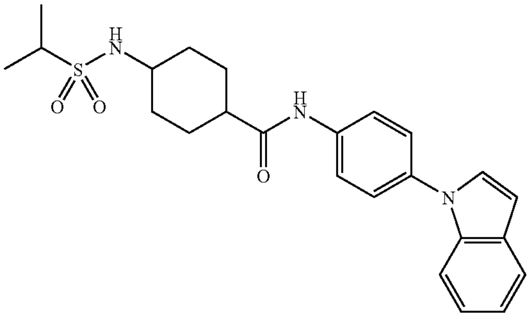
I-565
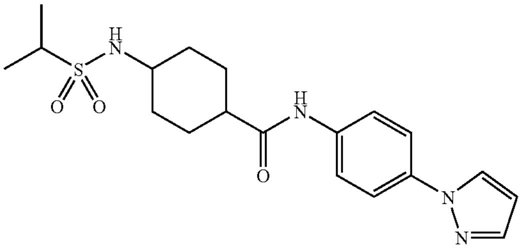

-continued
I-566
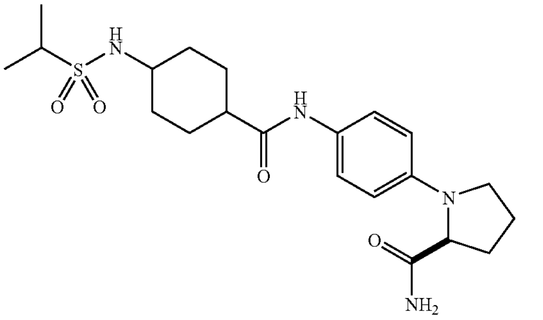
I-567
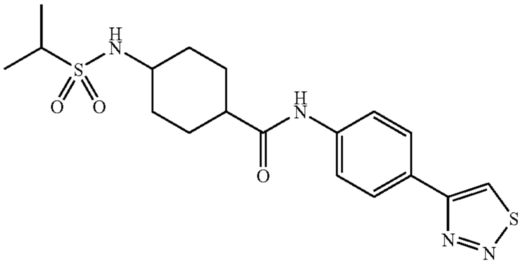
I-568
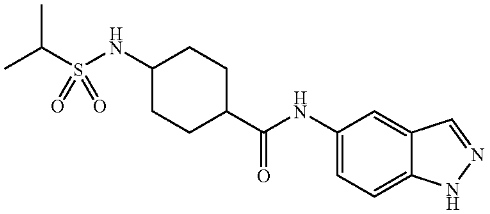
I-569
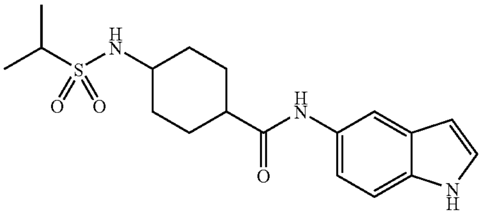
I-570
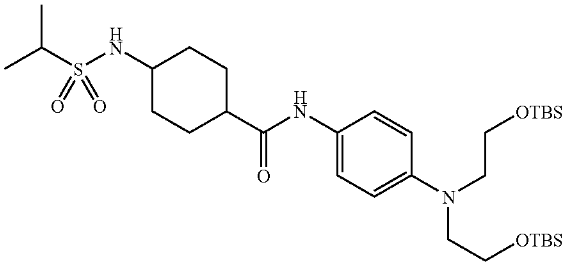
I-571
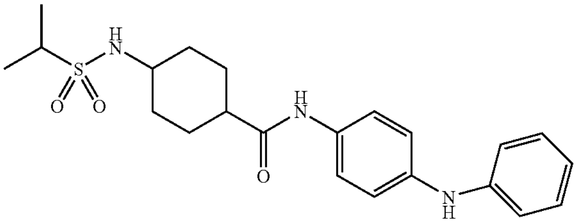
I-572
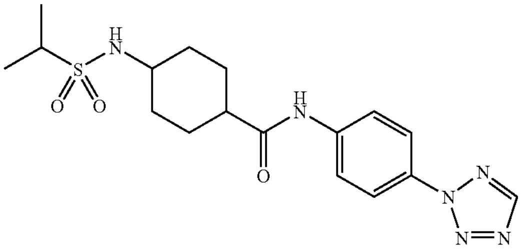
I-573
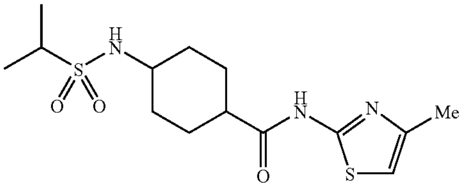
I-574
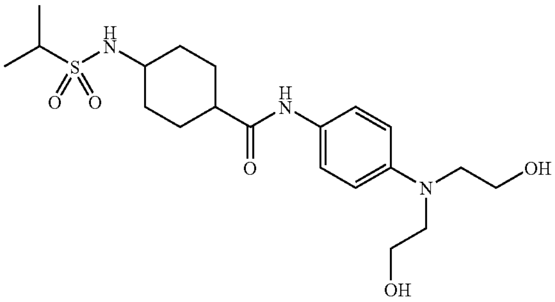
I-575
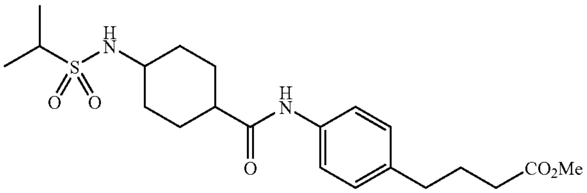

-continued
I-576
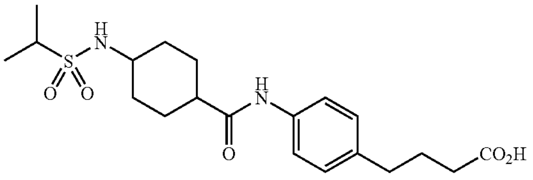
I-577
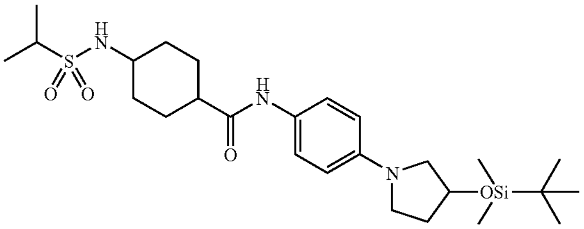
I-578
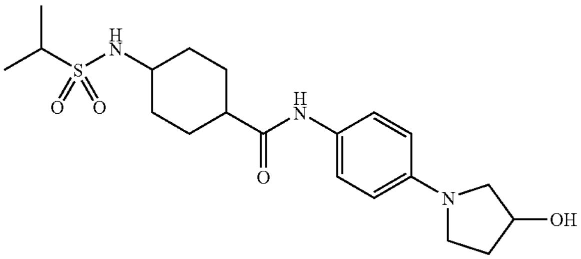
I-579
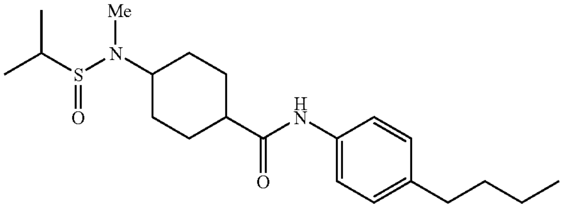
I-580
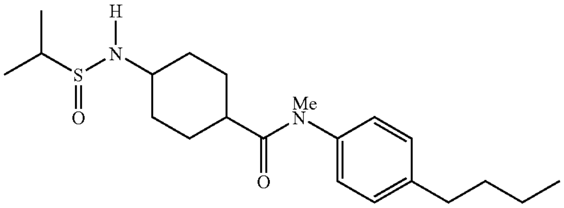
I-581
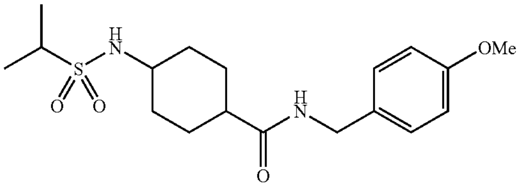
I-582
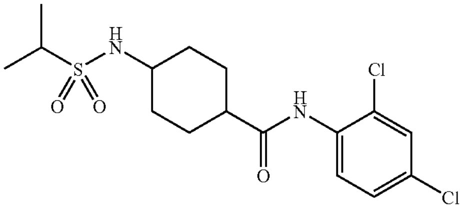
I-583
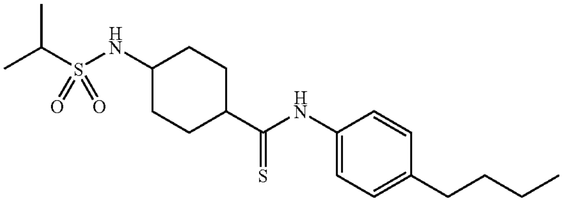
I-584
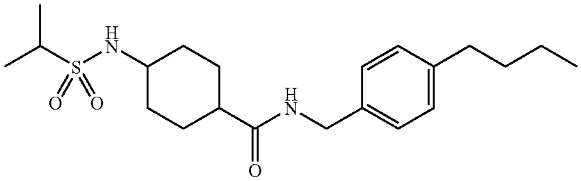
I-585
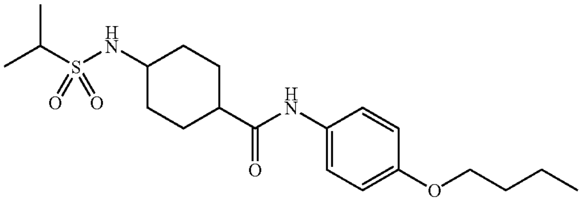
I-586
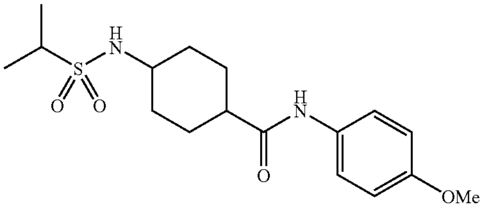

-continued
I-587
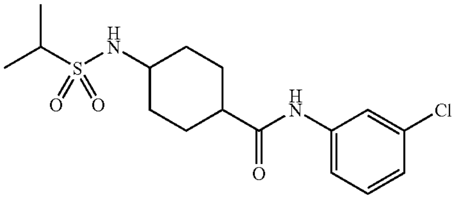
I-589
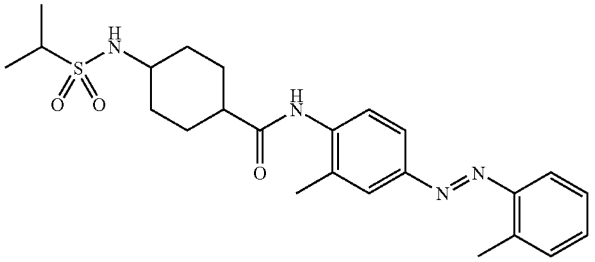
I-590
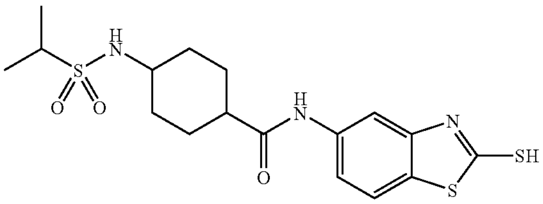
I-591
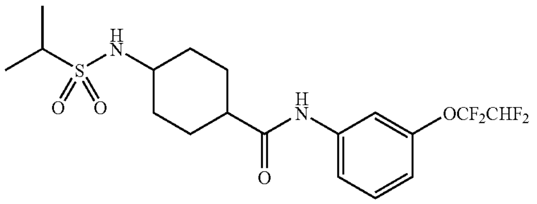
I-592
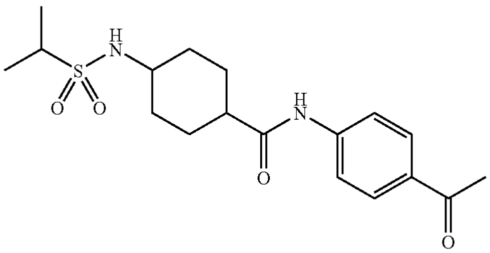
I-593
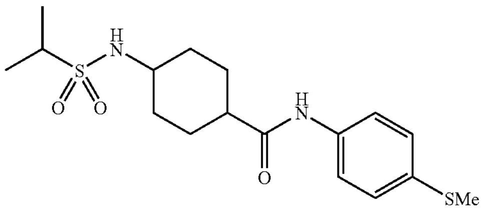
I-594
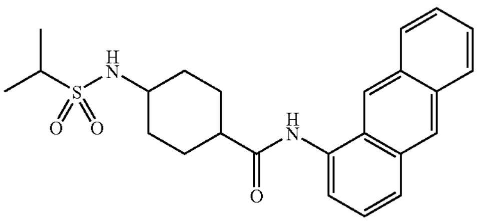
I-595
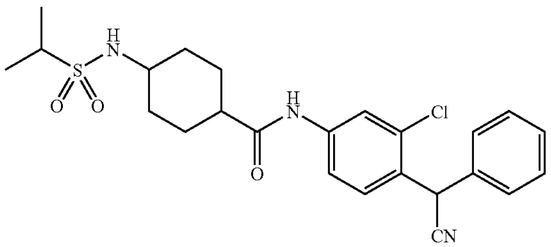
I-596
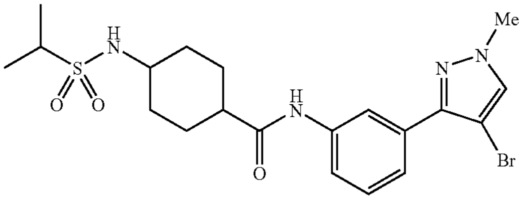
I-597
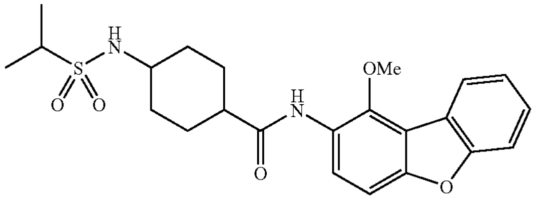
I-598
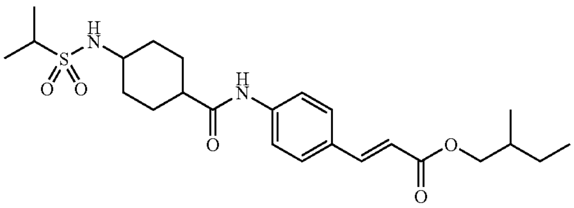
I-599
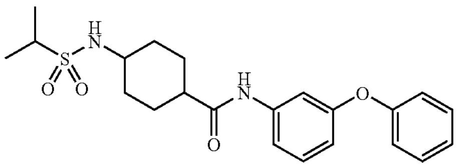

-continued
I-600
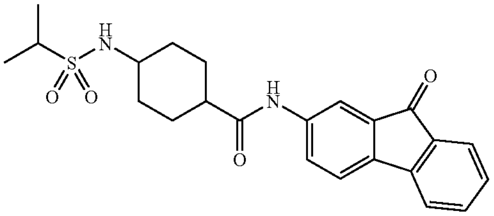
I-601
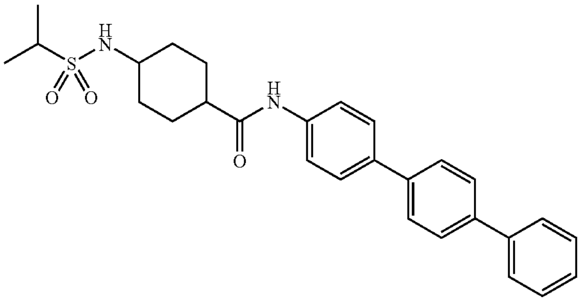
I-602
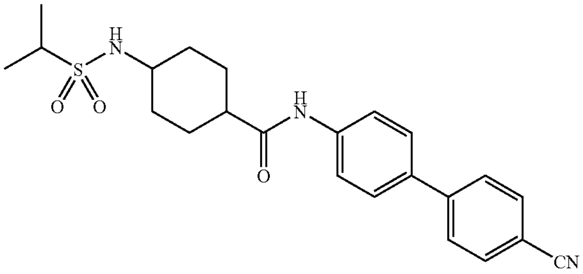
I-603
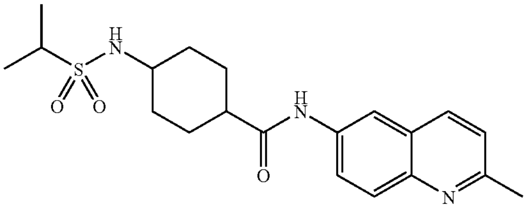
I-604
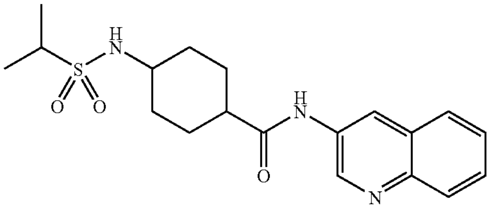
I-605
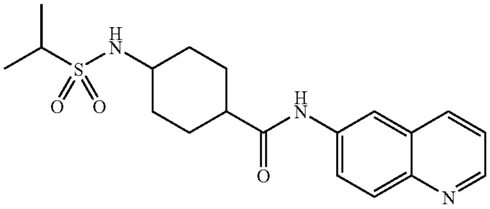
I-606
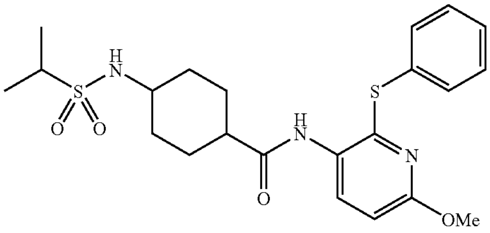
I-607
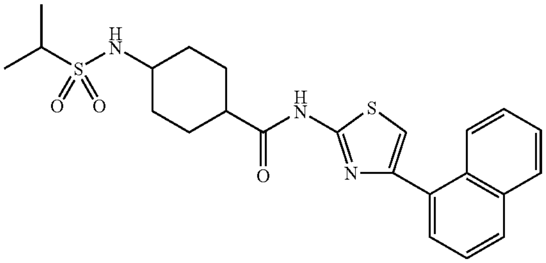
I-608
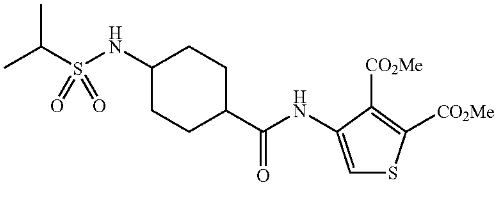
I-609
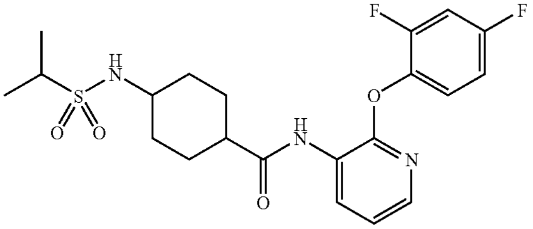
I-610
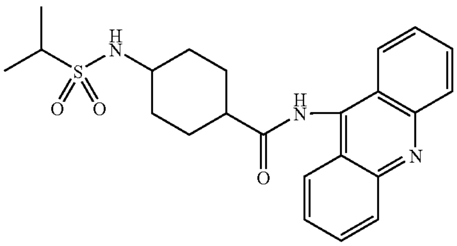
I-611
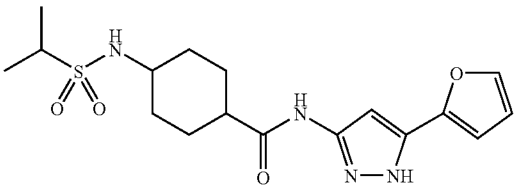

-continued
I-612
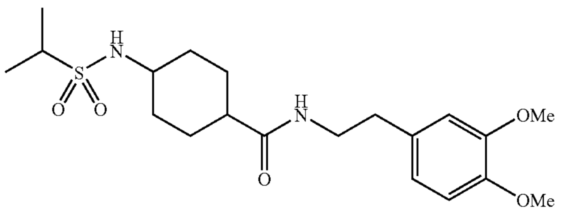
I-613
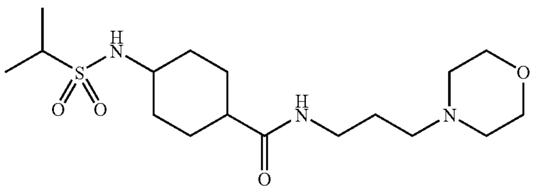
I-614
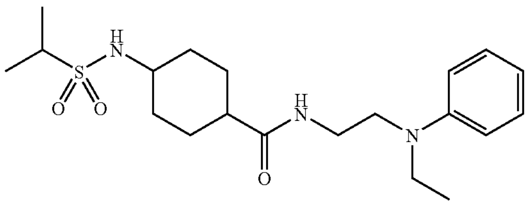
I-615
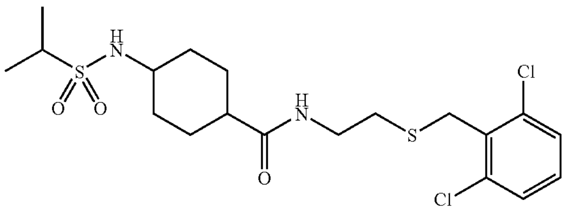
I-616
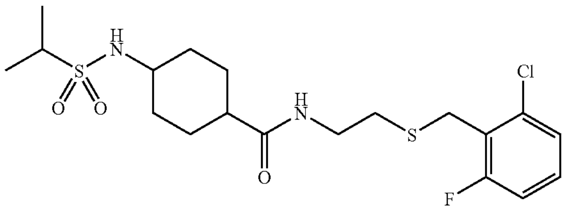
I-617
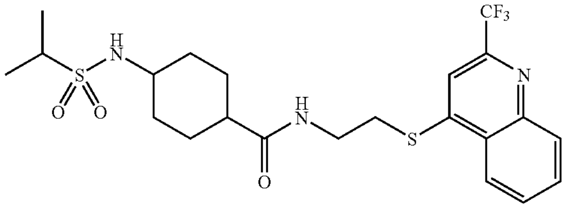
I-618
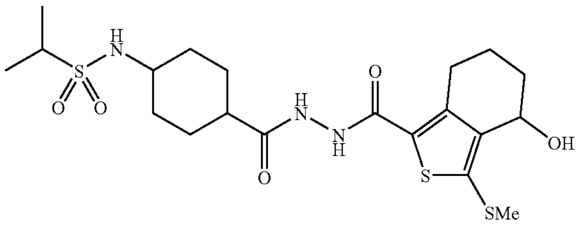
I-619
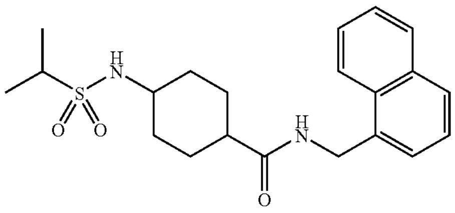
I-620
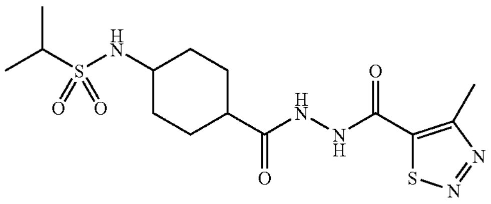
I-621
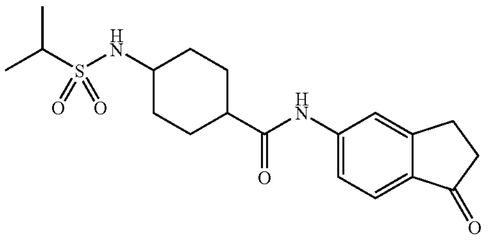
I-622
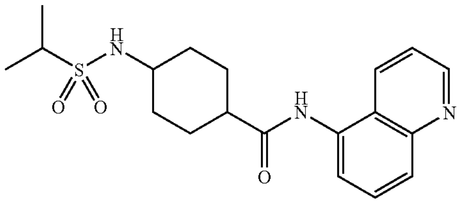
I-623
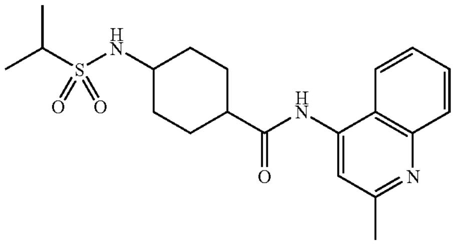

-continued
I-624
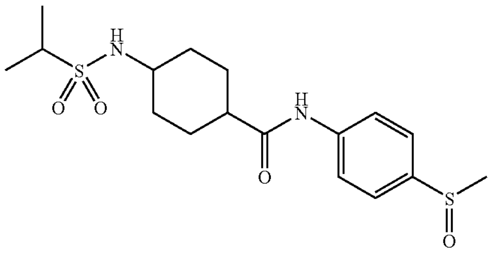
I-625
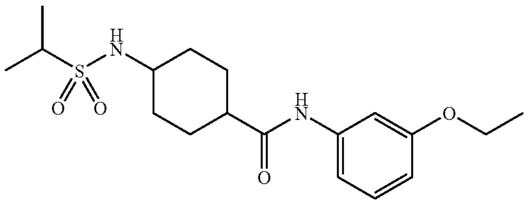
I-626
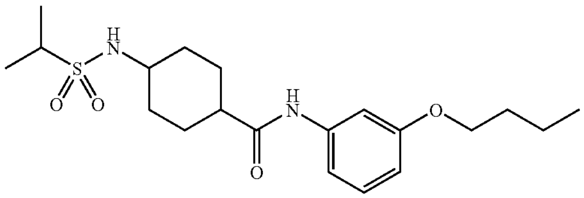
I-627
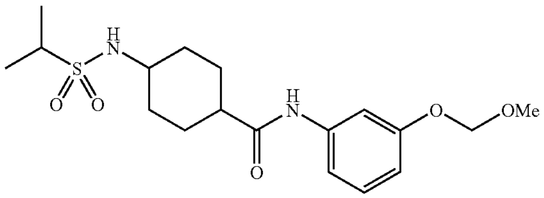
I-628
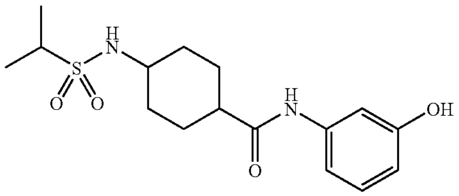
I-629
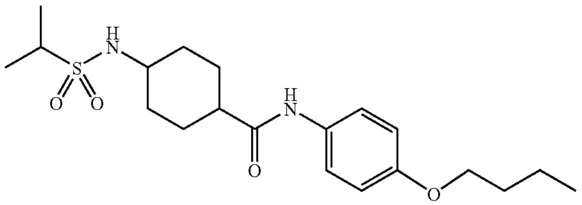
I-630
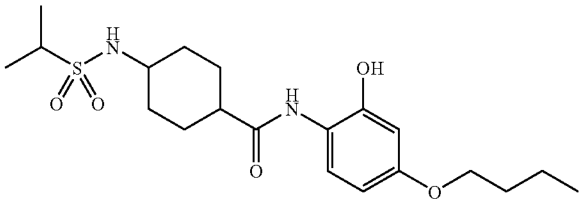
I-631
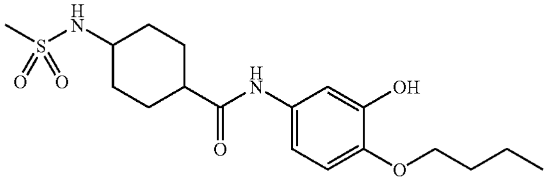
I-632
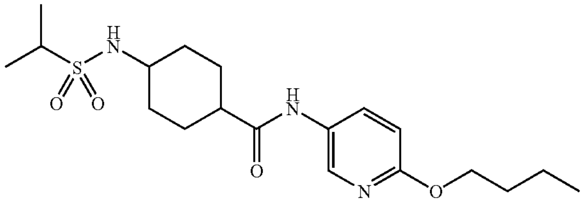
I-633
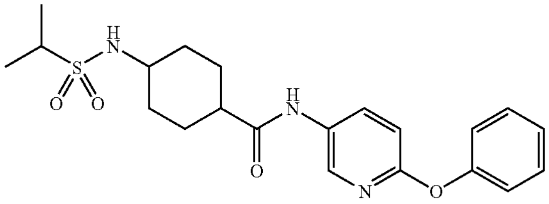
I-634
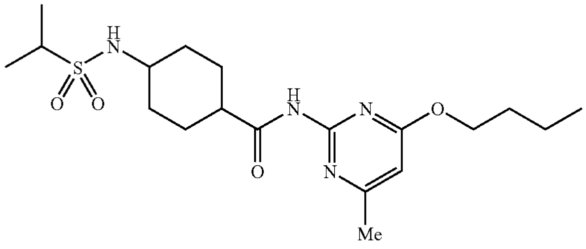
I-635
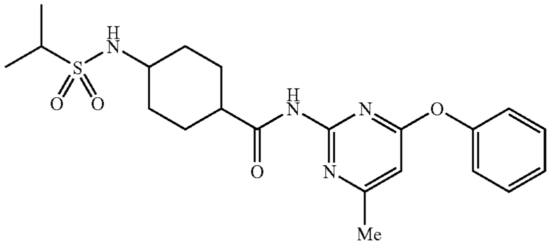

-continued
I-636
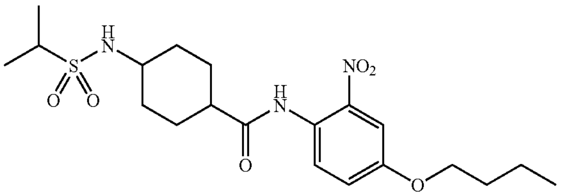
I-637
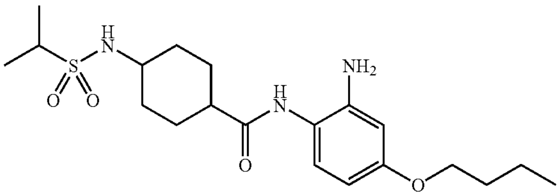
I-638
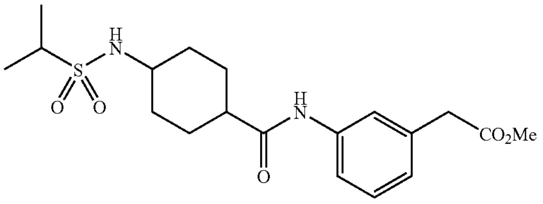
I-639
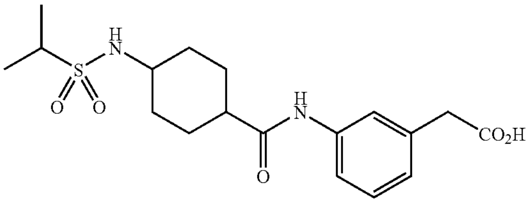
I-640
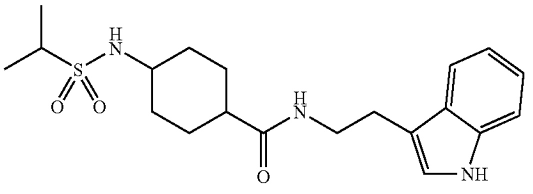
I-641
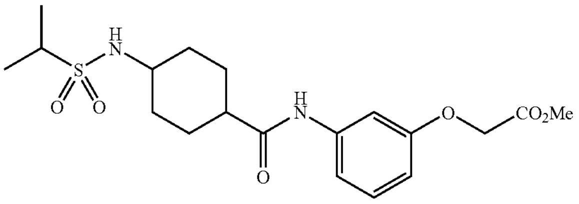
I-642
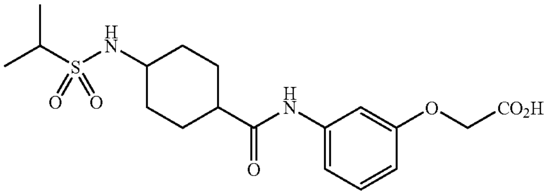
I-643
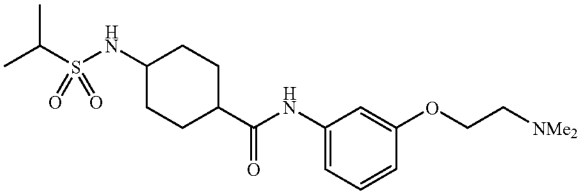
I-644
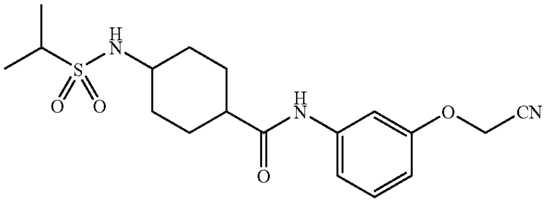
I-645
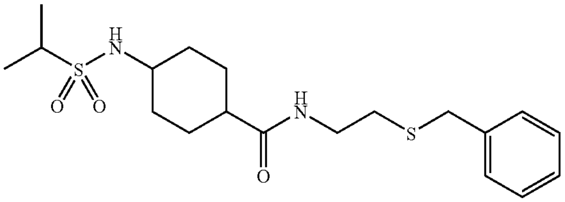
I-646
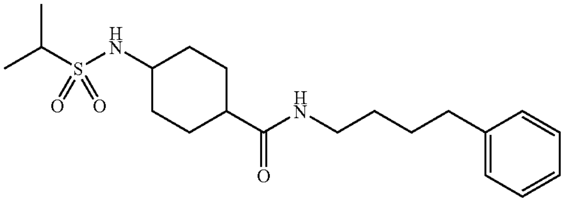
I-647
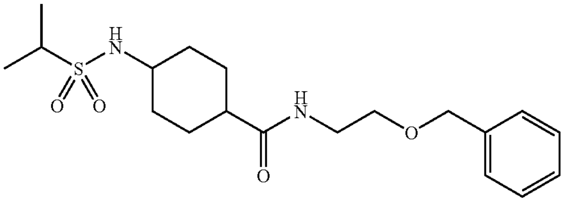
I-648
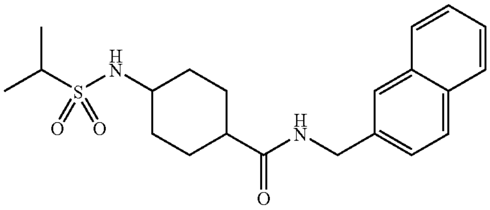
I-649
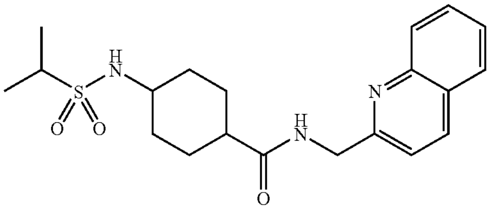

-continued
I-650
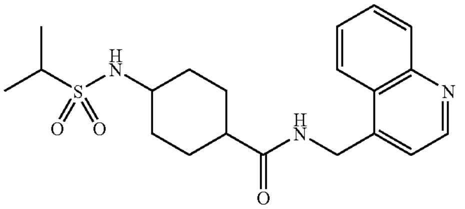
I-651
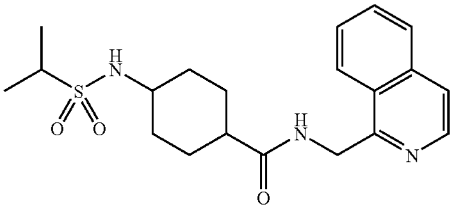
I-652
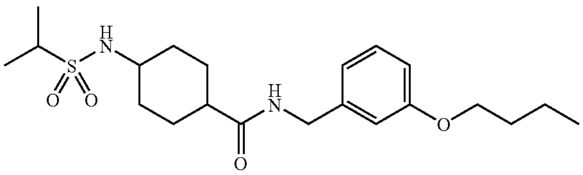
I-653
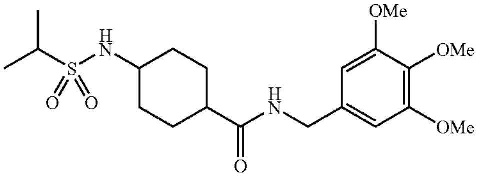
I-654
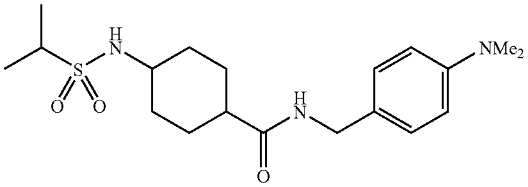
I-655
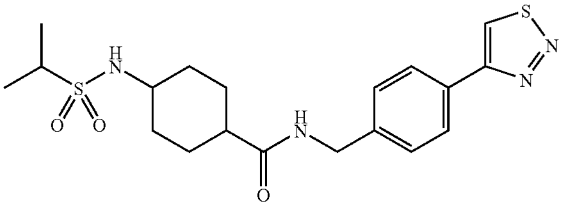
I-656
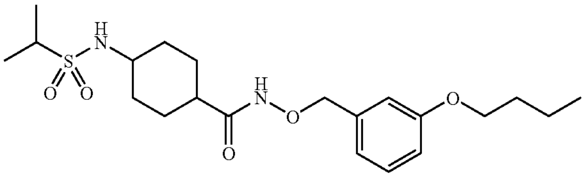
I-657
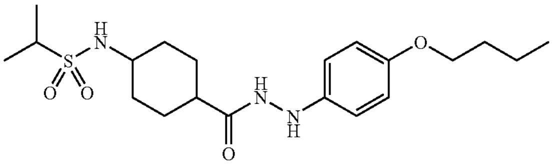
I-658
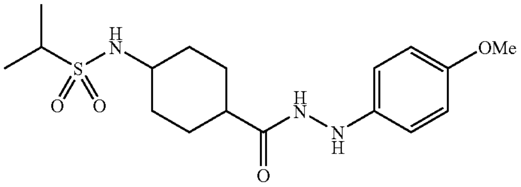
I-659
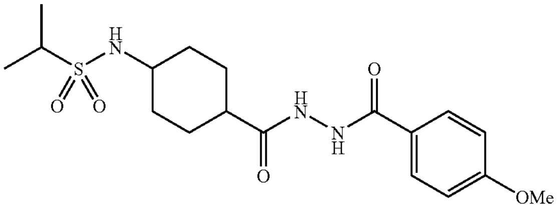
I-660
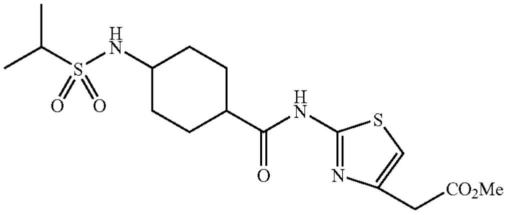
I-661
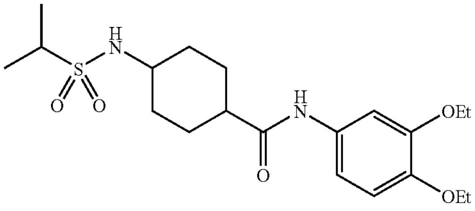
I-662
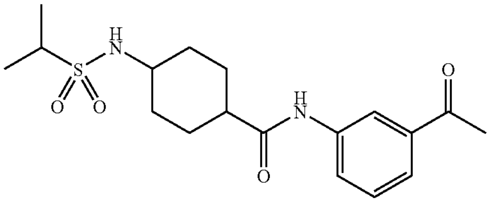
I-663
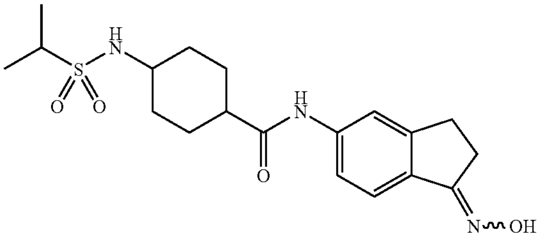

-continued
I-664
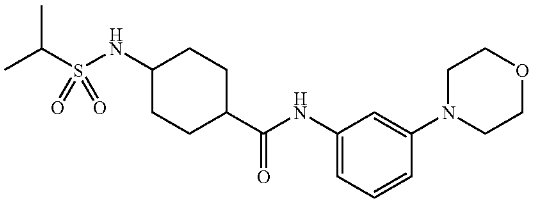
I-665
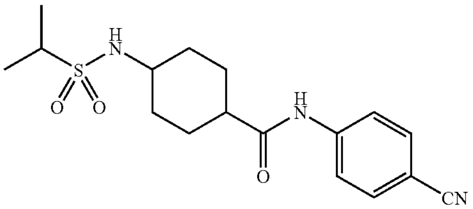
I-666
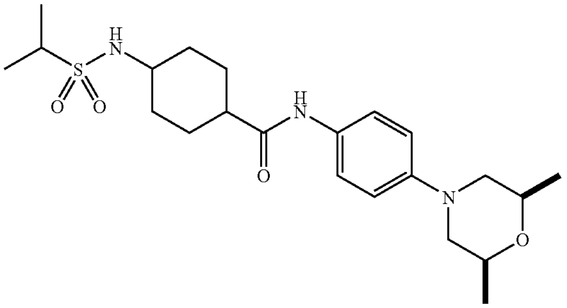
I-667
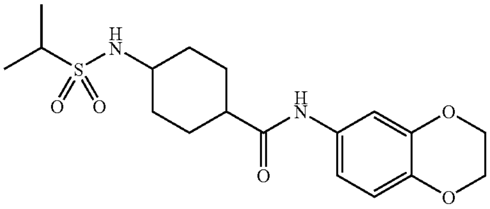
I-668
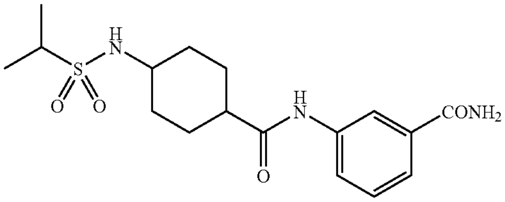
I-669
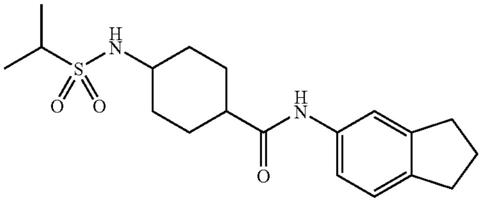
I-670
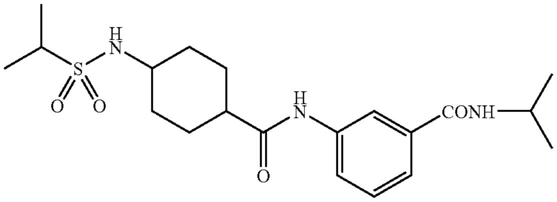
I-671
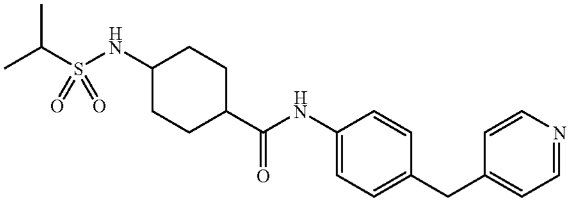
I-672
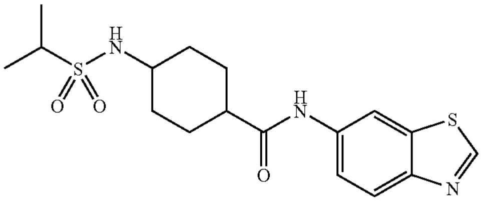
I-673
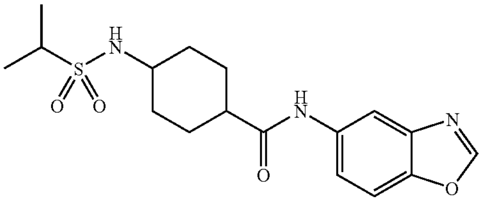
I-674
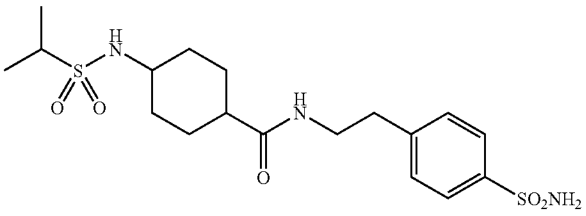
I-675
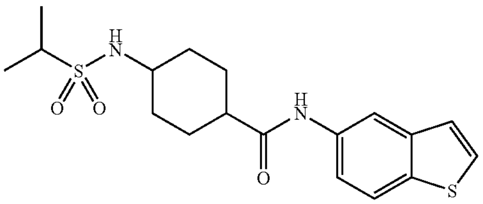

-continued
I-676
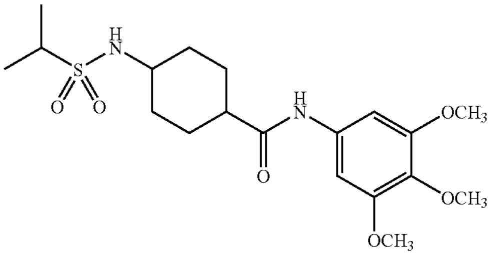
I-677
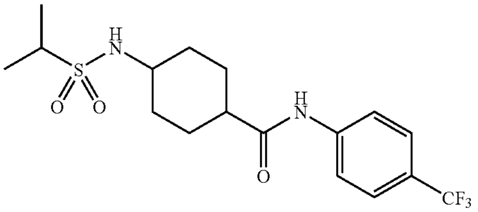
I-678
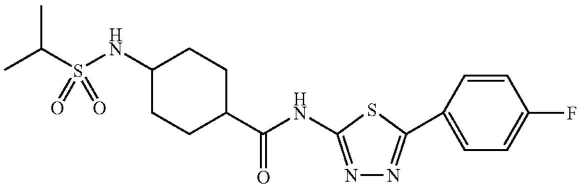
I-679
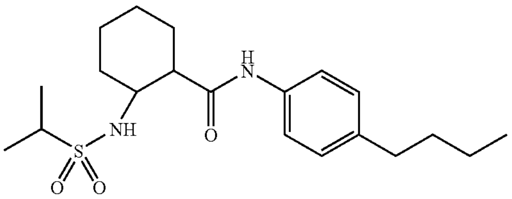
I-680
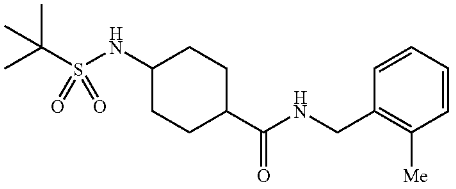
I-681
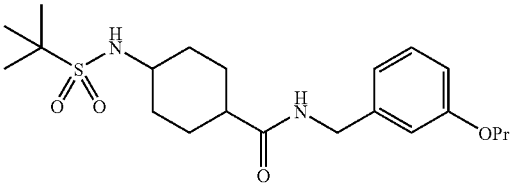
I-682
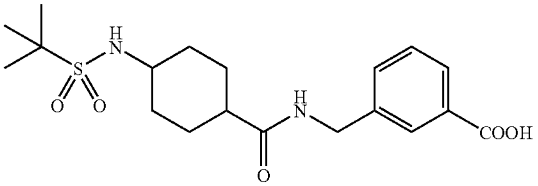
I-683
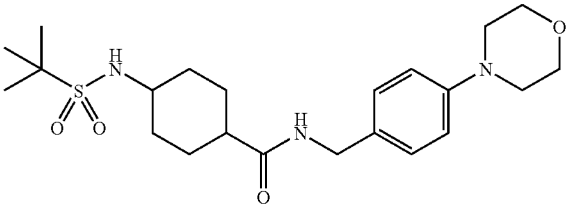
I-684
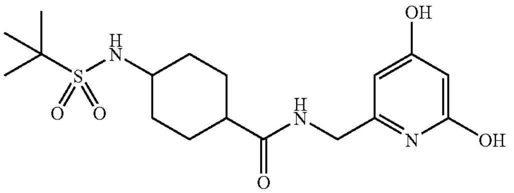
I-685
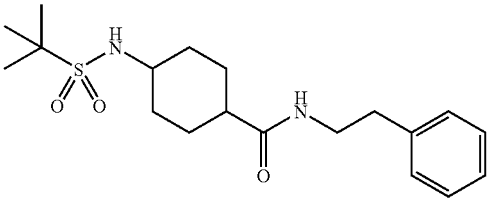
I-686
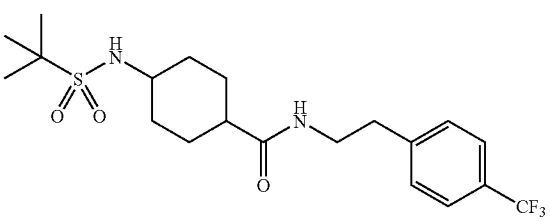
I-687
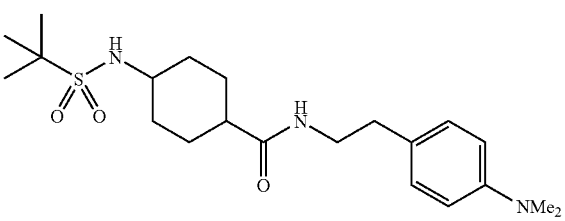

-continued
I-688
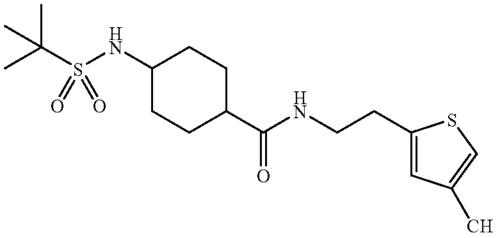
I-689
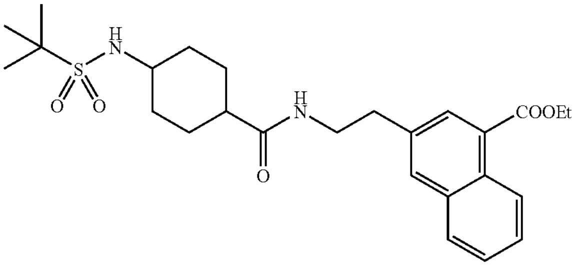
I-690
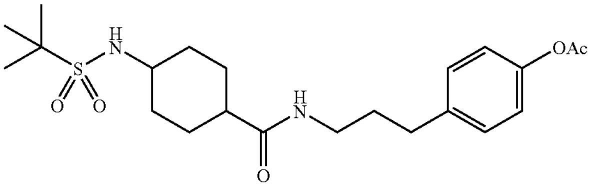
I-691
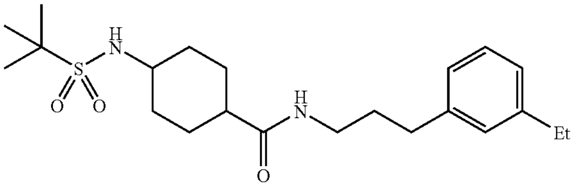
I-692
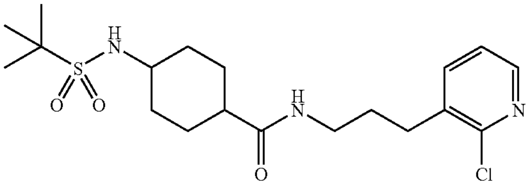
I-693
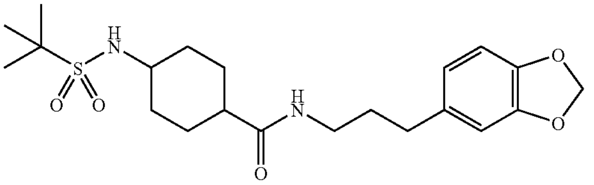
I-694
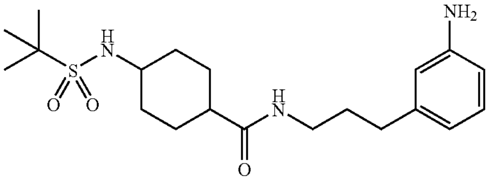
I-695
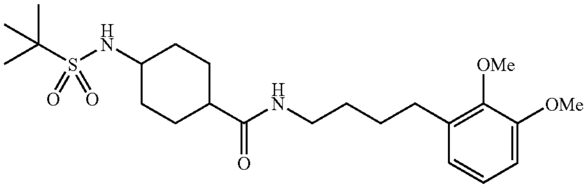
I-696
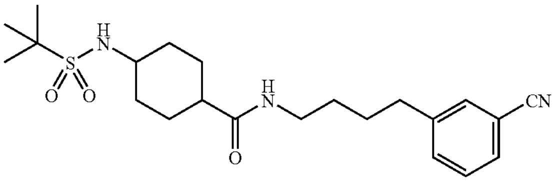
I-697
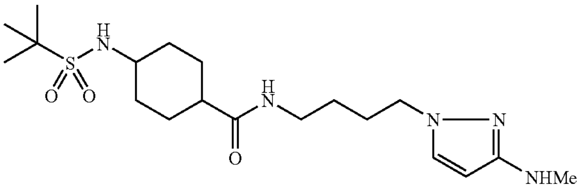
I-698
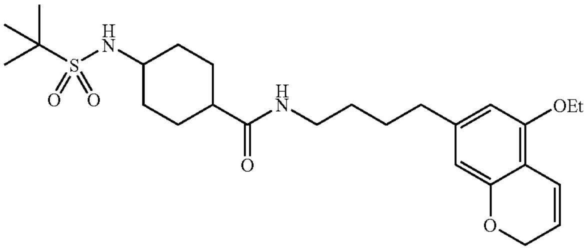
I-699
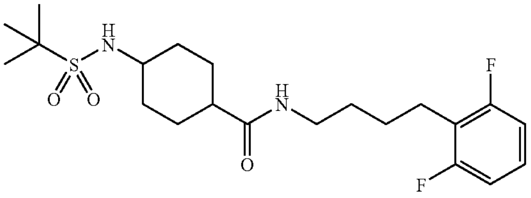

-continued
I-700
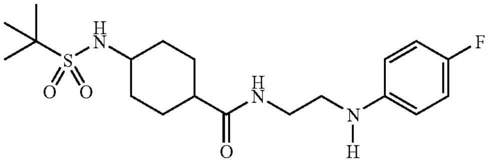
I-701
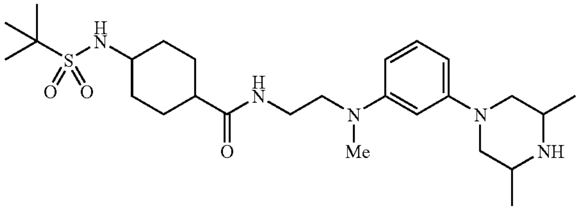
I-702
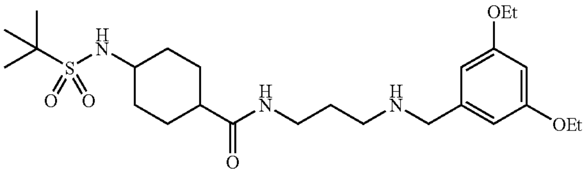
I-703
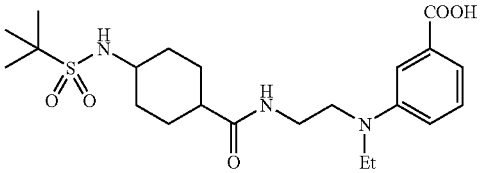
I-704
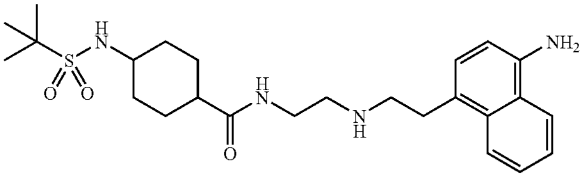
I-705
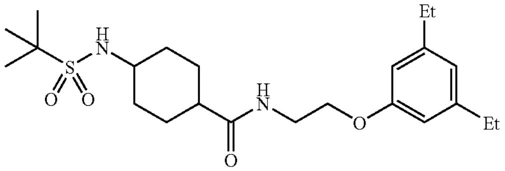
I-706
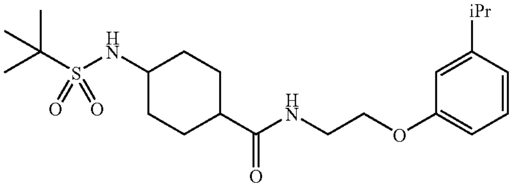
I-707
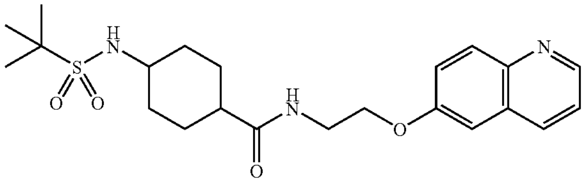
I-708
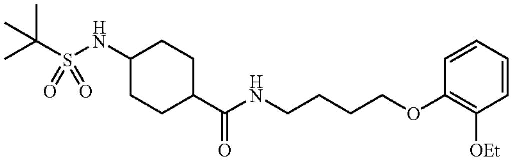
I-709
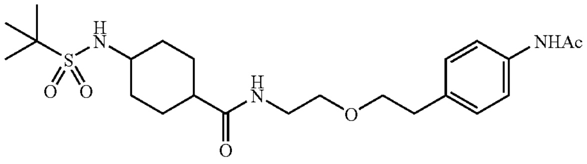
I-710
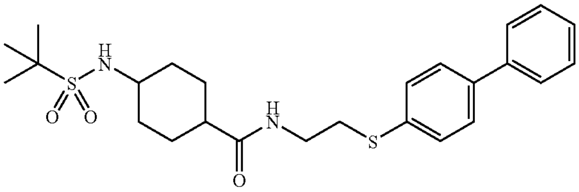
I-711
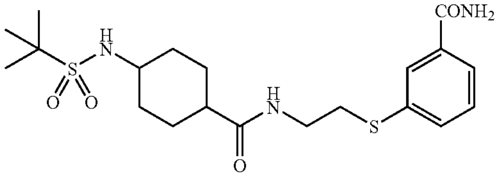
I-712
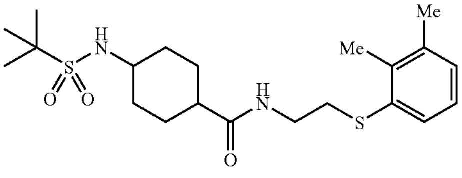
I-713
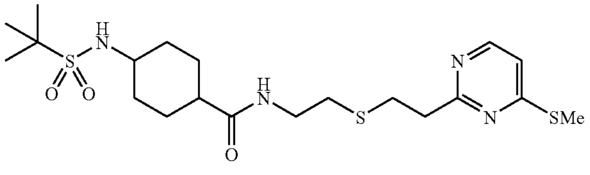

-continued
I-714
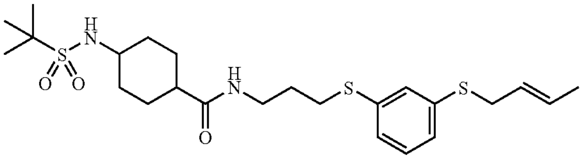
I-715
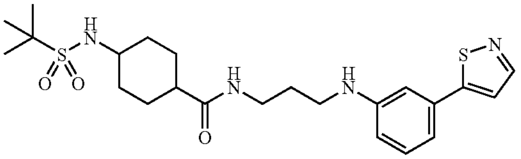
I-716
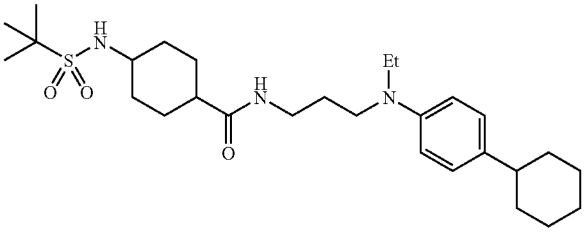
I-717
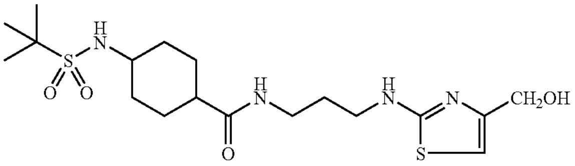
I-718
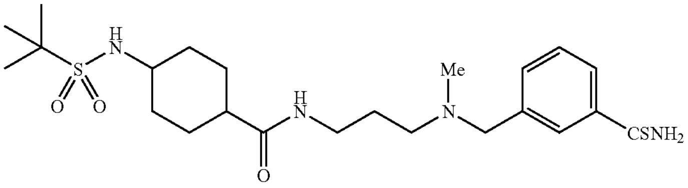
I-719
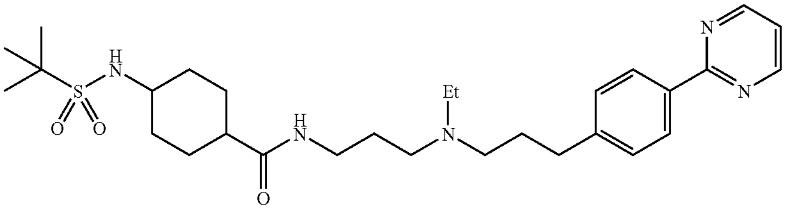
I-720
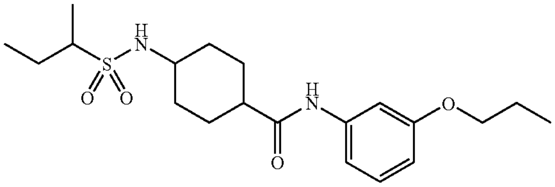
I-721
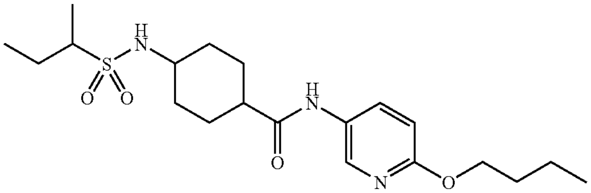
I-722
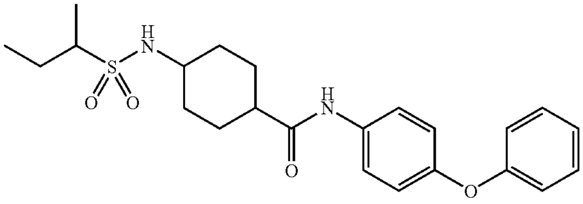
I-723
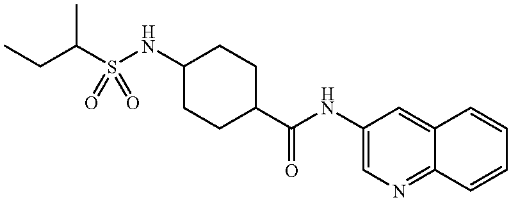
I-724
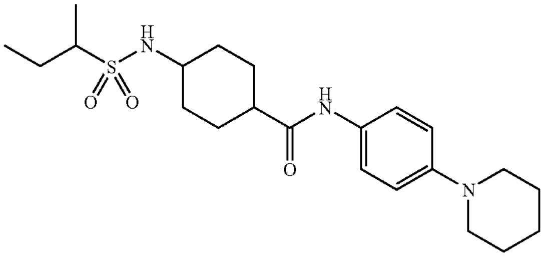
I-725
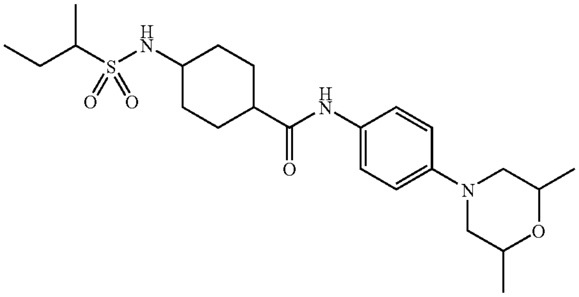

-continued
I-726
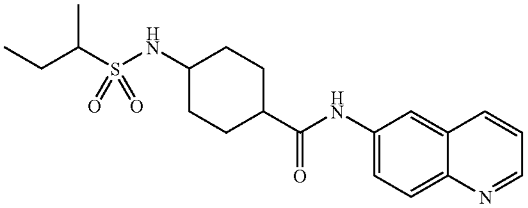
I-727
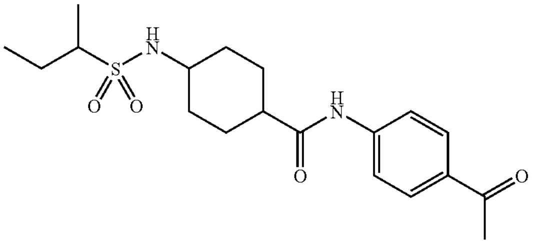
I-728
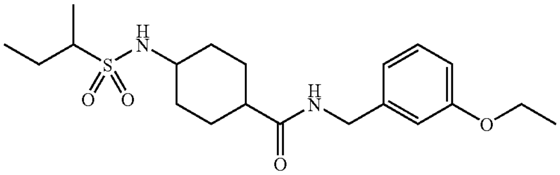
I-729
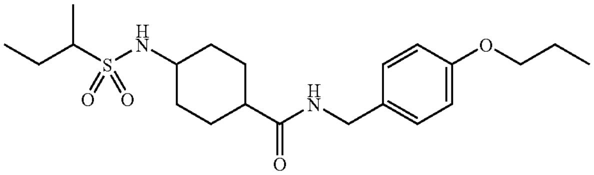
I-730
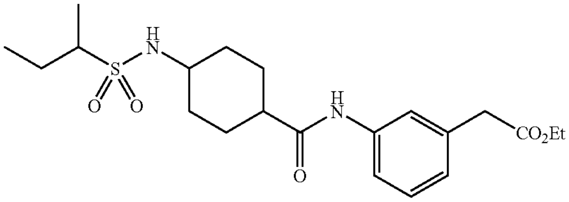
I-731
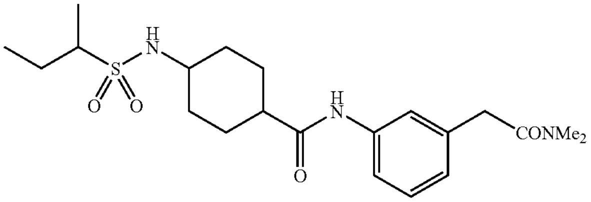
I-732
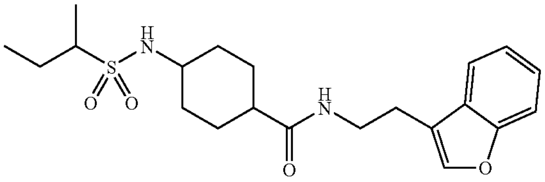
I-733
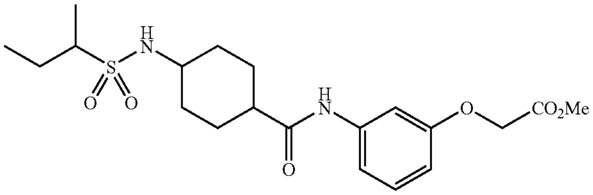
I-734
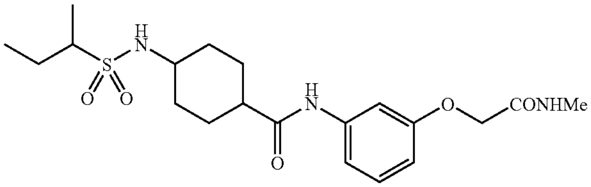
I-735
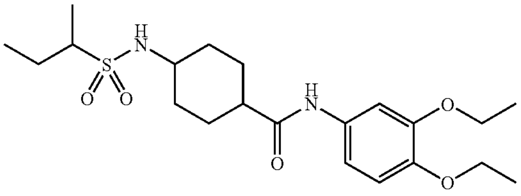
I-736
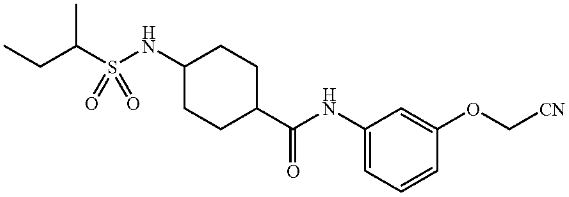
I-737
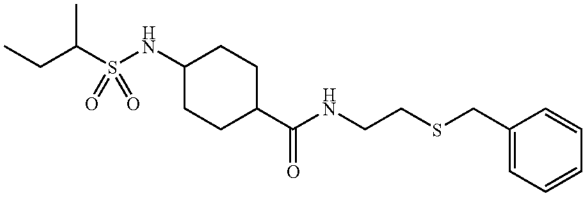
I-738
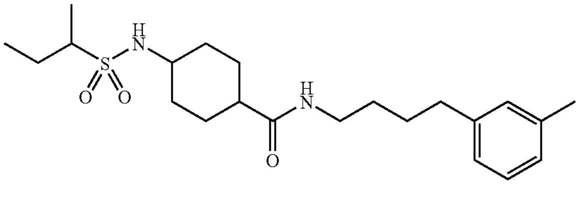
I-739
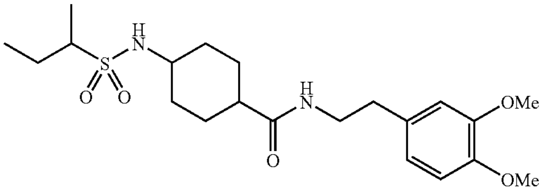

-continued
I-740
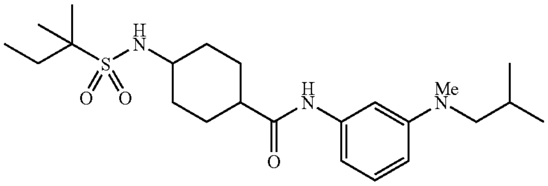
I-741
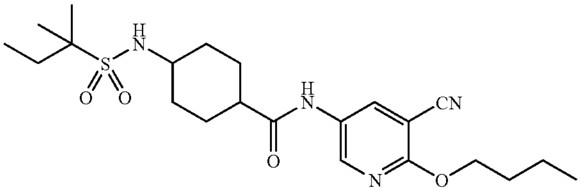
I-742
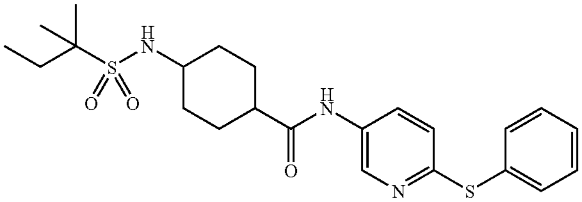
I-743
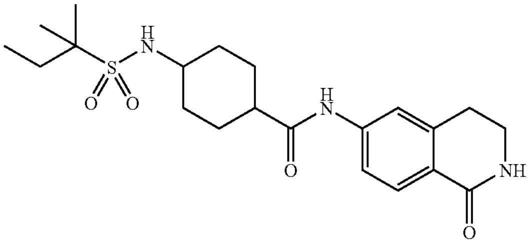
I-744
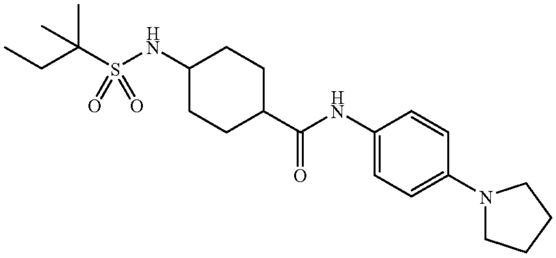
I-745
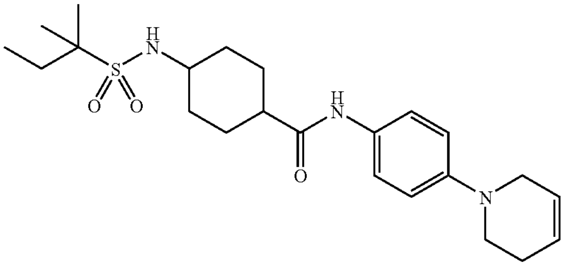
I-746
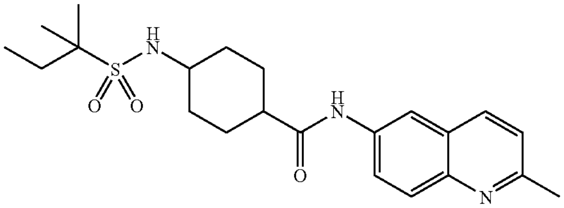
I-747
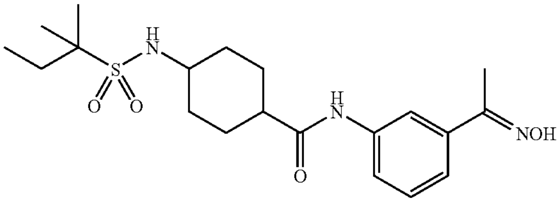
I-748
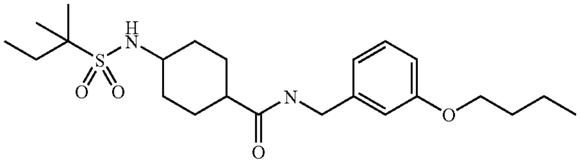
I-749
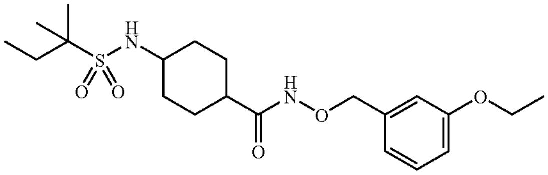
I-750
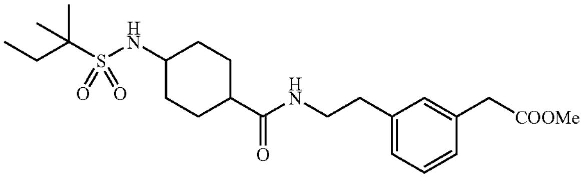
I-751
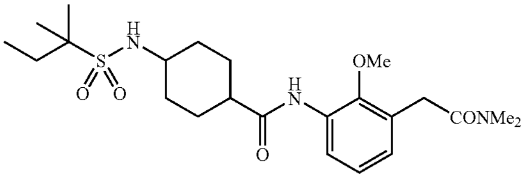

-continued
I-752
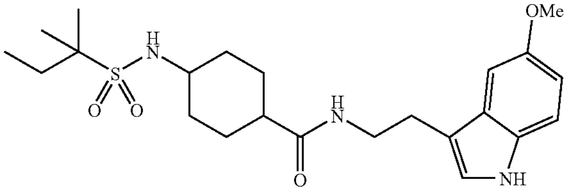
I-753
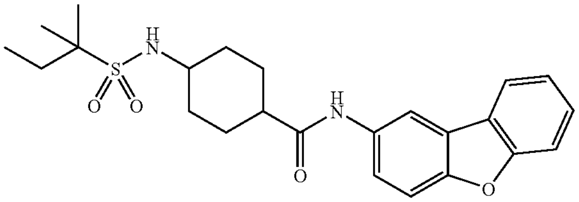
I-754
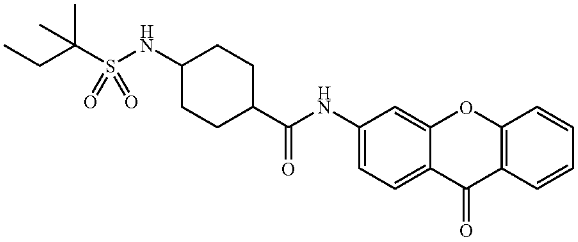
I-755
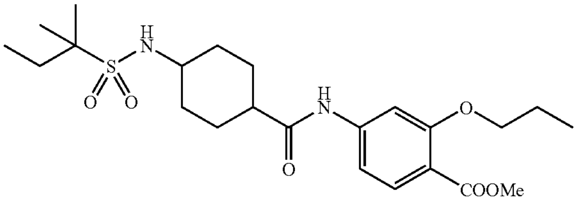
I-756
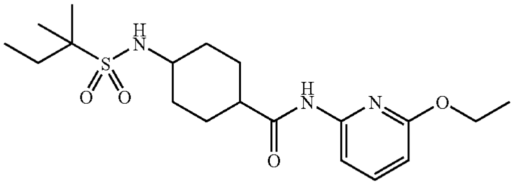
I-757
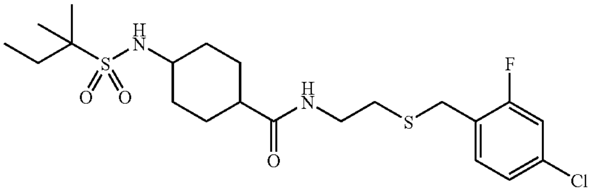
I-758
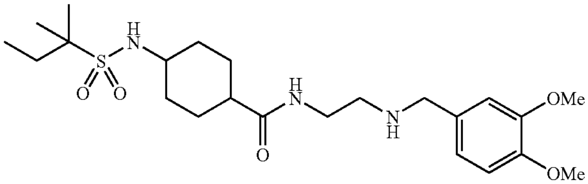
I-759
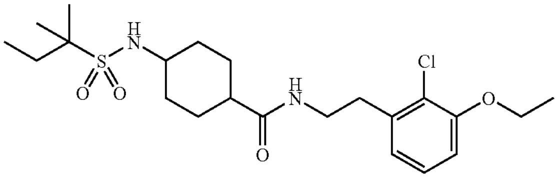
Ia-1
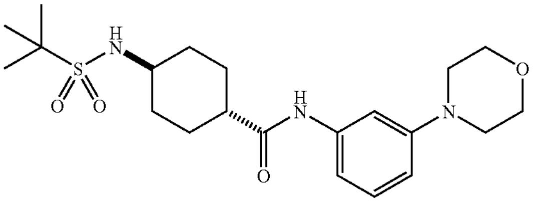
Ia-2
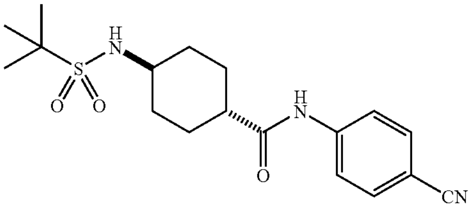
Ia-3
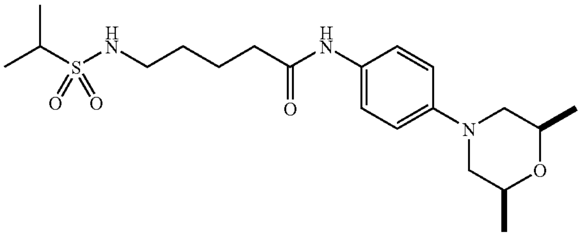
Ia-4
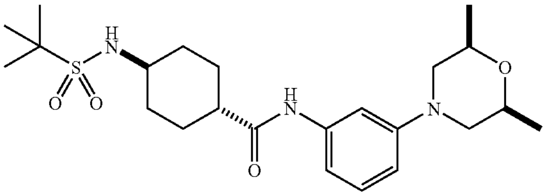

-continued
Ia-5
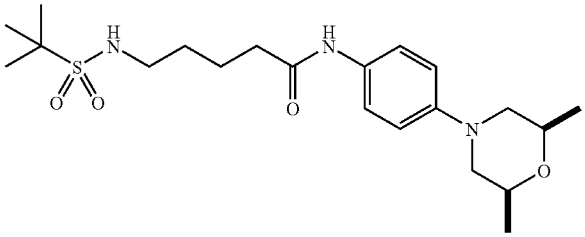
Ia-6
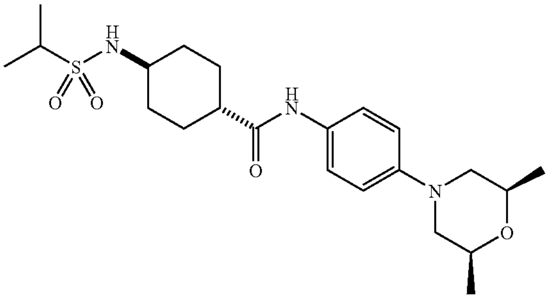
Ia-7
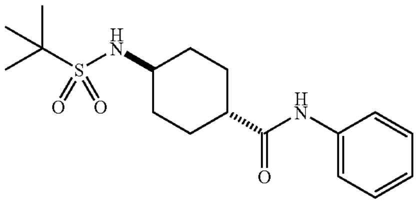
Ia-8
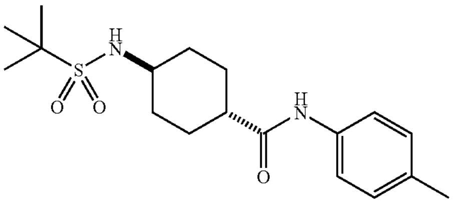
Ia-9
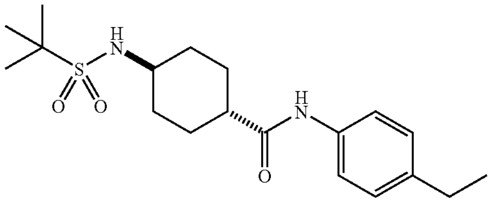
Ia-10
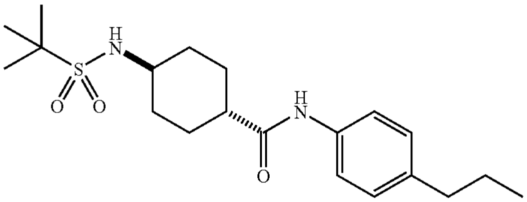
Ia-11
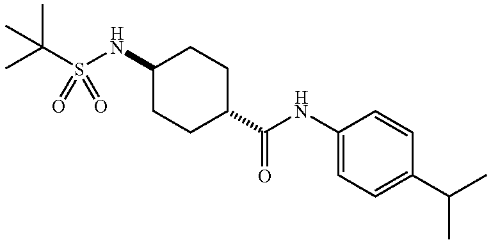
Ia-12
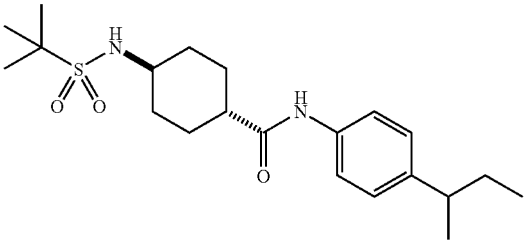
Ia-13
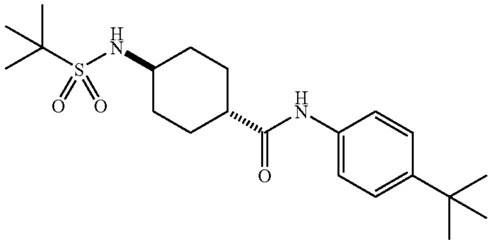
Ia-14
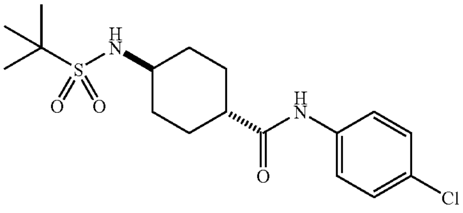
Ia-15
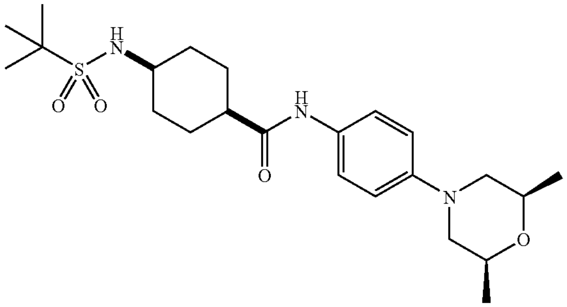
Ia-16
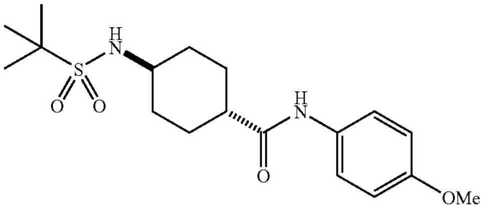

-continued
Ia-17
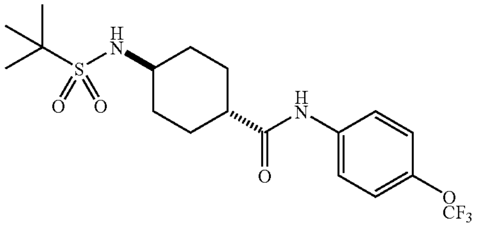
Ia-18
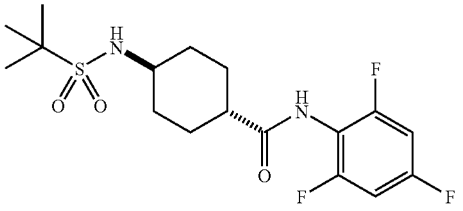
Ia-19
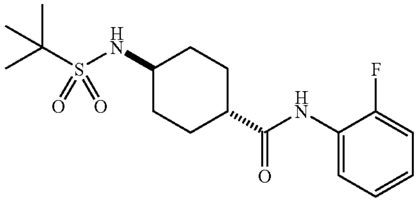
Ia-20
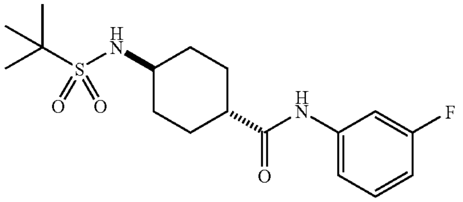
Ia-21
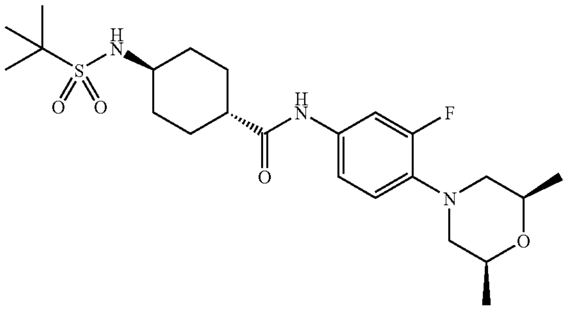
Ia-22
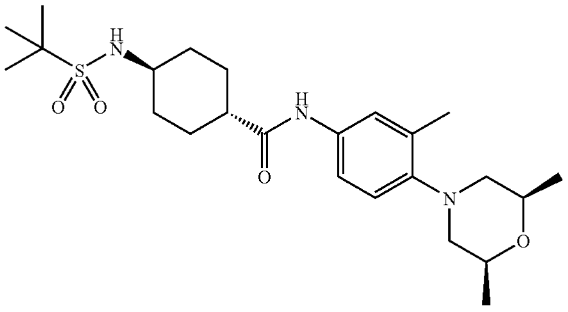
Ia-23
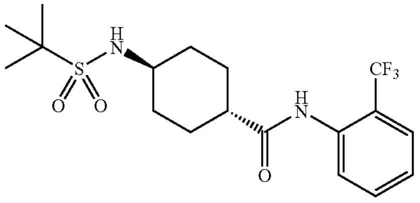
Ia-24
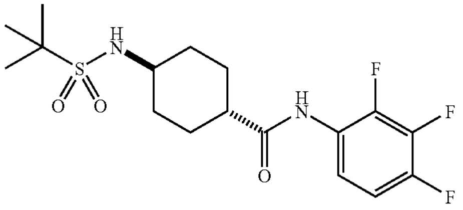
Ia-25
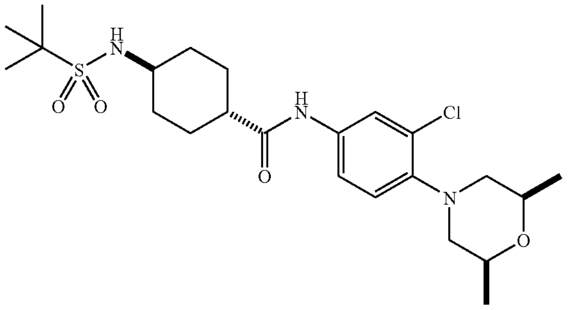
Ia-26
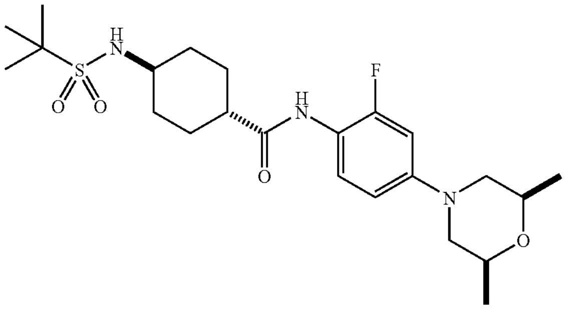

-continued
Ia-27
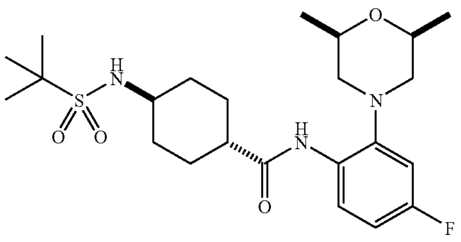
Ia-28
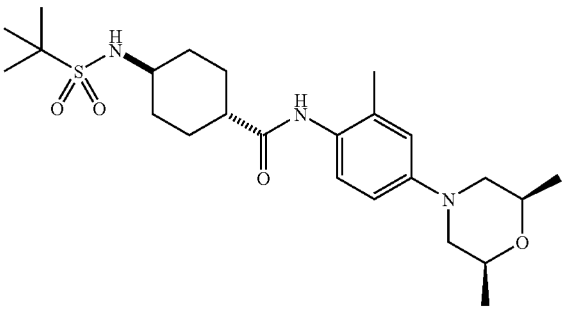
Ia-29
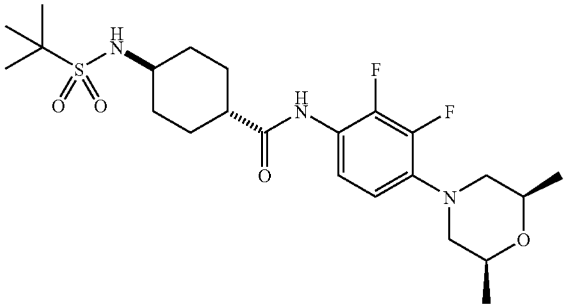
Ia-30
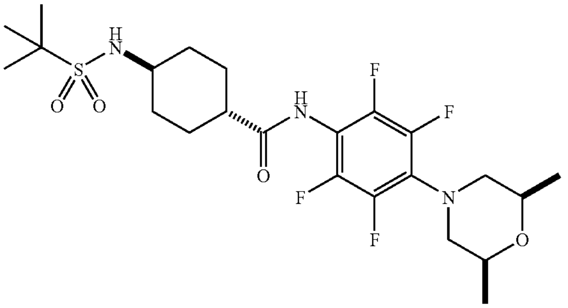
Ia-31
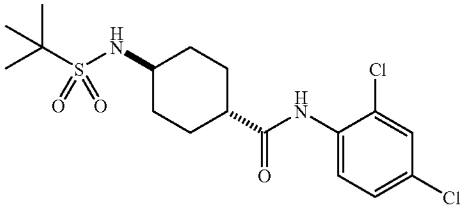
Ia-32
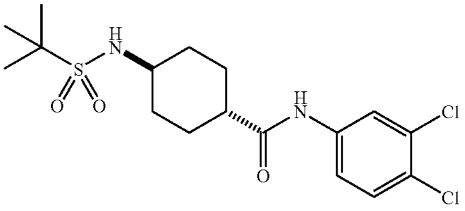
Ia-33
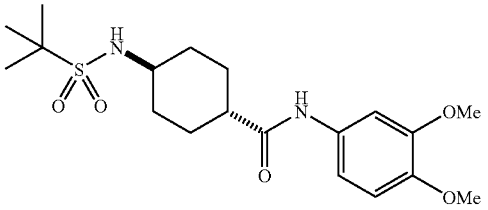
Ia-35
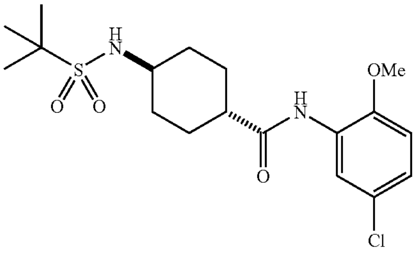
Ia-36
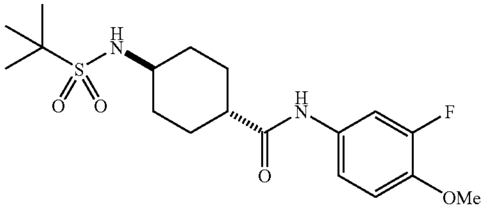
Ia-37
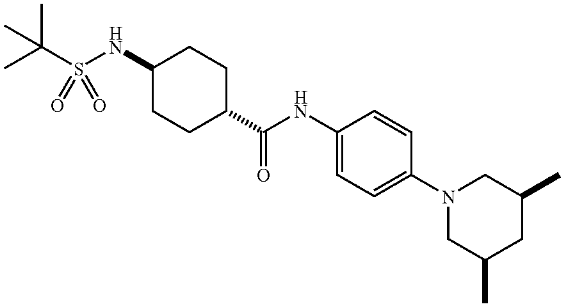

-continued
Ia-38
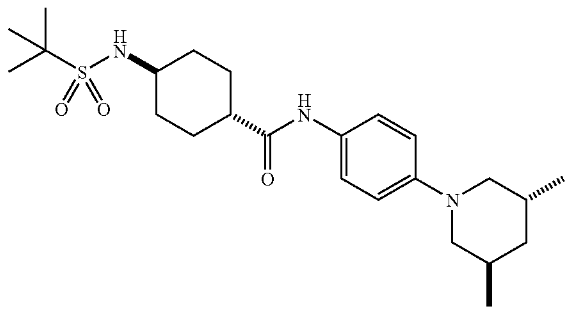
Ia-39
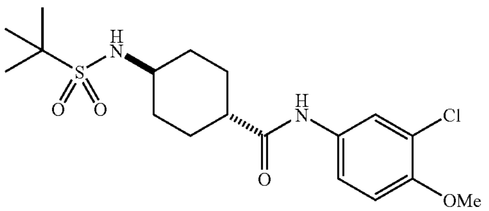
Ia-40
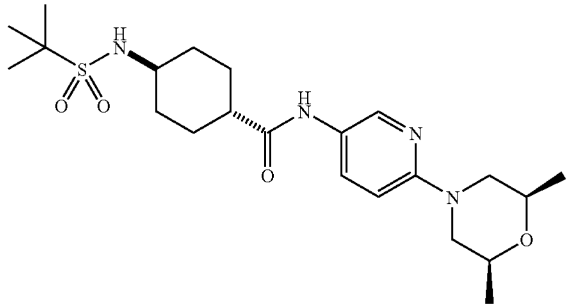
Ia-41
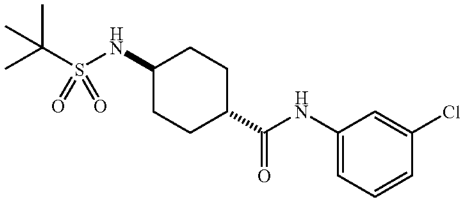
Ia-42
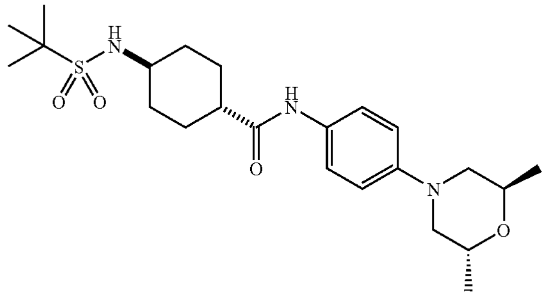
Ia-43
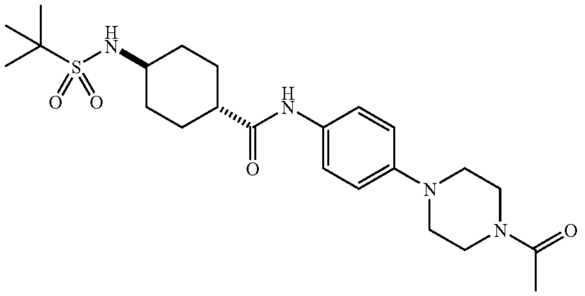
Ia-44
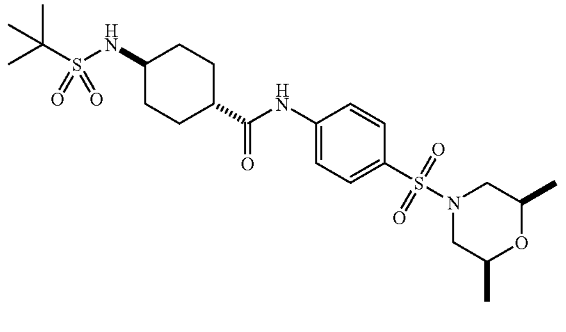
Ia-45
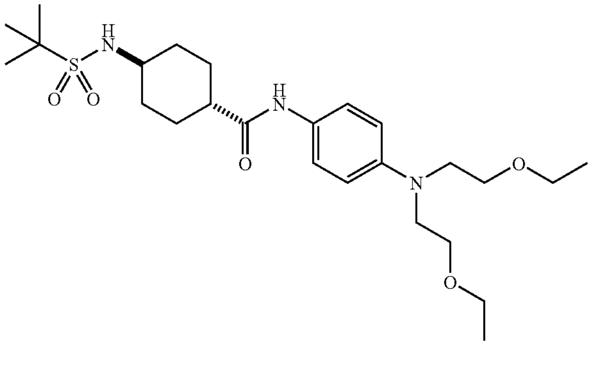

-continued
Ia-46
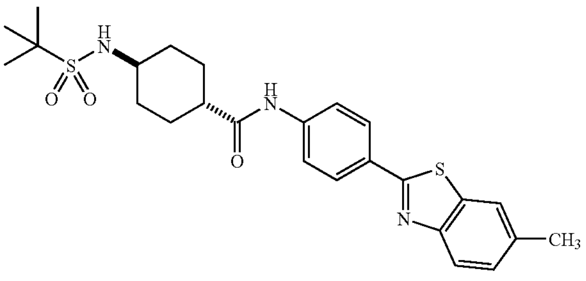
Ia-47
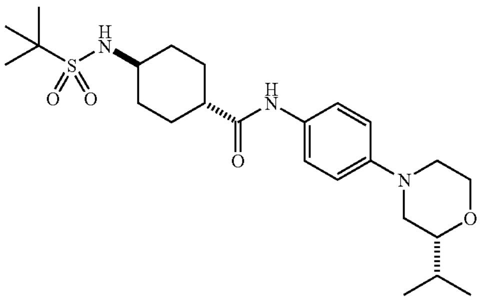
Ia-48
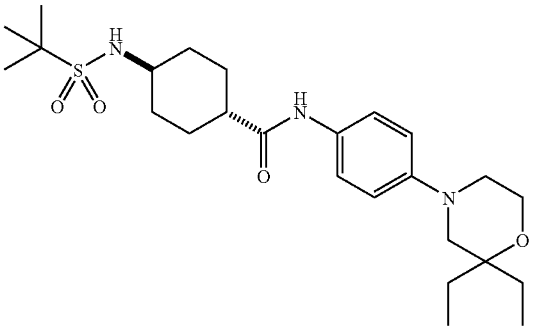
Ia-49
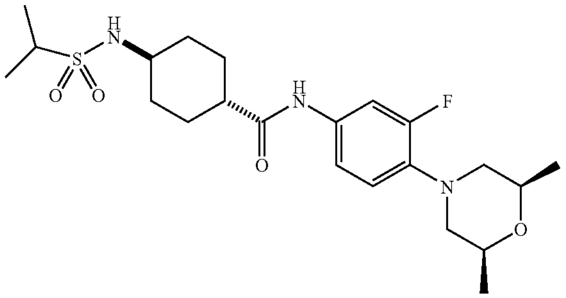
Ia-50
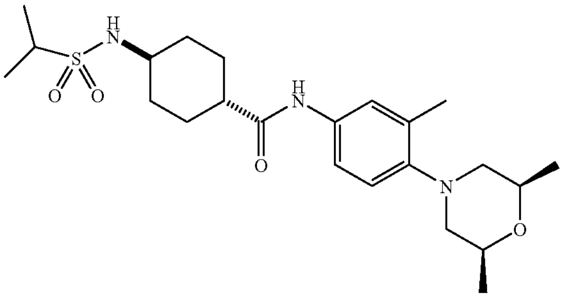
Ia-51
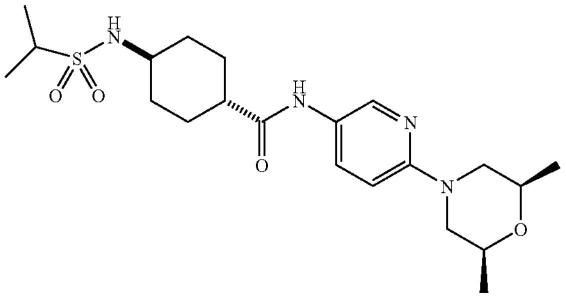
Ia-52
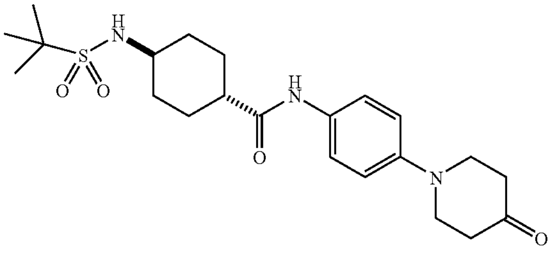
Ia-53
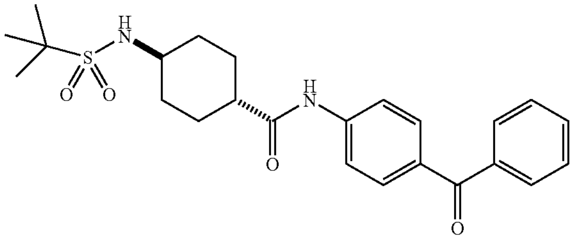
Ia-54
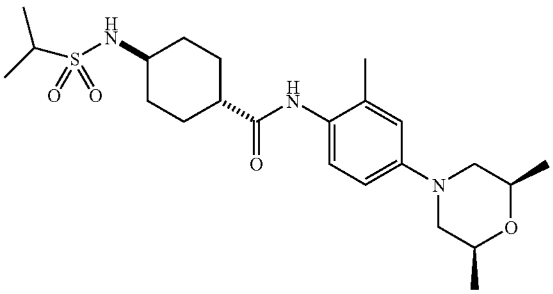
Ia-55
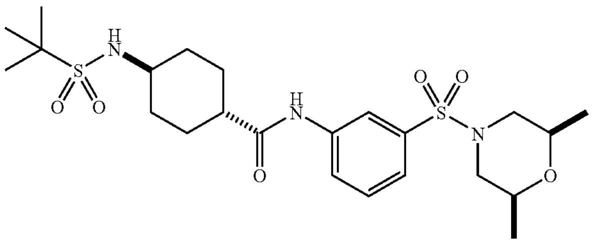

-continued
Ia-56
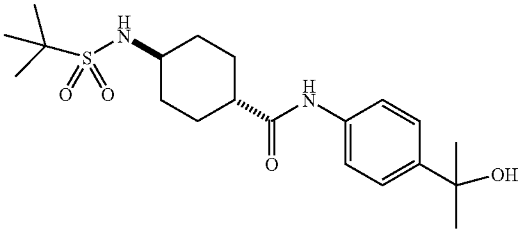
Ia-57
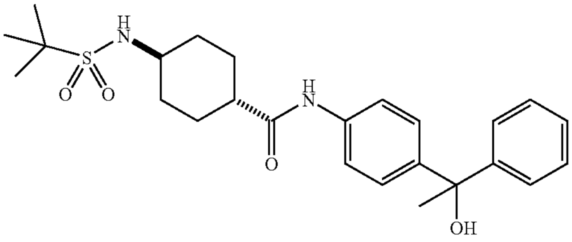
Ia-58
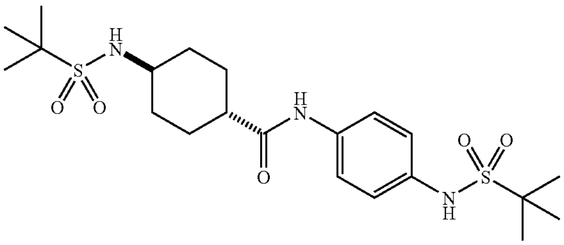
Ia-59
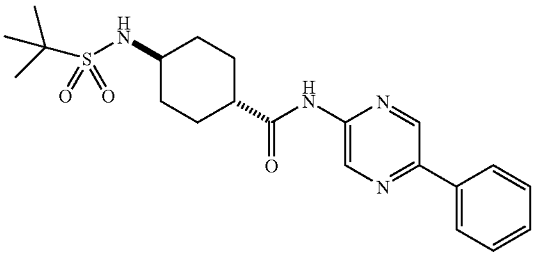
Ia-60
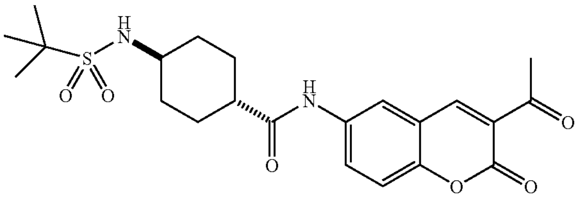
Ia-61
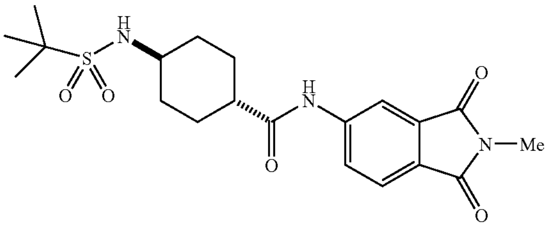
Ia-62
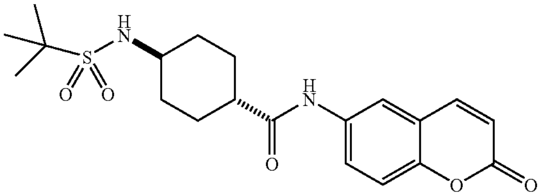
Ia-63
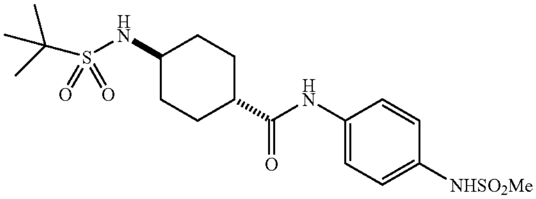
Ia-64
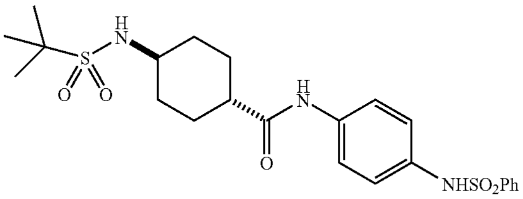
Ia-65
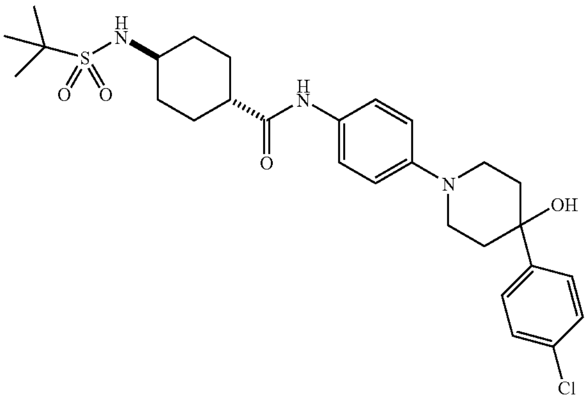

-continued
Ia-66
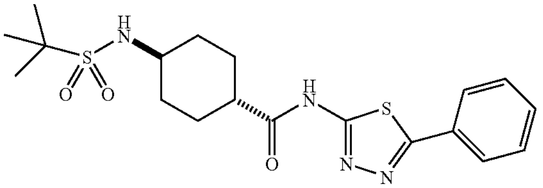
Ia-67
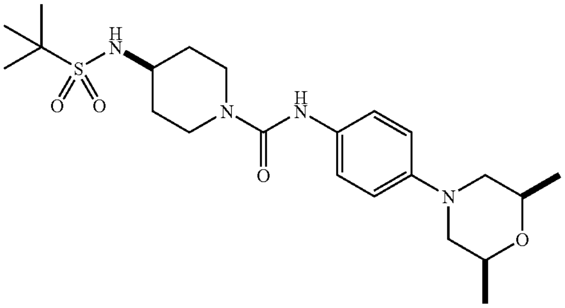
Ia-68
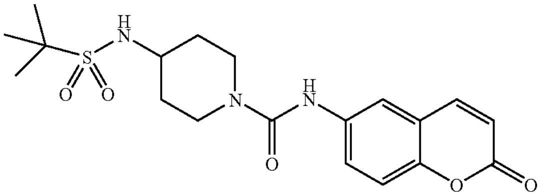
Ia-69
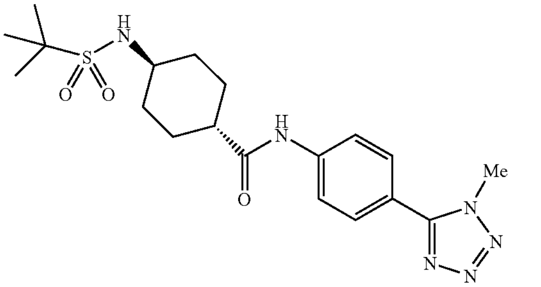
Ia-70
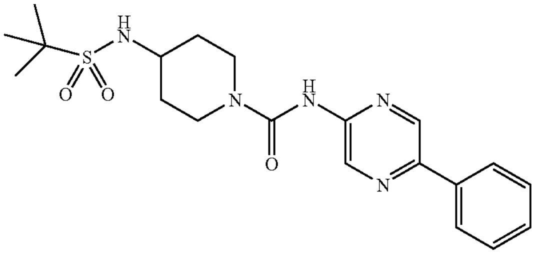
Ia-71
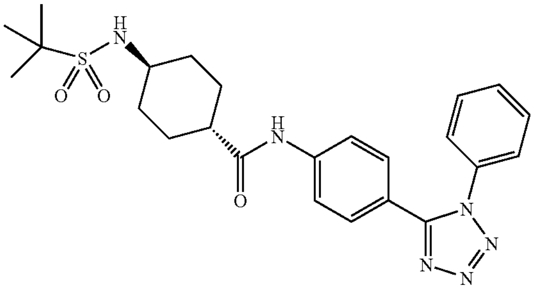
Ia-72
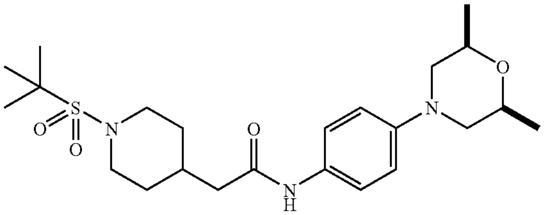
Ia-73
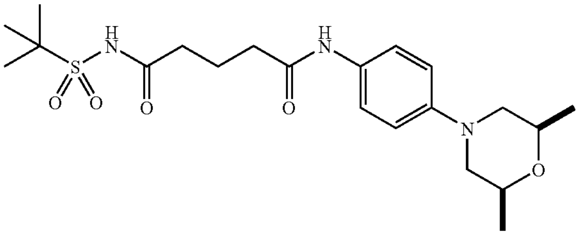
Ia-74
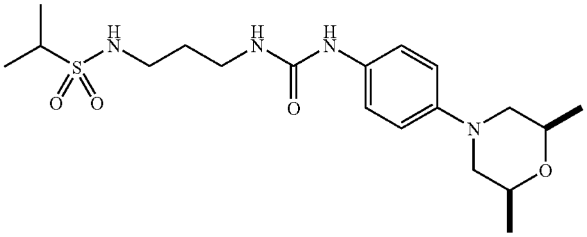
Ia-75
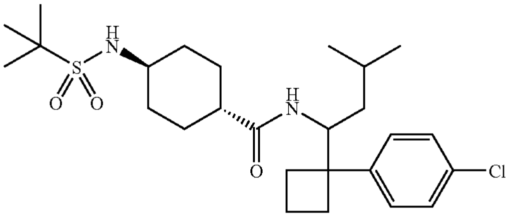

-continued
Ia-76
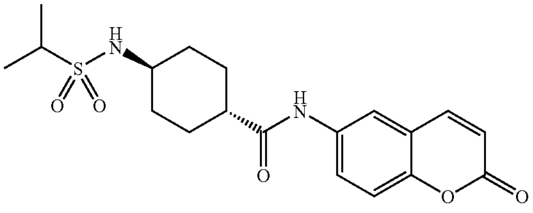
Ia-77
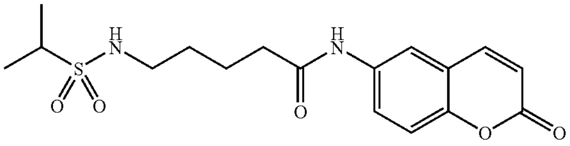
Ia-78
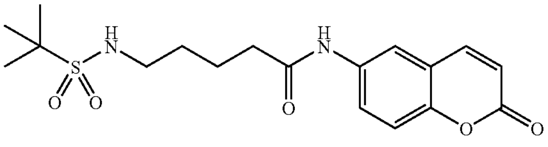
Ia-79
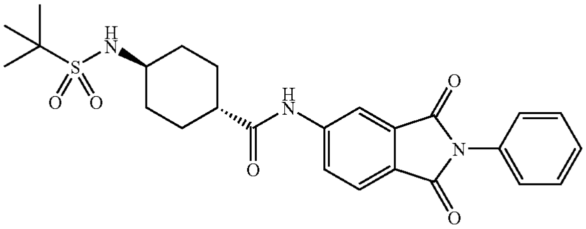
Ia-80
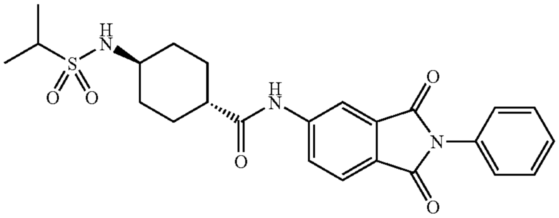
Ia-81
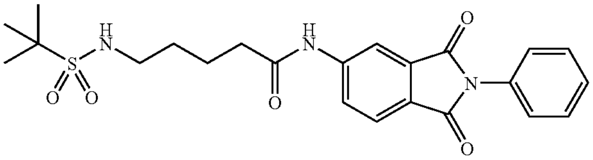
Ia-82
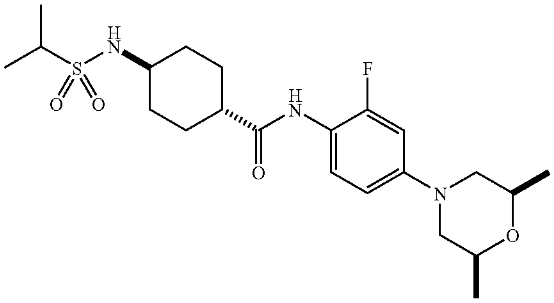
Ia-83
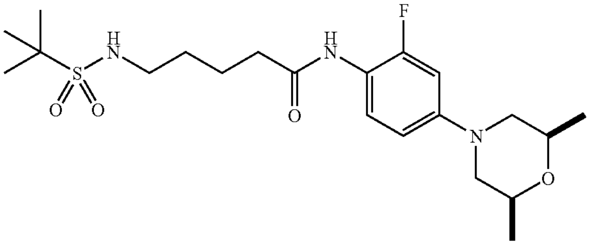
Ia-84
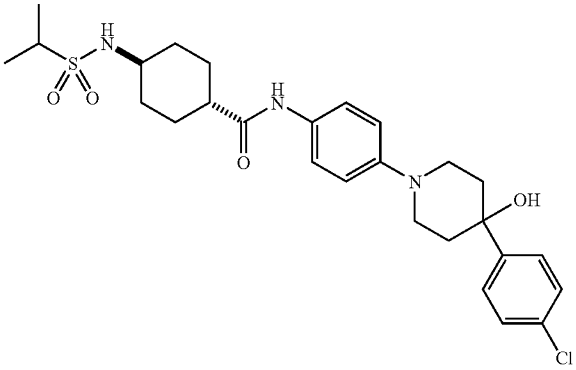
Ia-85
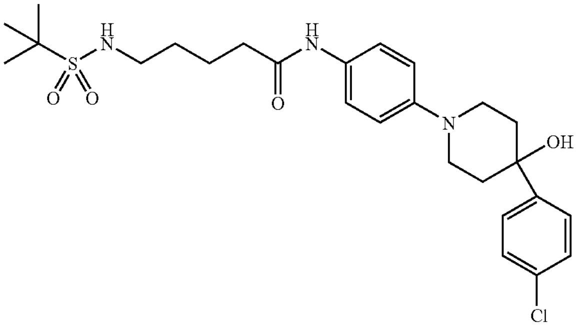

-continued
Ia-86
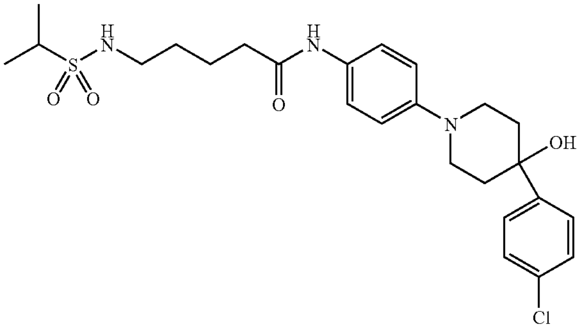
Ia-87
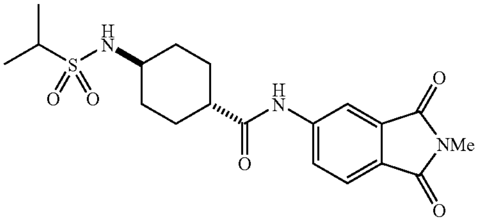
Ia-88
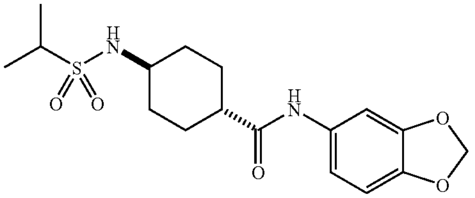
Ia-89
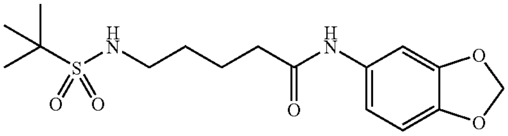
Ia-90
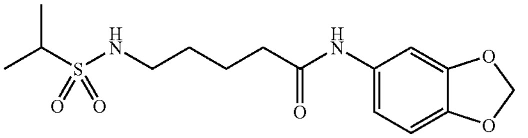
Ia-91
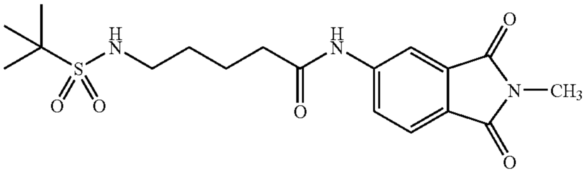
Ia-104
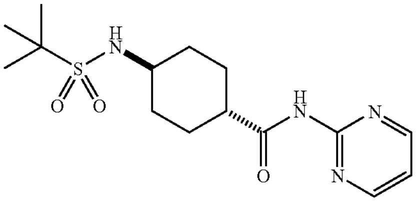
Ia-105
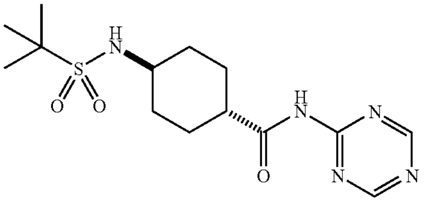
Ia-106
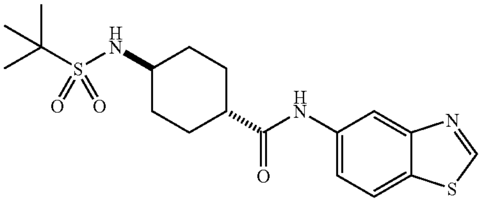
Ia-107
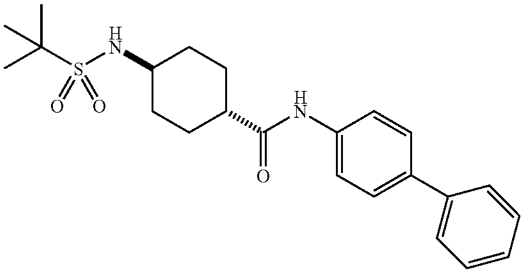
Ia-108
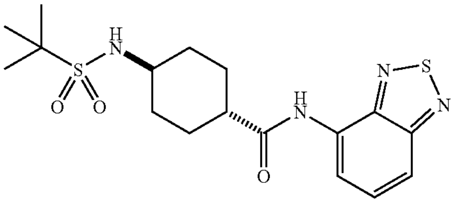
Ia-109
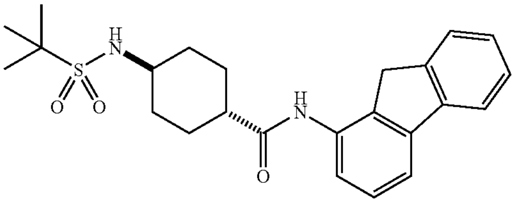

-continued
Ia-110
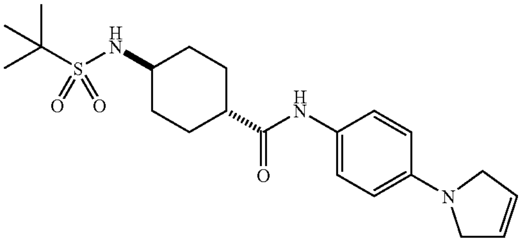
Ia-111
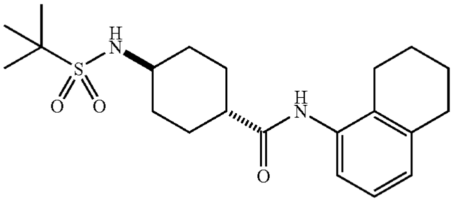
IA-122
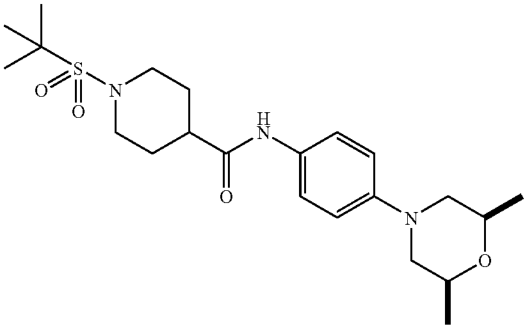
IA-123
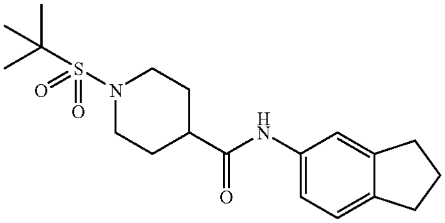
Ia-124
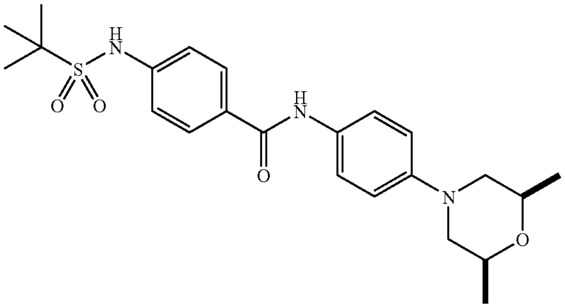
Ia-125
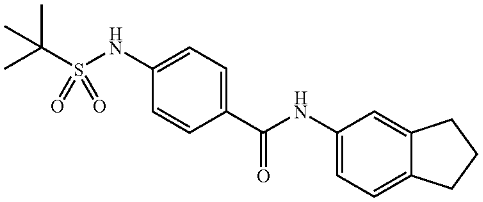
Ia-126
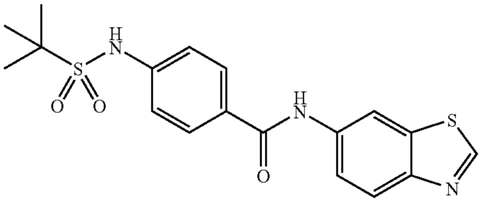
Ia-127
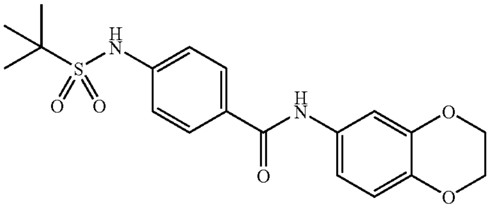
Ia-128
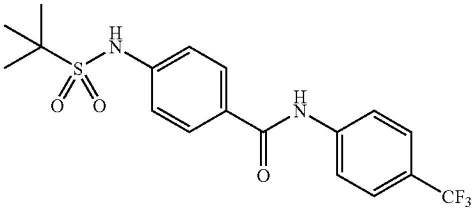
Ia-129
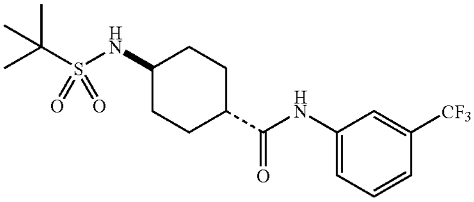
Ia-130
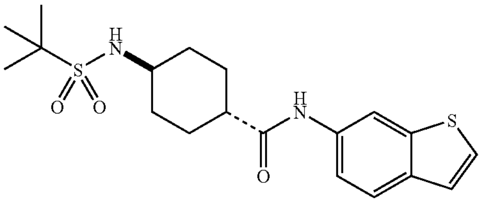
Ia-131
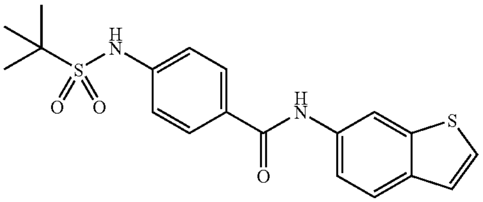

-continued
Ia-132
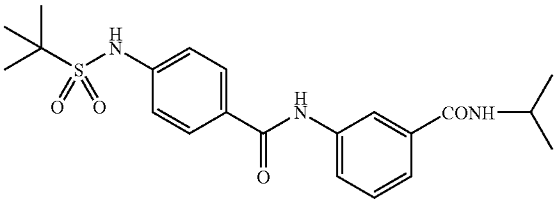
Ia-133
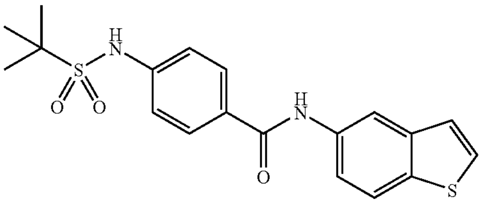
Ia-134
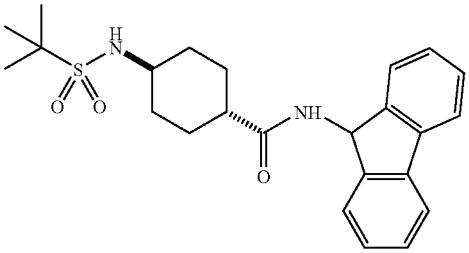
Ia-135
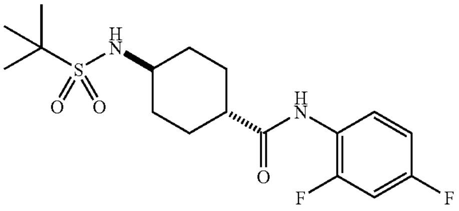
Ia-136
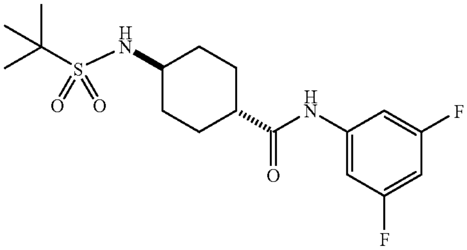
Ia-137
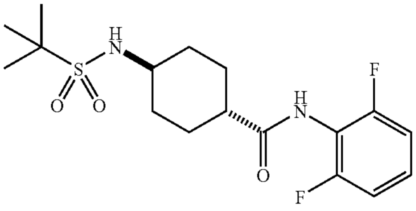
Ia-138
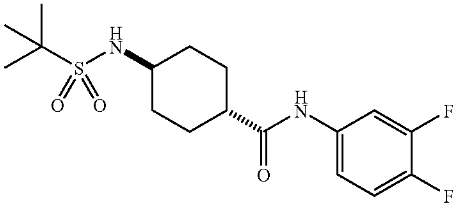
Ia-139
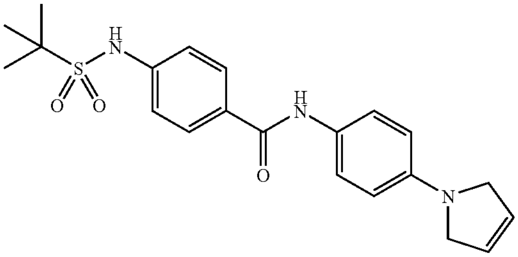
Ia-140
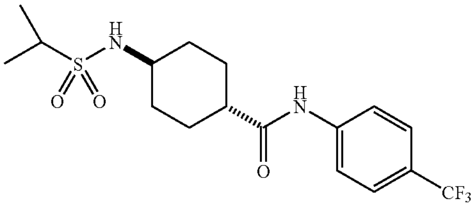
Ia-141
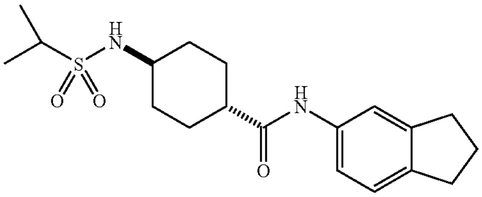
Ia-142
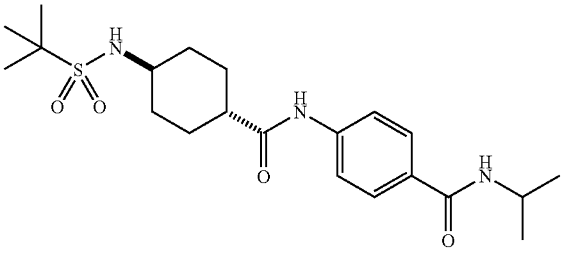
Ia-143
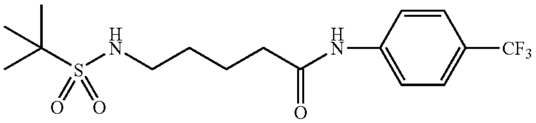

-continued
Ia-144
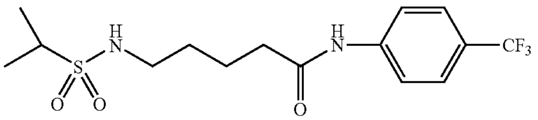
Ia-145
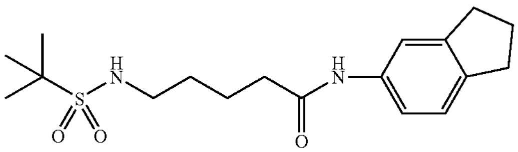
Ia-146
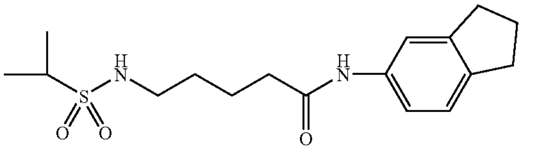
Ia-147
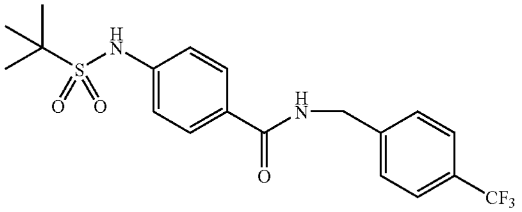
Ia-148
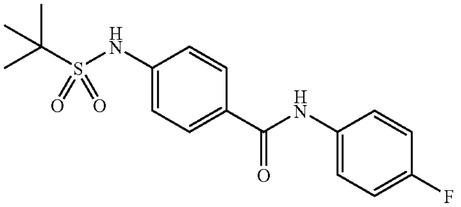
Ia-149
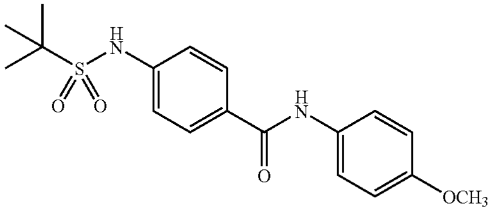
Ia-150
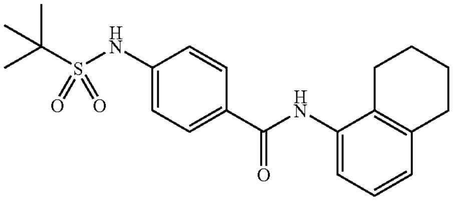
Ia-151
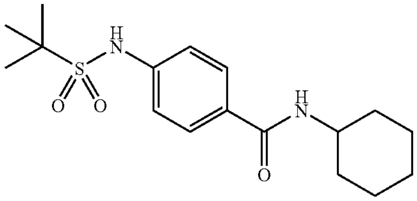
Ia-152
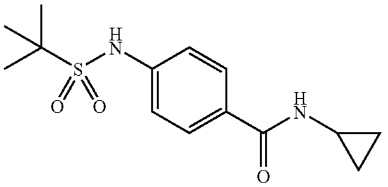
Ia-153
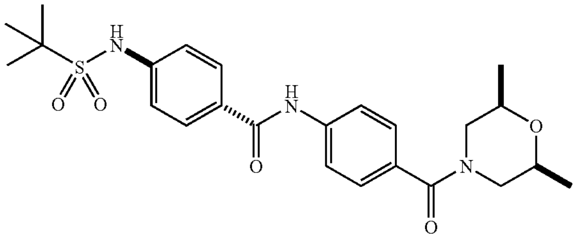
Ia-154
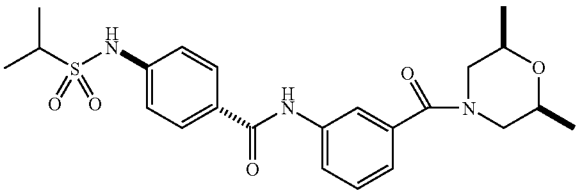
Ia-155
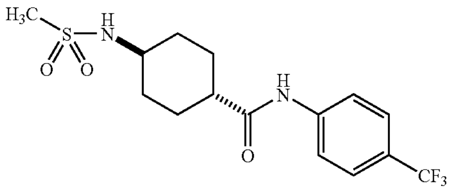
Ia-156
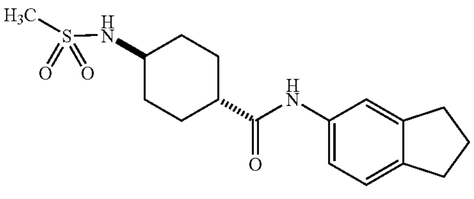
Ia-157
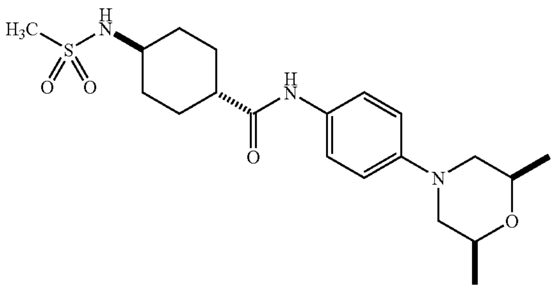

-continued
Ia-158
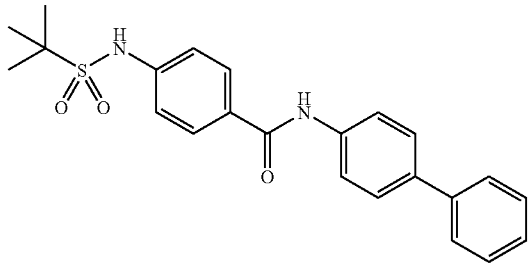
Ia-159
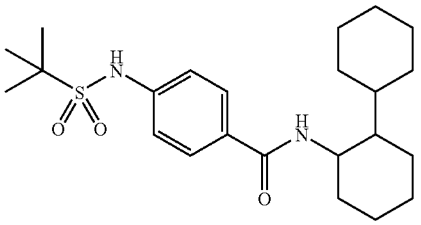
Ia-160
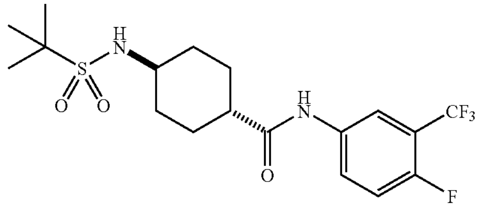
Ia-161
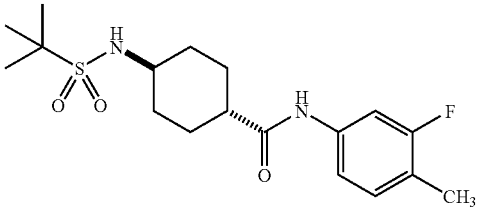
Ia-162
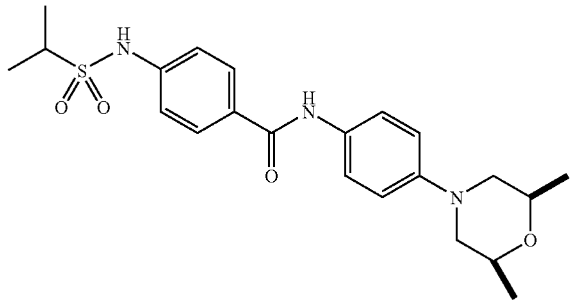
Ia-163
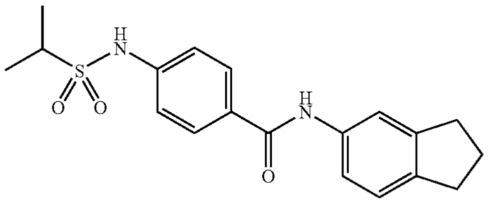
Ia-164
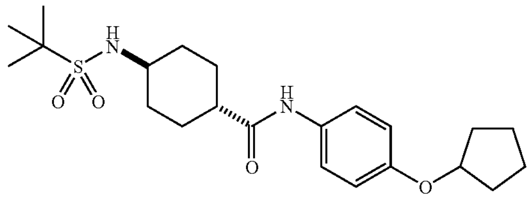
Ia-165
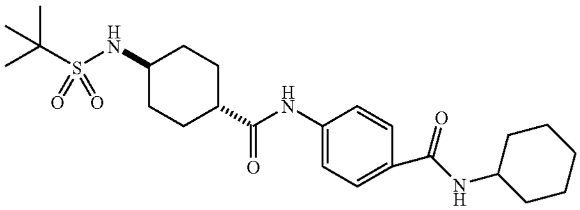
Ia-166
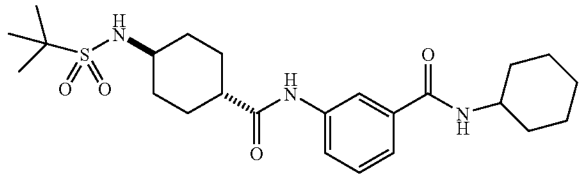
Ia-167
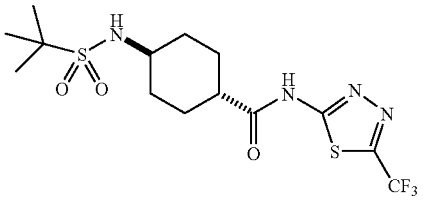
Ia-168
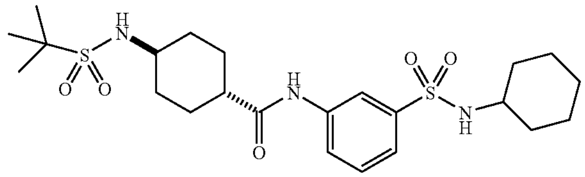
Ia-169
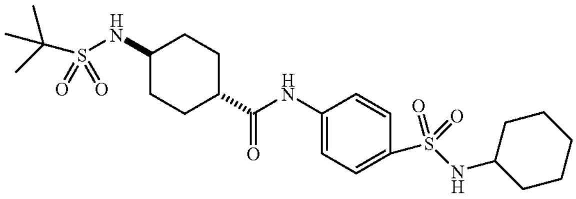

-continued
Ia-171
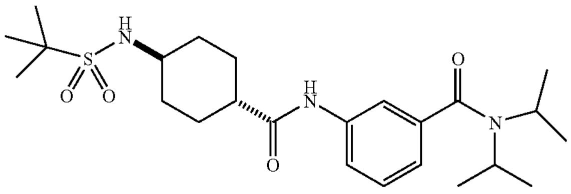
Ia-172
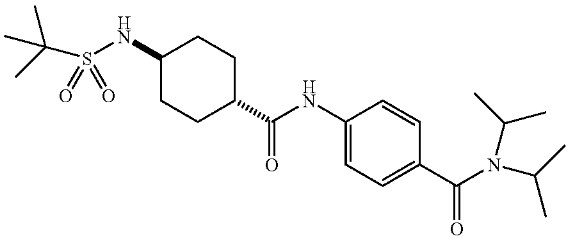
Ia-173
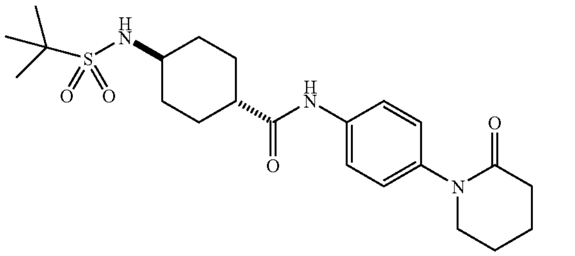
Ia-174
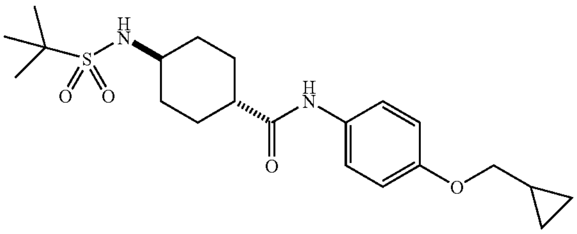
Ia-175
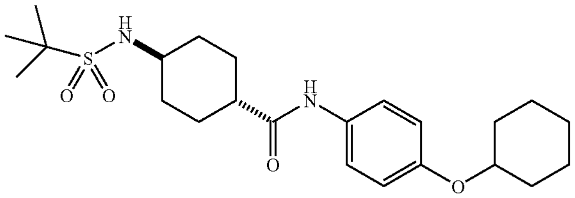
Ia-176
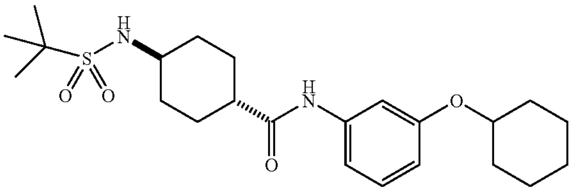
Ia-177
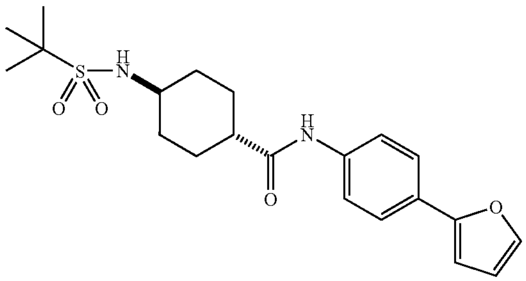
Ia-178
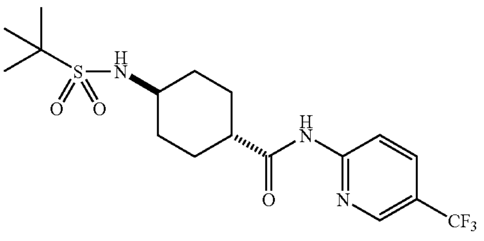
-continued
Ia-179
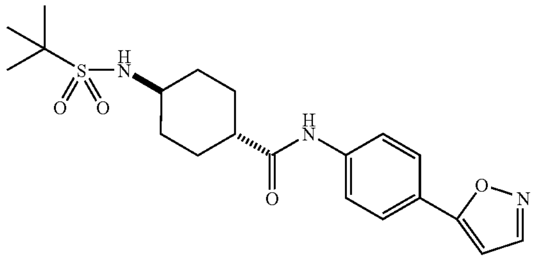
Ia-180
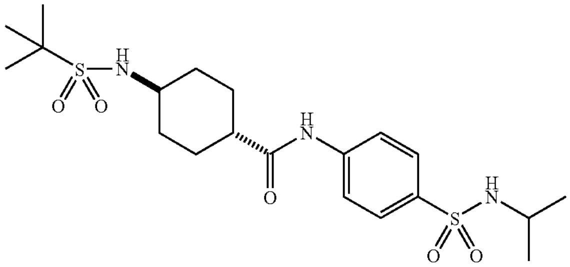

-continued
Ia-181
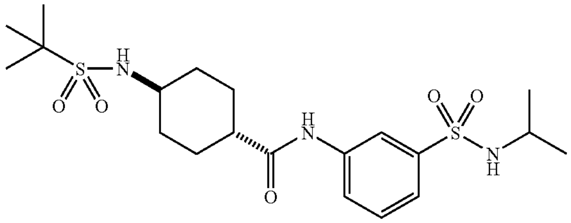
Ia-182
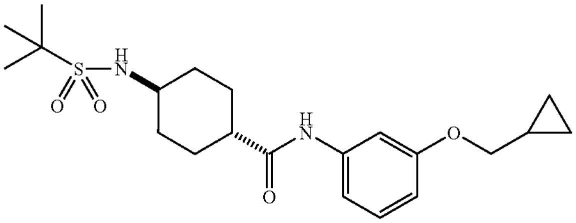
Ia-183
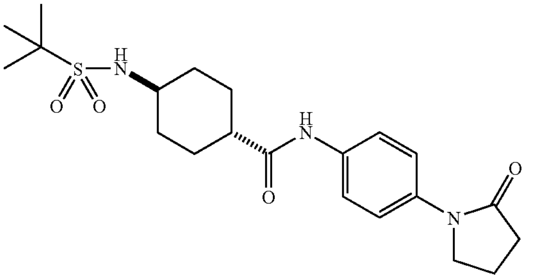
Ia-184
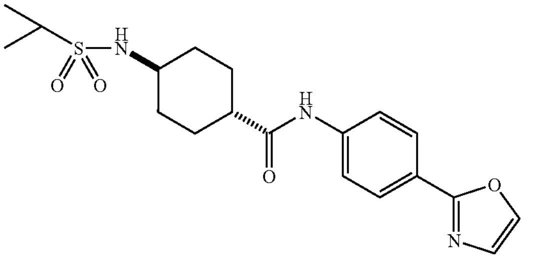
Ia-185
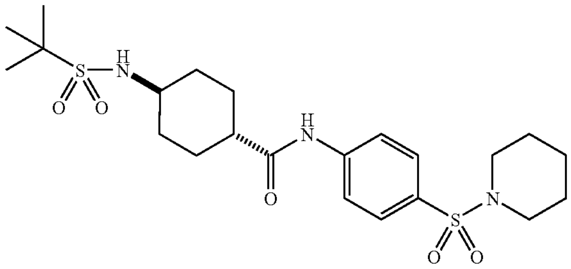
-continued
Ia-186
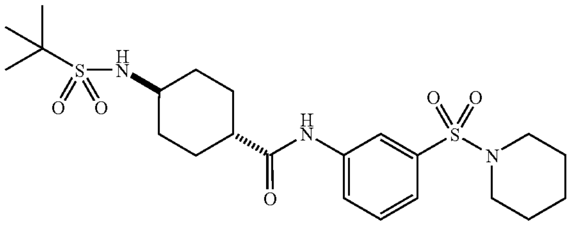
Ia-187
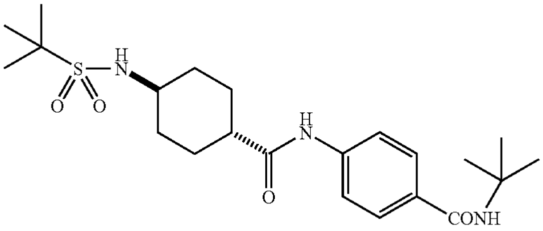
Ia-188
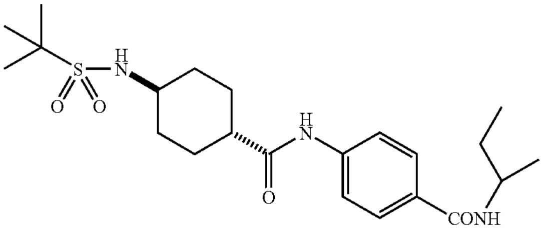
Ia-189
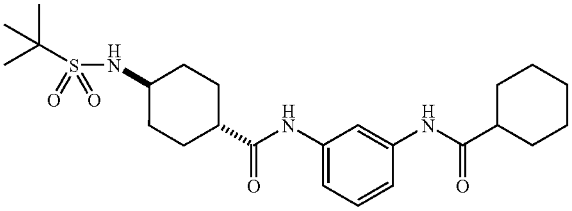
Ia-190
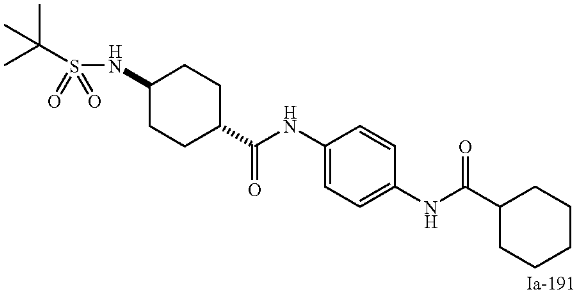
Ia-191
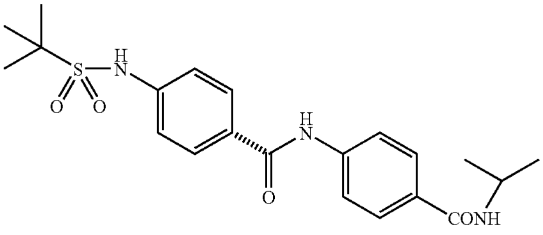

-continued
Ia-192
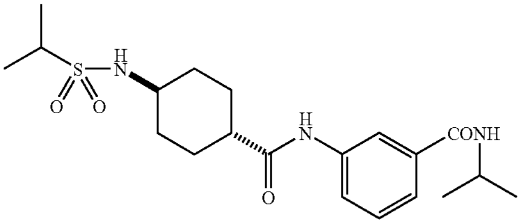
Ia-193
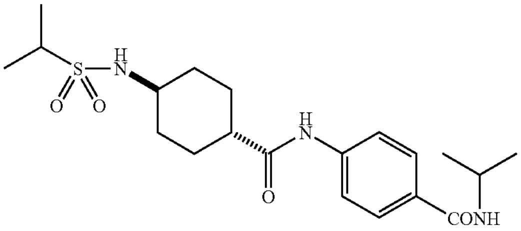
Ia-194
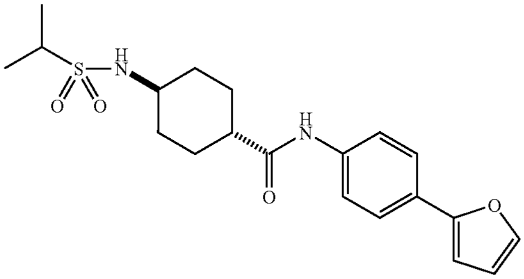
Ia-195
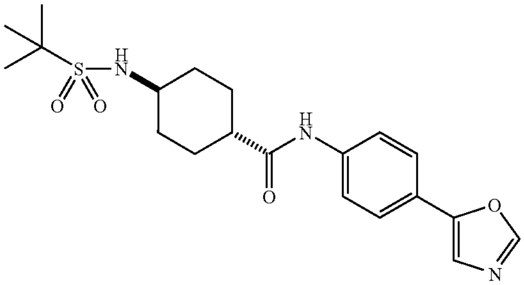
Ia-196
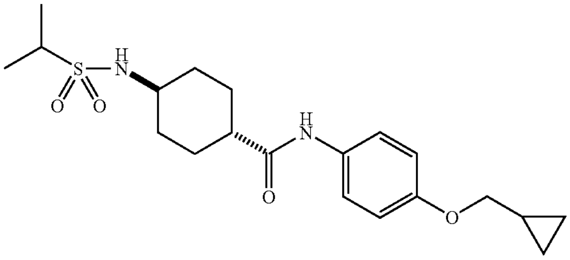
-continued
Ia-197
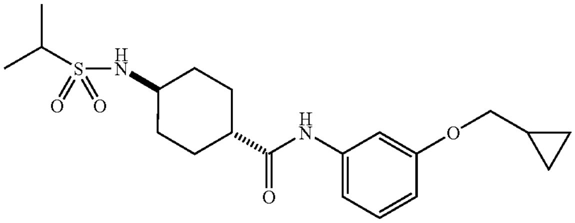
Ia-198
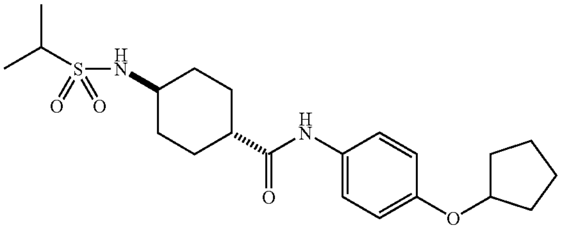
Ia-199
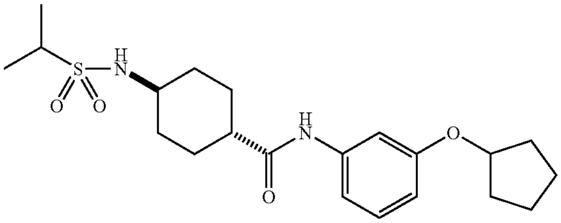
Ia-200
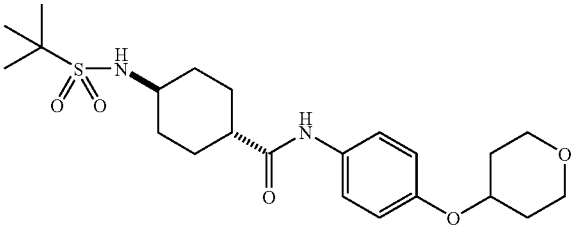
Ia-201
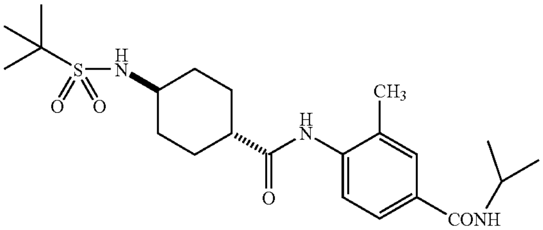
Ia-202
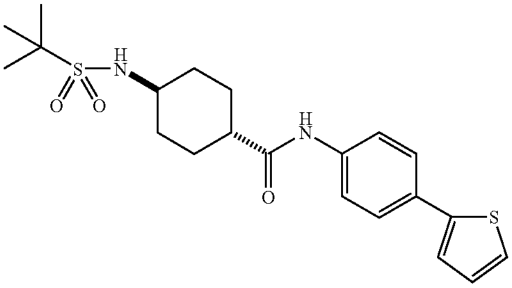

-continued
Ia-203
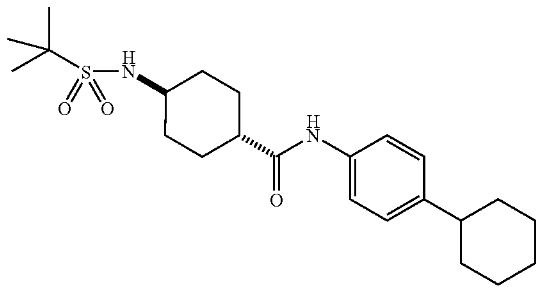
Ia-204
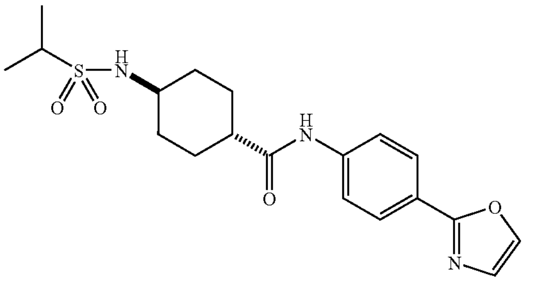
Ia-205
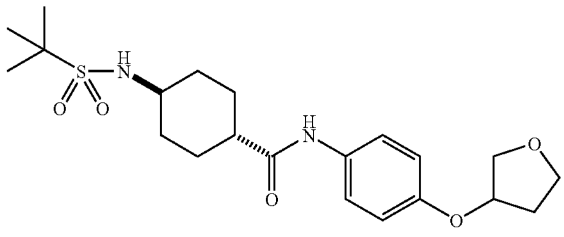
Ia-206
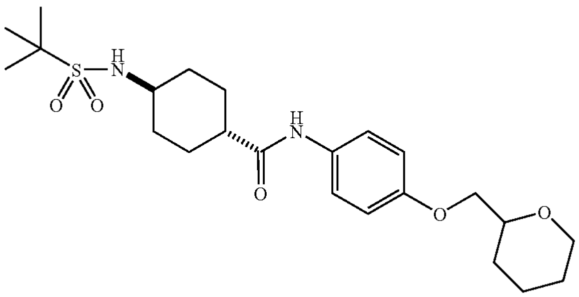
Ia-207
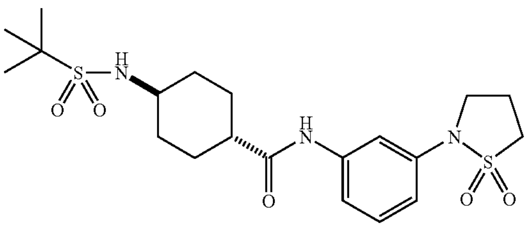
-continued
Ia-208
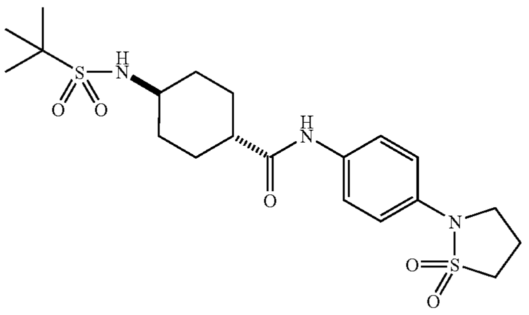
Ia-209
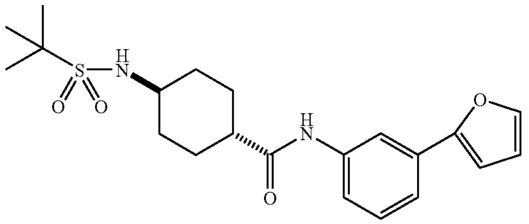
Ia-210
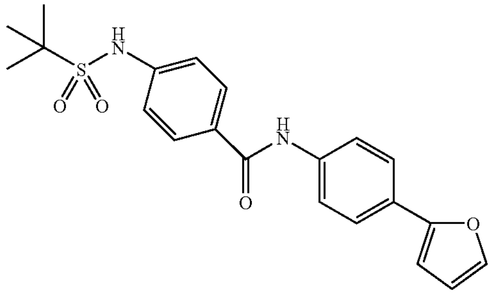
Ia-211
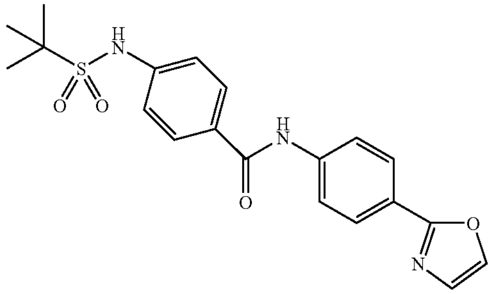
Ia-212
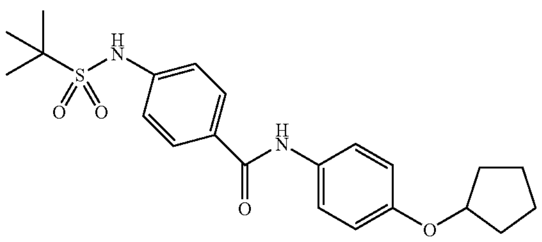

-continued
Ia-213
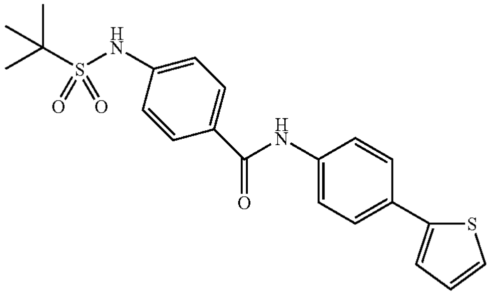
Ia-214
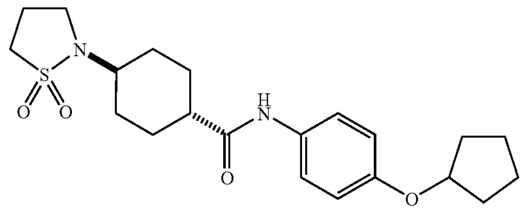
Ia-215
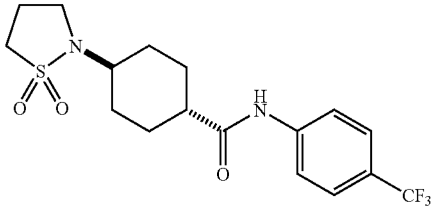
Ia-216
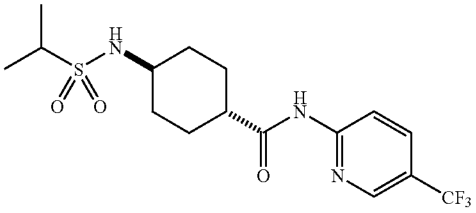
Ia-219
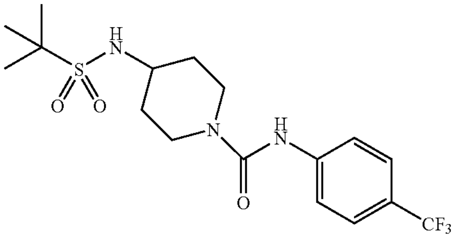
Ia-220
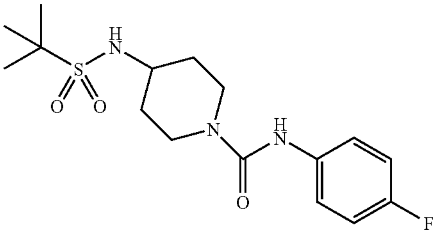
-continued
Ia-221
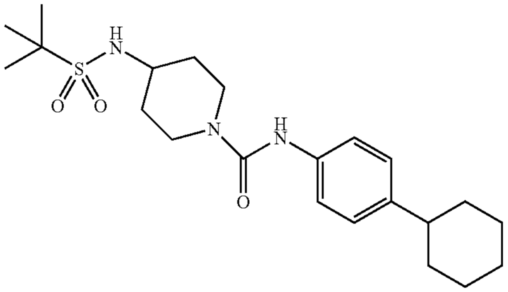
Ia-222
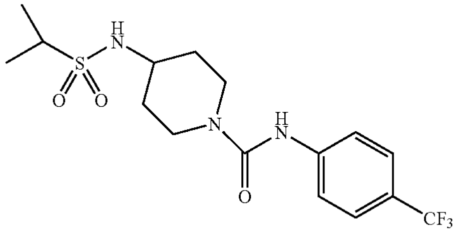
Ia-223
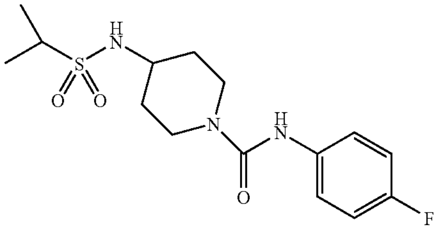
Ia-224
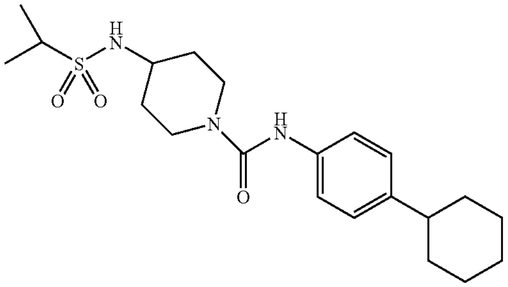
Ia-225
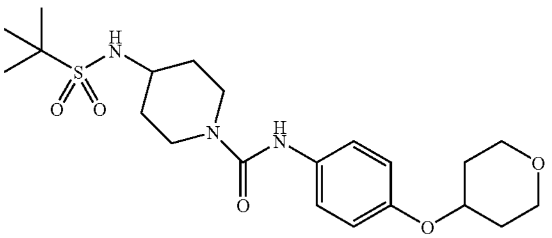
Ia-226
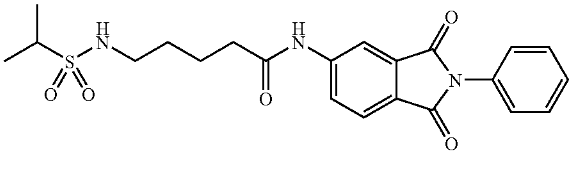

-continued
Ia-227
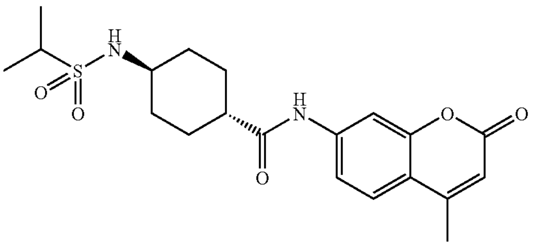
Ia-228
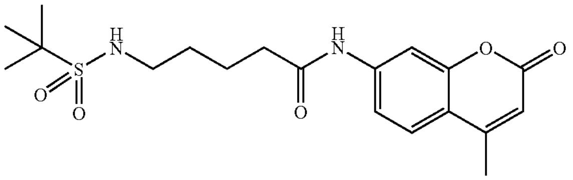
Ia-229
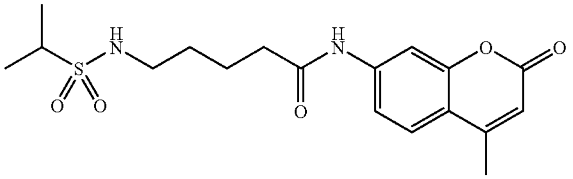
Ia-230
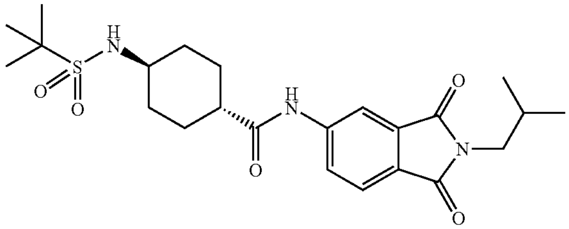
Ia-231
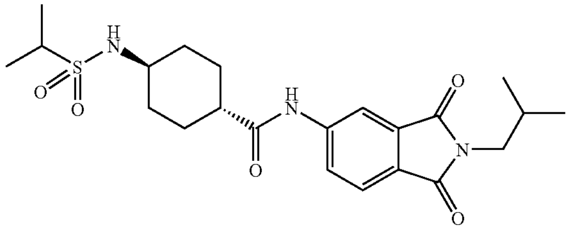
Ia-232
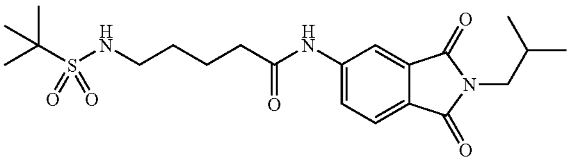
Ia-233
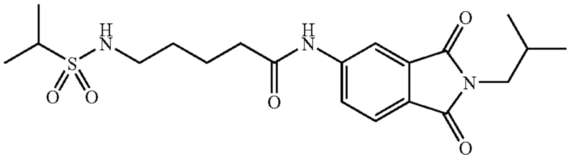
-continued
Ia-234
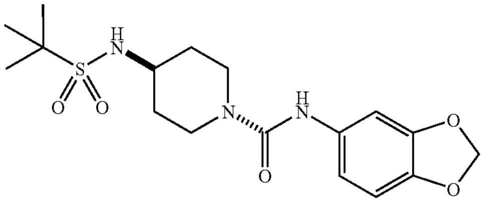
Ia-235
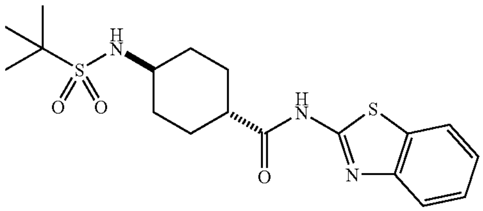
Ia-236
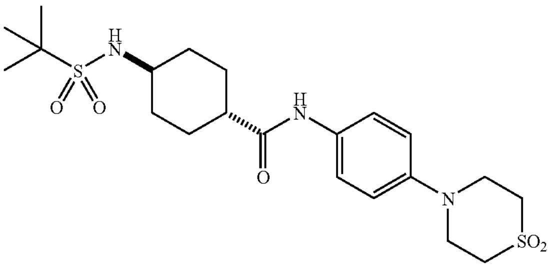
Ia-237
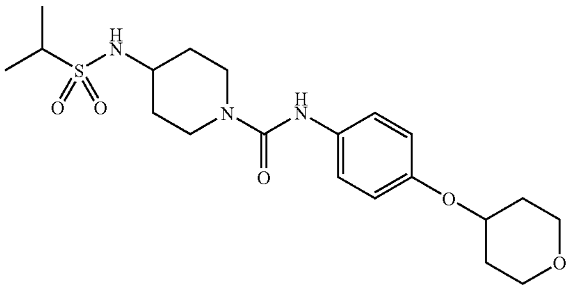
Ia-238
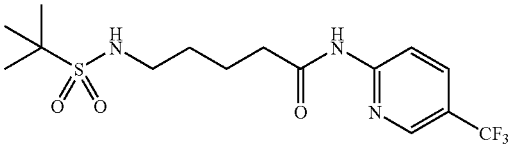
Ia-239
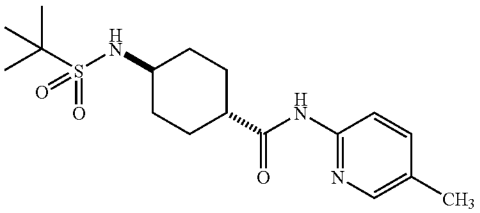

-continued
Ia-240
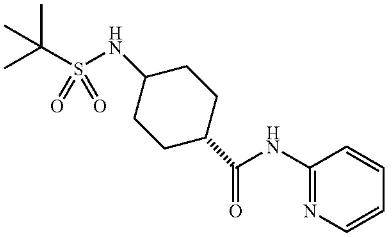
Ia-241
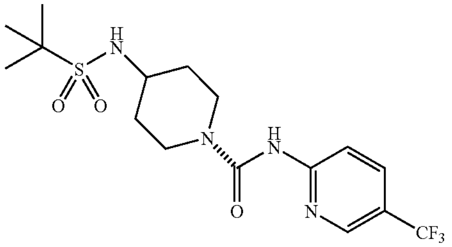
Ia-242
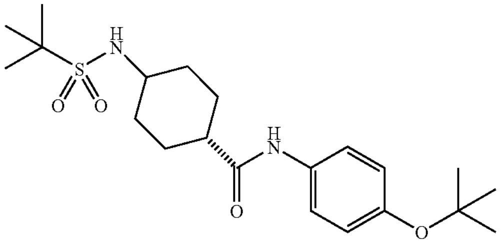
Ia-243
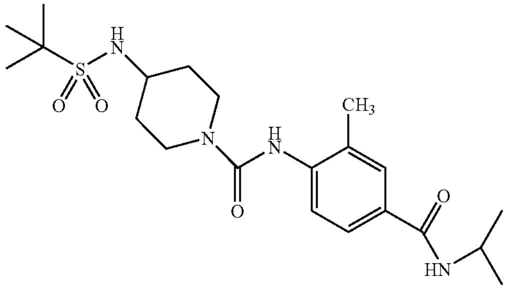
Ia-244
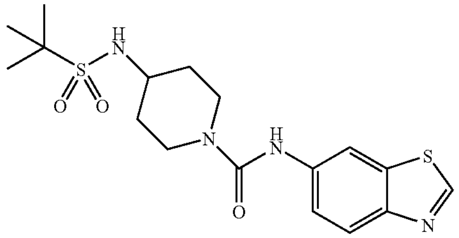
Ia-245
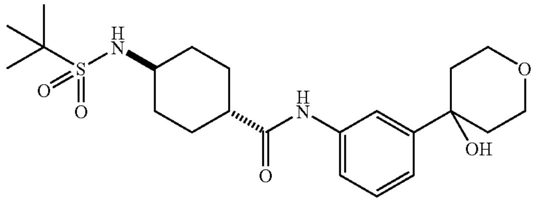
-continued
Ia-246
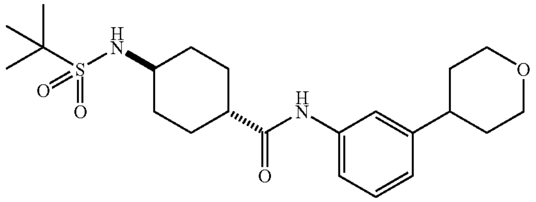
Ia-247
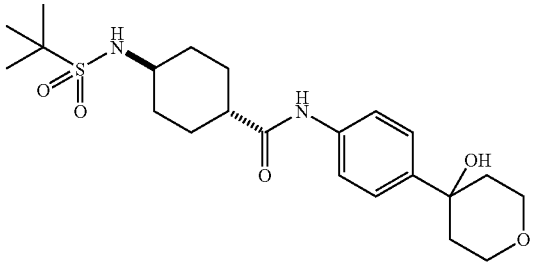
Ia-248
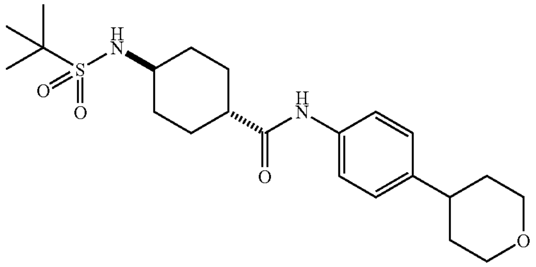
Ia-249
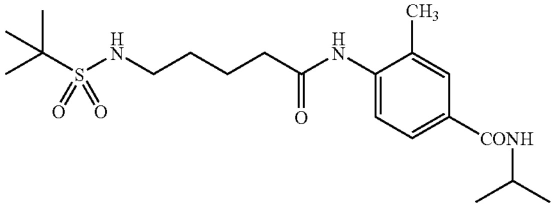
Ia-250
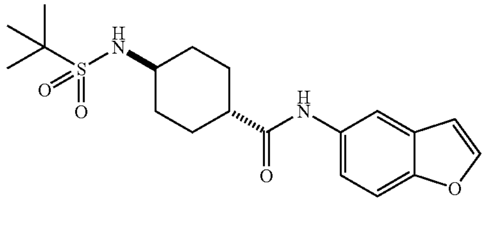
Ia-252
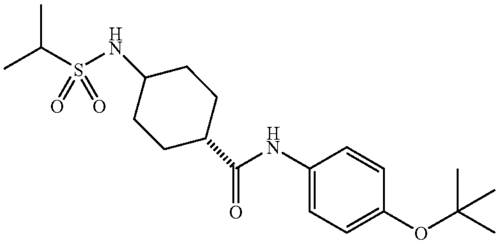

-continued
Ia-253
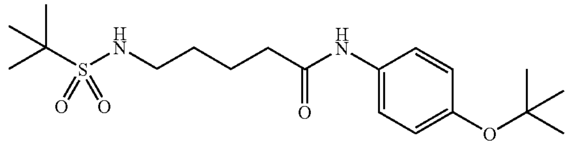
Ia-254
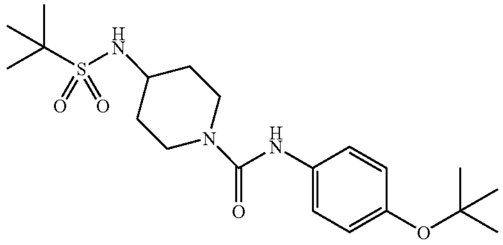
Ia-255
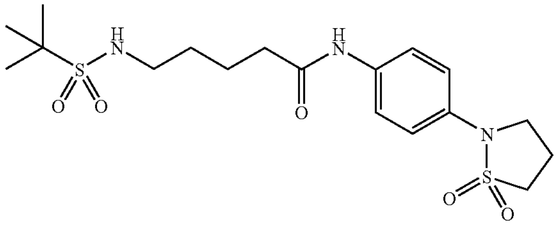
Ia-256
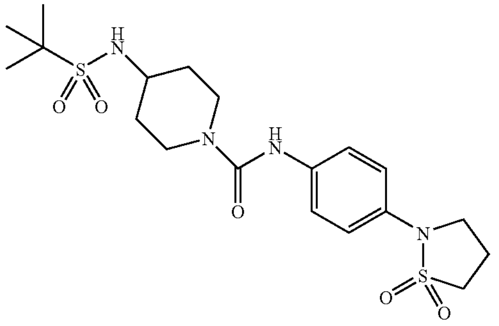
Ia-257
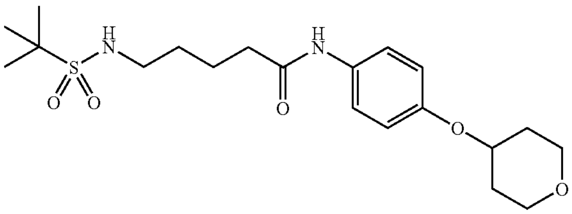
Ia-258
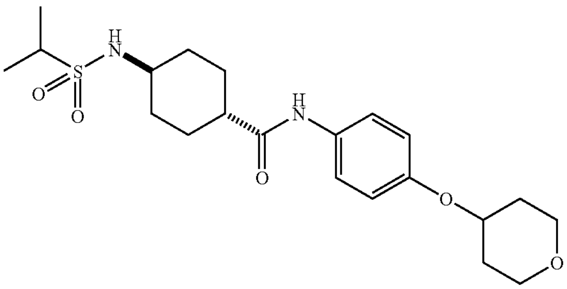
-continued
Ia-259
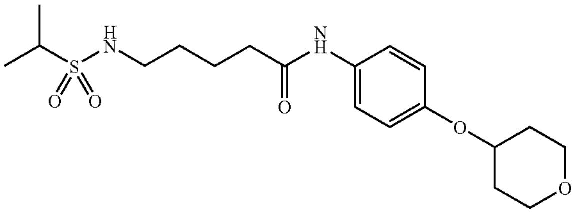
Ib-1
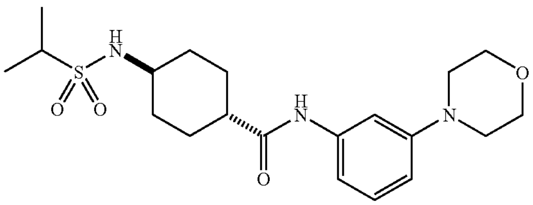
Ib-2
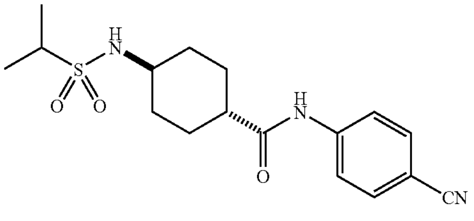
Ib-5
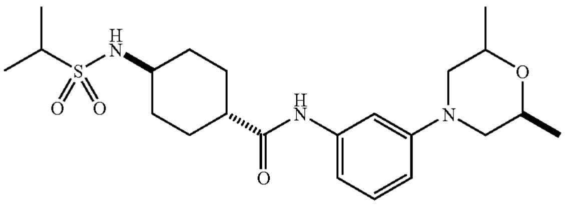
Ib-7
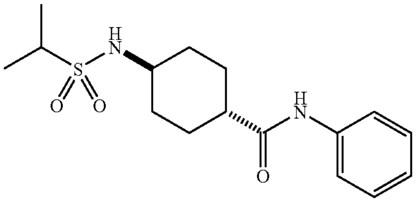
Ib-8
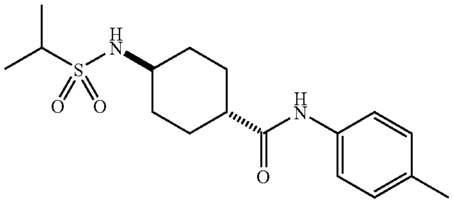
Ib-9
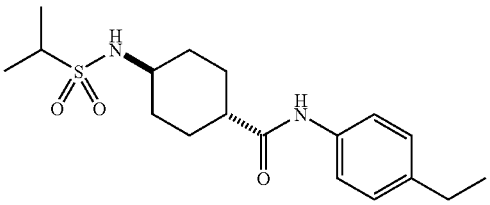

-continued
Ib-10
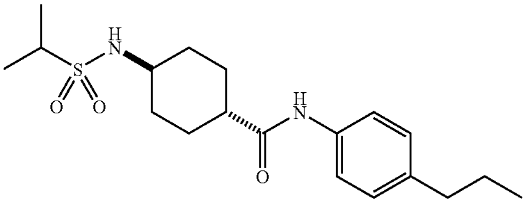
Ib-11
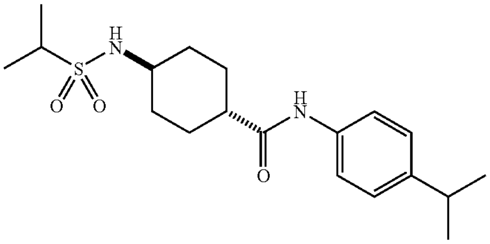
Ib-12
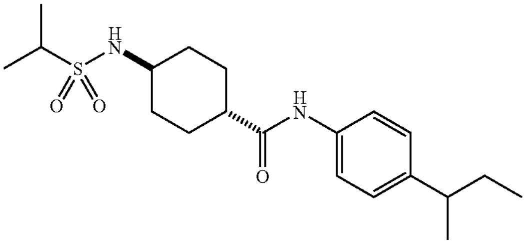
Ib-13
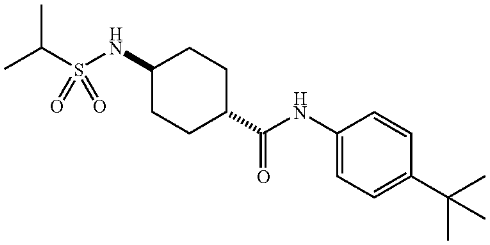
Ib-14
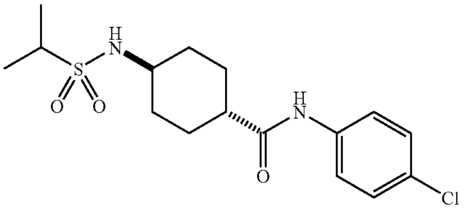
Ib-15
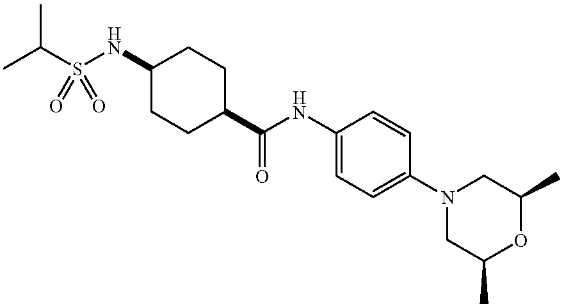
-continued
Ib-16
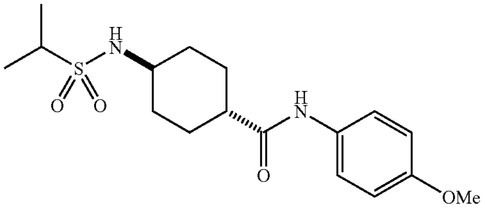
Ib-17
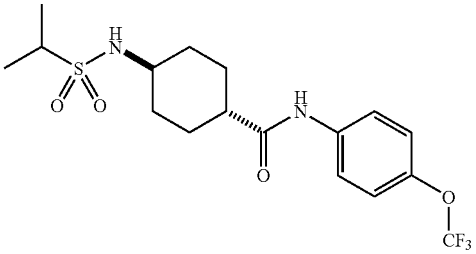
Ib-18
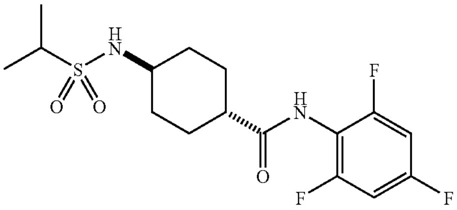
Ib-19
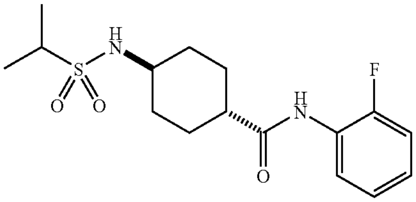
Ib-20
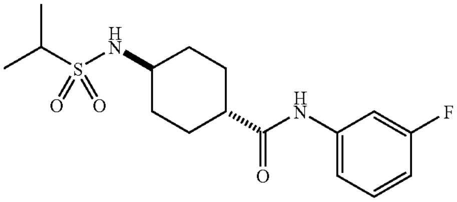
Ib-21
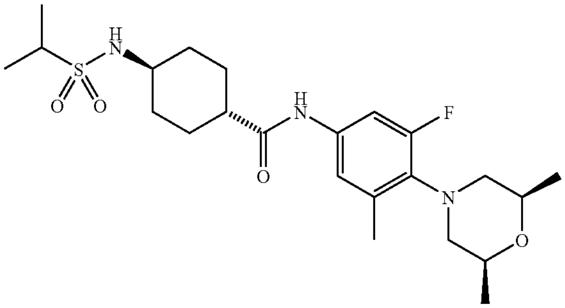

-continued
Ib-22
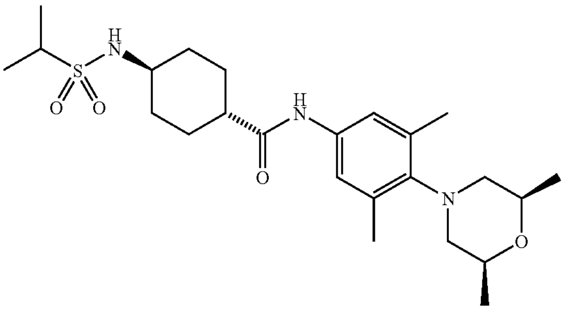
Ib-23
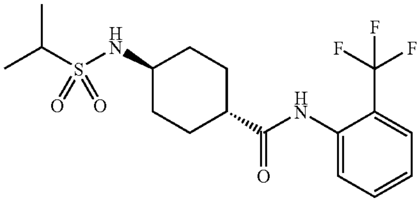
Ib-24
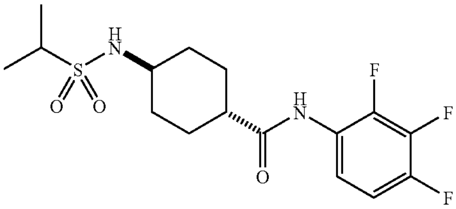
Ib-25
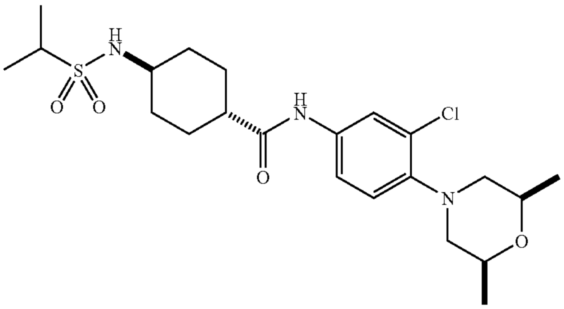
Ib-26
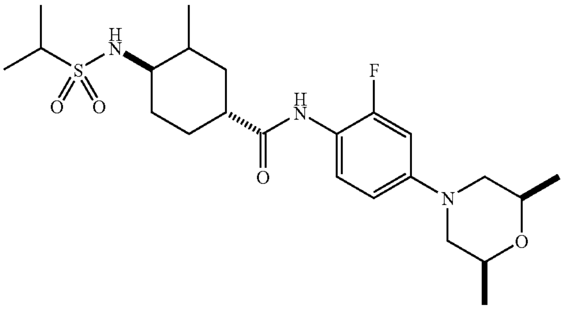
-continued
Ib-27
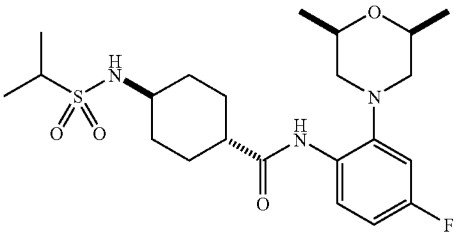
Ib-28
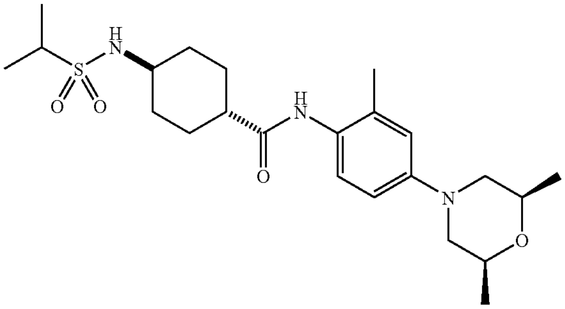
Ib-29
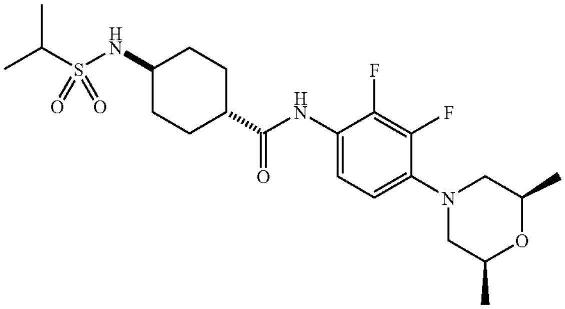
Ib-30
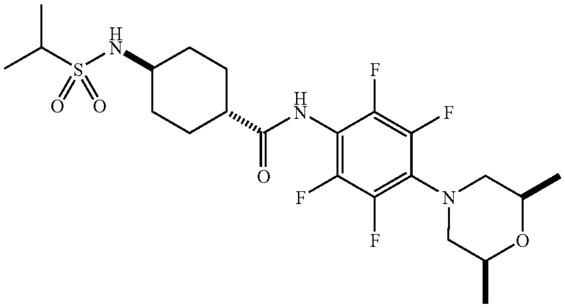
Ib-31
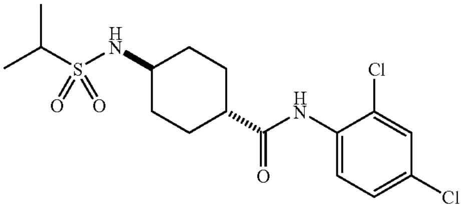

-continued
Ib-32
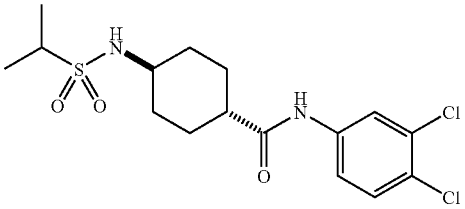
Ib-33
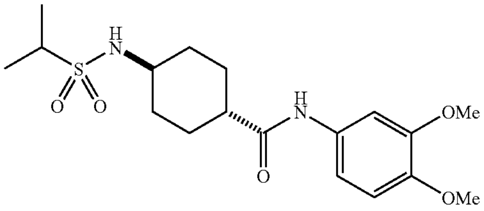
Ib-35
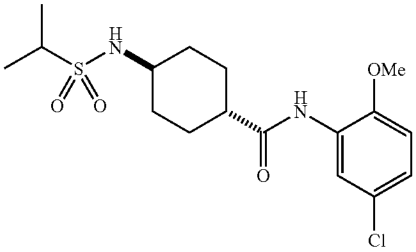
Ib-36
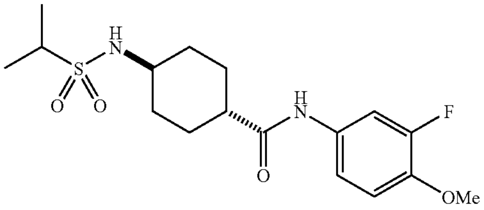
Ib-37
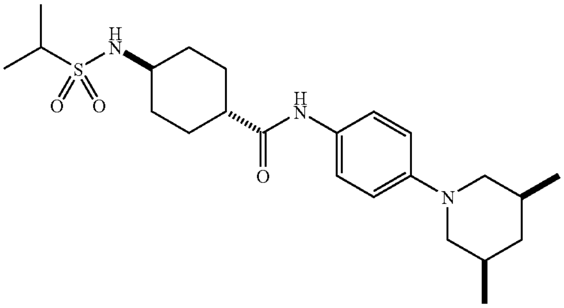
Ib-38
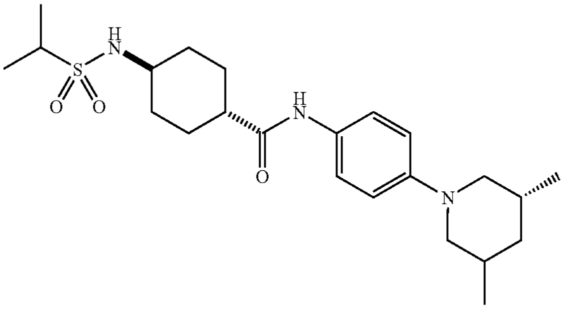
-continued
Ib-39
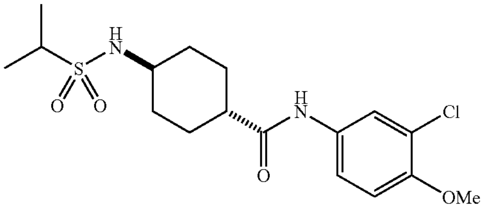
Ib-40
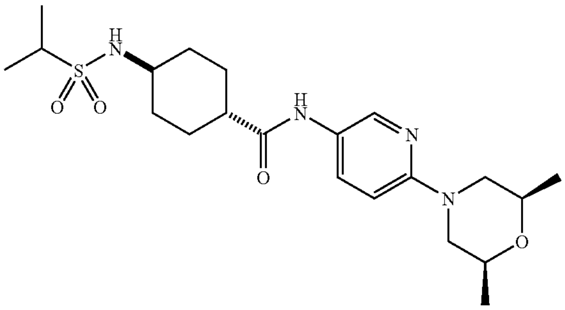
Ib-41
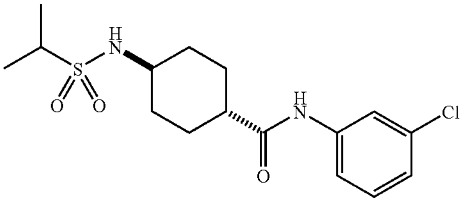
Ib-42
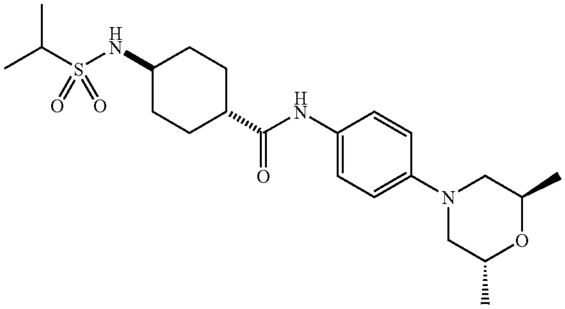
Ib-43
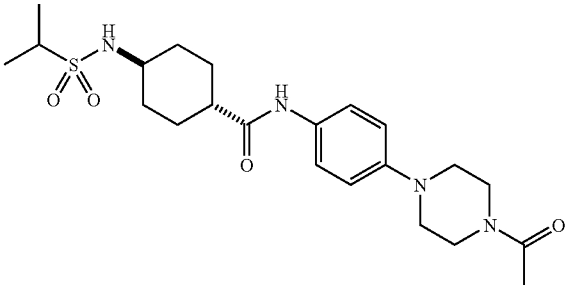

-continued
Ib-44
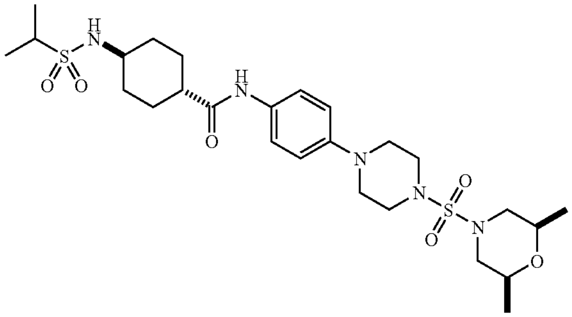
Ib-45
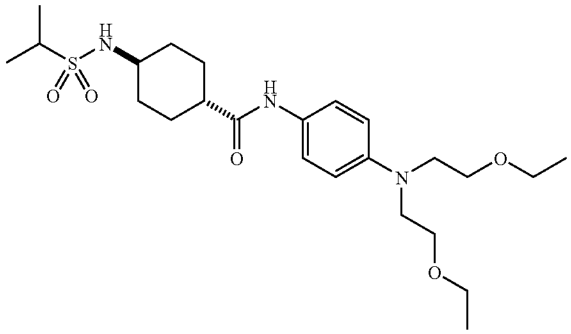
Ib-46
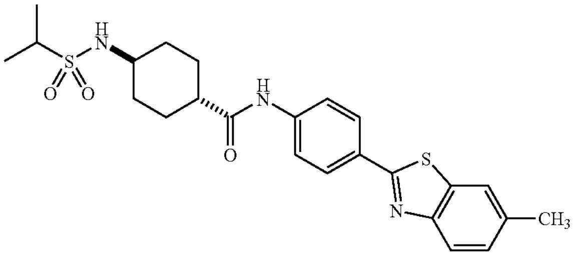
Ib-47
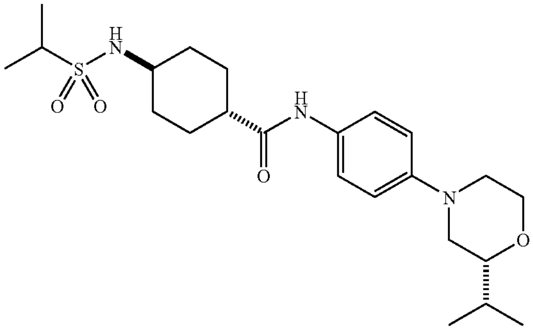
-continued
Ib-48
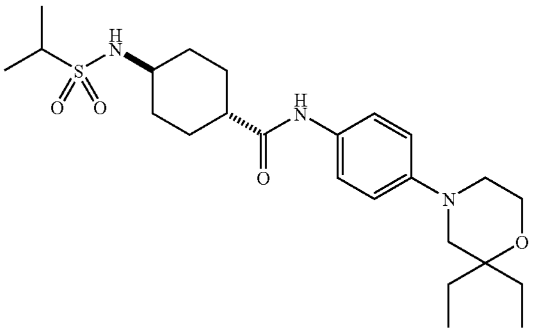
Ib-49
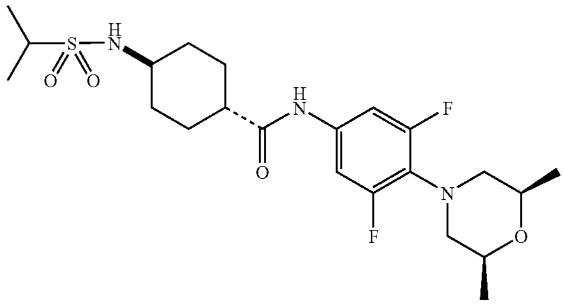
Ib-50
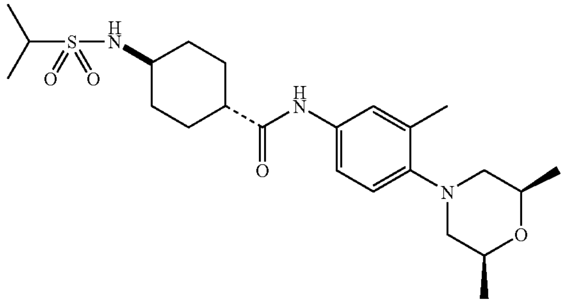
Ib-51
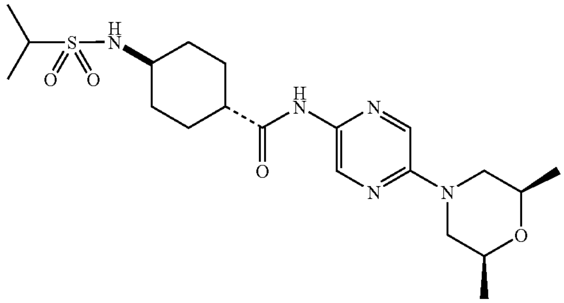
Ib-52
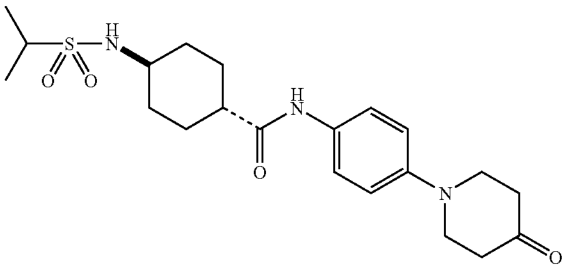

-continued
Ib-53
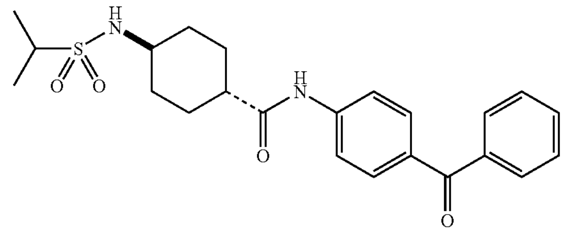
Ib-54
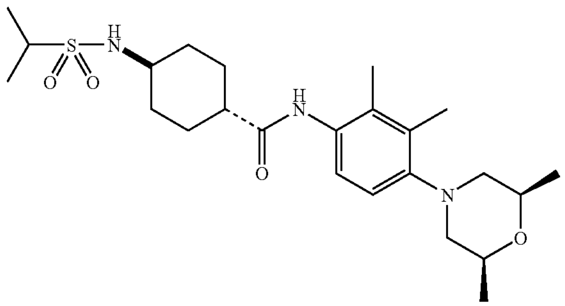
Ib-55
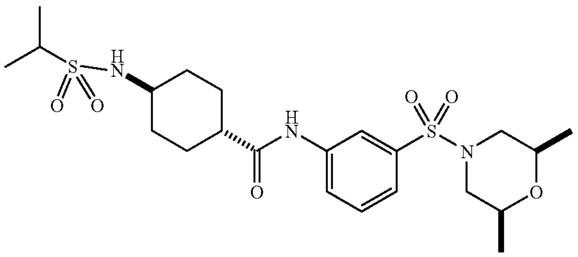
Ib-56
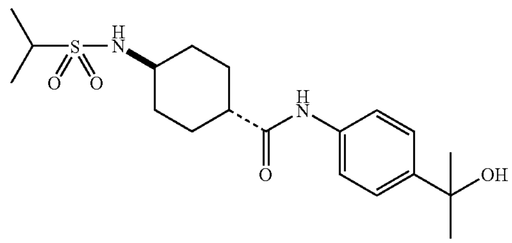
Ib-57
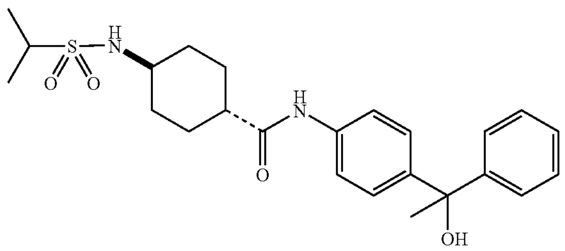
-continued
Ib-58
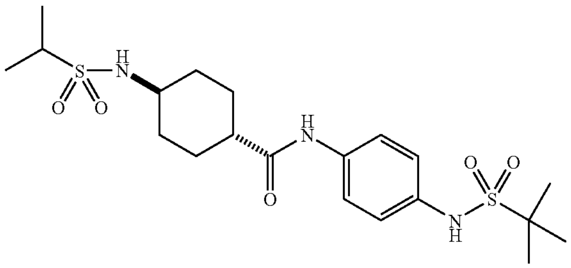
Ib-59
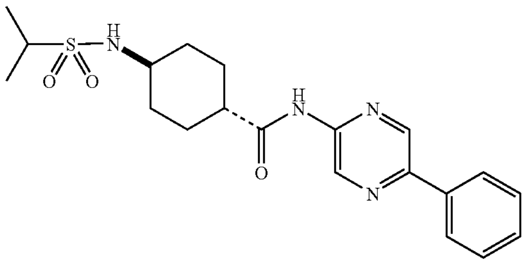
Ib-60
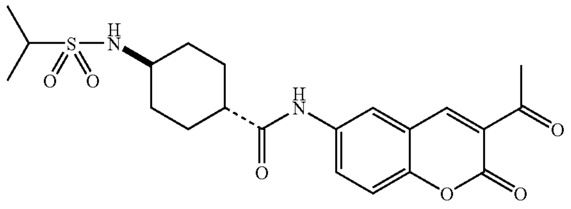
Ib-61
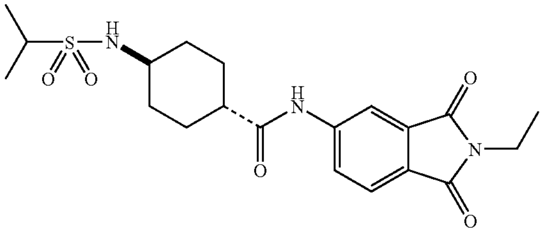
Ib-62
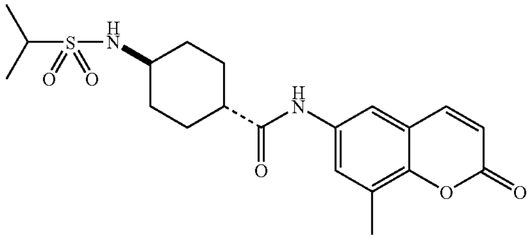
Ib-63
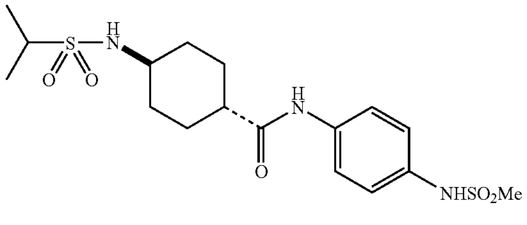

-continued
Ib-64
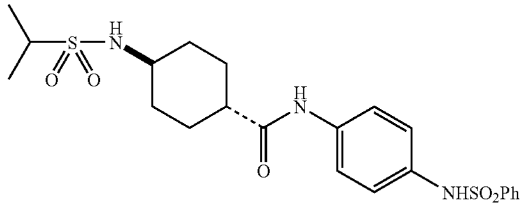
Ib-65
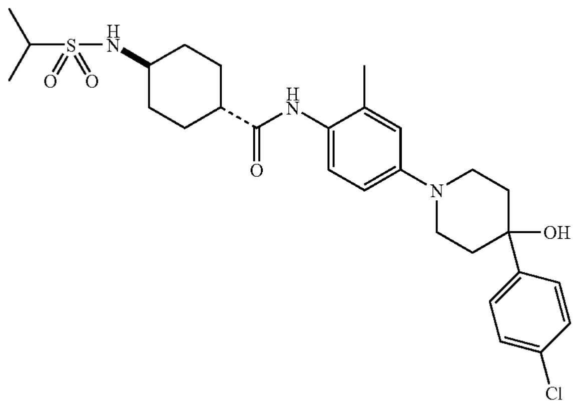
Ib-66
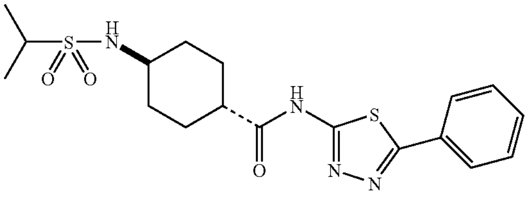
Ib-68
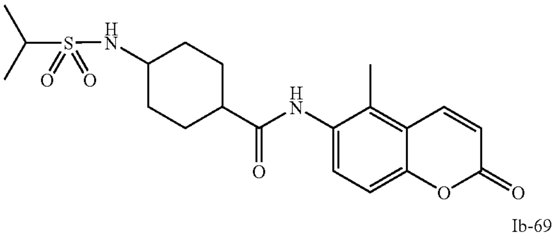
Ib-69
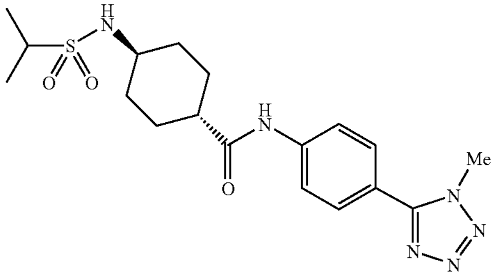
-continued
Ib-70
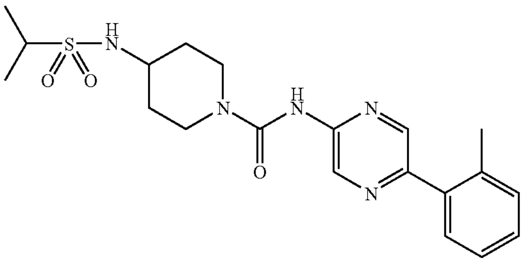
Ib-71
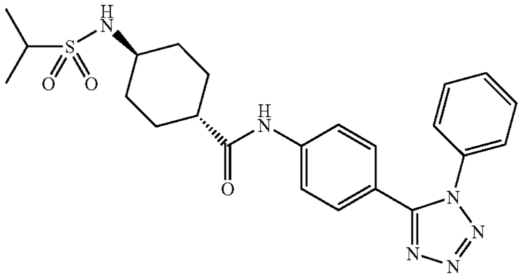
Ib-72
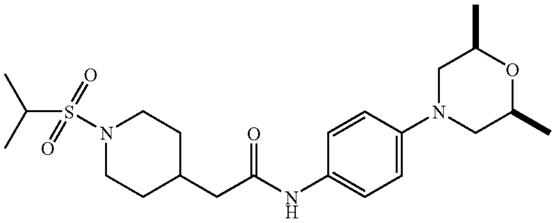
Ib-73
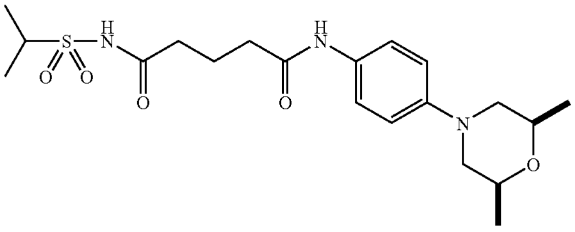
Ib-74
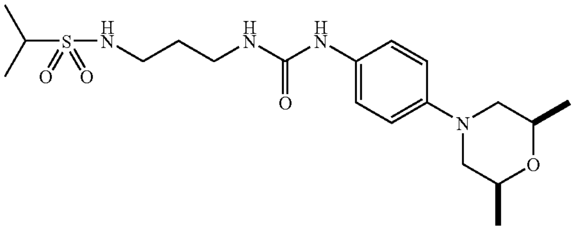
Ib-75
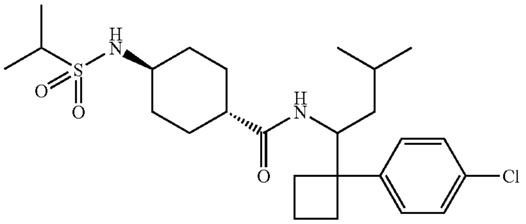

-continued
Ib-76
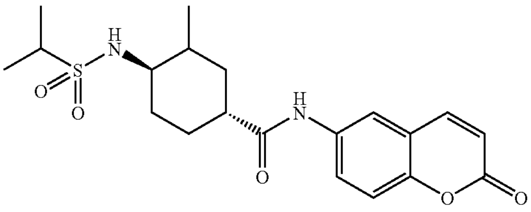
Ib-77
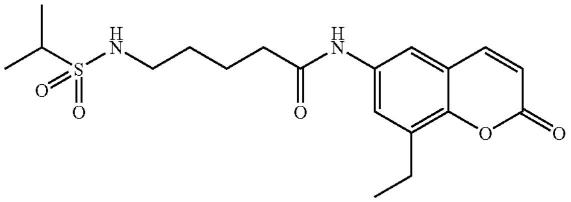
Ib-78
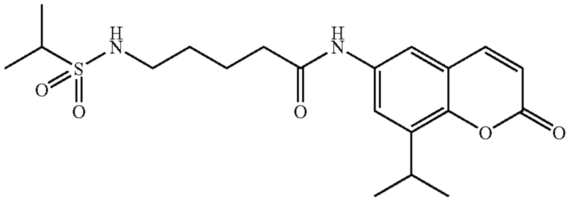
Ib-79
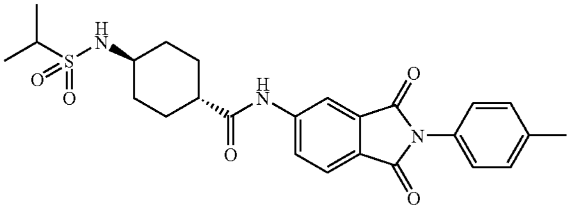
Ib-80
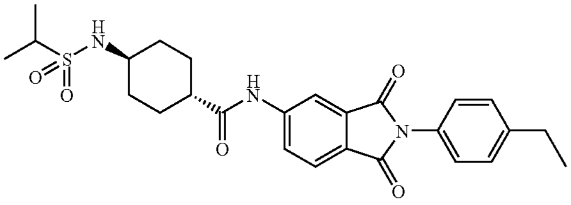
-continued
Ib-81
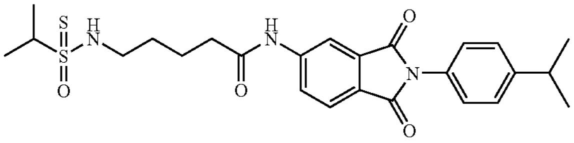
Ib-82
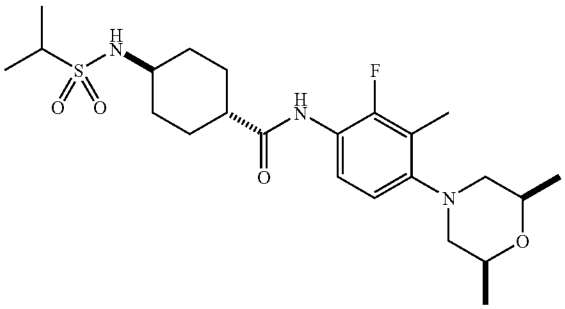
Ib-83
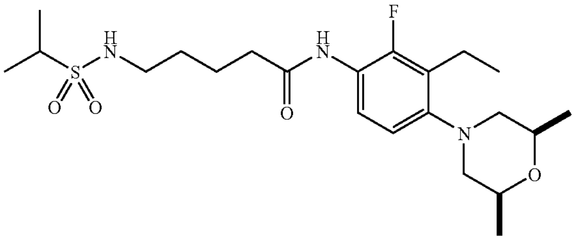
Ib-84
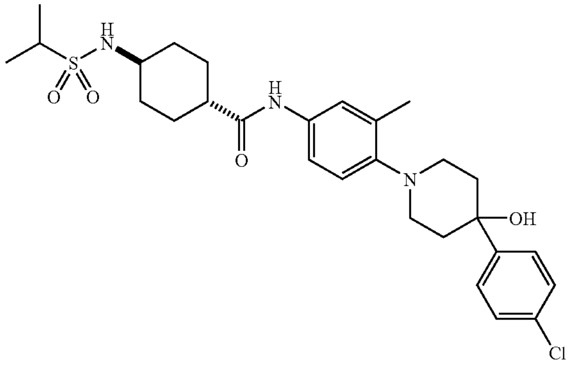
Ib-85
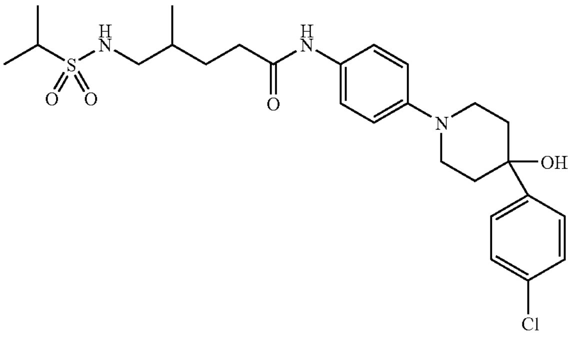

-continued
Ib-86
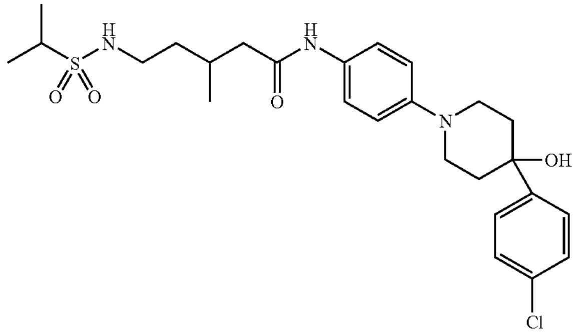
Ib-87
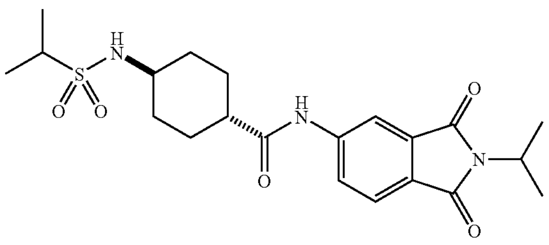
Ib-88
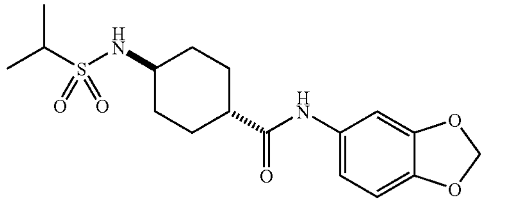
Ib-89
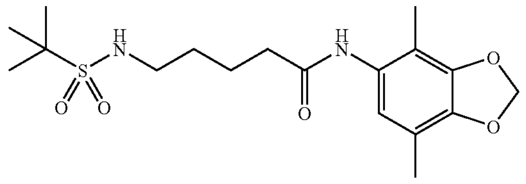
Ib-90
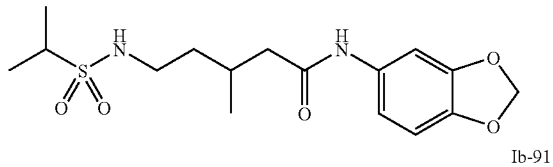
Ib-91
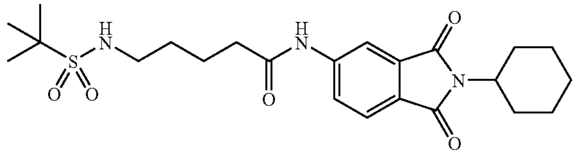
Ib-92
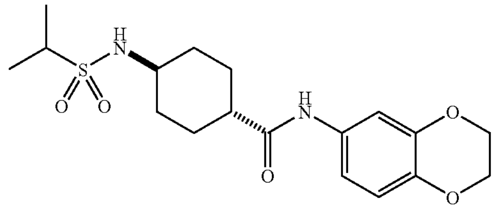
-continued
Ib-93
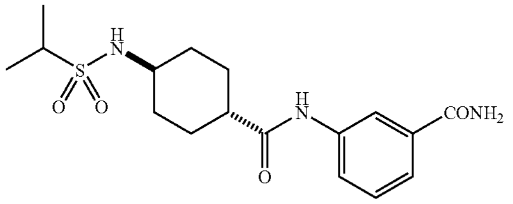
Ib-94
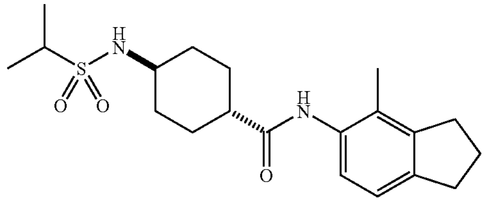
Ib-95
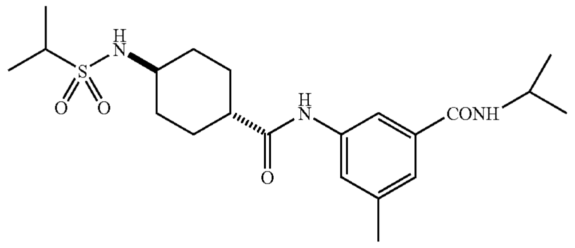
Ib-96
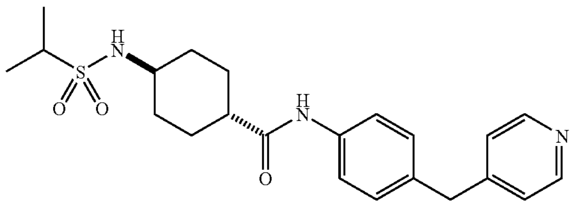
Ib-97
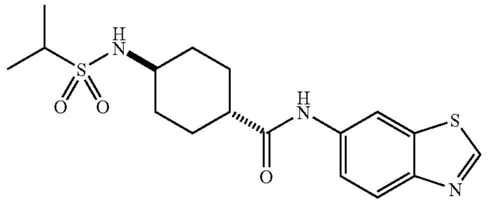
Ib-98
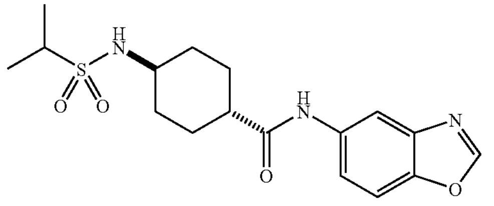
Ib-99
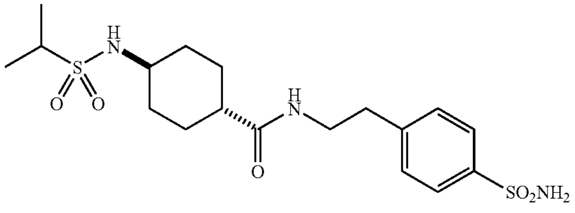

-continued
Ib-100
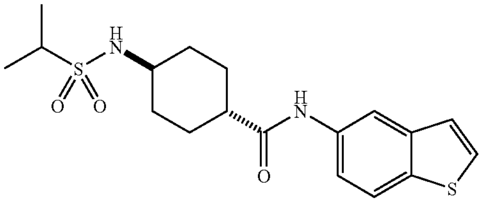
Ib-101
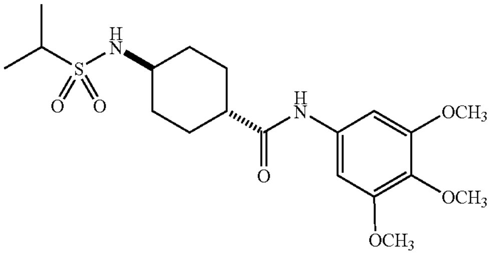
Ib-102
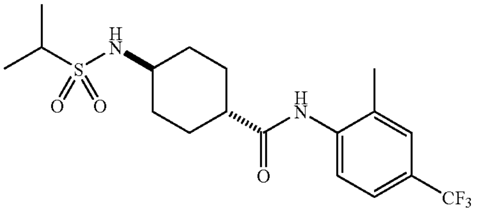
Ib-103
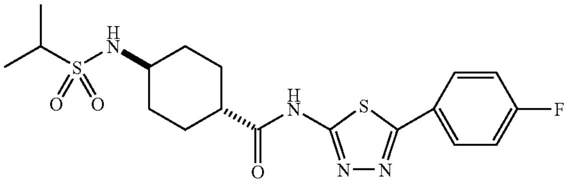
Ib-104
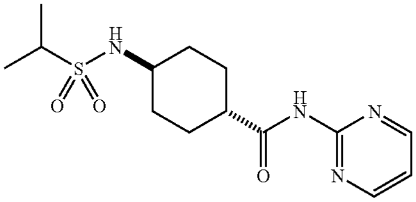
Ib-105
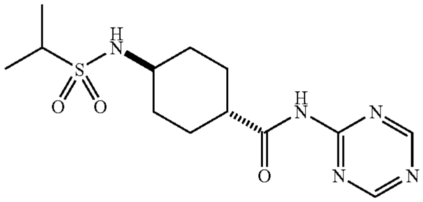
Ib-106
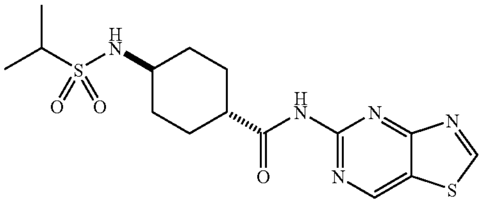
-continued
Ib-107
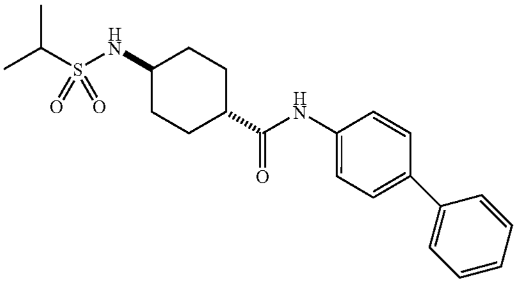
Ib-108
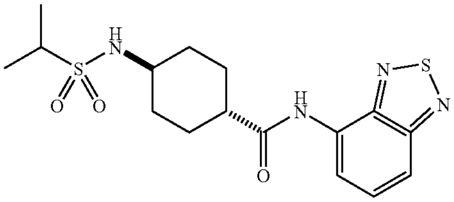
Ib-109
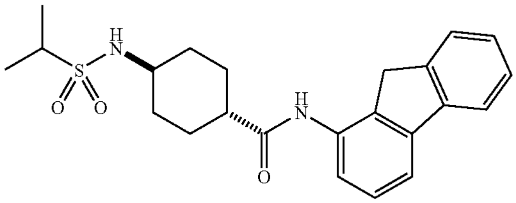
Ib-110
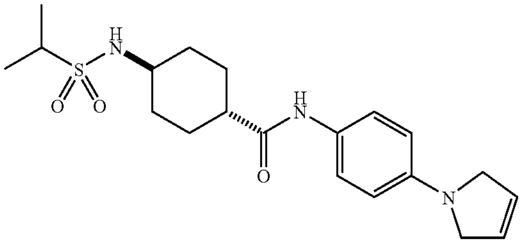
Ib-111
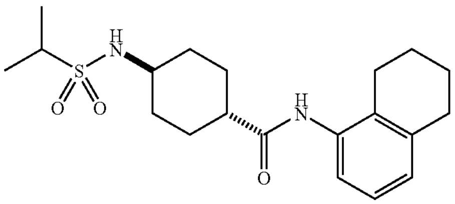
Ib-112
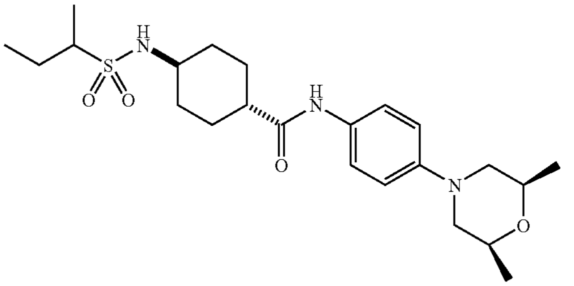

-continued
Ib-113
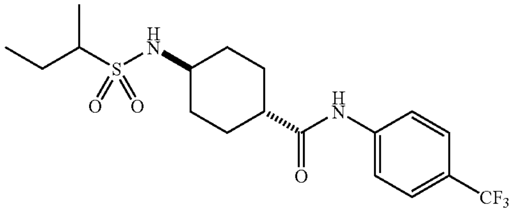
Ib-114
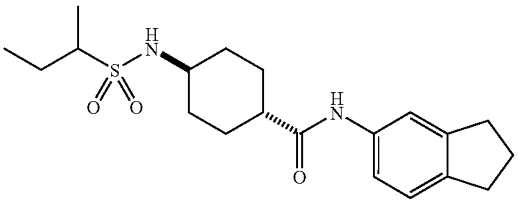
Ib-115
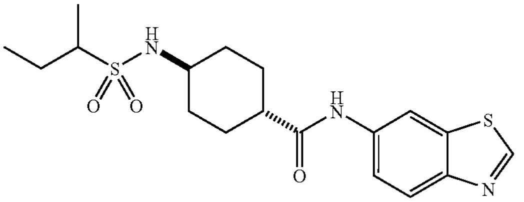
Ib-116
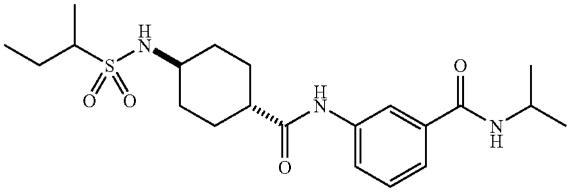
Ib-117
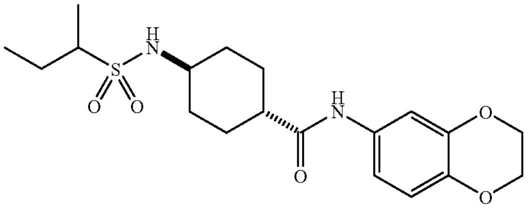
Ib-118
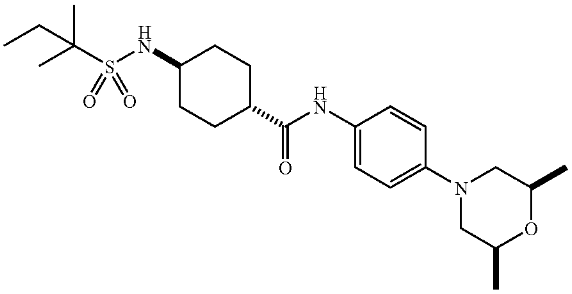
-continued
Ib-119
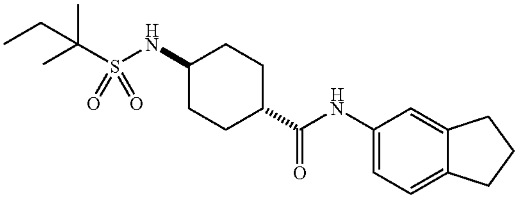
Ib-120
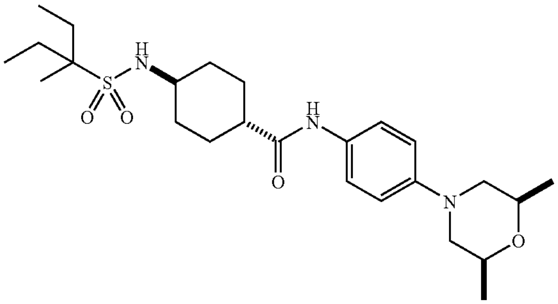
Ib-121
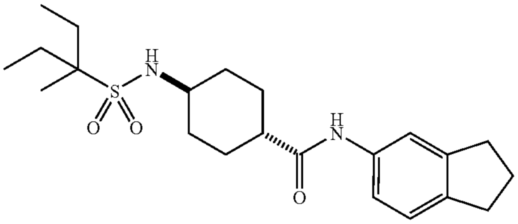
Ib-122
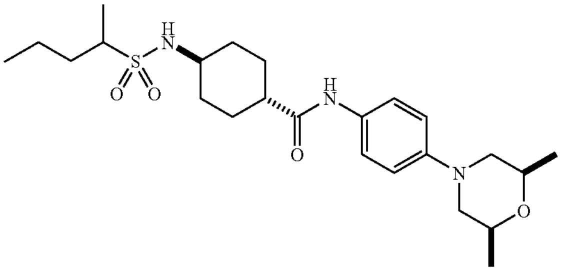
Ib-123
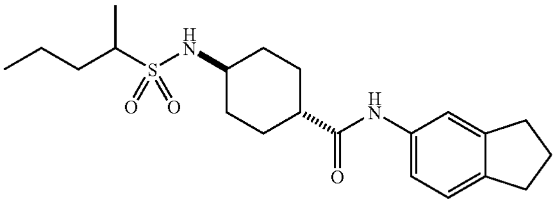
Ib-124
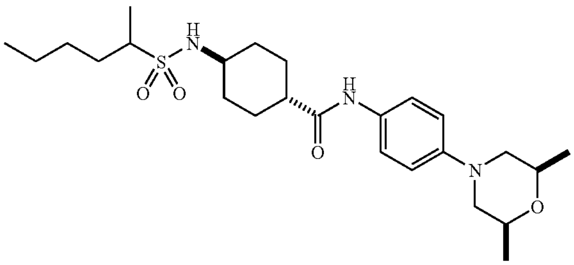

-continued
Ib-125
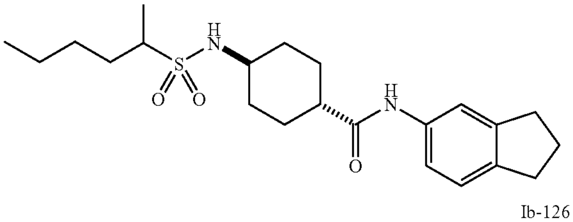
Ib-126
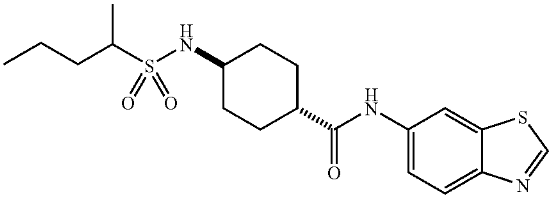
Ib-127
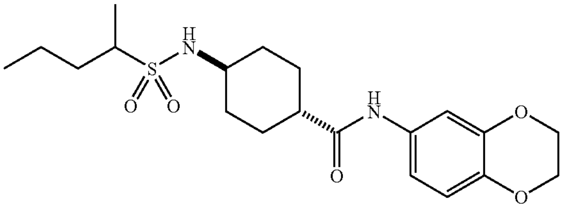
Ib-128
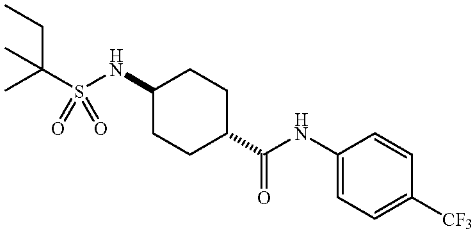
Ib-129
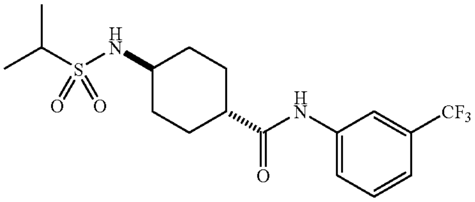
Ib-130
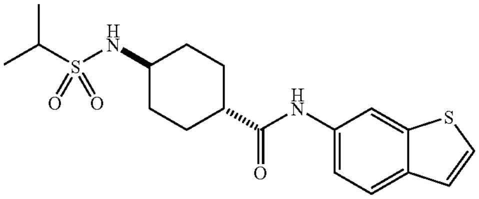
Ib-131
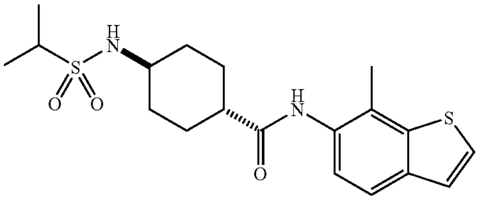
Ib-132
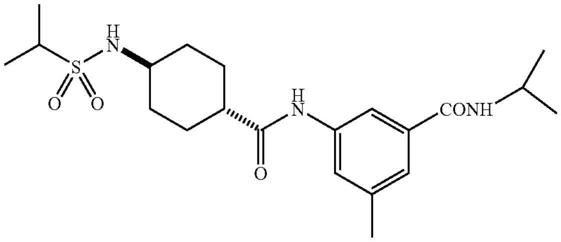
Ib-133
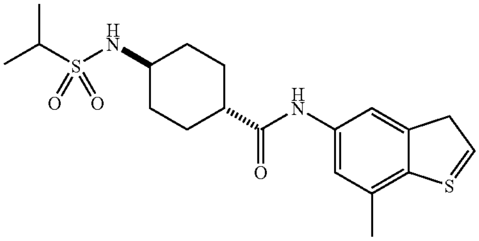
Ib-134
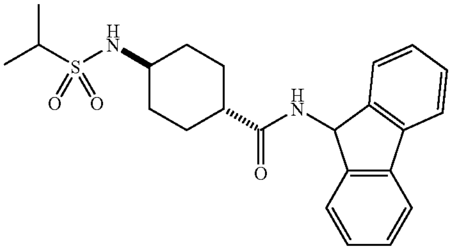
Ib-135
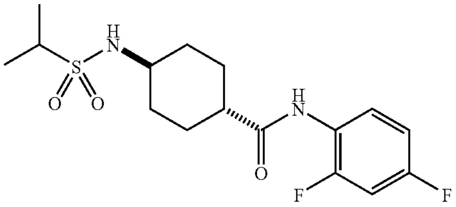
Ib-136
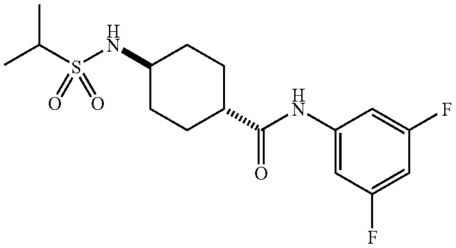
Ib-137
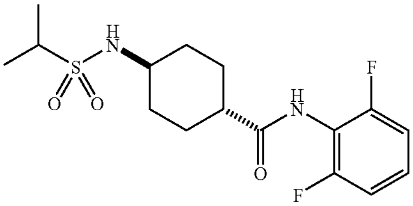

-continued
Ib-138
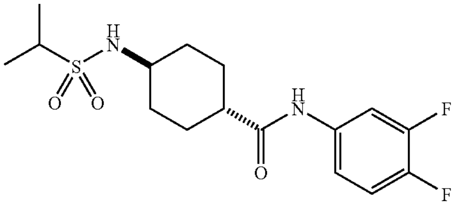
Ib-139
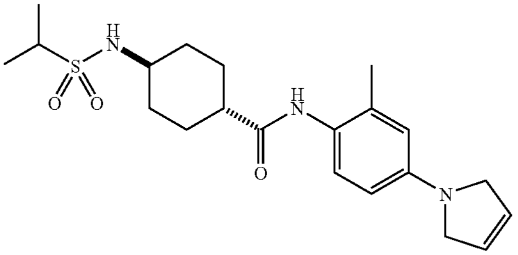
Ib-140
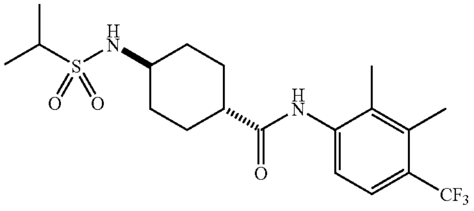
Ib-141
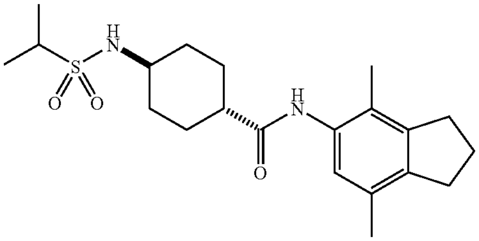
Ib-142
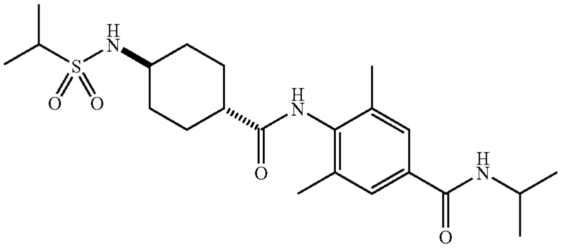
Ib-143
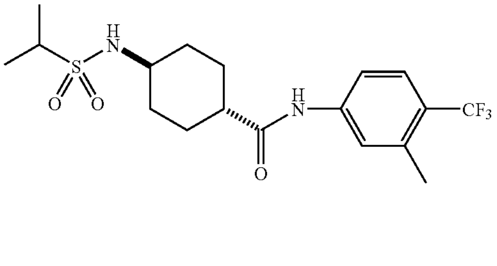
-continued
Ib-144
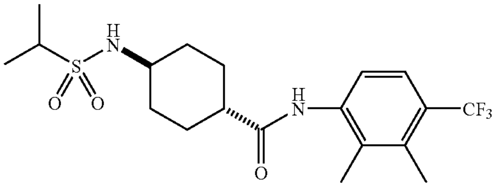
Ib-145
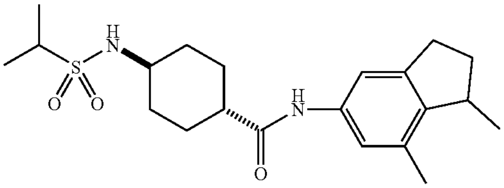
Ib-146
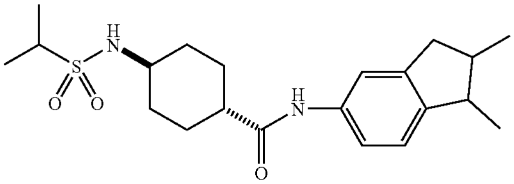
Ib-147
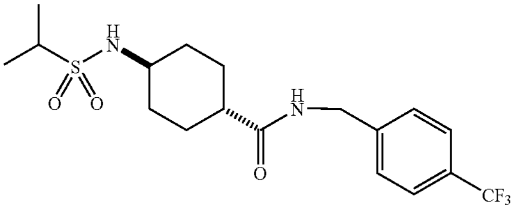
Ib-148
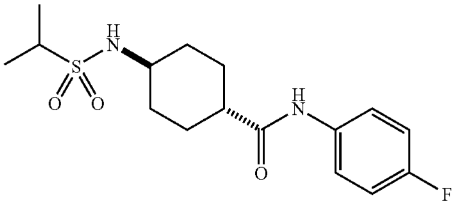
Ib-149
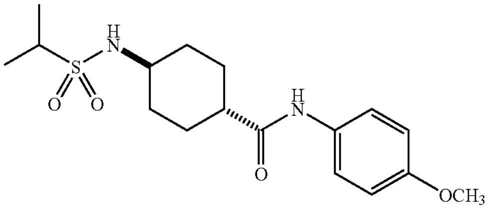
Ib-150
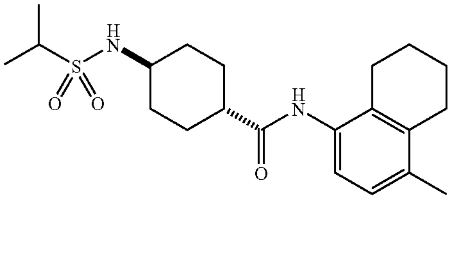

-continued
Ib-151
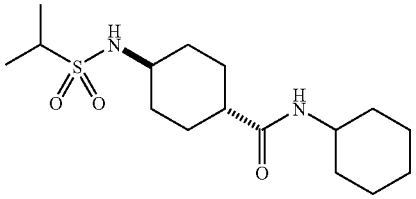
Ib-152
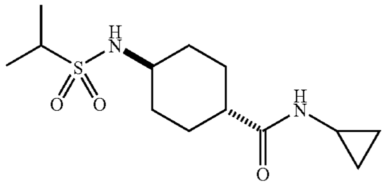
Ib-153
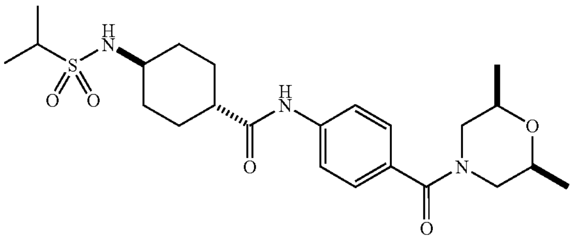
Ib-154
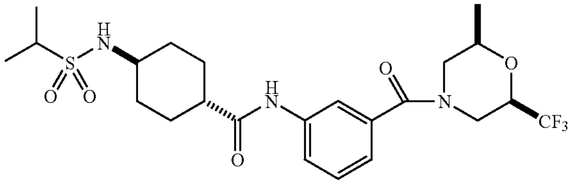
Ib-155
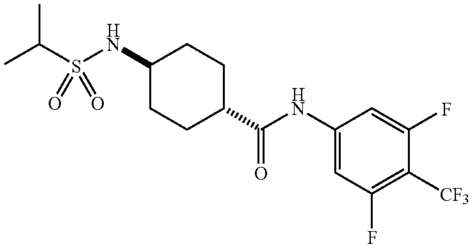
Ib-156
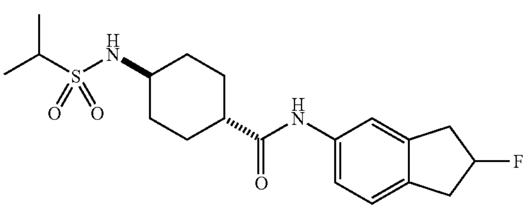
-continued
Ib-I57
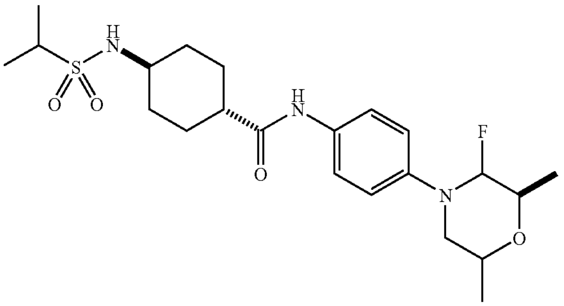
Ib-158
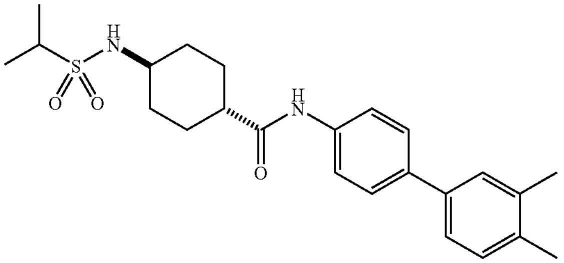
Ib-159
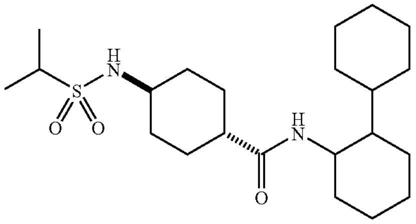
Ib-160
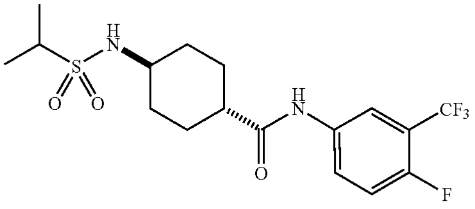
Ib-161
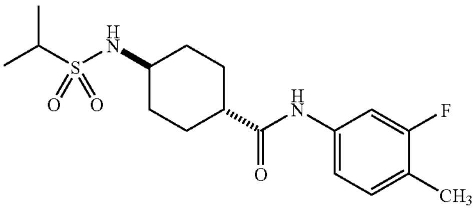
Ib-162
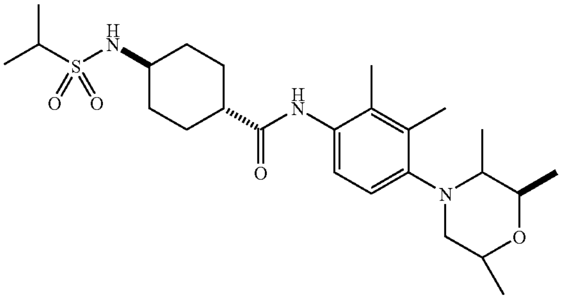

-continued
Ib-I63
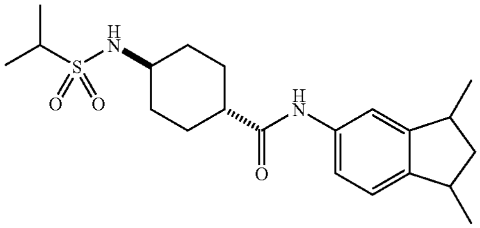
Ib-164
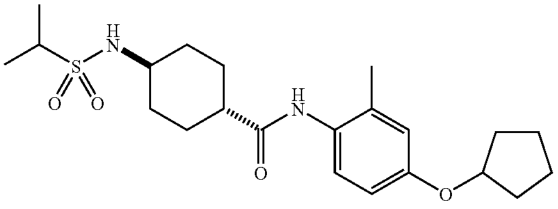
Ib-165
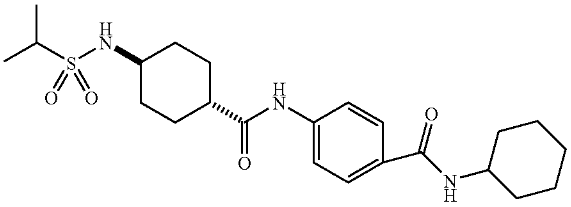
Ib-166
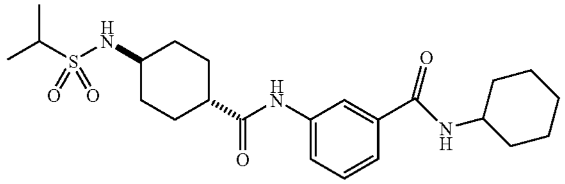
Ib-167
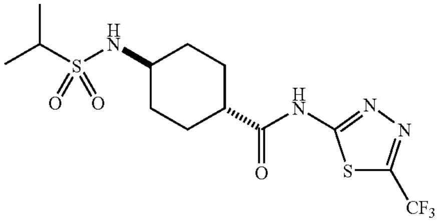
Ib-168
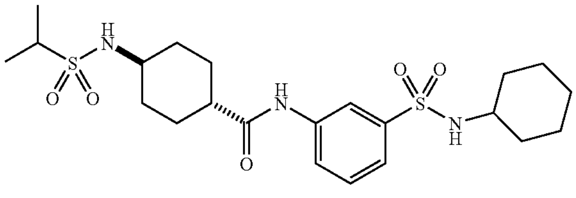
Ib-169
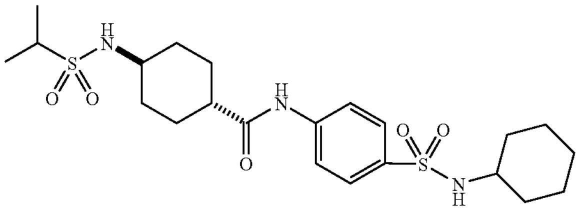
-continued
Ib-171
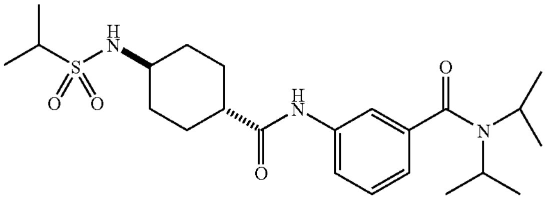
Ib-172
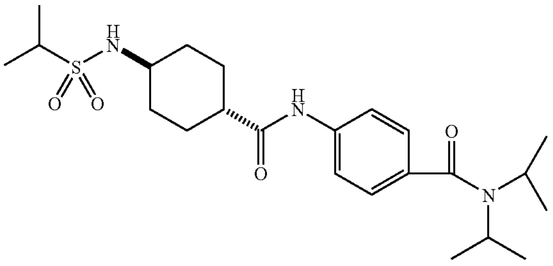
Ib-173
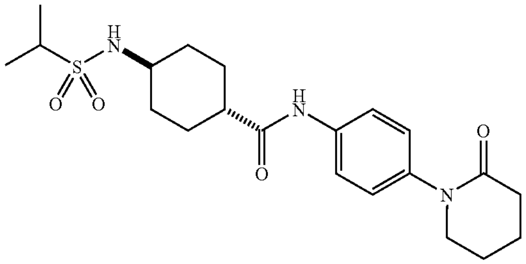
Ib-174
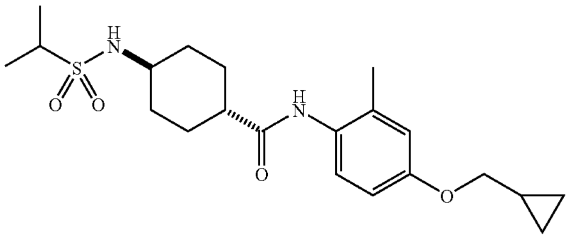
Ib-175
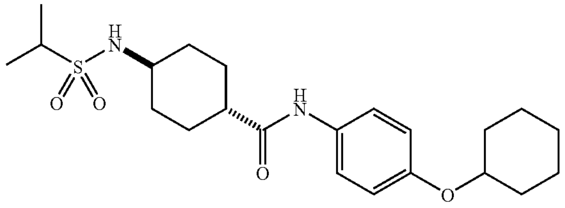
Ib-176
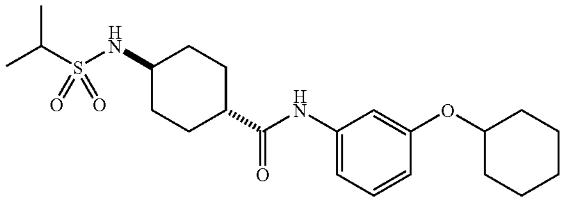

-continued
Ib-177
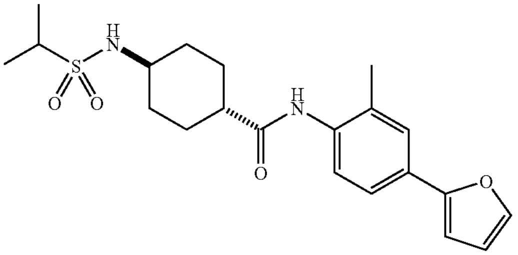
Ib-178
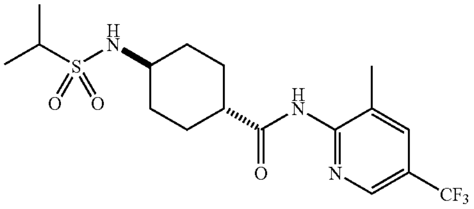
Ib-179
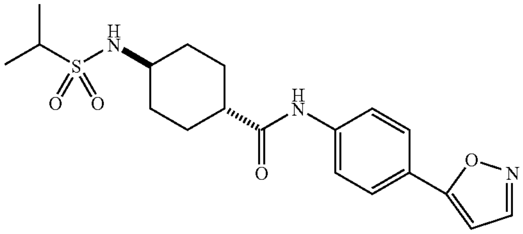
Ib-180
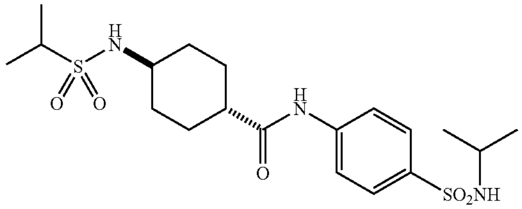
Ib-181
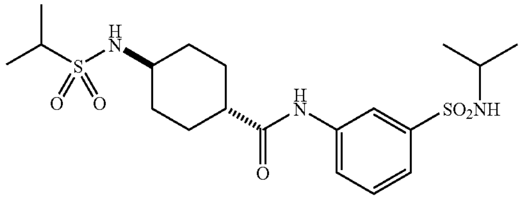
Ib-182
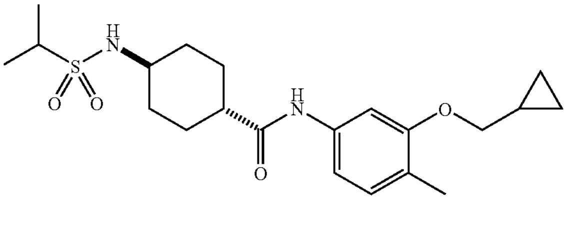
-continued
Ib-183
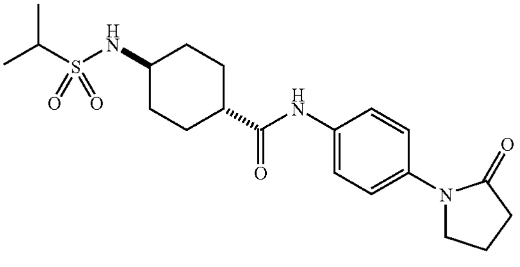
Ib-184
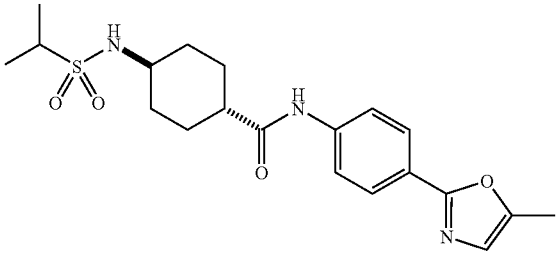
Ib-185
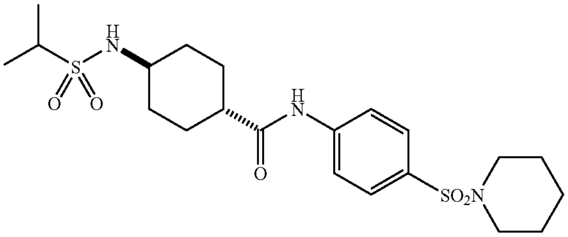
Ib-186
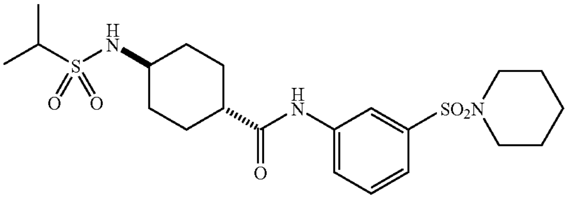
Ib-187
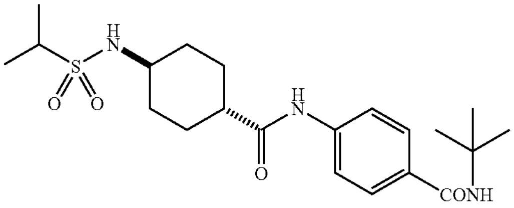
Ib-188
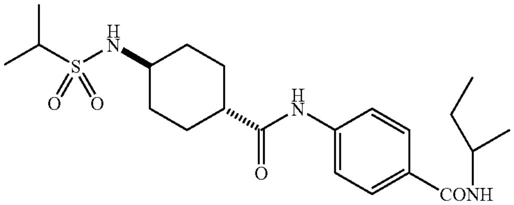

-continued
Ib-189
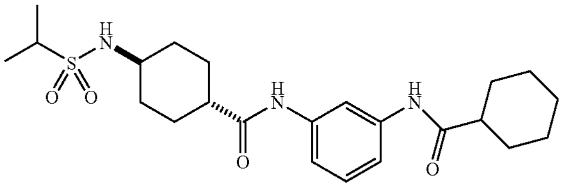
Ib-190
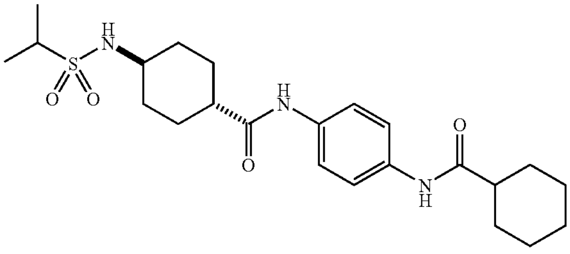
Ib-191
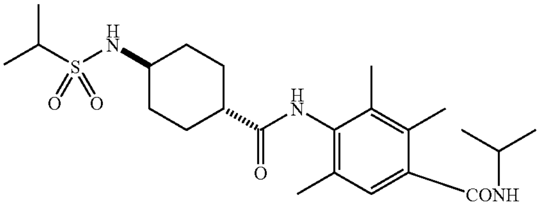
Ib-192
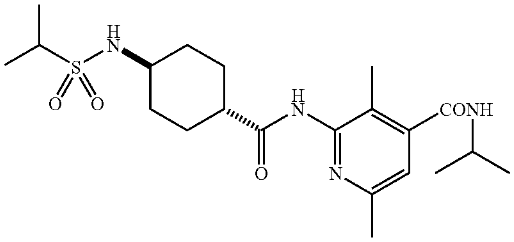
Ib-193
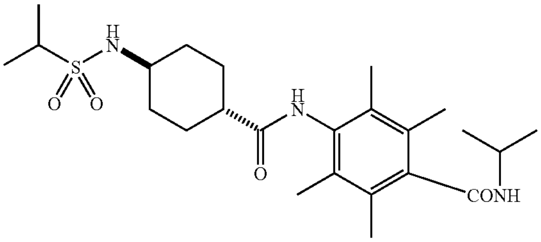
Ib-194
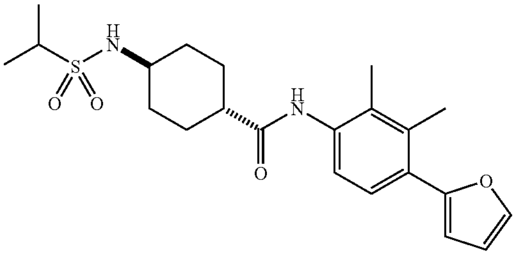
-continued
Ib-195
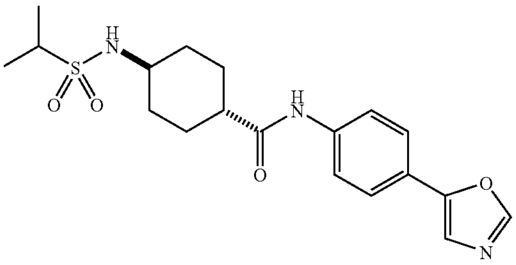
Ib-196
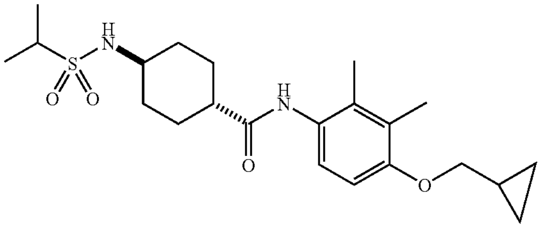
Ib-197
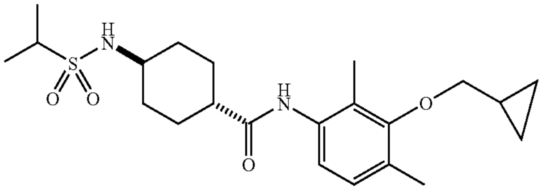
Ib-198
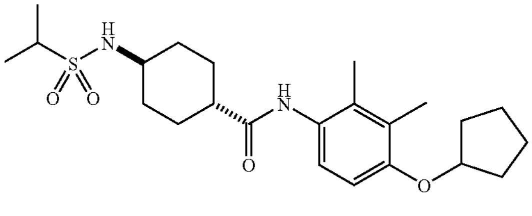
Ib-199
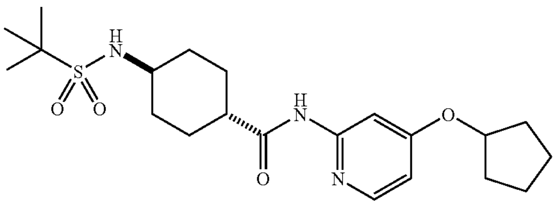
Ib-200
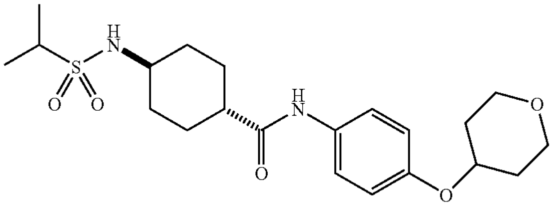

-continued
Ib-201
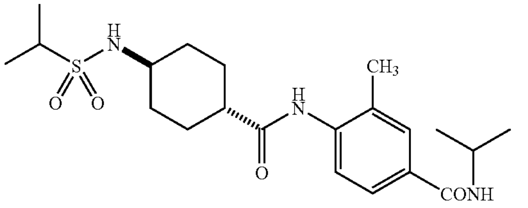
Ib-202
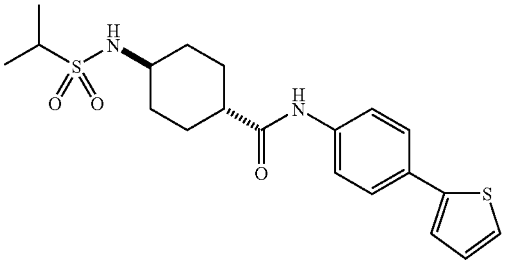
Ib-203
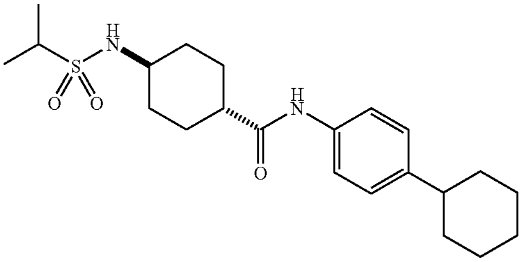
Ib-204
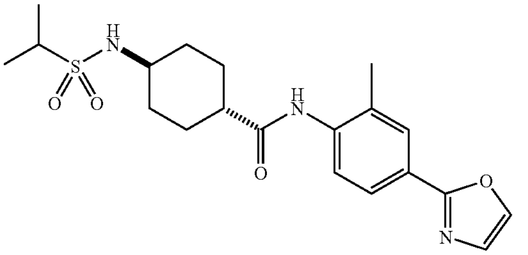
Ib-205
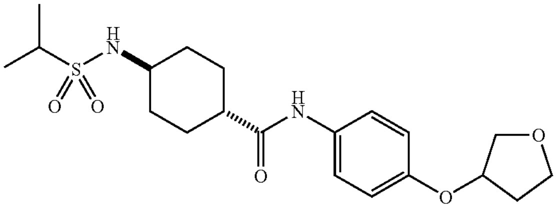
Ib-206
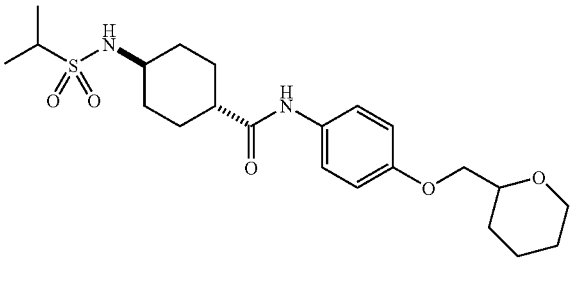
-continued
Ib-207
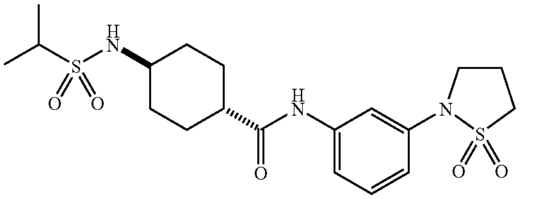
Ib-208
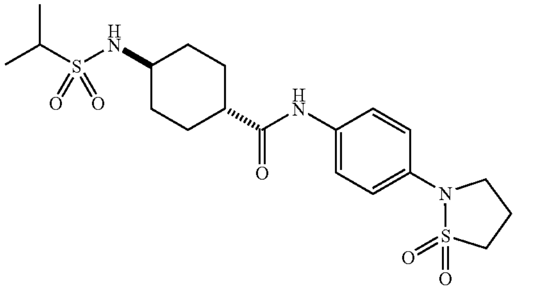
Ib-209
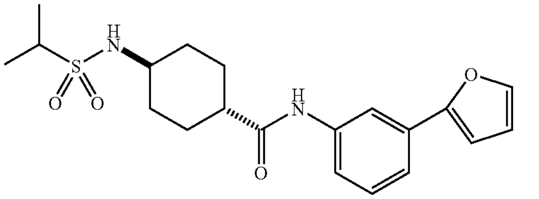
Ib-210
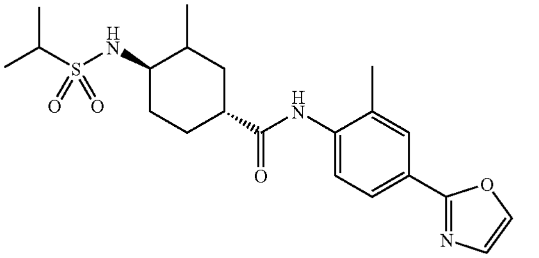
Ib-211
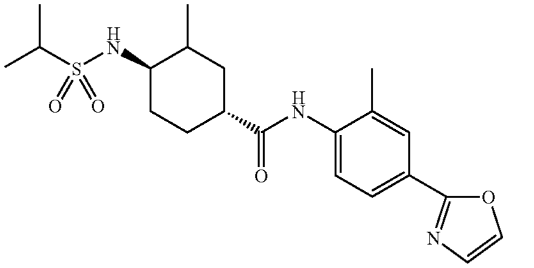
Ib-212
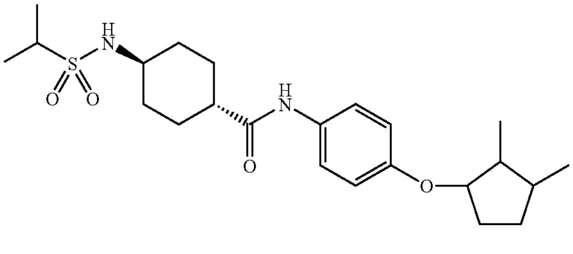

-continued
Ib-213
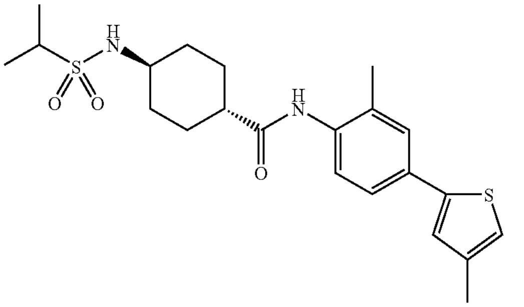
Ib-214
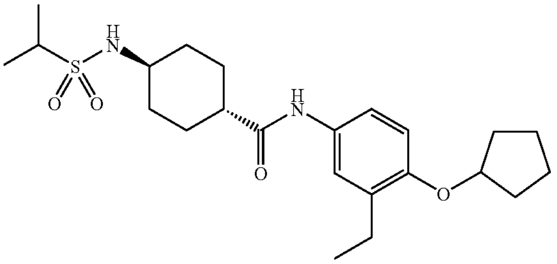
Ib-215
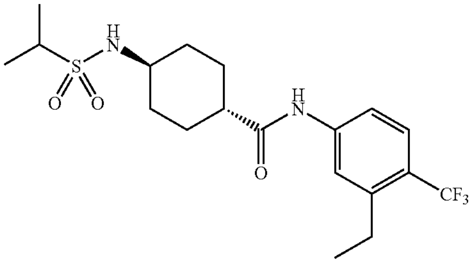
Ib-216
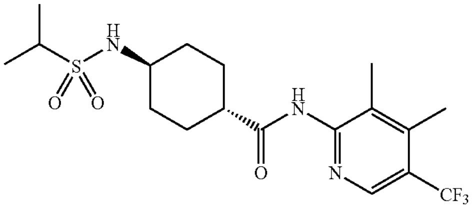
Ib-219
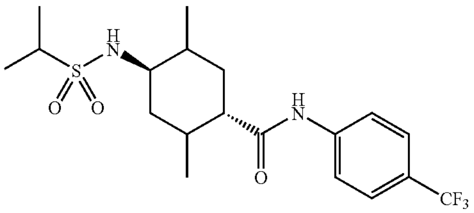
Ib-220
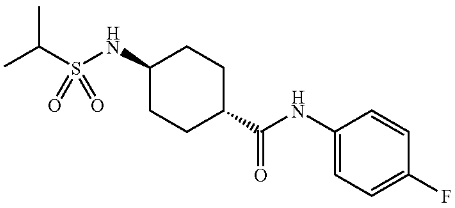
-continued
Ib-221
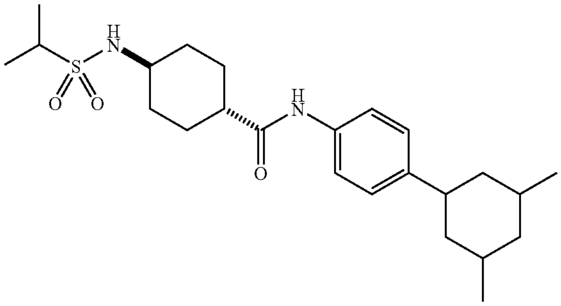
Ib-222
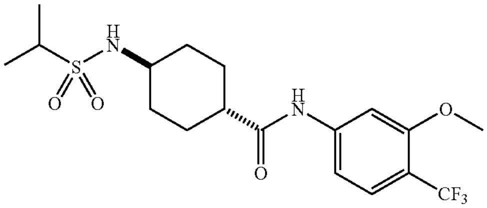
Ib-223
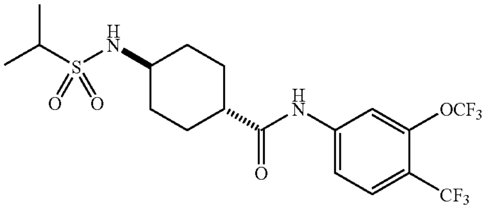
Ib-224
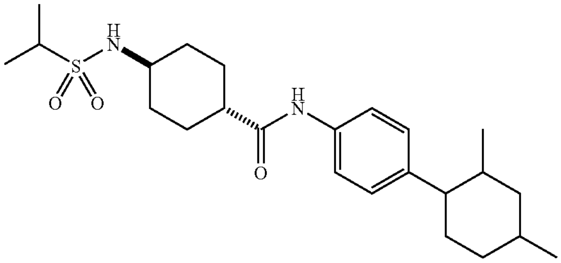
Ib-225
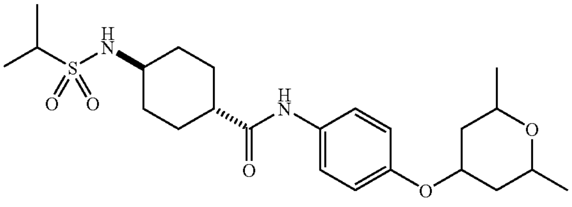
Ib-226
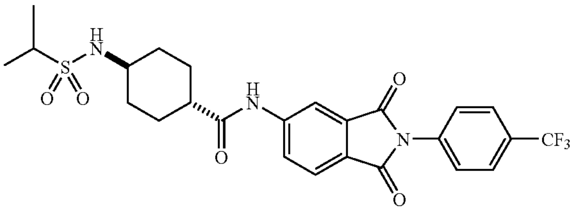

-continued
Ic-1
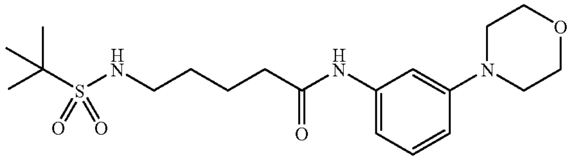
Ic-2
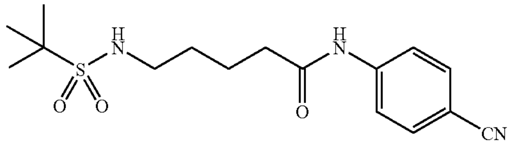
Ic-5
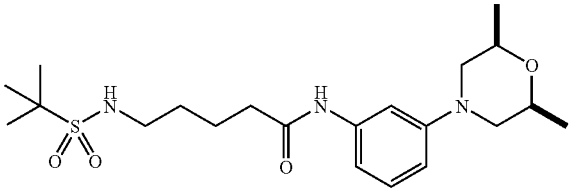
Ic-7
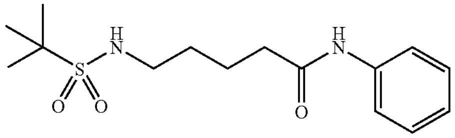
Ic-8
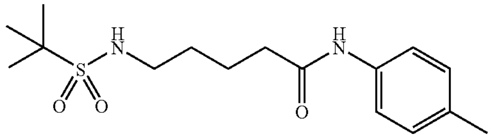
Ic-9
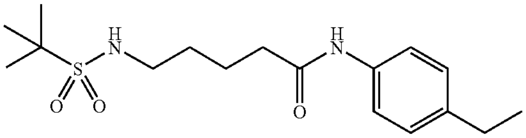
Ic-10
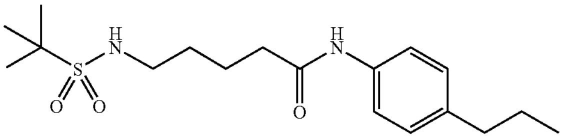
Ic-11
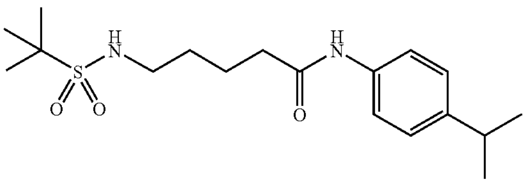
Ic-12
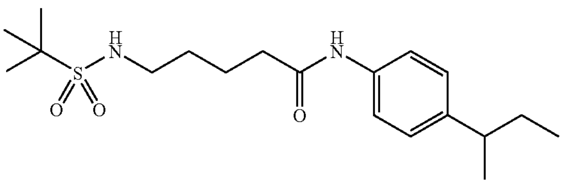
-continued
Ic-13
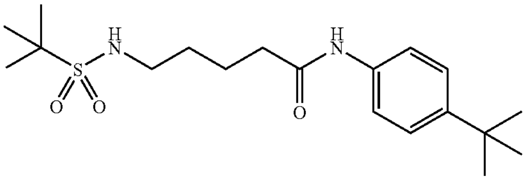
Ic-14
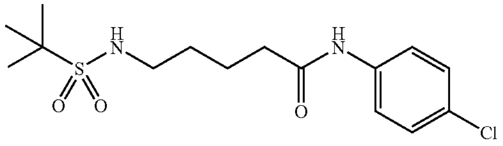
Ic-16
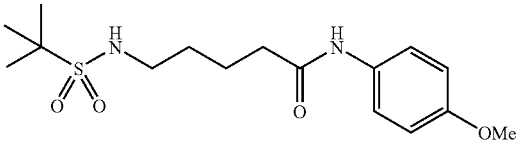
Ic-17
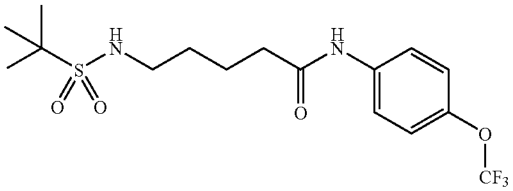
Ic-18
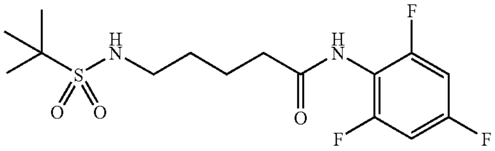
Ic-19
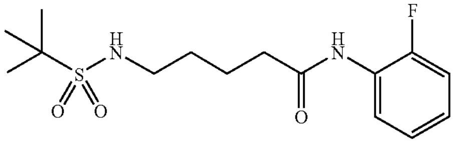
Ic-20
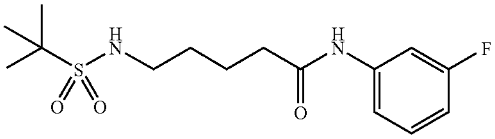
Ic-21
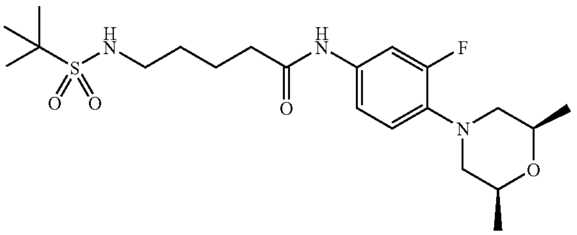

-continued
Ic-22
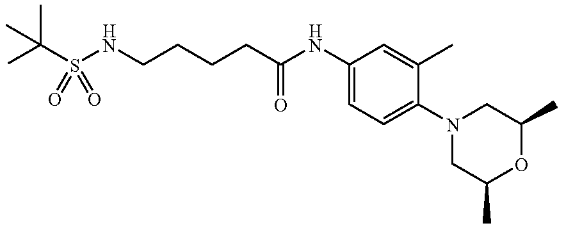
Ic-23
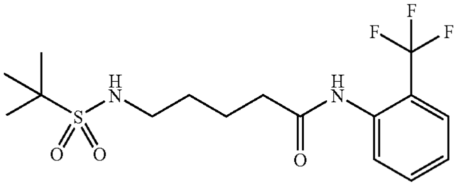
Ic-24
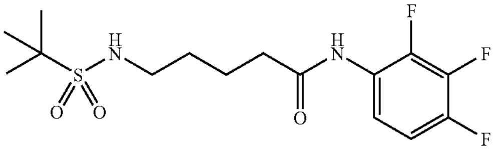
Ic-25
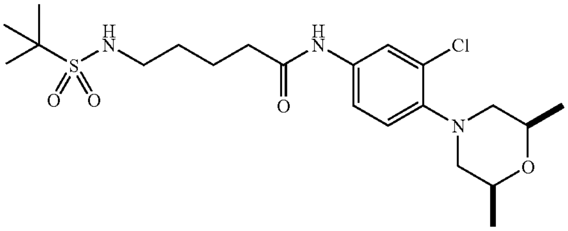
Ic-26
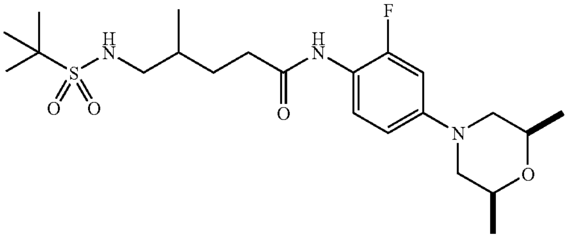
Ic-27
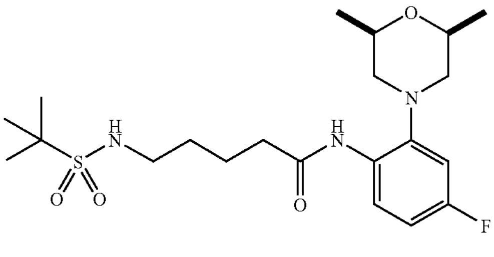
-continued
Ic-28
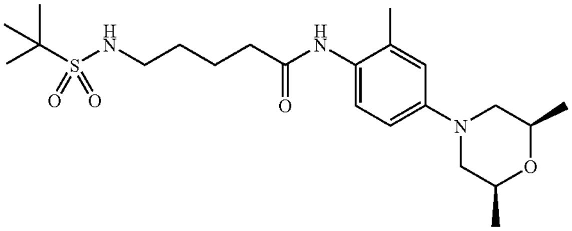
Ic-29
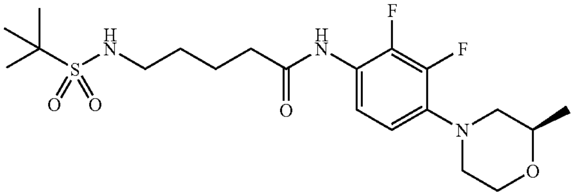
Ic-30
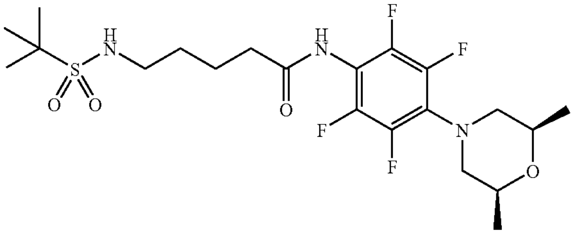
Ic-31
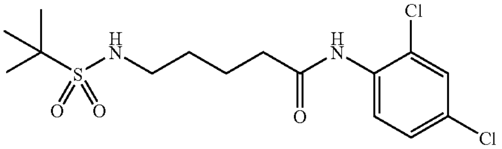
Ic-32
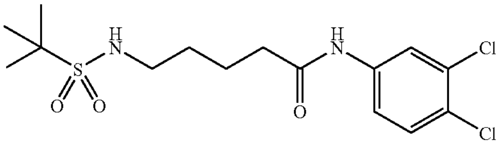
Ic-33
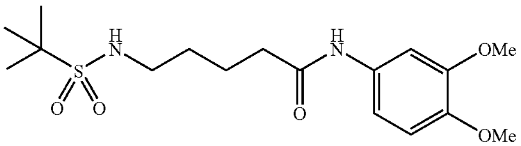
Ic-35
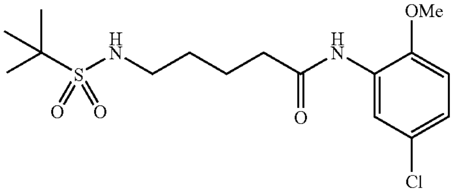
Ic-36
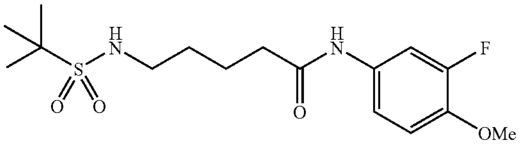

-continued
Ic-37
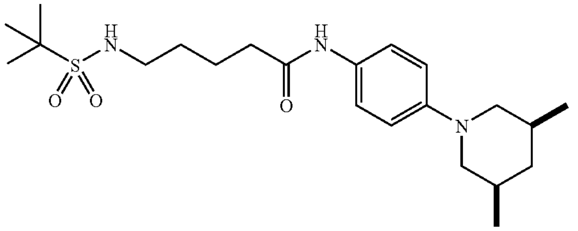
Ic-38
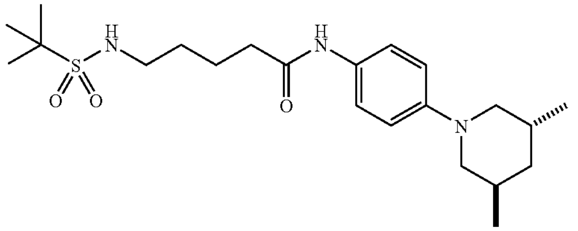
Ic-39
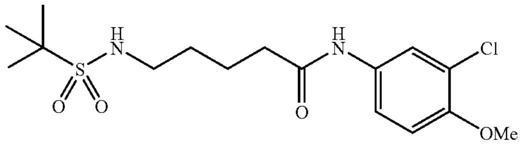
Ic-40
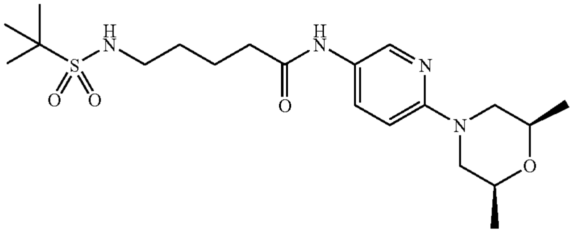
Ic-41
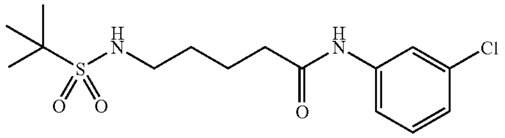
Ic-42
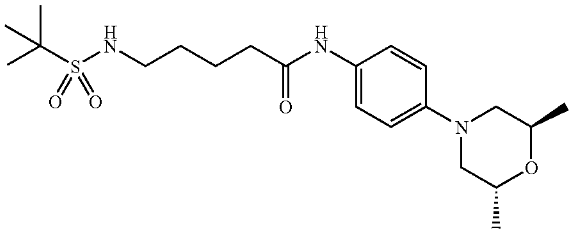
Ic-43
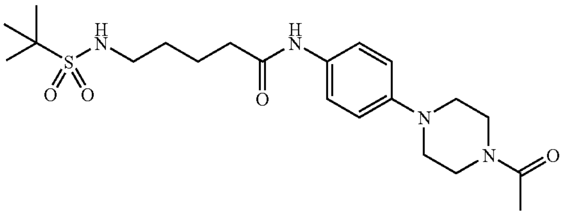
-continued
Ic-44
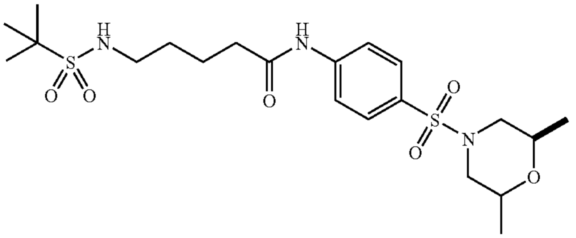
Ic-45
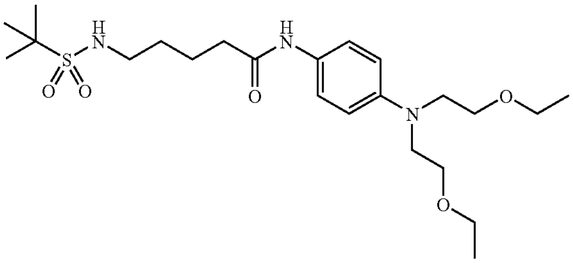
Ic-46
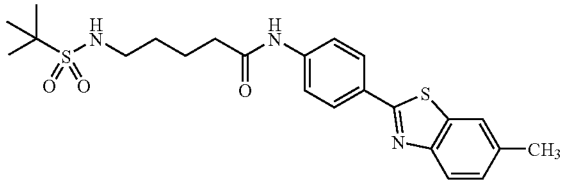
Ic-47
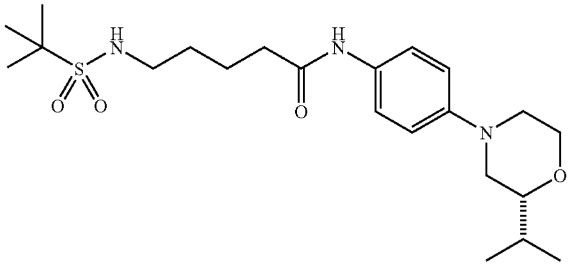
Ic-48
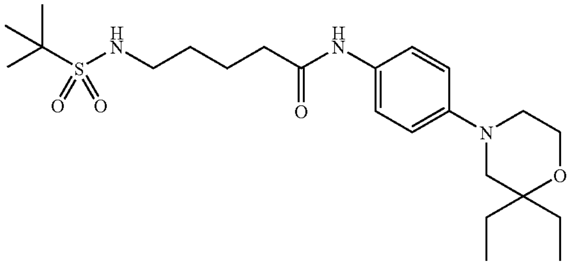
Ic-49
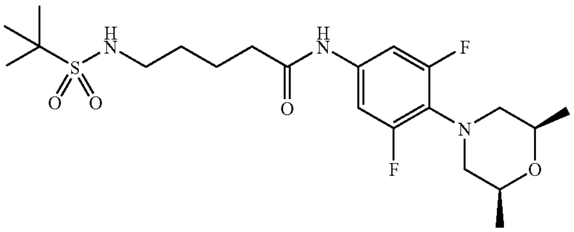

-continued
Ic-50
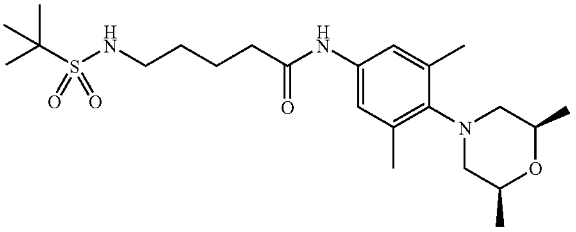
Ic-51
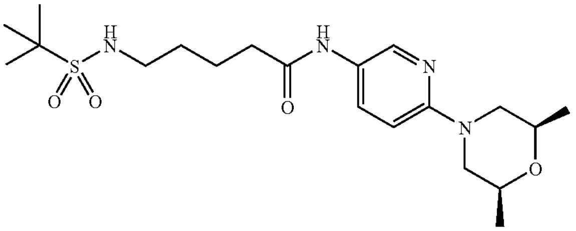
Ic-52
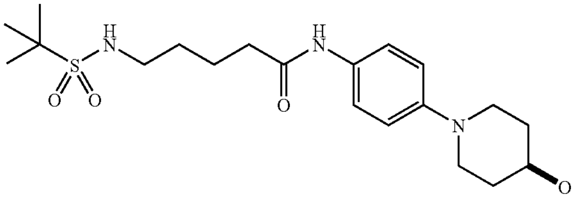
Ic-53
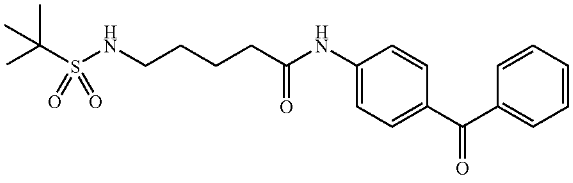
Ic-54
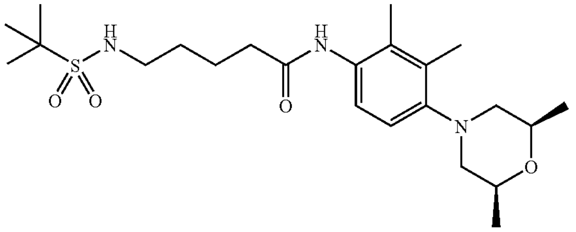
Ic-55
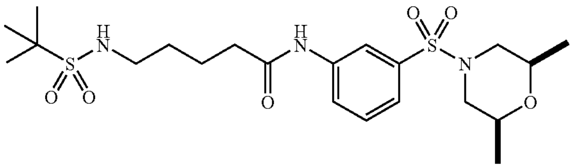
Ic-56
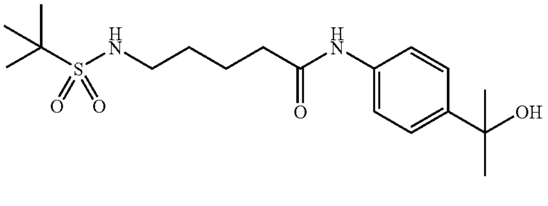
-continued
Ic-57
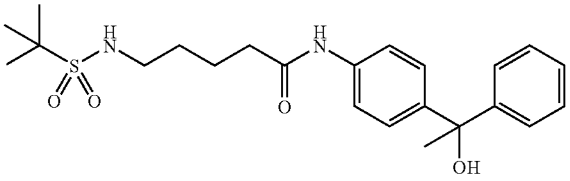
Ic-58
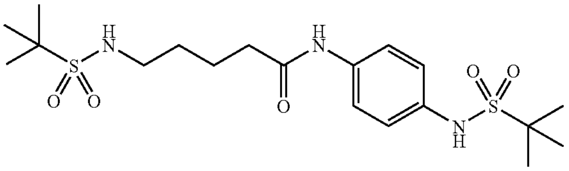
Ic-59
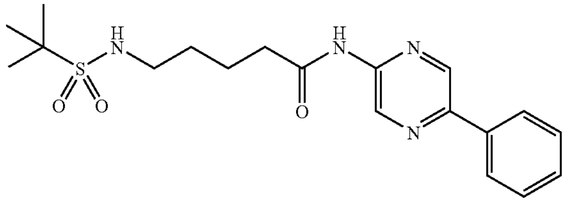
Ic-60
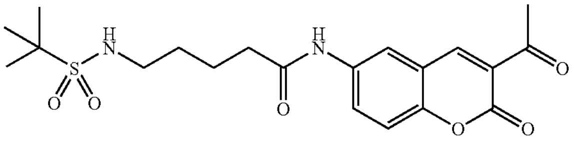
Ic-61
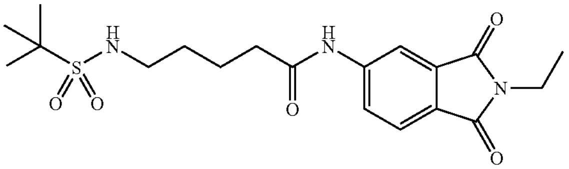
Ic-62
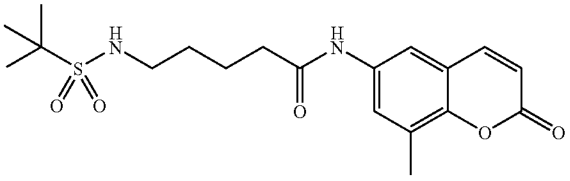
Ic-63
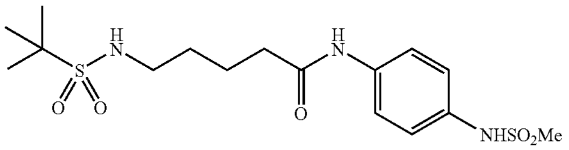
Ic-64
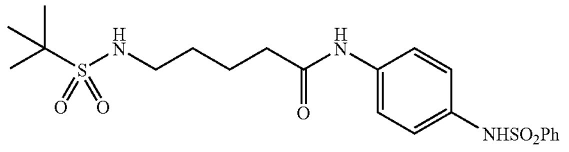

-continued
Ic-65
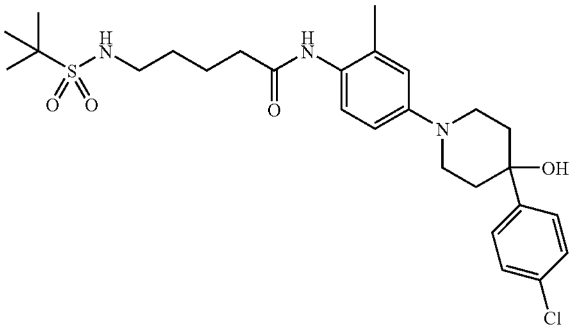
Ic-66
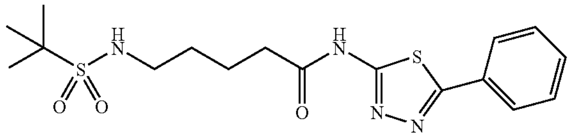
Ic-67
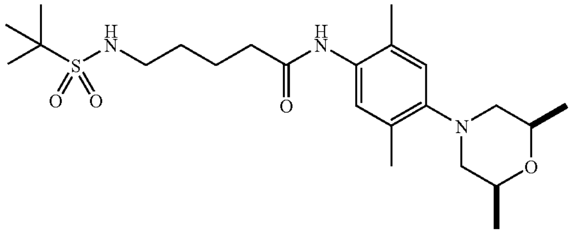
Ic-68
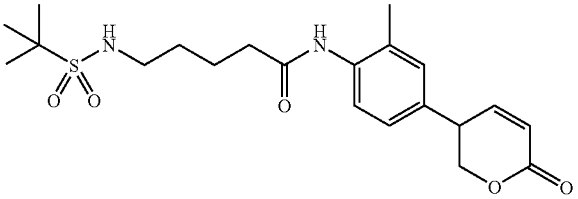
Ic-69
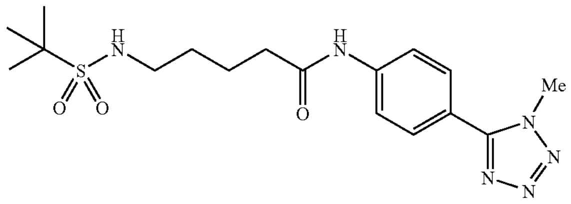
Ic-70
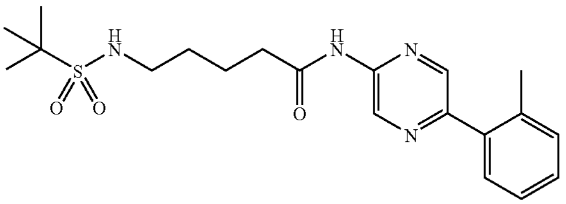
-continued
Ic-71
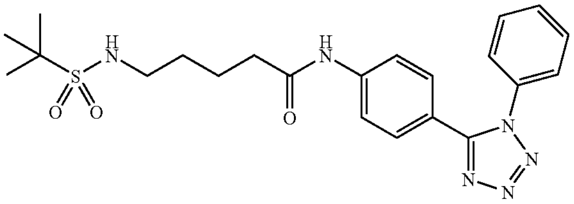
Ic-73
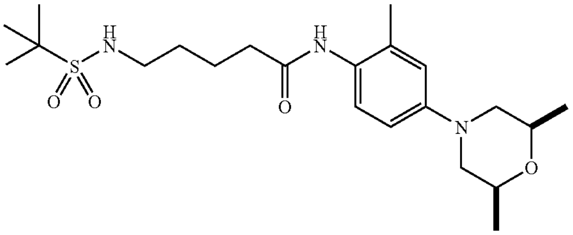
Ic-74
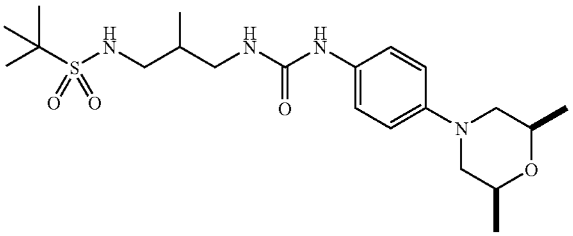
Ic-75
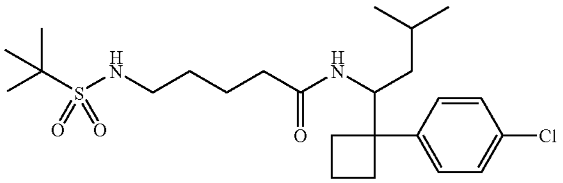
Ic-76
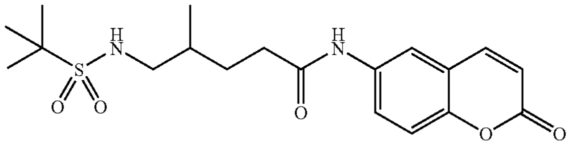
Ic-77
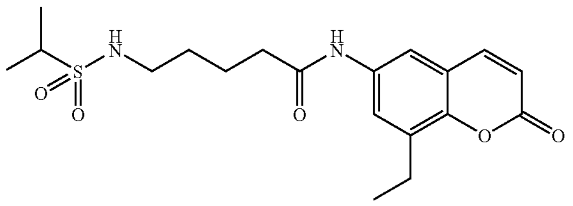
Ic-78
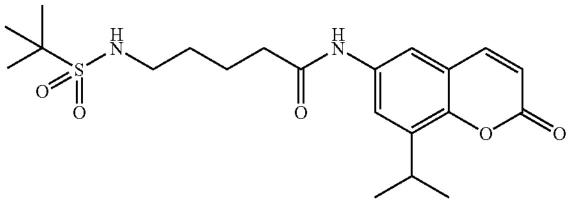

-continued
Ic-79
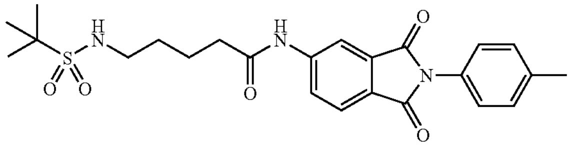
Ic-80
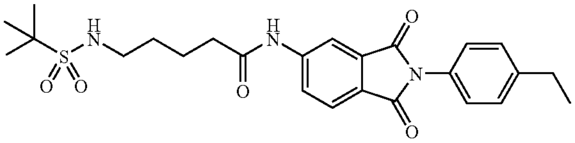
Ic-81
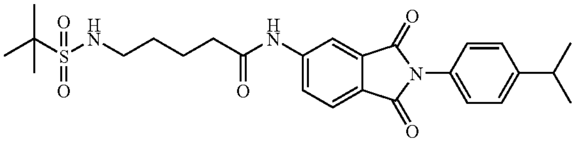
Ic-82
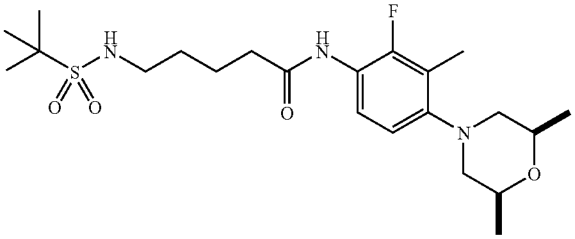
Ic-83
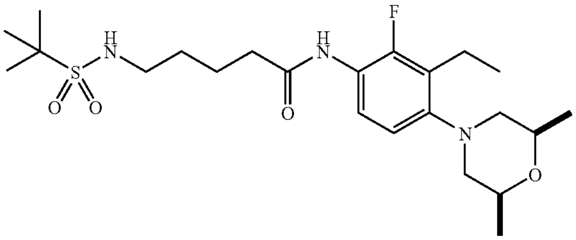
Ic-84
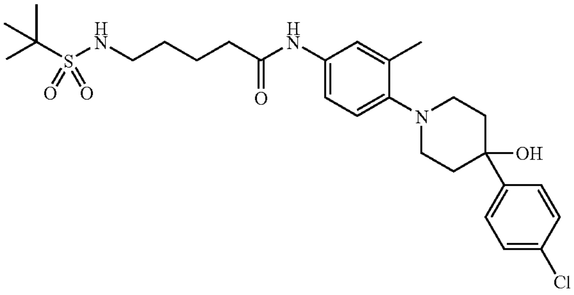
-continued
Ic-85
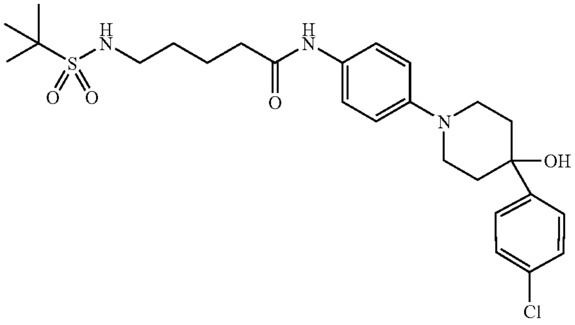
Ic-86
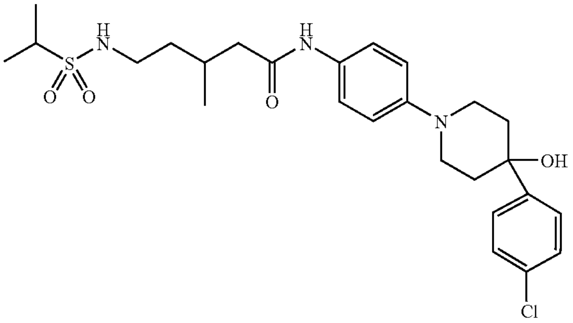
Ic-87
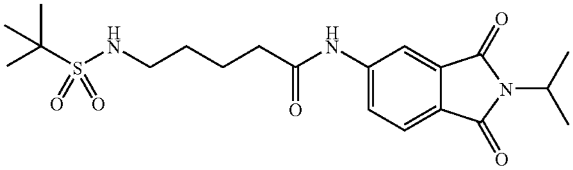
Ic-88
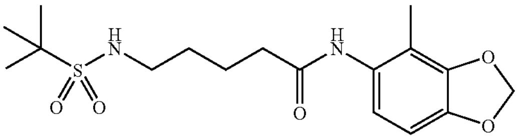
Ic-89
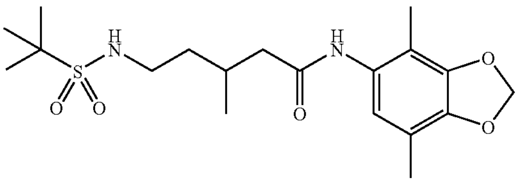
Ic-90
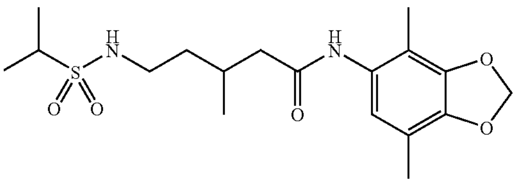

-continued
Ic-91
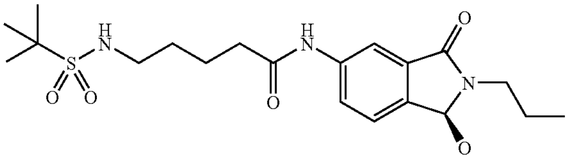
Ic-92
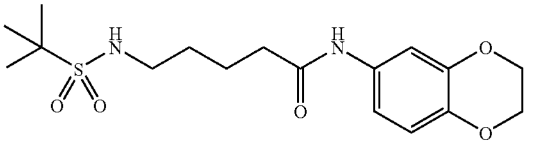
Ic-93
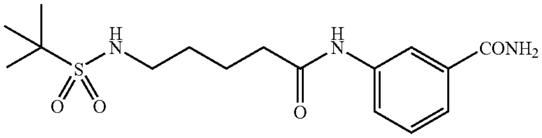
Ic-94
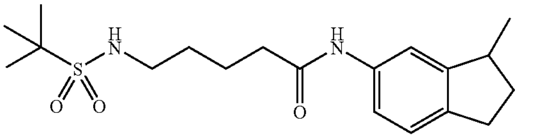
Ic-95
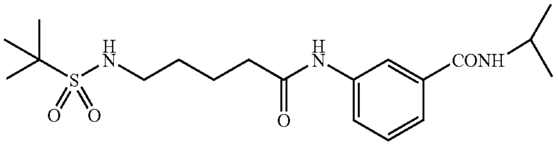
Ic-96
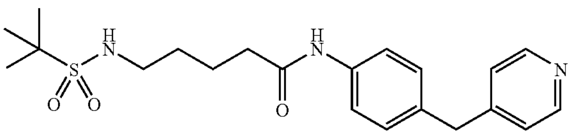
Ic-97
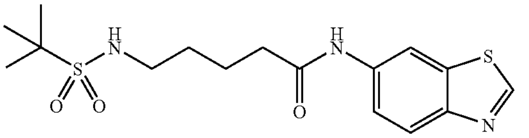
Ic-98
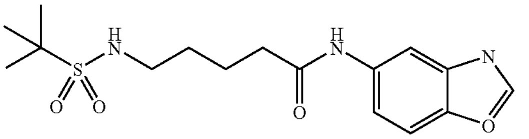
Ic-99
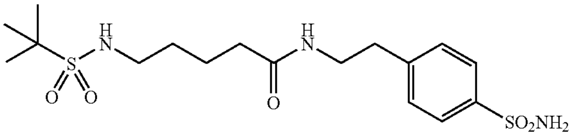
-continued
Ic-100
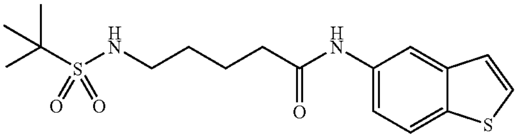
Ic-101
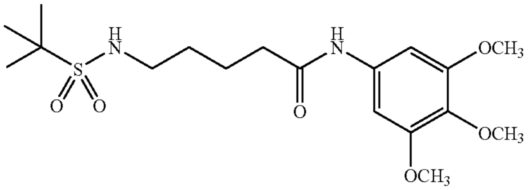
Ic-102
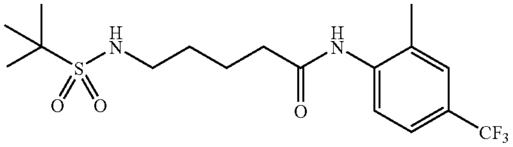
Ic-103
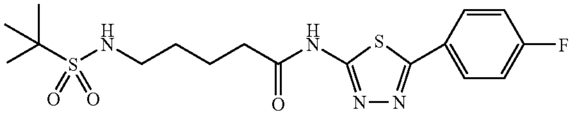
Ic-104
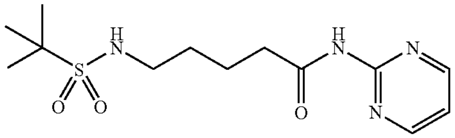
Ic-105
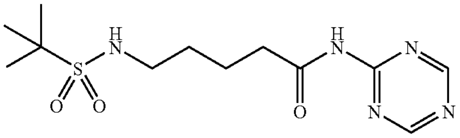
Ic-106
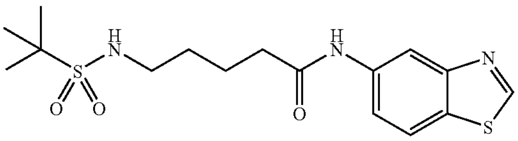
Ic-107
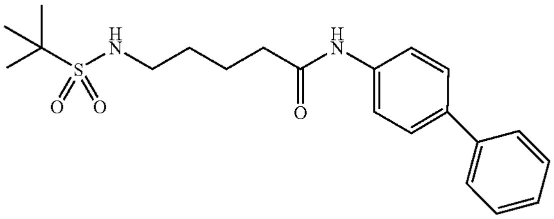
Ic-108
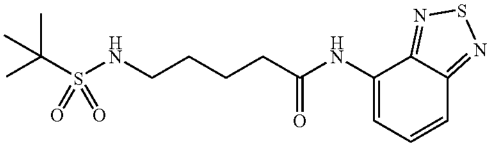

-continued
Ic-109
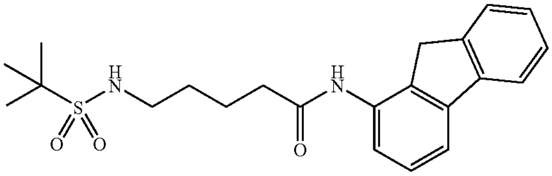
Ic-110
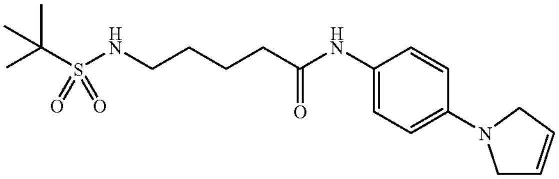
Ic-111
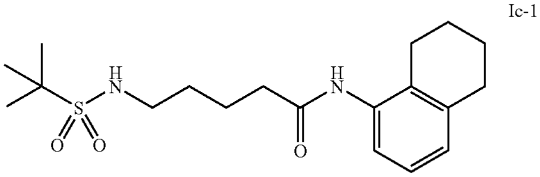
Ic-112
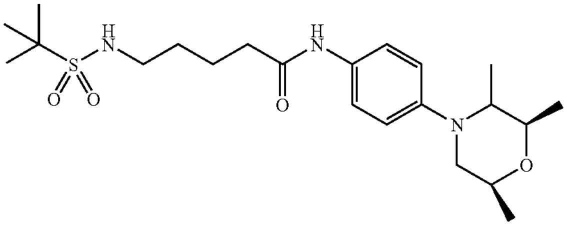
Ic-113
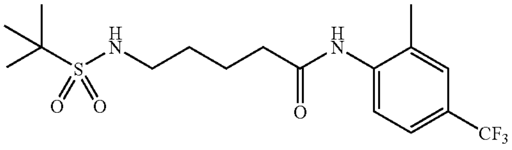
Ic-114
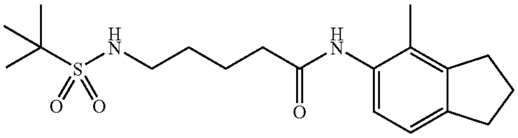
Ic-115
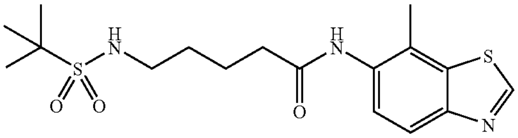
Ic-116
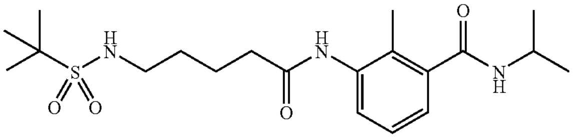
-continued
Ic-117
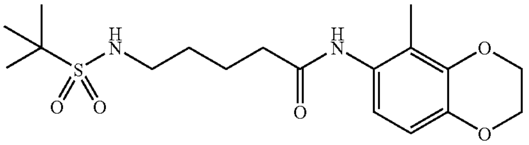
Ic-118
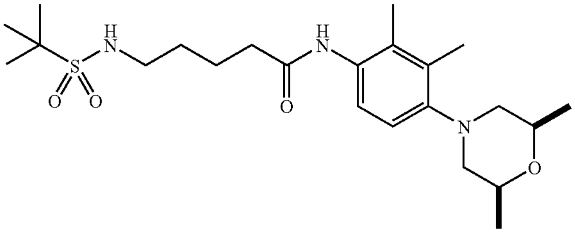
Ic-119
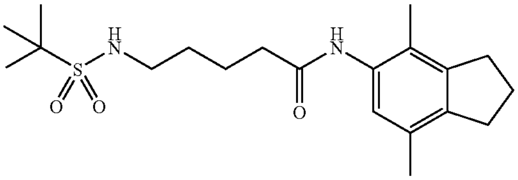
Ic-120
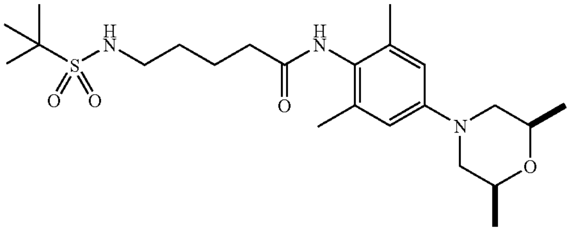
Ic-121
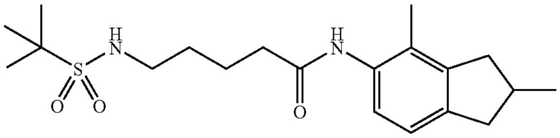
Ic-122
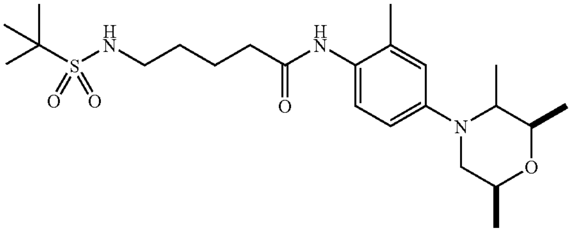
Ic-123
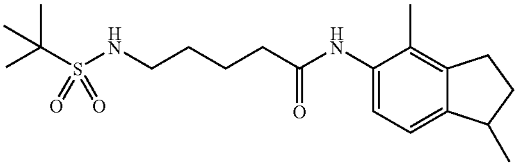

-continued
Ic-124
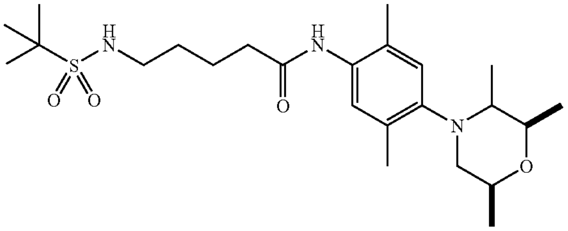
Ic-125
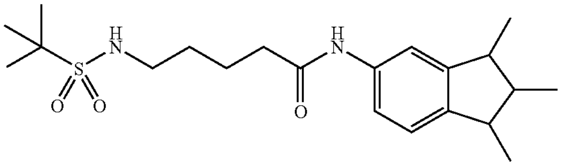
Ic-126
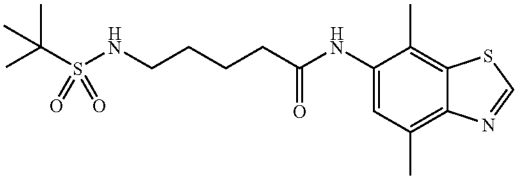
Ic-127
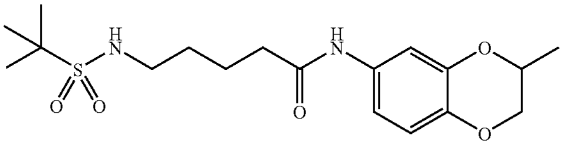
Ic-128
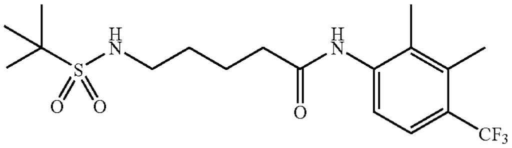
Ic-129
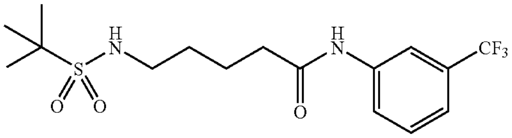
Ic-130
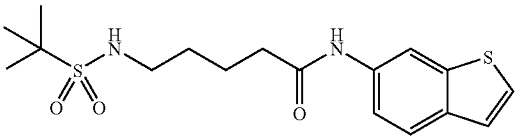
Ic-131
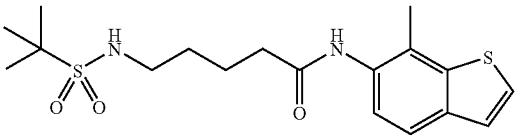
-continued
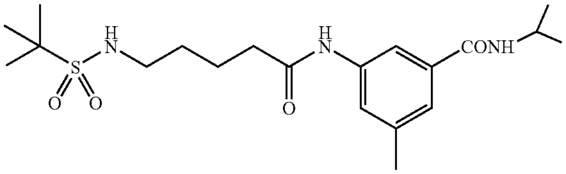
Ic-133
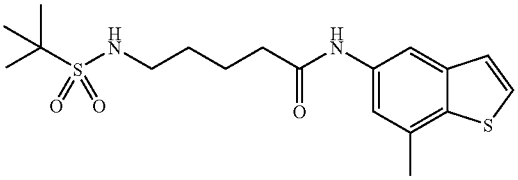
Ic-134
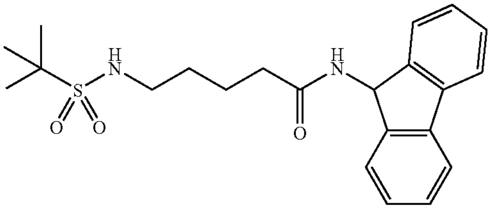
Ic-135
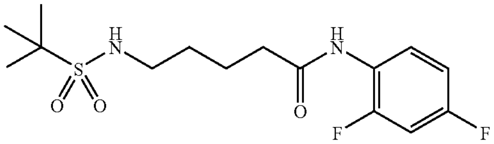
Ic-136
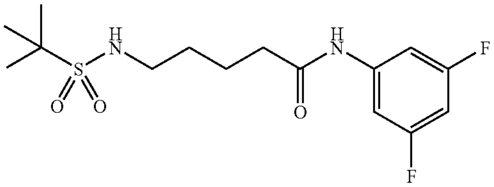
Ic-137
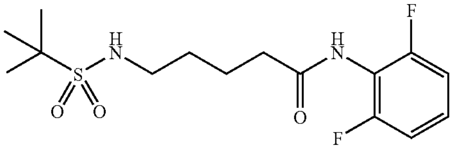
Ic-138
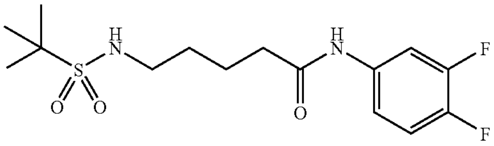
Ic-139
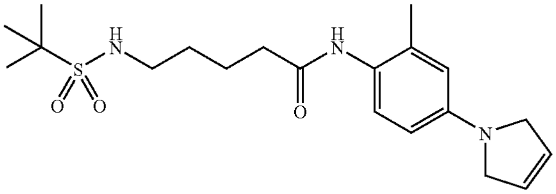

-continued
Ic-140
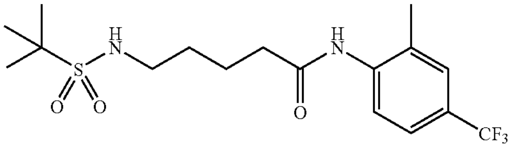
Ic-141
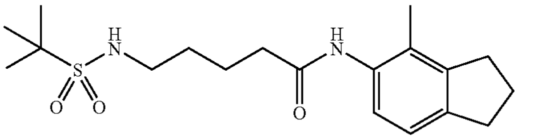
Ic-142
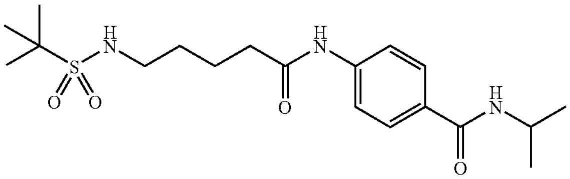
Ic-143
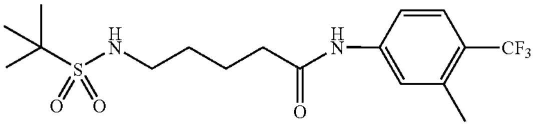
Ic-144
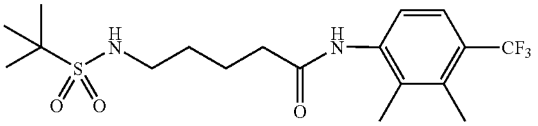
Ic-145
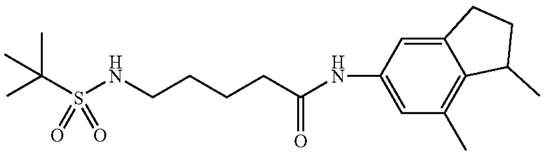
Ic-146
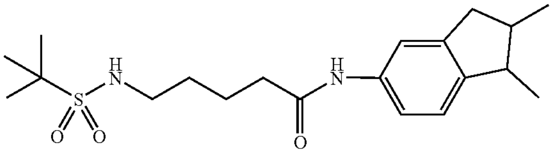
Ic-147
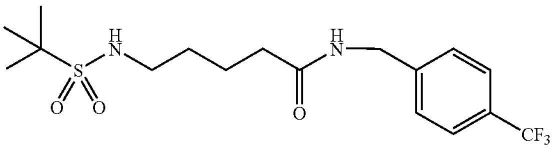
iC-148
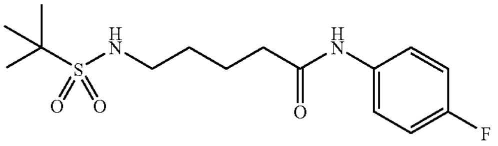
-continued
Ic-149
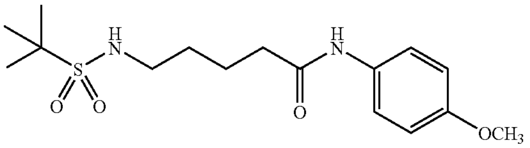
Ic-150
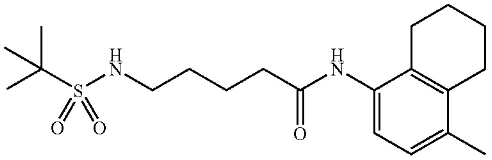
Ic-151
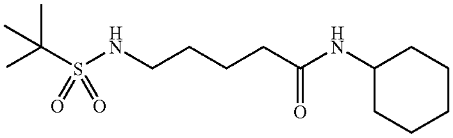
Ic-152
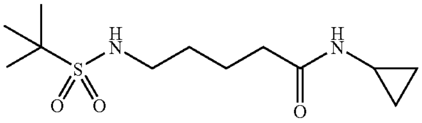
Ic-153
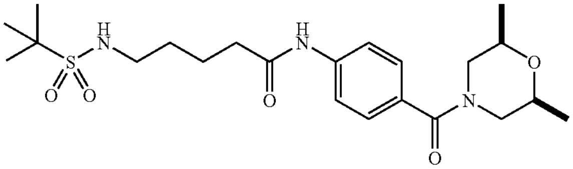
Ic-154
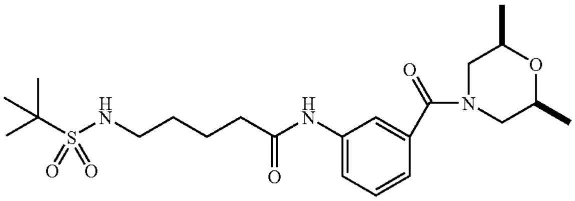
Ic-155
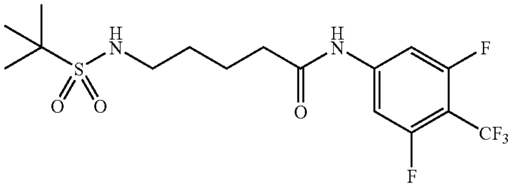
Ic-156
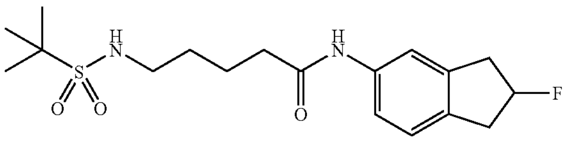

-continued
Ic-157
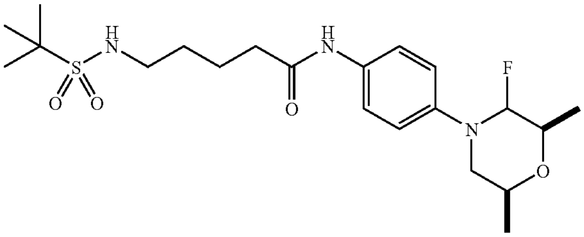
Ic-158
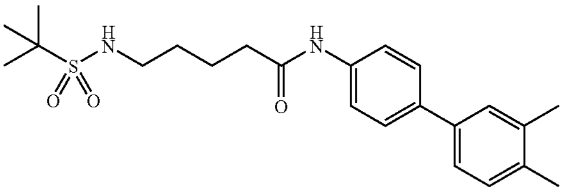
Ic-159
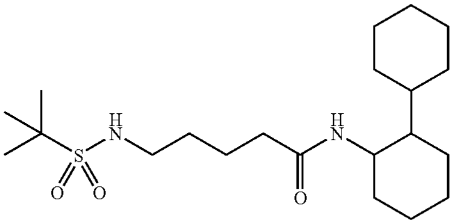
Ic-160
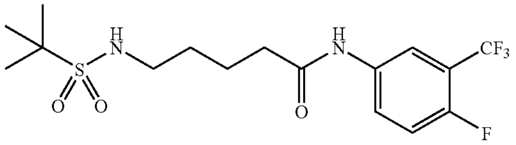
Ic-161
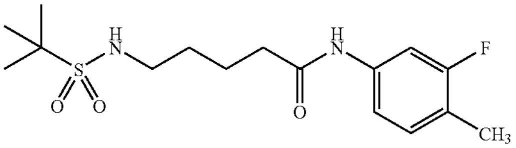
Ic-162
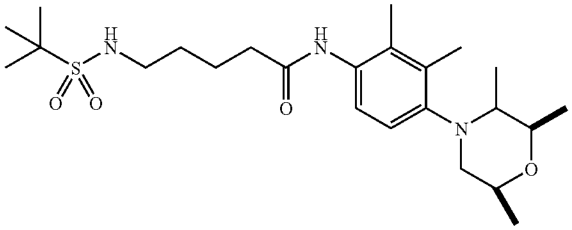
Ic-163
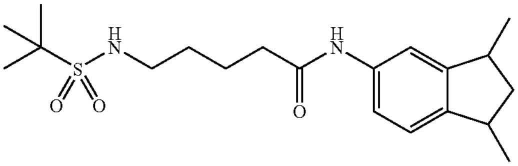
-continued
Ic-164
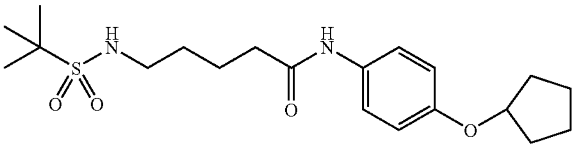
Ic-165
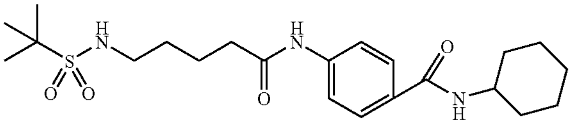
Ic-166
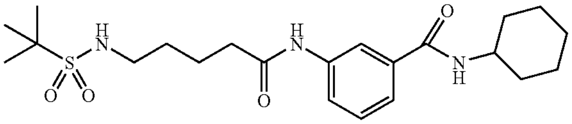
Ic-167
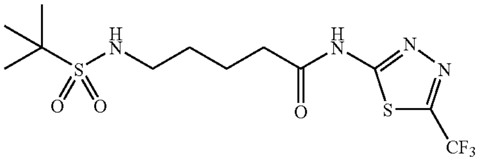
Ic-168
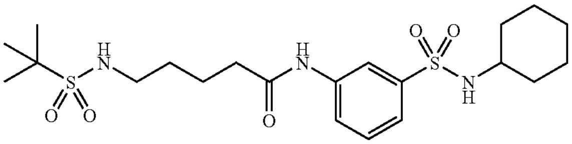
Ic-169
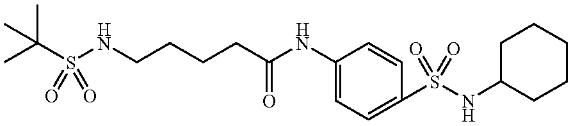
Ic-171
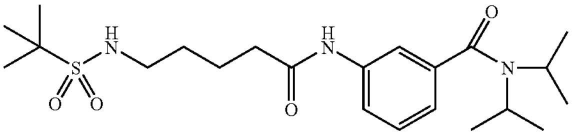
Ic-172
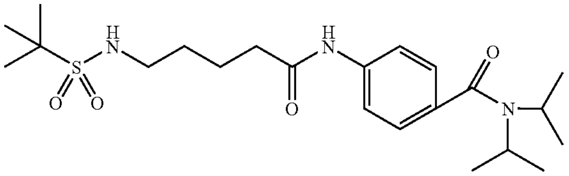
Ic-173
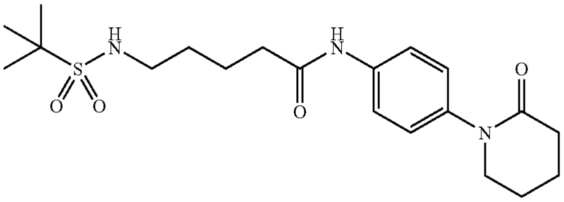

-continued
Ic-174
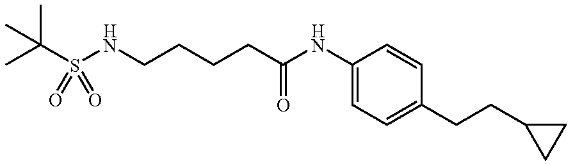
Ic-175
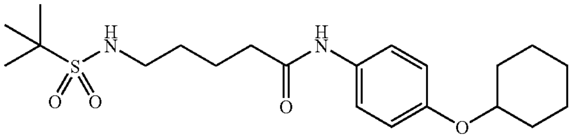
Ic-176
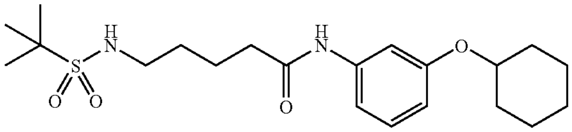
Ic-177
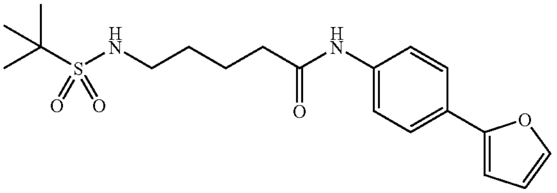
Ic-178
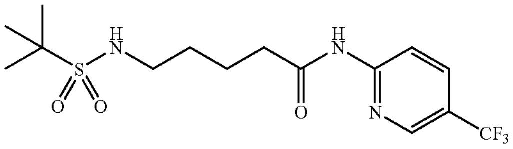
Ic-179
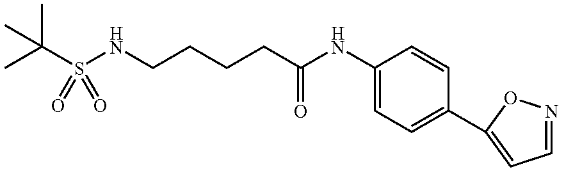
Ic-180
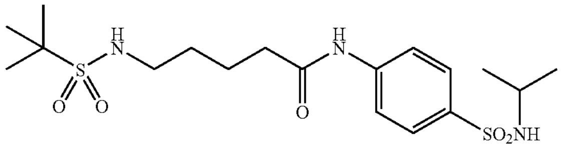
Ic-181
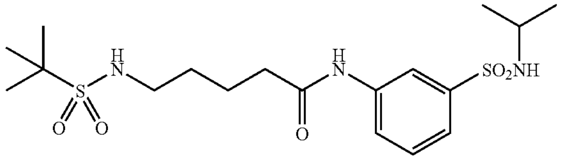
-continued
Ic-182
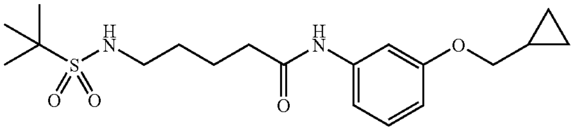
Ic-183
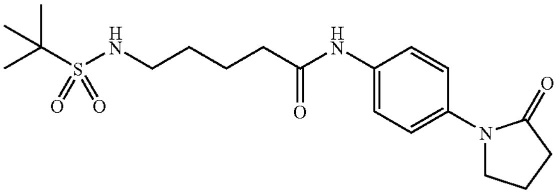
Ic-184
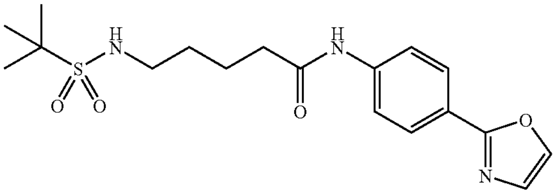
Ic-185
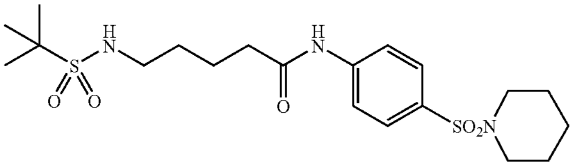
Ic-186
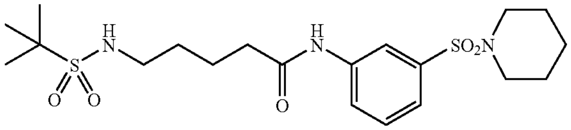
Ic-187
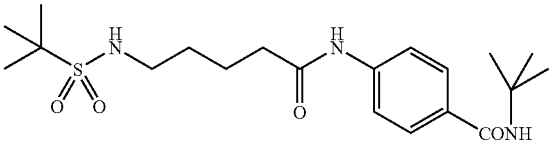
Ic-188
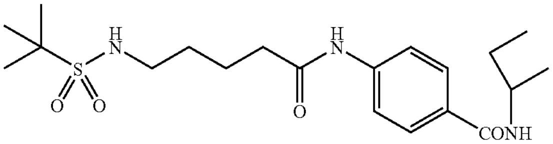
Ic-189
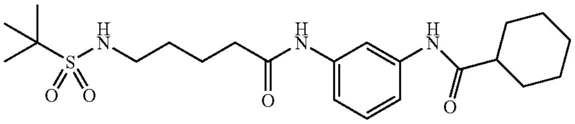

-continued
Ic-190
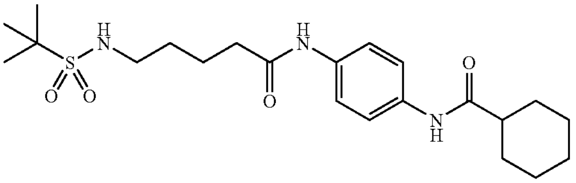
Ic-191
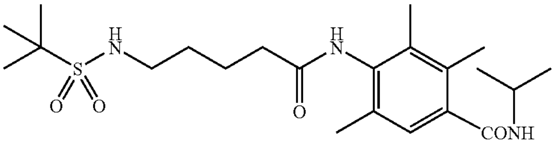
Ic-192
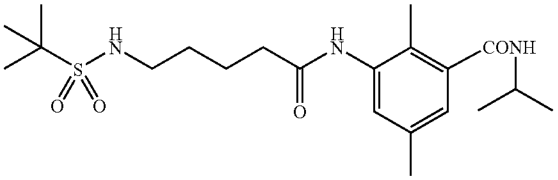
Ic-193
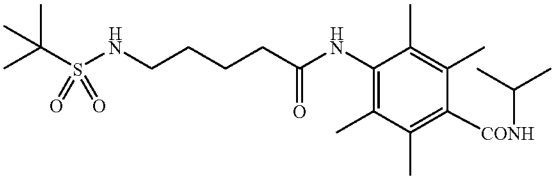
Ic-194
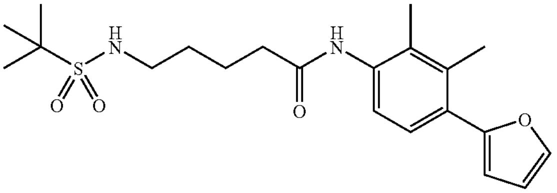
Ic-195
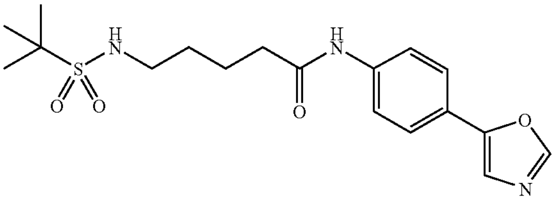
Ic-196
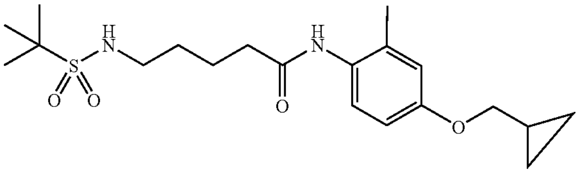
Ic-197
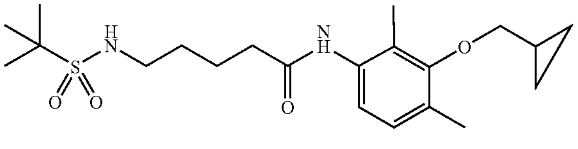
-continued
Ic-198
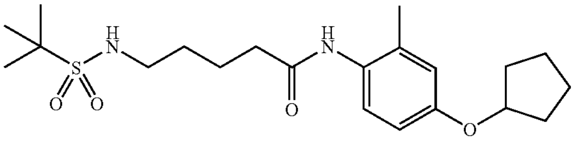
Ic-199
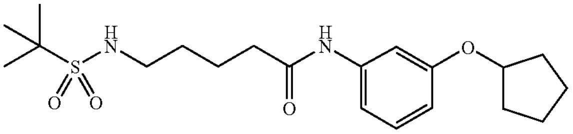
Ic-200
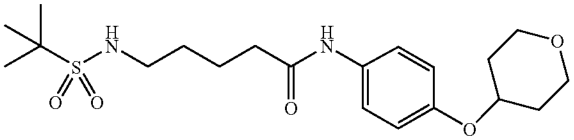
Ic-201
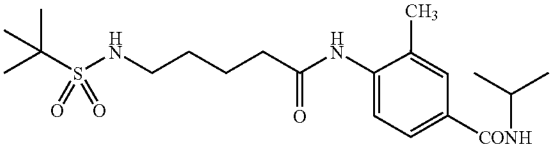
Ic-202
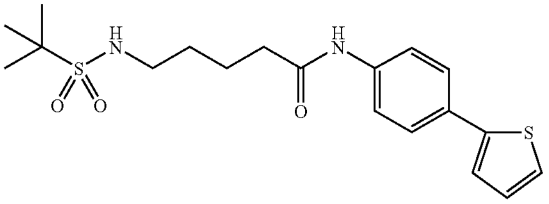
Ic-203
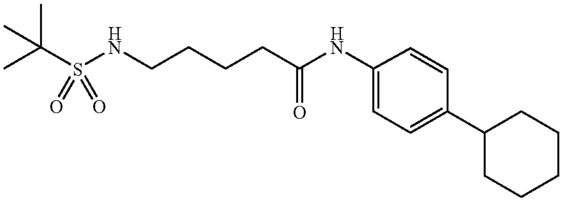
Ic-204
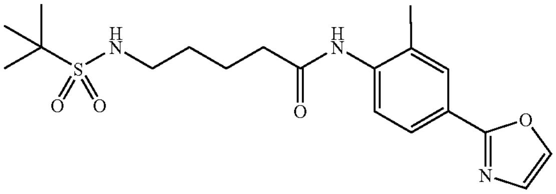
Ic-205
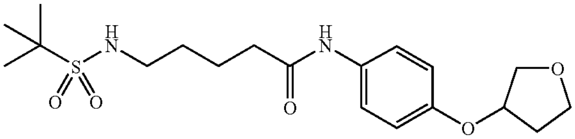

-continued
Ic-206
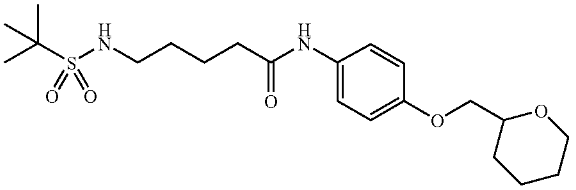
Ic-207
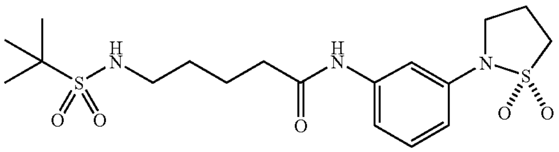
Ic-208
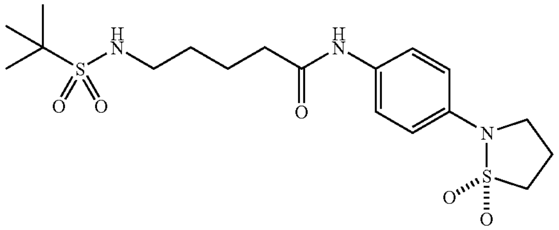
Ic-209
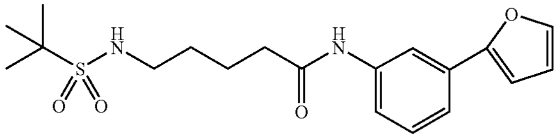
Ic-210
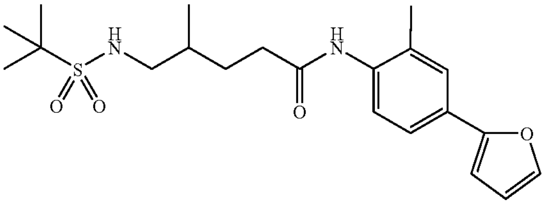
Ic-211
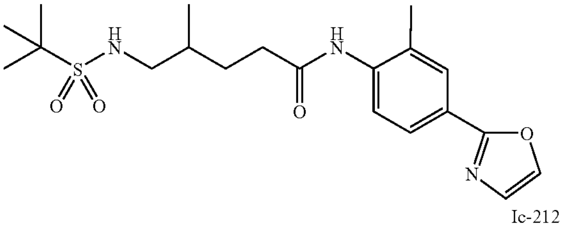
Ic-212
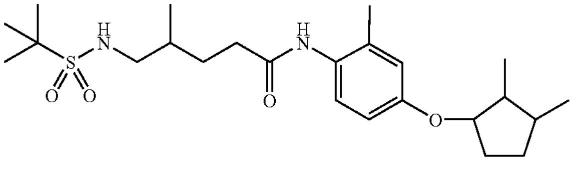
-continued
Ic-213
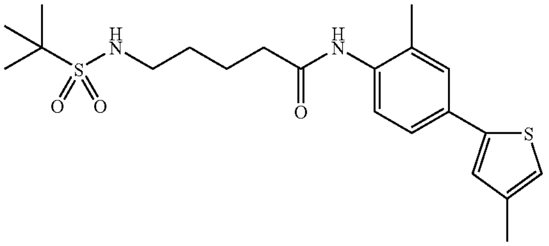
Ic-214
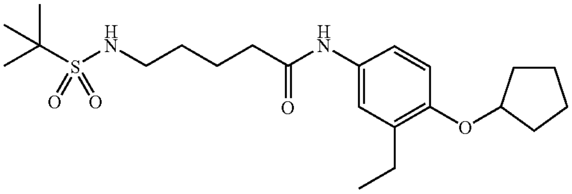
Ic-215
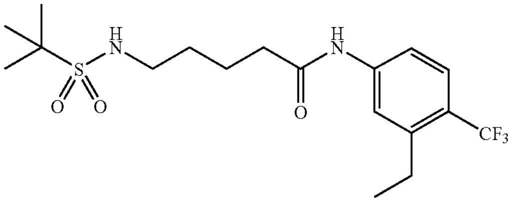
Ic-216
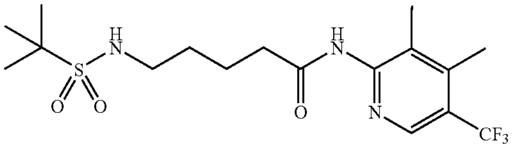
Ic-219
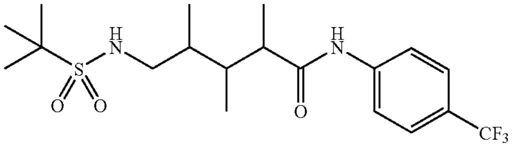
Ic-220
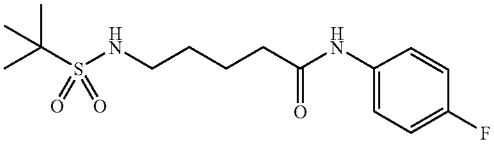
Ic-221
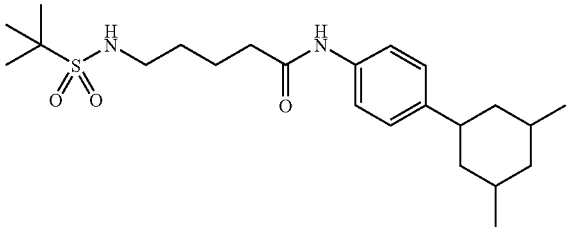

-continued
Ic-222
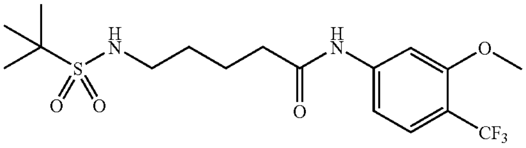
Ic-223
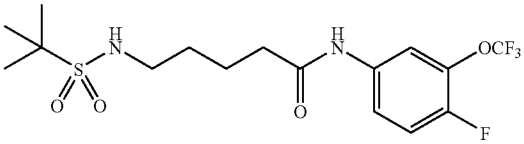
Ic-224
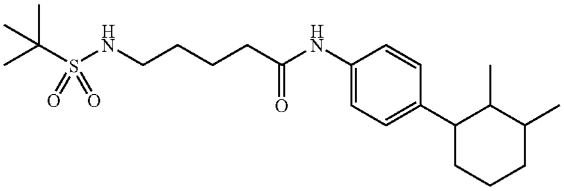
Ic-225
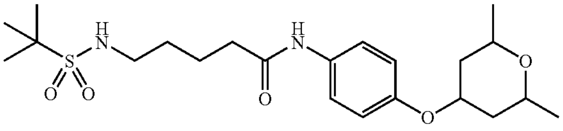
Ic-226
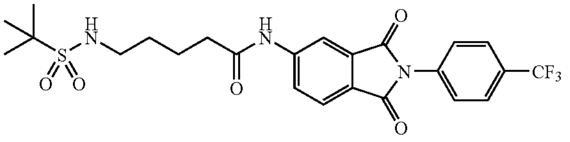
Id-1
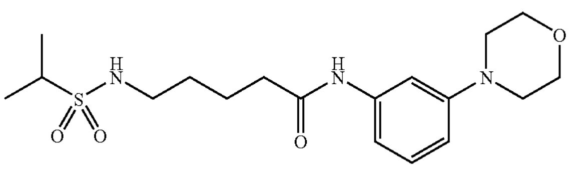
Id-2
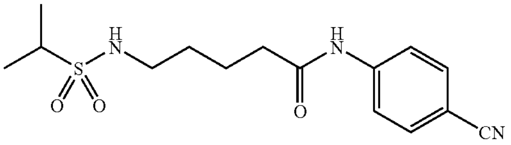
Id-4
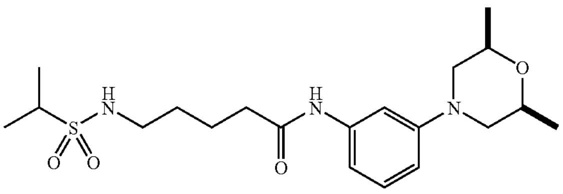
Id-7
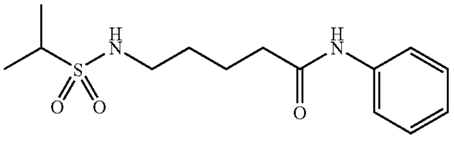
-continued
Id-8
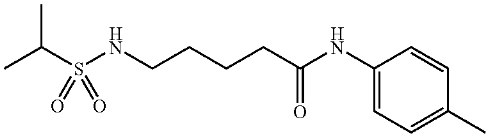
Id-9
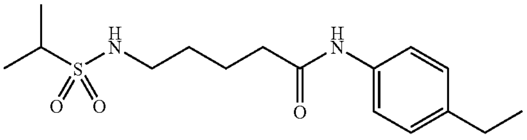
Id-10
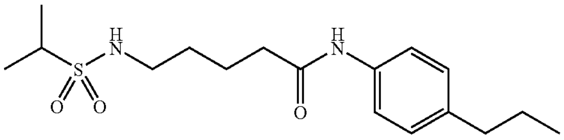
Id-11
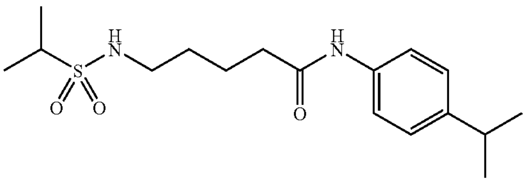
Id-12
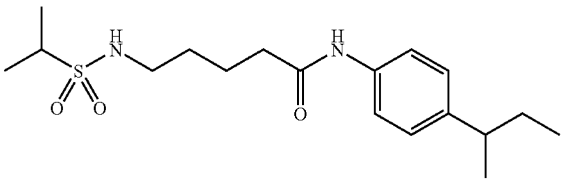
Id-13
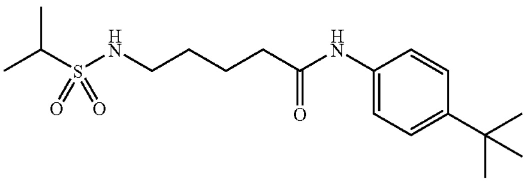
Id-14
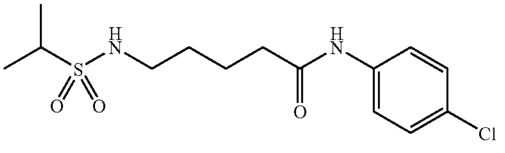
Id-16
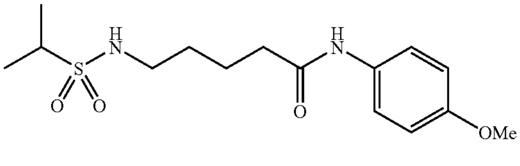

-continued
Id-17
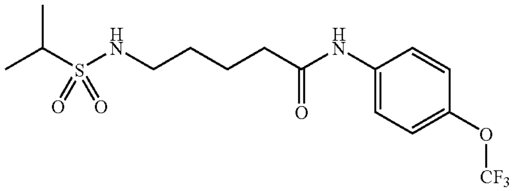
Id-18
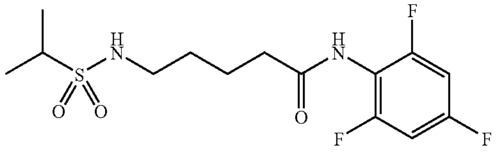
Id-19
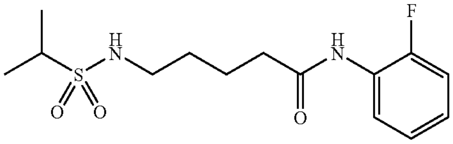
Id-20
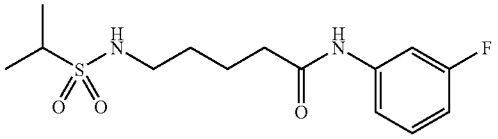
Id-21
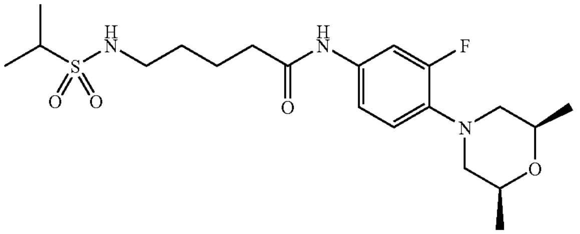
Id-22
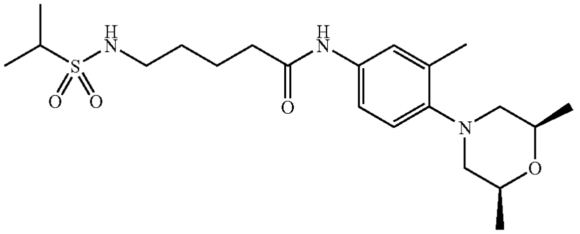
Id-23
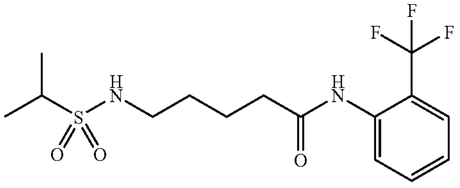
Id-24
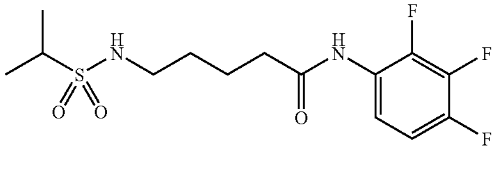
-continued
Id-25
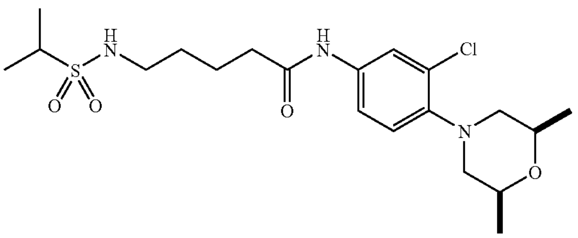
Id-26
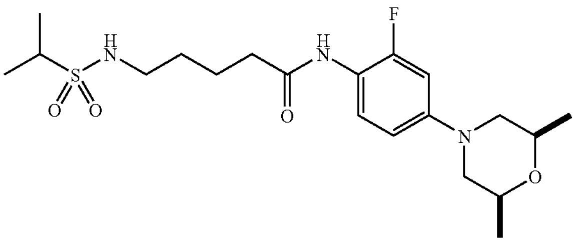
Id-27
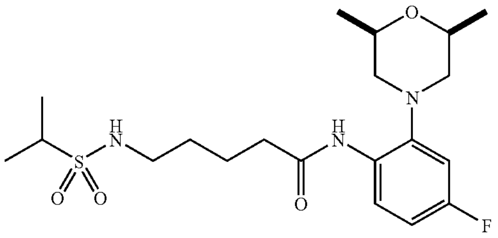
Id-28
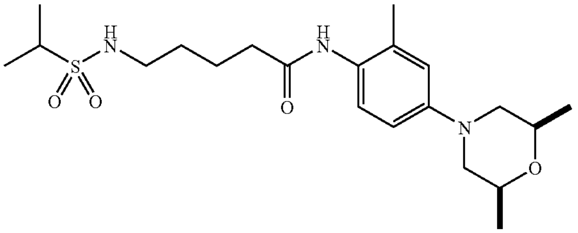
Id-29
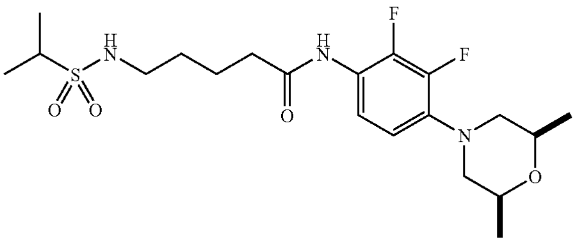
Id-30
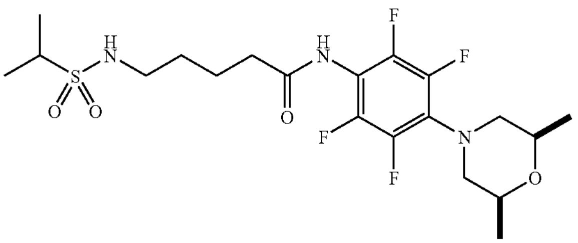

-continued
Id-31
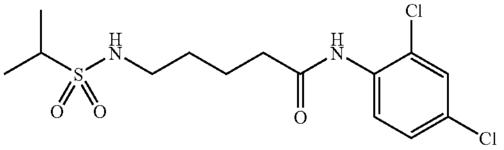
Id-32
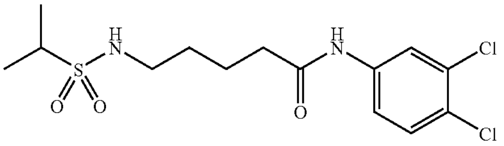
Id-33
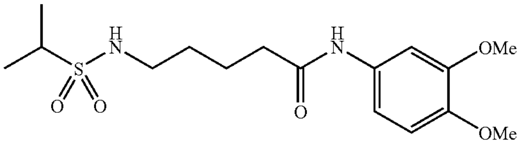
Id-35
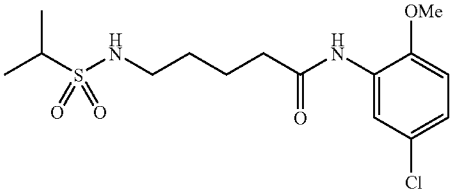
Id-36
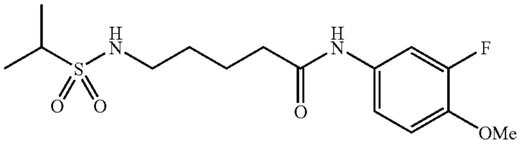
Id-37
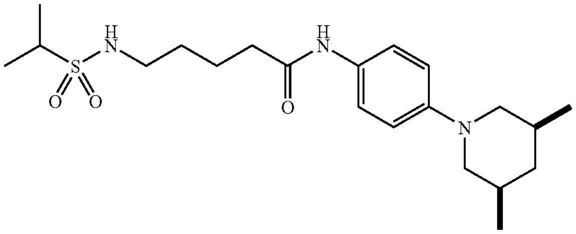
Id-38
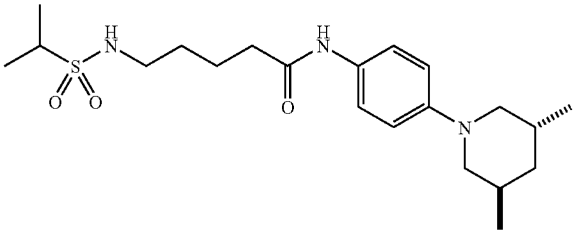
Id-39
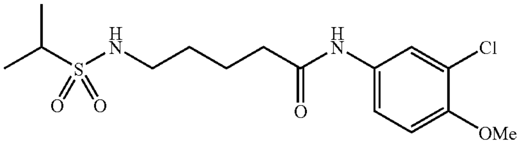
-continued
Id-40
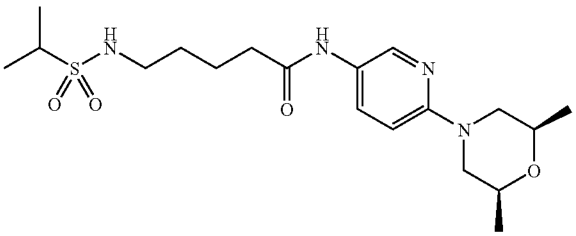
Id-41
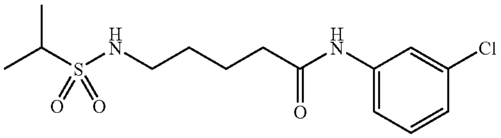
Id-42
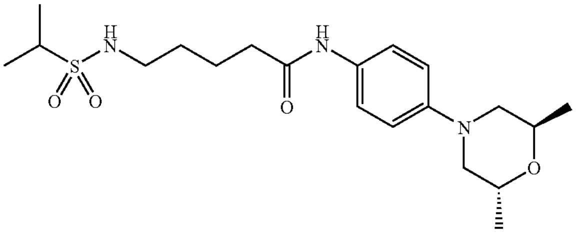
Id-43
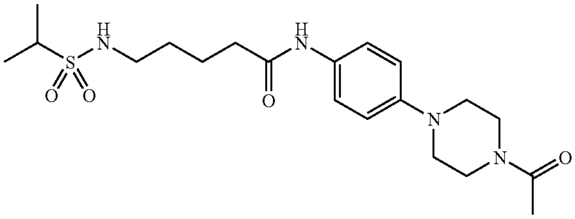
Id-44
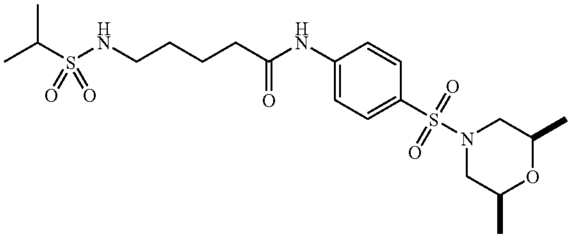
Id-45
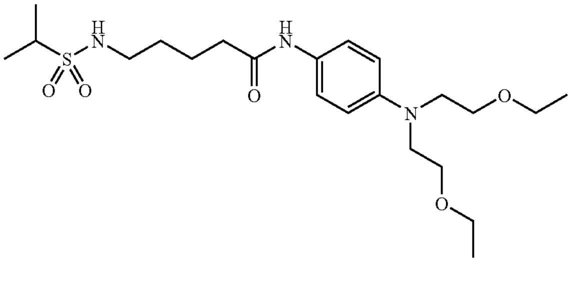

-continued
Id-46
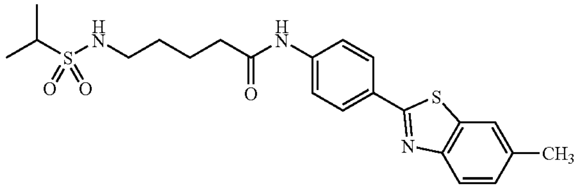
Id-47
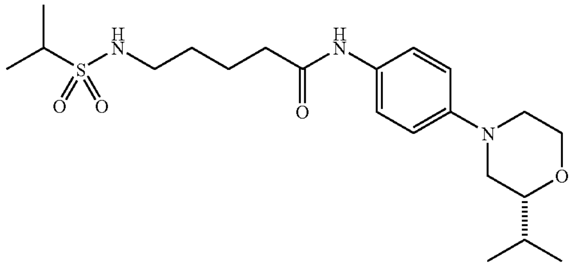
Id-48
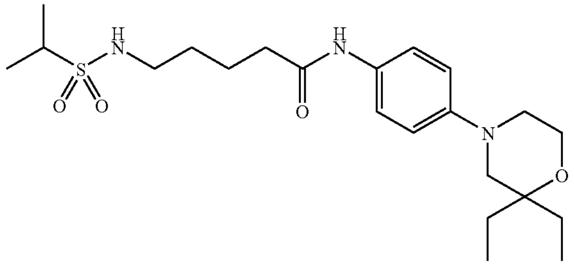
Id-49
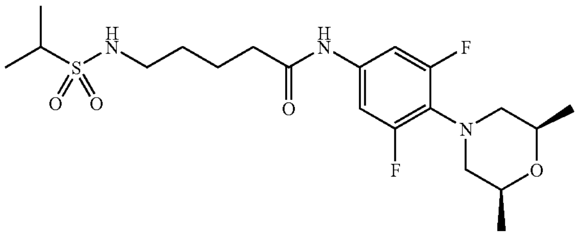
Id-50
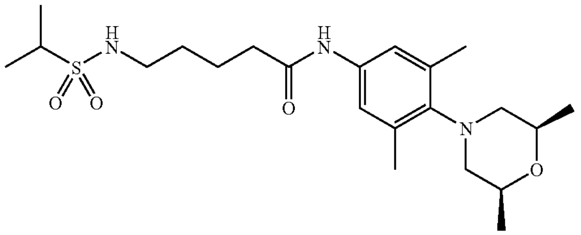
Id-51
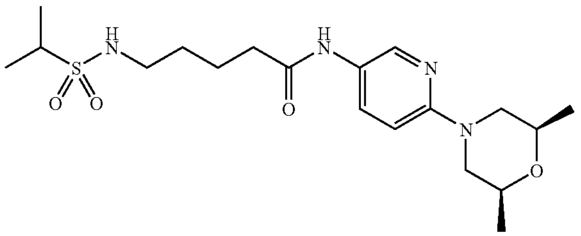
-continued
Id-52
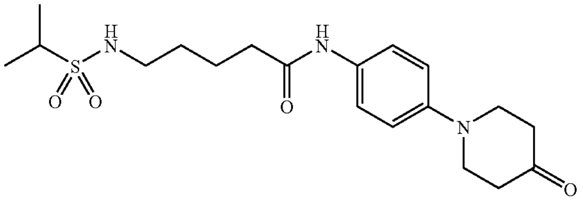
Id-53
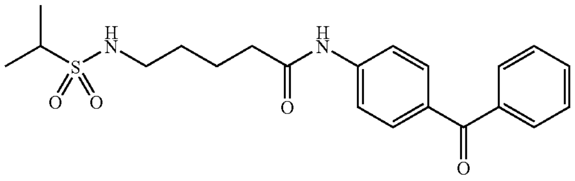
Id-54
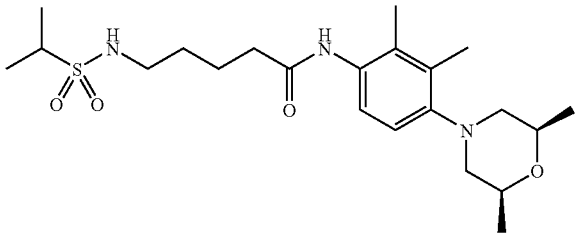
Id-55
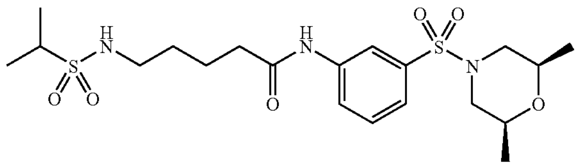
Id-56
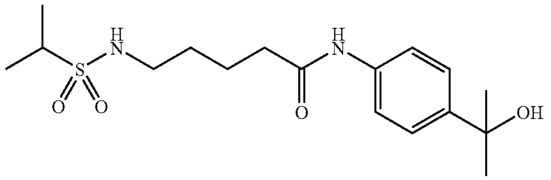
Id-57
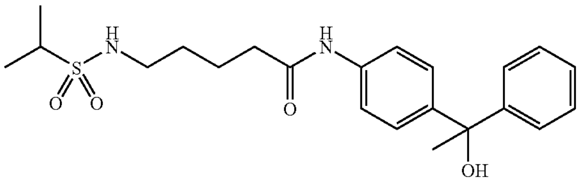
Id-58
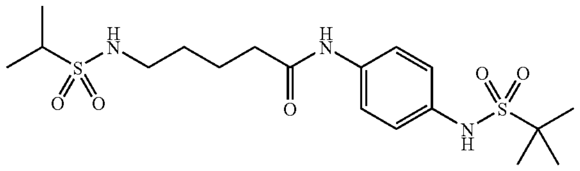

-continued
Id-59
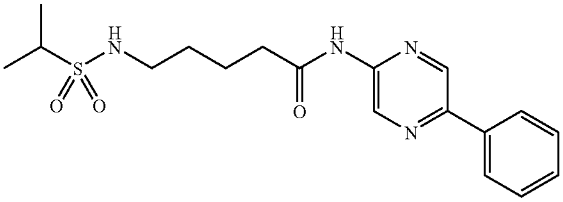
Id-60
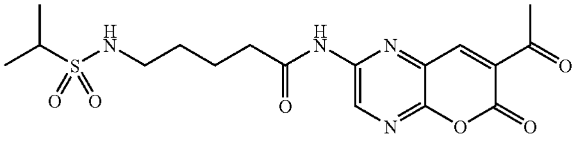
Id-61
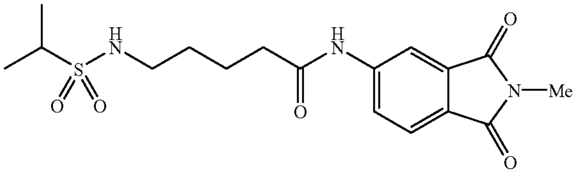
Id-62
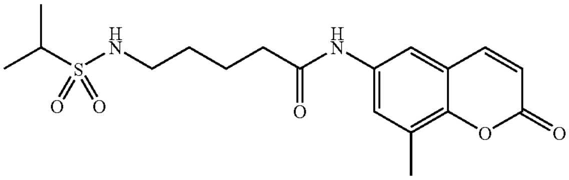
Id-63
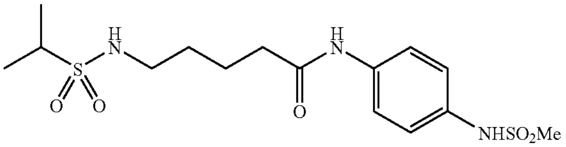
Id-64
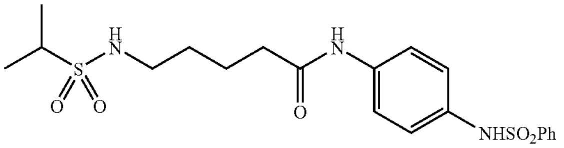
Id-65
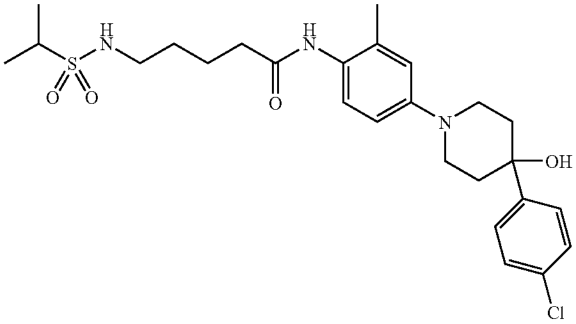
-continued
Id-66
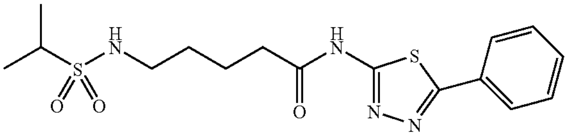
Id-67
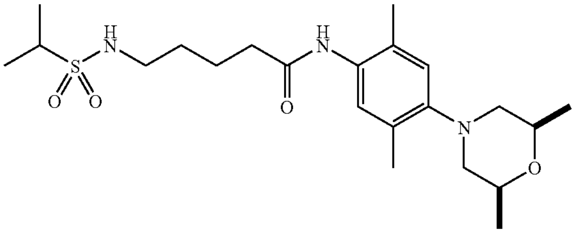
Id-68
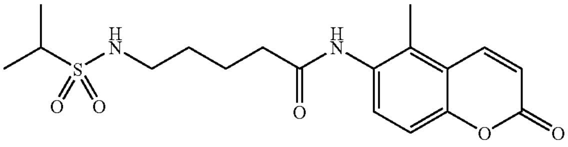
Id-69
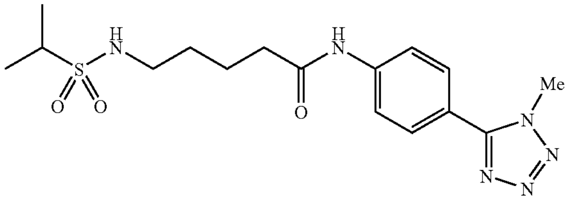
Id-70
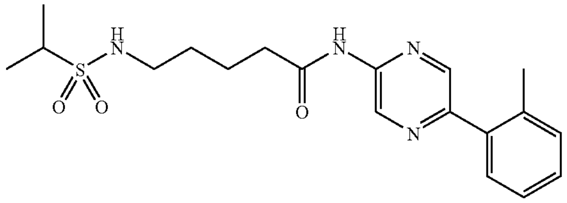
Id-71
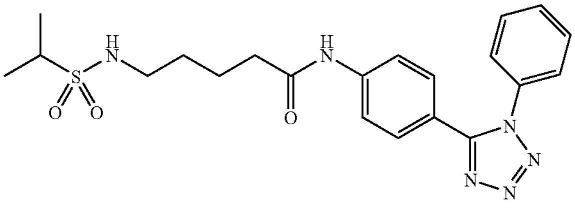
Id-73
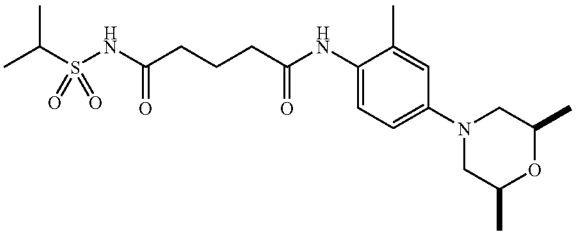

-continued
Id-74
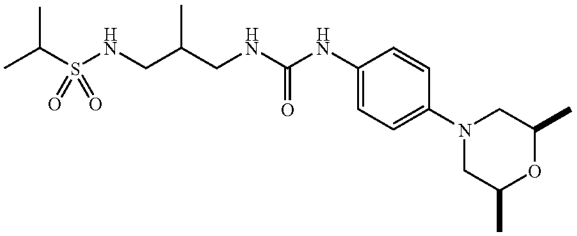
Id-75
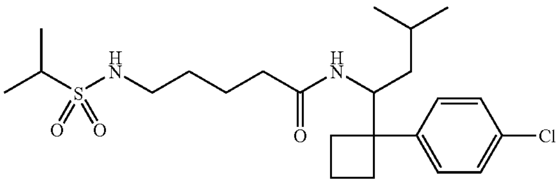
Id-76
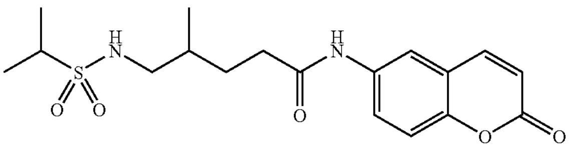
Id-77
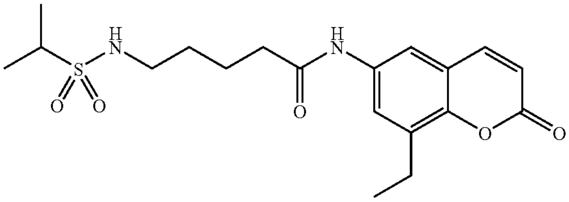
Id-78
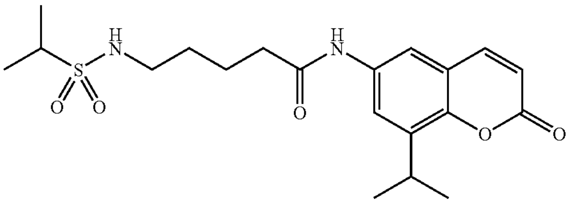
Id-79
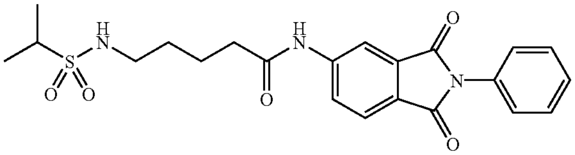
-continued
Id-80
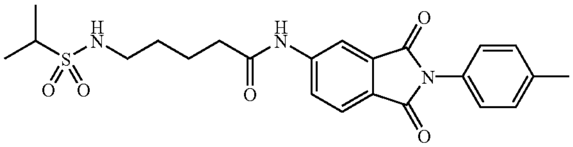
Id-81
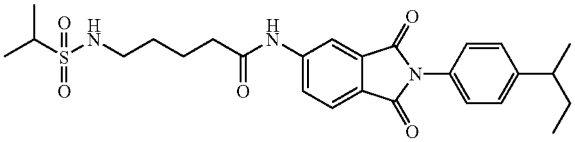
Id-82
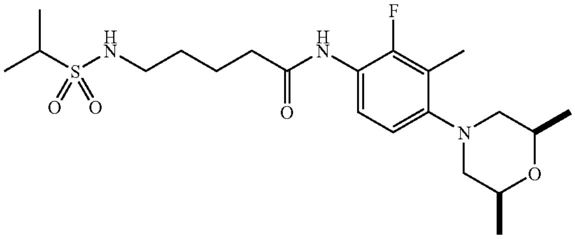
Id-83
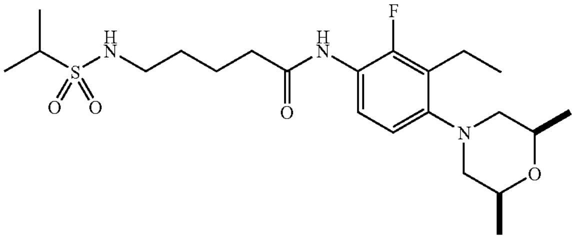
Id-84
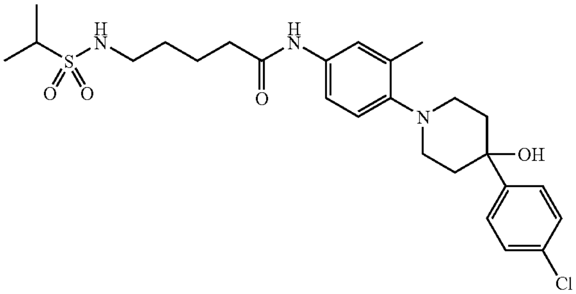
Id-85
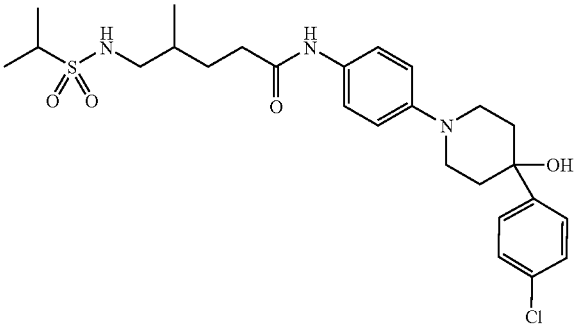

-continued
Id-86
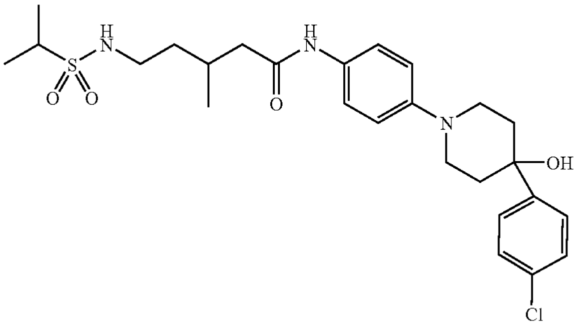
Id-87
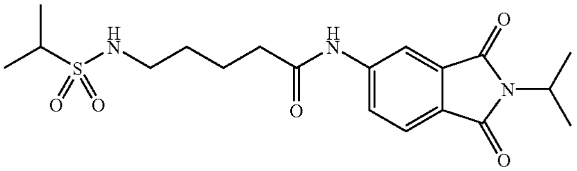
Id-88
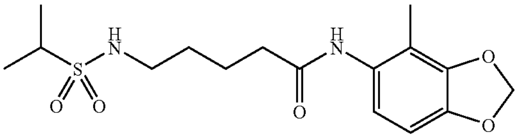
Id-89
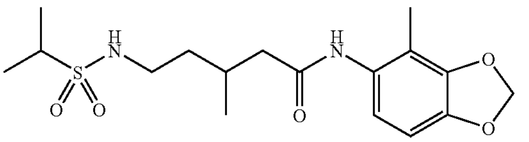
Id-90
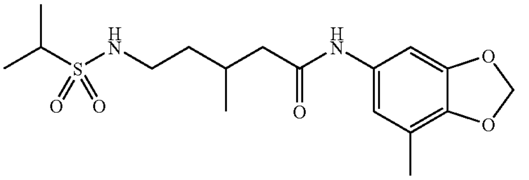
Id-91
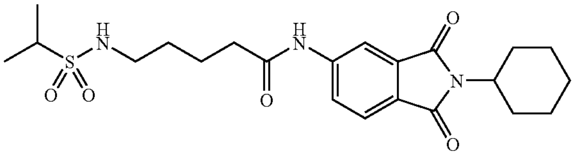
Id-92
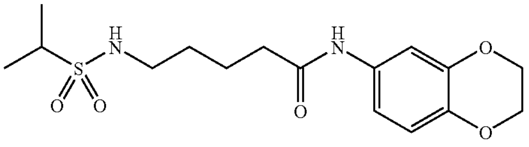
Id-93
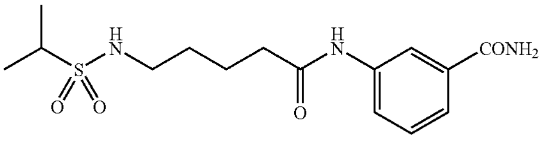
-continued
Id-94
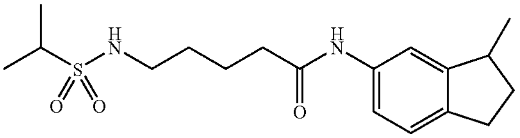
Id-95
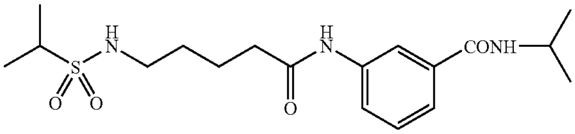
Id-96
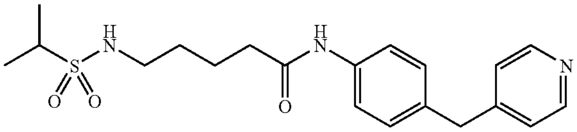
Id-97
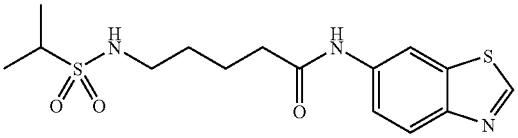
Id-98
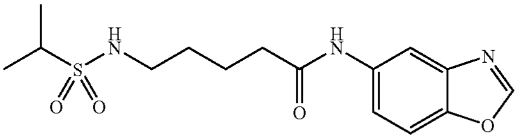
Id-99
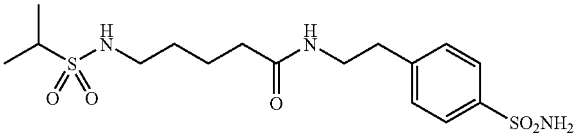
Id-100
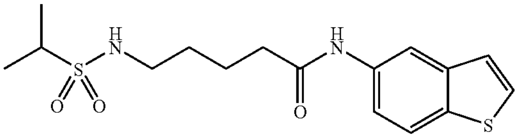
Id-101
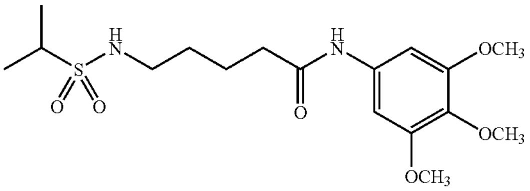
Id-102
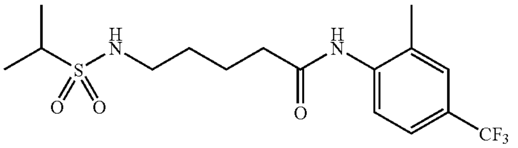

-continued
Id-103
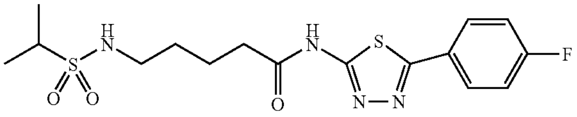
Id-104
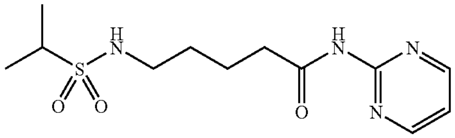
Id-105
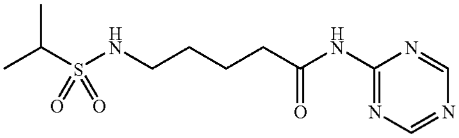
Id-106
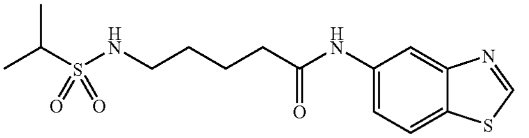
Id-107
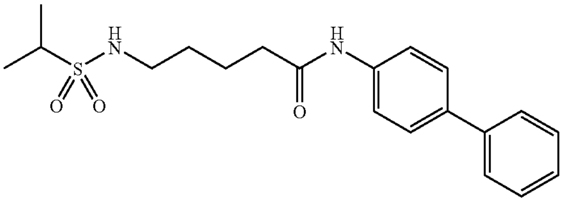
Id-108
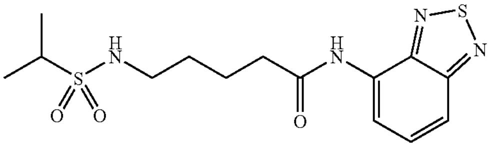
Id-109
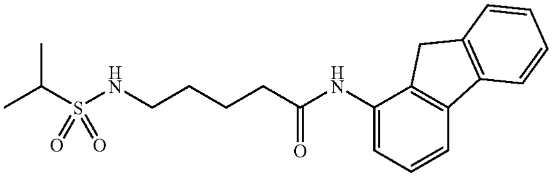
Id-110
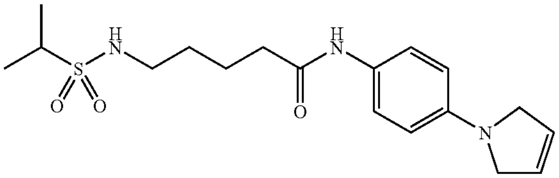
Id-111
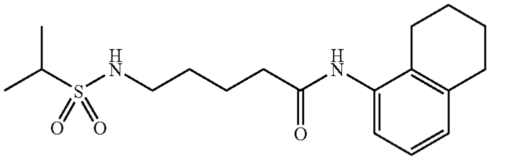
-continued
Id-112
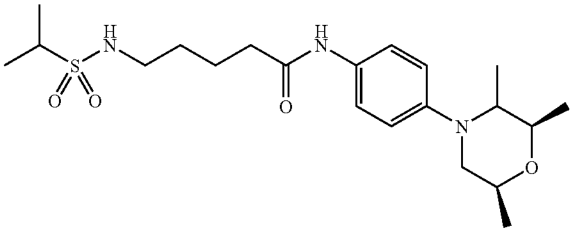
Id-113
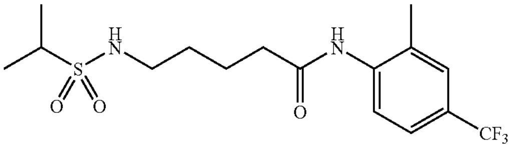
Id-114
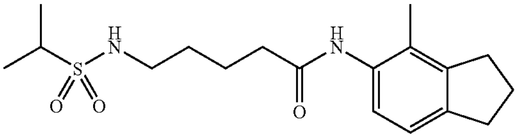
Id-115
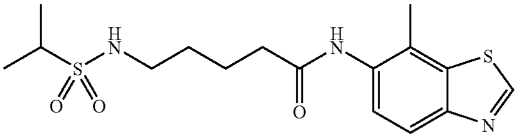
Id-116
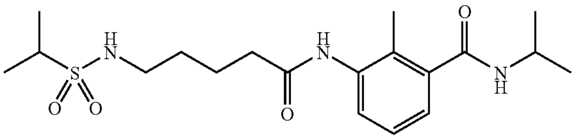
Id-117
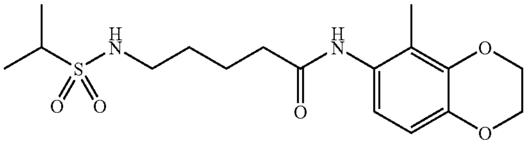
Id-118
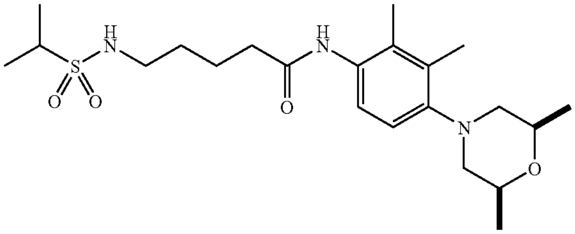
Id-119
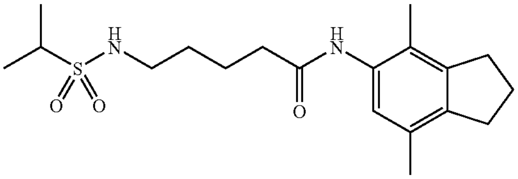

-continued
Id-120
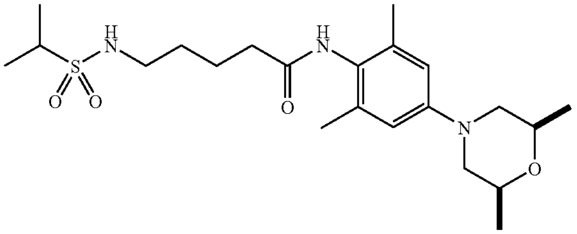
Id-121
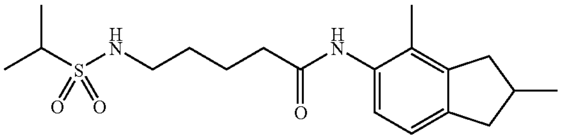
Id-122
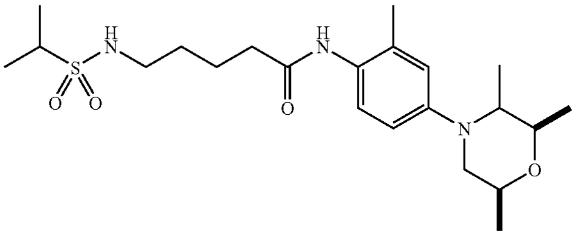
Id-123
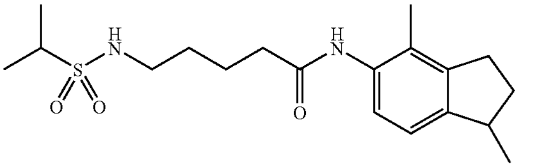
Id-124
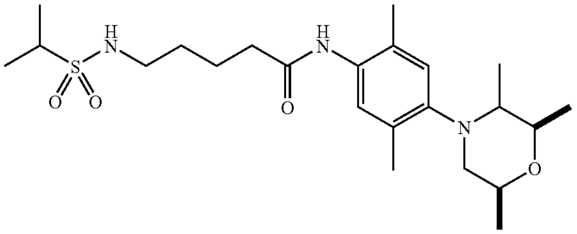
Id-125
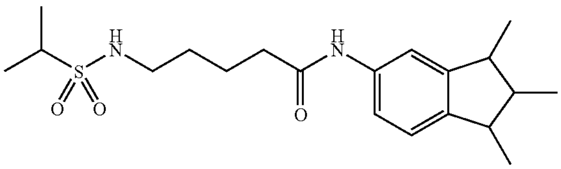
Id-126
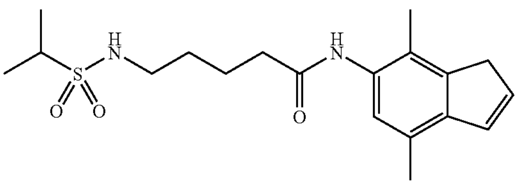
-continued
Id-127
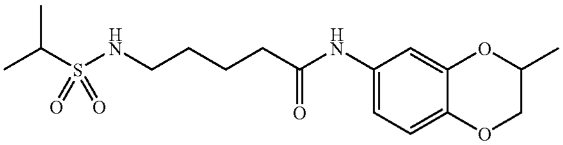
Id-128
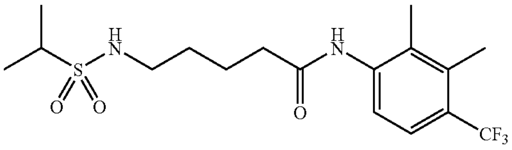
Id-129
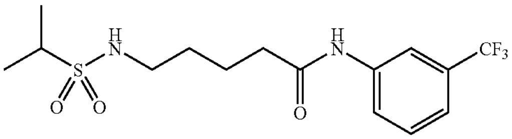
Id-130
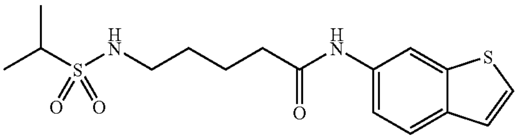
Id-131
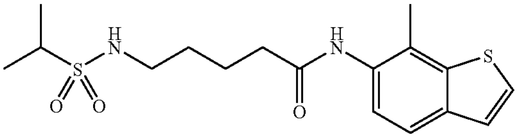
Id-132
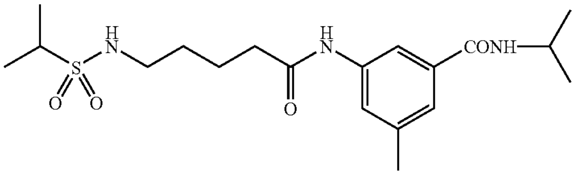
Id-133
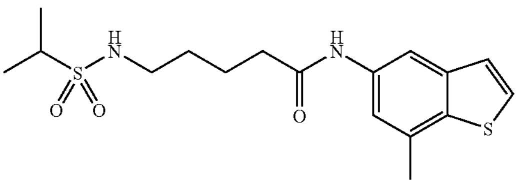
Id-134
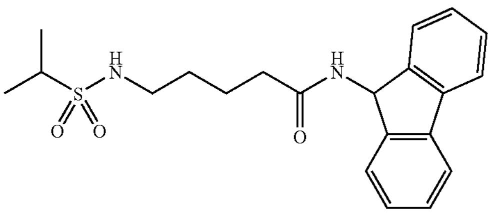

-continued
Id-135
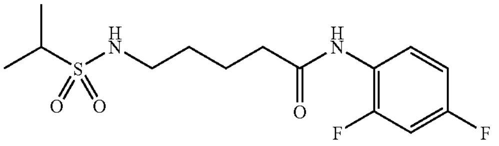
Id-136
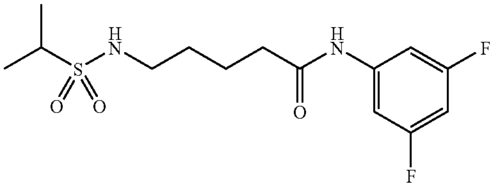
Id-137
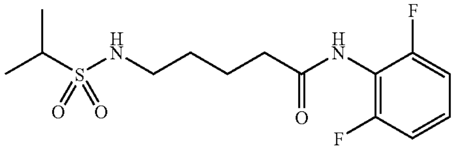
Id-138
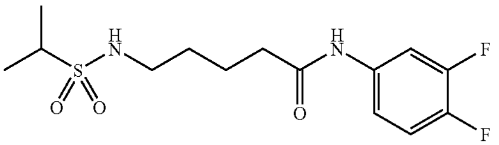
Id-139
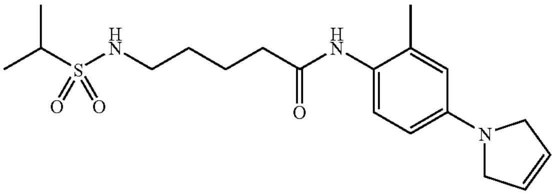
Id-140
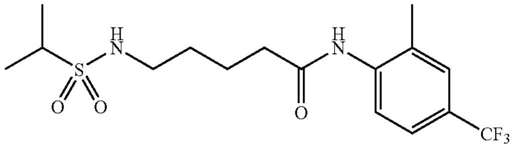
Id-141
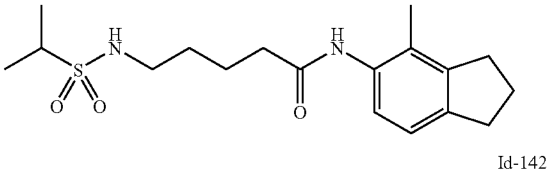
Id-142
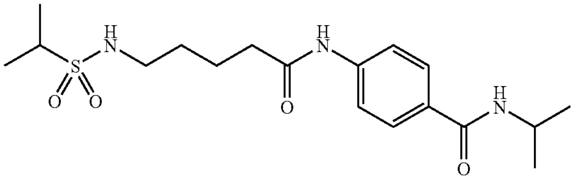
-continued
Id-143
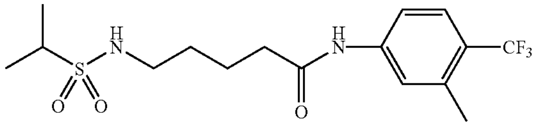
Id-144
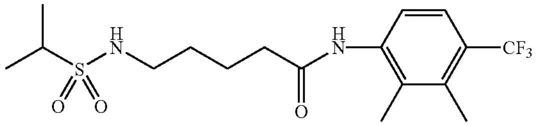
Id-145
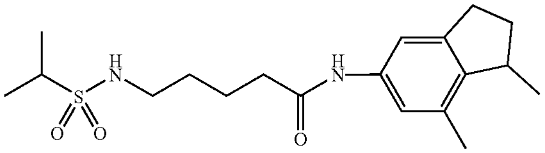
Id-146
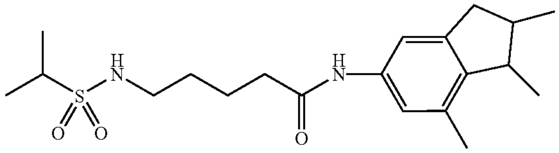
Id-147
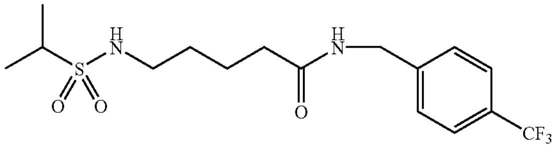
Id-148
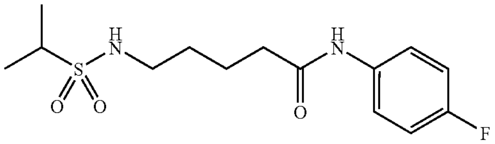
Id-149
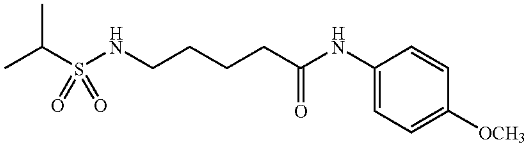
Id-150
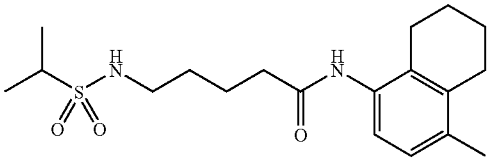
Id-151
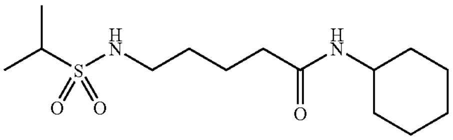

-continued
Id-152
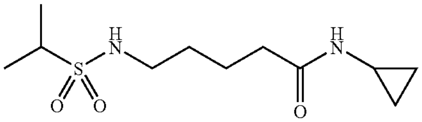
Id-153
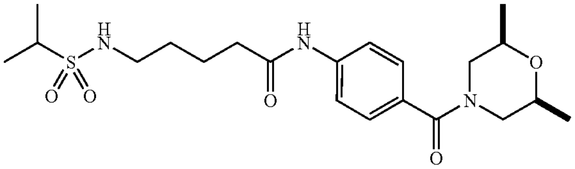
Id-154
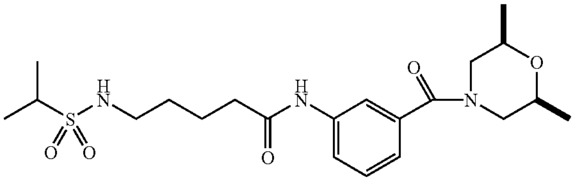
Id-155
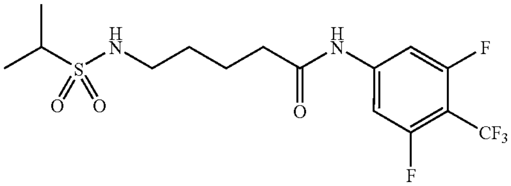
Id-156
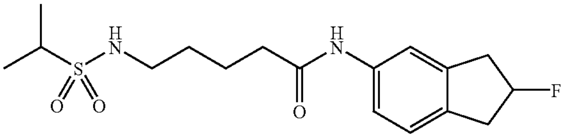
Id-157
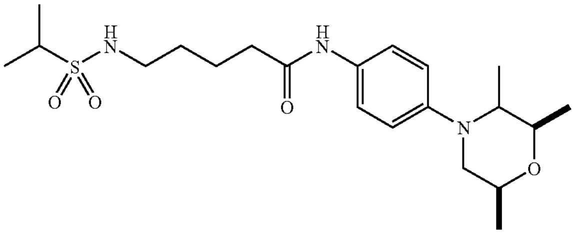
Id-158
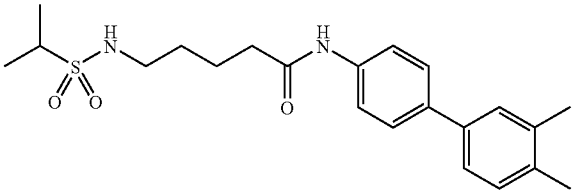
-continued
Id-159
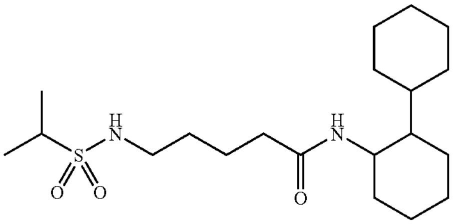
Id-160
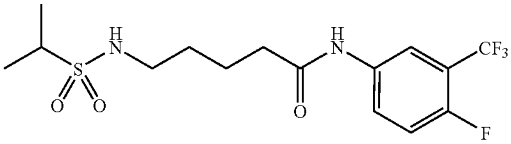
Id-161
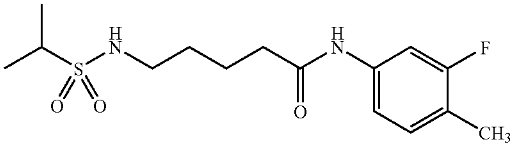
Id-162
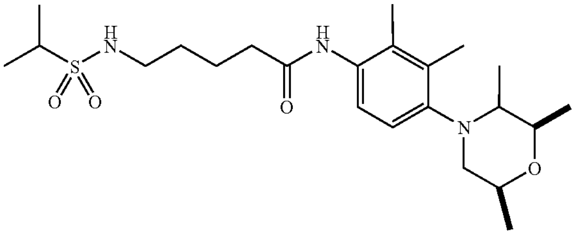
Id-163
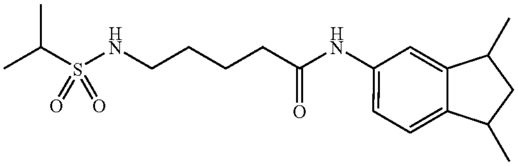
Id-164
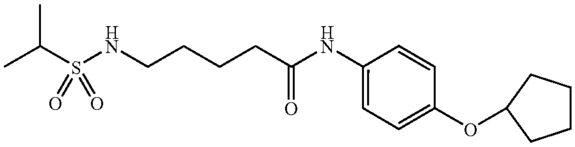
Id-165
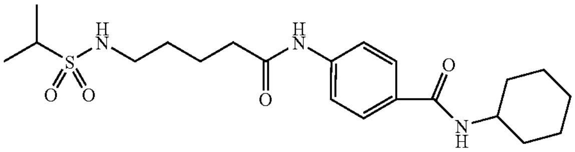
Id-166
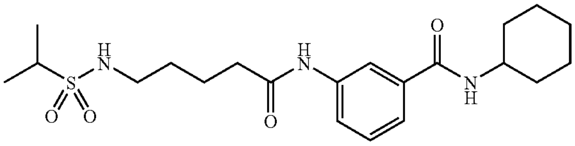

-continued
Id-167
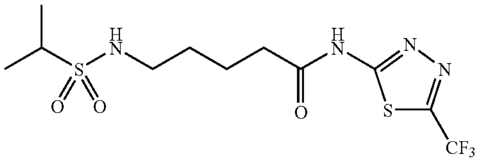
Id-168
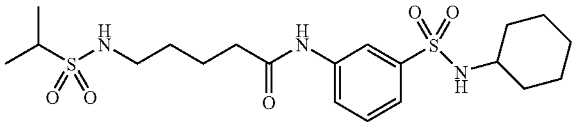
Id-169
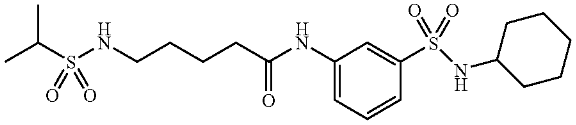
Id-171
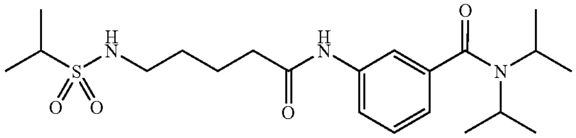
Id-172
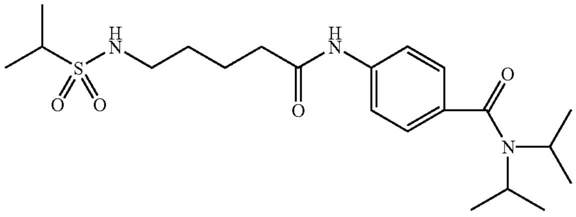
Id-173
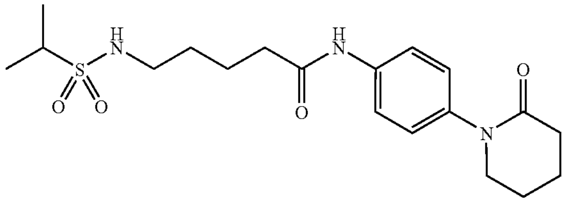
Id-174
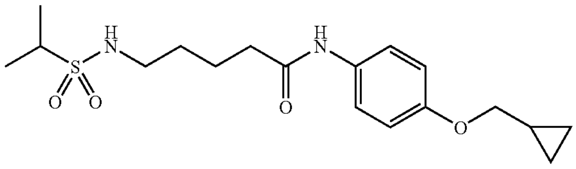
Id-175
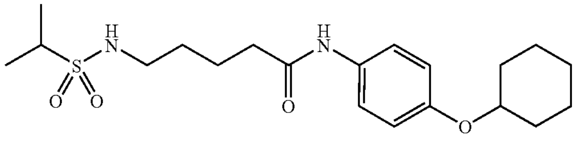
-continued
Id-176
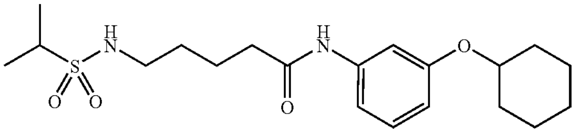
Id-177
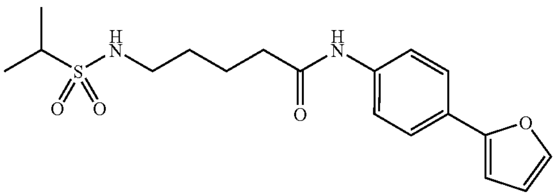
Id-178
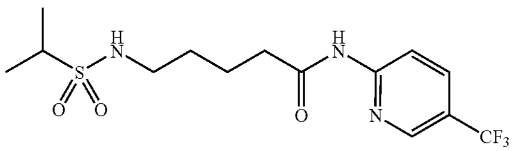
Id-179
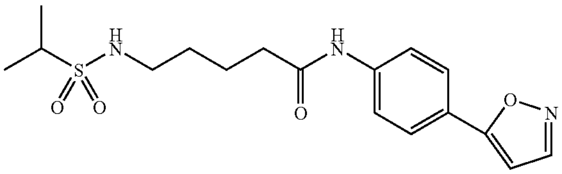
Id-180
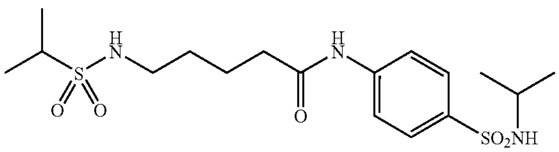
Id-181
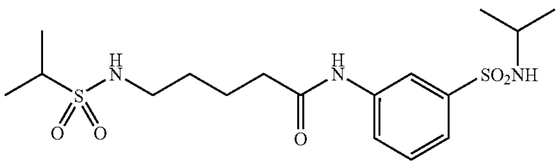
Id-182
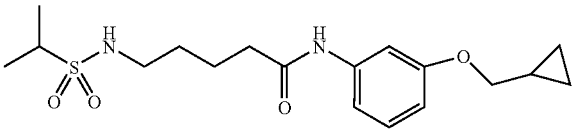
Id-183
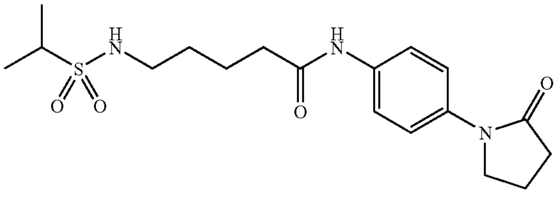

-continued
Id-184
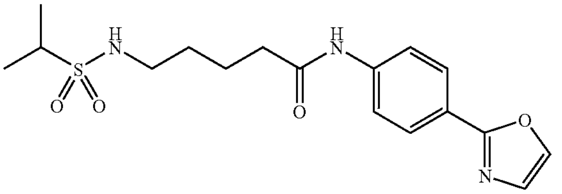
Id-185
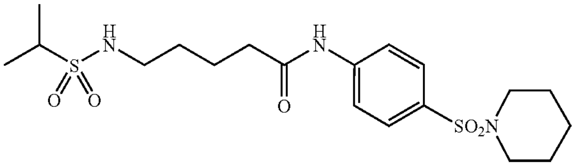
Id-186
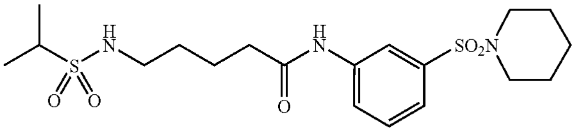
Id-187
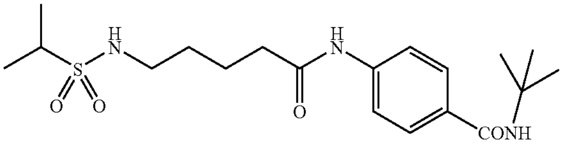
Id-188
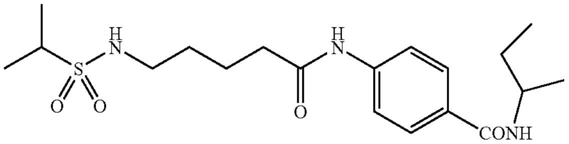
Id-189
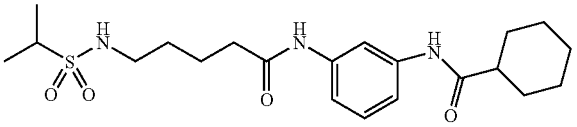
Id-190
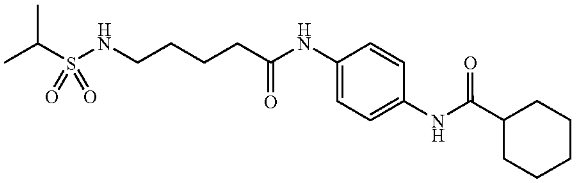
Id-191
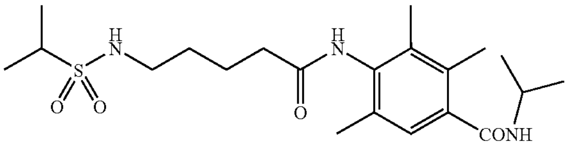
-continued
Id-192
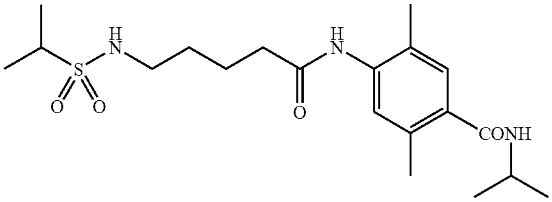
Id-193
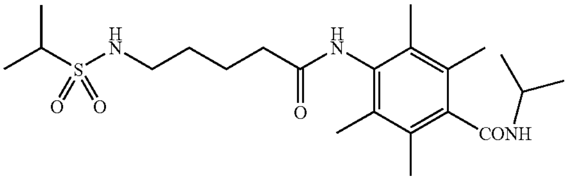
Id-194
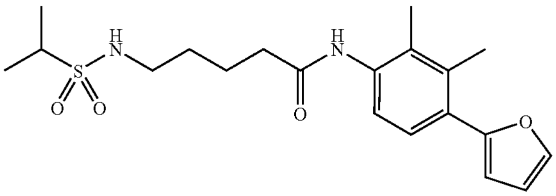
Id-195
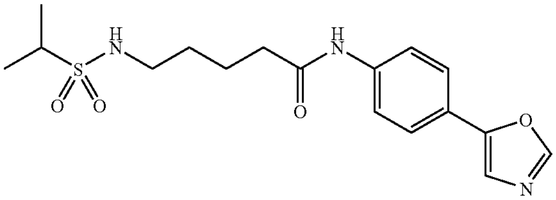
Id-196
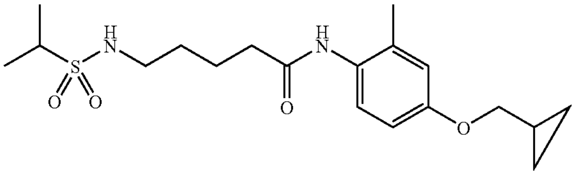
Id-197
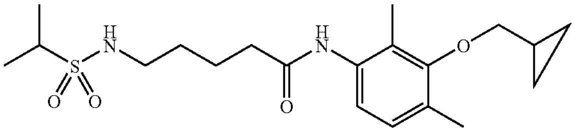
Id-198
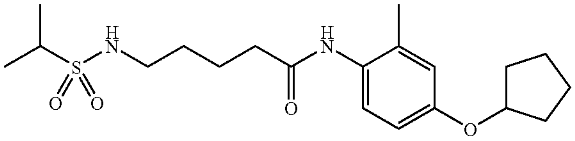
Id-199
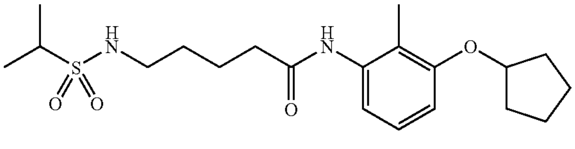

-continued
Id-200
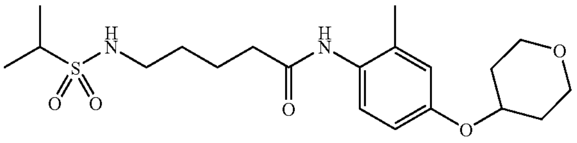
Id-201
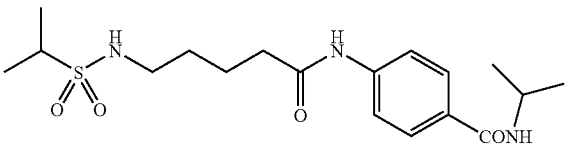
Id-202
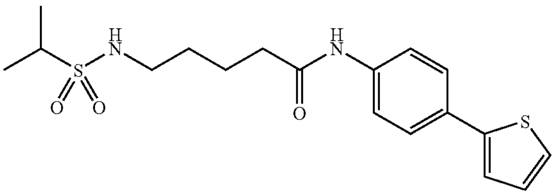
Id-203
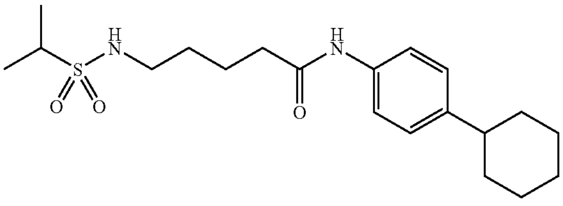
Id-204
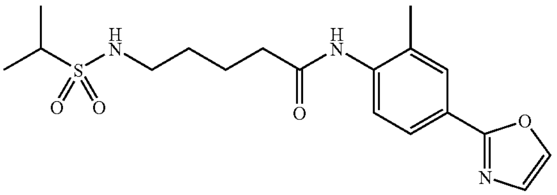
Id-205
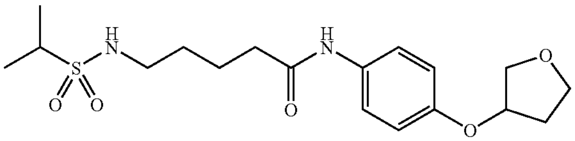
Id-206
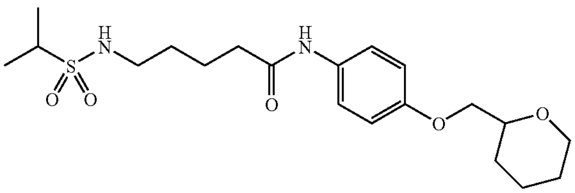
Id-207
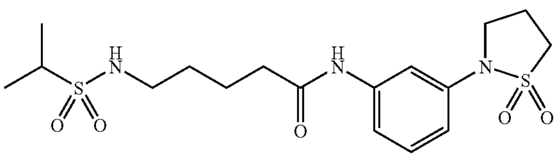
-continued
Id-208
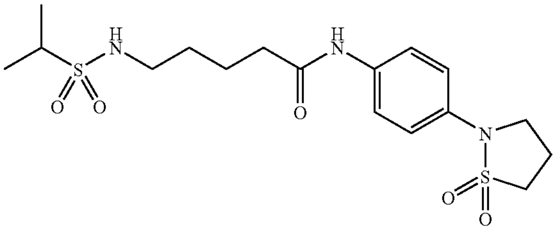
Id-209
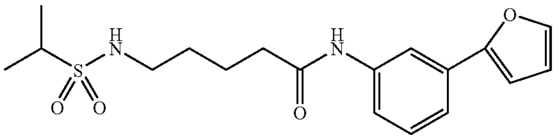
Id-210
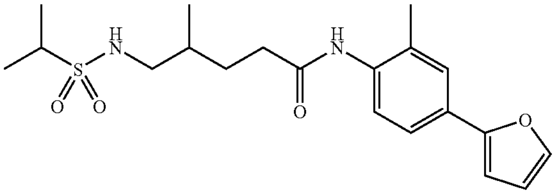
Id-211
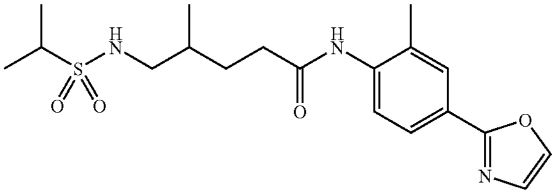
Id-212
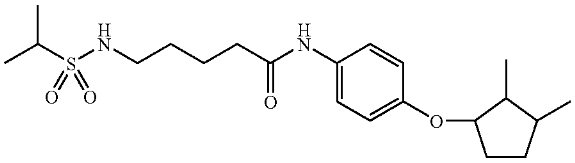
Id-213
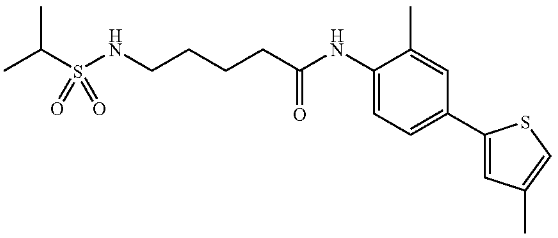
Id-214
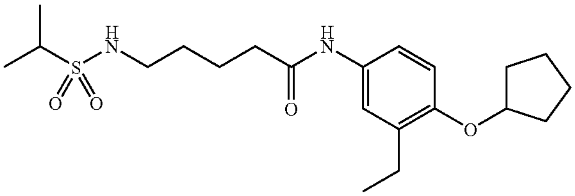

-continued
Id-215
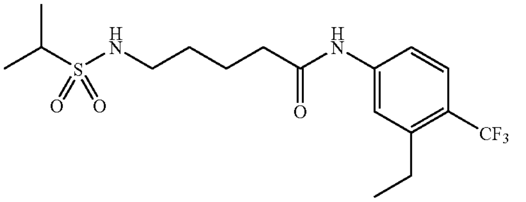
Id-216
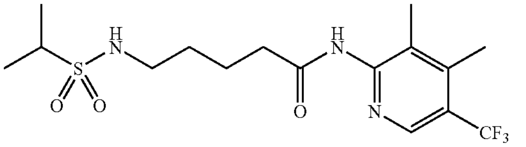
Id-219
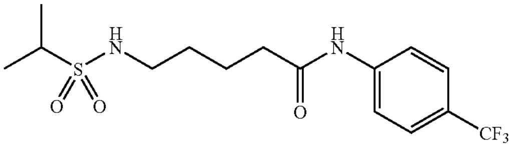
Id-220
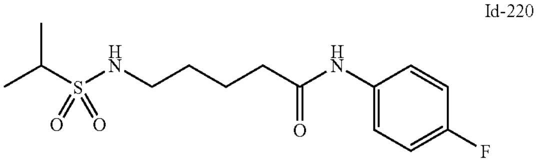
Id-221
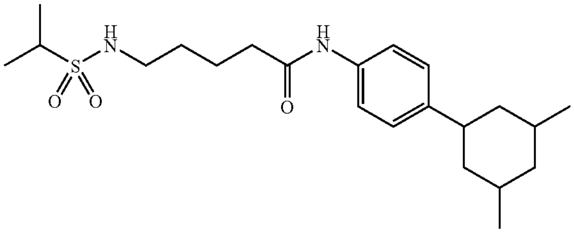
Id-222
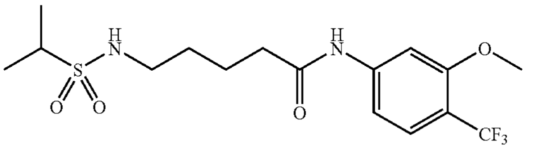
Id-223
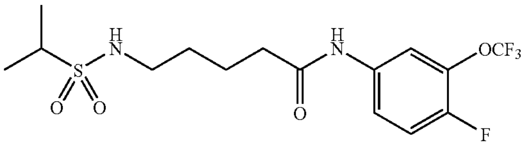
Id-224
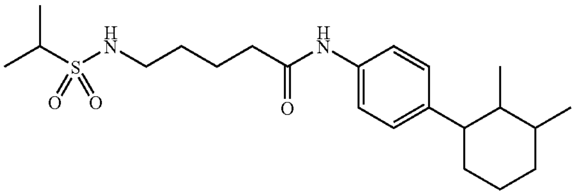
-continued
Id-225
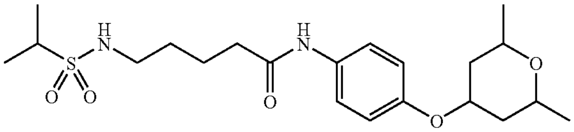
Id-226
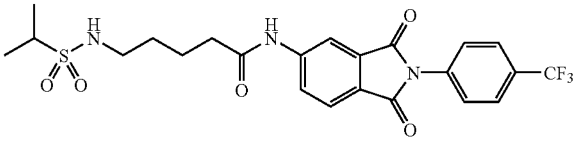
Ie-1
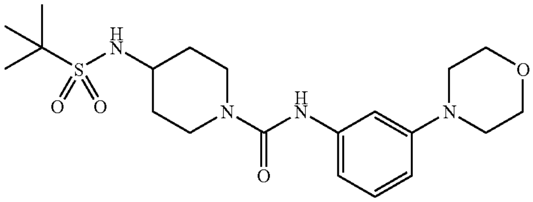
Ie-2
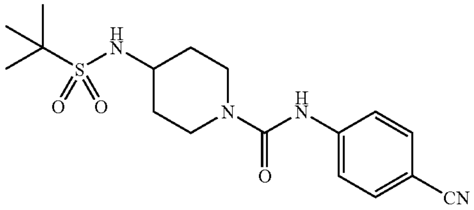
Ie-4
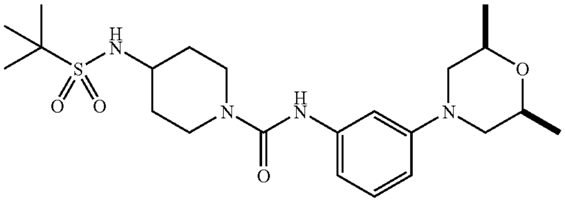
Ie-7
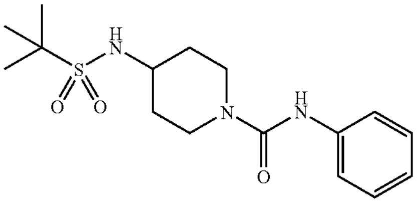
Ie-8
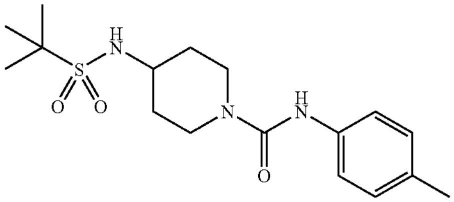

-continued
Ie-9
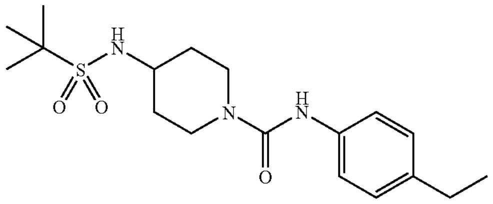
Ie-10
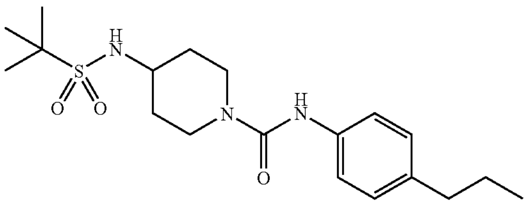
Ie-11
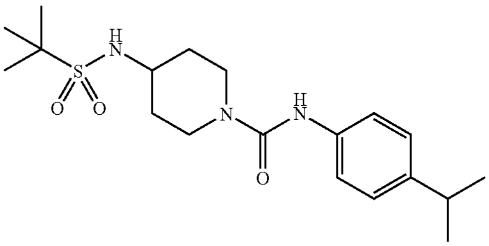
Ie-12
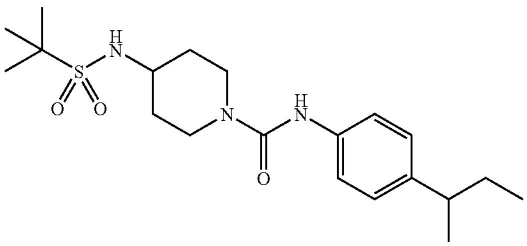
Ie-13
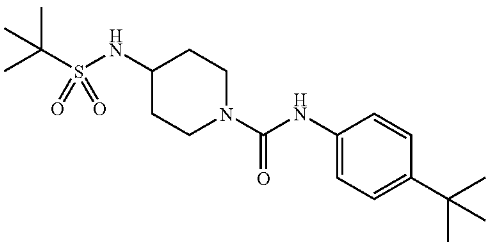
Ie-14
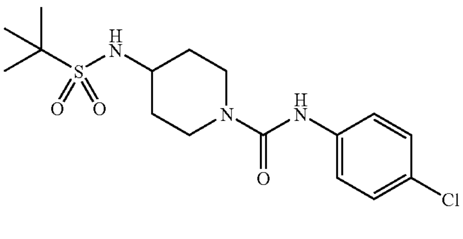
-continued
Ie-16
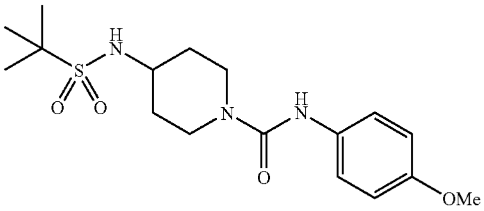
Ie-17
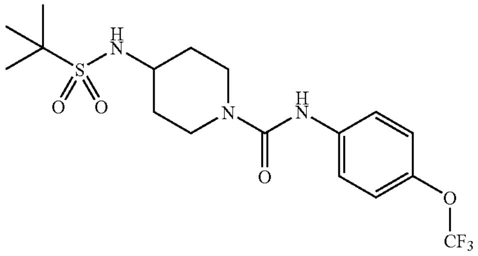
Ie-18
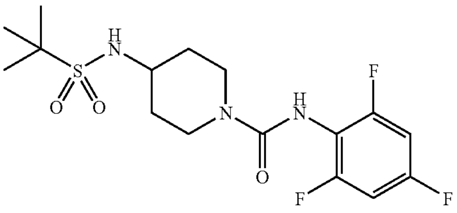
Ie-19
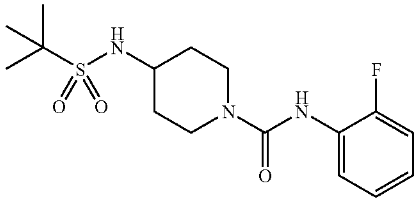
Ie-20
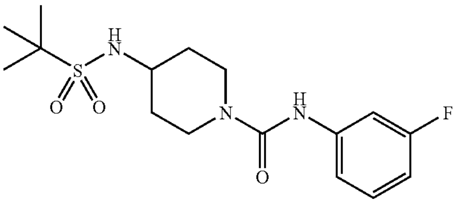
Ie-21
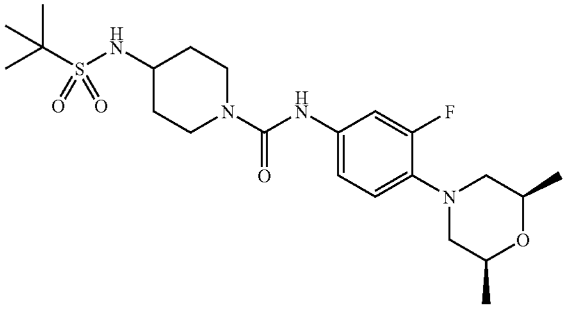

-continued
Ie-22
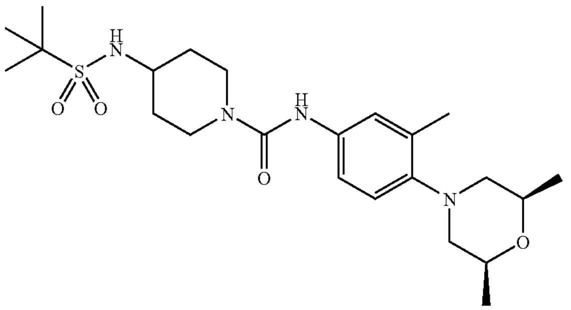
Ie-23
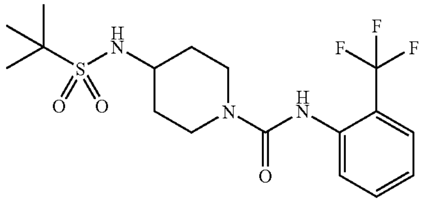
Ie-24
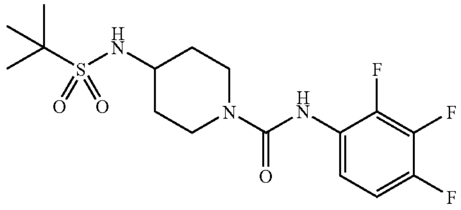
Ie-25
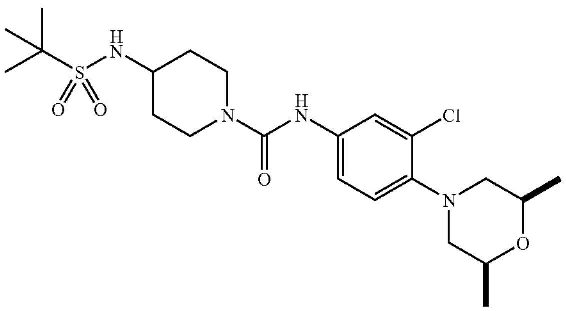
Ie-26
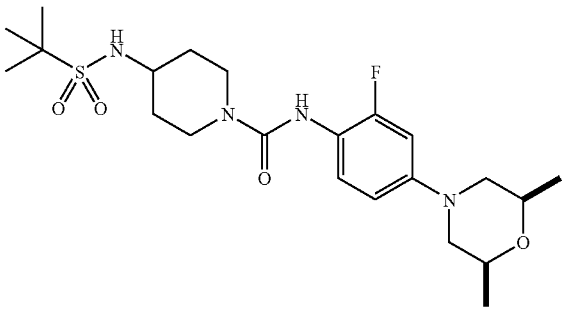
-continued
Ie-27
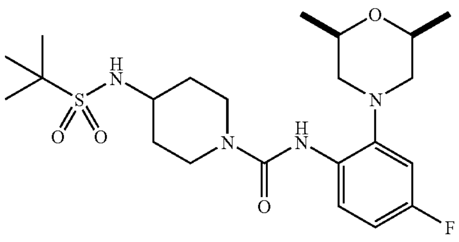
Ie-28
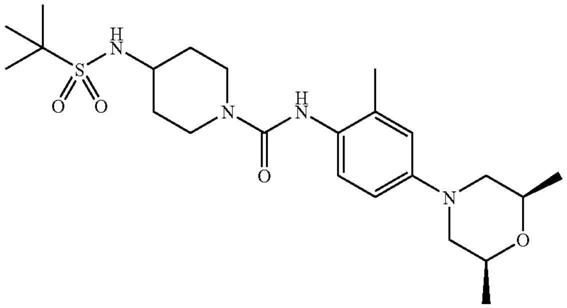
Ie-29
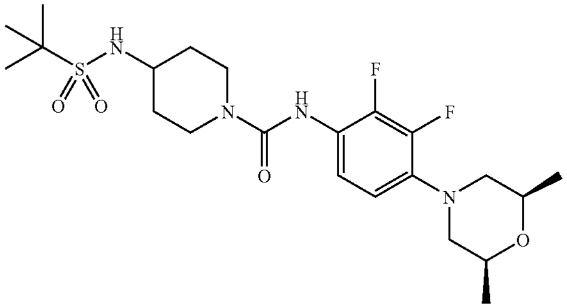
Ie-30
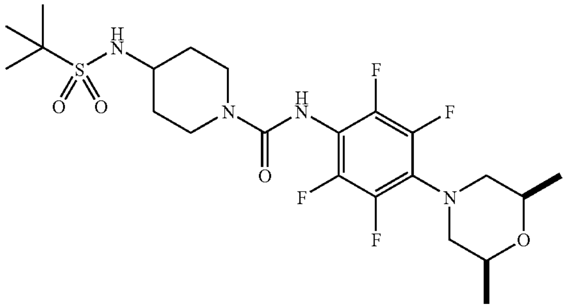
Ie-31
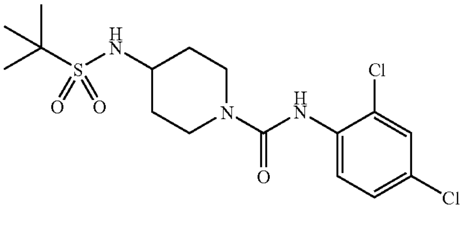

-continued
Ie-32
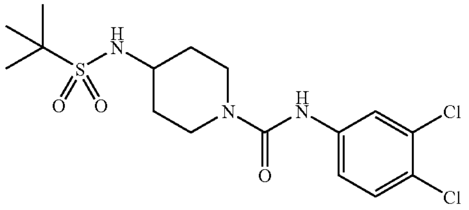
Ie-33
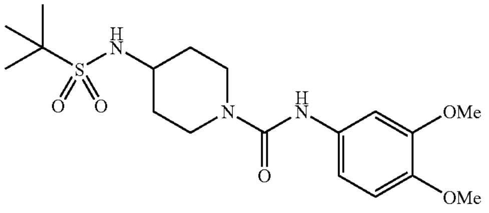
Ie-35
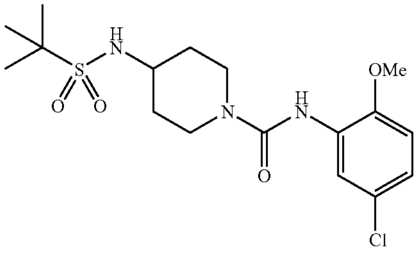
Ie-36
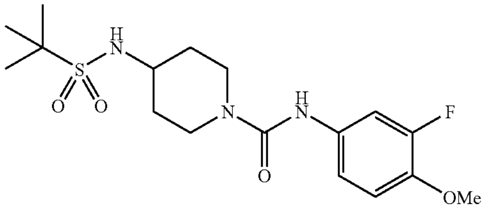
Ie-37
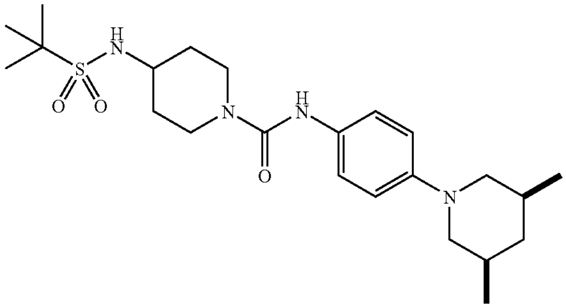
Ie-38
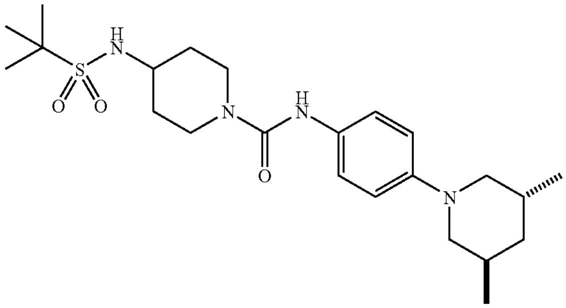
-continued
Ie-39
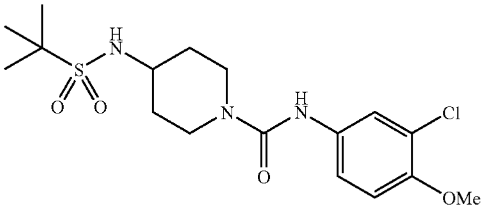
Ie-40
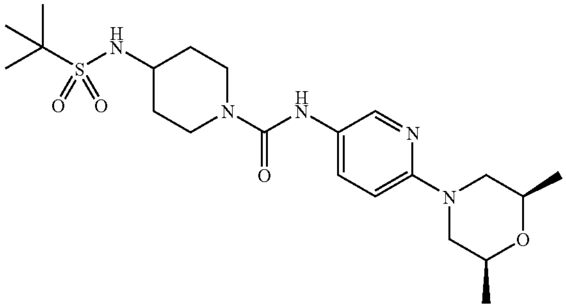
Ie-41
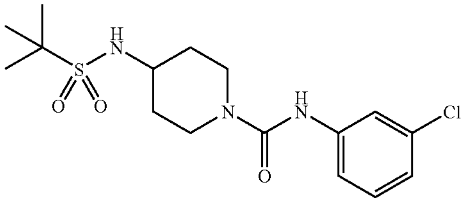
Ie-42
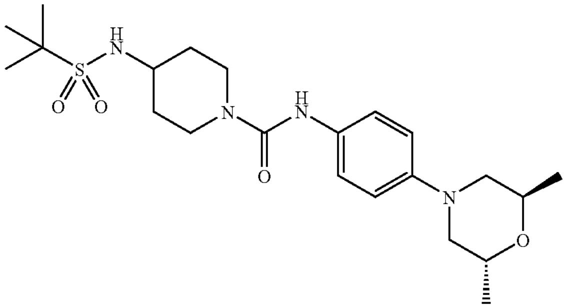
Ie-43
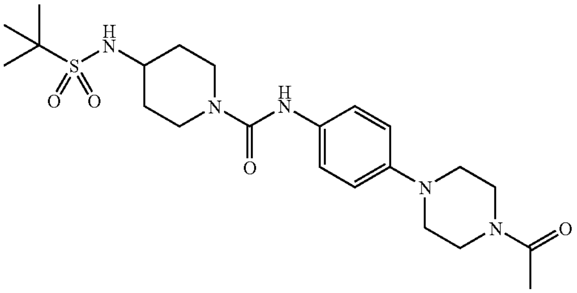

-continued
Ie-44
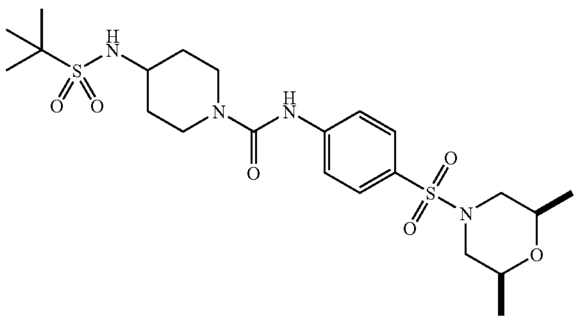
Ie-45
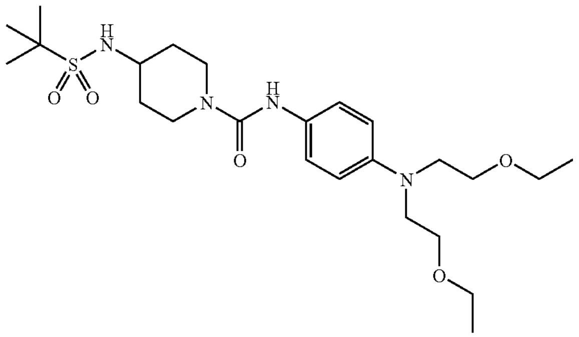
Ie-46
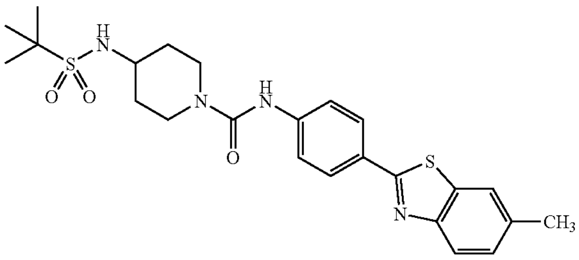
Ie-47
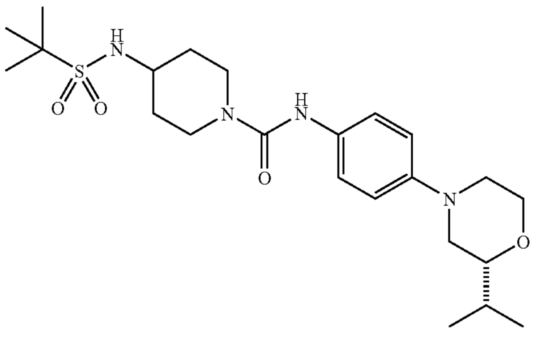
-continued
Ie-48
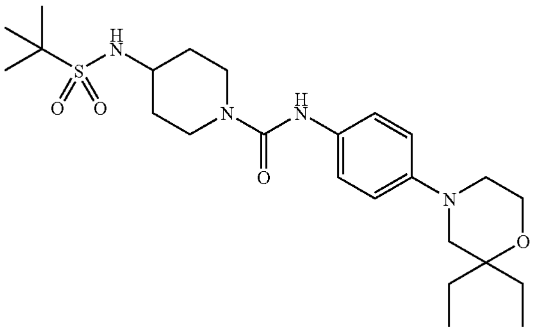
Ie-49
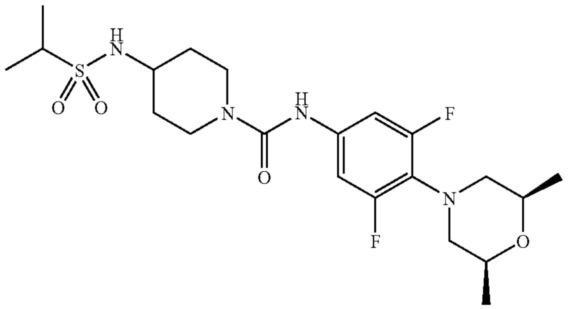
Ie-50
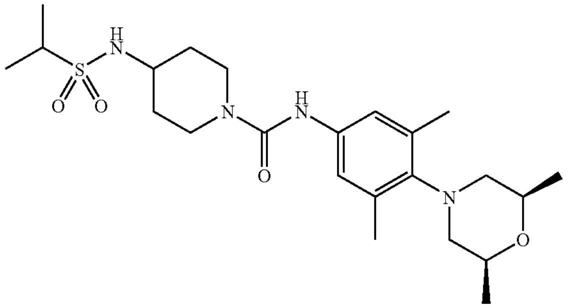
Ie-51
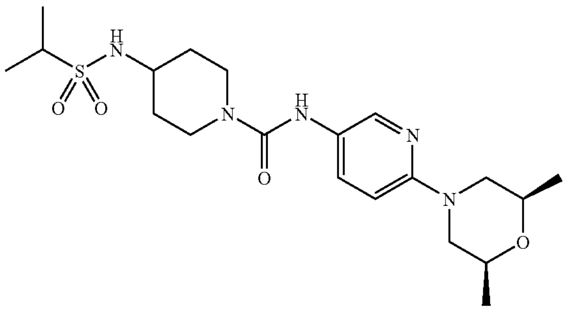

-continued
Ie-52
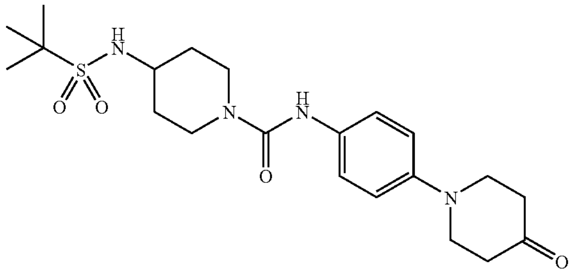
Ie-53
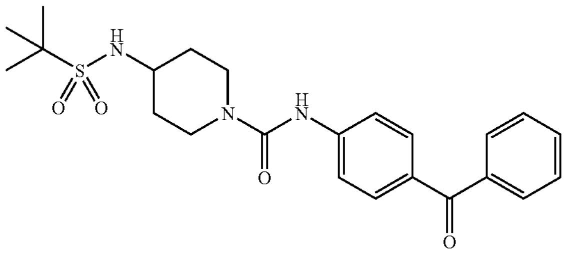
Ie-54
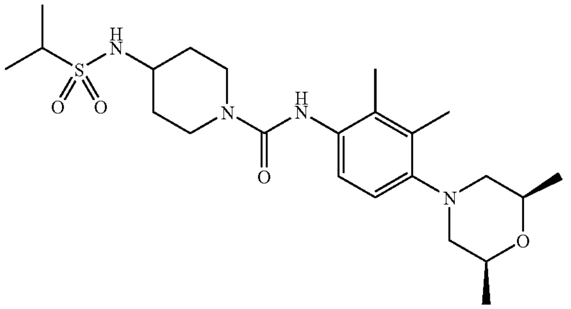
Ie-55
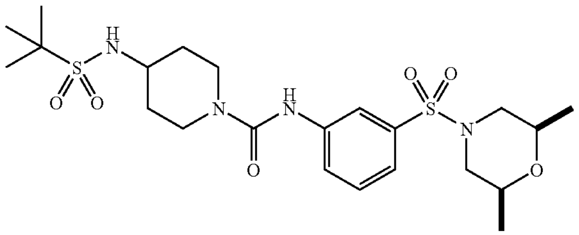
Ie-56
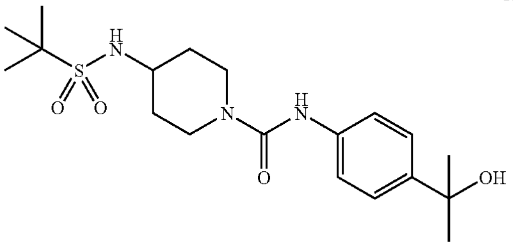
-continued
Ie-57
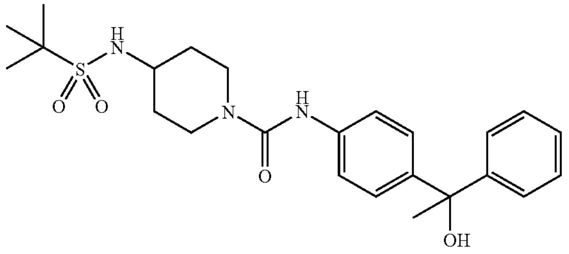
Ie-58
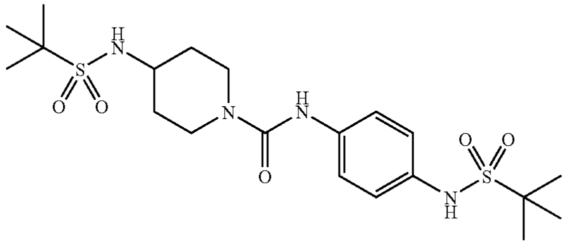
Ie-59
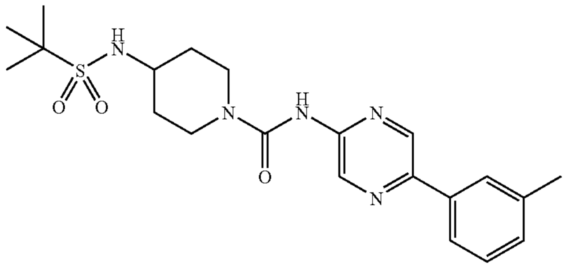
Ie-60
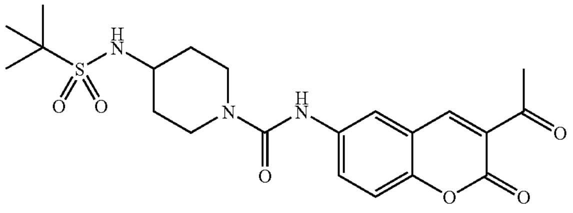
Ie-61
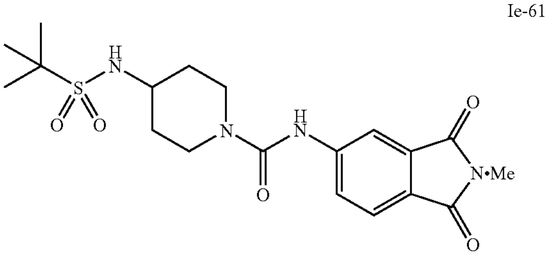
Ie-62
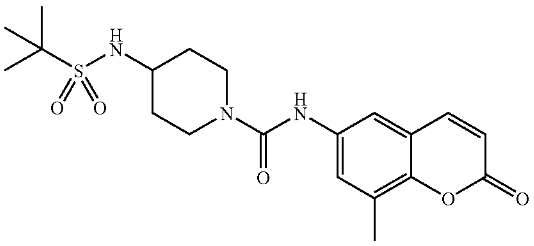

-continued
Ie-63
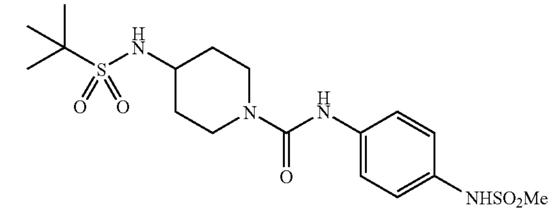
Ie-64
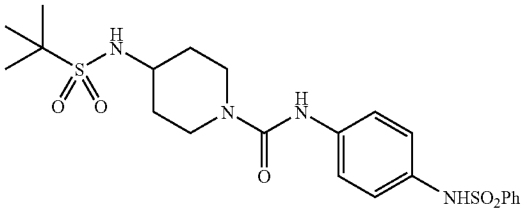
Ie-65
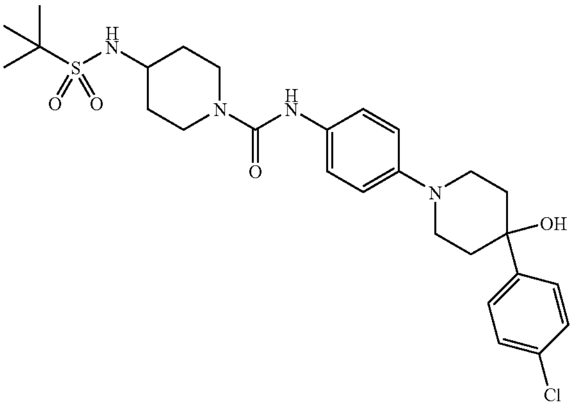
Ie-66
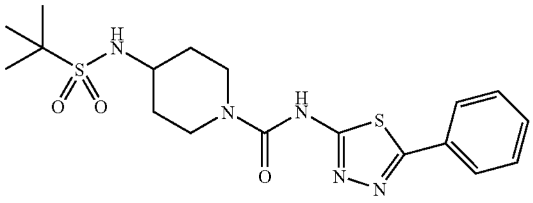
Ie-67
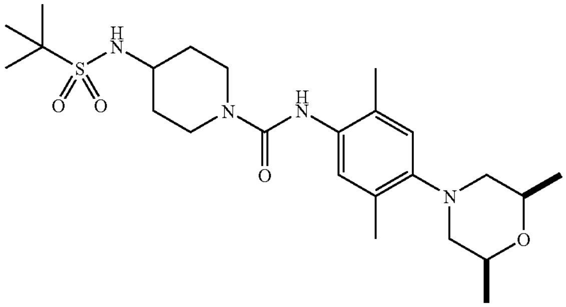
-continued
Ie-68
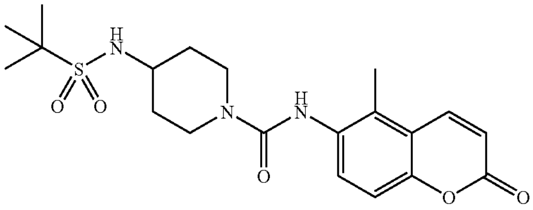
Ie-69
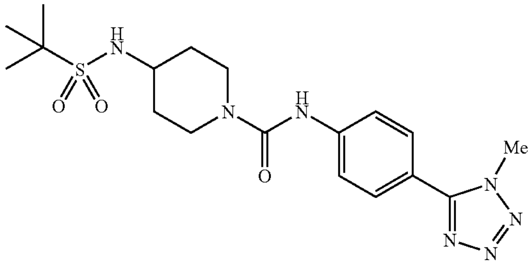
Ie-70
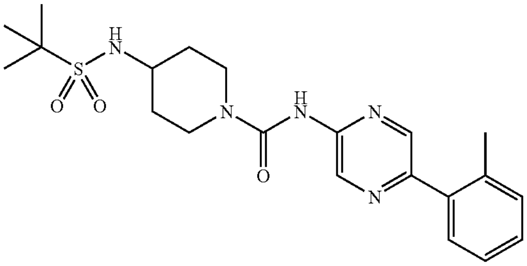
Ie-71
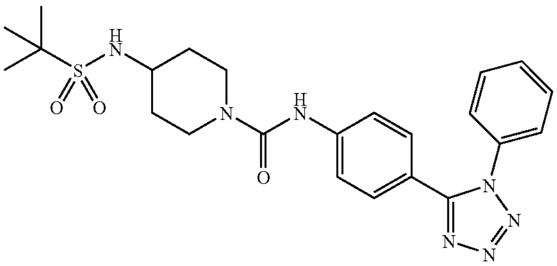
Ie-73
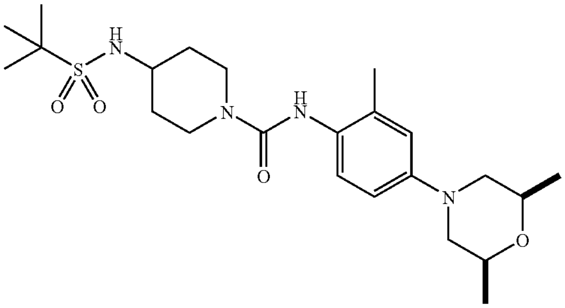

-continued
Ie-74
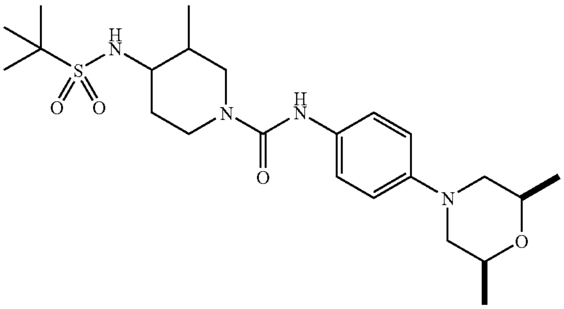
Ie-75
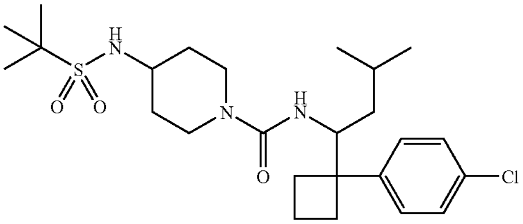
Ie-76
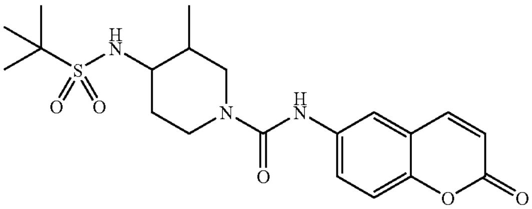
Ie-77
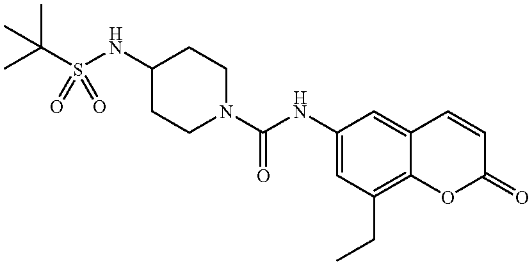
Ie-78
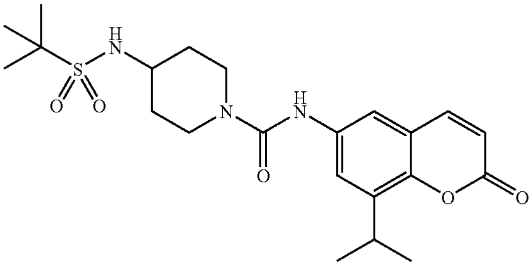
-continued
Ie-79
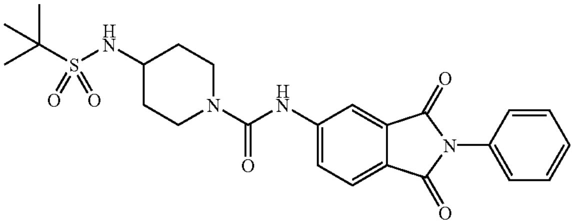
Ie-80
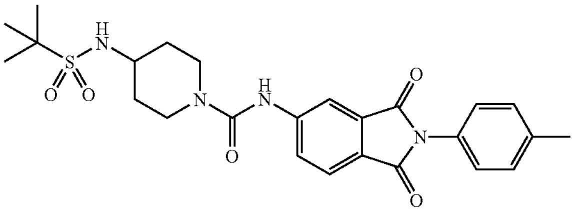
Ie-81
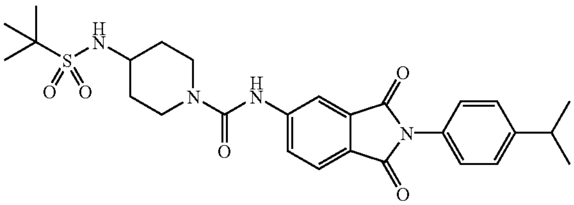
Ie-82
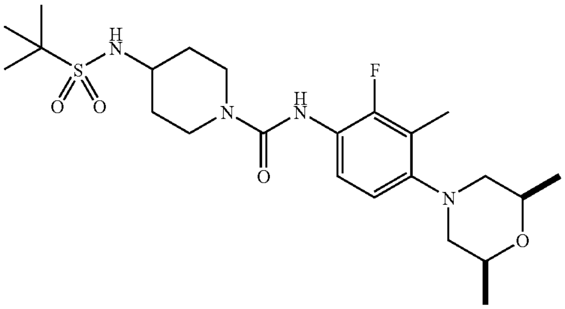
Ie-83
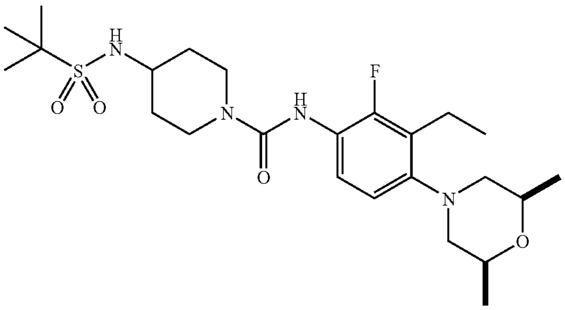

-continued
Ie-84
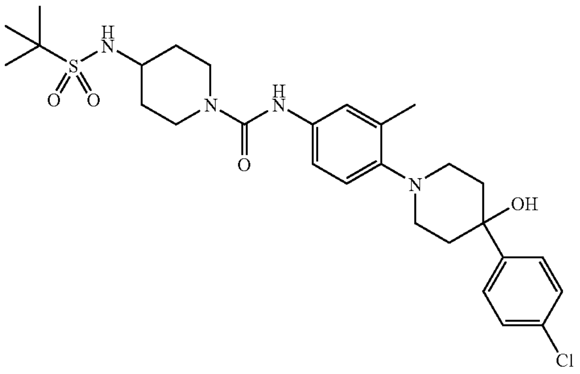
Ie-85
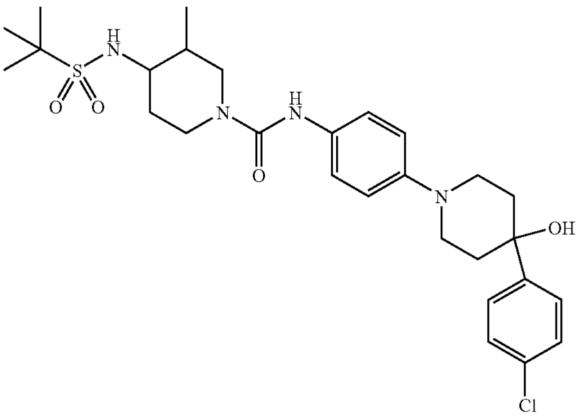
Ie-86
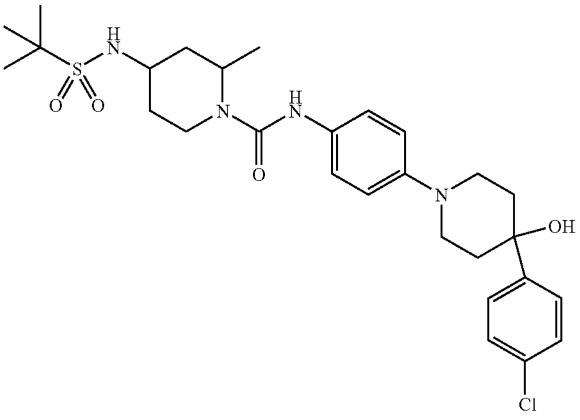
Ie-87
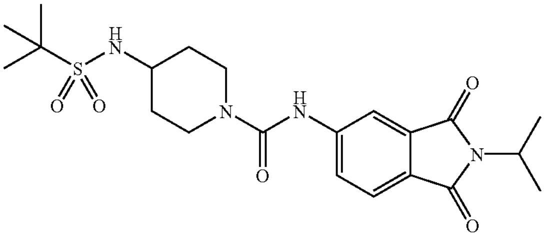
-continued
Ie-88
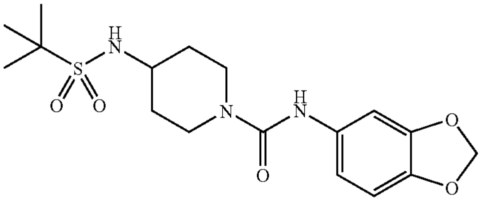
Ie-89
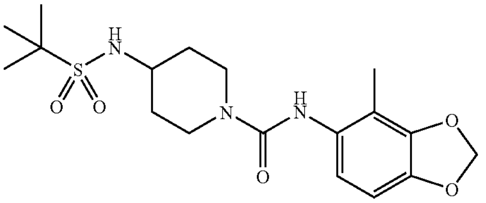
Ie-90
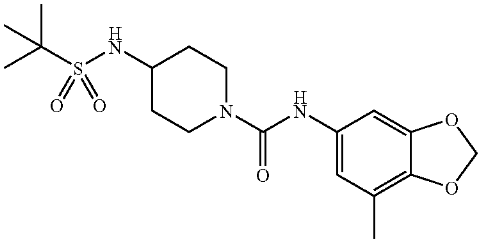
Ie-91
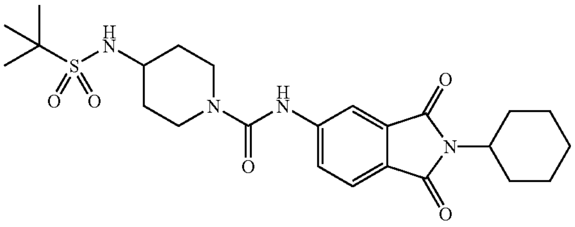
Ie-92
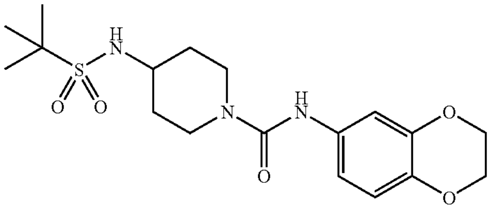
Ie-93
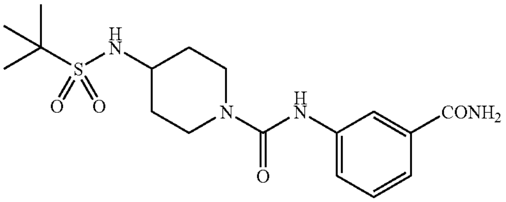
Ie-94
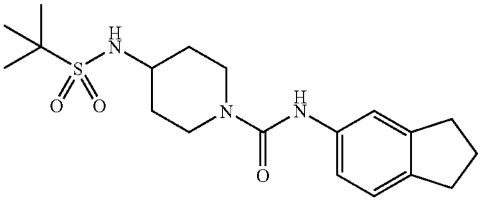

-continued
Ie-95
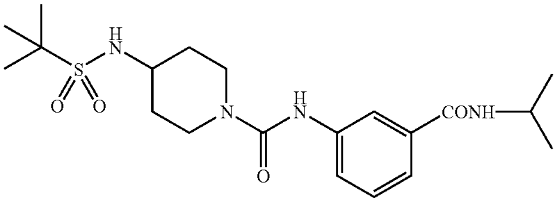
Ie-96
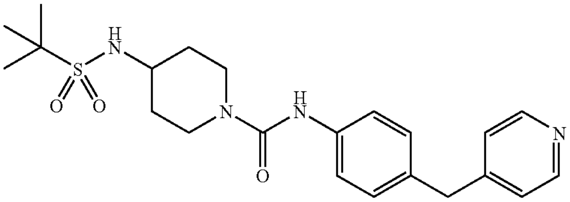
Ie-97
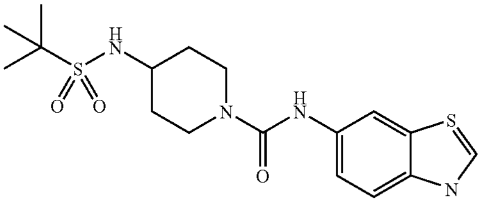
Ie-98
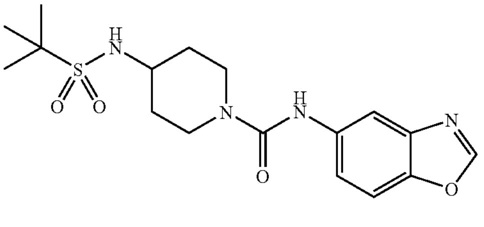
Ie-99
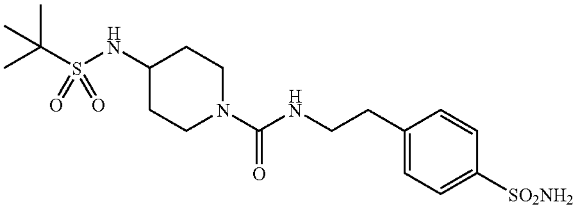
Ie-100
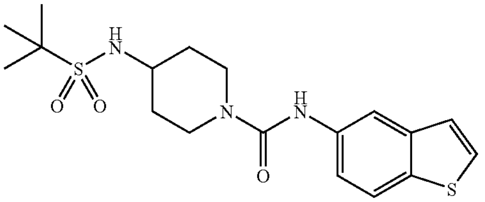
Ie-101
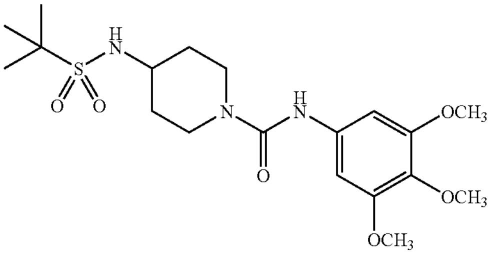
-continued
Ie-102
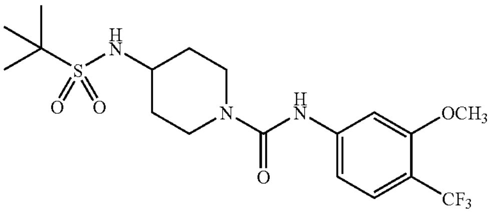
Ie-103
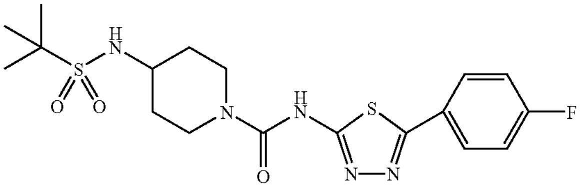
Ie-104
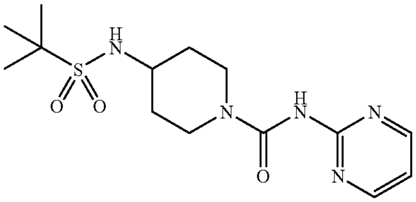
Ie-105
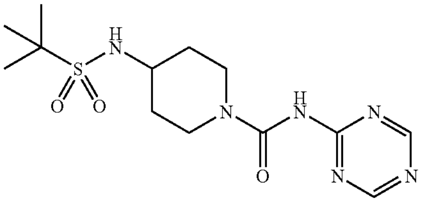
Ie-106
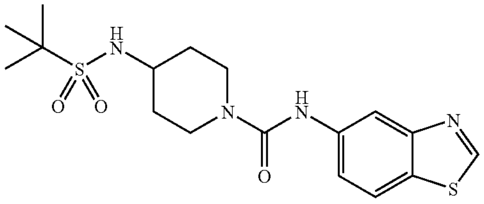
Ie-107
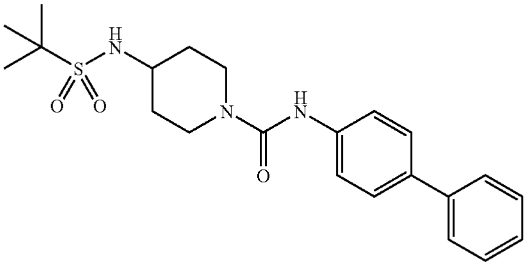
Ie-108
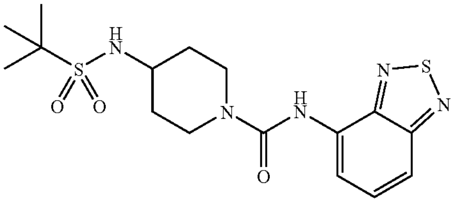

-continued
Ie-109
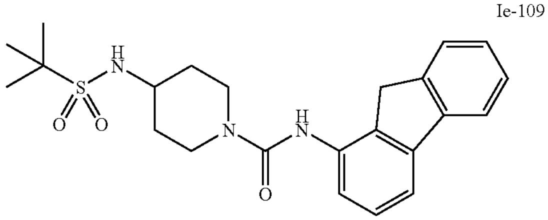
Ie-110
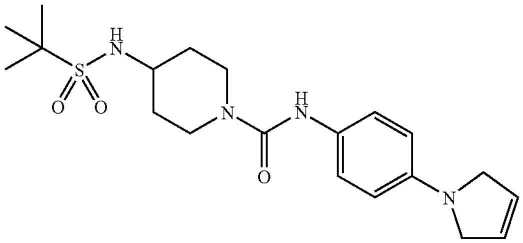
Ie-111
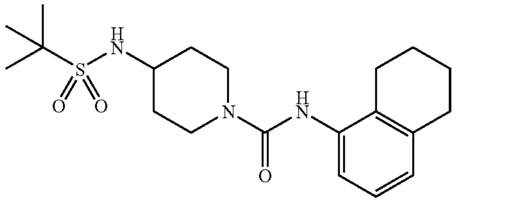
Ie-112
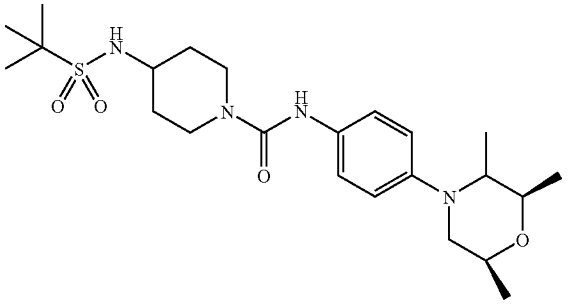
Ie-113
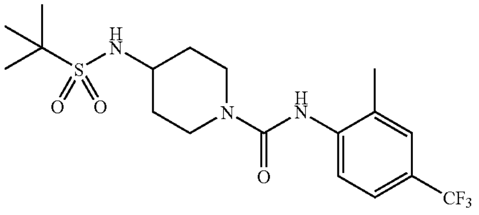
Ie-114
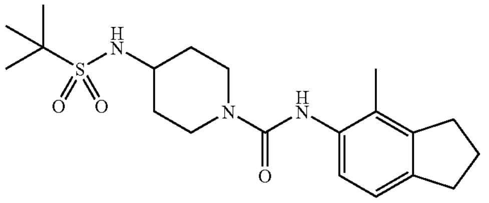
-continued
Ie-115
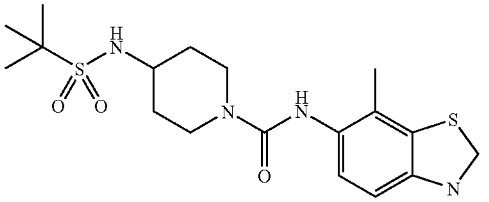
Ie-116
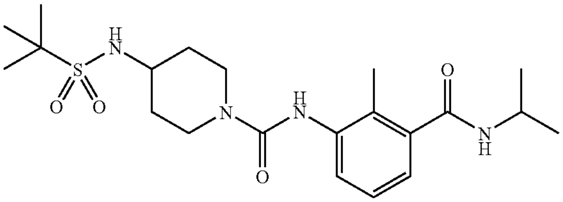
Ie-117
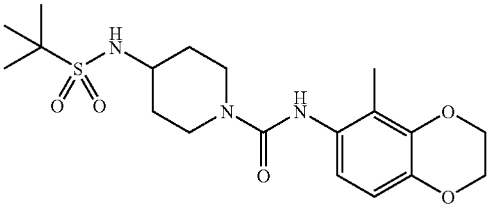
Ie-118
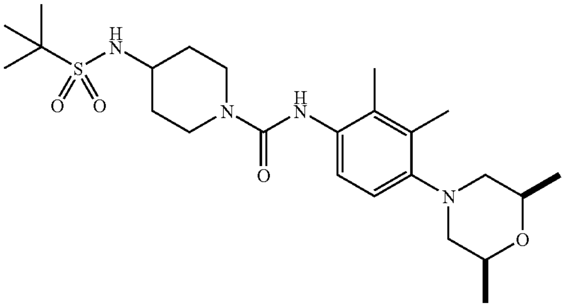
Ie-119
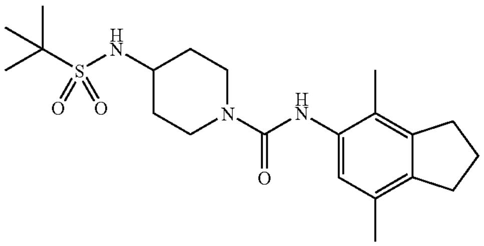
Ie-120
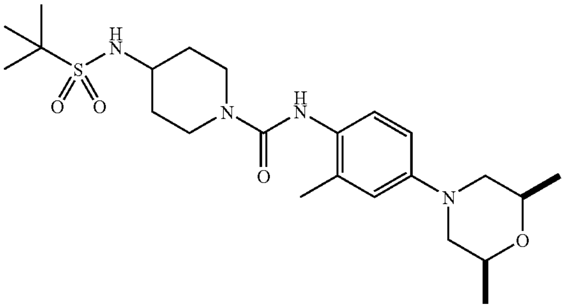

-continued
Ie-121
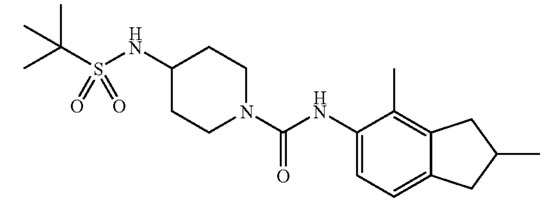
Ie-122
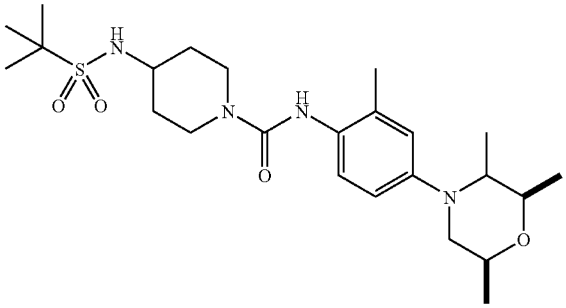
Ie-123
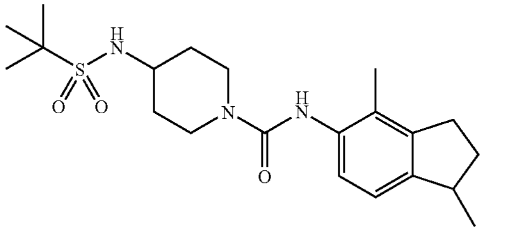
Ie-124
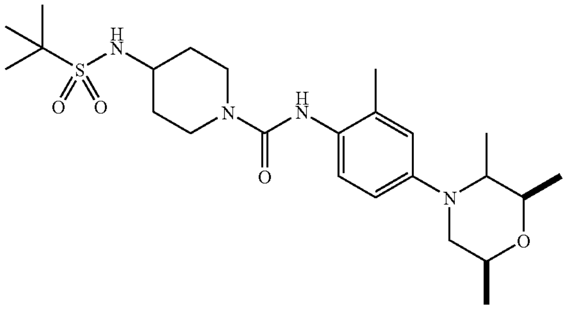
Ie-125
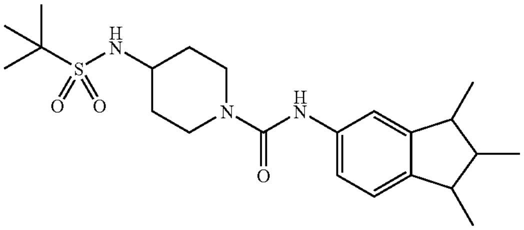
-continued
Ie-126
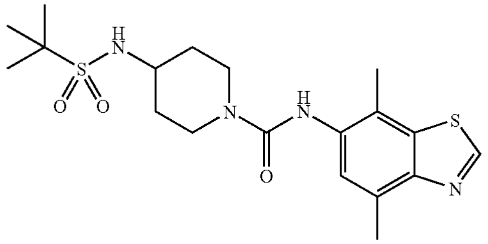
Ie-127
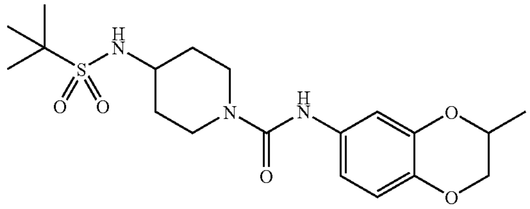
Ie-128
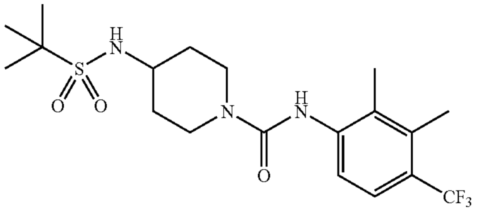
Ie-129
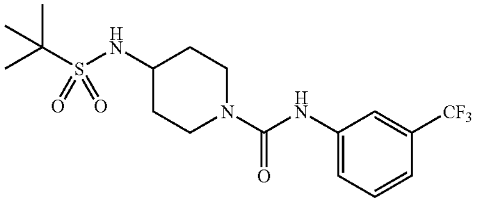
Ie-130
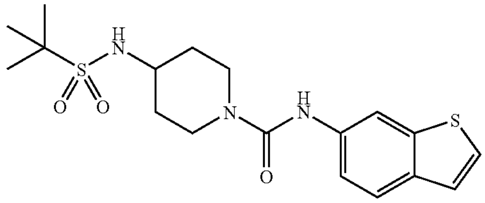
Ie-131
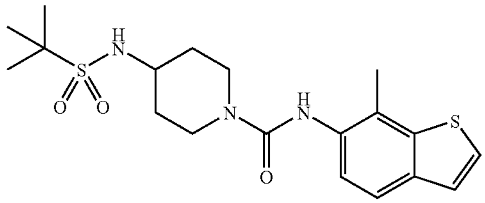
Ie-132
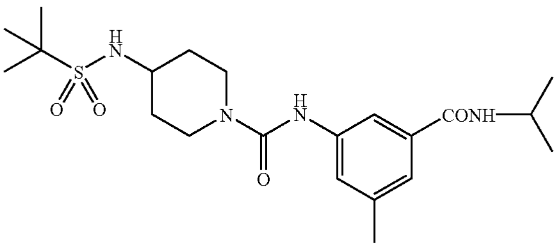

-continued
Ie-133
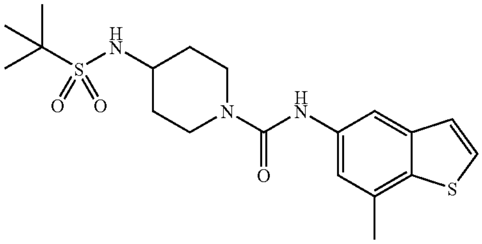
Ie-134
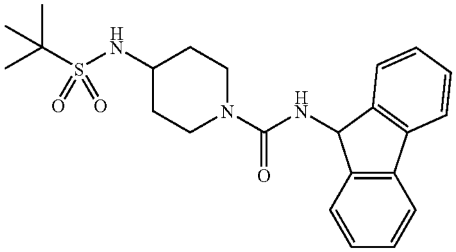
Ie-135
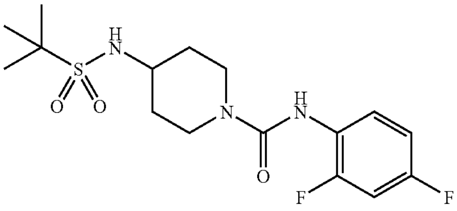
Ie-136
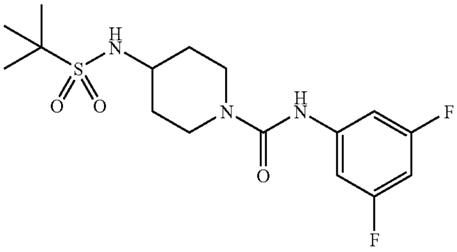
Ie-137
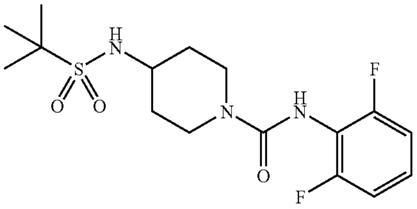
Ie-138
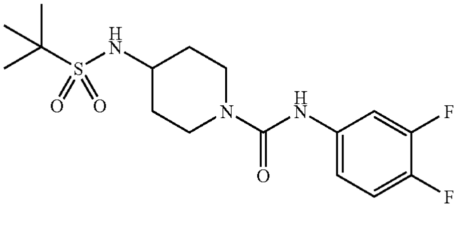
-continued
Ie-139
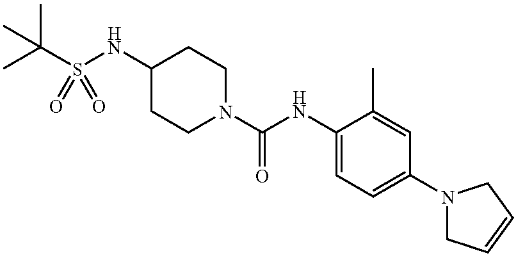
Ie-140
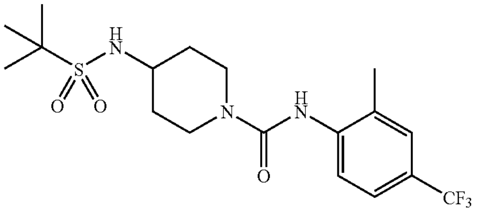
Ie-141
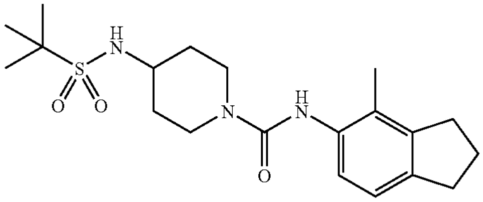
Ie-142
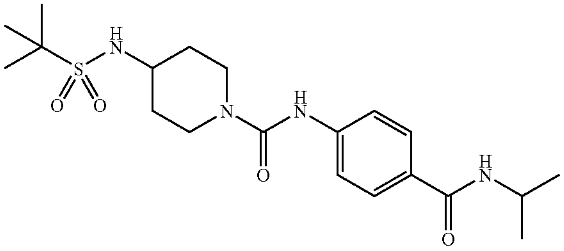
Ie-143
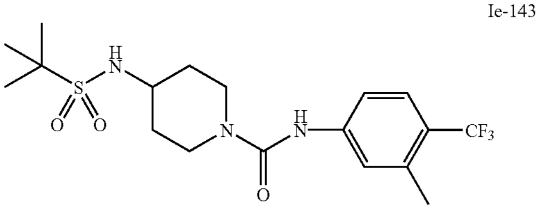
Ie_144
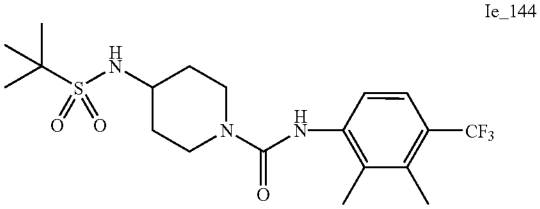
Ie-145
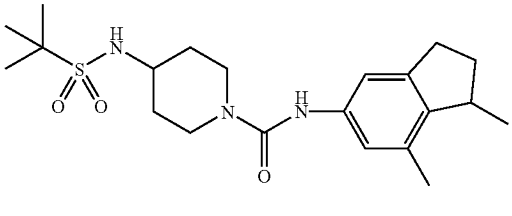

-continued
Ie-146
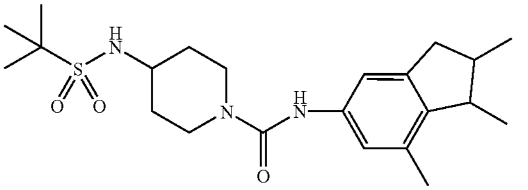
Ie-147
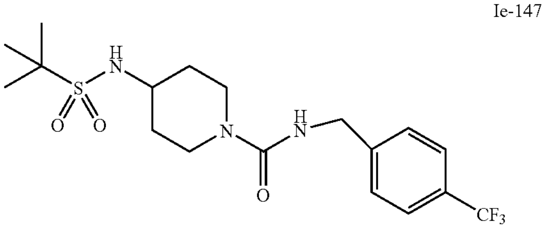
Ie-148
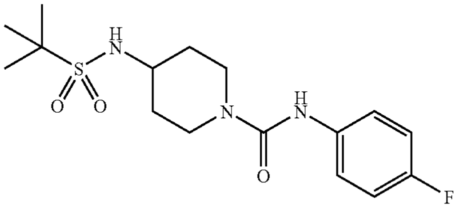
Ie-149
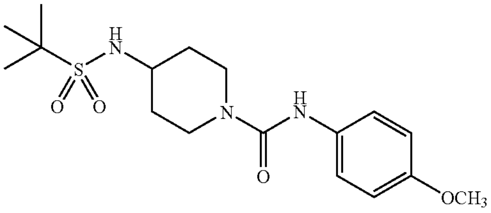
Ie-150
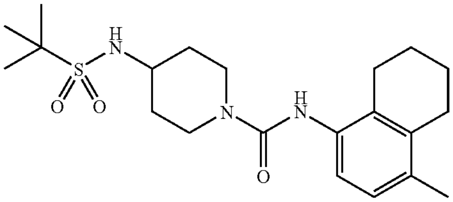
Ie-151
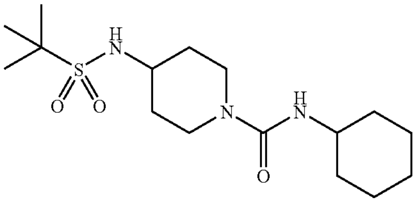
Ie-152
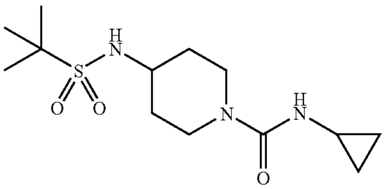
-continued
Ie-153
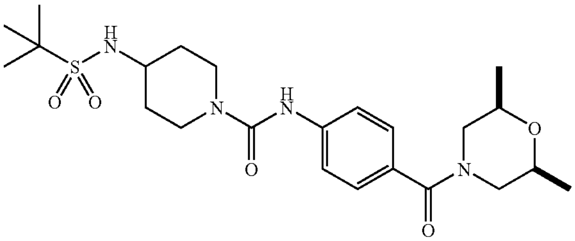
Ie-154
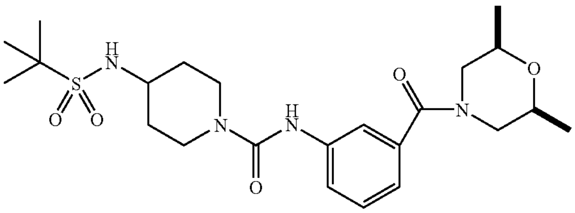
Ie-155
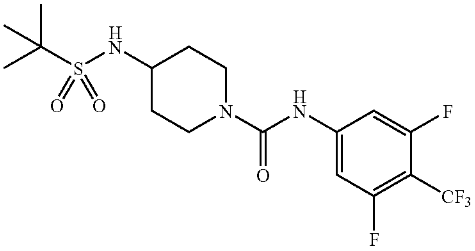
Ie-156
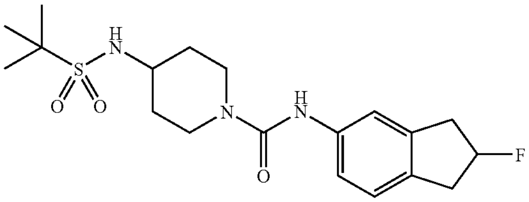
Ie-157
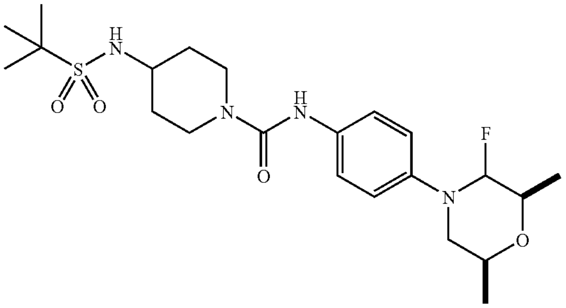

-continued
Ie-158
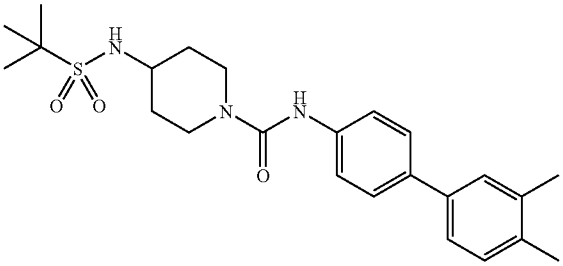
Ie-159
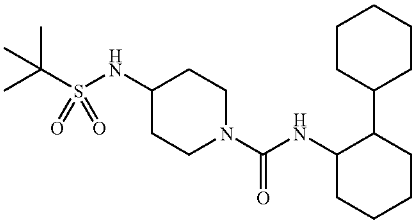
Ie-160
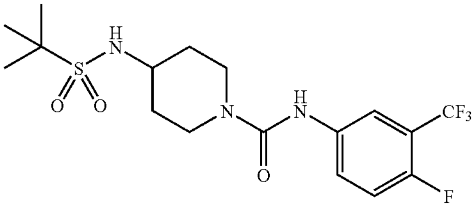
Ie-161
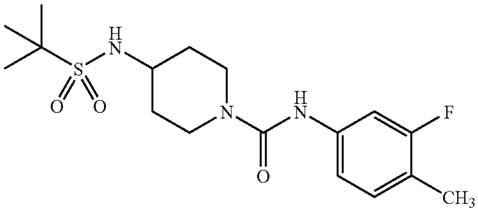
Ie-162
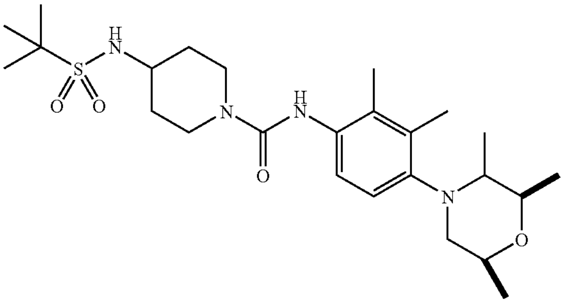
Ie-163
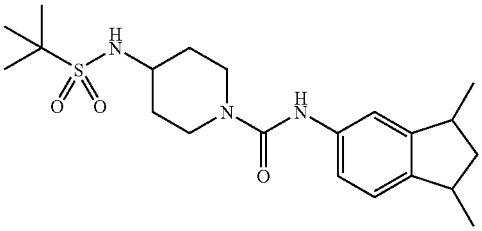
-continued
Ie-164
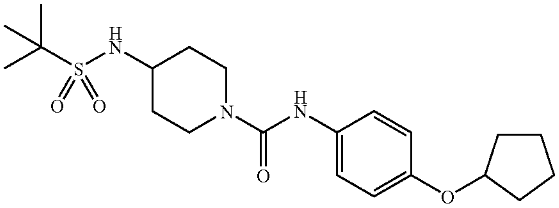
Ie-165
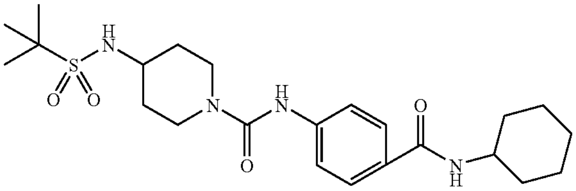
Ie-166
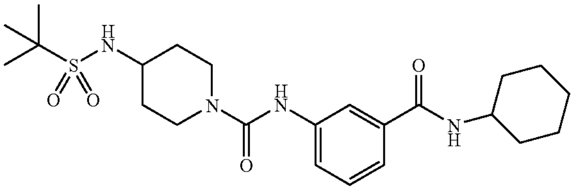
Ie-167
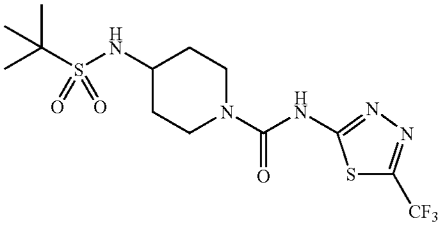
Ie-168
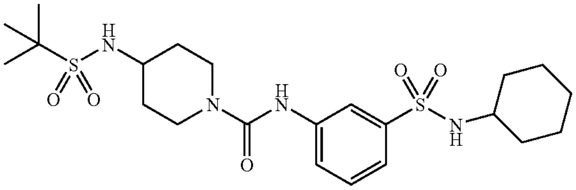
Ie-169
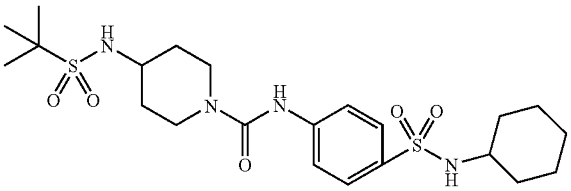
Ie-171
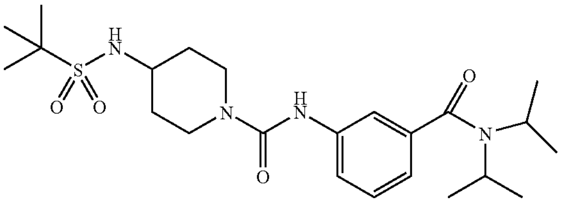

-continued
Ie-172
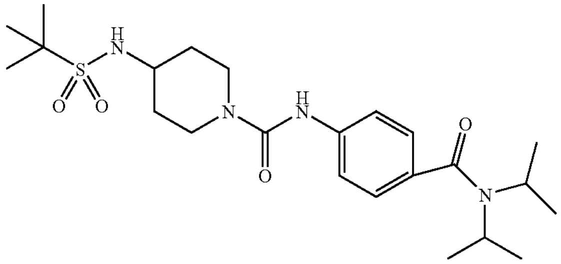
Ie-173
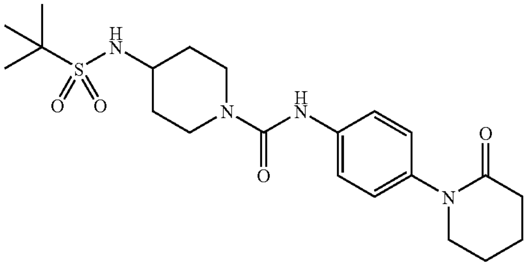
Ie-174
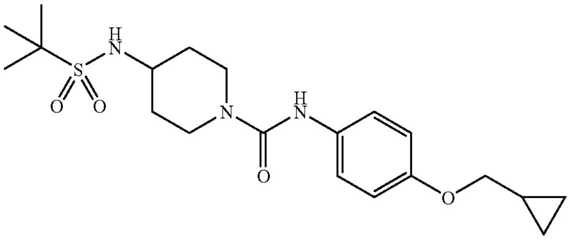
Ie-175
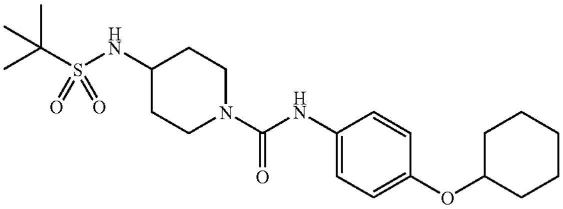
Ie-176
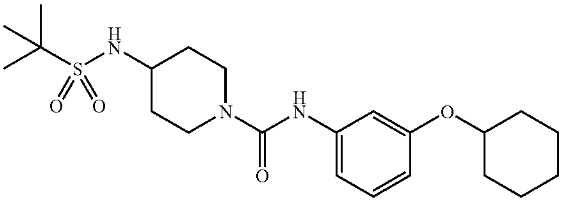
Ie-177
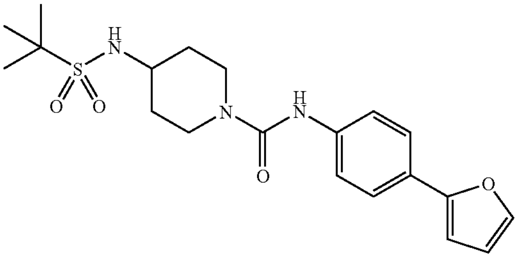
-continued
Ie-178
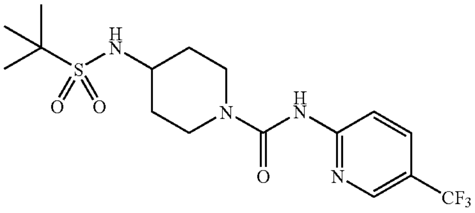
Ie-179
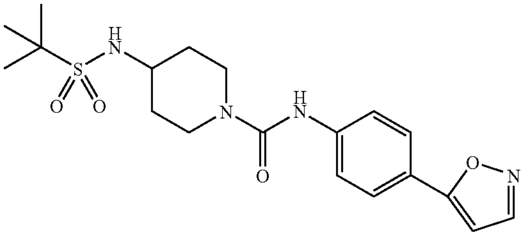
Ie-180
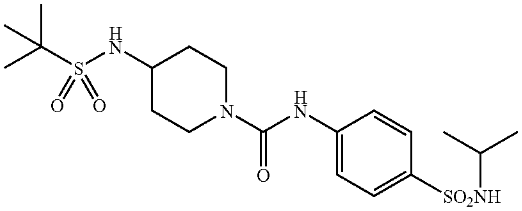
Ie-181
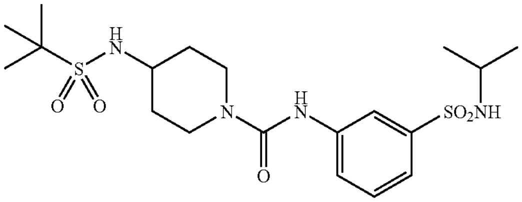
Ie-182
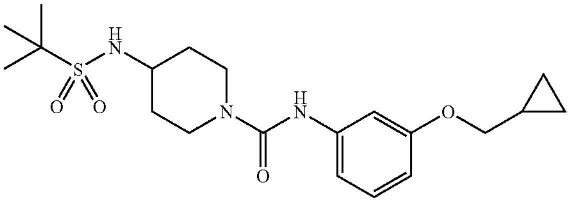
Ie-183
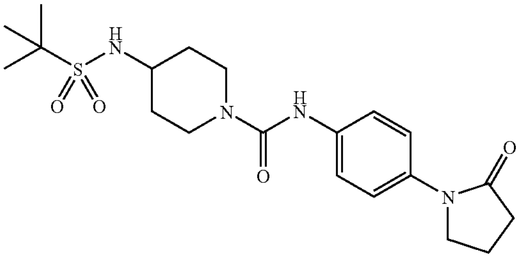

-continued
Ie-184
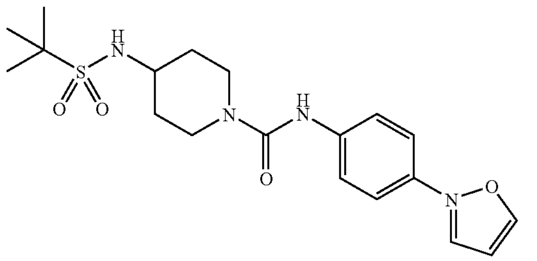
Ie-185
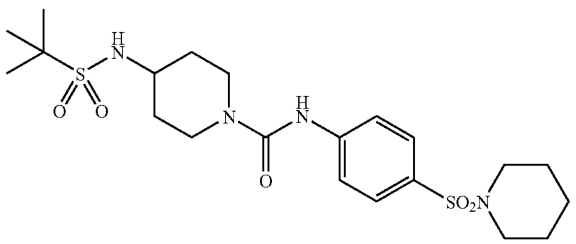
Ie-186
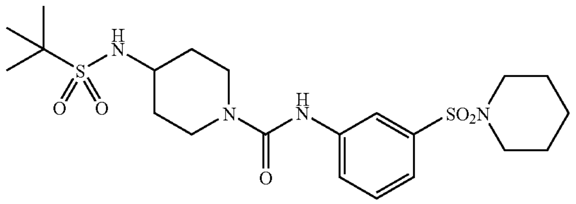
Ie-187
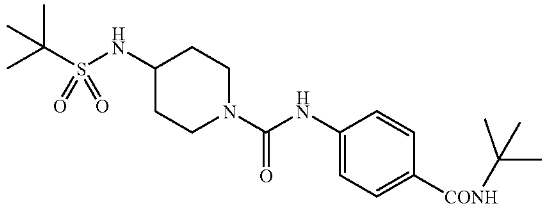
Ie-188
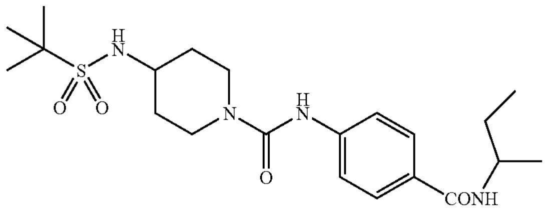
Ie-189
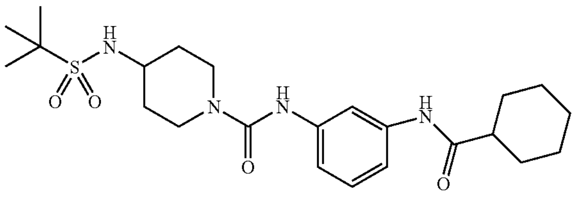
-continued
Ie-190
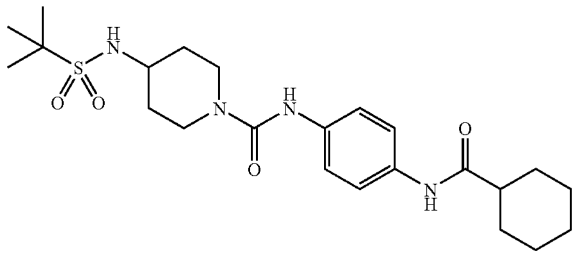
Ie-191
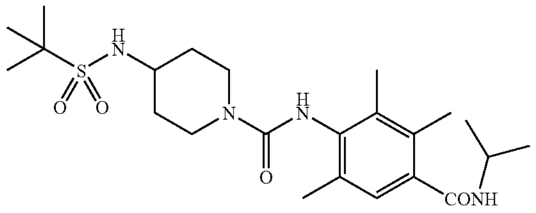
Ie-192
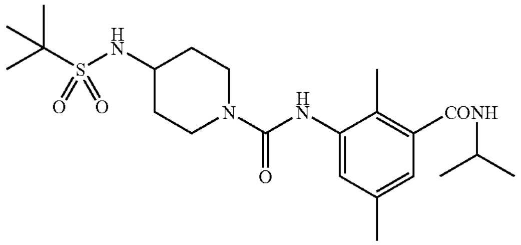
Ie-193
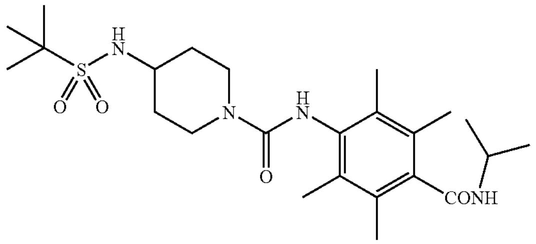
Ie-194
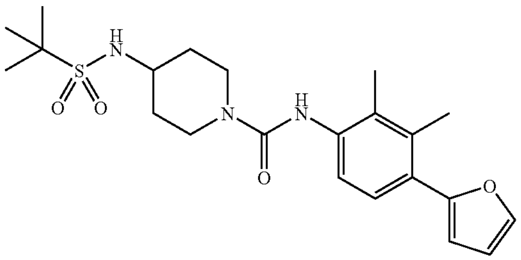
Ie-195
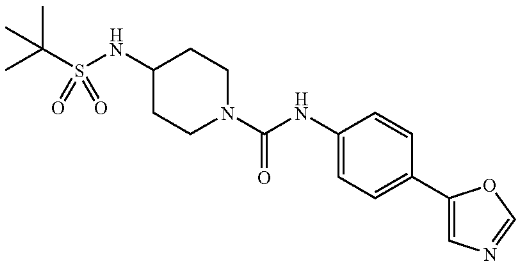

-continued
Ie-196
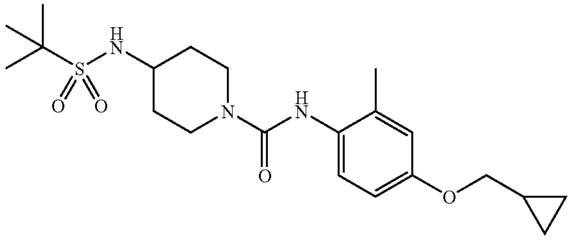
Ie-197
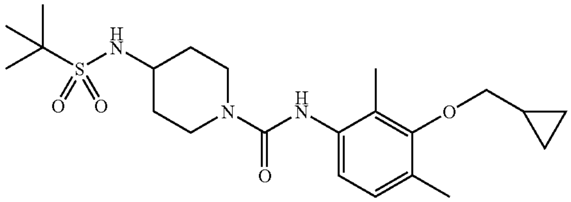
Ie-198
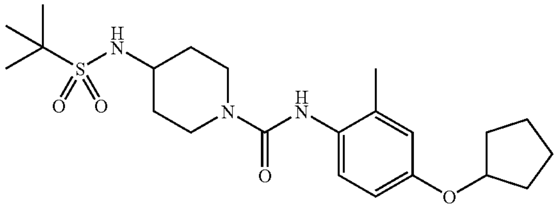
Ie-199
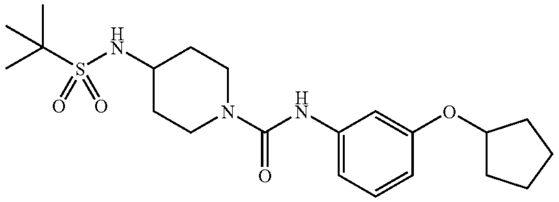
Ie-200
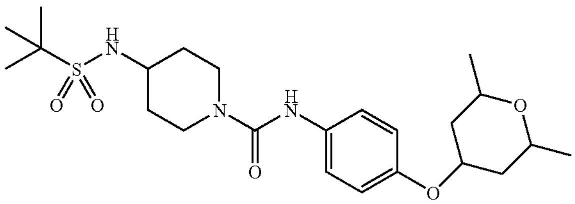
Ie-201
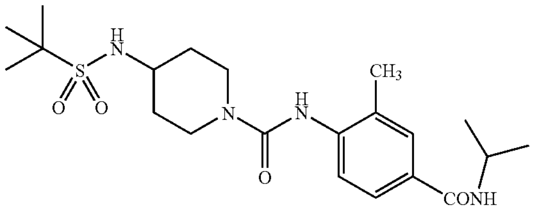
-continued
Ie-202
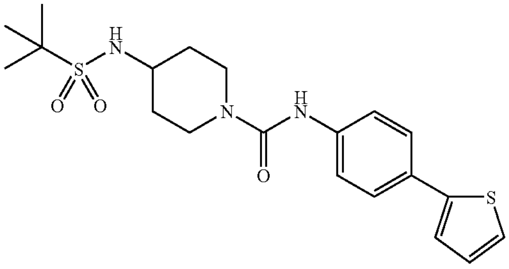
Ie-203
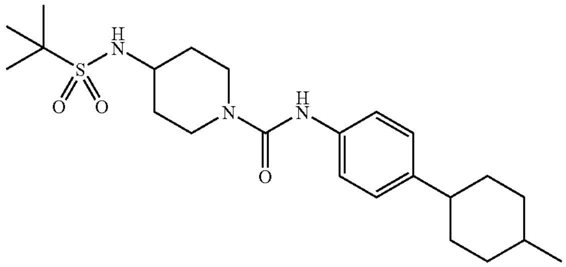
Ie-204
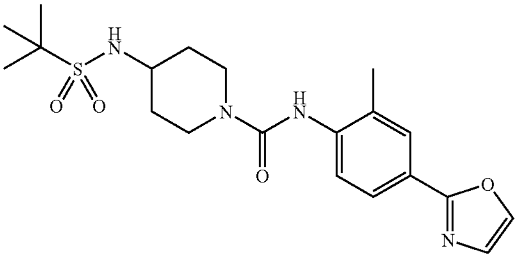
Ie-205
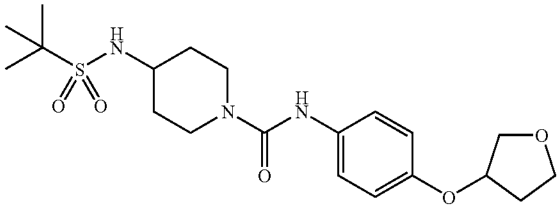
Ie-206
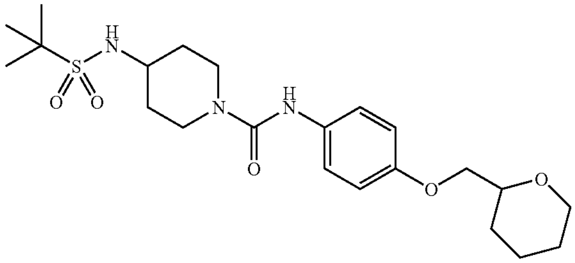
Ie-207
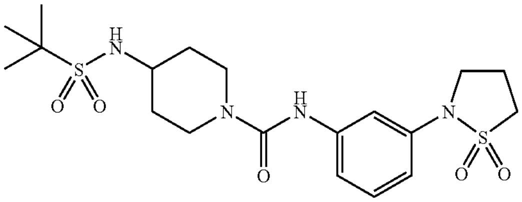

-continued
Ie-208
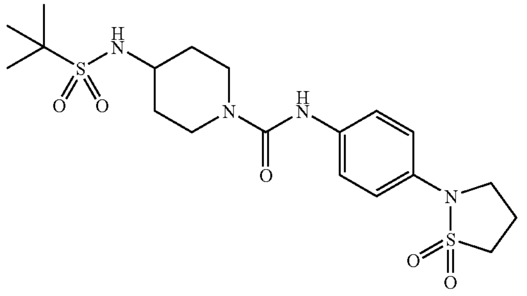
Ie-209
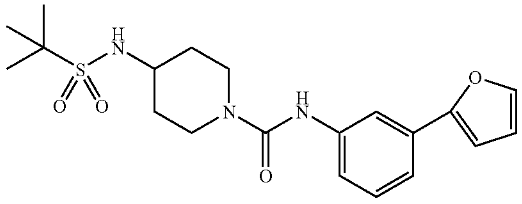
Ie-210
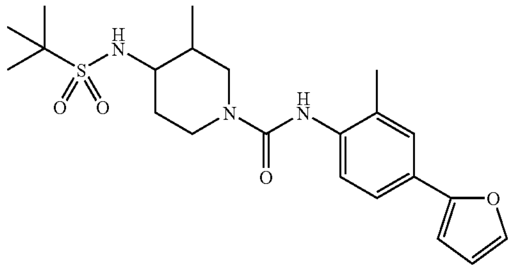
Ie-211
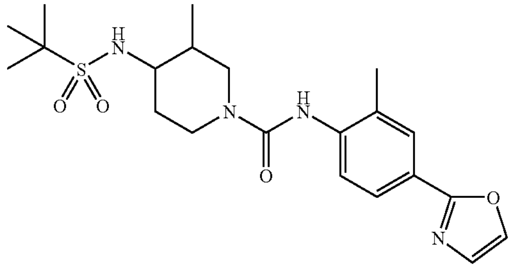
Ie-212
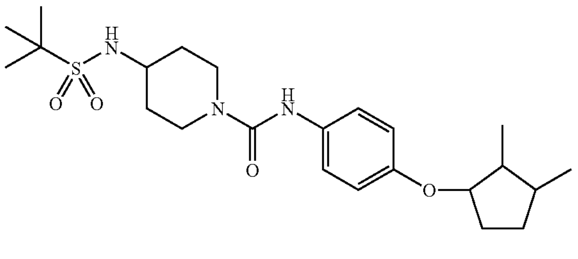
-continued
Ie-213
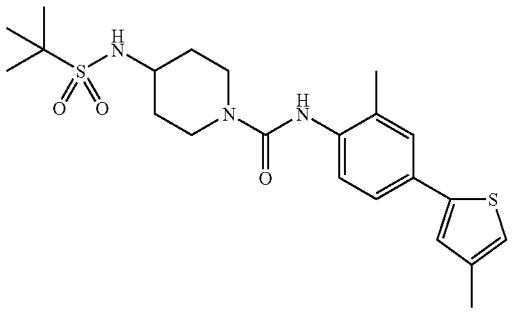
Ie-214
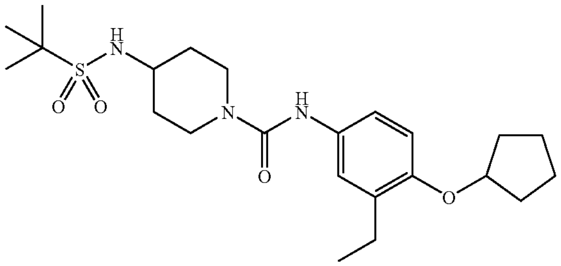
Ie-215
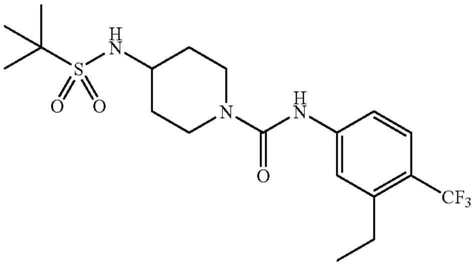
Ie-216
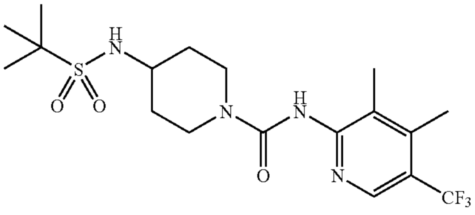
Ie-219
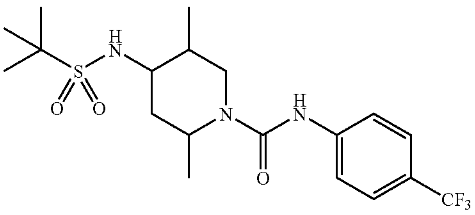
Ie-220
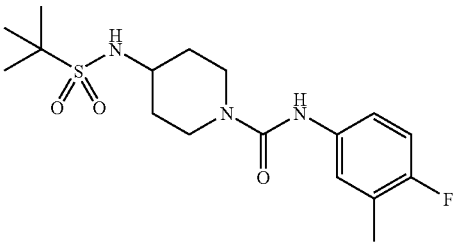

-continued
Ie-221
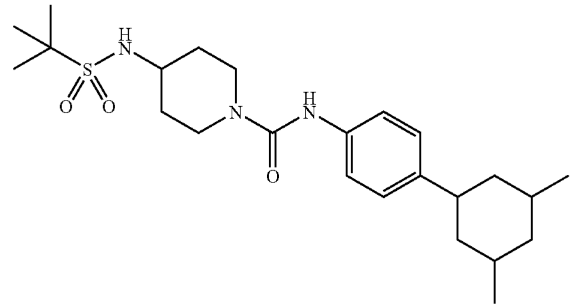
Ie-222
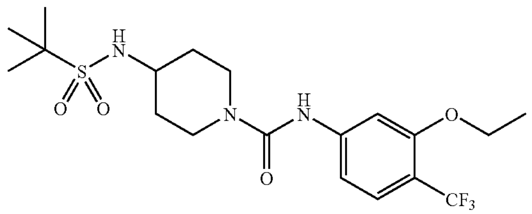
Ie-223
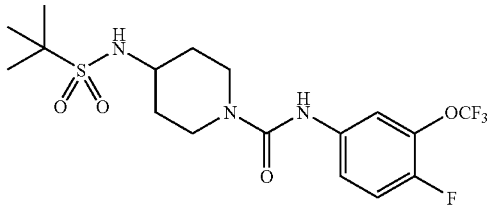
Ie-224
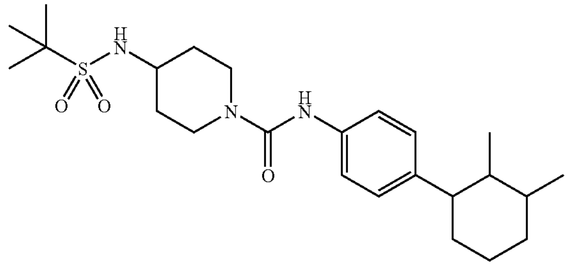
Ie-225
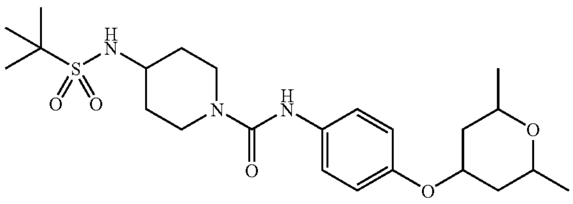
Ie-226
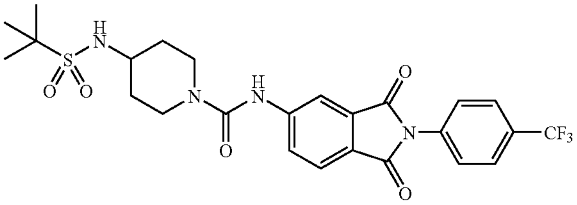
-continued
If-1
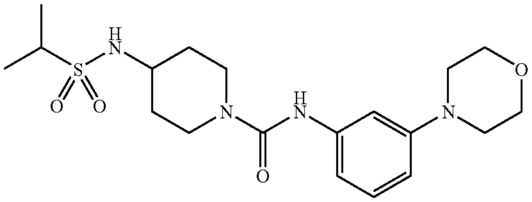
If-2
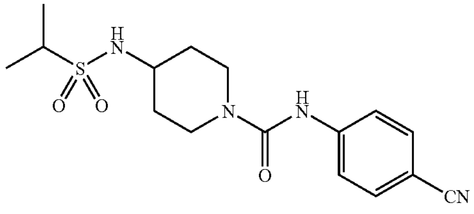
If-4
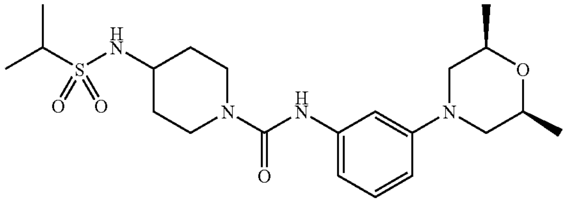
If-6
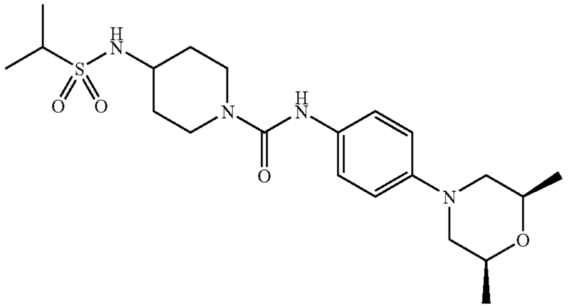
If-7
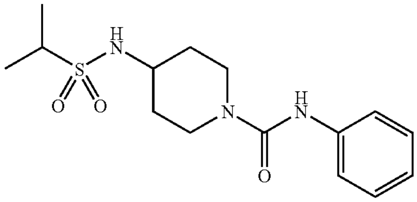
If-8
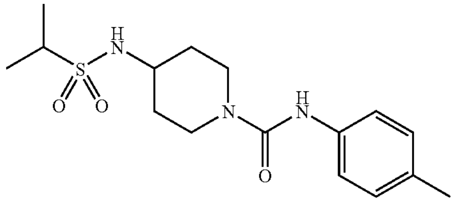

-continued
If-9
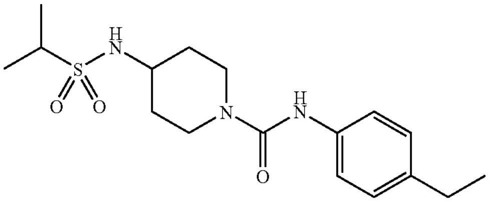
If-10
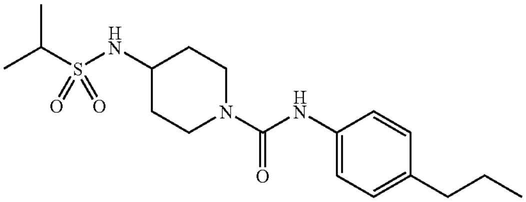
If-11
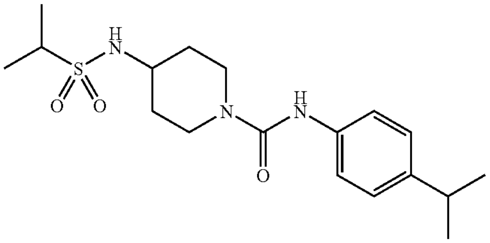
If-12
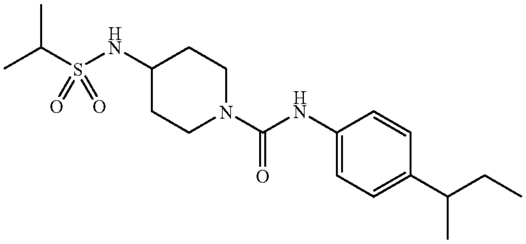
If-13
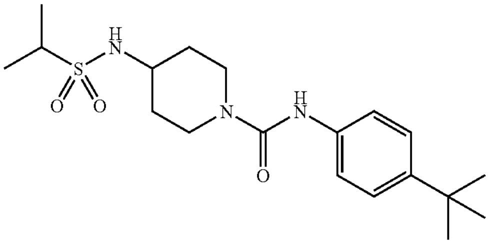
If-14
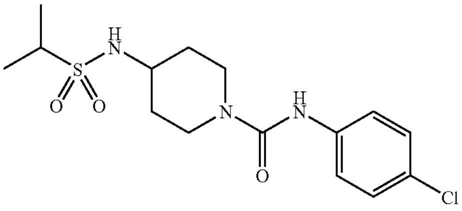
-continued
If-15
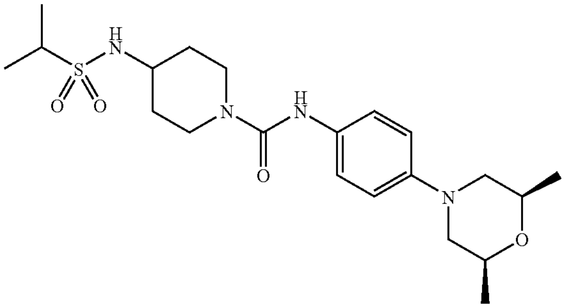
If-16
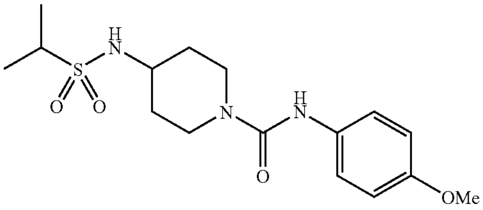
If-17
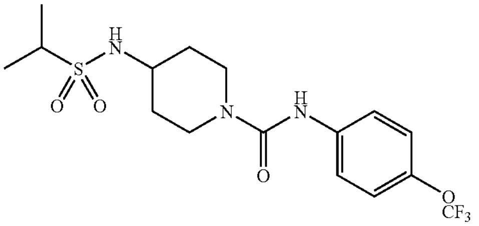
If-18
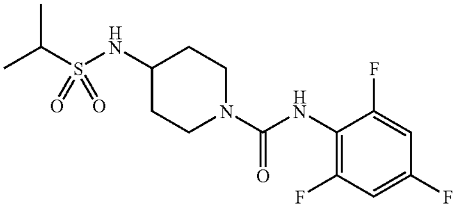
If-19
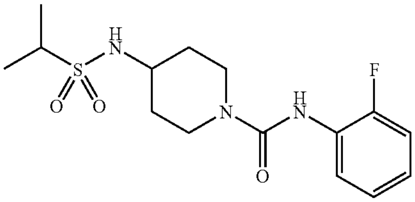
If-20
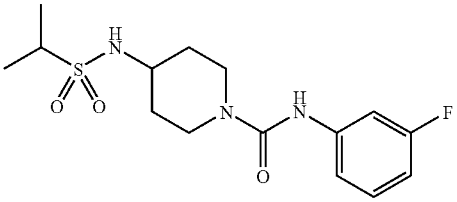

-continued
If-21
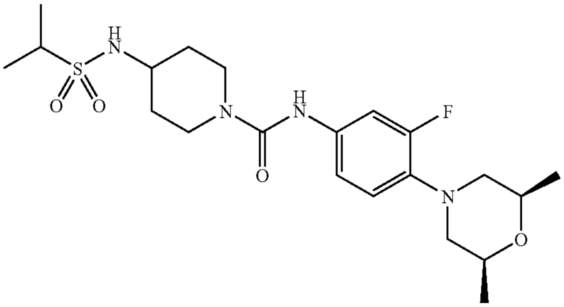
If-22
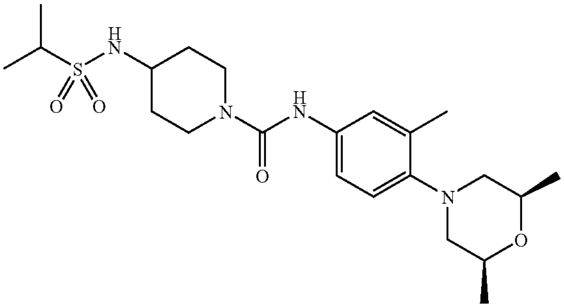
If-23
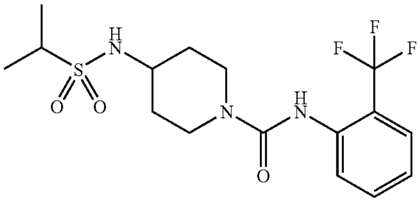
If-24
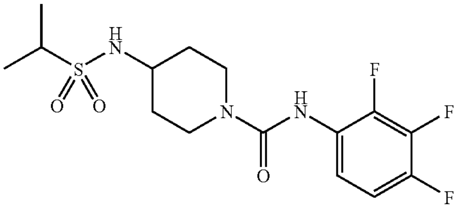
If-25
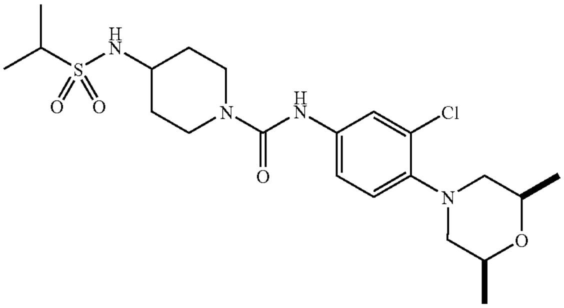
-continued
If-26
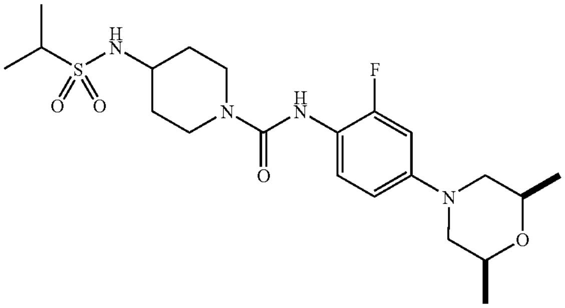
If-27
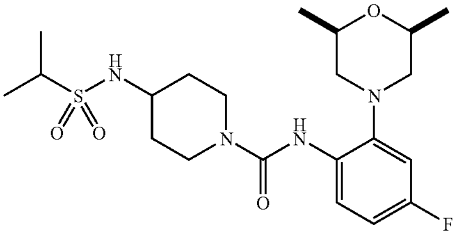
If-28
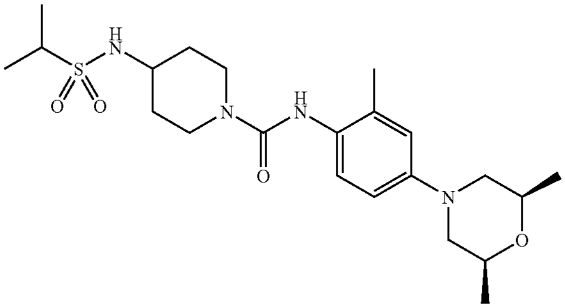
If-29
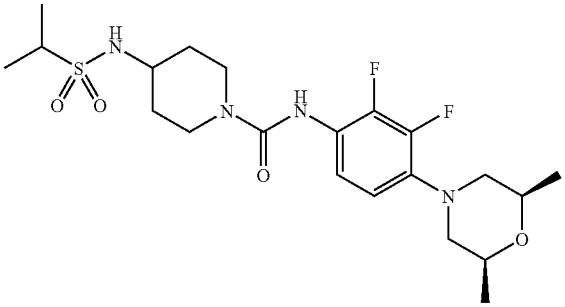
If-30
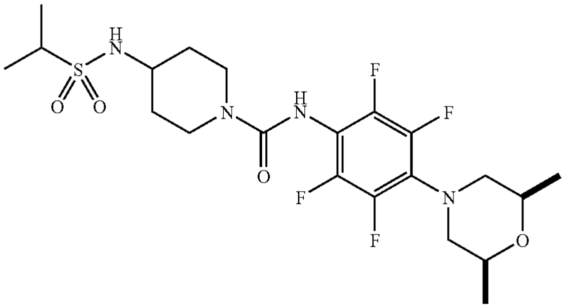

-continued
If-31
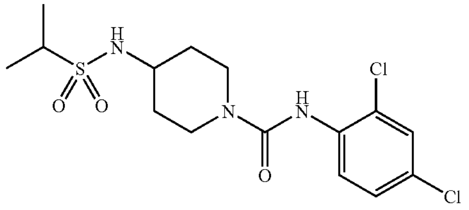
If-32
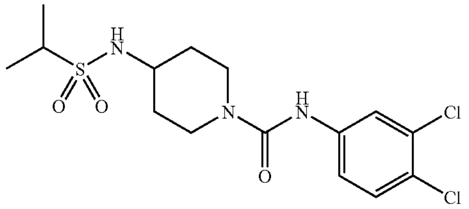
If-33
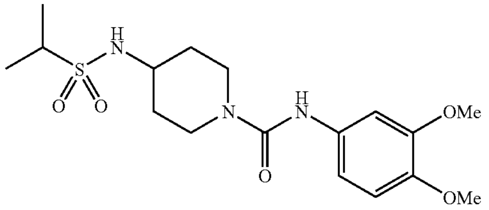
If-35
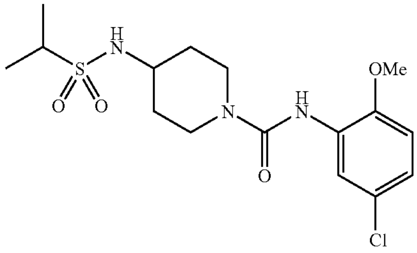
If-36
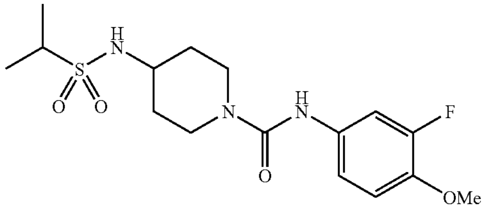
If-37
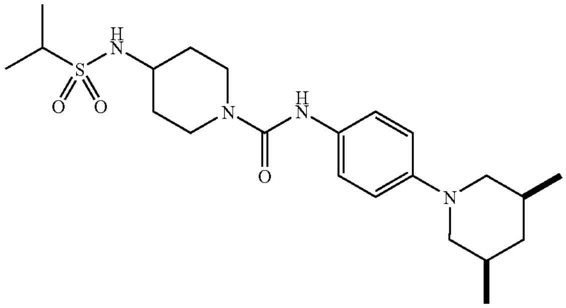
-continued
If-38
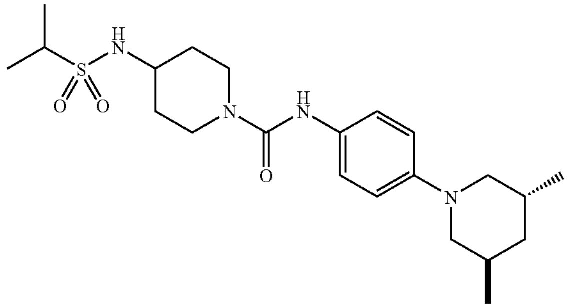
If-39
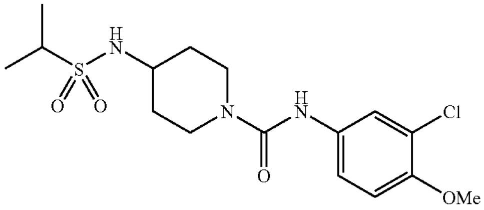
If-40
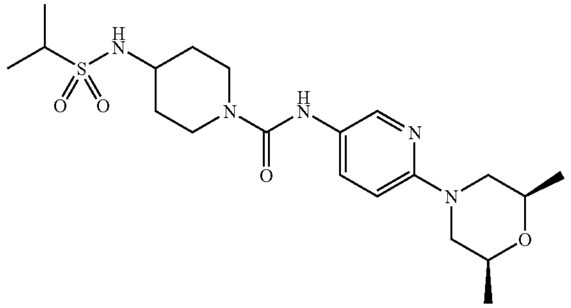
If-41
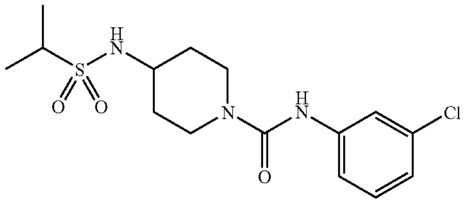
If-42
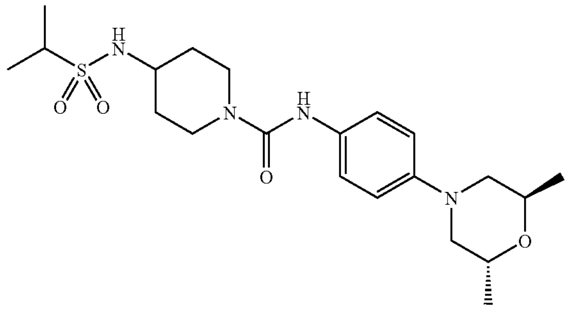

-continued
If-43
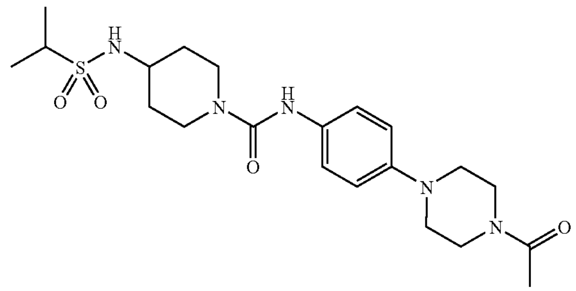
If-44
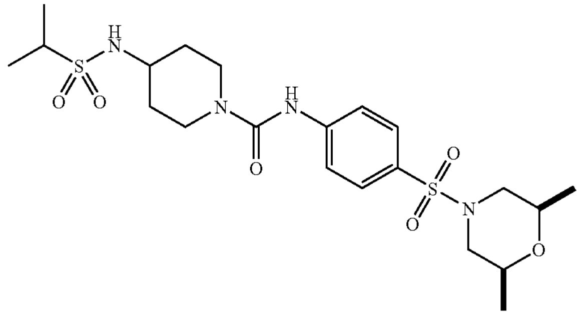
If-45
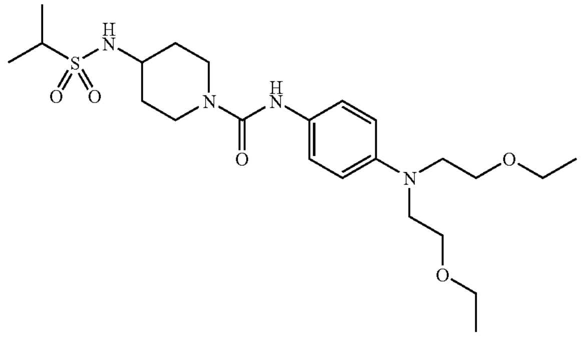
If-46
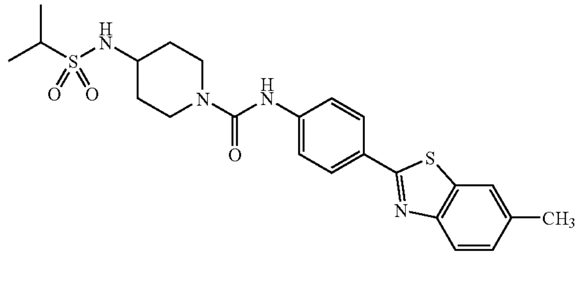
-continued
If-47
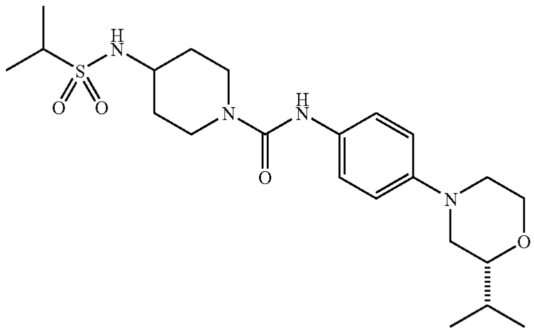
If-48
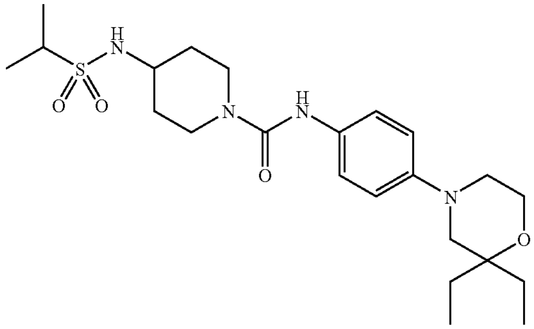
If-49
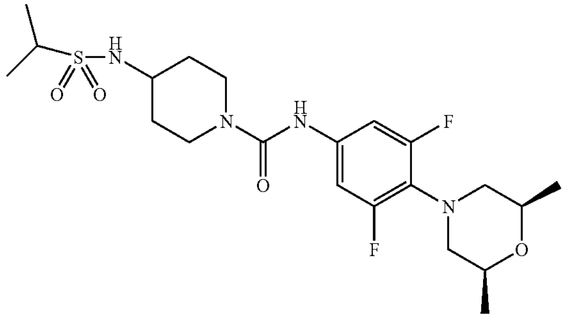
If-50
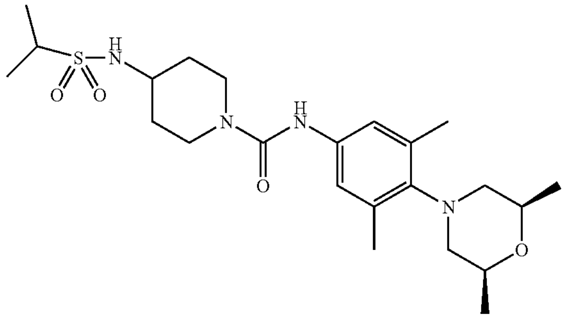

-continued
If-51
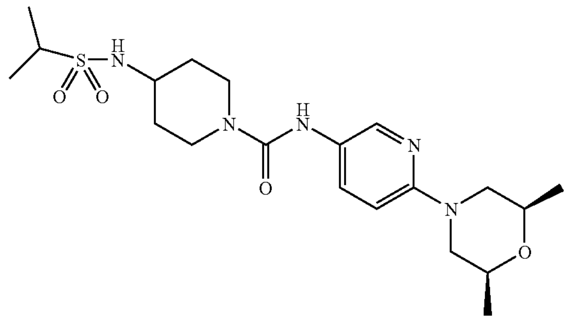
If-52
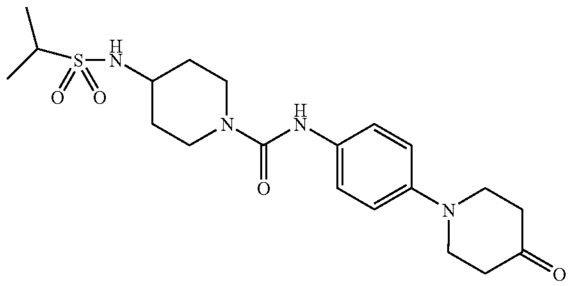
If-53
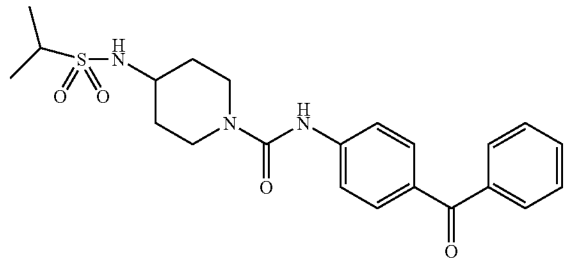
If-54
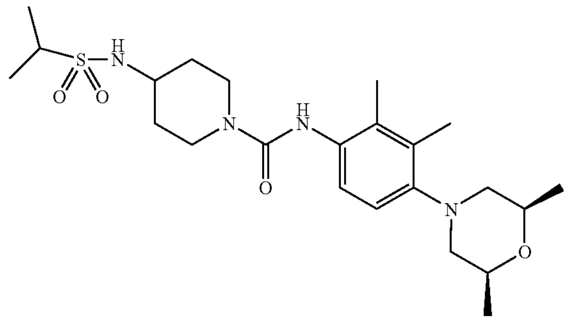
If-55
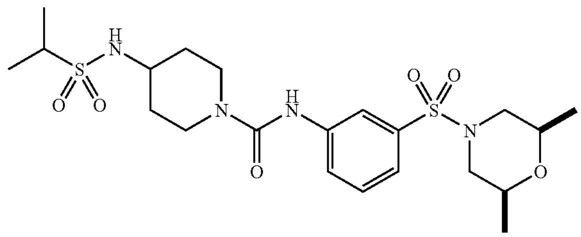
-continued
If-56
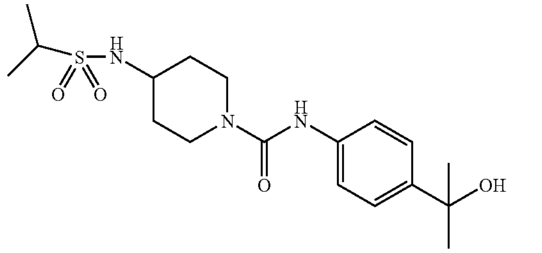
If-57
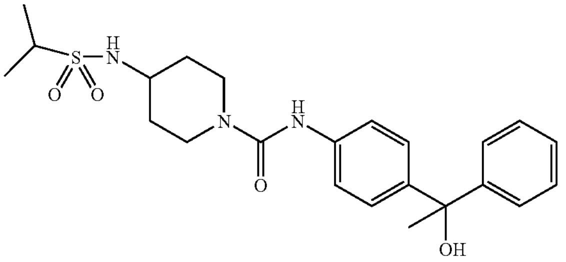
If-58
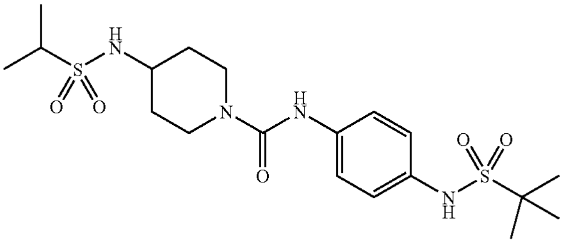
If-59
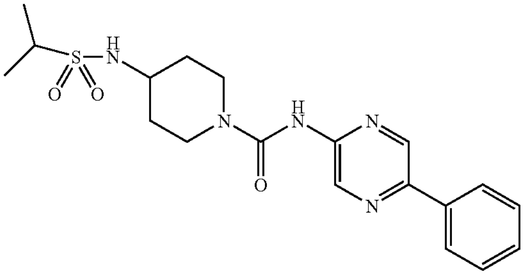
If-60
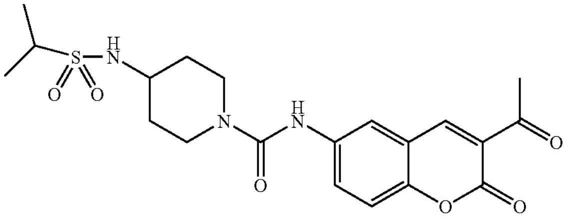

-continued
If-61
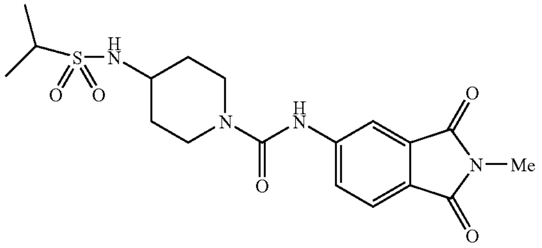
If-62
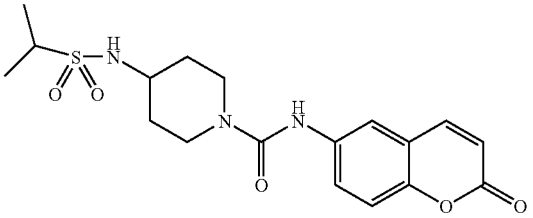
If-63
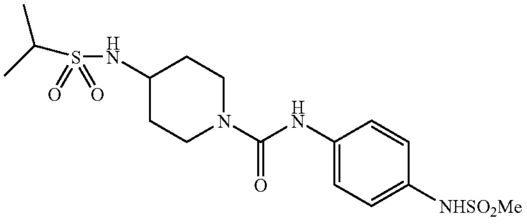
If-64
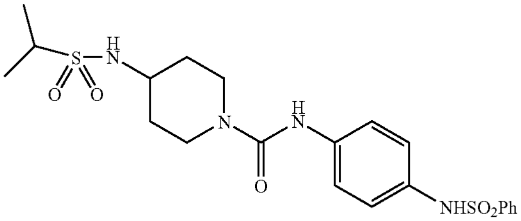
If-65
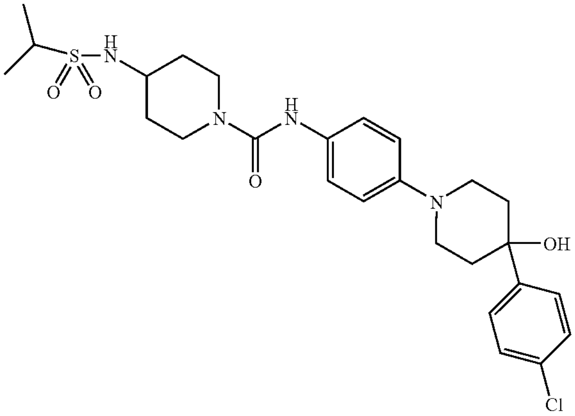
-continued
If-66
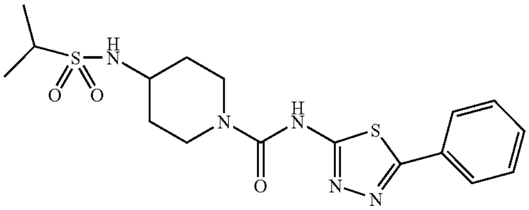
If-67
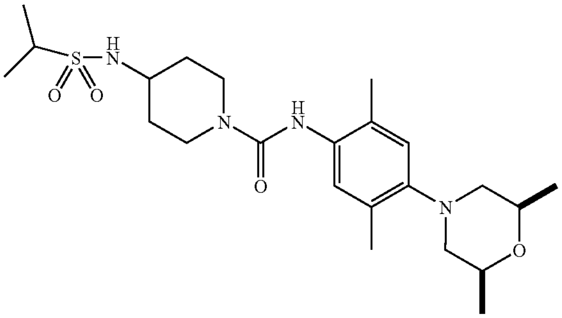
If-68
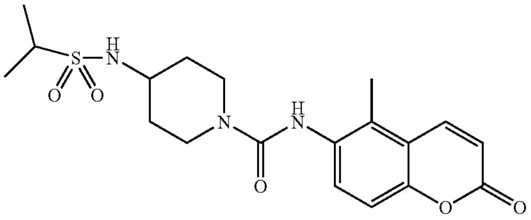
If-69
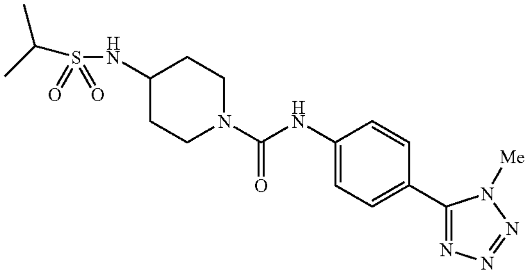
If-70
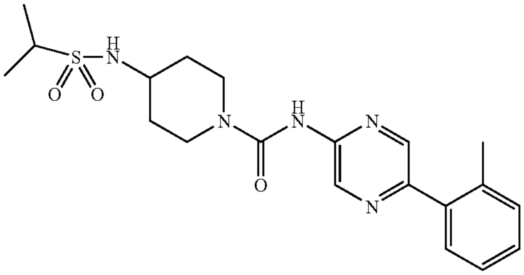

-continued
If-71
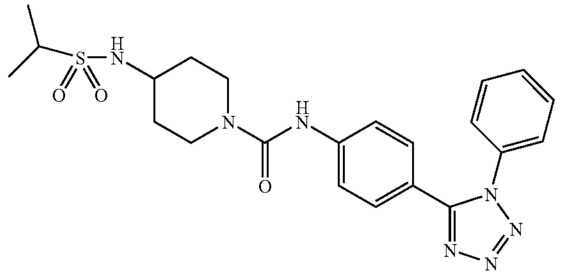
If-74
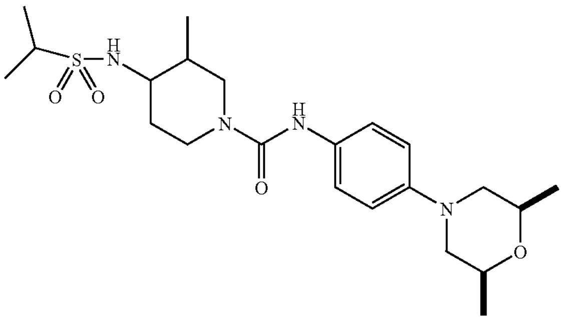
If-75
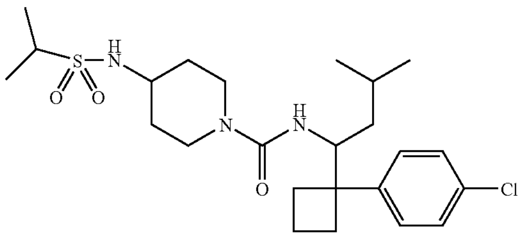
If-76
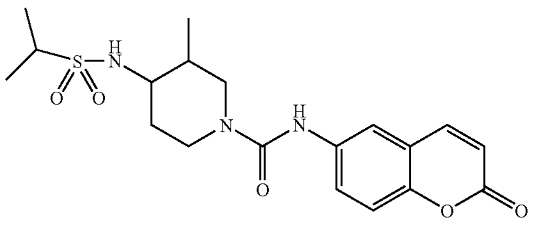
If-77
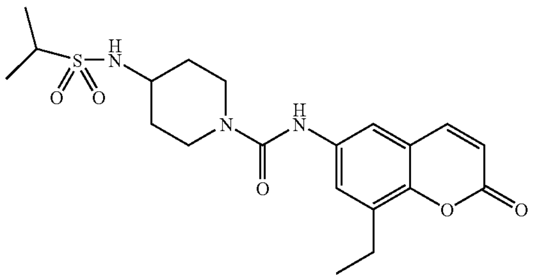
-continued
If-78
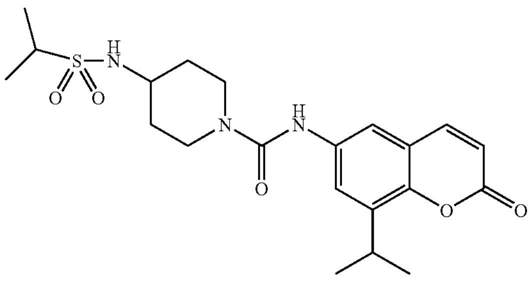
If-79
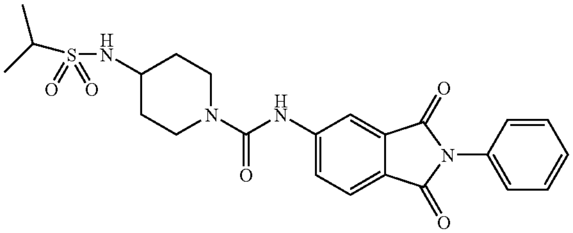
If-80
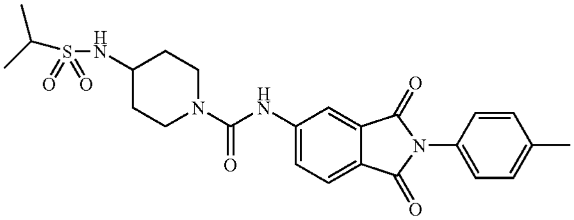
If-81
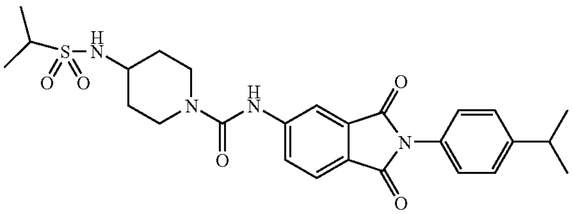
If-82
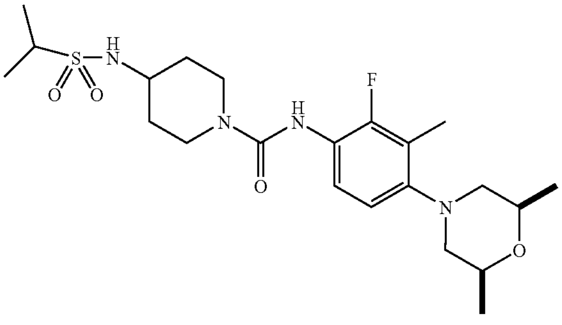

-continued
If-83
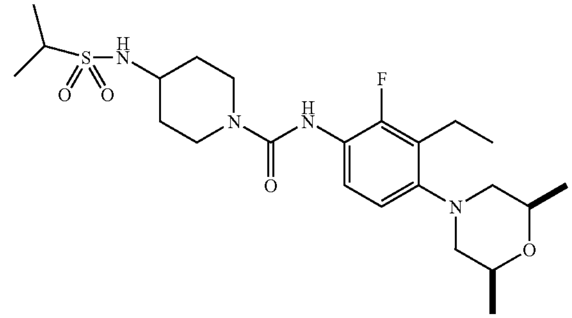
If-84
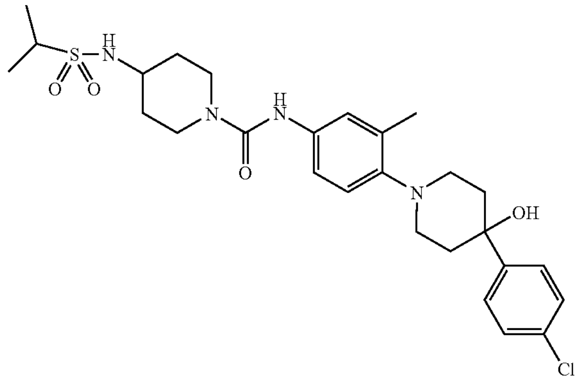
If-85
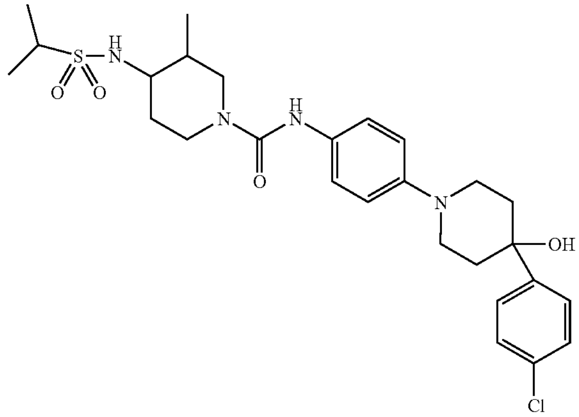
If-86
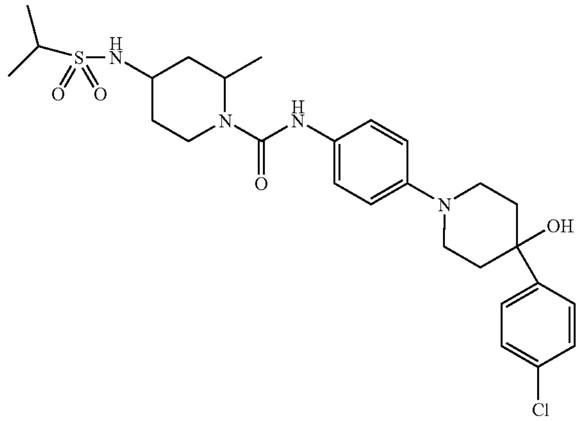
-continued
If-87
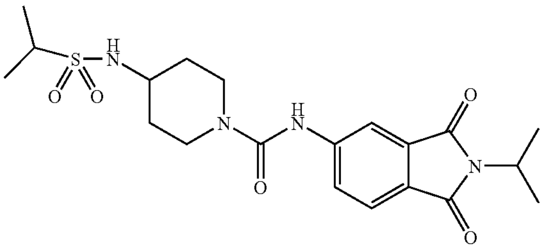
If-88
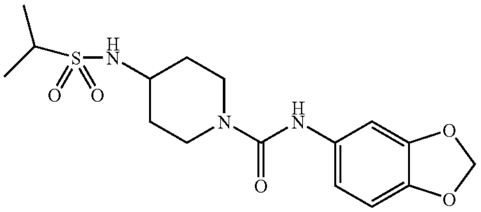
If-89
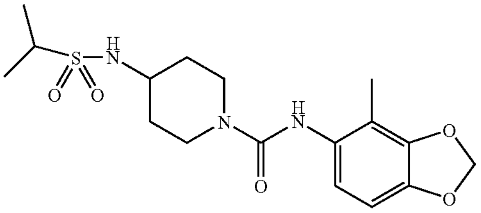
If-90
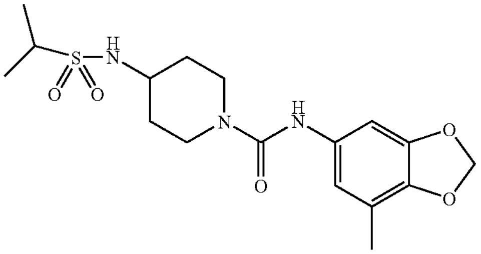
If-91
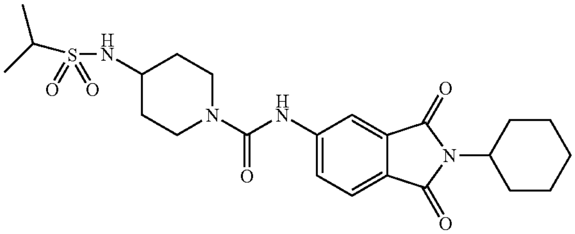
If-92
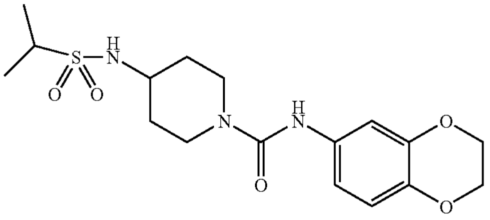

-continued
If-93
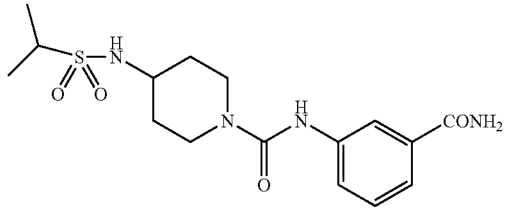
If-94
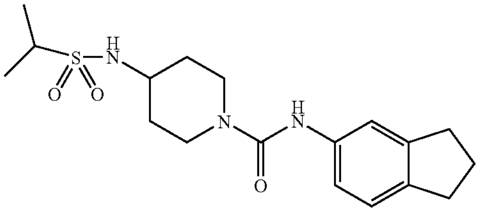
If-95
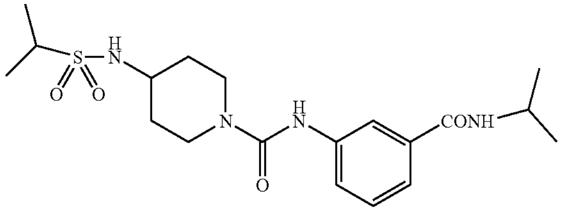
If-96
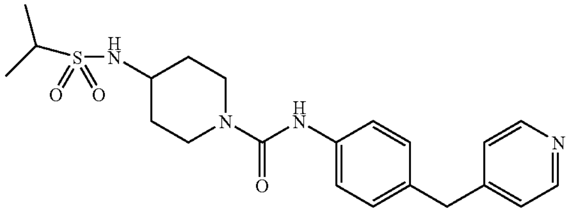
If-97
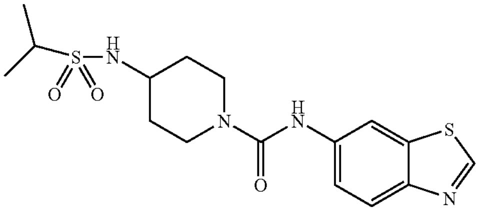
If-98
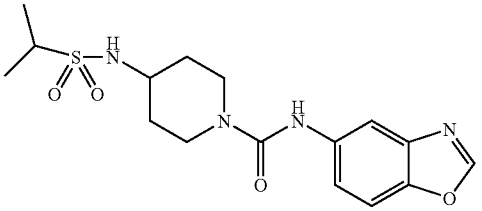
If-99
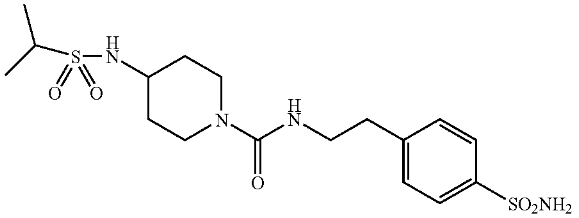
-continued
If-100
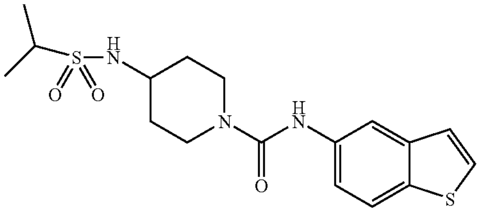
If-101
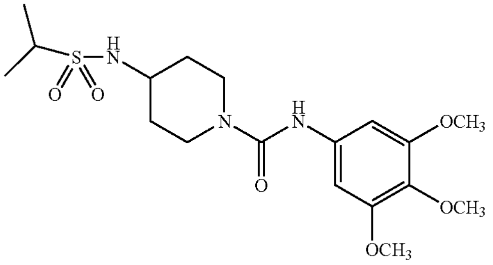
If-102
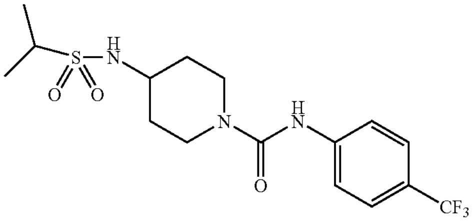
If-103
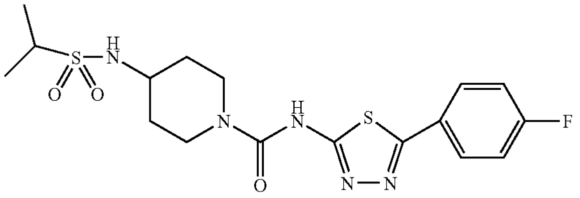
If-104
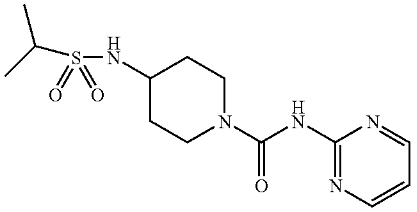
If-105
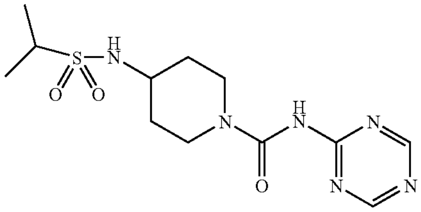
If-106
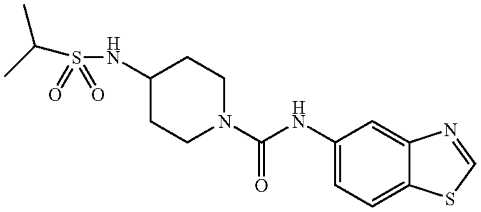

-continued
If-107
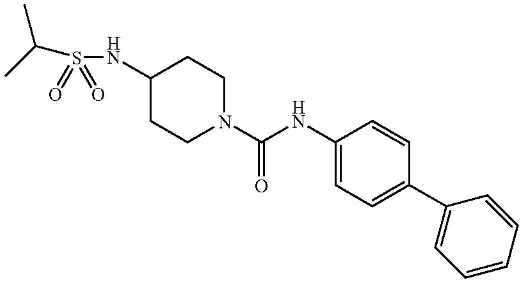
If-108
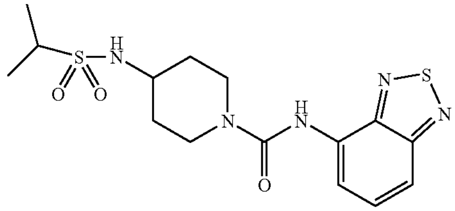
If-109
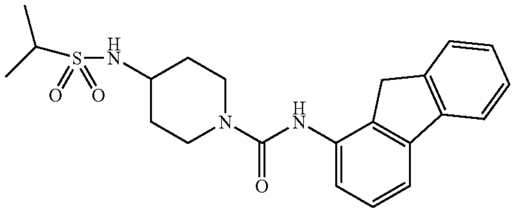
If-110
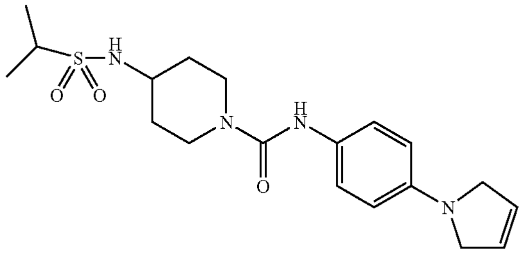
If-111
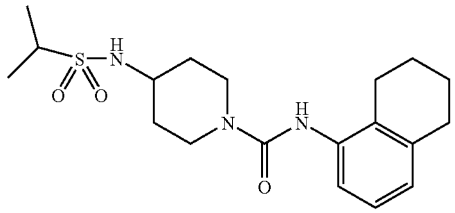
If-112
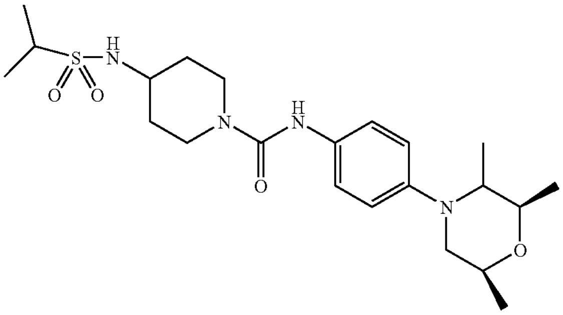
-continued
If-113
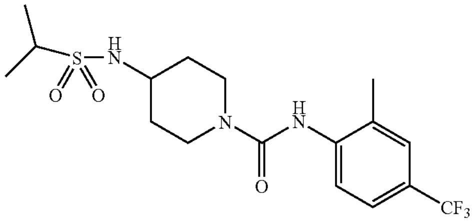
If-114
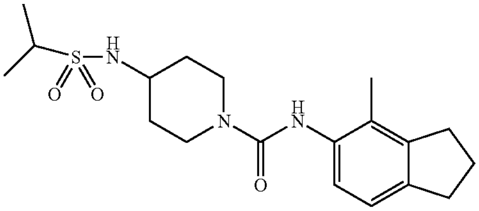
If-115
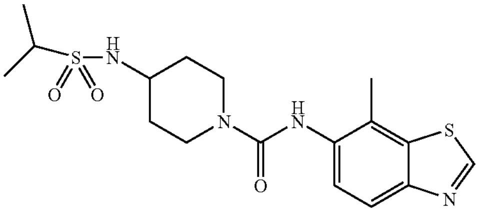
If-116
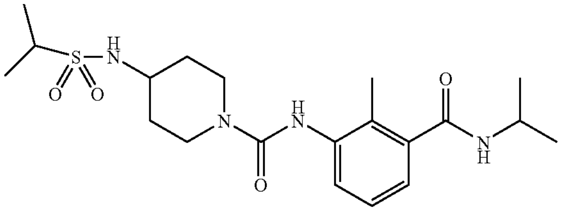
If-117
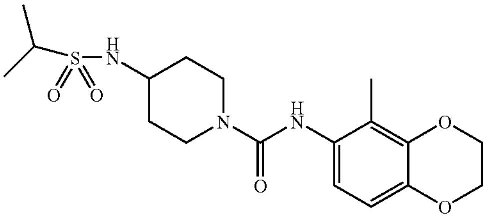
If-118
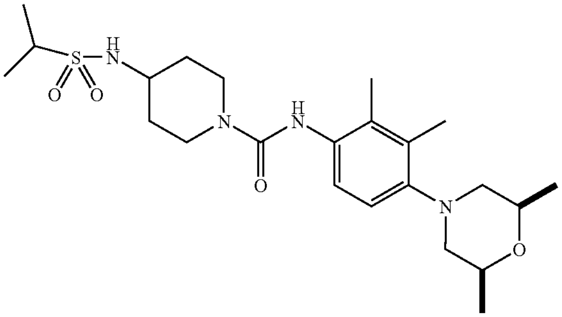

-continued
If-119
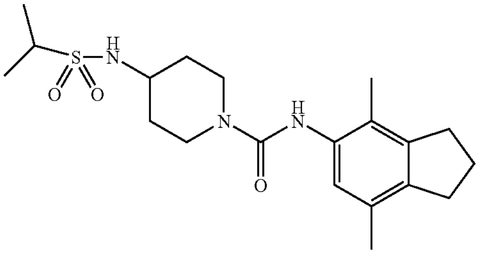
If-120
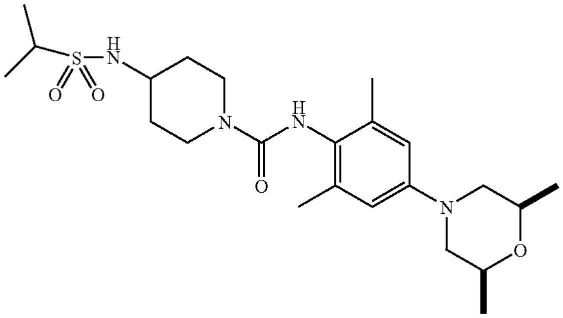
If-121
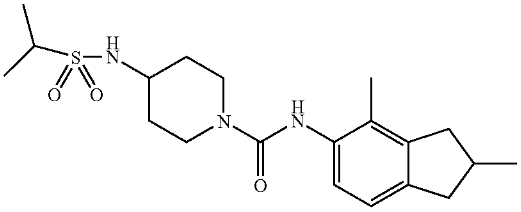
If-122
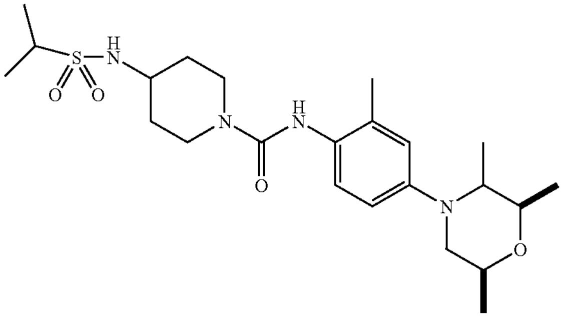
If-123
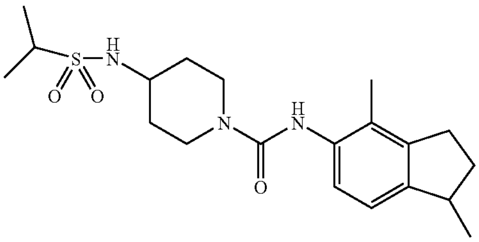
-continued
If-124
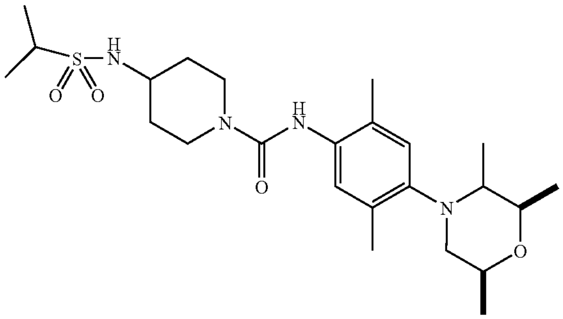
If-125
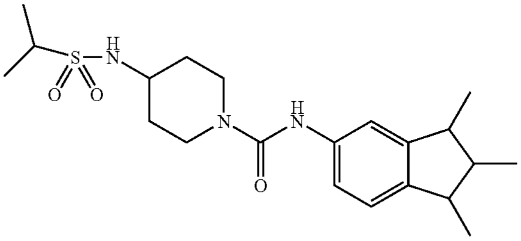
If-126
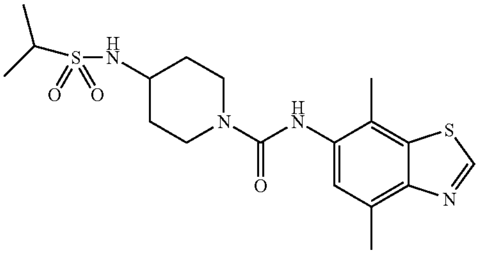
If-127
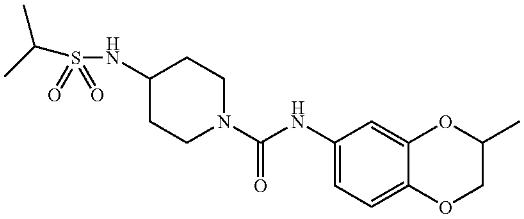
If-128
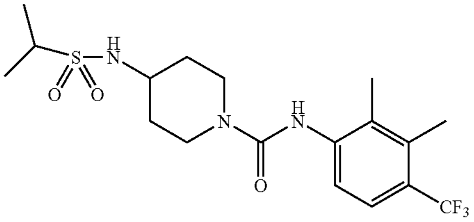
If-129
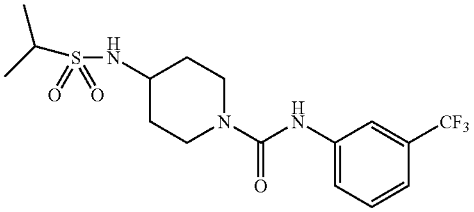

-continued
If-130
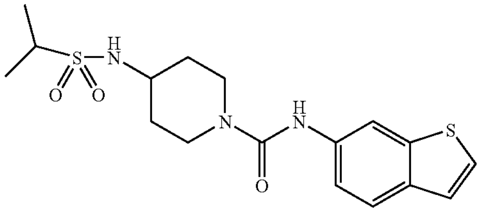
If-131
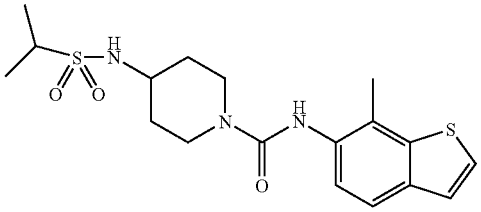
If-132
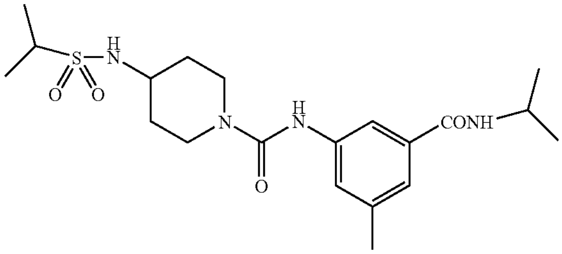
If-133
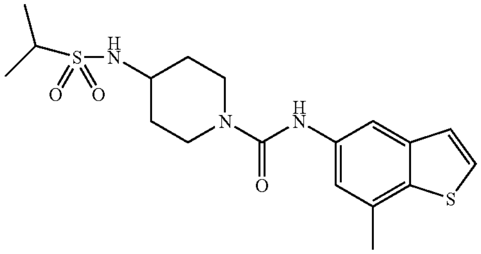
If-134
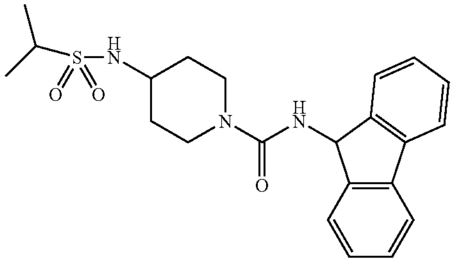
If-135
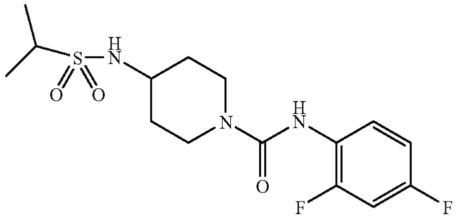
-continued
If-136
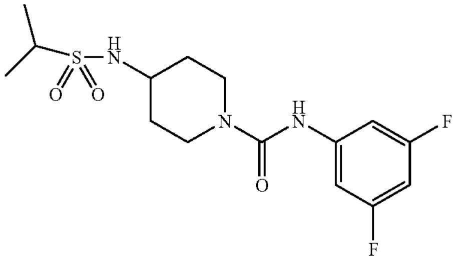
If-137
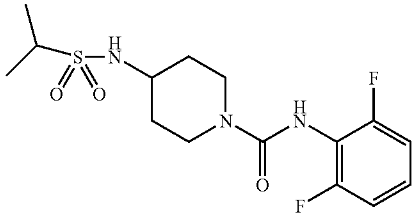
If-138
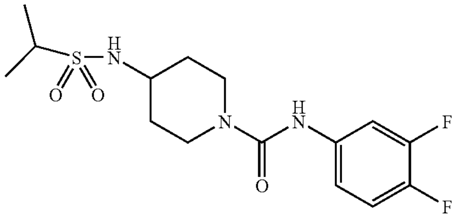
If-139
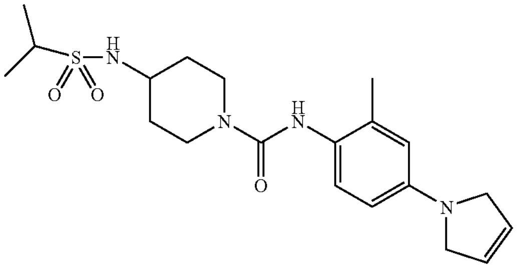
If-140
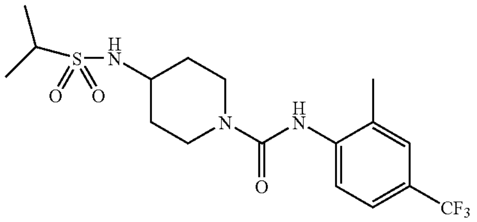
If-141
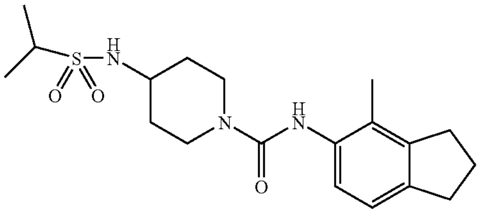

-continued
If-142
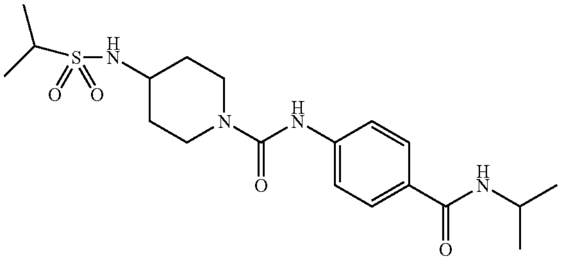
If-143
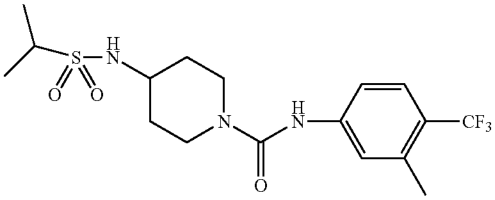
If-144
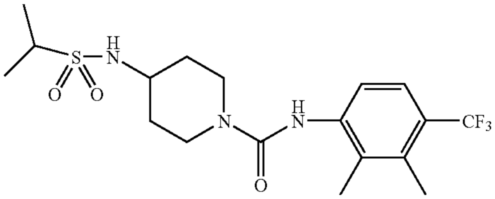
If-145
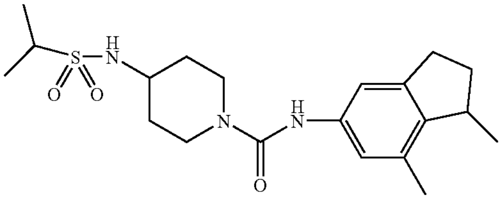
If-146
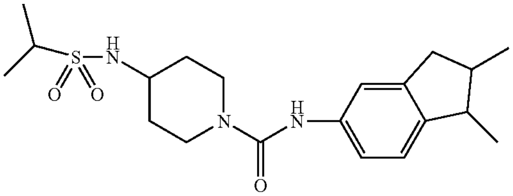
If-147
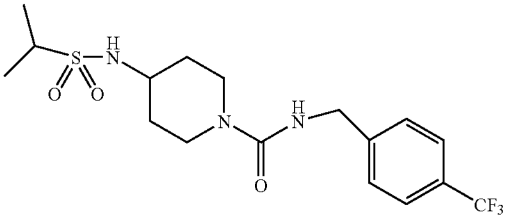
If-148
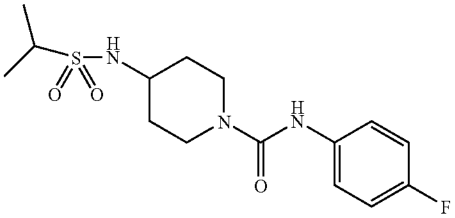
-continued
If-149
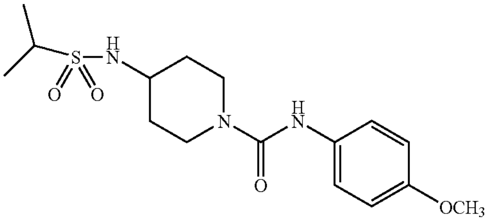
If-150
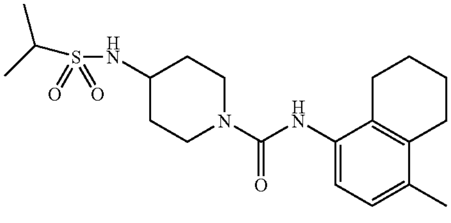
If-151
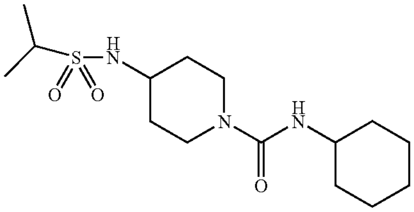
If-152
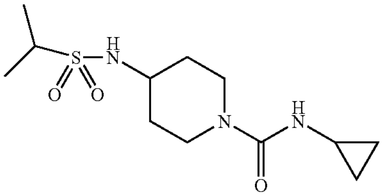
If-153
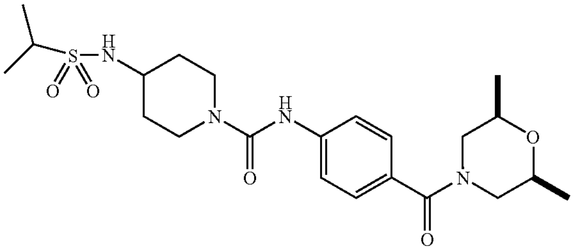
If-154
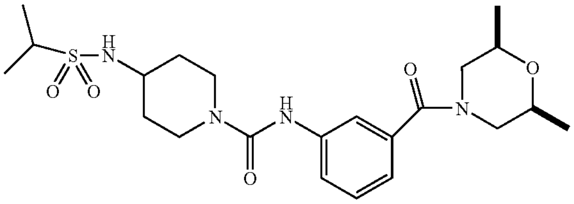
If-155
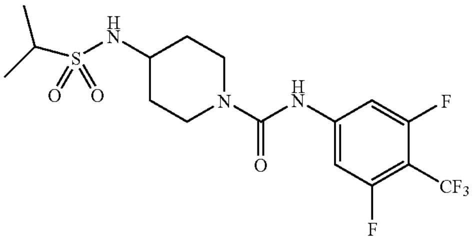

-continued
If-156
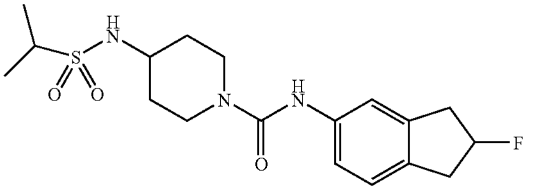
If-157
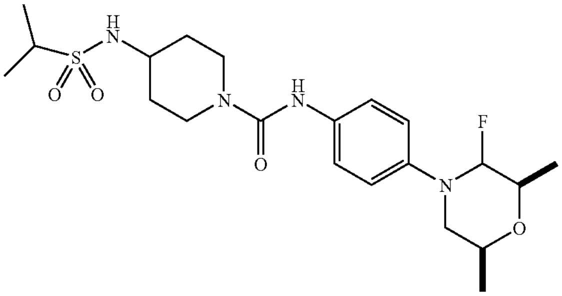
If-158
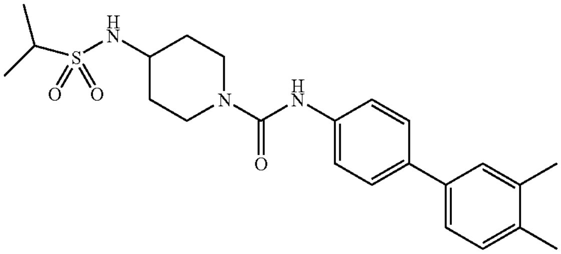
If-159
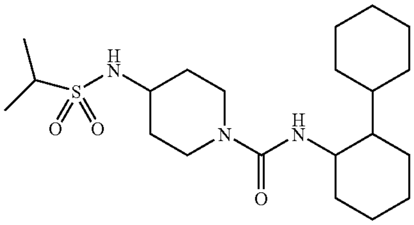
If-160
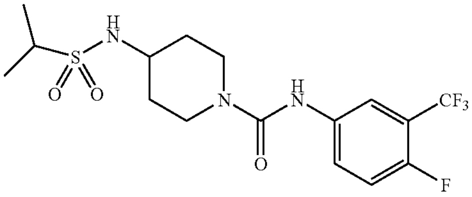
If-161
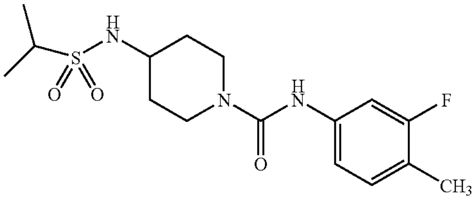
-continued
If-162
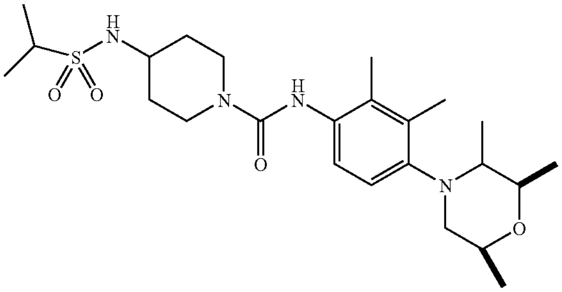
If-163
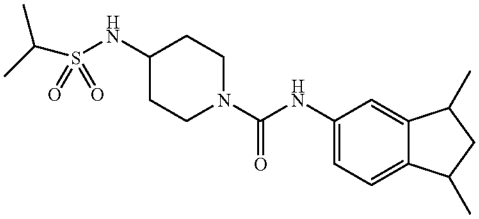
If-164
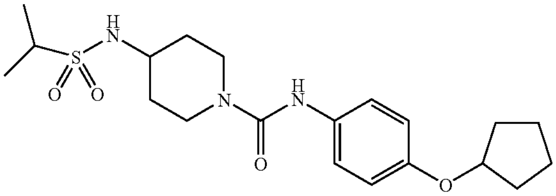
If-165
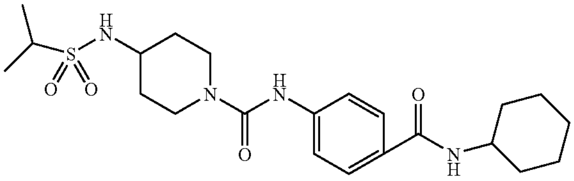
If-166
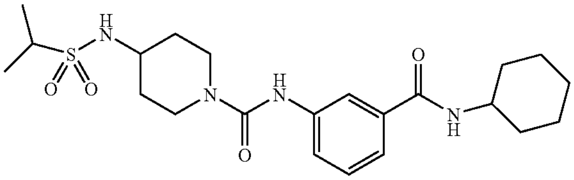
If-167
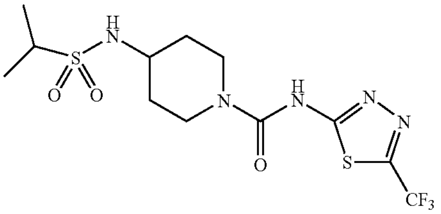
If-168
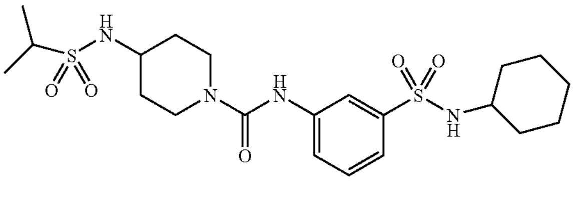

-continued
If-169
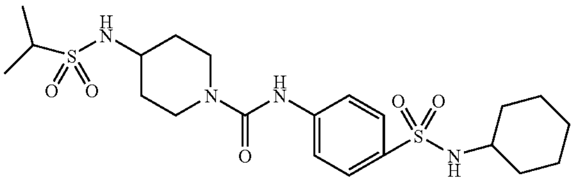
If-171
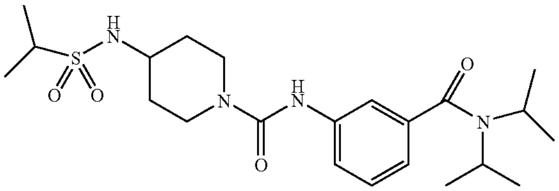
If-172
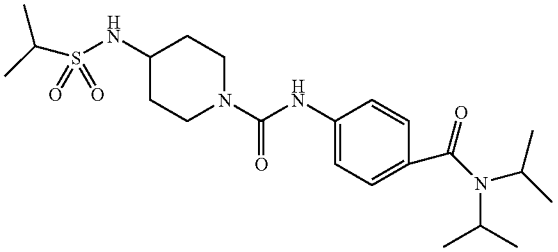
If-173
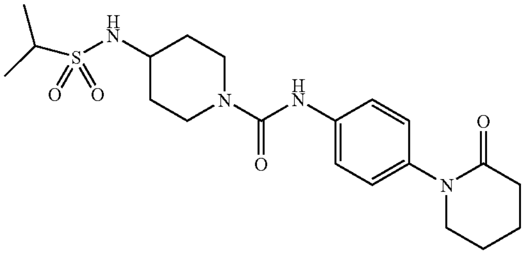
If-174
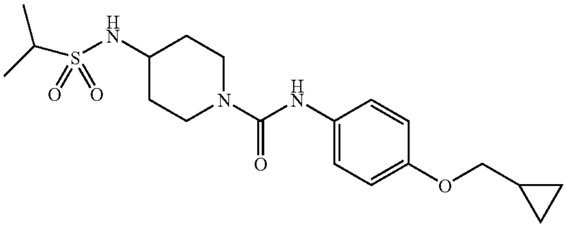
If-175
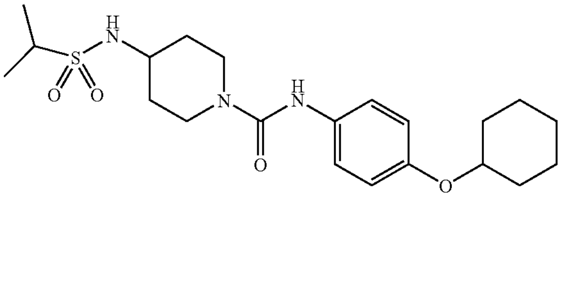
-continued
If-176
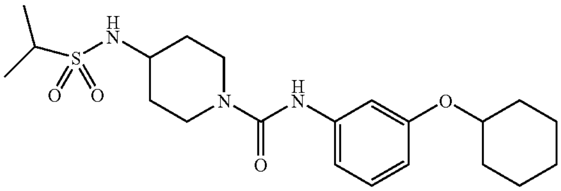
If-177
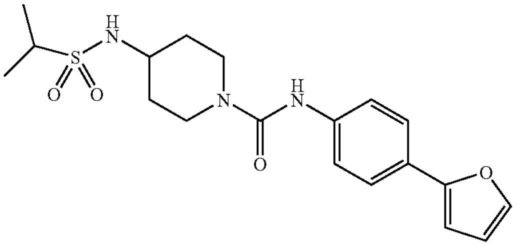
If-178
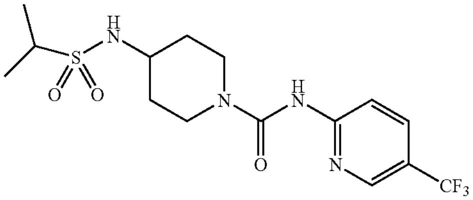
If-179
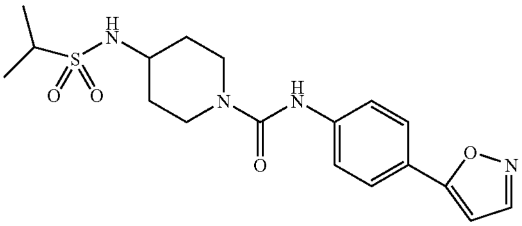
If-180
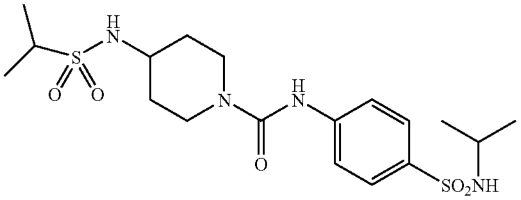
If-181
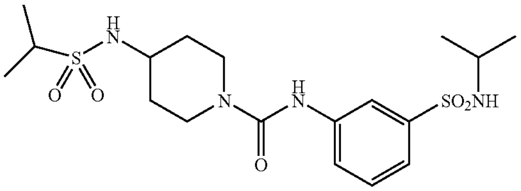
If-182
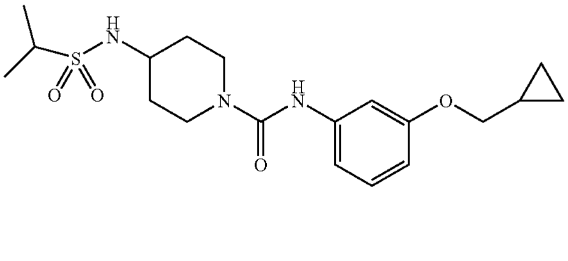

-continued
If-183
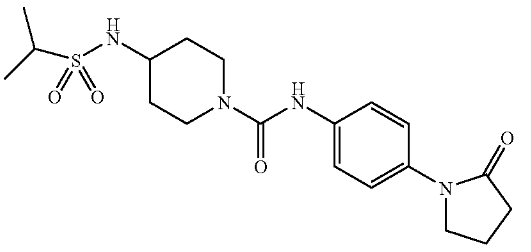
If-184
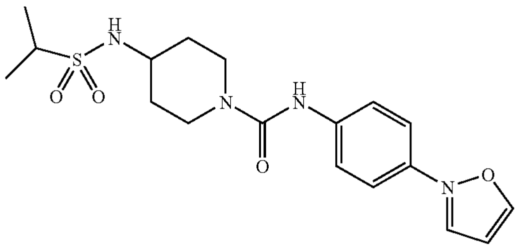
If-185
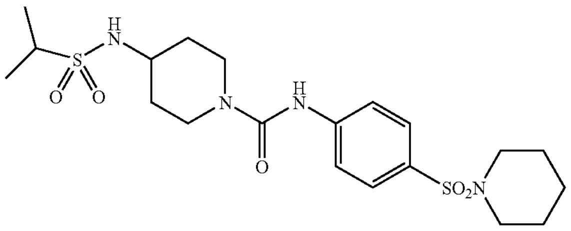
If-186
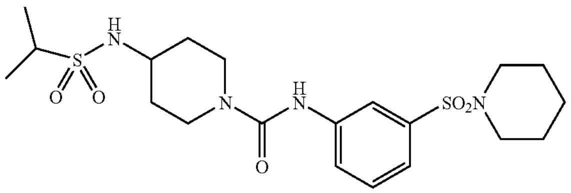
If-187
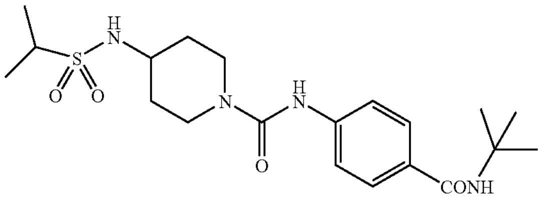
If-188
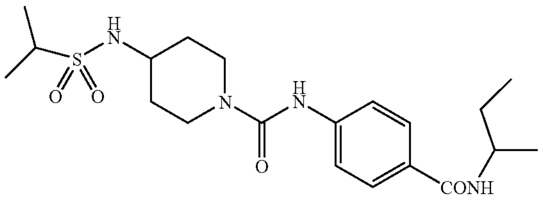
-continued
If-189
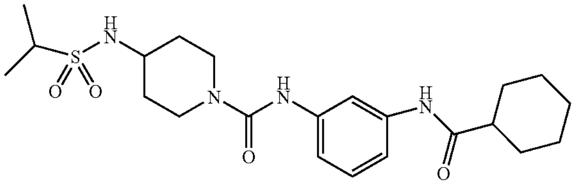
If-190
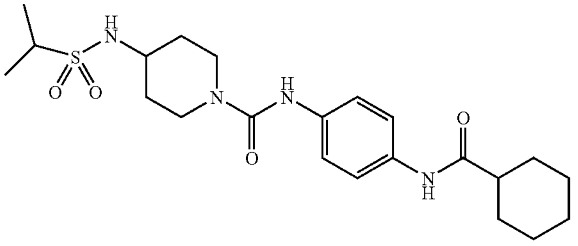
If-191
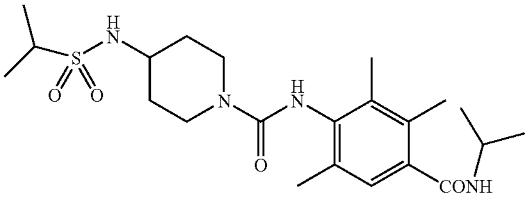
If-192
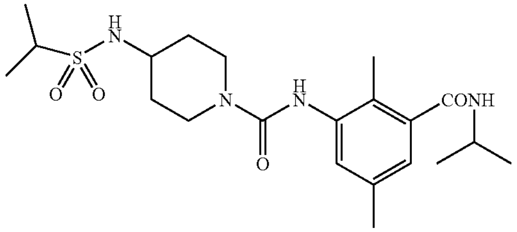
If-193
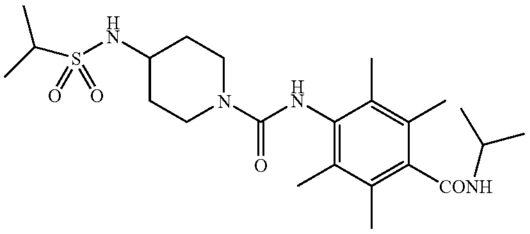
If-194
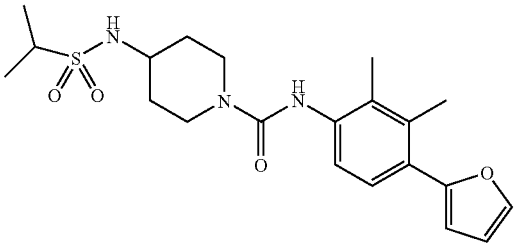

-continued
If-195
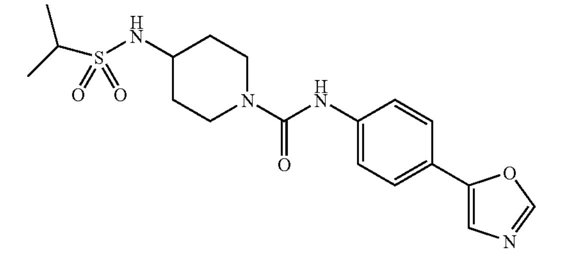
If-196
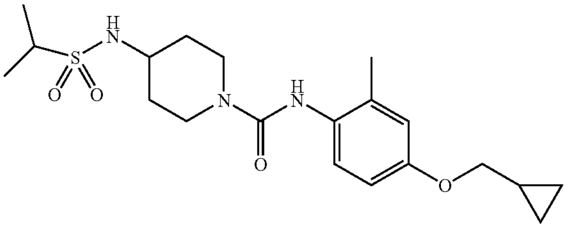
If-197
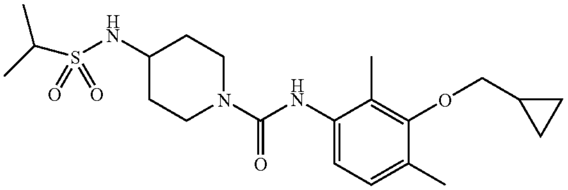
If-198
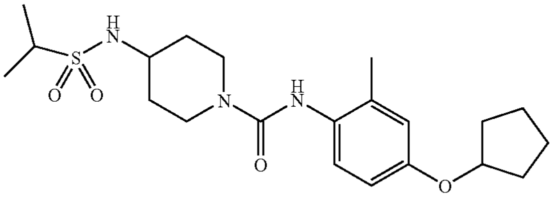
If-199
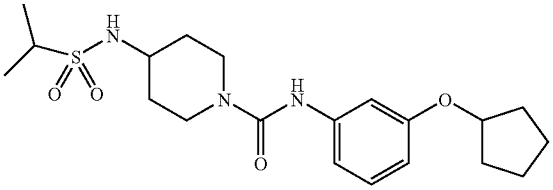
If-200
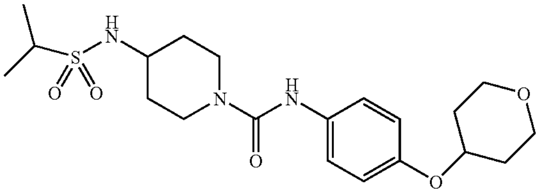
-continued
If-201
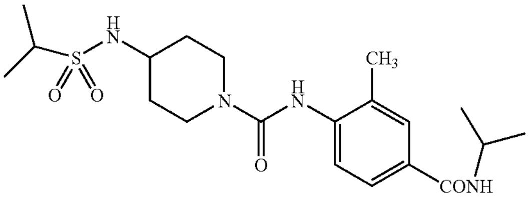
If-202
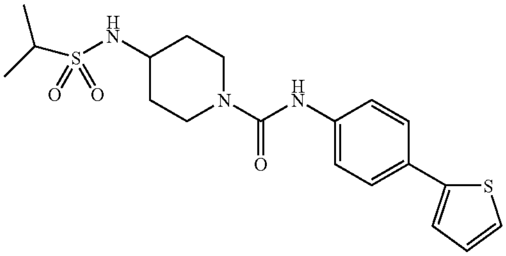
If-203
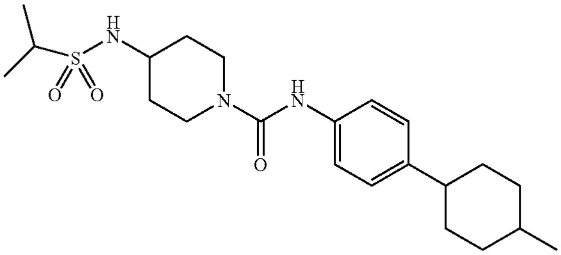
If-204
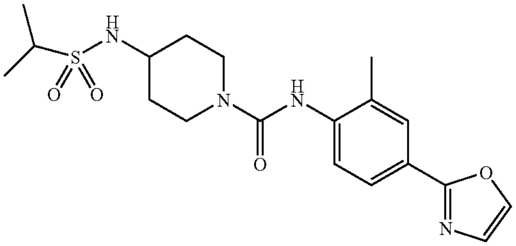
If-205
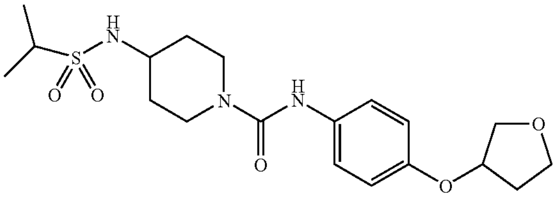
If-206
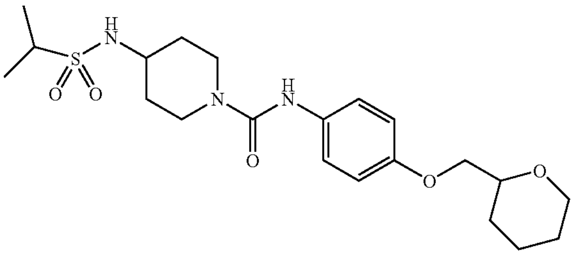

-continued
If-207
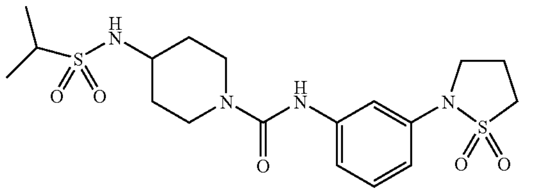
If-208
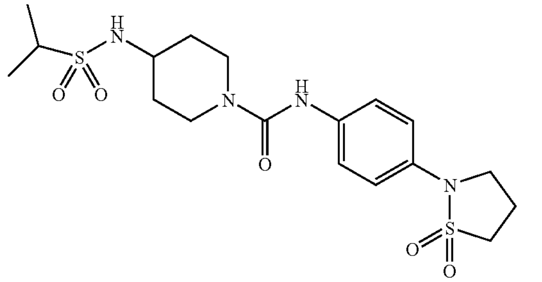
If-209
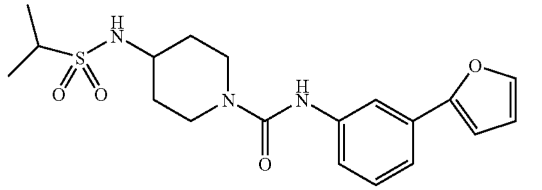
If-210
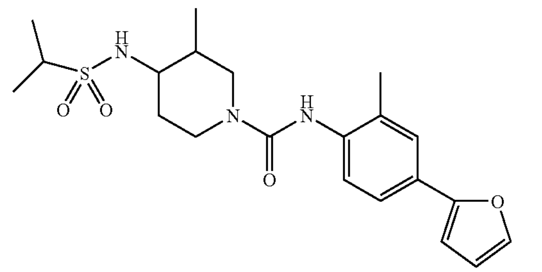
If-211
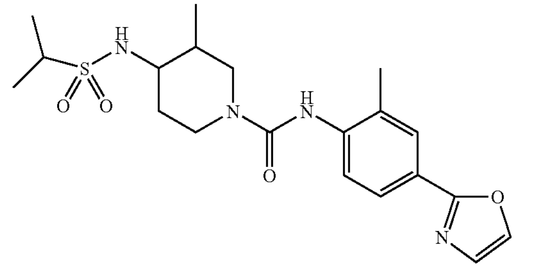
If-212
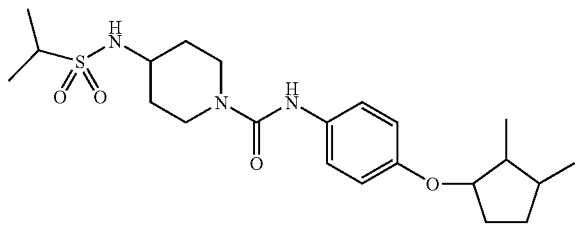
-continued
If-213
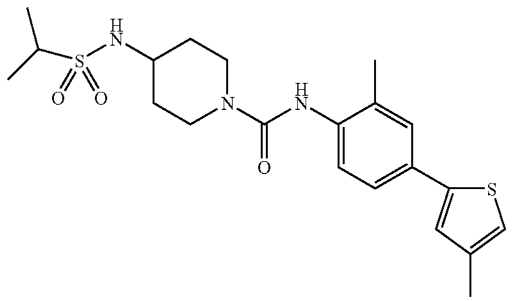
If-214
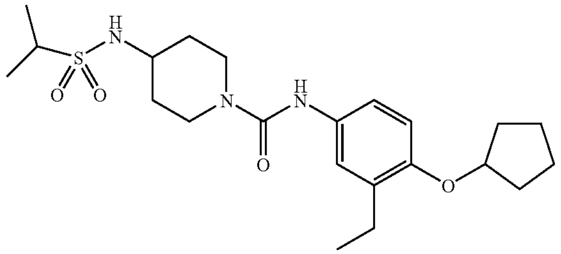
If-215
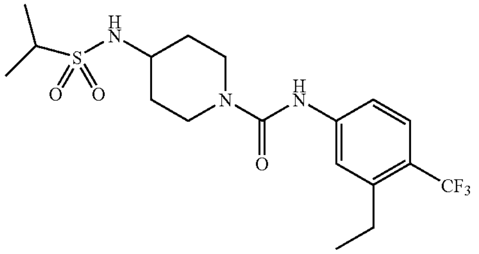
If-216
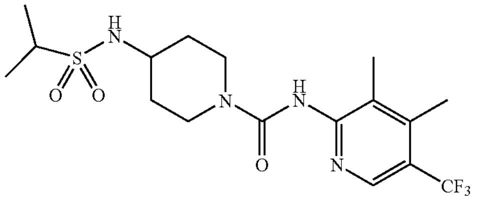
If-219
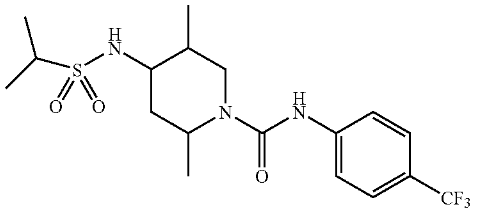
If-220
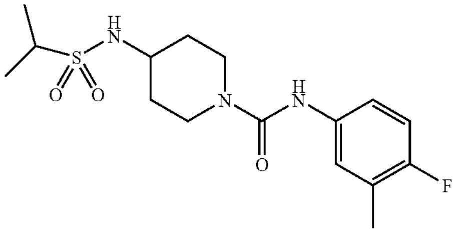

-continued
If-221
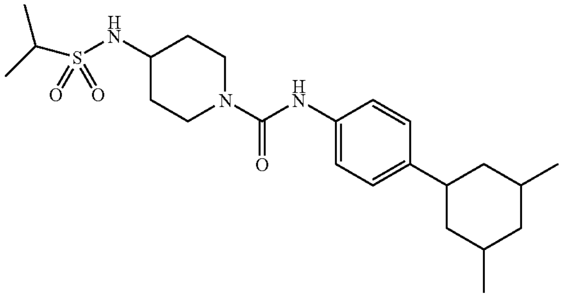
If-222
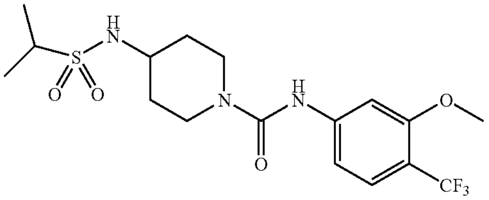
If-223
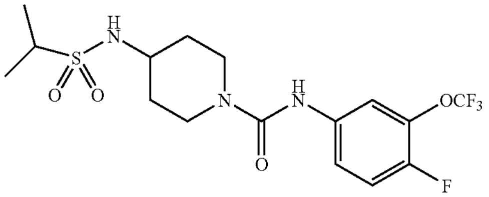
If-224
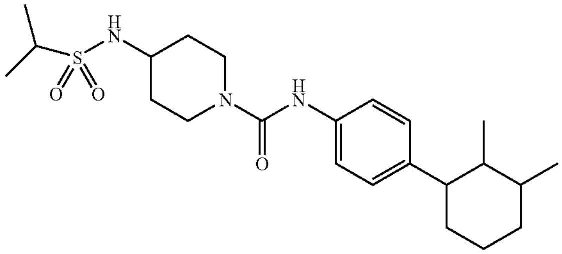
If-225
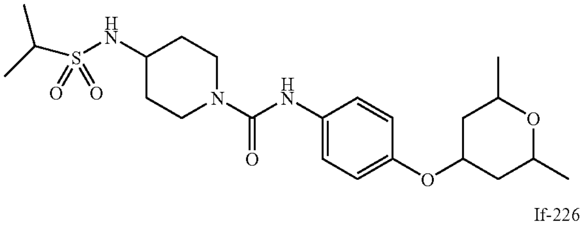
If-226
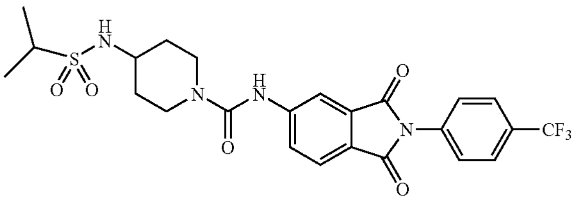
-continued
Ig-1
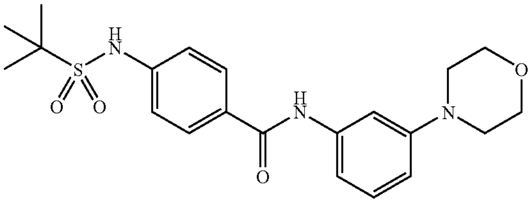
Ig-2
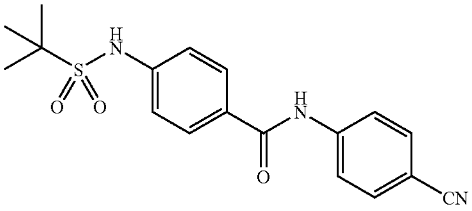
Ig-3
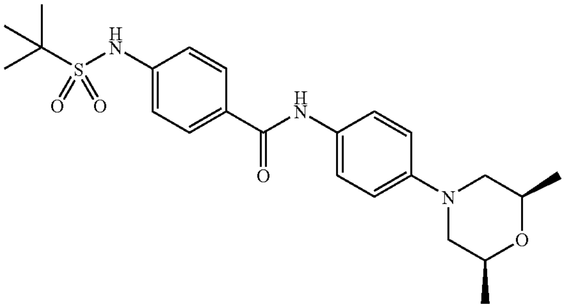
Ig-4
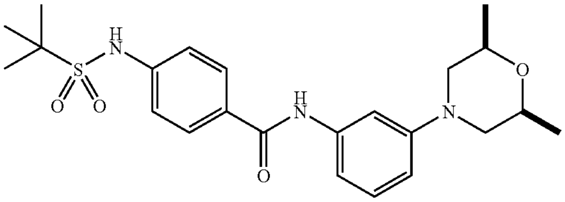
Ig-7
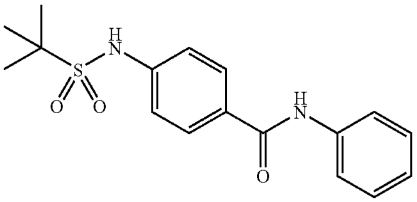
Ig-8
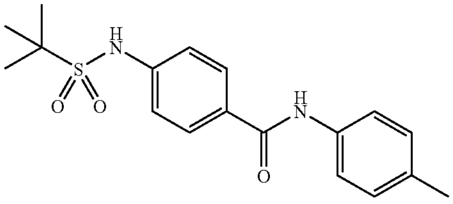

-continued
Ig-9
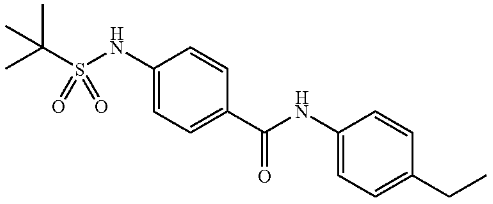
Ig-10
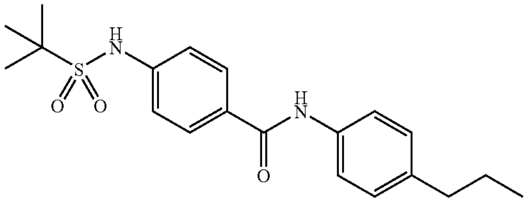
Ig-11
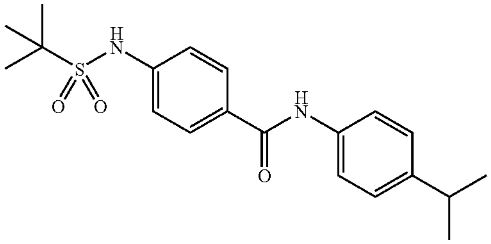
Ig-12
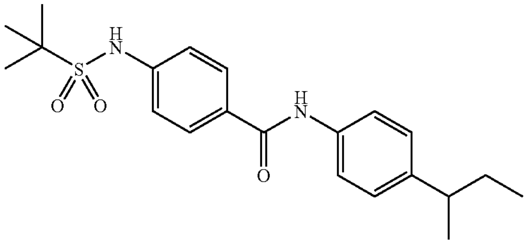
Ig-13
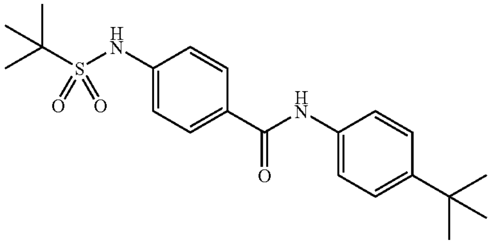
Ig-14
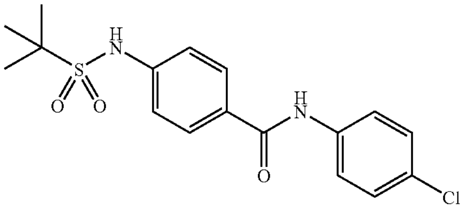
-continued
Ig-16
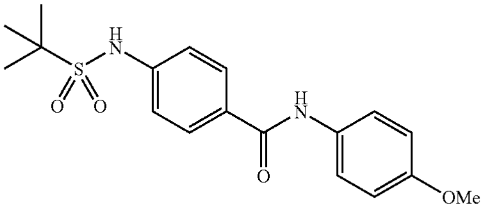
Ig-17
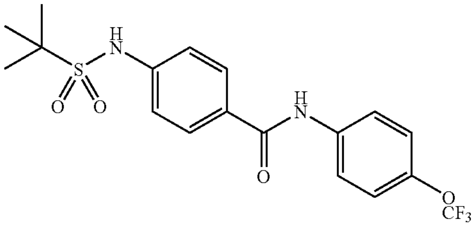
Ig-18
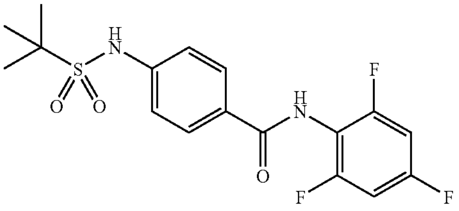
Ig-19
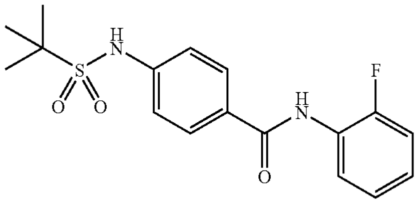
Ig-20
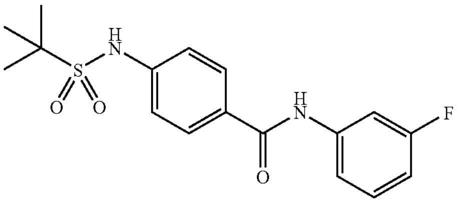
Ig-21
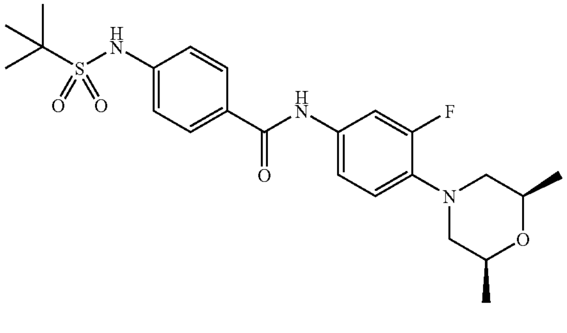

-continued
Ig-22
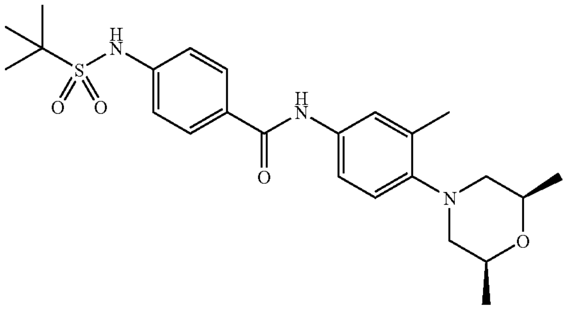
Ig-23
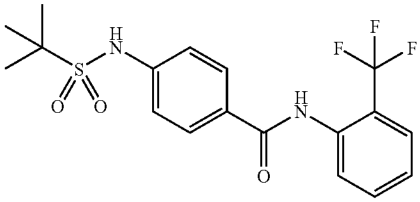
Ig-24
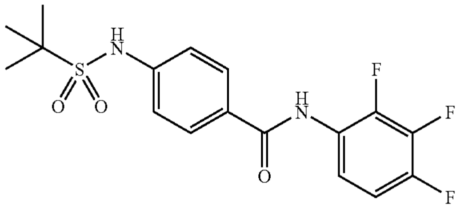
Ig-25
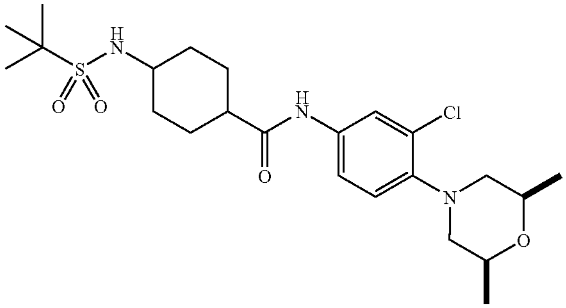
Ig-26
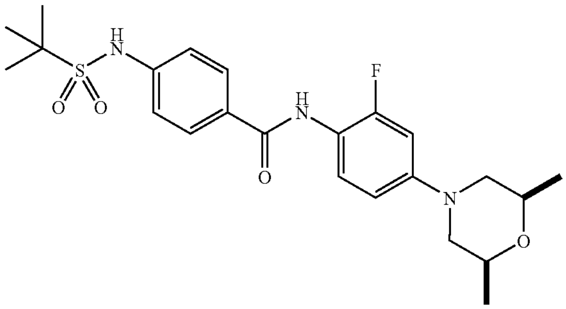
-continued
Ig-27
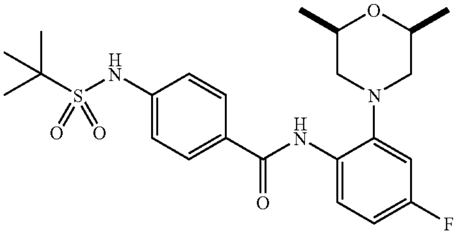
Ig-28
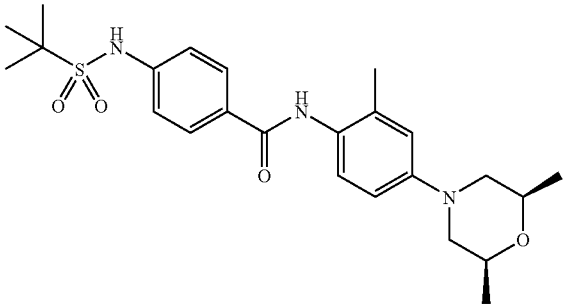
Ig-29
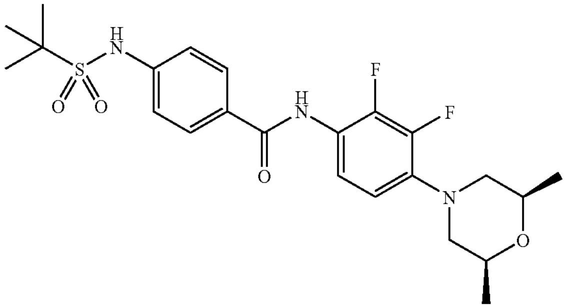
Ig-30
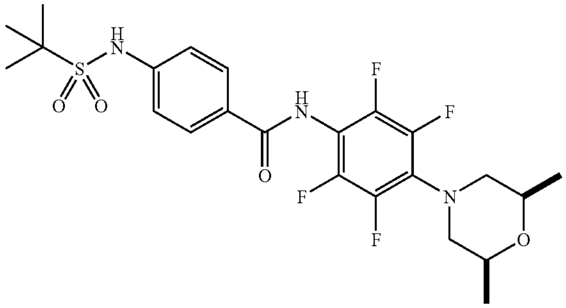
Ig-31
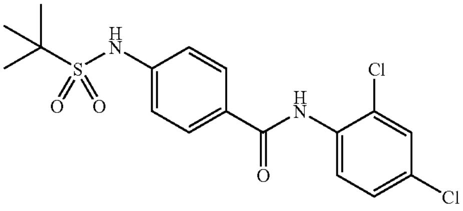

-continued
Ig-32
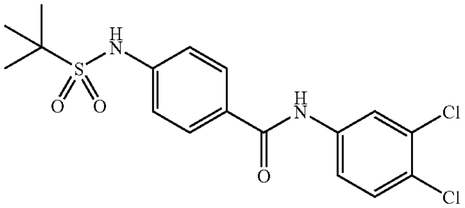
Ig-33
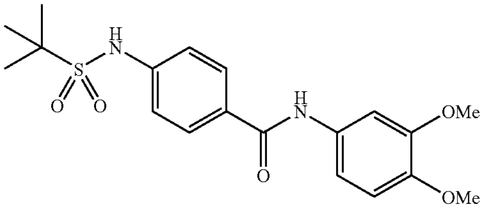
Ig-35
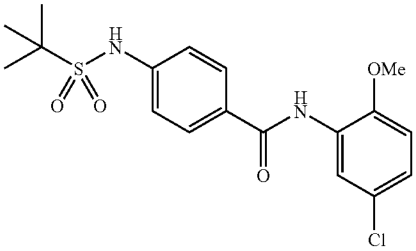
Ig-36
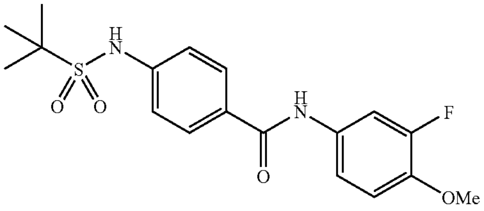
Ig-37
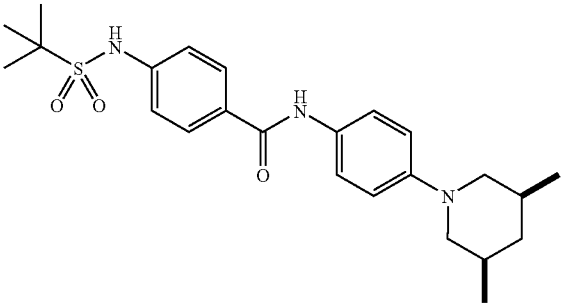
Ig-38
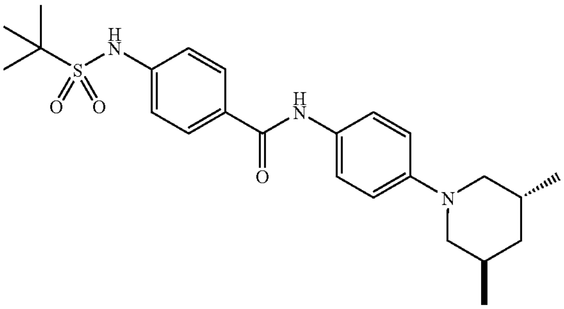
-continued
Ig-39
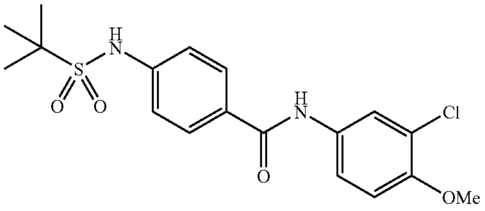
Ig-40
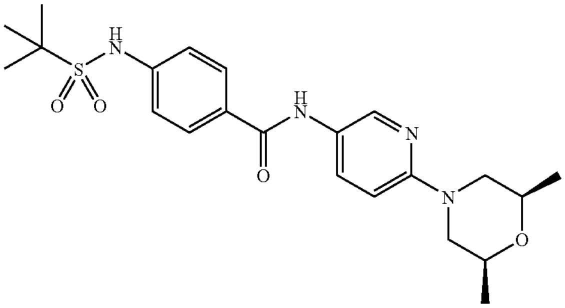
Ig-41
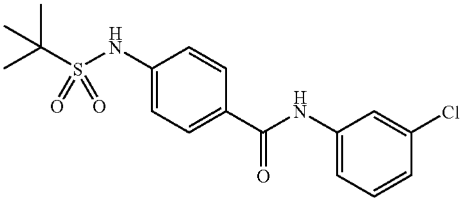
Ig-42
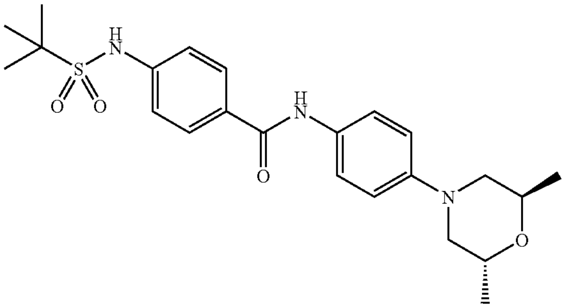
Ig-43
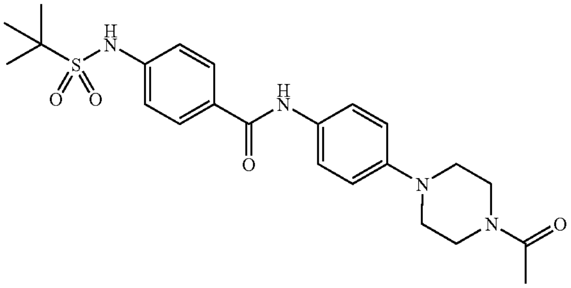

-continued
Ig-44
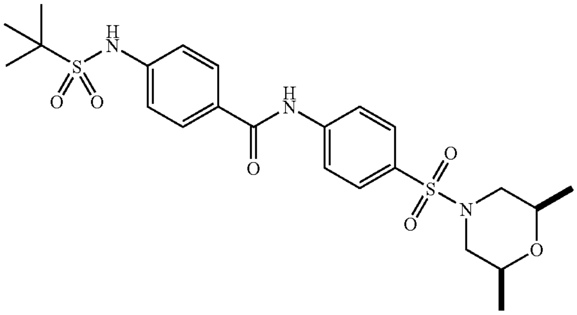
Ig-45
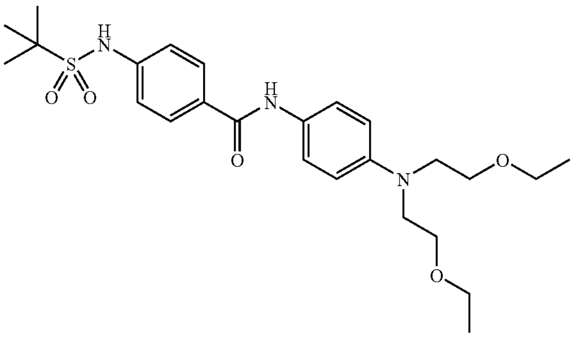
Ig-46
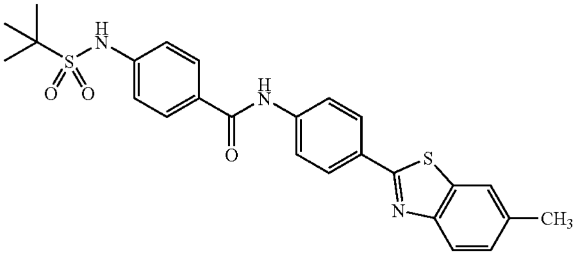
If-47
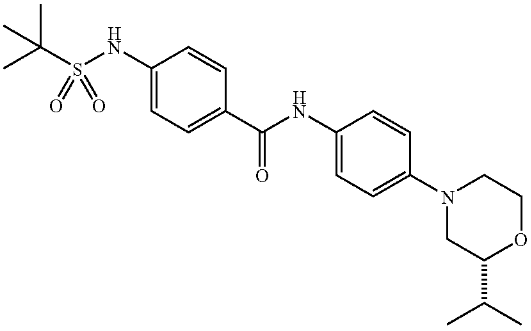
-continued
If-48
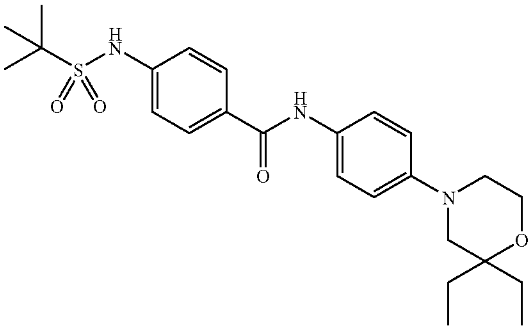
If-49
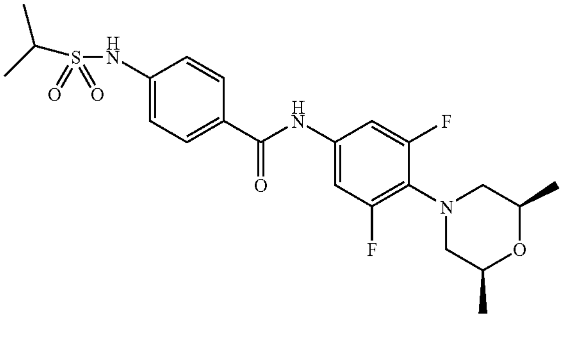
If-50
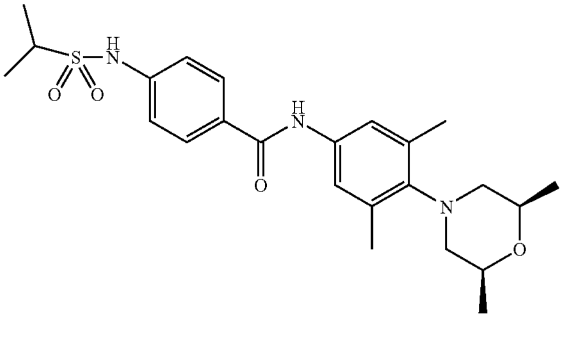
If-51
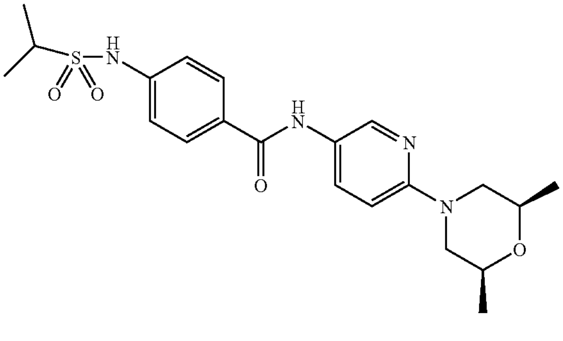

-continued
Ig-52
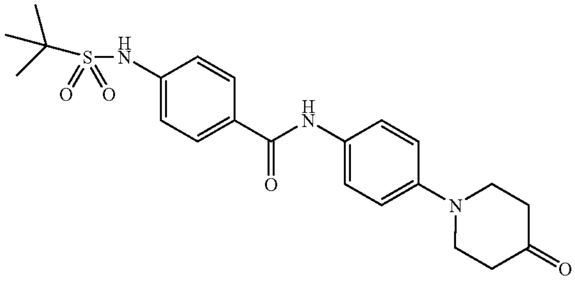
Ig-53
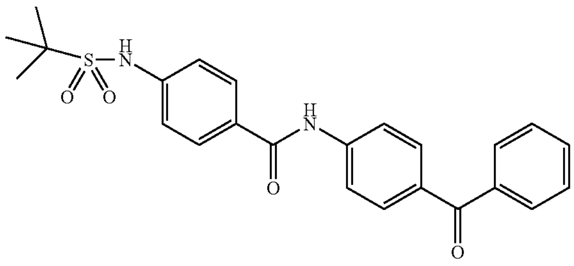
Ig-54
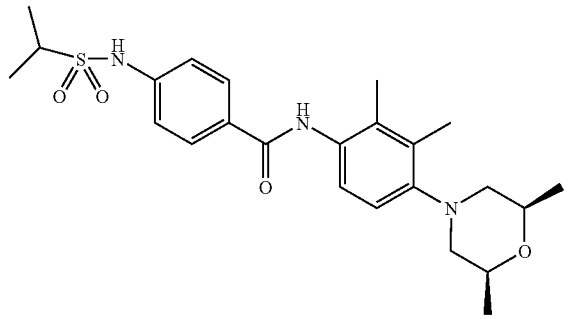
Ig-55
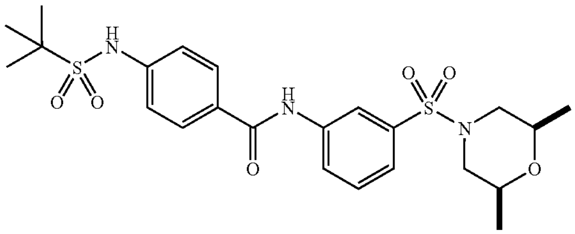
Ig-56
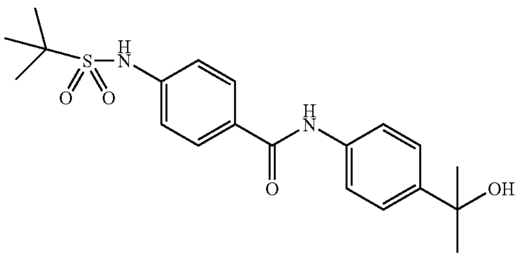
-continued
Ig-57
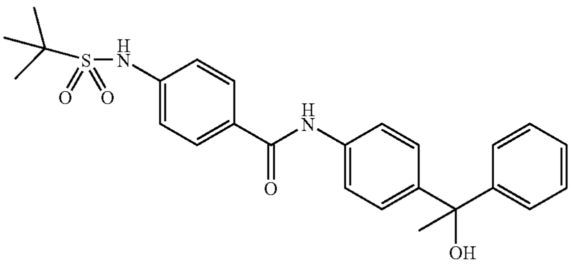
Ig-58
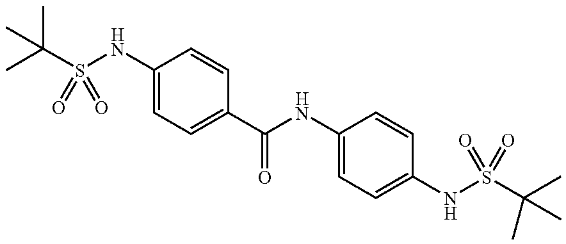
Ig-59
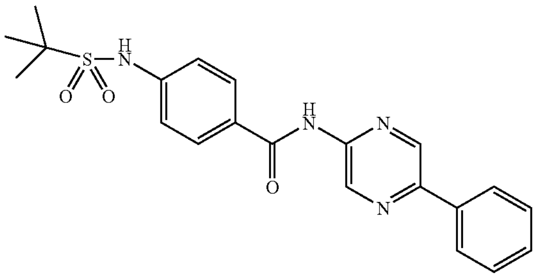
Ig-60
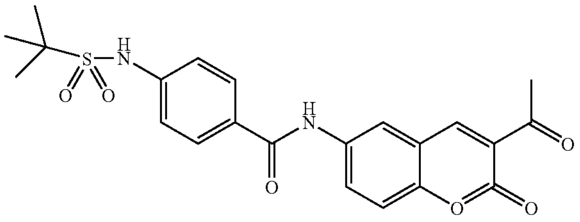
Ig-61
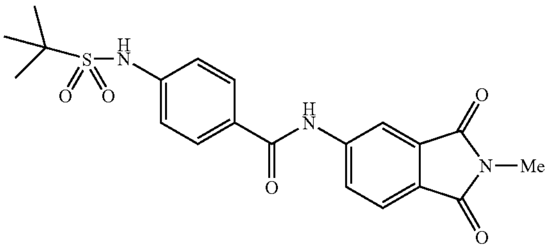
Ig-62
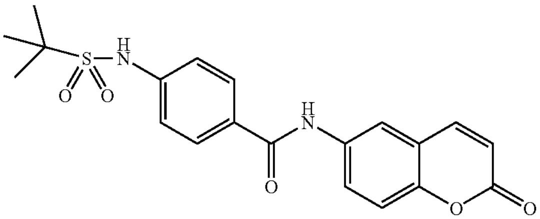

-continued
Ig-63
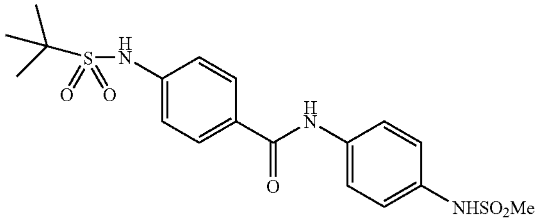
Ig-64
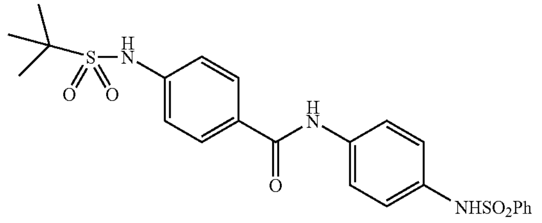
Ig-65
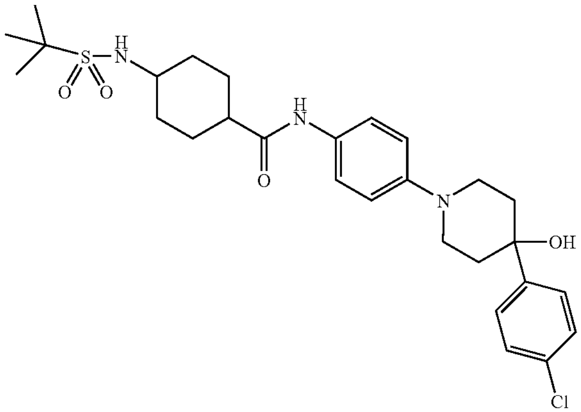
Ig-66
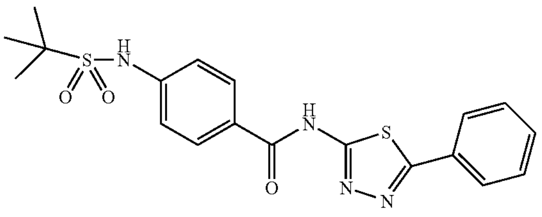
Ig-67
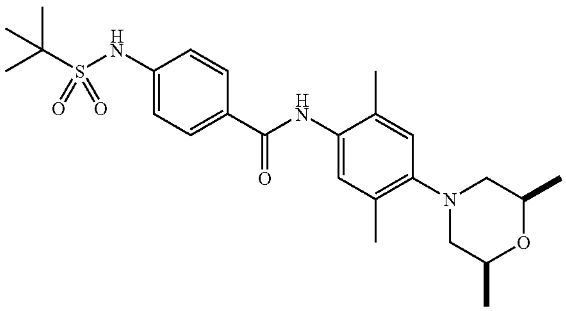
-continued
Ig-68
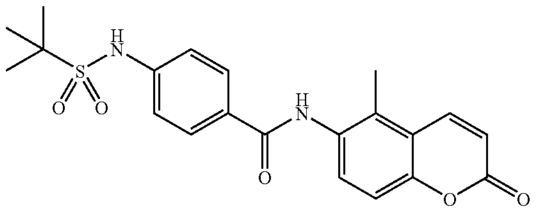
Ig-69
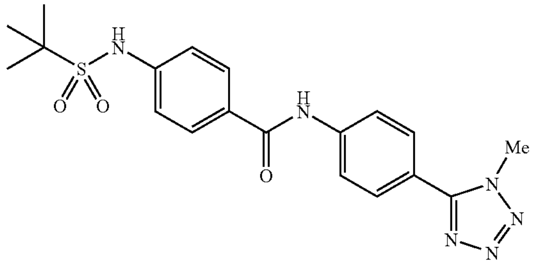
Ig-70
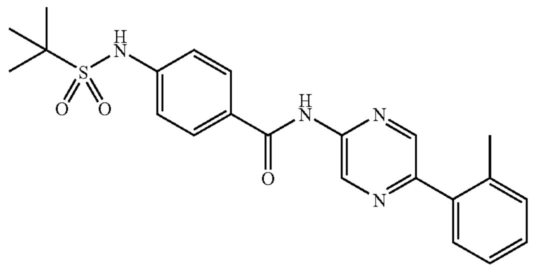
Ig-71
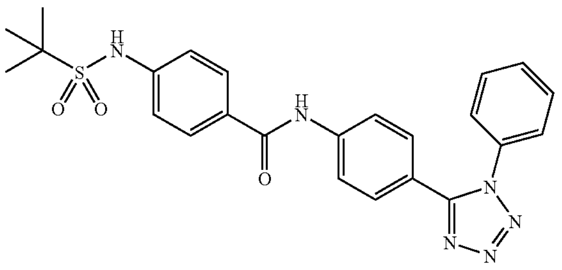
Ig-74
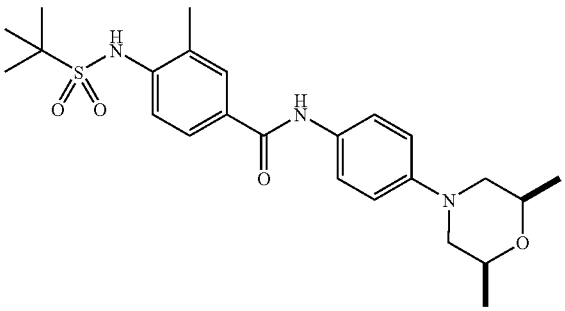

-continued
If-75
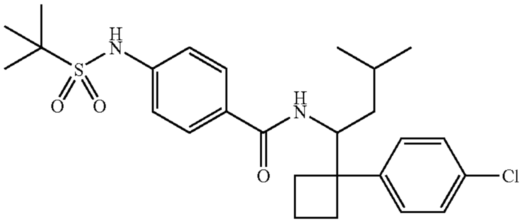
If-76
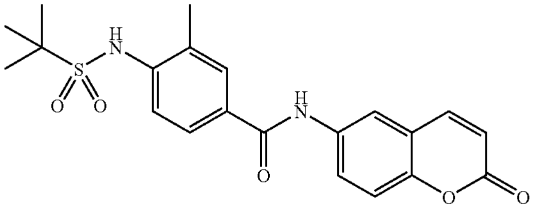
If-77
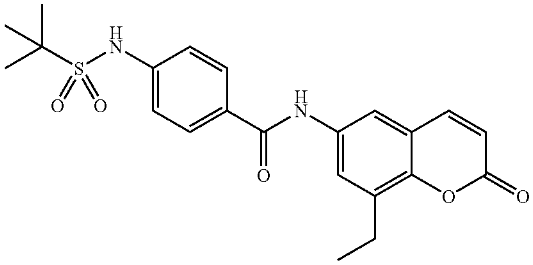
If-78
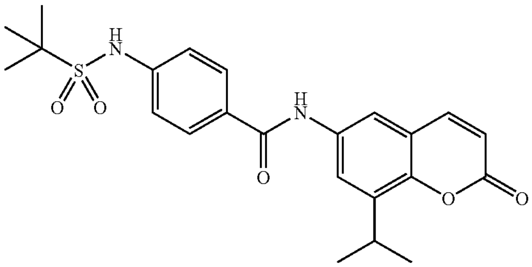
Ig-79
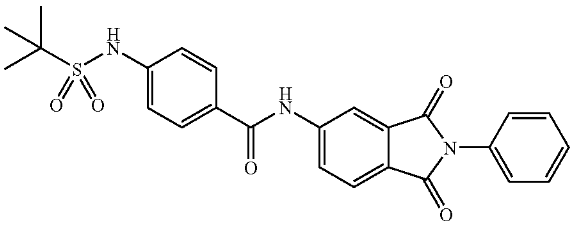
-continued
Ig-80
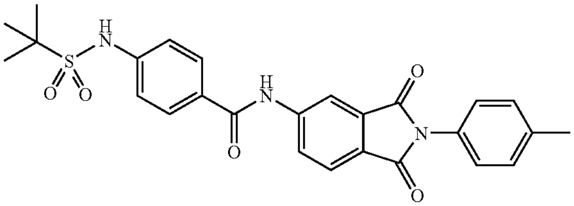
Ig-81
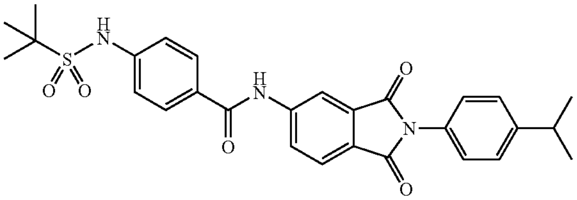
Ig-82
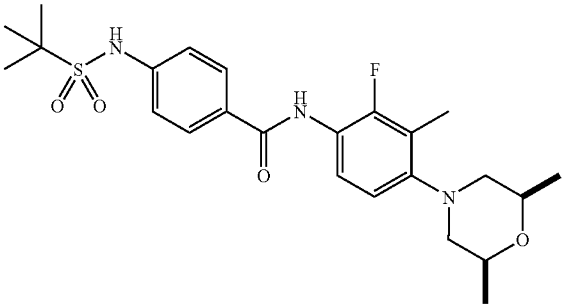
Ig-83
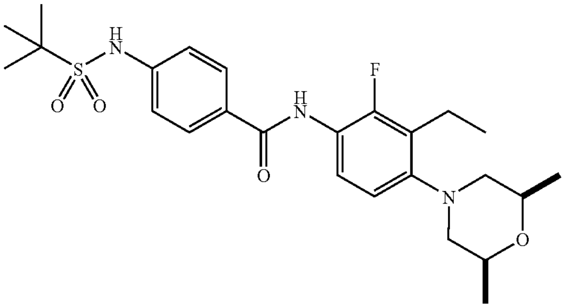
Ig-84
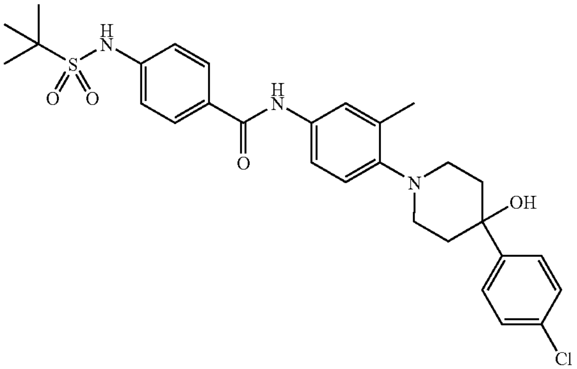

-continued
Ig-85
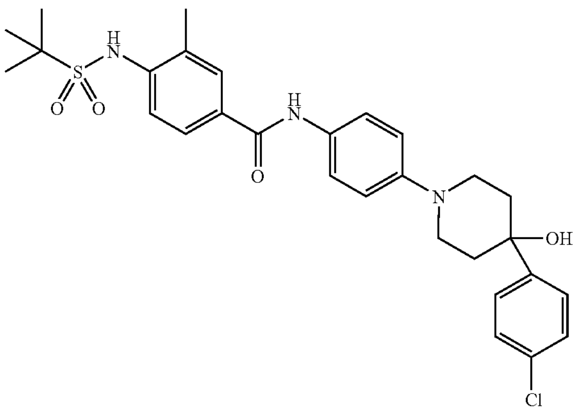
Ig-86
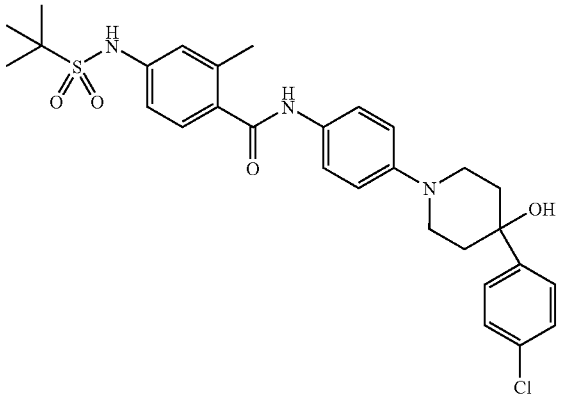
Ig-87
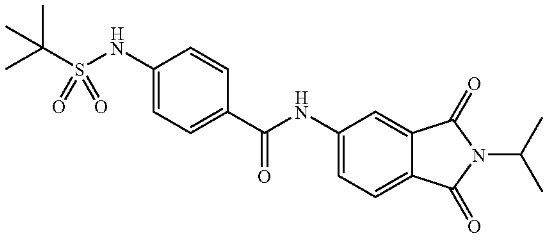
Ig-88
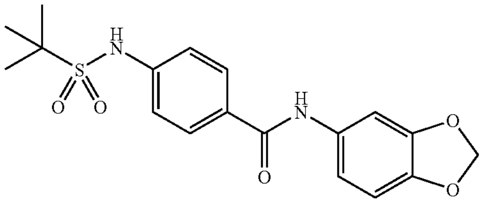
Ig-89
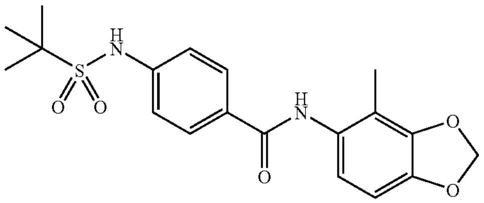
-continued
Ig-90
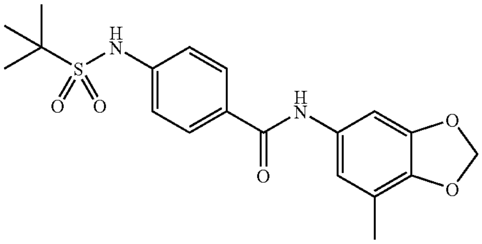
Ig-91
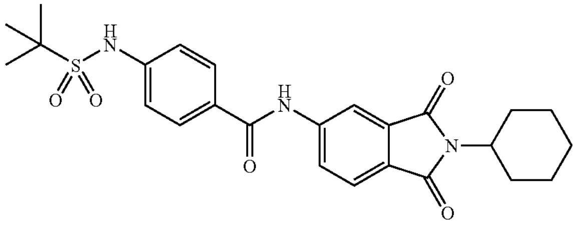
Ig-92
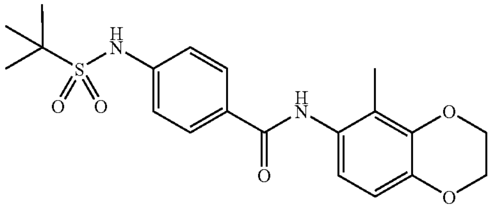
Ig-93
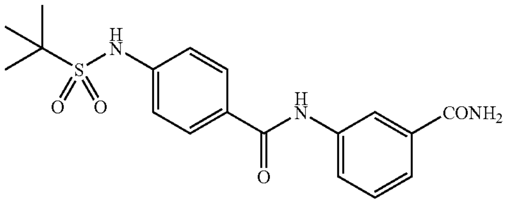
Ig-94
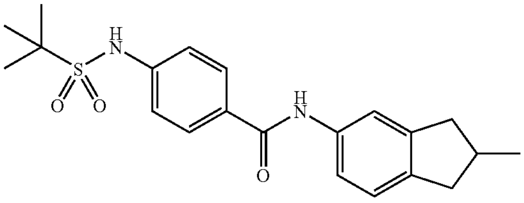
Ig-95
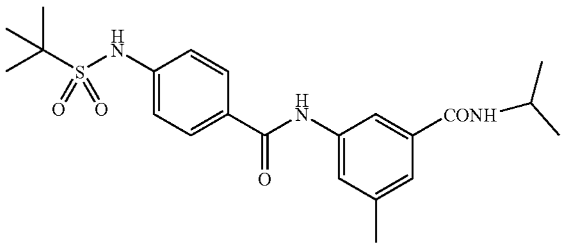

-continued
Ig-96
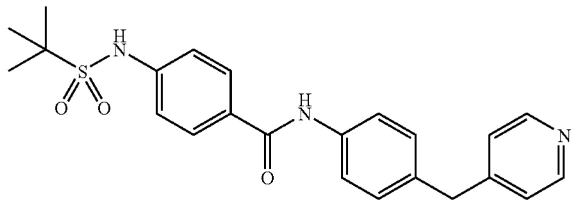
Ig-97
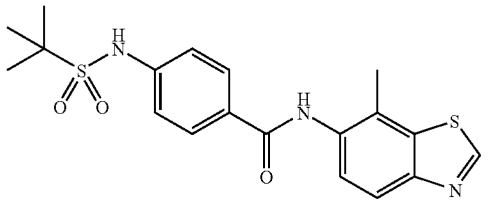
Ig-98
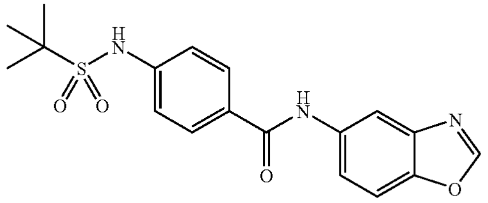
Ig-99
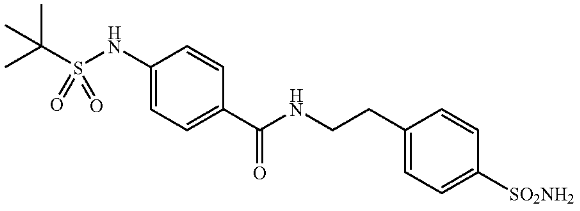
Ig-100
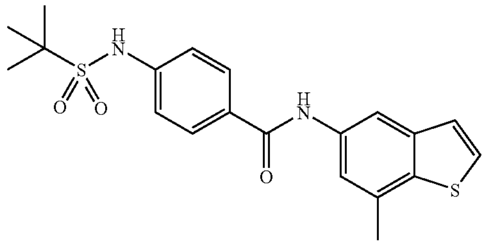
Ig-101
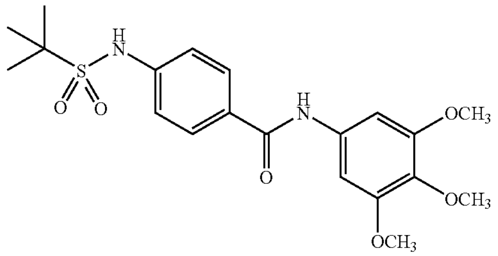
Ig-102
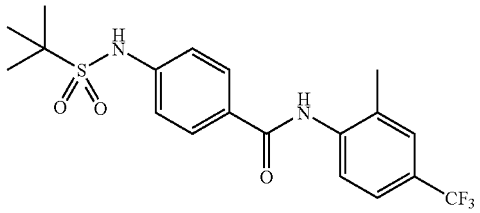
-continued
Ig-103
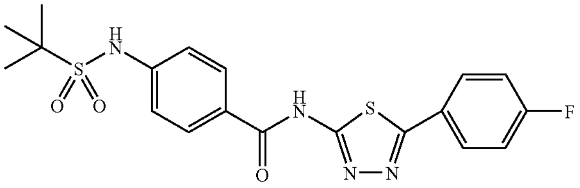
Ig-104
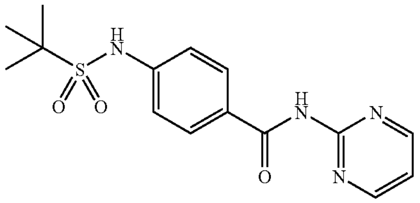
Ig-105
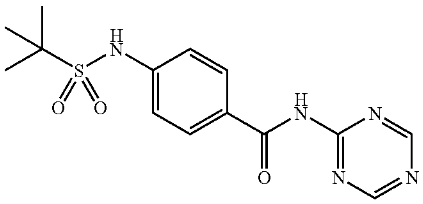
Ig-106
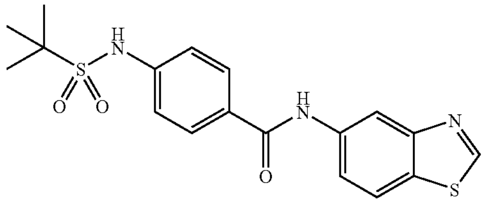
Ig-107
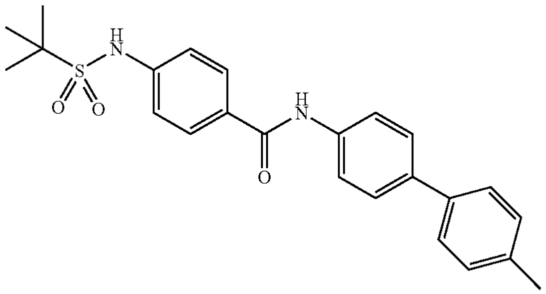
Ig-108
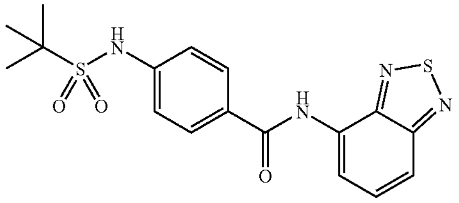
Ig-109
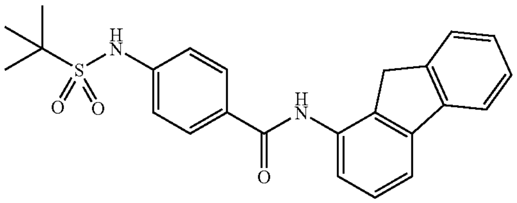

-continued
Ig-110
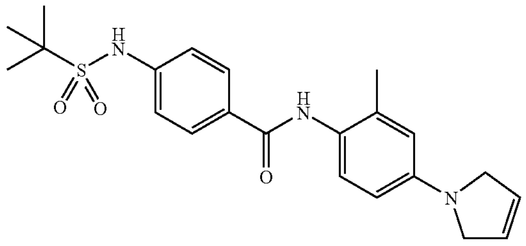
Ig-111
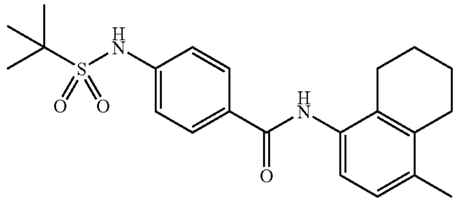
Ig-112
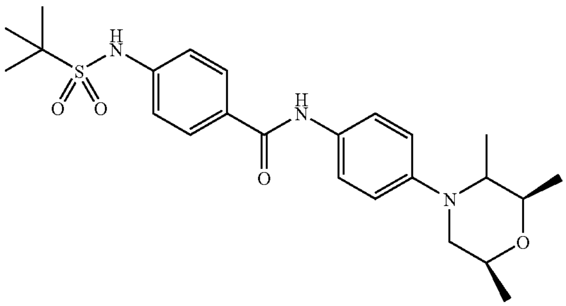
Ig-113
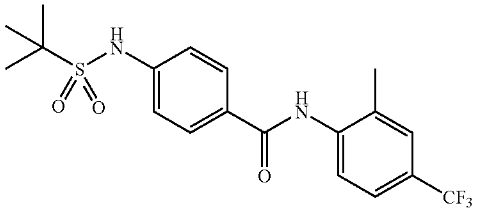
Ig-114
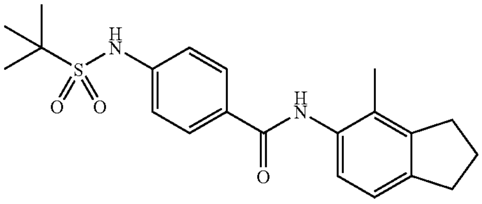
Ig-115
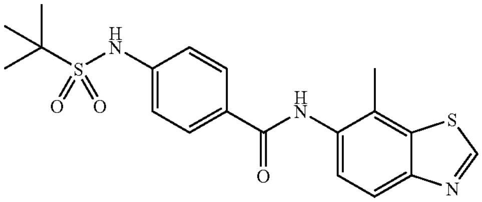
-continued
Ig-116
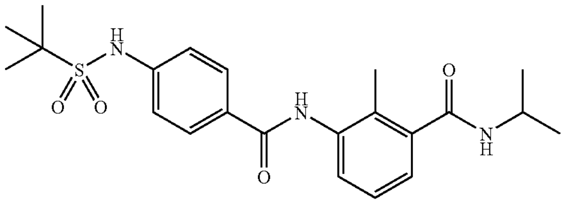
Ig-117
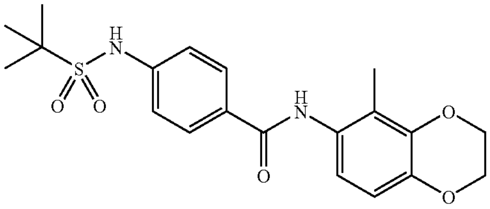
Ig-118
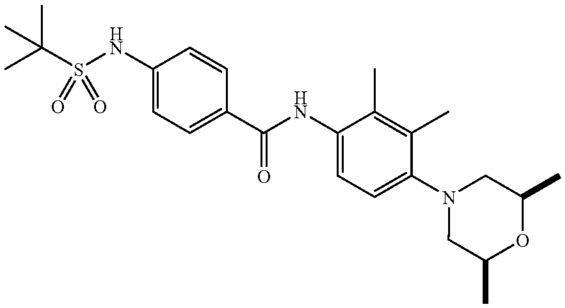
Ig-119
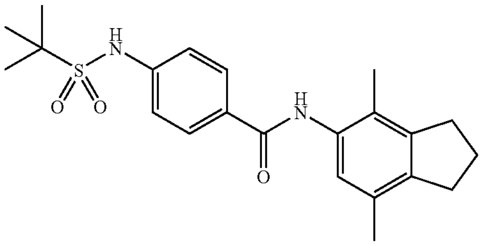
Ig-120
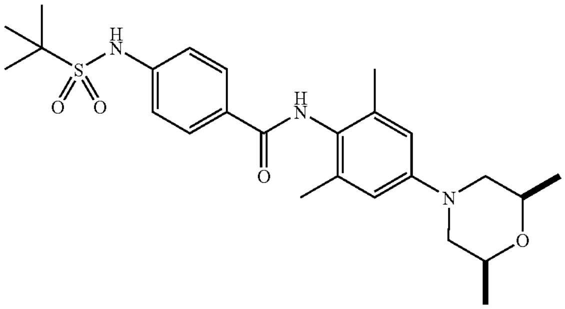
Ig-121
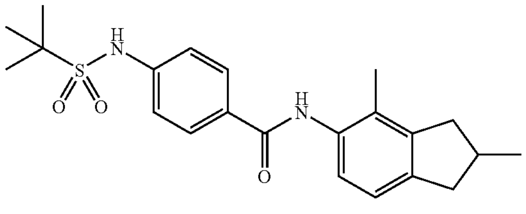

-continued
Ig-122
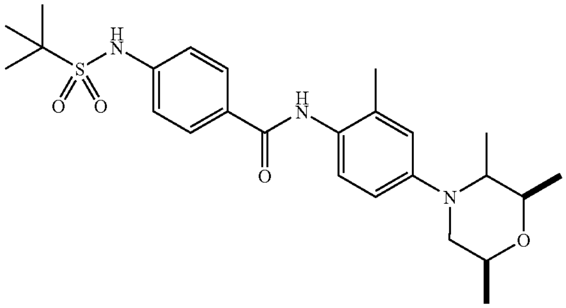
Ig-123
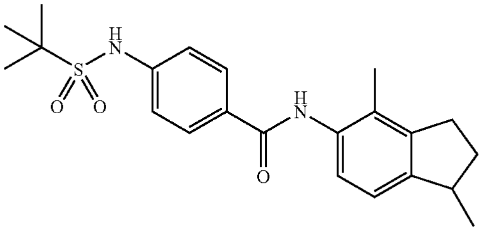
Ig-124
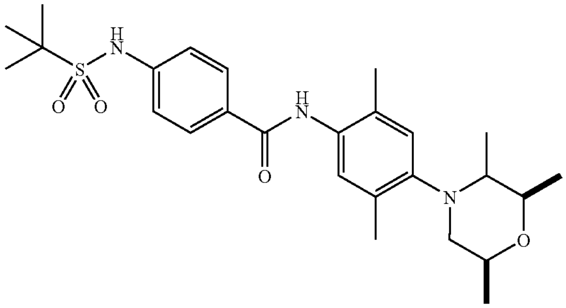
Ig-125
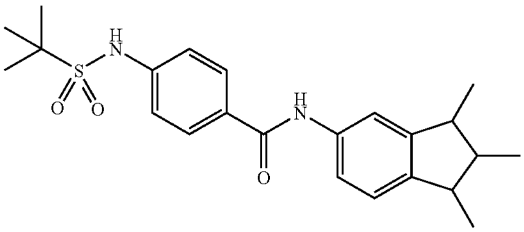
Ig-126
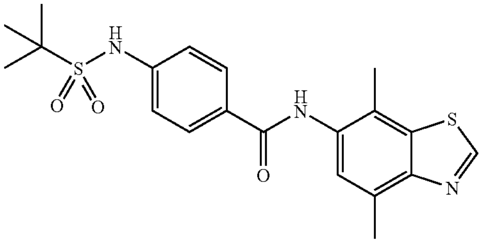
-continued
Ig-127
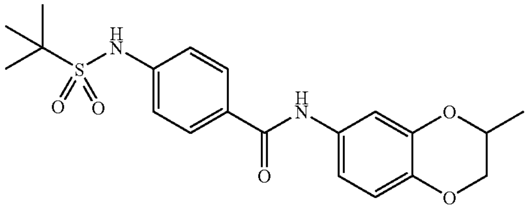
Ig-128
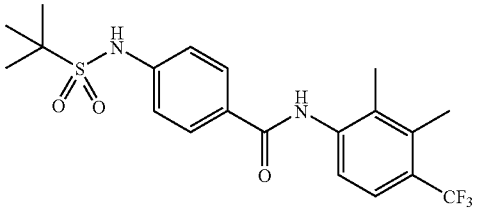
Ig-129
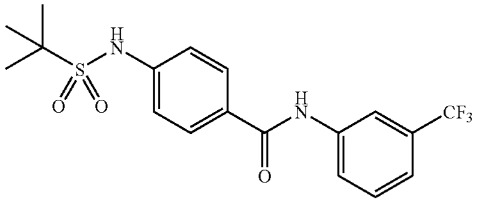
Ig-130
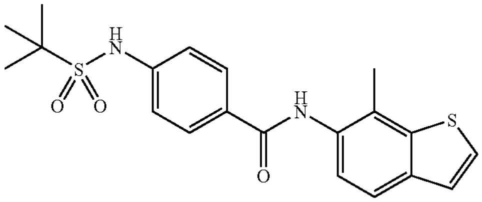
Ig-131
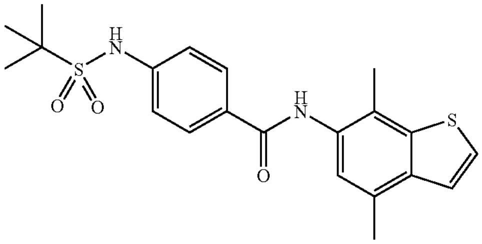
Ig-132
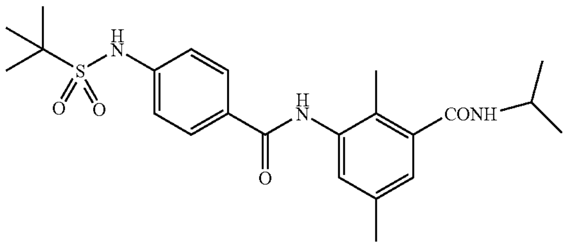

-continued
Ig-133
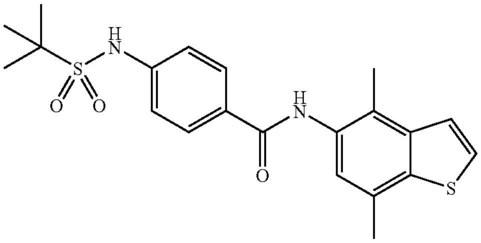
Ig-134
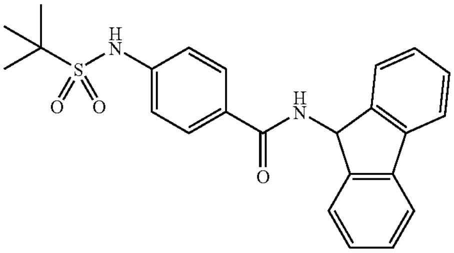
Ig-135
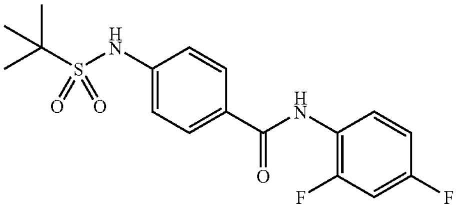
Ig-136
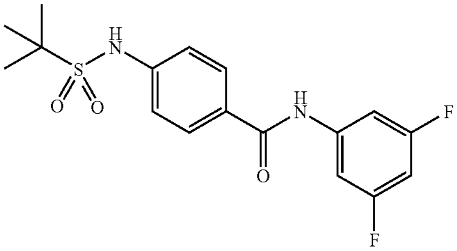
Ig-137
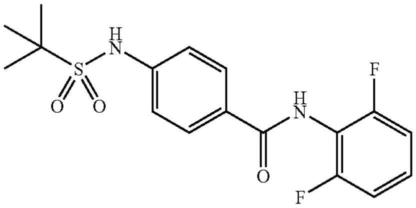
Ig-138
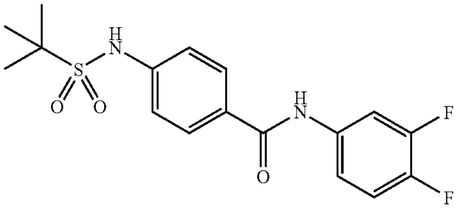
-continued
Ig-139
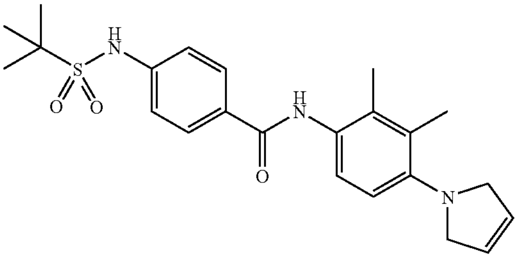
Ig-140
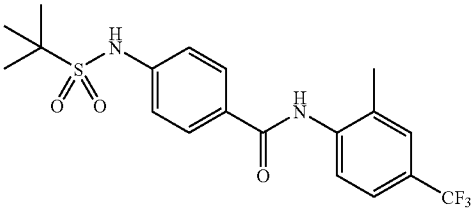
Ig-141
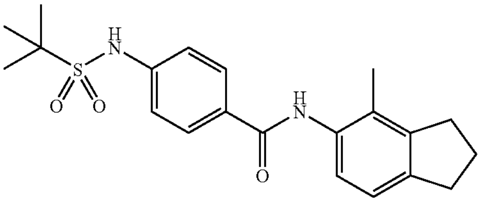
Ig-142
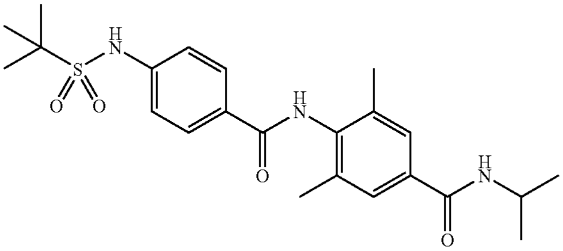
Ig-143
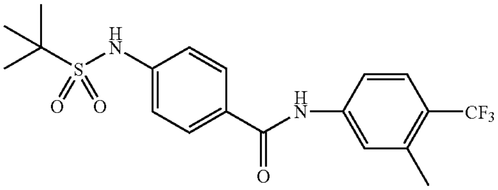
Ig-144
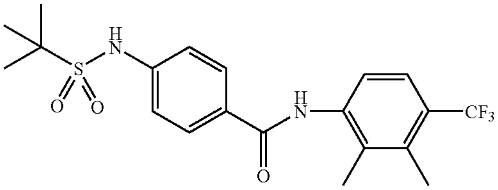

-continued
Ig-145
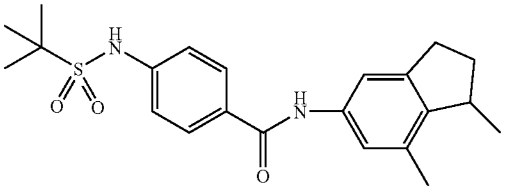
Ig-146
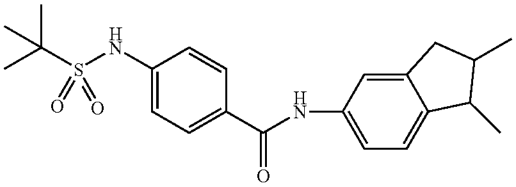
Ig-147
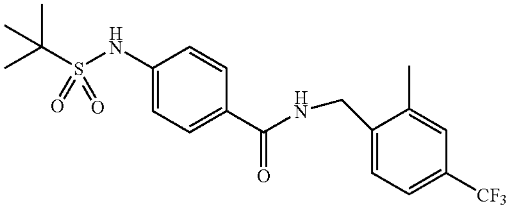
Ig-148
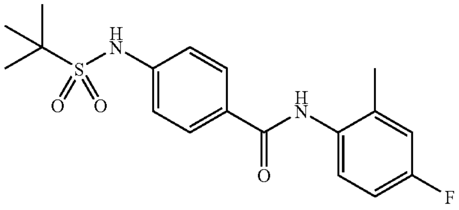
Ig-149
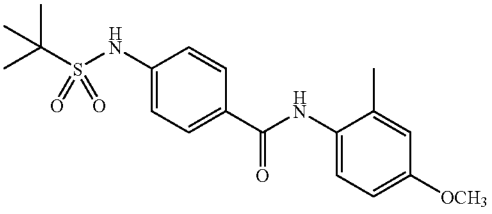
Ig-150
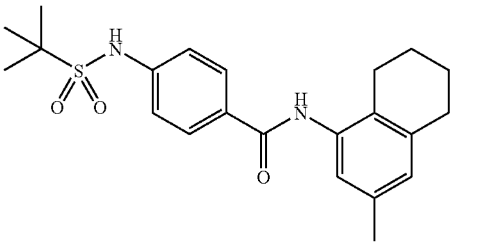
Ig-151
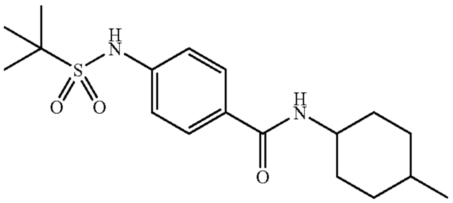
-continued
Ig-152
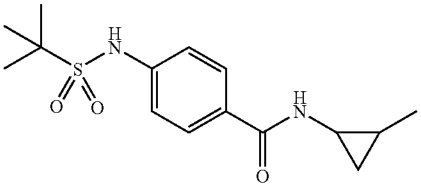
Ig-153
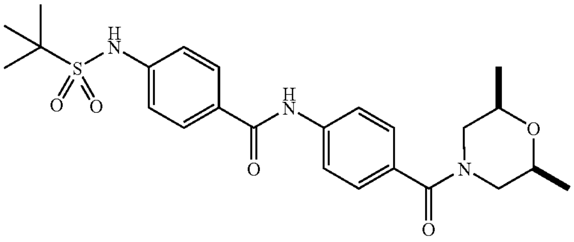
Ig-154
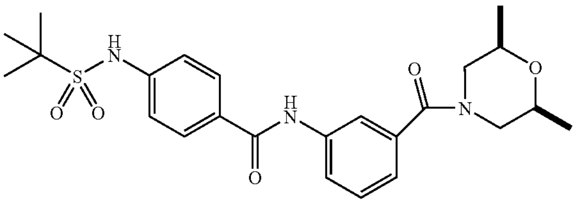
Ig-155
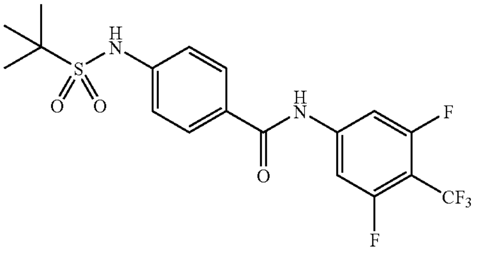
Ig-156
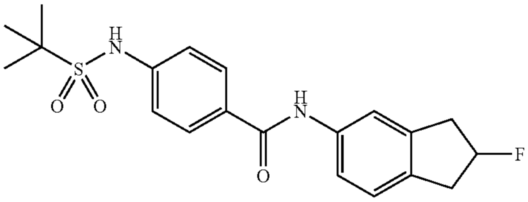
Ig-157
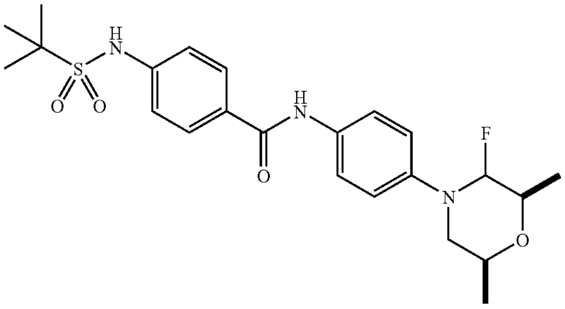

-continued
Ig-158
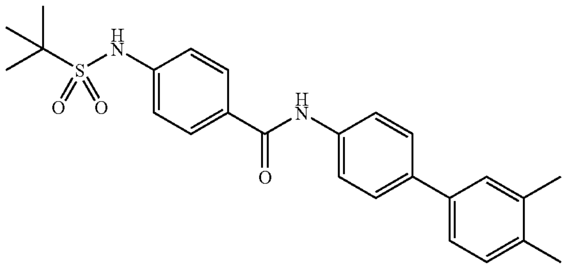
Ig-159
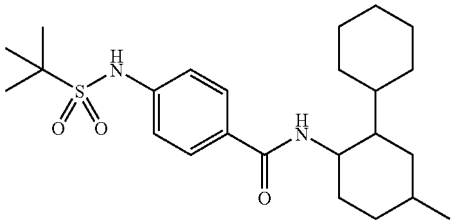
Ig-160
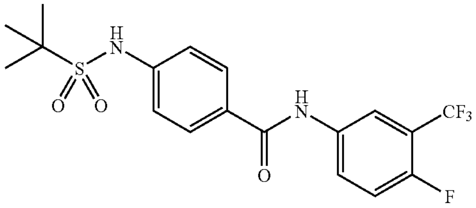
Ig-161
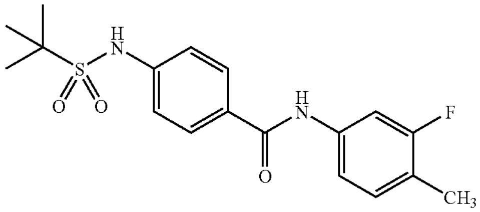
Ig-162
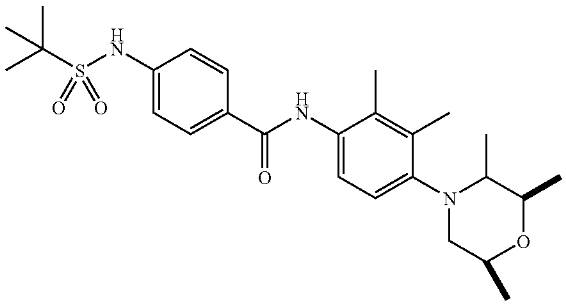
Ig-163
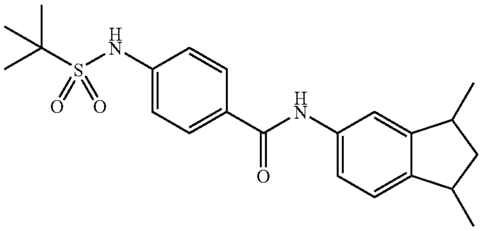
-continued
Ig-164
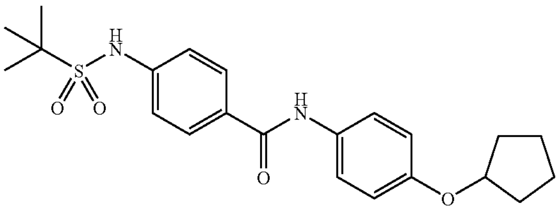
Ig-165
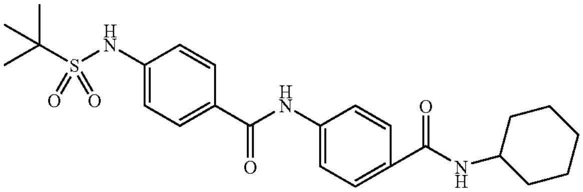
Ig-166
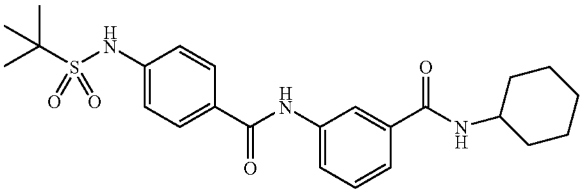
Ig-167
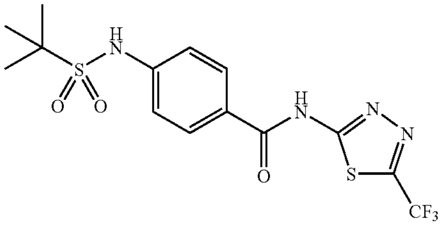
Ig-168
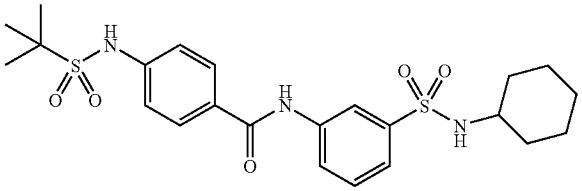
Ig-169
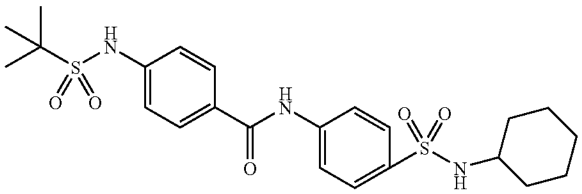
Ig-171
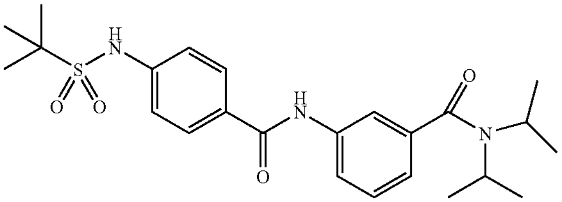

-continued
Ig-172
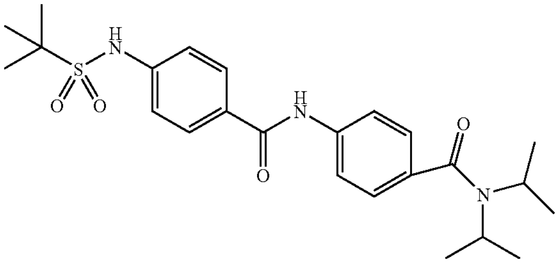
Ig-173
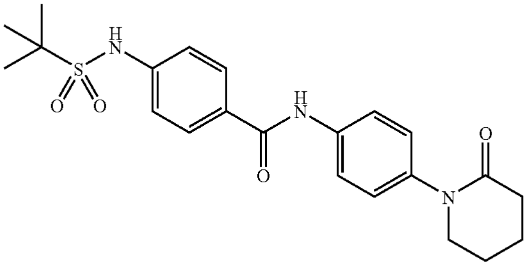
Ig-174
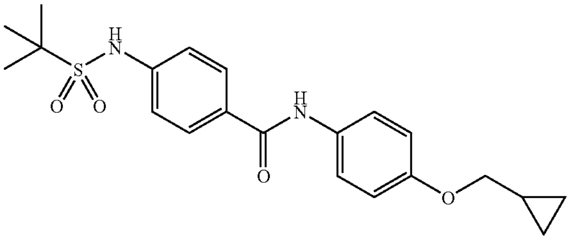
Ig-175
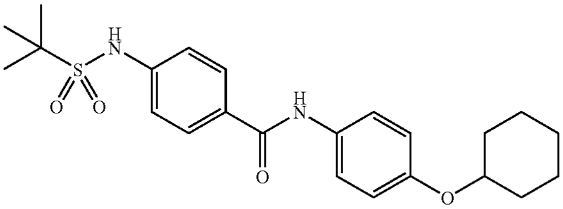
Ig-176
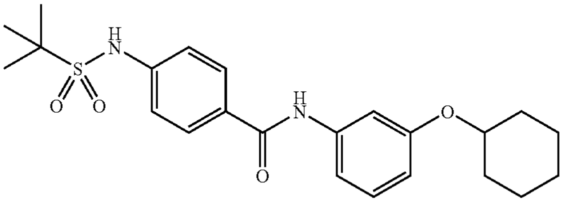
Ig-177
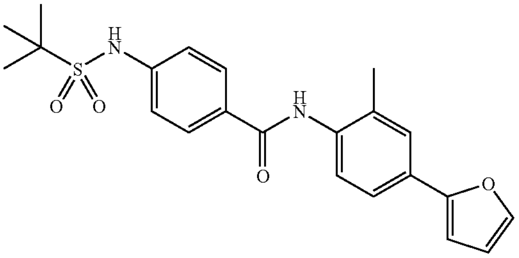
-continued
Ig-178
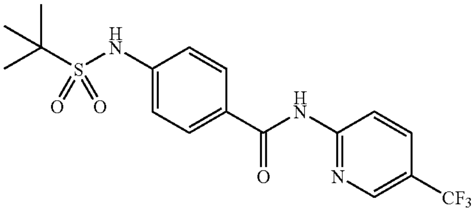
Ig-179
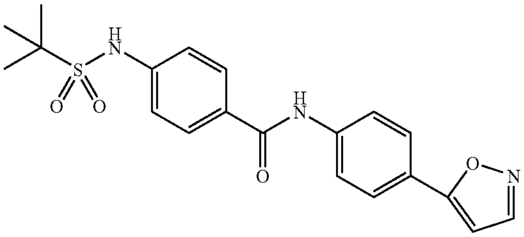
Ig-180
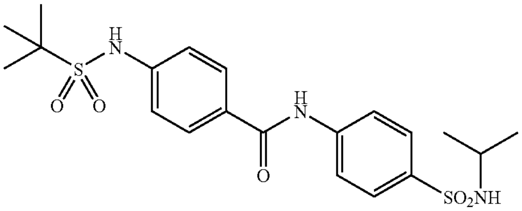
Ig-181
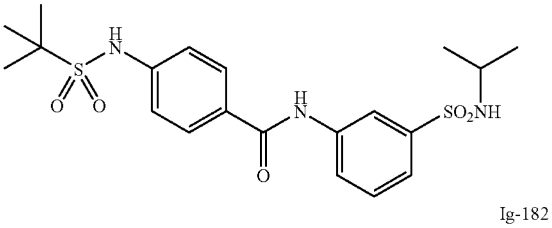
Ig-182
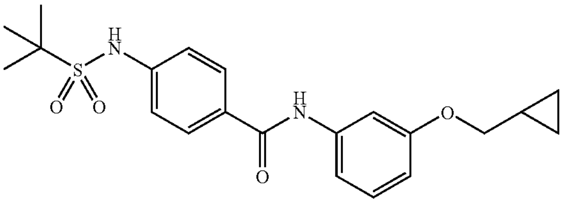
Ig-183
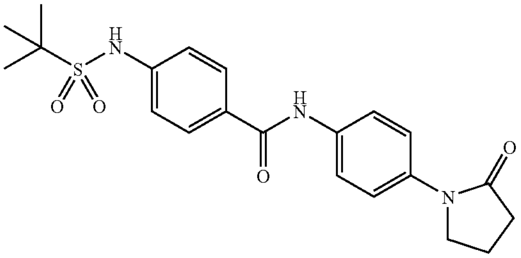

-continued
Ig-184
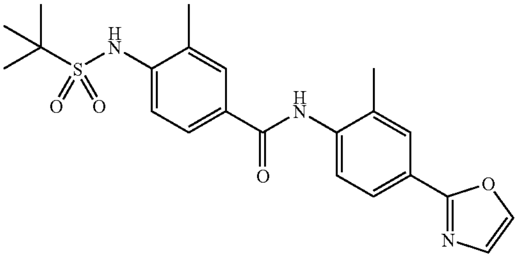
Ig-185
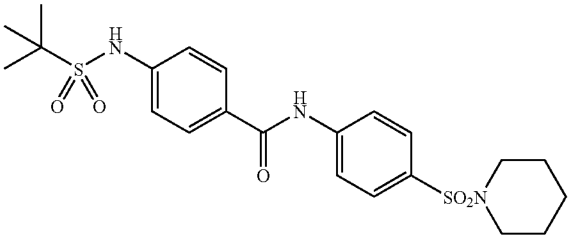
Ig-186
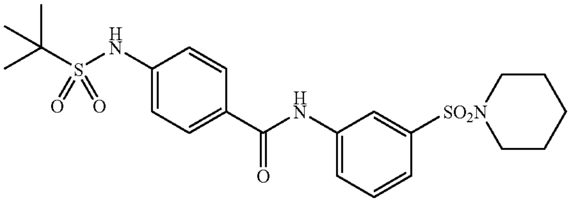
Ig-187
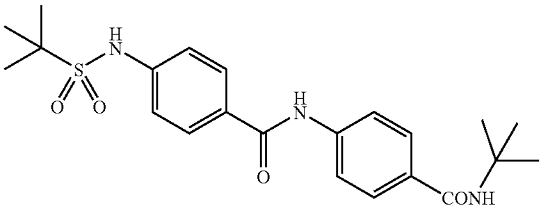
Ig-188
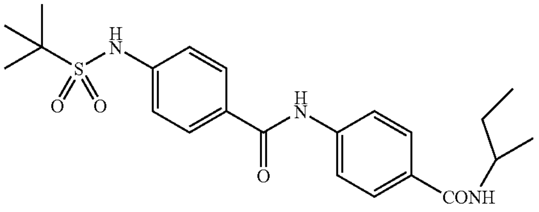
-continued
Ig-189
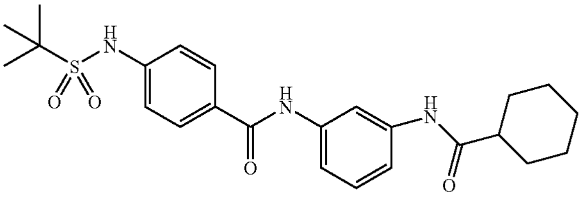
Ig-190
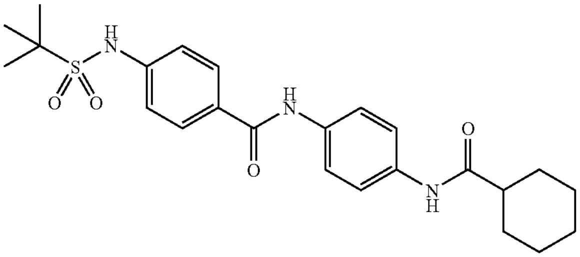
Ig-191
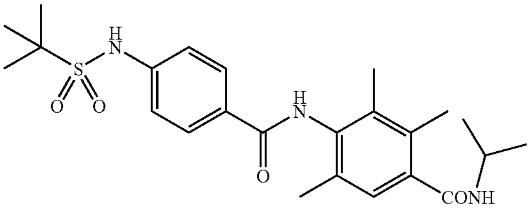
Ig-192
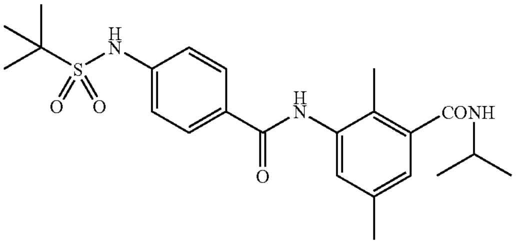
Ig-193
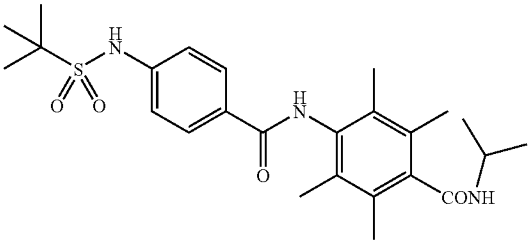
Ig-194
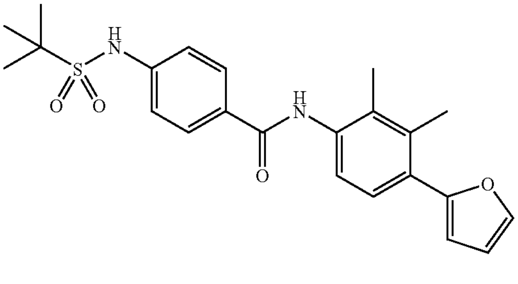

-continued
Ig-195
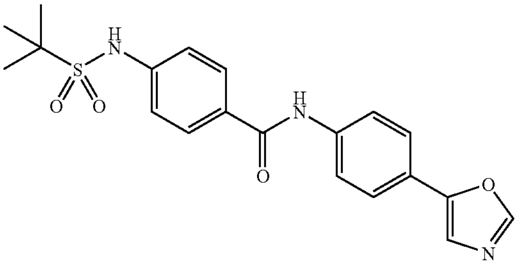
Ig-196
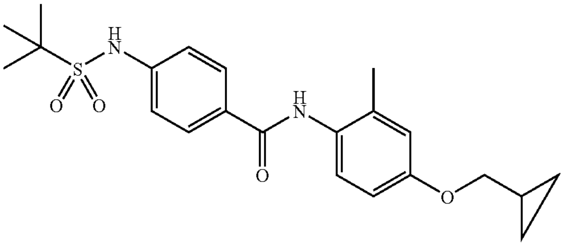
Ig-197
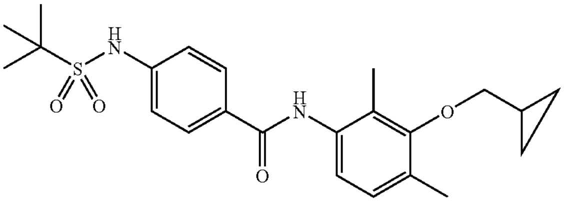
Ig-198
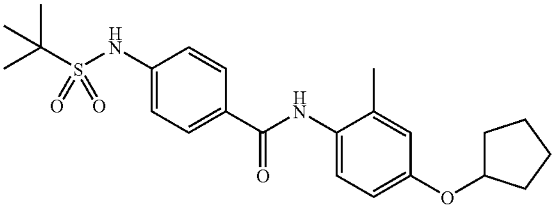
Ig-199
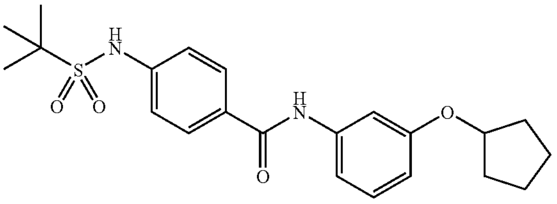
Ig-200
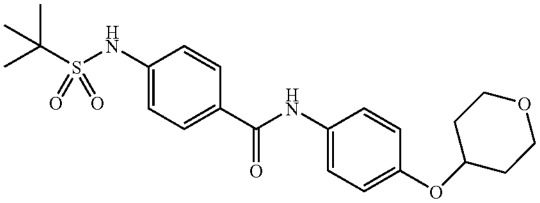
-continued
Ig-201
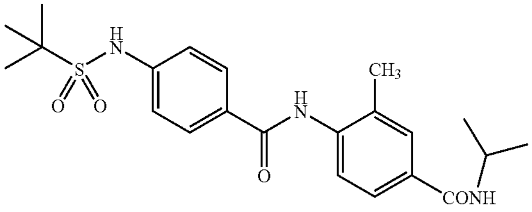
Ig-202
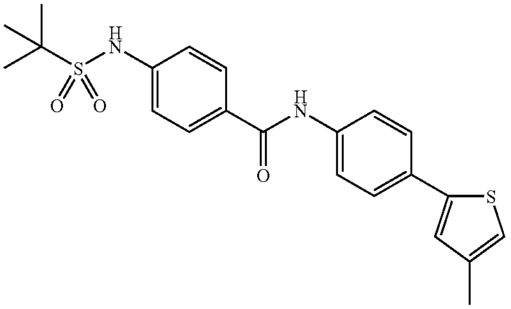
Ig-203
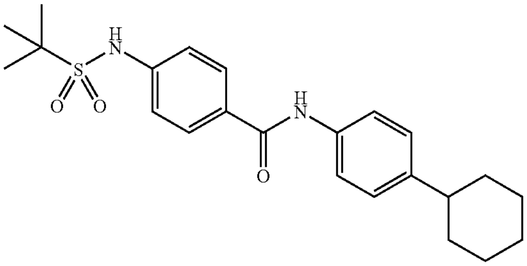
Ig-204
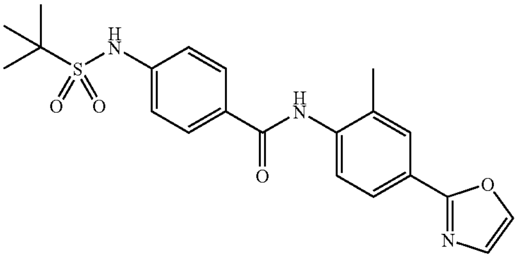
Ig-205
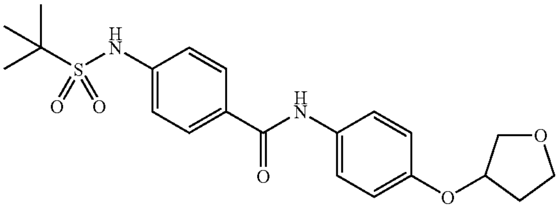

-continued
Ig-206
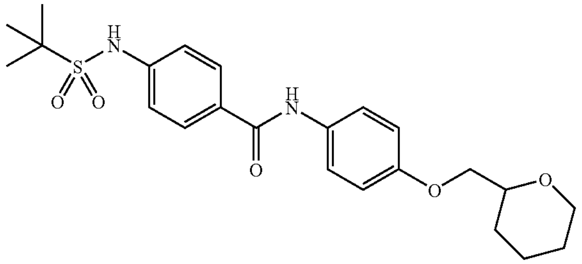
Ig-207
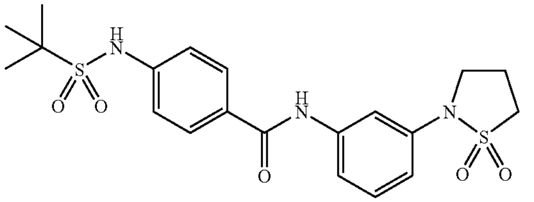
Ig-208
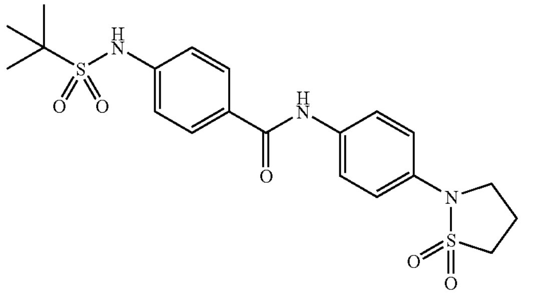
Ig-209
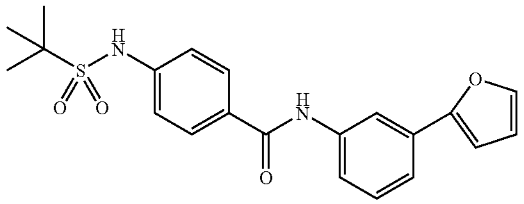
Ig-210
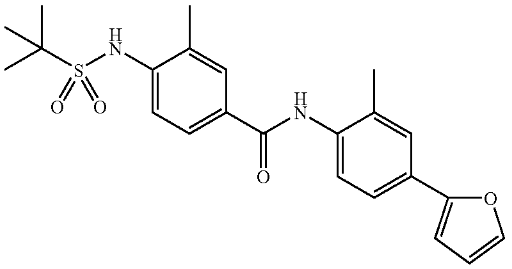
-continued
Ig-211
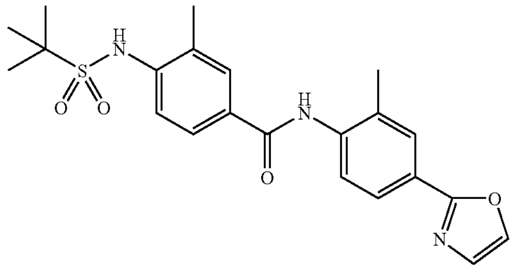
Ig-212
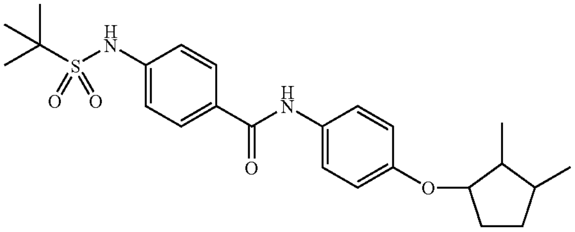
Ig-213
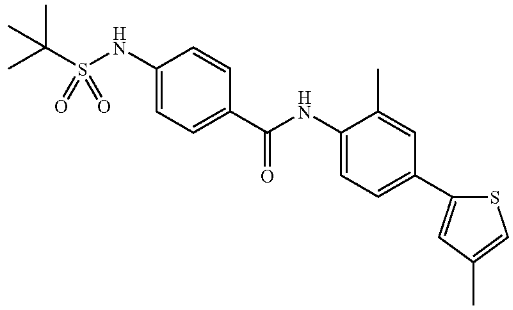
Ig-214
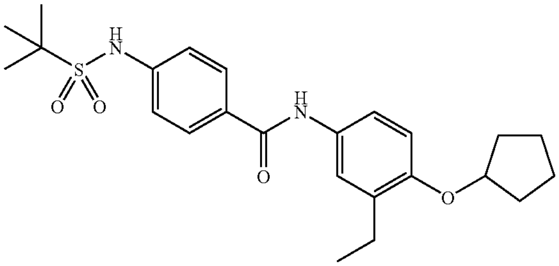
Ig-215
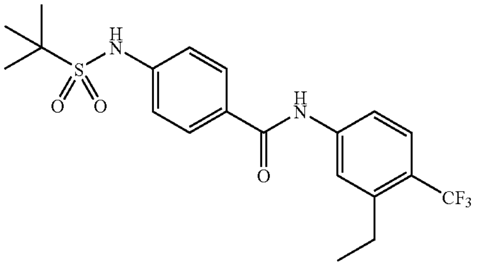

-continued
Ig-216
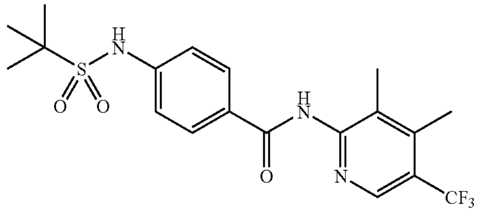
Ig-219
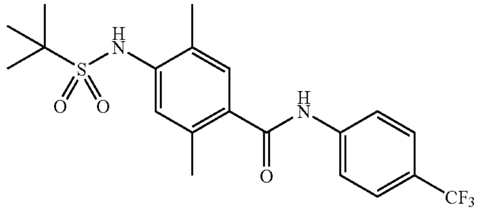
Ig-220
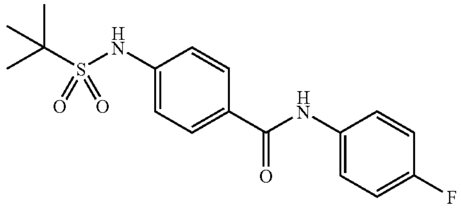
Ig-221
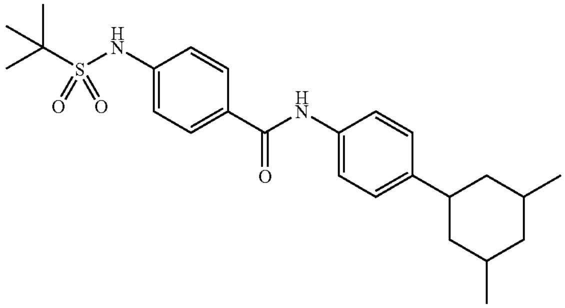
Ig-222
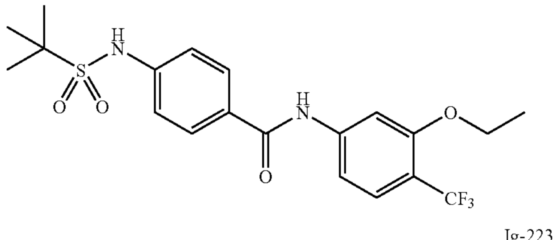
Ig-223
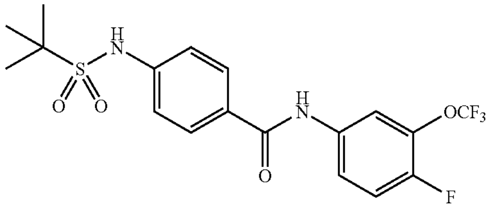
-continued
Ig-224
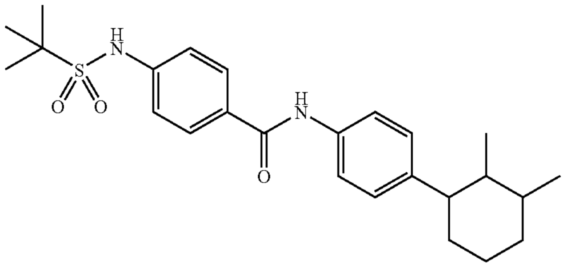
Ig-225
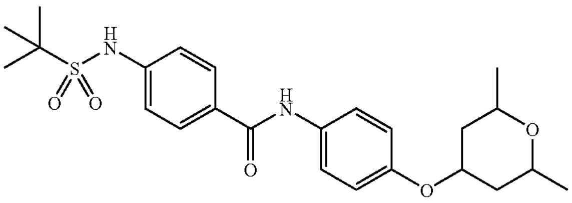
Ig-226
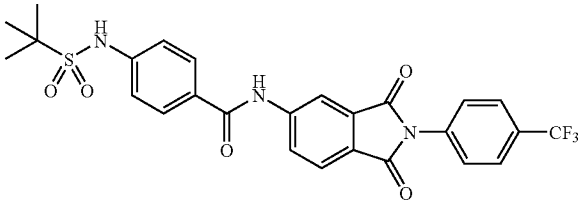
Ih-1
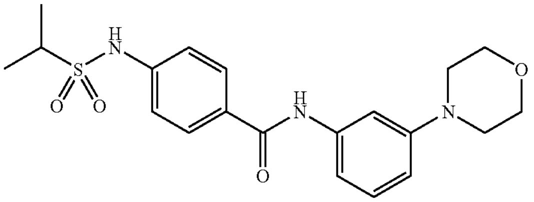
Ih-2
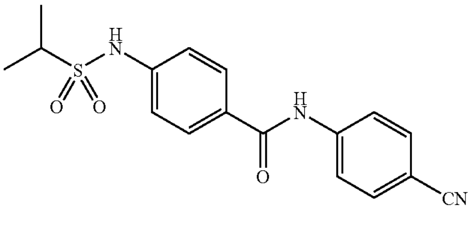
Ih-4
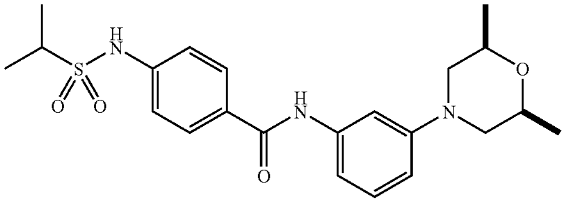

-continued
Ih-7
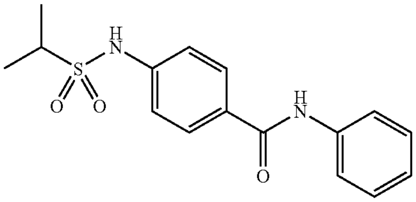
Ih-8
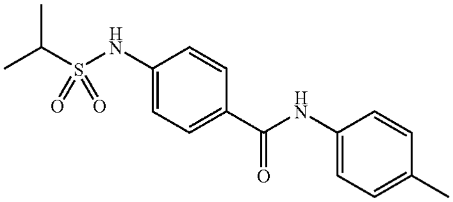
Ih-9
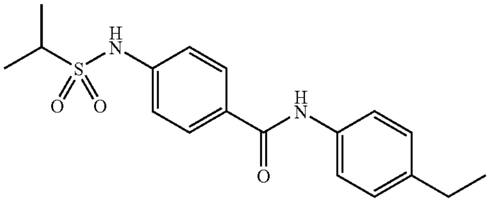
Ih-10
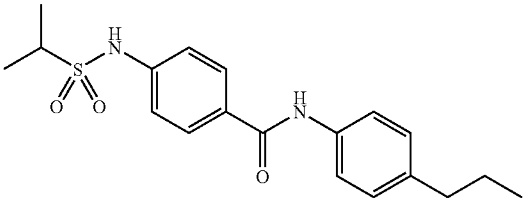
Ih-11
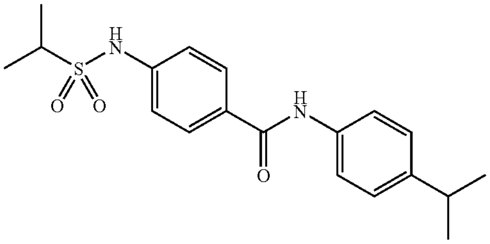
Ih-12
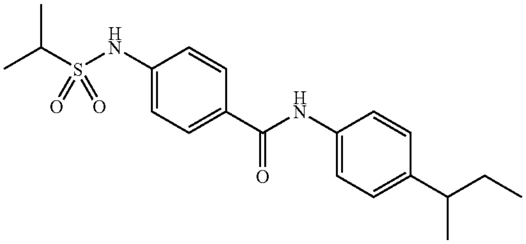
-continued
Ih-13
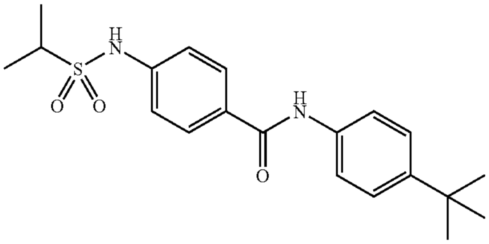
Ih-14
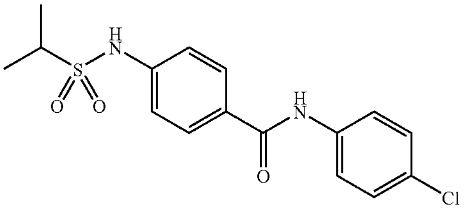
Ih-16
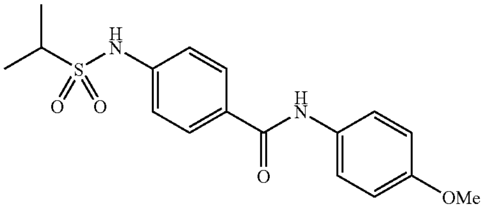
Ih-17
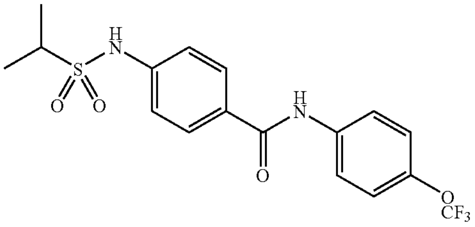
Ih-18
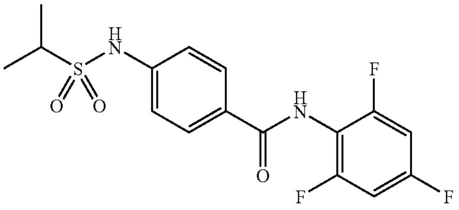
Ih-19
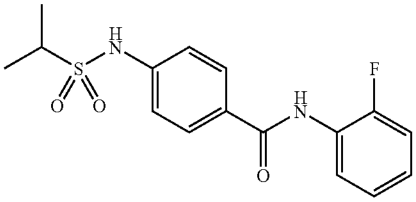
Ih-20
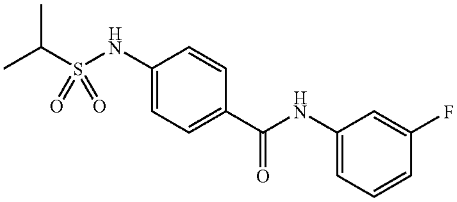

-continued
Ih-21
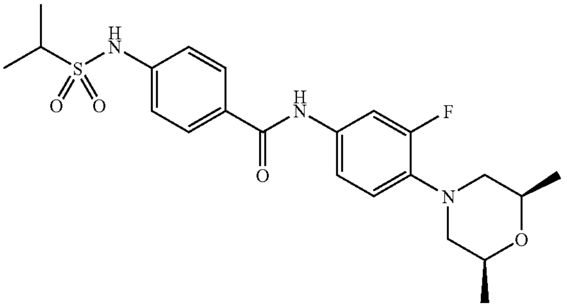
Ih-22
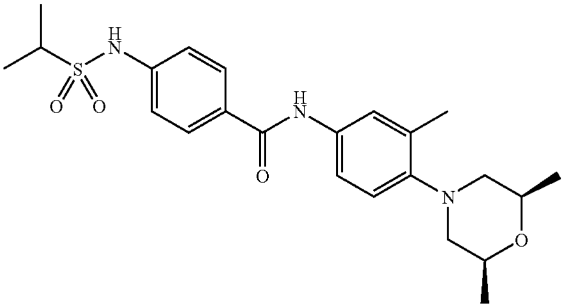
Ih-23
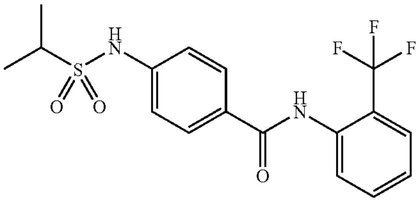
Ih-24
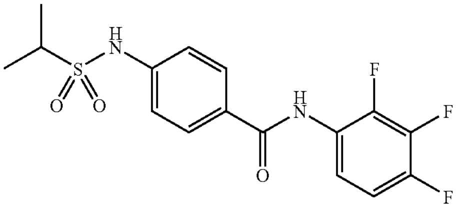
Ih-25
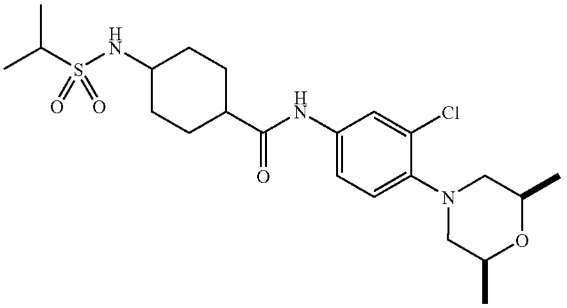
-continued
Ih-26
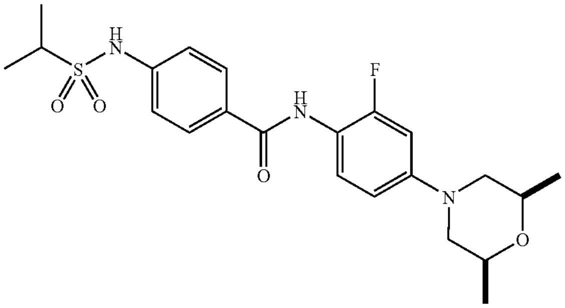
Ih-27
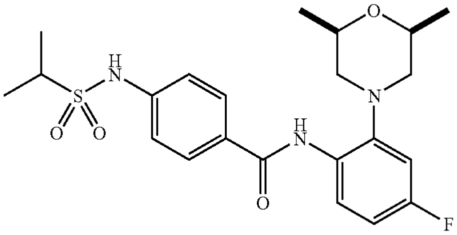
Ih-28
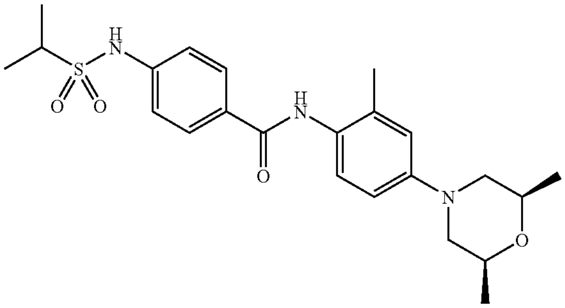
Ih-29
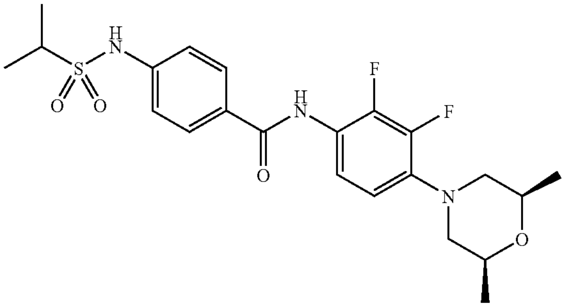
Ih-30
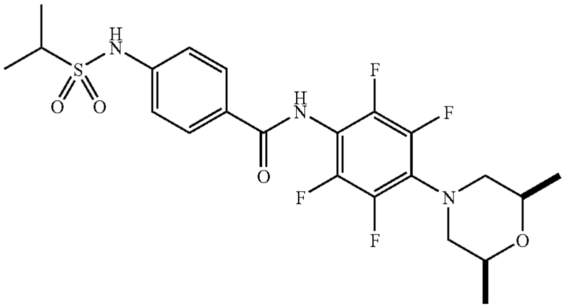

-continued
Ih-31
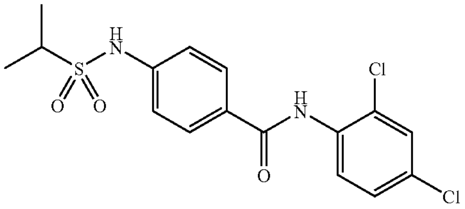
Ih-32
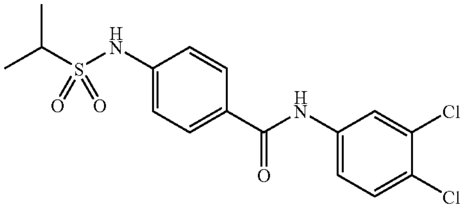
Ih-33
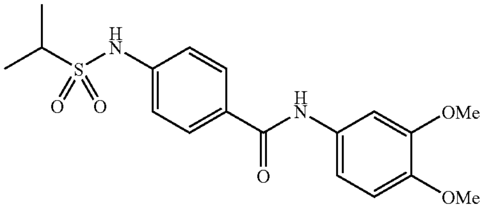
Ih-35
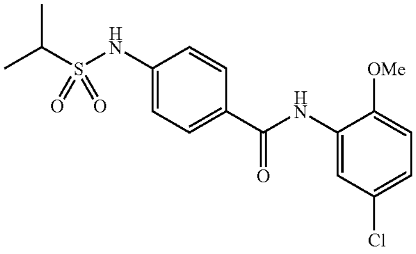
Ih-36
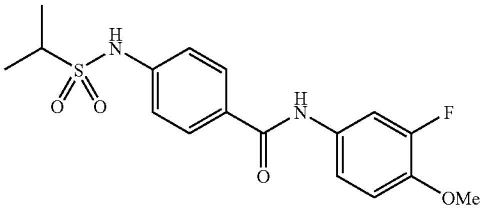
Ih-37
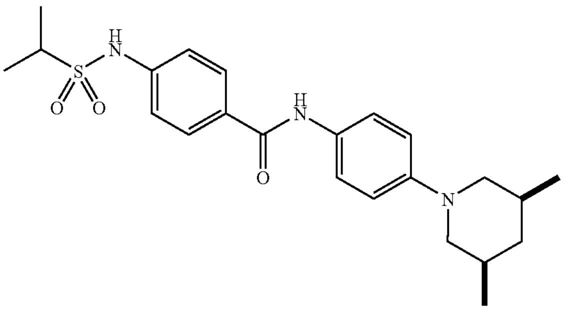
-continued
Ih-38
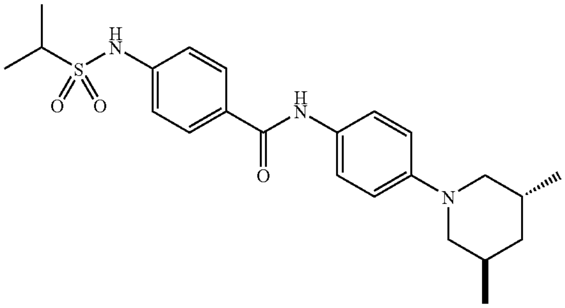
Ih-39
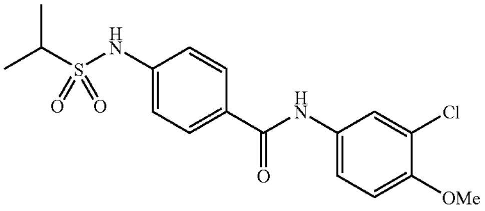
Ih-40
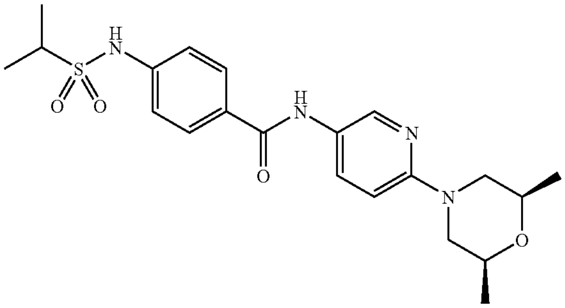
Ih-41
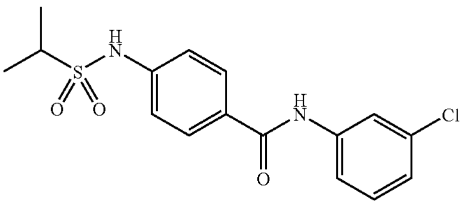
Ih-42
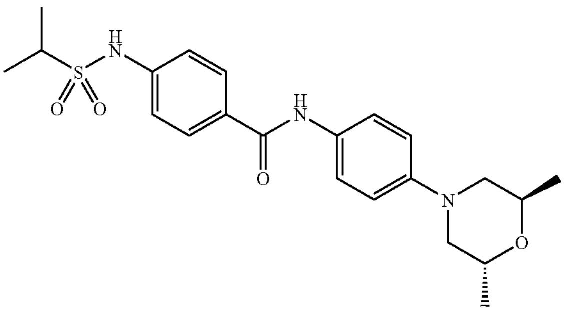

-continued
Ih-43
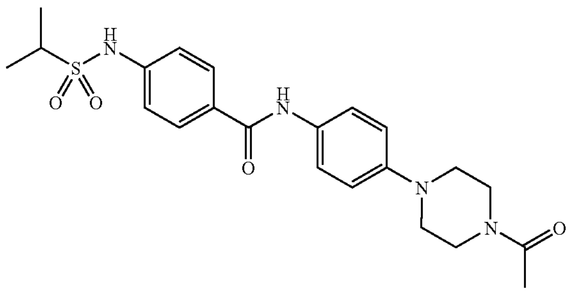
Ih-44
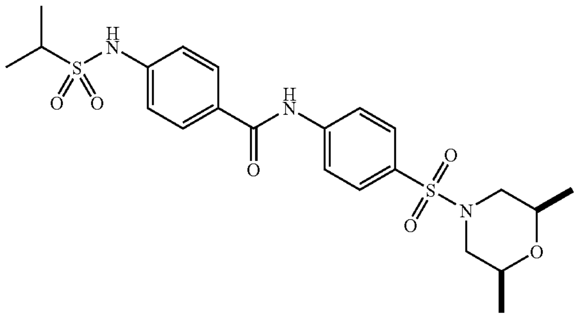
Ih-45
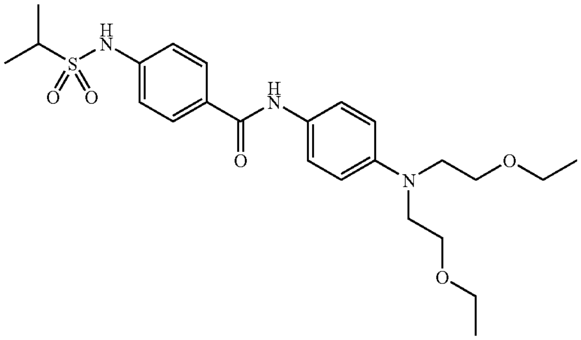
Ih-46
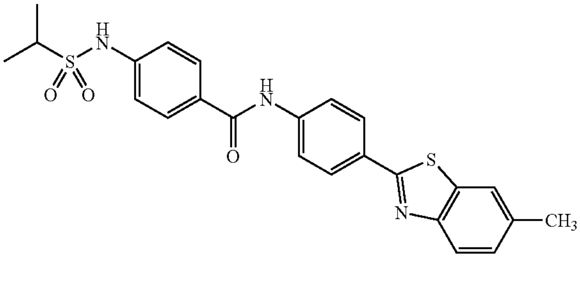
-continued
Ih-47
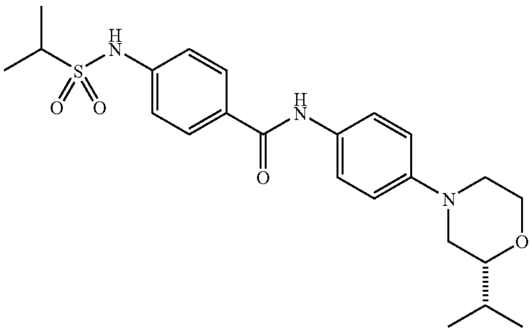
Ih-48
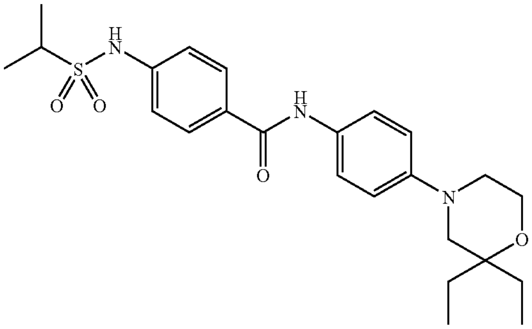
Ih-49
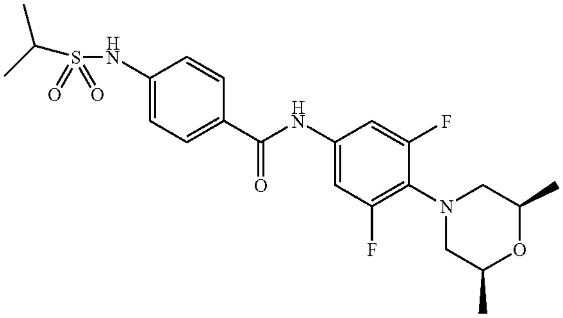
Ih-50
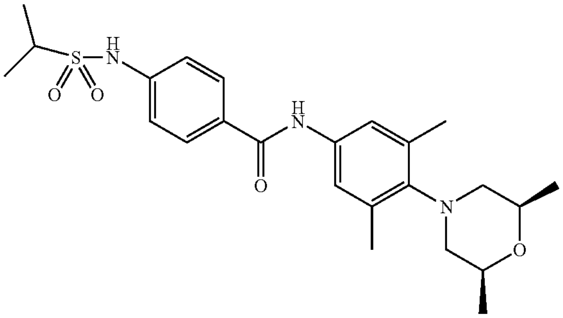

-continued
Ih-51
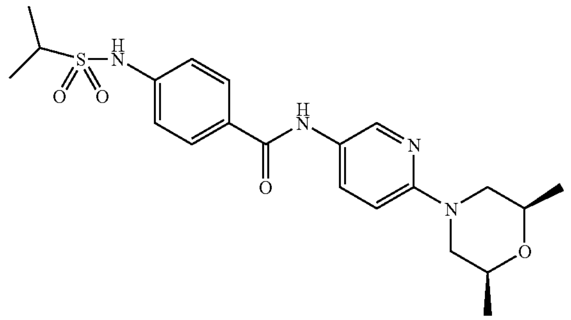
Ih-52
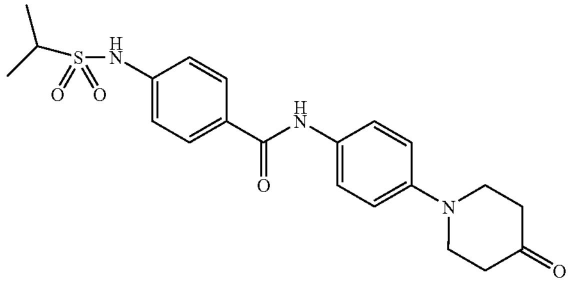
Ih-53
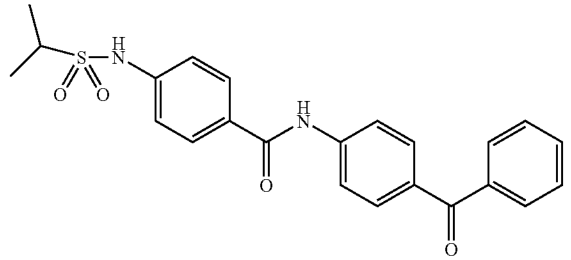
Ih-54
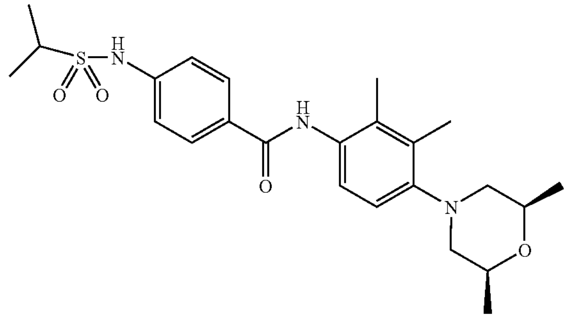
Ih-55
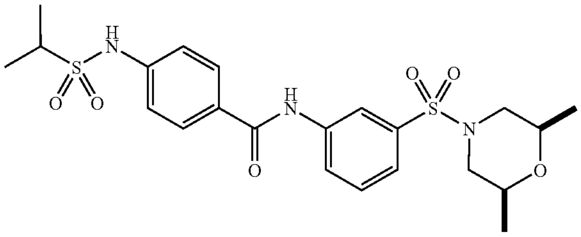
-continued
Ih-56
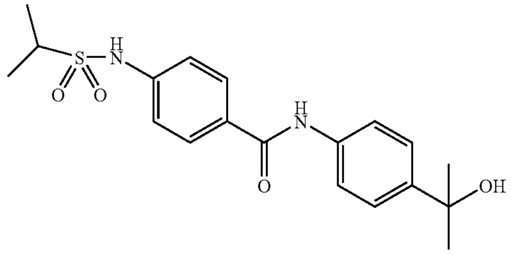
Ih-57
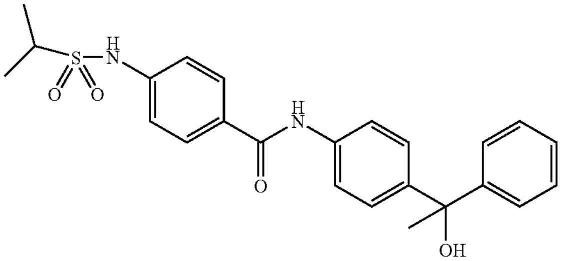
Ih-58
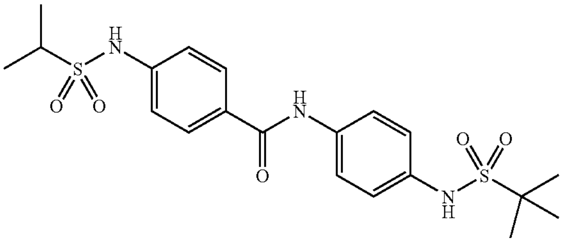
Ih-59
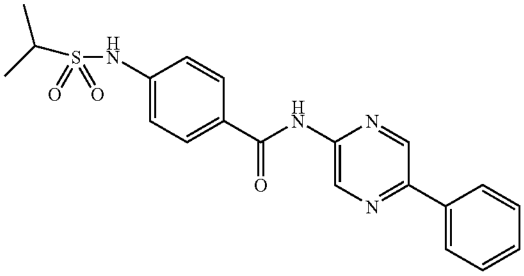
Ih-60
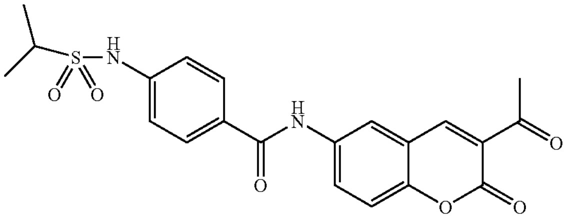

-continued
Ih-61
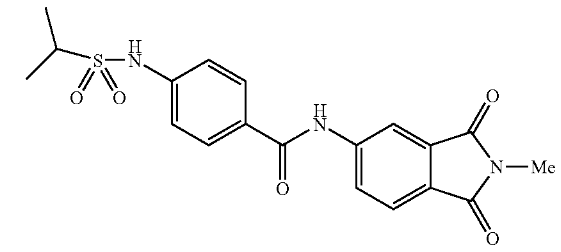
Ih-62
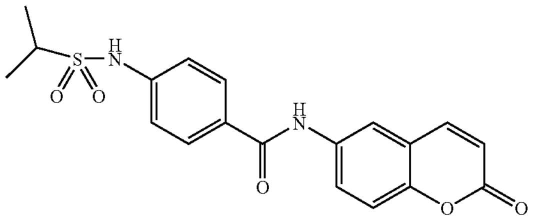
Ih-63
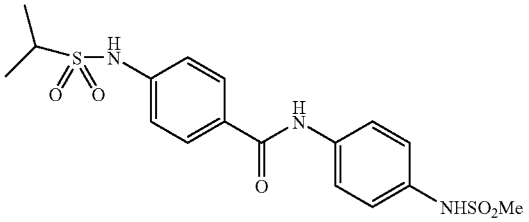
Ih-64
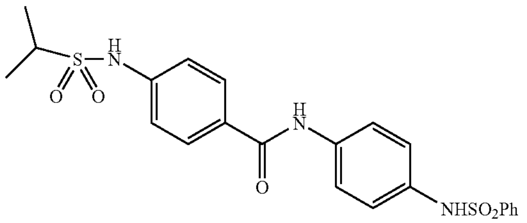
Ih-65
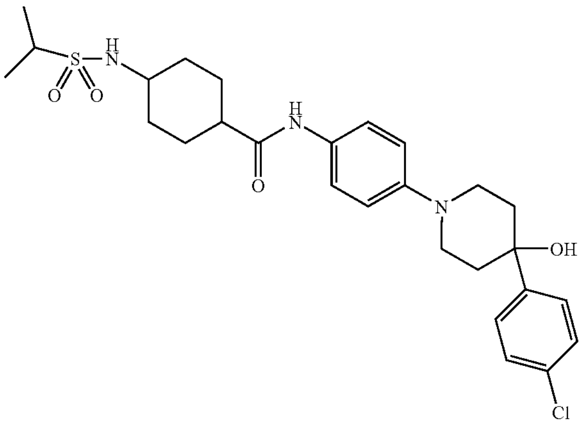
-continued
Ih-66
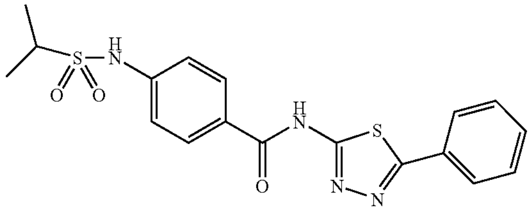
Ih-67
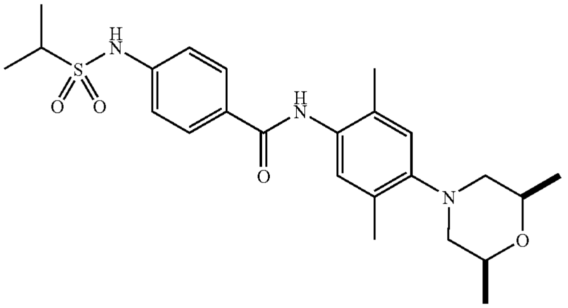
Ih-68
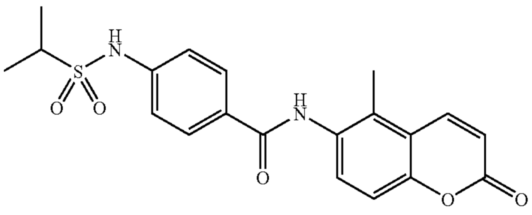
Ih-69
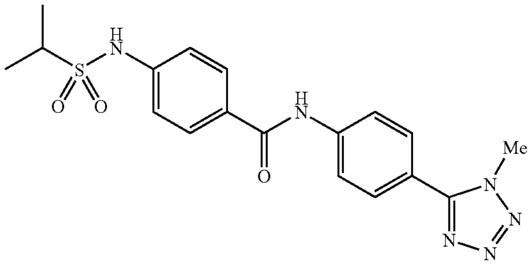
Ih-70
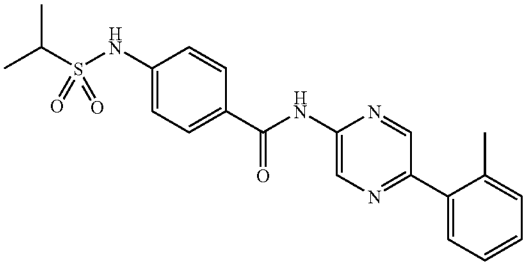

-continued
Ih-71
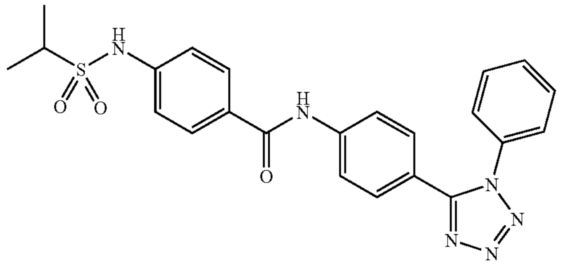
Ih-72
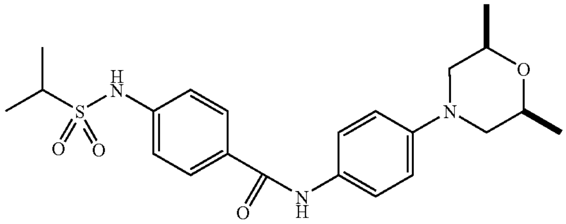
Ih-74
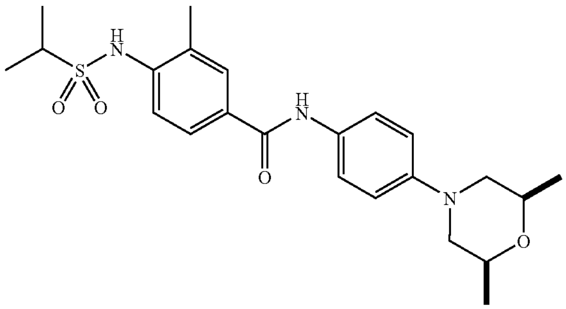
Ih-75
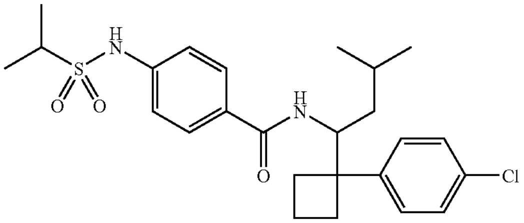
Ih-76
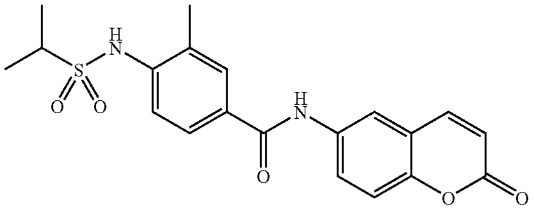
-continued
Ih-77
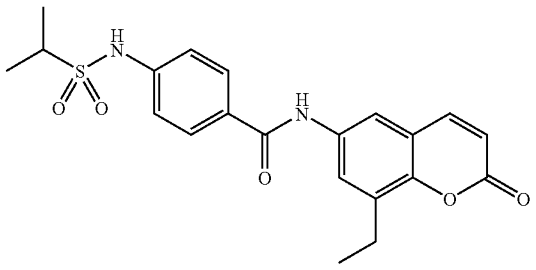
Ih-78
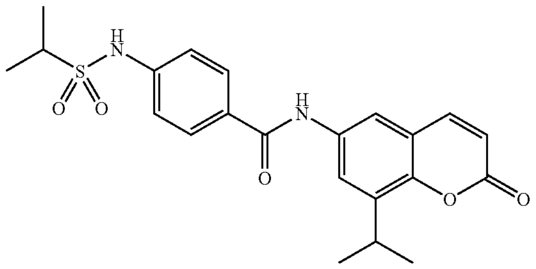
Ih-79
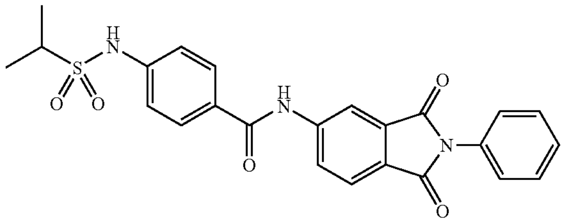
Ih-80
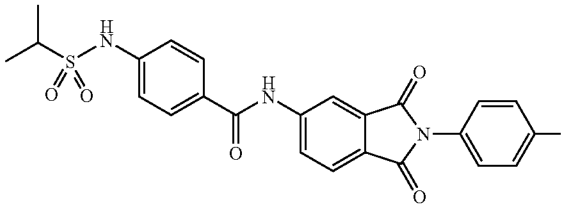
Ih-81
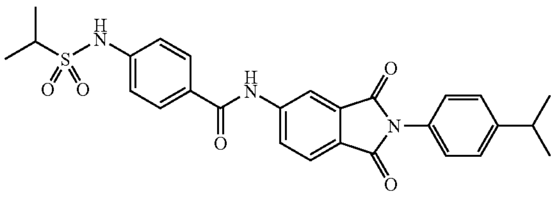
Ih-82
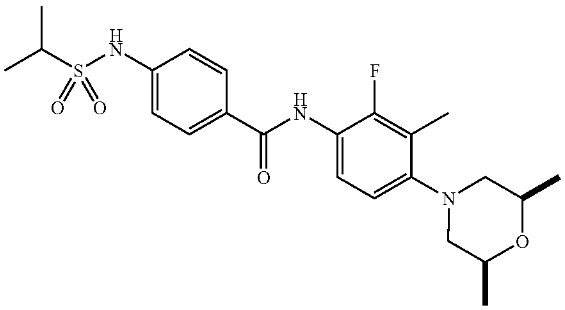

-continued
Ih-83
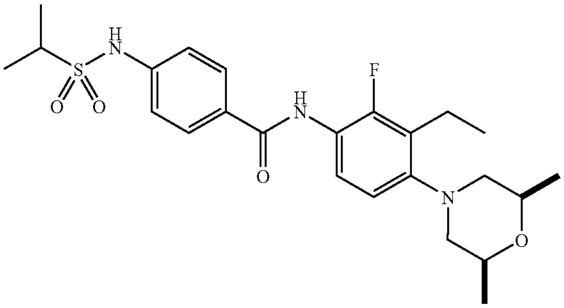
Ih-84
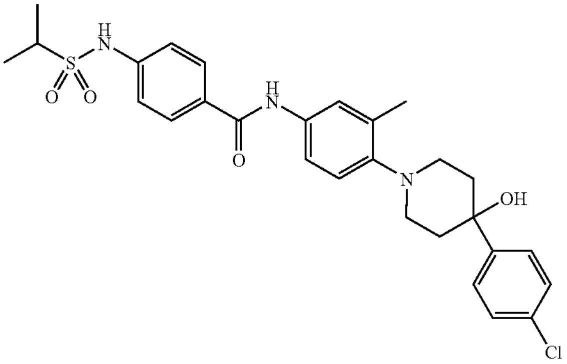
Ih-85
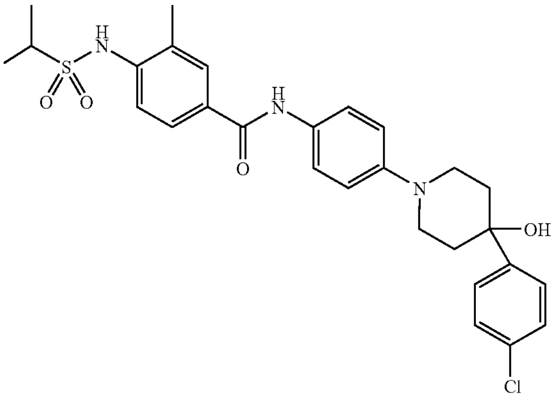
Ih-86
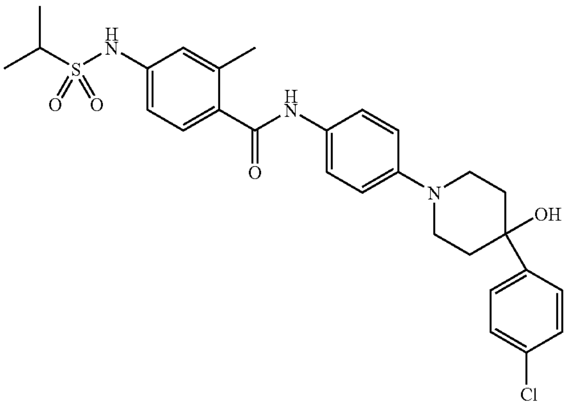
-continued
Ih-87
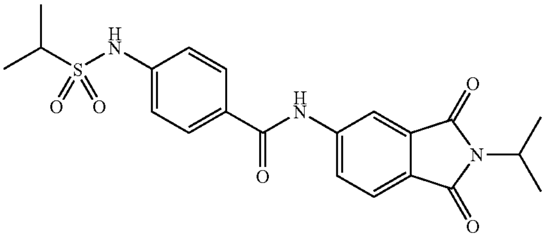
Ih-88
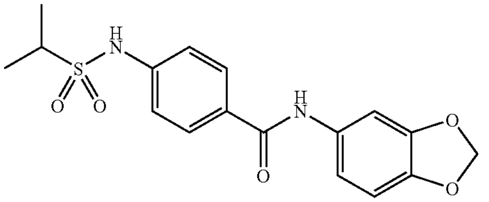
Ih-89
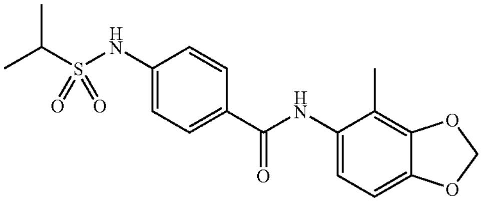
Ih-90
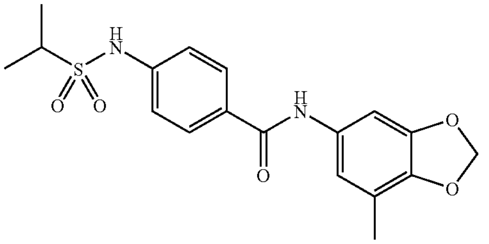
Ih-91
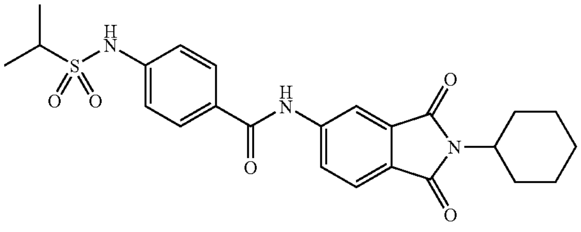
Ih-92
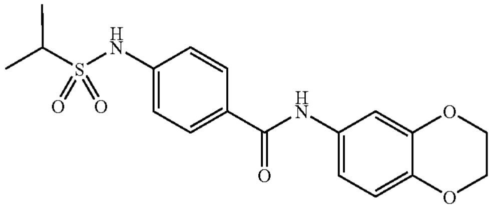

-continued
Ih-93
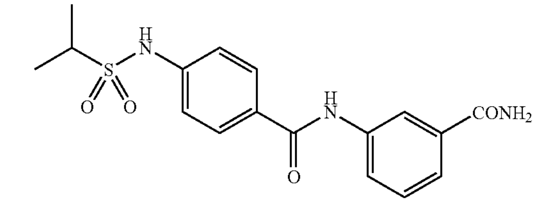
Ih-94
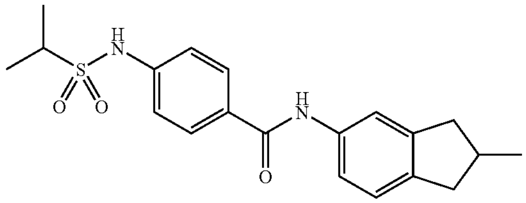
Ih-95
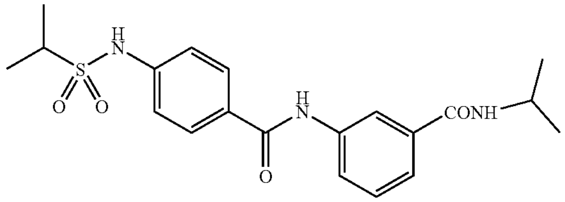
Ih-96
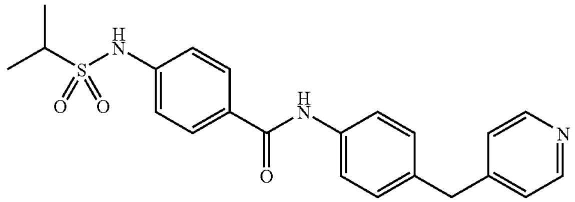
Ih-97
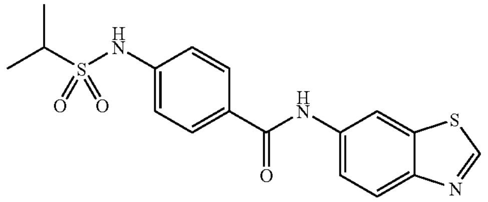
Ih-98
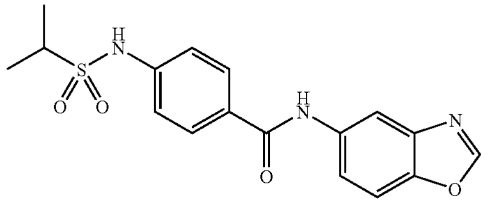
Ih-99
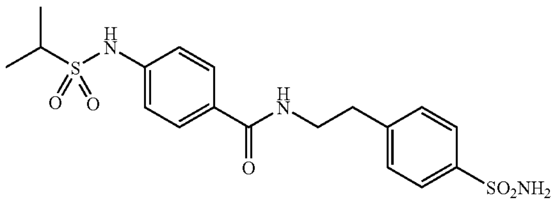
-continued
Ih-100
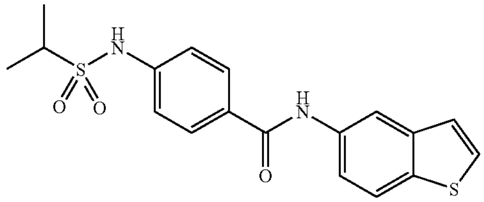
Ih-101
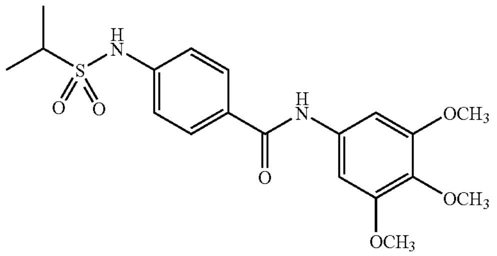
Ih-102
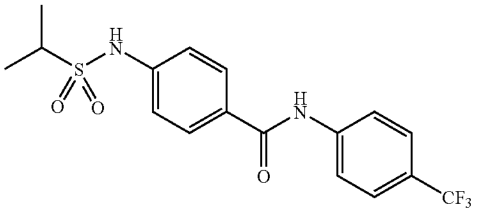
Ih-103
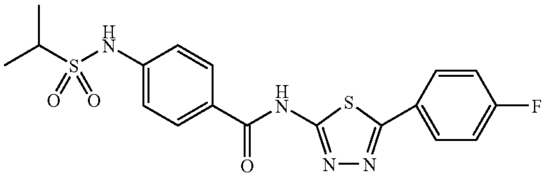
Ih-104
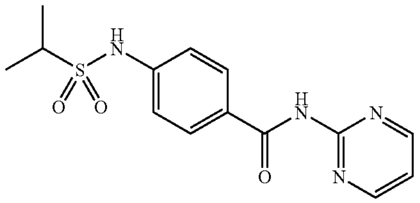
Ih-105
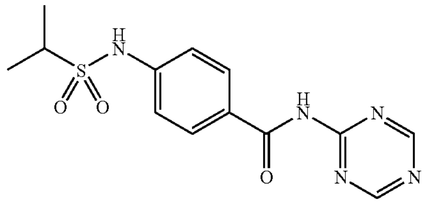
Ih-106
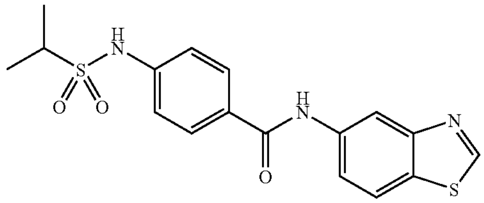

-continued
Ih-107
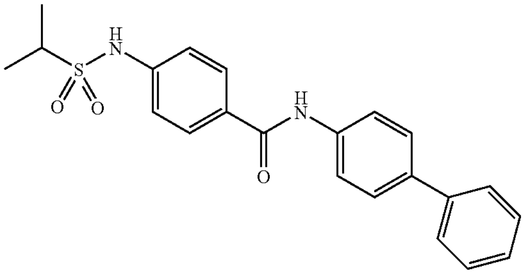
Ih-108
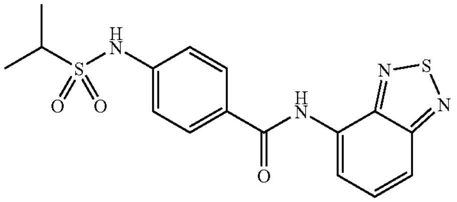
Ih-109
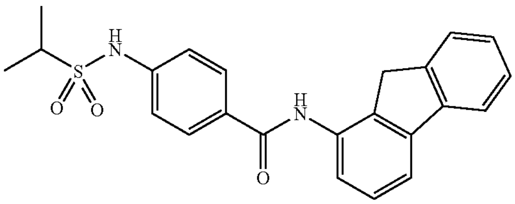
Ih-110
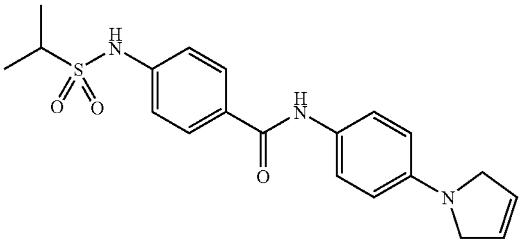
Ih-111
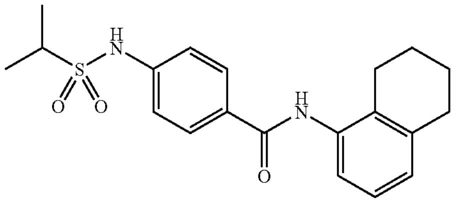
Ih-112
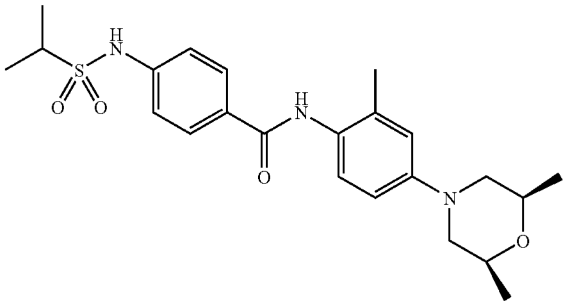
-continued
Ih-113
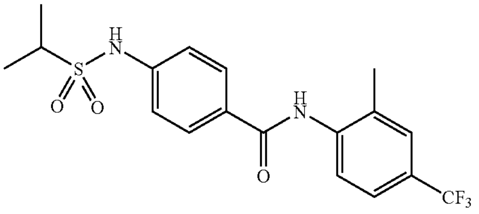
Ih-114
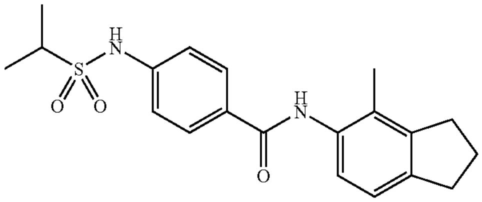
Ih-115
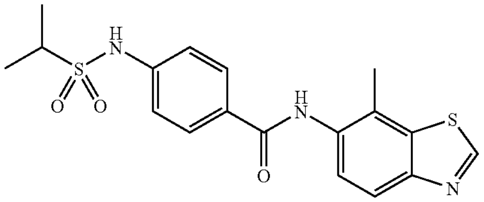
Ih-116
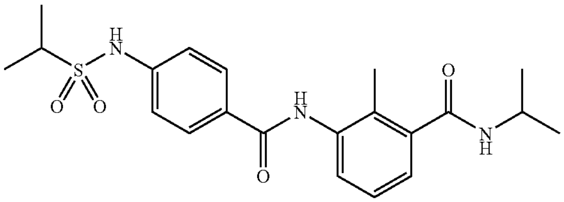
Ih-117
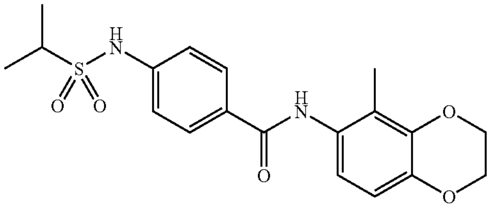
Ih-118
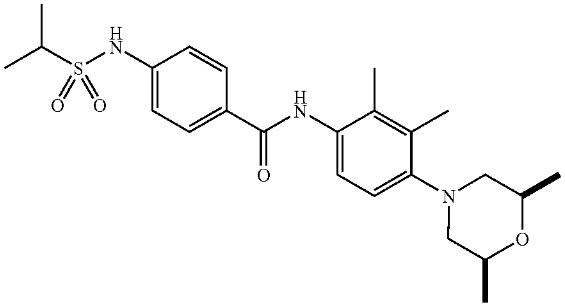

-continued
Ih-119
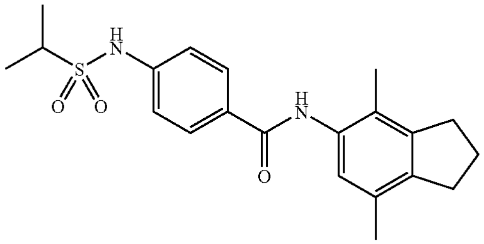
Ih-120
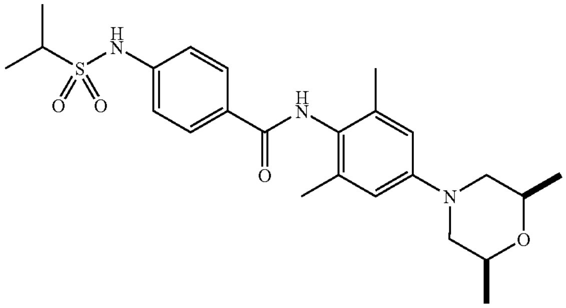
Ih-121
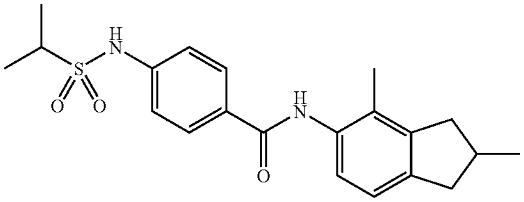
Ih-122
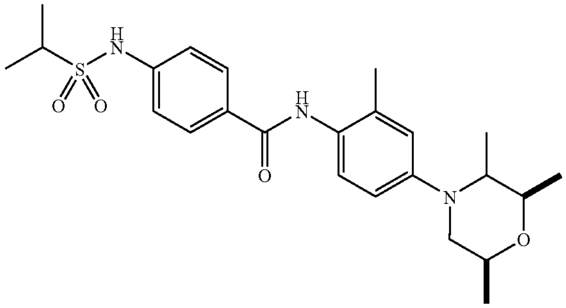
Ih-123
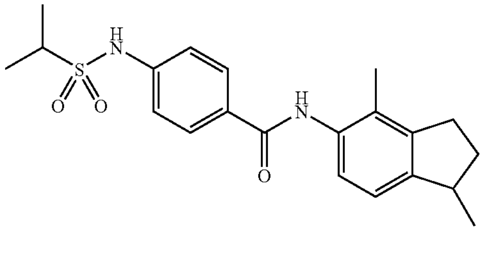
-continued
Ih-124
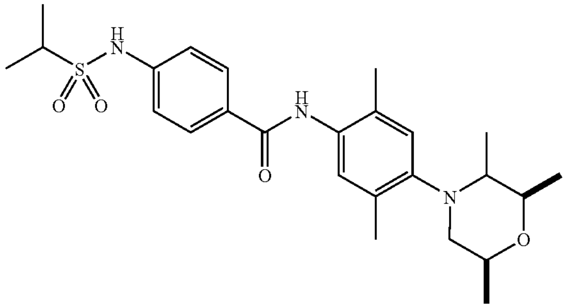
Ih-125
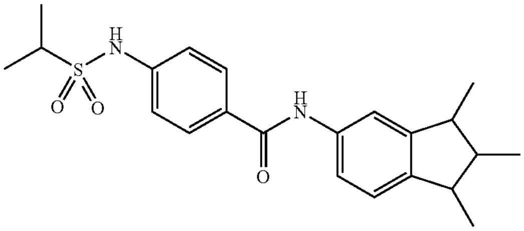
Ih-126
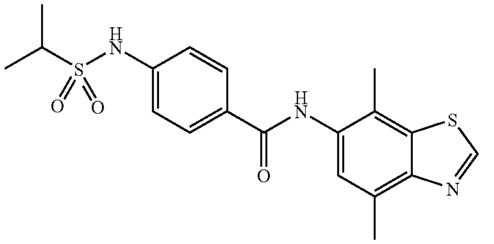
Ih-127
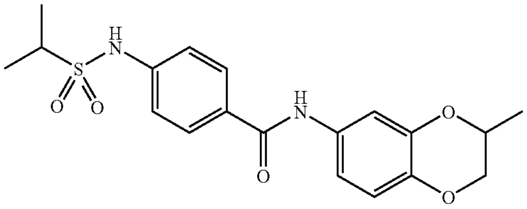
Ih-128
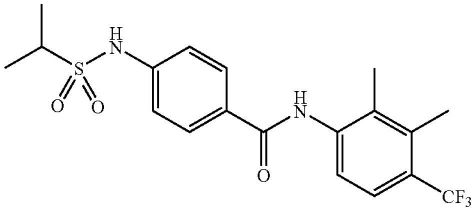
Ih-129
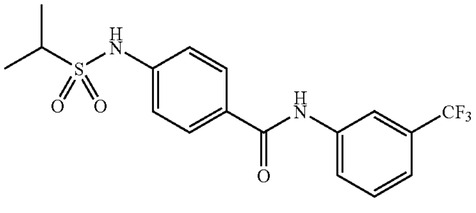

-continued
Ih-130
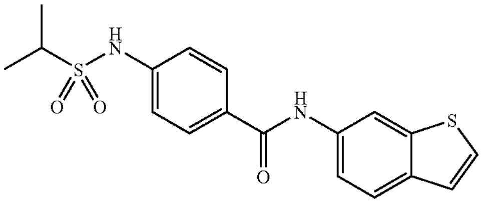
Ih-131
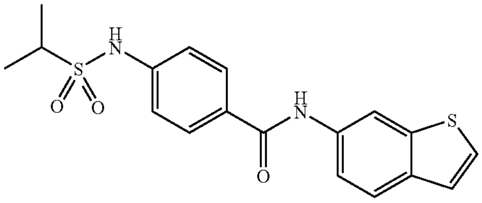
Ih-132
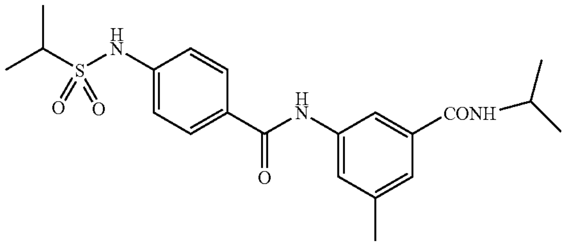
Ih-133
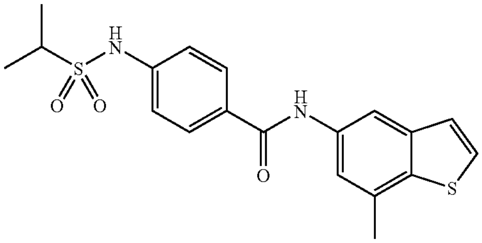
Ih-134
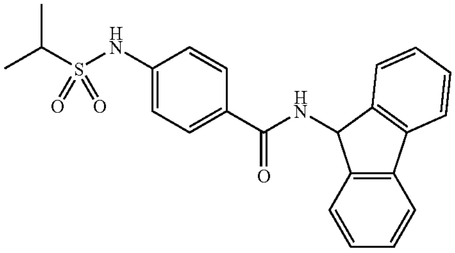
Ih-135
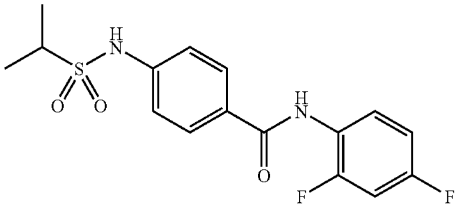
-continued
Ig-136
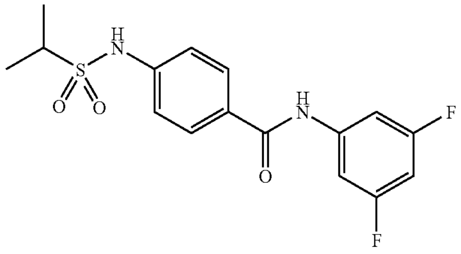
Ig-137
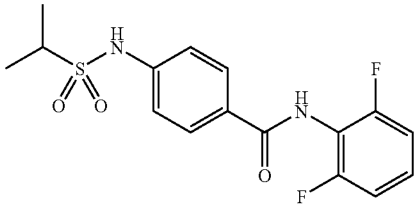
Ig-138
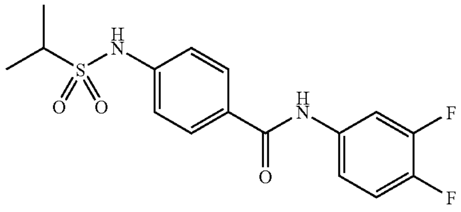
Ig-139
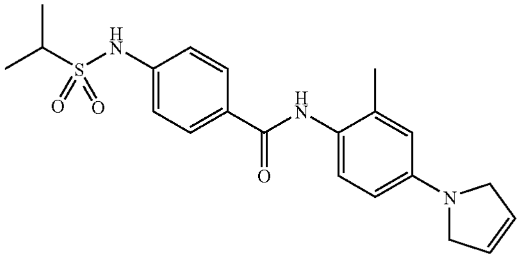
Ig-140
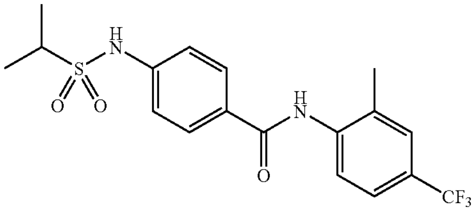
Ig-141
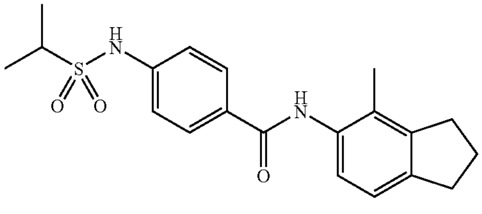

-continued
Ih-142
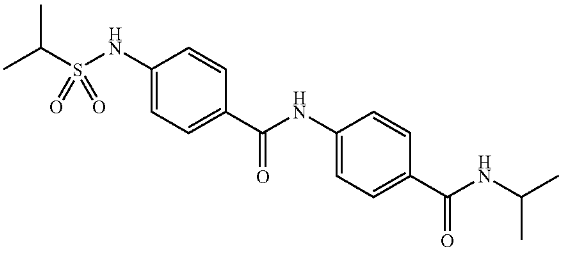
Ih-143
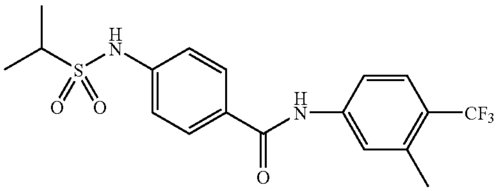
Ih-144
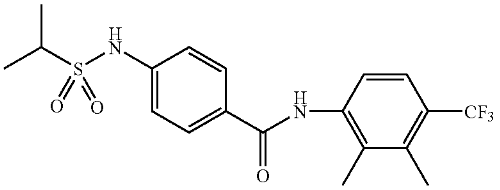
Ih-145
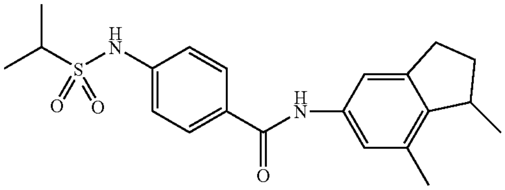
Ih-146
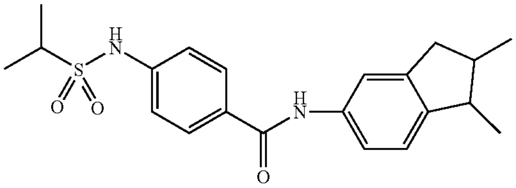
Ih-147
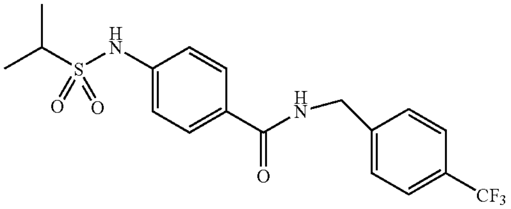
Ih-148
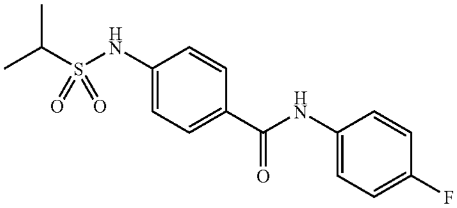
-continued
Ih-149
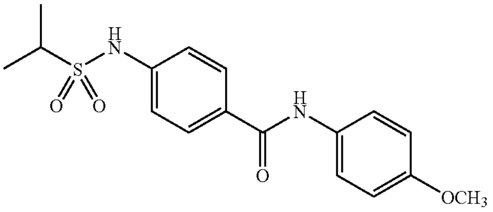
Ih-150
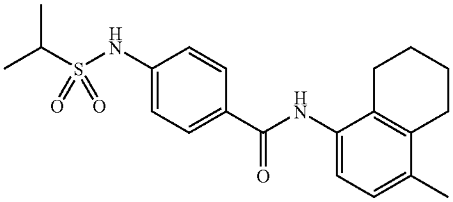
Ih-151
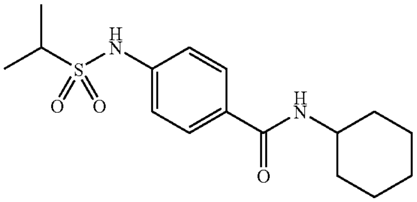
Ih-152
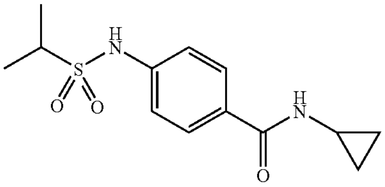
Ih-153
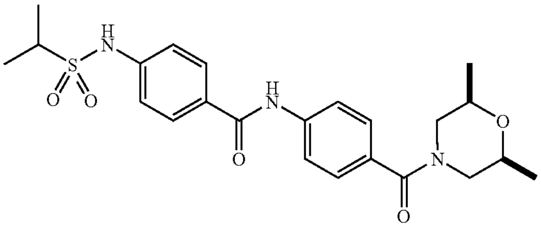
Ih-154
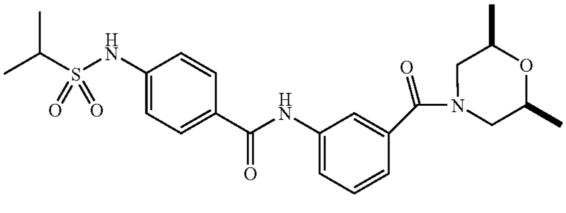
Ih-155
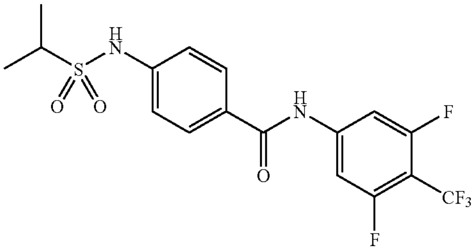

-continued
Ih-156
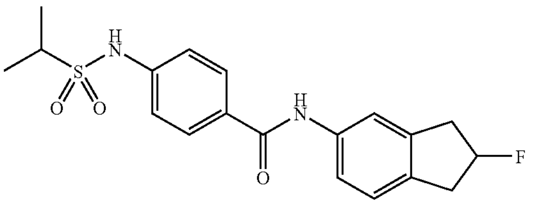
Ih-157
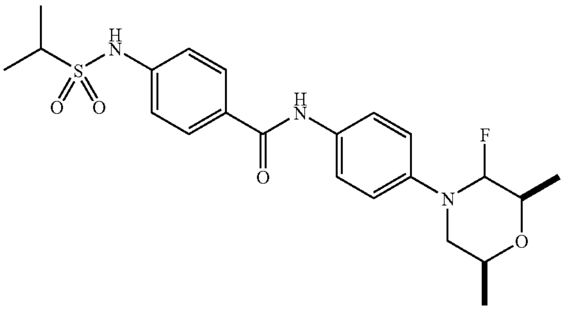
Ih-158
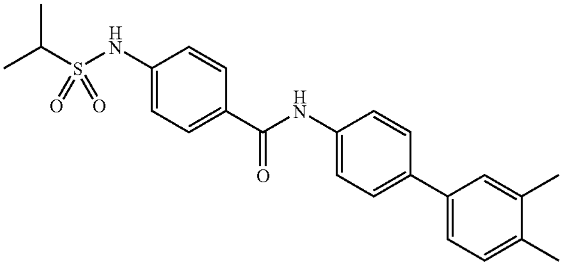
Ih-159
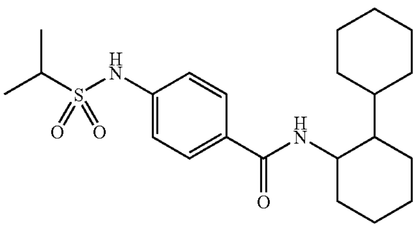
Ih-160
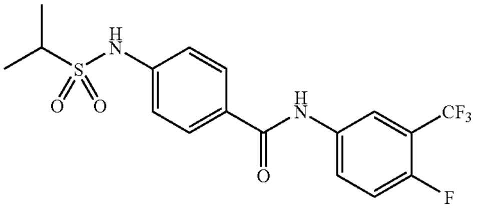
Ih-161
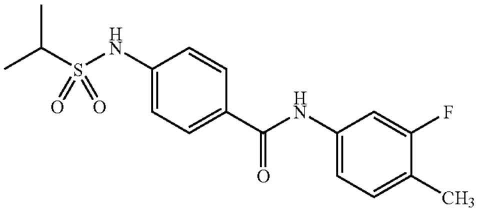
-continued
Ih-162
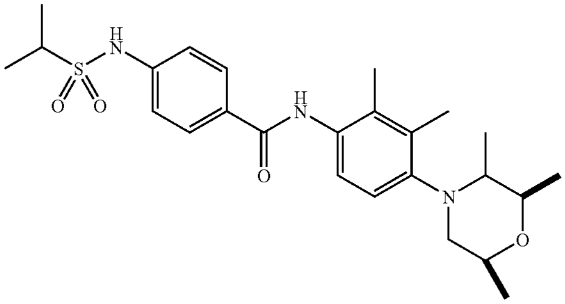
Ih-163
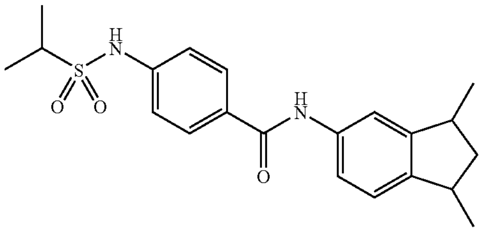
Ih-164
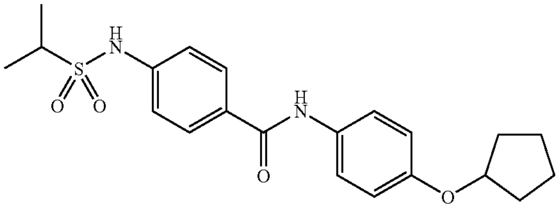
Ih-165
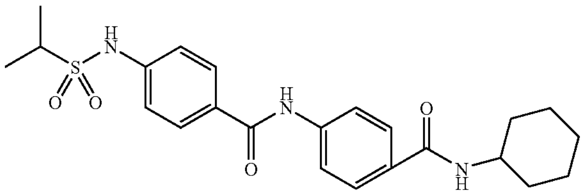
Ih-166
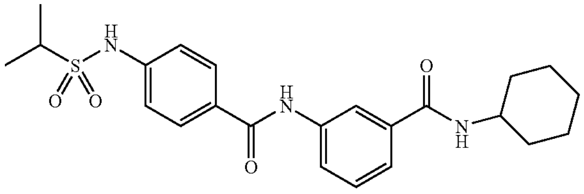
Ih-167
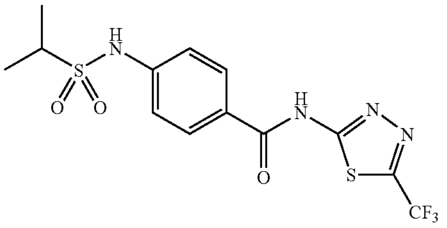

-continued
Ih-168
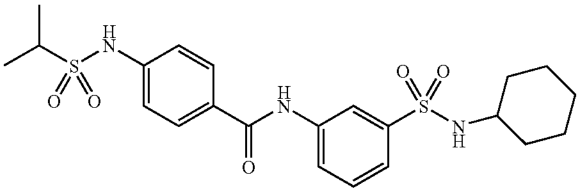
Ih-169
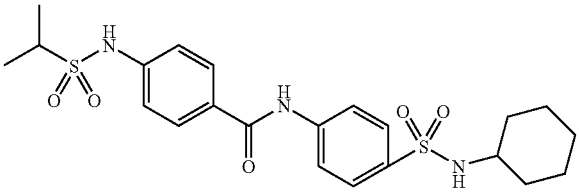
Ih-171
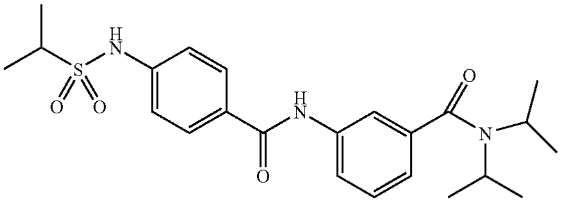
Ih-172
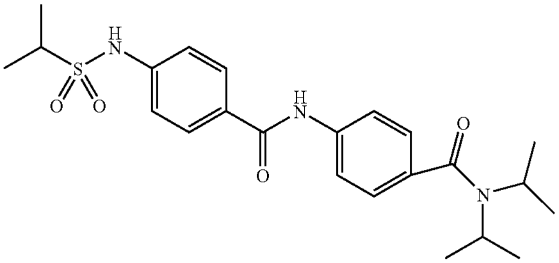
Ih-173
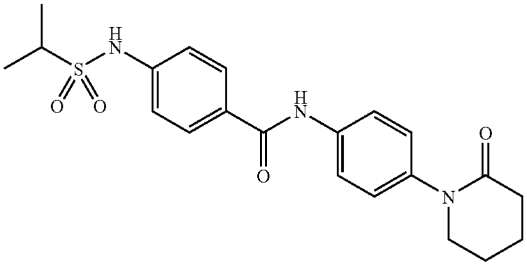
Ih-174
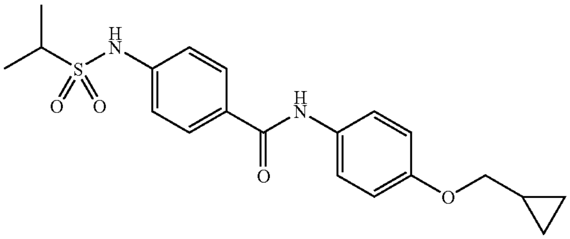
-continued
Ih-175
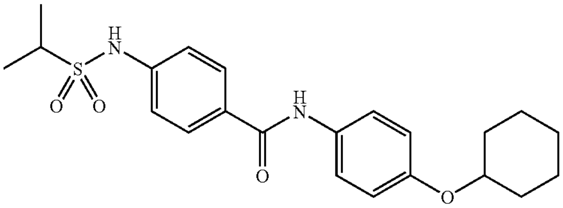
Ih-176
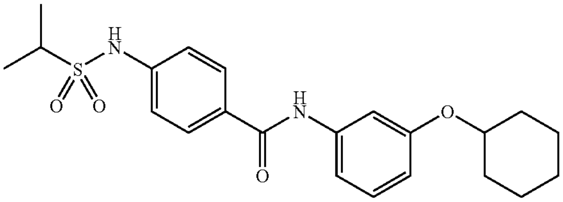
Ih-177
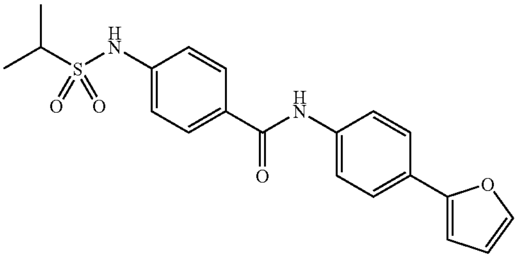
Ih-178
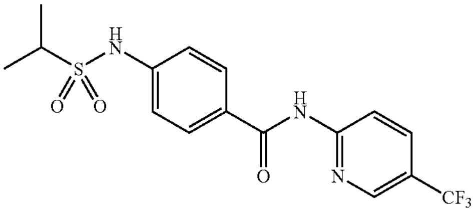
Ih-179
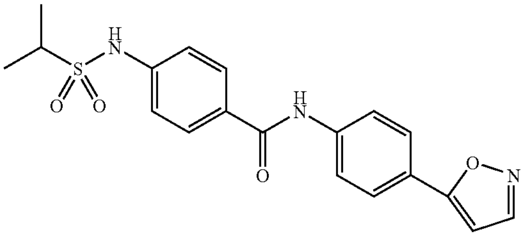
Ih-180
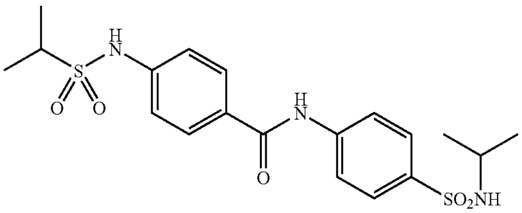

-continued
Ih-181
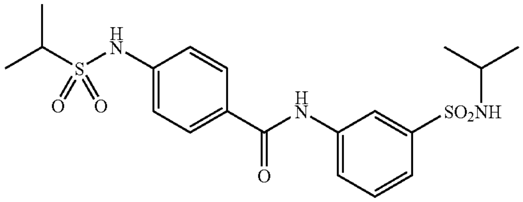
Ih-182
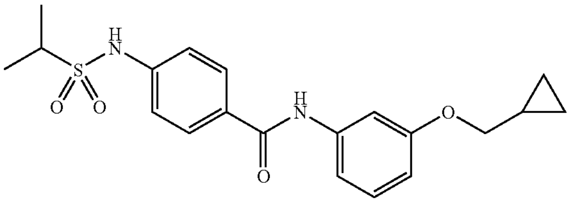
Ih-183
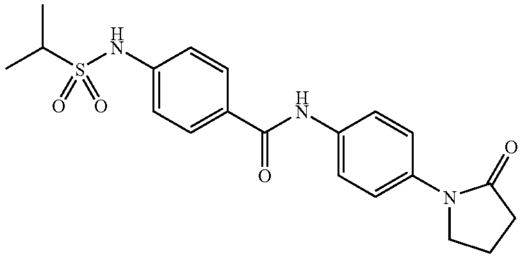
Ih-184
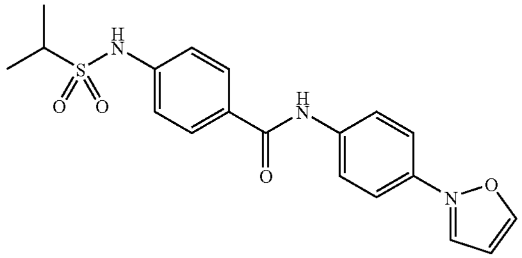
Ih-185
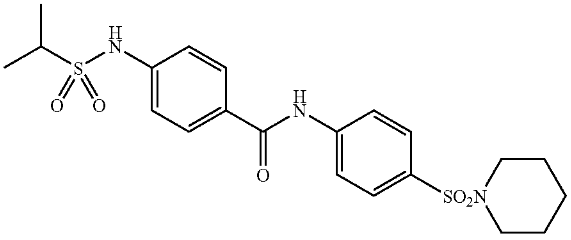
Ih-186
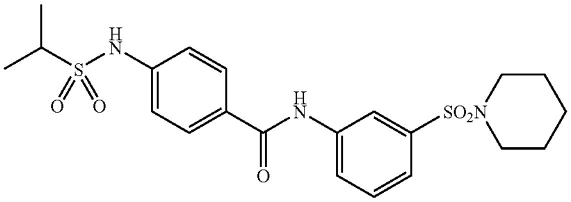
-continued
Ih-187
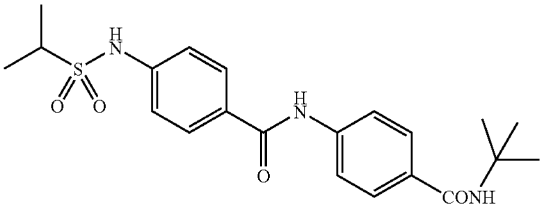
Ih-188
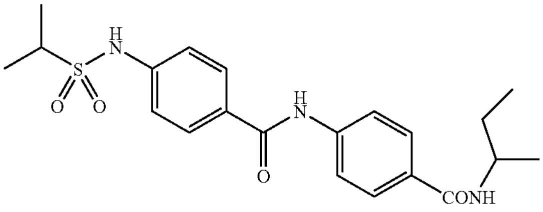
Ih-189
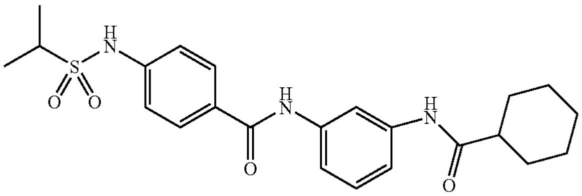
Ih-190
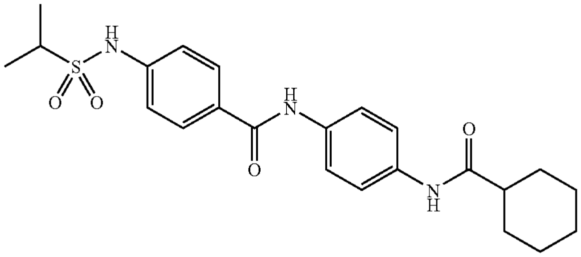
Ih-191
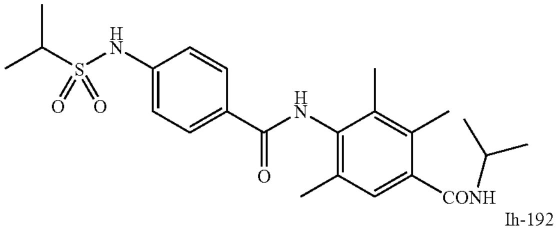
Ih-192
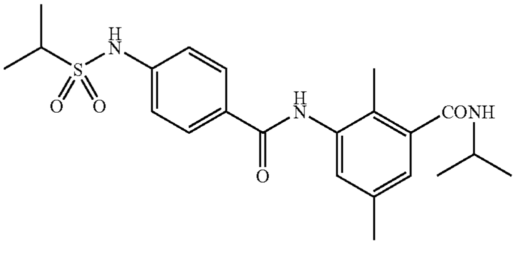

-continued
Ih-193
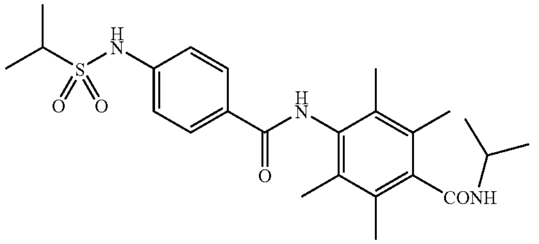
Ih-194
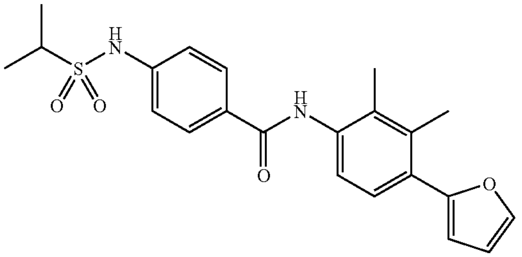
Ih-195
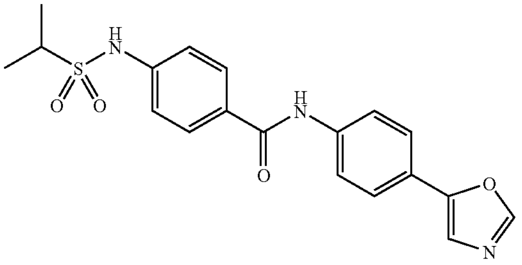
Ih-196
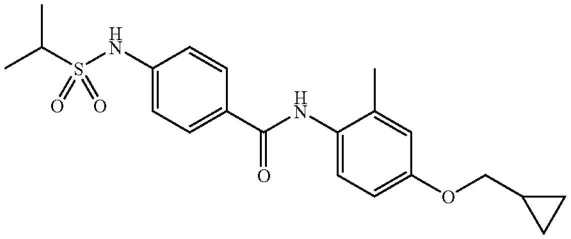
Ih-197
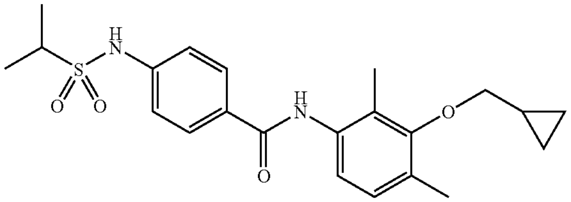
Ih-198
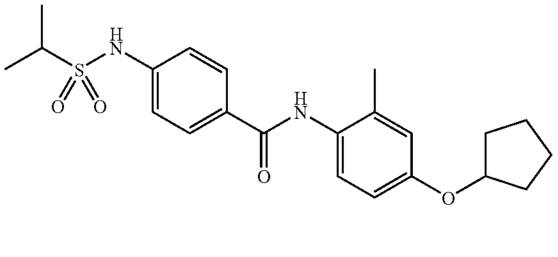
-continued
Ih-199
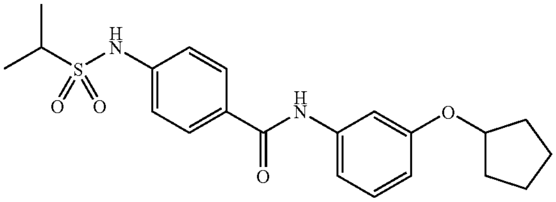
Ih-200
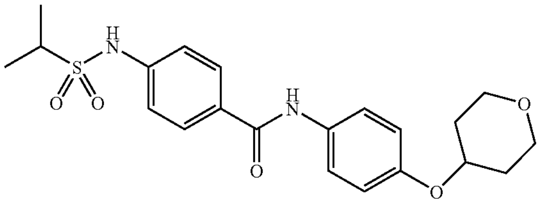
Ih-201
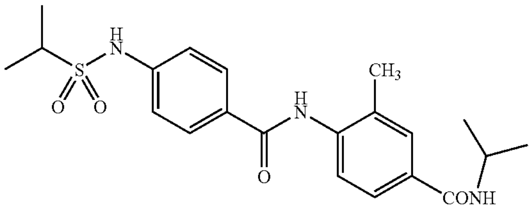
Ih-202
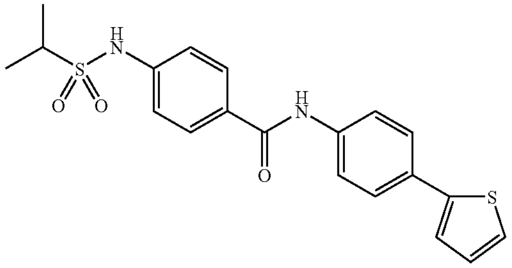
Ih-203
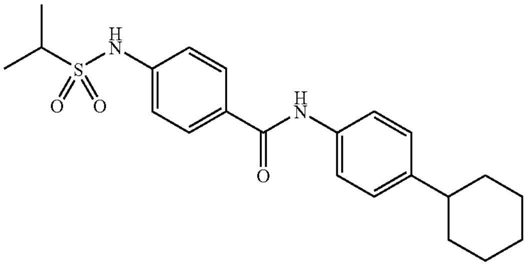
Ih-204
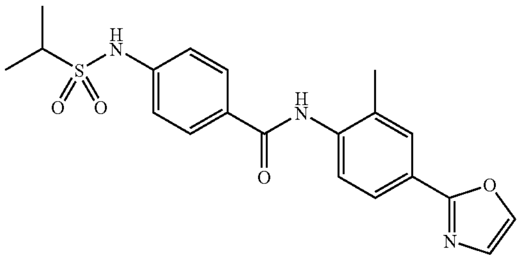

-continued
Ih-205
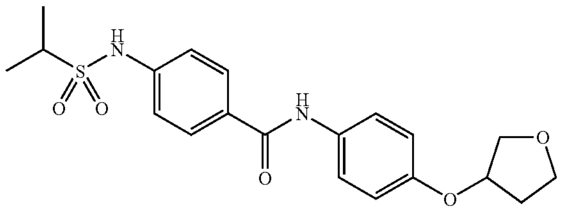
Ih-206
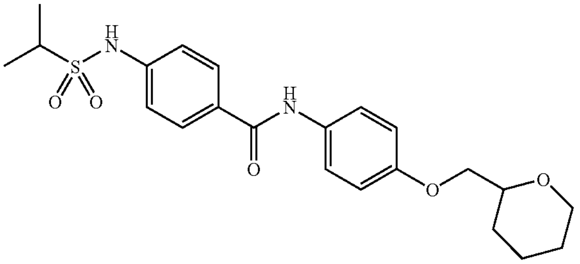
Ih-207
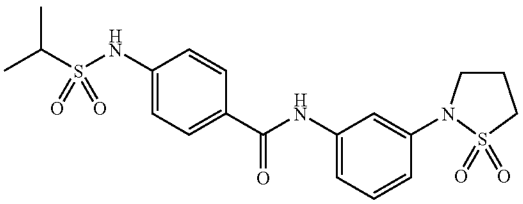
Ih-208
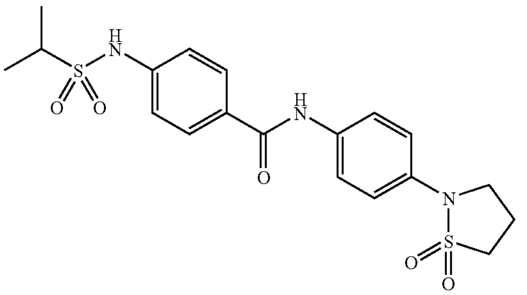
Ih-209
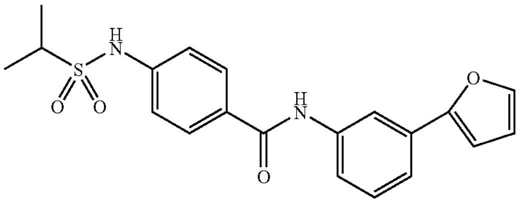
Ih-210
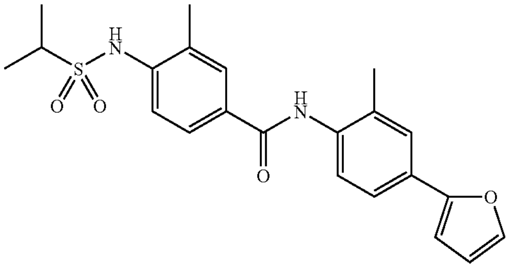
-continued
Ih-211
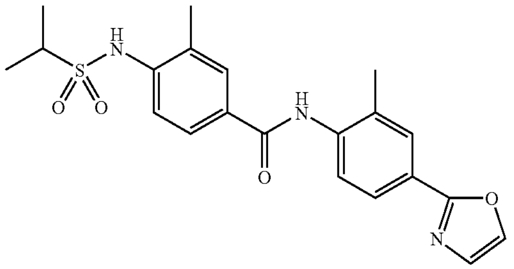
Ih-212
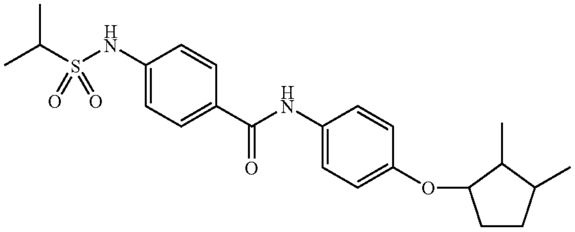
Ih-213
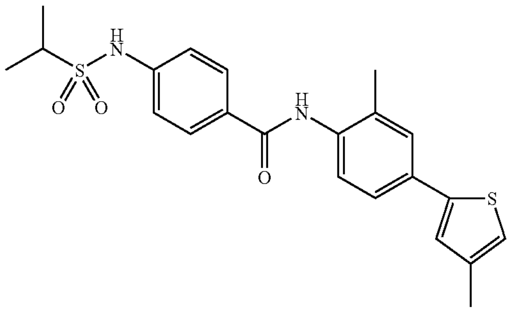
Ih-214
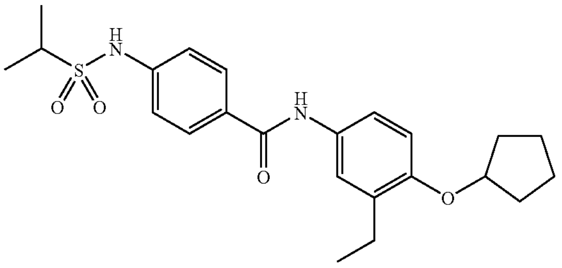
Ih-215
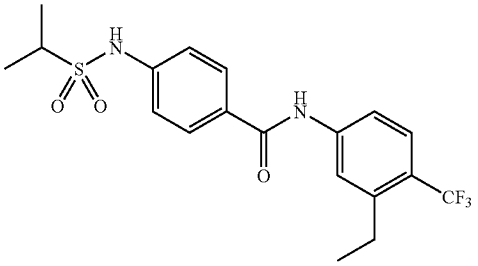

-continued

Ih-216

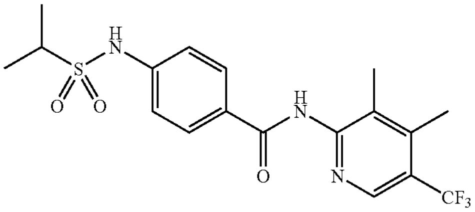

Ih-219

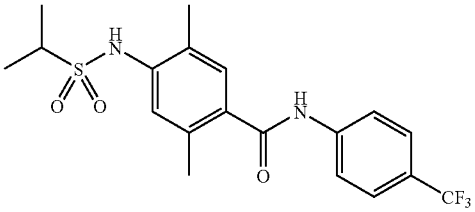

Ih-220

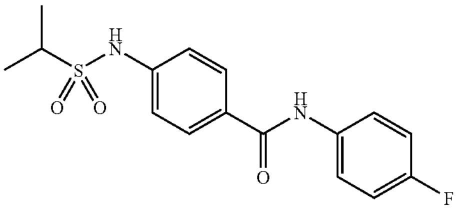

Ih-221

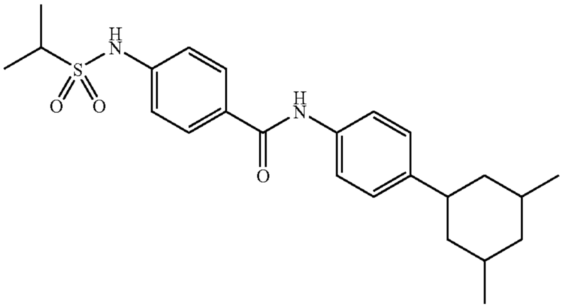

Ih-222

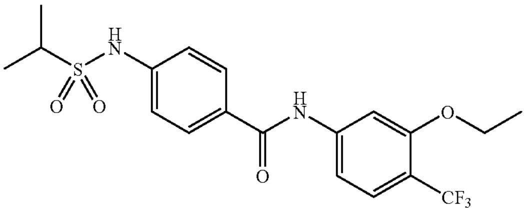

Ih-223

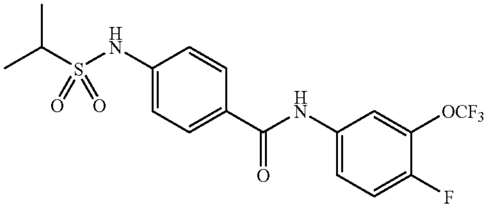

-continued

Ih-224

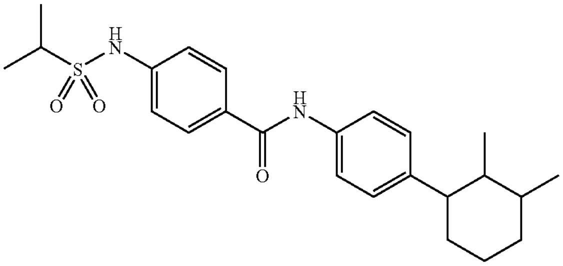

Ih-225

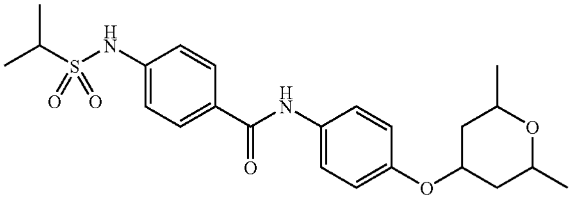

Ih-226

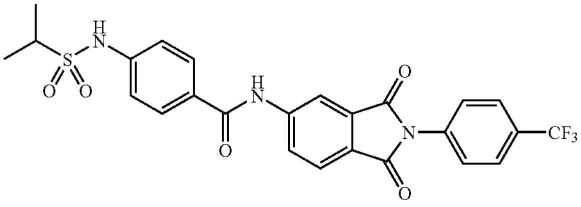

I-2

$^1$H-NMR ($CDCl_3$) δ ppm: 0.94 (t, 3H, J=7.5 Hz), 1.34-1.44 (m, 2H), 1.40 (d, 6H, J=6.6 Hz), 1.59-1.68 (m, 2H), 2.69 (t, 2H, J=7.8 Hz), 3.24-3.35 (m, 1H), 6.49 (s, 1H), 7.23-7.32 (m, 4H), 7.6 (d, 2H, J=8.7 Hz), 7.79 (d, 2H, J=8.1 Hz), 7.85 (s, 1H).

I-3

$^1$H-NMR ($CDCl_3$) δ ppm: 0.92 (t, 3H, J=7.2 Hz), 1.30-1.39 (m, 2H), 1.37 (d, 6H, J=6.9 Hz), 1.57 (quint, 2H, J=7.5 Hz), 1.96 (quint, 2H, J=6.6 Hz), 2.49 (t, 2H, J=6.6 Hz), 2.57 (t, 2H, J=7.8 Hz), 3.16-3.26 (m, 3H), 4.62 (brs, 1H), 7.12 (d, 2H, J=8.1 Hz), 7.43 (d, 2H, J=8.4 Hz), 7.64 (s, 1H).

I-4

$^1$H-NMR ($CD_3OD$) δ ppm: 0.92 (t, 3H, J=6.9 Hz), 1.28-1.41 (m, 2H), 1.46 (d, 6H, J=6.3 Hz), 1.53-1.63 (m, 2H), 2.58 (t, 2H, J=7.8 Hz), 3.33-3.43 (m, 1H), 6.27-6.29 (m, 1H), 7.14-7.16 (m, 3H), 7.50 (d, 2H, J=8.4 Hz), 7.90 (s, 1H).

I-5

$^1$H-NMR ($CDCl_3$) δ ppm: 0.92 (t, 3H, J=7.2 Hz), 1.28-1.41 (m, 2H), 1.46 (d, 6H, J=6.9 Hz), 1.53-1.63 (m, 2H), 2.59 (t, 2H, J=7.8 Hz), 3.35-3.44 (m, 1H), 7.15 (d, 2H, J=8.7 Hz), 7.38 (s, 1H), 7.45 (d, 2H, J=8.7 Hz), 7.57 (s, 1H).

I-6

$^1$H-NMR ($CDCl_3$) δ ppm: 0.91 (t, 3H, J=7.5 Hz), 1.29-1.39 (m, 2H), 1.37 (d, 6H, J=6.9 Hz), 1.55 (quint, 2H, J=7.5 Hz), 2.55 (t, 2H, J=5.1 Hz), 3.18-3.27 (m, 1H), 3.92 (d, 2H, J=6.0 Hz), 5.51 (t, 1H, J=5.7 Hz), 7.10 (d, 2H, J=8.4 Hz), 7.39 (d, 2H, J=8.4 Hz), 8.23 (s, 1H).

I-7

$^1$H-NMR ($CDCl_3$) δ ppm: 0.91 (t, 3H, J=7.2 Hz), 1.28-1.38 (m, 2H), 1.37 (d, 6H, J=6.9 Hz), 1.51-1.67 (m, 4H), 1.78-1.88 (m, 2H), 2.39 (t, 2H, J=7.2 Hz), 2.57 (t, 2H, J=7.5 Hz), 3.12-3.22 (m, 3H), 4.30-4.37 (m, 1H), 7.12 (d, 2H, J=8.4 Hz), 7.36-7.42 (m, 3H).

I-8

$^1$H-NMR ($CDCl_3$) δ ppm: 0.91 (t, 3H, J=7.5 Hz), 1.21-1.47 (m, 4H), 1.35 (d, 6H, J=6.6 Hz), 1.51-1.63 (m, 4H), 1.67-1.77 (m, 2H), 2.34 (t, 2H, J=7.5 Hz), 2.55 (t, 2H, J=7.8 Hz), 3.08-3.17 (m, 3H), 4.71 (t, 1H, J=6.0 Hz), 7.09 (d, 2H, J=8.1 Hz), 7.43 (d, 2H, J=8.4 Hz), 7.74 (s, 1H).

I-9

$^1$H-NMR ($CDCl_3$) δ ppm: 0.91 (t, 3H, J=7.2 Hz), 1.29-1.39 (m, 2H), 1.35 (d, 6H, J=6.9 Hz), 1.50-1.60 (m, 2H), 2.54 (t, 2H, J=7.8 Hz), 2.64 (t, 2H, J=5.7 Hz), 3.14-3.23 (m, 1H), 3.41-3.47 (m, 2H), 5.29 (t, 1H, J=6.3 Hz), 7.10 (d, 2H, J=8.4 Hz), 7.39 (d, 2H, J=8.4 Hz), 7.91 (s, 1H).

I-10

$^1$H-NMR ($CDCl_3$) δ ppm: 0.91 (t, 3H, J=7.5 Hz), 1.22 (s, 9H), 1.30-1.37 (m, 2H), 1.51-1.68 (m, 4H), 1.76-1.86 (m, 2H), 2.31-2.40 (m, 2H), 2.56 (t, 2H, J=7.5 Hz), 3.15-3.26 (m, 3H), 7.11 (t, 2H, J=8.7 Hz), 7.42 (d, 2H, J=8.1 Hz), 7.54 (s, 1H).

I-11 mp: 128-129° C. $^1$H-NMR ($CDCl_3$) δ ppm: 0.91 (t, 3H, J=7.5 Hz), 1.29-1.39 (m, 2H), 1.39 (s, 9H), 1.51-1.68 (m, 4H), 1.76-1.84 (m, 2H), 2.37 (t, 2H, J=7.5 Hz), 2.56 (t, 2H, J=7.8 Hz), 3.19-3.26 (m, 2H), 4.20 (t, 1H, J=5.7 Hz), 7.11 (d, 2H, J=8.1 Hz), 7.42 (d, 2H, J=8.7 Hz), 7.46 (s, 1H).

I-12

$^1$H-NMR ($CDCl_3$) δ ppm: 0.91 (t, 3H, J=7.5 Hz), 1.28-1.37 (m, 2H), 1.47-1.68 (m, 6H), 2.23 (t, 2H, J=7.2 Hz), 2.56 (t, 2H, J=7.5 Hz), 2.90-2.97 (m, 2H), 5.10 (brs, 1H) 7.11 (d, 2H, J=8.4 Hz), 7.36 (d, 2H, J=8.1 Hz), 7.50-7.68 (m, 3H), 7.93 (d, 1H, J=8.1 Hz), 8.06 (d, 1H, J=8.4 Hz), 8.24 (d, 1H, J=7.5 Hz), 8.66 (d, 1H, J=8.7 Hz).

I-13

$^1$H-NMR ($CDCl_3$) δ ppm: 0.91 (t, 3H, J=7.5 Hz), 1.28-1.40 (m, 2H), 1.45-1.73 (m, 6H), 2.23 (t, 2H, J=7.5 Hz), 2.56 (t, 2H, J=7.8 Hz), 2.88 (s, 6H), 2.88-2.95 (m, 2H), 5.04 (brs, 1H), 7.10 (d, 2H, J=8.1 Hz), 7.17 (d, 1H, J=7.2 Hz), 7.37 (d, 2H, J=8.4 Hz), 7.48-7.54 (m, 2H), 8.23 (d, 1H, J=7.2 Hz), 8.30 (d, 1H, J=8.7 Hz), 8.53 (d, 1H, J=8.4 Hz).

I-14

$^1$H-NMR ($CDCl_3$) δ ppm: 0.91 (t, 3H, J=7.2 Hz), 1.30-1.43 (m, 6H), 1.36 (d, 6H, J=6.6 Hz), 1.51-1.62 (m, 4H), 1.67-1.78 (m, 2H), 2.34 (t, 2H, J=7.5 Hz), 2.56 (t, 2H, J=7.8 Hz), 3.09-3.20 (m, 3H), 4.34 (brs, 1H), 7.10 (d, 2H, J=8.4 Hz), 7.41-7.44 (m, 3H).

I-15

$^1$H-NMR ($CDCl_3$) δ ppm: 0.91 (t, 3H, J=7.5 Hz), 1.23 (s, 9H), 1.27-1.80 (m, 12H), 2.30-2.38 (m, 2H), 2.56 (t, 2H, J=7.5 Hz), 3.15 (brs, 2H), 7.11 (d, 2H, J=7.8 Hz), 7.43 (d, 2H, J=7.8 Hz), 7.59 (s, 1H).

I-16

$^1$H-NMR ($CDCl_3$) δ ppm: 0.91 (t, 3H, J=7.5 Hz), 1.29-1.44 (m, 6H), 1.39 (s, 9H), 1.51-1.61 (m, 4H), 1.68-1.78 (m, 2H), 2.35 (t, 2H, J=7.5 Hz), 2.56 (t, 2H, J=8.1 Hz), 3.15-3.21 (m, 2H), 4.14-4.23 (m, 1H), 7.11 (d, 2H, J=7.8 Hz), 7.36-7.44 (m, 3H).

I-19

$^1$H-NMR ($CDCl_3$) δ ppm: 0.92 (t, 3H, J=7.5 Hz), 1.21 (s, 9H), 1.30-1.40 (m, 2H), 1.55-1.72 (m, 6H), 2.64 (t, 2H, J=7.8 Hz), 3.08-3.33 (m, 3H), 3.42-3.50 (m, 2H), 6.39 (s, 1H), 7.22 (d, 2H, J=8.4 Hz), 7.69 (d, 2H, J=8.1 Hz).

I-20

$^1$H-NMR ($CDCl_3$) δ ppm: 0.92 (t, 3H, J=7.2 Hz), 1.31-1.39 (m, 2H), 1.39 (s, 9H) 1.55-1.72 (m, 6H), 2.64 (t, 2H, J=7.8 Hz), 3.24 (quart, 2H, J=6.6 Hz), 3.48 (quart, 2H, J=6.6 Hz), 4.21 (t, 1H, J=6.3 Hz), 6.29 (s, 1H), 7.22 (d, 2H, J=7.8 Hz), 7.67 (d, 2H, J=8.1 Hz).

I-21

$^1$H-NMR ($CDCl_3$) δ ppm: 0.91 (t, 3H, J=7.2 Hz), 1.23 (s, 9H), 1.30-1.42 (m, 2H), 1.50-2.02 (m, 10H), 2.30-2.42 (m, 1H), 2.57 (t, 2H, J=8.1 Hz), 3.10 (brs, 1H), 3.57 (brs, 1H), 7.12 (d, 2H, J=8.4 Hz), 7.41 (d, 2H, J=7.8 Hz).

I-22 mp: 78-79° C. $^1$H-NMR ($CDCl_3$) δ ppm: 0.91 (t, 3H, J=7.2 Hz), 1.30-1.40 (m, 2H), 1.40 (s, 9H), 1.50-1.65 (m, 4H), 1.70-1.98 (m, 8H), 2.30-2.40 (m, 1H), 2.57 (t, 2H, J=7.5 Hz), 3.58-3.70 (m, 1H), 4.16 (d, 1H, J=9.3 Hz), 7.11-7.15 (m, 3H), 7.40 (d, 2H, J=8.1 Hz).

I-23

$^1$H-NMR ($CDCl_3$) δ ppm: 0.91 (t, 3H, J=7.2 Hz), 1.21 (s, 9H), 1.21-1.41 (m, 4H), 1.51-1.64 (m, 4H), 1.86-2.01 (m, 4H), 2.12-2.25 (m, 1H), 2.56 (t, 2H, J=7.5 Hz), 2.87-2.96 (m, 1H), 3.00-3.12 (m, 1H), 3.23-3.34 (m, 1H), 3.67-3.75 (m, 1H), 7.11 (d, 2H, J=8.1 Hz), 7.40 (d, 2H, J=8.4 Hz).

I-24

$^1$H-NMR ($CDCl_3$) δ ppm: 0.91 (t, 3H, J=7.2 Hz), 1.25-1.37 (m, 2H), 1.40 (s, 9H), 1.48-1.65 (m, 6H), 1.90 (d, 2H, J=11.7 Hz), 2.02 (d, 2H, J=11.7 Hz), 2.12-2.24 (m, 1H), 2.56 (t, 2H, J=7.5 Hz), 3.04 (t, 2H, J=6.3 Hz), 4.31 (t, 1H, J=5.7 Hz), 7.11 (d, 2H, J=8.1 Hz), 7.42 (d, 2H, J=8.4 Hz).

I-25 mp: 232-233° C. $^1$H-NMR ($CDCl_3$) δ ppm: 0.91 (t, 3H, J=7.5 Hz), 1.23-1.10 (m, 4H), 1.40 (s, 9H), 1.51-1.76 (m, 4H), 2.01-2.26 (m, 5H), 2.56 (t, 2H, J=7.5 Hz), 3.22-3.38 (m, 1H), 3.79 (d, 1H, J=9.3 Hz), 7.11 (d, 2H, J=8.7 Hz), 7.17 (s, 1H), 7.40 (d, 2H, J=8.4 Hz).

I-26

$^1$H-NMR ($CDCl_3$) δ ppm: 0.91 (t, 3H, J=7.2 Hz), 1.22 (s, 9H), 1.28-1.40 (m, 2H), 1.52-1.62 (m, 2H), 1.85-1.96 (m, 1H), 2.00-2.14 (m, 1H), 2.38-2.53 (m, 2H), 2.56 (t, 2H, J=7.5 Hz), 3.22-3.37 (m, 3H), 7.11 (d, 2H, J=8.4 Hz), 7.45 (d, 2H, J=8.4 Hz), 8.19 (s, 1H).

I-27

$^1$H-NMR ($CDCl_3$) δ ppm: 0.91 (t, 3H, J=7.2 Hz), 1.30-1.40 (m, 2H), 1.40 (s, 9H), 1.52-1.61 (m, 2H), 1.95 (quint, 2H, J=6.3 Hz), 2.50 (t, 2H, J=6.9 Hz), 2.56 (t, 2H, J=7.8 Hz), 3.31 (quart, 2H, J=6.0 Hz), 4.30-4.36 (m, 1H), 7.12 (d, 2H, J=8.4 Hz), 7.43 (d, 2H, J=8.4 Hz), 7.65 (s, 1H).

I-28

$^1$H-NMR ($CDCl_3$) δ ppm: 0.91 (t, 3H, J=7.2 Hz), 1.21 (s, 9H), 1.30-1.62 (m, 8H), 2.08 (d, 4H, J=11.1 Hz), 2.56 (t, 2H, J=7.8 Hz), 3.04 (d, 1H, J=4.8 Hz), 3.20-3.30 (m, 1H), 4.65-4.76 (m, 1H), 6.57 (s, 1H), 7.10 (d, 2H, J=8.7 Hz), 7.26 (d, 2H, J=8.1 Hz).

I-29

$^1$H-NMR ($CDCl_3$) δ ppm: 0.91 (t, 3H, J=7.2 Hz), 1.23-1.62 (m, 8H), 1.40 (s, 9H), 2.12 (d, 4H, J=14.4 Hz), 2.56 (t, 2H, J=7.8 Hz), 3.28-3.40 (m, 1H), 3.90 (s, 1H), 4.60-4.73 (m, 1H), 6.57 (s, 1H), 7.10 (d, 2H, J=8.4 Hz), 7.25 (d, 2H, J=8.4 Hz).

I-30

$^1$H-NMR ($CDCl_3$) δ ppm: 0.91 (t, 3H, J=7.5 Hz), 1.26-1.39 (m, 2H), 1.51-1.64 (m, 4H), 1.72-1.81 (m, 2H), 2.34 (t, 2H, J=6.9 Hz), 2.56 (t, 2H, J=7.8 Hz), 2.95-3.01 (m, 2H), 4.84 (t, 1H, J=5.7 Hz), 6.99-7.12 (m, 6H), 7.19-7.24 (m, 1H), 7.30 (s, 1H), 7.38-7.43 (m, 4H), 7.79 (d, 2H, J=8.7 Hz).

I-31

$^1$H-NMR ($CDCl_3$) δ ppm: 0.92 (t, 3H, J=7.5 Hz), 1.21 (s, 9H), 1.28-1.62 (m, 8H), 2.07-2.14 (m, 4H), 2.64 (t, 2H, J=7.8 Hz), 3.11 (d, 1H, J=5.1 Hz), 3.20 (brs, 1H), 3.90-4.04 (m, 1H), 6.06-6.14 (m, 1H), 7.21 (t, 2H, J=8.1 Hz), 7.67 (t, 2H, J=8.4 Hz).

I-32

$^1$H-NMR ($CDCl_3$) δ ppm: 0.92 (t, 3H, J=7.2 Hz), 1.27-1.65 (m, 8H), 1.40 (s, 9H), 2.10-2.23 (m, 4H), 2.65 (t, 2H, J=7.5 Hz), 3.23-3.35 (m, 1H) 3.49 (s, 1H), 3.88-4.02 (m, 1H), 5.84-5.92 (m, 1H), 7.13 (t, 2H, J=8.4 Hz), 7.65 (d, 2H, J=8.1 Hz).

I-33

$^1$H-NMR ($CDCl_3$) δ ppm: 0.94 (t, 3H, J=7.2 Hz), 1.30-1.42 (m, 2H), 1.32 (s, 9H), 1.57-1.66 (m, 2H), 2.67 (t, 2H, J=7.8 Hz), 5.61 (s, 1H), 6.93 (d, 2H, J=8.7 Hz), 2.5 (d, 2H, J=8.4 Hz), 7.49 (d, 2H, J=9.0 Hz), 7.80 (d, 2H, J=8.1 Hz), 8.22 (s, 1H).

I-34

$^1$H-NMR ($CD_3OD$) δ ppm: 0.95 (t, 3H, J=7.5 Hz), 1.35 (s, 9H), 1.35-1.44 (m, 2H), 1.57-1.69 (m, 2H), 2.69 (t, 2H, J=7.5 Hz), 7.28-7.33 (m, 4H), 7.56 (d, 2H, J=9.0 Hz), 7.83 (d, 2H, J=8.4 Hz).

I-36

$^1$H-NMR ($CDCl_3$) δ ppm: 0.92 (t, 3H, J=7.5 Hz), 1.31-1.70 (m, 11H), 1.39 (s, 9H), 1.75-1.85 (m, 1H), 2.65 (t, 2H, J=8.1 Hz), 3.13 (t, 2H, J=6.6 Hz), 3.40 (t, 2H, J=7.2 Hz), 4.10 (t, 1H, J=5.7 Hz), 6.21 (t, 1H, J=5.7 Hz), 7.2:3 (d, 2H, J=8.1 Hz), 7.67 (d, 2H, J=8.4 Hz).

I-37

$^1$H-NMR ($CDCl_3$) δ ppm: 0.92 (t, 3H, J=7.5 Hz), 0.95-1.10 (m, 2H), 1.31-1.40 (m, 2H), 1.39 (s, 9H), 1.55-1.63 (m, 4H), 1.80-1.92 (m, 4H), 2.65 (t, 2H, J=7.8 Hz), 3.03 (t, 2H, J=6.6 Hz), 3.31 (t, 2H, J=6.6 Hz), 4.06 (t, 1H, J=6.0 Hz), 6.22 (t, 1H, J=6.0 Hz), 7.23 (d, 2H, J=8.4 Hz), 7.67 (d, 2H, J=8.1 Hz).

I-39

$^1$H-NMR ($CDCl_3$) δ ppm: 1.13 (t, 3H, J=7.2 Hz), 1.39 (s, 9H), 1.69-1.97 (m, 8H), 2.27-2.38 (m, 1H), 3.29-3.35 (m, 4H), 3.60-3.70 (m, 1H), 4.52 (d, 1H, J=9.3 Hz), 6.64 (d, 2H, J=8.4 Hz), 7.22 (s, 1H), 7.31 (d, 2H, J=9.0 Hz).

I-40

$^1$H-NMR ($CDCl_3$) δ ppm: 1.38 (s, 9H), 1.68-1.96 (m, 8H), 2.30-2.40 (m, 1H), 3.11 (t, 4H, J=4.8 Hz), 3.60-3.72 (m, 1H) 3.86 (t, 4H, J=4.8 Hz), 4.51 (brs, 1H), 6.89 (d, 2H, J=9.0 Hz), 7.42 (d, 2H, J=8.7 Hz).

I-41 mp: >278° C. (dec.) $^1$H-NMR ($CDCl_3$) δ ppm: 1.18-1.40 (m, 2H), 1.40 (s, 9H), 1.62-1.75 (m, 2H), 2.01-2.27 (m, 5H), 3.10-3.13 (m, 4H), 3.22-3.38 (m, 1H), 3.72 (d, 1H, J=9.3 Hz), 3.85-3.88 (m, 4H), 6.87 (d, 2H, J=9.0 Hz), 7.10 (s, 1H), 7.40 (d, 2H, J=9.0 Hz).

I-42

$^1$H-NMR ($CDCl_3$) δ ppm: 1.40 (s, 9H), 1.61-1.97 (m, 8H), 2.16 (s, 3H), 2.33-2.43 (m, 1H), 3.60-3.70 (m, 1H), 4.66 (brs, 1H), 7.12 (d, 1H, J=8.7 Hz), 7.46-7.50 (m, 1H), 7.62 (s, H), 7.75-7.78 (m, 1H), 7.86-7.91 (m, 2H).

I-43

$^1$H-NMR ($CDCl_3$) δ ppm: 1.40 (s, 9H), 1.62-2.00 (m, 8H), 1.87 (s, 3H), 2.36-2.47 (m, 1H), 3.24 (s, 3H), 3.64-3.74 (m, 1H), 4.87 (brs, 1H), 7.13 (d, 2H, J=9.0 Hz), 7.64 (d, 2H, J=8.4 Hz), 7.81 (s, H).

I-44 mp: 235-236° C. $^1$H-NMR ($CDCl_3$) δ ppm: 1.13 (t, 6H, J=6.9 Hz), 1.18-1.33 (m, 2H), 1.40 (s, 9H), 1.60-1.77 (m, 2H), 2.00-2.26 (m, 5H), 3.28-3.35 (m, 4H), 3.73 (d, 1H, J=9.3 Hz), 6.60-6.70 (m, 2H), 7.03 (brs, 1H), 7.31 (d, 2H, J=7.8 Hz).

I-45 mp: >268° C. (dec.) $^1$H-NMR ($CDCl_3$) δ ppm: 120-1.34 (m, 2H), 1.40 (s, 9H), 1.56-1.76 (m, 8H), 2.00-2.26 (m, 5H), 3.06-3.14 (m, 4H), 3.24-3.36 (m, 1H), 3.72 (d, 1H, J=9.3 Hz), 6.90 (d, 2H, J=8.7 Hz), 7.09 (s, 1H), 7.36 (d, 2H, J=8.7 Hz).

I-46 mp: >272° C. (dec.) $^1$H-NMR (DMSO-$d_6$) δ ppm: 1.28 (s, 9H), 1.31-1.59 (m, 7H), 1.87-2.00 (m, 4H), 2.23-2.34 (m, 1H), 3.00-3.16 (m, 1H), 4.35-4.45 (m, 2H), 6.81 (d, 1H, J=9.0 Hz), 7.16 (t, 1H, J=7.2 Hz), 7.43 (t, 1H, J=8.4 Hz), 7.52-7.58 (m, 3H), 8.04 (d, 1H, J=7.8 Hz), 8.43 (s, 1H).

I-47

$^1$H-NMR ($CDCl_3$) δ ppm: 1.20-1.36 (m, 2H), 1.40 (s, 9H), 1.62-1.77 (m, 2H), 1.98-2.32 (m, 5H), 3.31-3.40 (m, 1H), 3.62 (d, 1H, J=9.0 Hz), 7.08 (s, 1H), 7.29 (d, 2H, J=9.0 Hz), 7.61 (d, 2H, J=9.0 Hz).

I-48

$^1$H-NMR ($CDCl_3$) δ ppm: 1.22-1.36 (m, 2H), 1.40 (s, 9H), 1.62-1.77 (m, 2H), 2.00-2.31 (m, 5H), 3.24-3.40 (m, 1H), 3.62 (d, 1H, J=10.2 Hz), 7.01 (t, 2H, J=8.7 Hz), 7.09 (s, 1H), 7.42-7.50 (m, 2H).

I-49 mp: 270° C. (dec.) $^1$H-NMR ($CDCl_3$) δ ppm: 1.20-1.36 (m, 2H), 1.40 (s, 9H), 1.61-1.77 (m, 2H), 1.95-2.30 (m, 9H), 3.17-338 (m, 5H), 3.67 (d, 1H, J=9.3 Hz), 6.50 (d, 2H, J=9.0 Hz), 6.97 (s, 1H), 7.30 (d, 2H, J=9.0 Hz).

I-50 mp: 252-253° C. $^1$H-NMR ($CDCl_3$) δ ppm: 1.21-1.37 (m, 2H), 1.40 (s, 9H), 1.62-1.78 (m, 2H), 1.98-2.32 (m, 5H), 3.26-3.40 (m, 1H), 3.68 (d, 1H, J=9.6 Hz), 6.94-7.02 (m, 4H), 7.08 (t, 1H, J=7.5 Hz), 7.13 (s, 1H), 7.31 (t, 2H, J=7.5 Hz), 7.46 (d, 2H, J=9.0 Hz).

I-51 mp: 278-279° C. $^1$H-NMR ($CDCl_3$) δ ppm: 1.02 (d, 6H, J=6.9 Hz), 1.35 (s, 9H), 1.39-1.71 (m, 6H), 1.90-2.09 (m, 2H), 3.16-3.30 (m, 1H) 3.46 (d, 1H, J=9.0 Hz), 4.92-5.01 (m, 1H), 6.91-6.95 (m, 2H), 7.00-7.07 (m, 3H), 7.13-7.16 (m, 2H), 7.30-7.36 (m, 2H).

I-52 mp: 276-277° C. $^1$H-NMR ($CDCl_3$) δ ppm: 1.20-1.36 (m, 2H), 1.40 (s, 9H), 1.60-1.78 (m, 2H), 1.98-2.30 (m, 5H), 2.36 (s, 3H), 2.58 (t, 4H, J=4.5 Hz), 3.17 (t, 4H, J=4.5 Hz), 3.21-3.40 (m, 1H), 3.64 (d, 1H, J=9.0 Hz), 6.88 (d, 2H, J=9.0 Hz), 7.01 (s, 1H), 7.37 (d, 2H, J=9.0 Hz).

I-53 mp: >300° C. $^1$H-NMR (DMSO-$d_6$) δ ppm: 1.20-1.54 (m, 4H), 1.27 (s, 9H), 1.73-1.88 (m, 2H), 1.89-2.01 (m, 2H), 2.13-2.25 (m, 1H), 2.98-3.12 (m, 1H), 3.15-3.31 (m, 8H), 6.76-6.84 (m, 2H), 6.93 (d, 2H, J=9.0 Hz), 6.99 (d, 2H, J=8.1 Hz), 7.24 (d, 2H, J=8.1 Hz), 7.46 (d, 2H, J=9.0 Hz), 9.60 (s, 1H).

I-54 mp: >215° C. (dec.) $^1$H-NMR (DMSO-$d_6$) δ ppm: 1.27 (s, 9H), 1.27-2.00 (m, 18H), 2.14-2.26 (m, 1H), 2.53-2.84 (m, 4H), 2.86-3.30 (m, 2H), 3.46-3.54 (m, 1H), 3.62-3.74 (m, 2H), 6.78 (d, 1H, J=8.7 Hz), 6.87 (d, 2H, J=7.8 Hz), 7.42 (d, 2H, J=8.7 Hz), 9.58 (s, 1H).

I-55 mp: >290° C. (dec.) $^1$H-NMR ($CDCl_3$) δ ppm: 1.23-1.40 (m, 2H), 1.40 (s, 9H), 1.60-1.76 (m, 2H), 2.02-2.27 (m, 5H), 3.20 (t, 4H, J=5.4 Hz), 3.21-3.32 (m, 1H), 3.67 (d, 1H, J=9.3

Hz), 3.98 (t, 4H, J=4.8 Hz), 6.52 (t, 1H, J=4.8 Hz), 6.93 (d, 2H, J=8.4 Hz), 7.06 (s, 1H), 7.41 (d, 2H, J=8.7 Hz), 8.33 (d, 2H, J=4.8 Hz).

I-56 mp: >232° C. (dec.) $^1$H-NMR (DMSO-$d_6$) δ ppm: 1.27 (s, 9H), 1.27-1.48 (m, 4H), 1.80-1.99 (m, 4H), 2.14-2.25 (m, 1H), 3.04-3.24 (m, 8H), 3.68 (s, 3H), 3.76 (s, 3H), 6.44-6.47 (m, 1H), 6.66 (s, 1H), 6.76-6.84 (m, 2H), 6.92 (d, 2H, J=8.4 Hz), 7.46 (d, 2H, J=8.4 Hz), 9.61 (s, 1H).

I-57 mp: 284-285° C. (dec.) $^1$H-NMR ($CDCl_3$) δ ppm: 1.27 (t, 3H, J=7.2 Hz), 1.40 (s, 9H) 1.61-2.24 (m, 9H), 2.35-2.49 (m, 1H), 2.76 (t, 2H, J=10.2 Hz), 3.04-3.15 (m, 2H), 3.20-3.36 (m, 1H), 3.55-3.59 (m, 2H), 3.87 (d, 1H, J=9.6 Hz), 4.12-4.19 (m, 2H), 6.90 (d, 2H, J=8.7 Hz), 2.79 (s, 1H), 7.40 (d, 2H, J=8.7 Hz).

I-58 mp: >299° C. (dec.) $^1$H-NMR ($CDCl_3$) δ ppm: 1.26-1.33 (m, 2H), 1.40 (s, 9H), 1.56-2.42 (m, 19H), 2.73-2.81 (m, 4H), 3.16-3.26 (m, 4H), 3.64 (d, 1H, J=9.6 Hz), 6.87 (d, 2H, J=8.7 Hz), 7.04 (s, 1H), 7.37 (d, 2H, J=9.0 Hz).

I-59 mp: >270° C. (dec.) $^1$H-NMR ($CDCl_3$) δ ppm: 1.26-1.47 (m, 2H), 1.47 (s, 9H), 1.60-1.80 (m, 4H), 2.01-2.32 (m, 5H), 3.28-3.40 (m, 3H), 3.62-3.74 (m, 3H), 5.74-5.96 (m, 2H), 6.92 (d, 2H, J=8.7 Hz), 7.13 (s, 1H), 7.39 (d, 2H, J=9.0 Hz).

I-60 mp: 247-250° C. (dec.) $^1$H-NMR ($CDCl_3$) δ ppm: 1.20-1.37 (m, 2H), 1.40 (s, 9H), 1.60-1.78 (m, 2H), 1.98-2.33 (m, 5H), 2.93-3.03 (m, 2H), 3.22-3.40 (m, 1H), 3.52 (t, 2H, J=6.0 Hz), 3.62 (d, 1H, J=8.4 Hz), 4.36 (s, 2H), 6.93 (d, 2H, J=8.7 Hz), 7.00 (s, 1H), 7.11-7.22 (m, 4H), 7.39 (d, 2H, J=8.7 Hz).

I-61 mp: 280-281° C. $^1$H-NMR ($CDCl_3$) δ ppm: 1.21-1.38 (m, 2H), 1.41 (s, 9H), 1.64-1.80 (m, 2H), 2.02-2.33 (m, 5H), 3.24-3.40 (m, 1H), 3.61 (d, 1H, J=9.0 Hz), 6.33 (t, 2H, J=2.1 Hz), 7.04 (t, 2H, J=2.1 Hz), 7.14 (s, 1H), 7.34 (d, 2H, J=9.0 Hz), 7.56 (d, 2H, J=9.0 Hz).

I-62 mp: 260-262° C. $^1$H-NMR ($CDCl_3$) δ ppm: 1.22-1.39 (m, 2H), 1.41 (s, 9H), 1.64-1.82 (m, 2H), 2.02-2.35 (m, 5H), 3.24-3.40 (m, 1H), 3.62 (d, 1H, J=9.6 Hz), 7.31 (d, 2H, J=9.0 Hz), 7.51 (s, 1H), 7.69 (d, 2H, J=9.0 Hz).

I-63 mp: 248° C. $^1$H-NMR ($CDCl_3$) δ ppm: 1.20-1.38 (m, 2H), 1.40 (s, 9H), 1.61-1.78 (m, 2H), 1.98-2.32 (m, 5H), 3.22-3.45 (m, 1H), 3.64 (d, 1H, J=9.3 Hz), 7.11 (s, 1H), 7.37-7.46 (m, 4H).

I-64 mp: 272-275° C. (dec.) $^1$H-NMR (DMSO-$d_6$) δ ppm: 1.20-1.53 (m, 4H), 1.27 (s, 9H), 1.75-1.88 (m, 2H), 1.88-2.00 (m, 2H), 2.11-2.24 (m, 1H), 2.96-3.12 (m, 1H), 5.96 (s, 2H), 6.77 (d, 1H, J=8.7 Hz), 6.82 (d, 1H, J=8.4 Hz), 6.95 (dd, 1H, J=1.8, 8.4 Hz), 7.29 (d, 1H, J=1.8 Hz), 9.70 (s, 1H).

I-65 mp: 293-296° C. (dec.) $^1$H-NMR (DMSO-$d_6$) δ ppm: 1.20-1.70 (m, 10H), 1.27 (s, 9H), 1.79-2.038 (m, 4H), 2.18-2.33 (m, 1H), 2.98-3.30 (m, 5H), 6.79 (d, 1H, J=9.0 Hz), 6.97 (d, 2H, J=8.1 Hz), 7.43-7.57 (m, 4H), 7.62 (d, 2H, J=8.1 Hz), 9.82 (s, 1H).

I-66 mp: >300° C. $^1$H-NMR (DMSO-$d_6$) δ ppm: 1.27 (s, 9H), 1.27-1.53 (m, 4H), 1.86-1.99 (m, 4H), 2.22-2.34 (m, 1H), 2.39 (s, 3H), 3.00-3.14 (m, 1H), 6.25 (s, 1H), 6.79 (d, 1H, J=9.0 Hz), 7.47-7.50 (m, 1H), 7.69-7.76 (m, 1H), 10.27 (s, 1H).

I-67 mp: 248-249° C. $^1$H-NMR (DMSO-$d_6$) δ ppm: 1.20-1.54 (m, 4H), 1.27 (s, 9H), 1.77-1.90 (m, 2H), 1.90-2.02 (m, 2H), 2.02 (s, 3H), 2.17-2.32 (m, 1H), 2.96-3.13 (m, 1H), 6.78 (d, 1H, J=8.7 Hz), 7.12-7.30 (m, 3H), 7.89 (s, 1H), 9.79 (s, 1H), 9.88 (s, 1H).

I-68 mp: >300° C. $^1$H-NMR (DMSO-$d_6$) δ ppm: 1.20-1.54 (m, 4H), 1.27 (s, 9H), 1.77-1.89 (m, 2H), 1.89-2.03 (m, 2H), 2.00 (s, 3H), 2.14-2.28 (m, 1H), 2.95-3.13 (m, 1H), 6.78 (d, 1H, J=8.7 Hz), 7.40-7.54 (m, 4H), 9.72 (s, 1H), 9.83 (s, 1H).

I-69 mp: 199-201° C. $^1$H-NMR (DMSO-$d_6$) δ ppm: 1.21-1.53 (m, 4H), 1.27 (s, 9H), 1.76-1.89 (m, 2H), 1.89-2.02 (m, 2H), 2.13-2.30 (m, 1H), 2.85 (s, 6H), 2.94-3.14 (m, 1H), 6.40 (dd, 1H, J=2.4, 8.4 Hz), 6.78 (d, 1H, J=8.7 Hz), 6.90 (d, 1H, J=8.4 Hz), 7.05 (t, 2H, J=8.4 Hz), 9.60 (s, 1H).

I-70 mp: 227-230° C. $^1$H-NMR (DMSO-$d_6$) δ ppm: 1.22-1.52 (m, 4H), 1.27 (s, 9H), 1.72-1.87 (m, 2H), 1.87-2.01 (m, 2H), 2.12-2.29 (m, 1H), 2.96-3.12 (m, 1H), 5.00 (s, 2H), 6.22 (d, 1H, J=7.5 Hz), 6.66 (d, 1H, J=7.5 Hz), 6.78 (d, 1H, J=9.0 Hz), 6.86 (d, 1H, J=7.5 Hz), 6.89-6.95 (m, 1H), 9.46 (s, 1H).

I-71 mp: 270-272° C. $^1$H-NMR (DMSO-$d_6$) δ ppm: 1.22-1.52 (m, 4H), 1.26 (s, 9H), 1.73-1.86 (m, 2H), 1.88-2.00 (m, 2H), 2.08-2.22 (m, 1H), 2.95-3.11 (m, 1H), 4.80 (s, 2H), 6.47 (d, 2H, J=8.4 Hz), 6.77 (d, 1H, J=8.4 Hz), 7.20 (d, 2H, J=8.4 Hz), 9.35 (s, 1H).

I-72 mp: 262-263° C. $^1$H-NMR ($CDCl_3$) δ ppm: 1.25 (d, 6H, J=6.3 Hz), 1.17-1.42 (m, 2H), 1.40 (s, 9H), 1.60-1.78 (m, 2H), 1.98-2.43 (m, 7H), 3.20-3.43 (m, 3H), 3.67 (d, 1H, J=9.6 Hz), 3.74-3.86 (m, 2H), 6.86 (d, 2H, J=9.0 Hz), 7.04 (s, 1H), 7.38 (d, 2H, J=9.0 Hz).

I-73 mp: 218-219° C. $^1$H-NMR ($CD_3OD$) δ ppm: 1.36 (s, 9H), 1.36-1.69 (m, 4H), 1.45 (s, 9H), 1.88-2.02 (m, 3H), 2.06-2.30 (m, 4H), 3.05-3.44 (m, 3H), 3.46-3.56 (m, 1H), 4.16-4.26 (m, 1H), 6.61 (d, 2H, J=9.0 Hz), 7.30 (d, 2H, J=8.7 Hz).

I-74 mp: 295-296° C. (dec.) $^1$H-NMR ($CD_3OD$) δ ppm: 1.36 (s, 9H), 1.36-1.67 (m, 4H), 1.92-2.13 (m, 4H), 2.26-2.40 (m, 2H), 2.62-2.75 (m, 1H), 3.16-3.25 (m, 1H), 3.58-3.98 (m, 4H), 4.16-4.25 (m, 1H), 7.20-7.30 (m, 2H), 7.62 (d, 2H, J=9.0 Hz).

I-75 mp: 250-251° C. $^1$H-NMR (DMSO-$d_6$) δ ppm: 1.23-1.55 (m, 4H), 1.27 (s, 9H), 1.78-1.90 (m, 2H), 1.90-2.02 (m, 2H), 2.15-2.28 (m, 1H), 2.98-3.14 (m, 1H), 3.06 (t, 2H, J=8.4 Hz), 3.87 (t, 2H, J=8.4 Hz), 6.67 (dd, 1H, J=1.5, 7.2 Hz), 6.80 (d, 1H, J=8.4 Hz), 6.94-7.05 (m, 2H), 7.12-7.19 (m, 1H), 7.16 (d, 2H, J=9.3 Hz), 7.57 (d, 2H, J=9.3 Hz), 9.73 (s, 1H).

I-76 mp: 265-266° C. $^1$H-NMR (DMSO-$d_6$) δ ppm: 1.23-1.58 (m, 4H), 1.28 (s, 9H), 1.83-2.04 (m, 4H), 2.20-2.36 (m, 1H), 2.97-3.16 (m, 1H), 6.67 (d, 1H, J=3.0 Hz), 6.82 (d, 1H, J=8.4 Hz), 7.07-7.22 (m, 2H), 7.47-7.53 (m, 1H), 7.50 (d, 2H, J=9.0 Hz), 7.58 (d, 1H, J=3.0 Hz), 7.64 (d, 1H, J=7.5 Hz), 7.79 (d, 2H, J=9.0 Hz), 10.02 (s, 1H).

I-77 mp: 281° C. $^1$H-NMR (DMSO-$d_6$) δ ppm: 1.21-1.56 (m, 4H), 1.27 (s, 9H), 1.80-2.03 (m, 4H), 2.18-2.31 (m, 1H), 2.97-3.14 (m, 1H), 6.51 (dd, 1H, J=2.1, 2.7 Hz), 6.81 (d, 1H, J=9.0 Hz), 7.67-7.78 (m, 5H), 8.41 (d, 1H, J=2.1 Hz), 9.96 (s, 1H).

I-78 mp: >300° C. (dec.) $^1$H-NMR (DMSO-$d_6$) δ ppm: 1.27 (s, 9H), 1.27-1.52 (m, 4H), 1.74-2.04 (m, 7H), 2.10-2.25 (m, 2H), 2.96-3.20 (m, 2H), 3.48-3.58 (m, 1H), 3.75-3.84 (m, 1H), 6.39 (d, 2H, J=8.4 Hz), 6.79 (d, 1H, J=8.4 Hz), 7.02 (s, 1H), 7.30 (s, 1H), 7.36 (d, 2H, J=8.1 Hz), 9.48 (s, 1H).

I-79 mp: 248-250° C. (dec.) $^1$H-NMR (DMSO-$d_6$) δ ppm: 1.27 (s, 9H), 1.27-1.54 (m, 4H), 1.85-1.99 (m, 4H), 2.24-2.33 (m, 1H), 3.00-3.14 (m, 1H), 6.82 (d, 1H, J=8.7 Hz), 7.77 (d, 2H, J=8.4 Hz), 8.07 (d, 2H, J=8.4 Hz).

I-80 mp: >300° C. $^1$H-NMR (DMSO-$d_6$) δ ppm: 1.22-1.58 (m, 4H), 1.27 (s, 9H), 1.80-2.03 (m, 4H), 2.18-2.32 (m, 1H), 2.98-3.14 (m, 1H), 6.80 (d, 1H, J=8.7 Hz), 7.35-7.50 (m, 2H), 7.99 (s, 1H), 8.11 (s, 1H), 9.79 (s, 1H), 12.94 (s, 1H).

I-81 mp: 261-262° C. $^1$H-NMR (DMSO-$d_6$) δ ppm: 1.21-1.57 (m, 4H), 1.27 (s, 9H), 1.78-2.02 (m, 4H), 2.17-2.30 (m, 1H), 2.96-3.16 (m, 1H), 6.34 (s, 1H), 6.80 (d, 1H, J=8.7 Hz), 7.14-7.32 (m, 3H), 7.85 (s, 1H), 9.58 (s, 1H), 10.95 (s, 1H).

I-82

$^1$H-NMR ($CDCl_3$) δ ppm: 0.86 (s, 18H), 1.24-1.37 (m, 2H), 1.37 (s, 9H), 1.56-1.74 (m, 2H), 1.95-2.19 (m, 5H), 3.18-3.32 (m, 1H), 3.44 (t, 4H, J=6.3 Hz), 3.70 (t, 4H, J=6.3 Hz), 4.39 (d, 1H, J=9.0 Hz), 6.59 (d, 2H, J=9.0 Hz), 7.31 (d, 2H, J=8.7 Hz), 7.43 (s, 1H).

I-83 mp: 264-265° C. $^1$H-NMR (DMSO-$d_6$) δ ppm: 1.27 (s, 9H), 1.27-1.52 (m, 4H), 1.78-1.88 (m, 2H), 1.90-2.00 (m, 2H), 2.14-2.26 (m, 1H), 2.96-3.14 (m, 1H), 6.72-6.82 (m, 2H), 6.99 (t, 4H, J=7.8 Hz), 7.18 (t, 2H, J=7.5 Hz), 7.46 (d, 2H, J=9.0 Hz), 8.00 (s, 1H), 9.65 (s, 1H).

I-84 mp: 257° C. (dec.) $^1$H-NMR (DMSO-$d_6$) δ ppm: 1.23-1.57 (m, 4H), 1.27 (s, 9H), 1.83-2.03 (m, 4H), 2.23-2.35 (m, 1H), 2.98-3.15 (m, 1H), 6.80 (d, 1H, J=8.1 Hz), 7.87 (d, 2H, J=9.0 Hz), 8.34 (d, 2H, J=9.0 Hz), 9.21 (s, 1H), 10.20 (s, 1H).

I-85 mp: 256-258° C. $^1$H-NMR (DMSO-$d_6$) δ ppm: 1.22-1.53 (m, 4H), 1.26 (s, 9H), 1.79-2.01 (m, 4H), 2.25 (s, 3H), 2.28-2.42 (m, 1H), 2.97-3.02 (m, 1H), 6.71 (d, 1H, J=0.9 Hz), 6.80 (d, 1H, J=8.1 Hz), 11.91 (s, 1H).

I-86 mp: 228-230° C. $^1$H-NMR ($CD_3OD$) δ ppm: 1.36 (s, 9H), 1.36-1.48 (m, 2H), 1.55-1.70 (m, 2H), 1.87-1.98 (m, 2H), 2.08-2.17 (m, 2H), 2.20-2.32 (m, 1H), 3.15-3.27 (m, 1H), 3.50 (t, 4H, J=5.7 Hz), 3.69 (t, 4H, J=5.7 Hz), 6.72 (d, 2H, J=9.0 Hz), 7.29-7.33 (m, 2H).

I-87 mp: 183-184° C. $^1$H-NMR (DMSO-$d_6$) δ ppm: 1.27 (s, 9H), 1.27-1.48 (m, 4H), 1.73-1.89 (m, 4H), 1.90-2.00 (m, 2H), 2.16-2.28 (m, 1H), 2.28 (t, 2H, J=7.5 Hz), 2.51-2.54 (m, 2H), 2.97-3.13 (m, 1H), 3.58 (s, 3H), 6.79 (d, 1H, J=8.7 Hz), 7.08 (d, 2H, J=8.7 Hz), 7.49 (d, 2H, J=8.4 Hz), 9.73 (s, 1H).

I-88 mp: 217-218° C. $^1$H-NMR ($CD_3OD$) δ ppm: 1.36 (s, 9H), 1.36-1.46 (m, 2H), 1.55-1.69 (m, 2H), 1.83-2.00 (m, 4H), 2.07-2.18 (m, 2H), 2.26-2.36 (m, 3H), 2.61 (t, 2H, J=7.5 Hz), 3.14-3.26 (m, 1H), 7.13 (d, 2H, J=8.1 Hz), 7.44 (d, 2H, J=8.1 Hz).

I-89

$^1$H-NMR ($CDCl_3$) δ ppm: 0.08 (d, 6H, J=3.3 Hz), 0.88 (s, 9H), 1.21-1.36 (m, 2H), 1.39 (s, 9H), 1.6 1-1.74 (m, 2H), 1.88-2.23 (m, 6H), 3.06-3.11 (m, 1H), 3.24-3.74 (m, 4H), 3.92 (d, 1H, J=9.6 Hz), 4.48-4.56 (m, 1H), 6.47 (d, 2H, J=9.0 Hz), 7.17 (s, 1H), 7.32 (d, 2H, J=9.0 Hz).

I-90 mp: amorphous $^1$H-NMR ($CD_3OD$) δ ppm: 1.36 (s, 9H), 1.36-1.47 (m, 2H), 1.56-1.70 (m, 3H), 1.88-2.30 (m, 6H), 3.05-3.49 (m, 5H), 4.50 (brs, 1H), 6.50 (d, 2H, J=9.0 Hz), 7.29 (d, 2H, J=9.0 Hz).

I-91 mp: 105-106° C. $^1$H-NMR ($CDCl_3$) δ ppm: 0.92 (t, 3H, J=7.3 Hz), 1.25-1.27 (m, 2H), 1.36 (d, 6H, J=6.9 Hz), 1.51-1.59 (m, 2H), 2.56 (t, 2H, J=7.8 Hz), 3.27 (sept, 1H, J=6.9 Hz), 7.12 (d, 2H, J=8.6 Hz), 7.32 (t, 1H, J=7.8 Hz), 7.45 (brd, 1H, J=7.8 Hz), 7.53 (d, 2H, J=8.6 Hz), 7.58 (d, 1H, J=7.8 Hz), 7.71-7.72 (m, 2H), 8.27 (s, 1H).

I-92 mp: 163-164° C. $^1$H-NMR ($CDCl_3$) δ ppm: 0.93 (t, 3H, J=7.3 Hz), 1.32-1.39 (m, 2H), 1.55-1.65 (m, 2H), 1.87 (s, 3H), 1.95 (s, 3H), 2.60 (t, 2H, J=7.6 Hz), 7.07 (d, 2H, J=8.4 Hz), 7.18 (d, 2H, J=8.5 Hz), 7.54 (d, 2H, J=8.5 Hz), 7.91 (brs, 1H), 8.18 (d, 2H, J=8.4 Hz), 8.77 (s, 1H).

I-93 mp: 173° C. $^1$H-NMR ($CDCl_3$) δ ppm: 0.93 (t, 3H, J=7.3 Hz), 1.32-1.40 (m, 2H), 1.39 (d, 6H, J=6.9 Hz), 1.55-1.62 (m, 2H), 2.60 (t, 2H, J=7.8 Hz), 3.13 (sept, 1H, J=6.9 Hz), 4.39 (d, 2H, J=6.3 Hz), 4.45 (t, 1H, J=6.3 Hz), 7.18 (d, 2H, J=8.7 Hz), 7.46 (d, 2H, J=8.7 Hz), 7.54 (d, 2H, J=8.7 Hz), 7.80 (s, 1H), 7.85 (d, 2H, J=8.7 Hz).

I-94 mp: 159-160° C. $^1$H-NMR ($CDCl_3$) δ ppm: 0.93 (t, 3H, J=7.3 Hz), 1.32-1.39 (m, 2H), 1.54-1.80 (m, 2H), 1.79 (s, 3H), 1.80 (s, 3H), 2.60t, 2H, J=7.7 Hz), 3.18 (s, 3H), 7.18 (d, 2H, J=8.35 Hz), 7.30 (d, 2H, J=8.8 Hz), 7.52 (d, 2H, J=8.5 Hz), 7.70 (brs, 1H), 7.84 (d, 2H, J=8.8 Hz), 8.77 (s, 1H).

I-95 mp: 177-178° C. $^1$H-NMR ($CDCl_3$) δ ppm: 0.94 (t, 3H, J=7.2 Hz), 1.31-1.48 (m, 8H), 1.54-1.66 (m, 2H), 2.55 (s, 3H), 2.62 (t, 9H, J=7.6 Hz), 3.92 (sept, 1H, J=6.6 Hz), 7.20 (d, 2H, J=8.45 Hz), 7.74 (d, 2H, J=8.5 Hz), 9.01 (brs, 1H), 9.17 (s, 1H).

I-96 mp: 220-223° C. $^1$H-NMR ($CDCl_3$) δ ppm: 0.93 (t, 3H, J=7.3 Hz), 1.28-1.42 (m, 2H), 1.50 (d, 6H, J=6.8 Hz), 1.54-1.65 (m, 2H), 2.62 (t, 2H, J=7.6 Hz), 4.08 (sept, 1H, J=7.1 Hz), 7.20(d, 2H, J=8.5 Hz), 7.48 (d, 2H, J=8.5 Hz), 7.71 (brs, 1H), 8.51 (hrs, 1H), 8.95 (s, 1H).

I-97 mp: 195-197° C. $^1$H-NMR ($CDCl_3$) δ ppm: 0.91 (t, 3H, J=7.6 Hz), 0.94 (t, 3H, J=7.3 Hz), 1.32-1.44 (m, 6H), 1.54-1.64 (m, 2H), 1.66-1.78 (m, 2H), 2.62 (t, 2H, J=7.7 Hz), 2.86 (brs, 2H), 3.98 (sept, 1H, J=7.1 Hz), 7.19 (d, 2H, J=8.5 Hz), 7.63 (d, 2H, J=8.4 Hz), 8.72 (brs, 1H), 8.81 (brs, 1H).

I-98 mp: 216-218° C. $^1$H-NMR ($CDCl_3$+$CD_3OD$) δ ppm: 0.93 (t, 3H, J=7.4 Hz), 1.29-1.40 (m, 2H), 1.43 (d, 2H, J=6.9 Hz), 1.51-1.63 (m, 2H), 2.60 (t, 2H, J=7.8 Hz), 3.65 (sept, 1H, J=6.9 Hz), 7.18 (d, 2H, J=8.5 Hz), 7.22 (d, 1H, J=8.8 Hz), 7.55 (d, 2H, J=8.51 Hz), 8.18 (dd, 1H, J=8.8, 2.4 Hz), 8.63 (d, 1H, J=2.4 Hz).

I-99 mp: 201-202° C. $^1$H-NMR ($CDCl_3$) δ ppm: 0.93 (t, 3H, J=7.3 Hz), 1.22-1.40 (m, 2H), 1.49 (d, 2H), J=7.1 Hz), 1.51-1.63 (m, 2H), 2.59 (t, 2H, J=7.7 Hz), 4.22 (sept, 1H, J=7.1 Hz), 7.16(d, 2H, J=8.4 Hz), 7.41 (brs, 1H), 7.52 (d, 2H, J=8.4 Hz), 8.10 (brs, 1H), 8.13 (d, 1H, J=2.2 Hz), 8.61 (brs, 1H).

I-100 mp: 160-162° C. $^1$H-NMR ($CDCl_3$) δ ppm: 0.93 (t, 3H, J=7.3 Hz), 1.22-1.42 (m, 2H), 1.45 (d, 2H, J=6.9 Hz), 1.51-1.63 (m, 2H), 2.61 (t, 2H, J=7.8 Hz), 3.37 (sept, 1H, J=6.9 Hz), 6.89(brs, 1H), 7.19 (d, 2H, J=8.4 Hz), 7.65 (d, 2H, J=8.4 Hz), 7.80 (dd, 1H, J=8.4, 2.4 Hz), 8.27 (d, 1H, J=8.4 Hz), 8.45 (d, 1H, J=2.4 Hz), 9.75 (brs, 1H).

I-101, I-214 mp: 192-194° C. $^1$H-NMR ($CDCl_3$) δ ppm: 0.93 (t, 3H, J=7.3 Hz), 1.27-1.41 (m, 2H), 1.35 (s, 9H), 1.50-1.66 (m, 2H), 2.60 (t, 2H, J=7.6 Hz), 5.58 (brs, 1H), 7.07 (d, 2H, J=8.5 Hz), 7.17 (d, 2H, J=8.5 Hz), 7.52 (d, 2H, J=8.5 Hz), 7.71 (brs, 1H), 7.79 (d, 2H, J=8.5 Hz).

I-102 mp: 216-217° C. $^1$H-NMR ($CDCl_3$) δ ppm: 0.93 (t, 3H, J=7.3 Hz), 1.26-1.42 (m, 2H), 1.45 (s, 9H), 1.70-1.83 (m, 2H), 2.60 (t, 2H, J=7.7 Hz), 6.42 (brs, 1H), 7.18 (d, 2H, J=8.5 Hz), 7.35 (d, 2H, J=8.5 Hz), 7.51 (d, 2H, J=8.5 Hz), 7.68 (brs, 1H), 7.82 (d, 2H, J=8.5 Hz).

I-103

$^1$H-NMR ($CDCl_3$) δ ppm: 0.91 (t, 3H, J=7.3 Hz), 1.28-1.36 (m, 2H), 1.32 (d, 6H, J=6.9 Hz), 1.49-1.59 (m, 2H), 2.54 (t, 2H, J=7.7 Hz), 3.23 (sept, 1H, J=6.9 Hz), 3.46 (s, 3H), 6.76 (brs, 1H), 6.91 (d, 2H, J=8.2 Hz), 6.99 (d, 2H, J=8.8 Hz), 7.03 (d, 2H, J=8.2 Hz), 7.25 (d, 2H, J=8.8 Hz).

I-104 mp: 182-183° C. $^1$H-NMR ($CDCl_3$) δ ppm: 0.93 (t, 3H, J=7.31 Hz), 1.28-1.40 (m, 2H), 1.51-1.63 (m, 2H), 1.64-1.88 (m, 4H), 1.90-2.23 (m, 4H), 2.60 (t, 2H, J=7.6 Hz), 3.39 (m, 1H), 6.16 (brs, 1H), 7.07 (d, 2H, J=8.5 Hz), 7.16 (d, 2H, J=8.5 Hz), 7.52 (d, 2H, J=8.5 Hz), 7.74 (brs, 1H), 7.77 (d, 2H, J=8.5 Hz).

I-105 mp: 190-191° C. $^1$H-NMR ($CDCl_3$) δ ppm: 0.93 (t, 3H, J=7.3 Hz), 1.28-1.41 (m, 2H), 1.52-1.69 (m, 4H), 1.75-1.90 (m, 2H), 1.92-2.07 (m, 4H), 2.58 (t, 2H, J=7.6 Hz), 3.59 (m, 1H), 6.53 (brs, 1H), 7.18 (d, 2H, J=8.5 Hz), 7.31 (d, 2H, J=8.5 Hz), 7.52 (d, 2H, J=8.5 Hz), 7.67 (brs, 1H), 7.84 (d, 2H, J=8.5 Hz).

I-106 mp: 194-497° C. $^1$H-NMR ($CDCl_3$) δ ppm: 0.93 (t, 3H, J=7.3 Hz), 1.22-1.41 (m, 2H), 1.53-1.65 (m, 2H), 1.90 (s, 6H), 2.60 (t, 2H, J=7.8 Hz), 6.86 (brs, 1H), 7.18 (d, 2H, J=8.5 Hz), 7.43 (d, 2H, J=8.5 Hz), 7.51 (d, 2H, J=8.5 Hz), 7.71 (brs, 1H), 7.84 (d, 2H, J=8.5 Hz).

I-107 mp: 211-212° C. $^1$H-NMR ($CDCl_3$) δ ppm: 0.93 (t, 3H, J=7.3 Hz), 1.24-1.40 (m, 2H), 1.50-1.62 (m, 2H), 2.60 (t, 2H, J=7.6 Hz), 6.19 (brs, 1H), 7.17 (d, 2H, J=8.5 Hz), 7.18 (d, 2H, J=8.5 Hz), 7.51 (d, 2H, J=8.5 Hz), 7.66 (brs, 1H), 7.86 (d, 2H, J=8.5 Hz).

I-108 mp: 298-300° C. $^1$H-NMR (DMSO-$d_6$) δ ppm: 0.90 (t, 3H, J=7.3 Hz), 1.22-1.39 (m, 2H), 1.48-1.60 (m, 2H), 2.54 (t, 2H, J=7.3 Hz), 7.04 (d, 2H, J=8.8 Hz), 7.12 (d, 2H, J=8.5 Hz), 7.64 (d, 2H, J=8.5 Hz), 7.69 (d, 2H, J=8.8 Hz), 9.80 (s, 1H).

I-109 mp: 122-123° C. $^1$H-NMR ($CDCl_3$) δ ppm: 0.90 (t, 3H, J=7.4 Hz), 0.97 (t, 3H, J=7.7 Hz), 1.26-1.38 (m, 2H), 1.30 (s, 6H), 1.50-1.66 (m, 4H), 1.72-1.83 (m, 4H), 2.34 (t, 2H, J=7.1 Hz), 2.55 (t, 2H, J=7.6 Hz), 3. 19 (q, 1H, J=6.0 Hz), 4.60 (brs, 1H), 7.08 (d, 2H, J=8.5 Hz), 7.42 (d, 2H, J=8.5 Hz), 7.85 (s, 1H).

I-110 mp: 109-110° C. $^1$H-NMR ($CDCl_3$) δ ppm: 0.91 (t, 3H, J=7.4 Hz), 1.10 (d, 6H, J=6.7 Hz), 1.29-1.38 (m, 2H), 1.55 (s, 9H), 1.60-1.70 (m, 2H), 1.78-1.89 (m, 2H), 2.26 (m, 1H ), 2.39 (t, 2H, J=7.0 Hz), 2.57 (t, 2H, J=7.7 Hz), 2.90 (d, 2H, J=6.6 Hz), 3.16 (brs, 1H) 4.24 (brs, 1H), 7.12 (d, 2H, J=8.5 Hz), 7.40 (d, 2H, J=8.5 Hz).

I-111 mp: 64-65° C. $^1$H-NMR ($CDCl_3$) δ ppm: 0.91 (t, 3H, J=7.3 Hz), 1.02 (t, 3H, J=7.5 Hz), 1.35 (d, 3H, J=6.7 Hz), 1.26-1.38 (m, 2H), 1.48-1.69 (m, 5H), 1.76-1.87 (m, 2H), 2.04 (m, 1H), 2.38 (t, 2H, J=7.3 Hz), 2.56 (t, 2H, J=7.6 Hz), 2.91 (m, 1H), 3.16 (brs, 2H), 4.42 (brs, 1H), 7.11 (d, 2H, J=8.5 Hz), 7.42 (d, 2H, J=8.5 Hz), 7.47 (brs, 1H).

I-112 mp: 79-80° C. $^1$H-NMR ($CDCl_3$) δ ppm: 1.36 (s, 9H), 1.52-1.62 (m, 2H), 1.67-1.76 (m, 2H), 2.22 (t, 2H, J=7.4 Hz), 3.16 (q, 2H, J=6.3 Hz), 3.78 (s, 3H), 4.33 (d, 2H, J=5.4 Hz), 4.62 (brs, 1H), 6.20 (brs, 1H), 6.85 (d, 2H, J=8.8 Hz), 7.19 (d, 2H, J=8.8 Hz).

I-113 mp: 125-126° C. $^1$H-NMR ($CDCl_3$) δ ppm: 1.38 (s, 9H), 1.62-1.70 (m, 2H), 1.76-1.88 (m, 2H), 2.46 (t, 2H, J=7.4 Hz), 3.22 (q, 2H, J=6.1 Hz), 4.22 (t, 1H, J=6.1 Hz), 7.24 (dd, 1H, J=8.9, 2.3 Hz), 7.36 (d, 1H, J=2.3 Hz), 7.65 (brs, 1H), 8.29 (d, 1H, J=8.9 Hz).

I-114 mp: 89-91° C. $^1$H-NMR ($CDCl_3$) δ ppm: 0.92 (t, 3H, J=7.0 Hz), 1.06 (d, 6H, J=7.0 Hz), 1.36 (m, 1H), 1.50-1.72 (m, 5H), 1.94-2.06 (m, 2H), 2.26 (m, 1H), 2.60 (t, 2H, J=7.7 Hz), 2.84 (t, 2H, J=7.7 Hz), 2.93 (d, 2H, J=6.3 Hz), 3.20 (t, 2H, J=6.6 Hz), 4.30 (brs, 1H), 7.19 (d, 2H, J=8.5 Hz), 7.63 (d, 2H, J=8.5 Hz), 9.15 (brs, 1H).

I-115 mp: 94-95° C. $^1$H-NMR ($CDCl_3$) δ ppm: 0.92 (t, 3H, J=7.5 Hz), 1.03 (t, 3H, J=7.5 Hz), 1.23-1.40 (m, 5H), 1.42-1.65 (m, 6H), 1.75 (m, 1H), 2.02 (m, 1H), 2.24 (t, 2H, J=7.0 Hz), 2.59 (t, 2H, J=8.0 Hz), 2.90 (m, 1H), 3.14 (q, 2H, J=6.6 Hz), 4.20 (m, 1H), 4.40 (d, 2H, J=5.4 Hz), 5.70 (brs, 1H), 7.14 (d, 2H, J=8.1 Hz), 7.18 (d, 2H, J=8.1 Hz).

I-116 mp: 89-91° C. $^1$H-NMR ($CDCl_3$) δ ppm: 0.97 (t, 3H, J=7.3 Hz), 1.02 (t, 3H, J=7.5 Hz), 1.35 (d, 3H, J=7.0 Hz), 1.40-1.90 (m, 9H), 2.04 (m, 1H), 2.37 (t, 2H, J=7.0 Hz), 2.90 (m, 1H), 3.17 (q, 2H, J=6.6 Hz), 3.93 (t, 2H, J=6.6 Hz), 4.32 (m, 1H), 6.84 (d, 2H, J=9.0 Hz), 7.31 (brs, 1H), 7.40 (d, 2H, J=9.0 Hz).

I-117 mp: 110-111° C. $^1$H-NMR ($CDCl_3$) δ ppm: 1.02 (t, 3H, J=7.5 Hz), 1.34 (d, 3H, J=6.6 Hz), 1.45-1.70 (m, 3H), 1.75-1.85 (m, 2H), 2.05 (m, 1H), 2.36 (t, 2H, J=7.5 Hz), 2.90 (m, 1H), 3.16 (q, 2H, J=6.6 Hz), 3.78 (s, 3H), 4.50 (m, 1H), 6.84 (d, 2H, J=6.8 Hz), 7.42 ((d, 2H, J=6.8 Hz), 7.48 (brs, 1H).

I-118 mp: 113-115° C. $^1$H-NMR ($CDCl_3$) δ ppm: 0.92 (t, 3H, J=7.0 Hz), 1.20-1.34 (m, 1H), 1.37 (d, 6H, J=7.0 Hz), 1.48-1.70 (m, 3H), 2.43 (q, 2H, J=6.6 Hz), 2.58 (t, 2H, J=7.7 Hz), 3.10-3.31 (m, 3H), 4.75 (m, 1H), 6.04 (d, 1H, J=15.0 Hz), 6.77 (dt, 1H, J=7.7, 15.0 Hz), 7.14 (d, 2H, J=8.4 Hz), 7.55 (d, 2H, J=8.4 Hz), 7.85 (brs, 1H).

I-119 mp: 139-140° C. $^1$H-NMR ($CDCl_3$) δ ppm: 1.19 (s, 9H), 1.47 (m, 2H), 1.61 (m, 2H), 2.18 (t, 2H, J=7.6 Hz), 3.03 (q, 2H, J=6.3 Hz), 4.09 (t, 1H, J=5.9 Hz), 6.85 (brd, 1H, J=8.0 Hz), 7.00 (t, 1H, J=8.0 Hz), 7.16 (brd, 1H, J=8.0), 7.48 (brs, 1H), 757 (brs, 1H).

I-120 mp: 183° C. $^1$H-NMR ($CDCl_3$) δ ppm: 0.91 (t, 3H, J=7.3 Hz), 1.20-1.58 (m, 6H), 1.40 (s, 9H), 2.07 (dd, 1H, J=12.9, 3.1 Hz), 2.52 (t, 2H, J=7.7 Hz), 2.95 (dd, 2H, J=11.5, 2.5 Hz), 3.46(m, 1H), 3.88-4.07 (m, 3H), 6.47 (s, 1H), 7.08 (d, 2H, J=8.5 Hz), 7.22 (d, 2H, J=8.5 Hz).

I-121 mp: 163-166° C. $^1$H-NMR ($CDCl_3$) δ ppm: 0.91 (t, 3H, J=7.3 Hz), 1.32-1.62 (m, 6H), 1.45 (s, 9H), 1.95-2.07 (m, 3H), 2.20 (m, 1H), 2.46 (td, 1H, J=10.4, 3.7 Hz), 2.37 (t, 2H, J=7.6 Hz), 3.43 (brd, 2H, J=10.4 Hz), 4.80 (s, 1H), 7.12 (d, 2H, J=8.4 Hz), 7.14 (s, 1H), 7.39 (d, 2H, J=8.4 Hz).

I-122 mp: 188-189° C. $^1$H-NMR ($CDCl_3$) δ ppm: 0.91 (t, 3H, J=7.5 Hz), 1.25-1.41 (m, 2H), 1.42 (s, 9H), 1.50-1.62 (m, 2H), 1.78-1.95 (m, 4H), 2.00-2.20 (m, 6H), 2.57 (t, 2H, J=7.5 Hz), 3.99 (brs, 1H), 7.10 (brs, 1H), 7.12 (d, 2H, J=6.5 Hz), 7.41 (d, 2H, J=6.5 Hz).

I-123 mp: 197-198° C. $^1$H-NMR ($CDCl_3$) δ ppm: 0.91 (t, 3H, J=7.5 Hz), 1.24-1.40 (m, 2H), 1.39 (s, 9H), 1.50-1.70 (m, 2H), 1.99 (brs, 12H), 2.56 (t, 2H, J=7.5 Hz), 3.47 (brs, 1H), 7.10 (s, 1H), 7.11 (d, 2H, J=8.5 Hz), 7.38 (d, 2H, J=8.5 Hz).

I-124 mp: 258-260° C. $^1$H-NMR ($CDCl_3$) δ ppm: 1.20-1.40 (m, 2H), 1.41 (s, 9H), 1.62-1.81 (m, 2H), 2.03-2.35 (m, 5H), 2.37 (s, 3H), 2.71 (s, 3H), 3.32 (m, 1H), 3.64 (d, 1H, J=8.4 Hz), 7.08 (brs, 1H), 7.24 (m, 1H), 7.33 (m, 2H), 7.60 (d, 1H, J=8.1 Hz), 7.77 (s, 1H), 7.80 (d, 1H, J=8.1 Hz), 8.14 (m, 1H).

I-125 mp: 297-299° C. $^1$H-NMR (DMSO-$d_6$) δ ppm: 1.27 (s, 9H), 1.28-1.56 (m, 4H), 1.80-2.01 (m, 4H), 2.47 (m, 1H), 2.76 (brs, 1H), 3.05 (m, 2H), 6.78 (d, 1H, J=9.0 Hz), 7.23 (d, 1H, J=9.0 Hz), 7.46 (dd, 1H, J=2.0, 9.0 Hz), 8.03 (d, 1H, J=2.0 Hz).

I-126 mp: 198-199° C. $^1$H-NMR ($CDCl_3$) δ ppm: 1.18-1.39 (m, 2H), 1.40 (s, 9H), 1.60-1.79 (m, 2H), 1.98-2.35 (m, 5H), 3.30 (m, 1H), 3.67 (d, 1H, J=9.6 Hz), 5.89 (tt, 1H, J=3.0, 50.0 Hz), 6.97 (d, 1H, J=7.8 Hz), 7.21 (s, 1H), 7.30-7.40 (m, 2H), 7.55 (s, 1H)

I-127 mp: 262-264° C. $^1$H-NMR ($CDCl_3$) δ ppm: 1.20-1.39 (m, 2H), 1.41 (s, 9H), 1.60-1.80 (m, 2H), 2.00-2.36 (m, 5H), 2.57 (s, 3H), 3.33 (m, 1H), 3.62 (d, 1H, J=8.7 Hz), 7.28 (brs, 1H), 7.62 (d, 2H, J=8.7 Hz), 7.94 (d, 2H, J=8.7 Hz).

I-128 mp: 252-254° C. $^1$H-NMR ($CDCl_3$) δ ppm: 1.18-1.39 (m, 2H), 1.40 (s, 9H), 1.58-1.79 (m, 2H), 1.99-2.30 (m, 5H), 2.46 (s, 3H), 3.32 (m, 1H), 3.64 (m, 1H), 7.11 (brs, 1H), 7.23 (d, 2H, J=9.0 Hz), 7.44 (d, 2H, J=9.0 Hz).

I-129 mp: >300° C. $^1$H-NMR ($CDCl_3$+$CD_3OD$) δ ppm: 1.30-1.45 (m, 2H), 1.42 (s, 91H), 1.70-1.88 (m, 2H), 2.10-2.37 (m, 4H), 2.52 (m, 1H), 3.34 (m, 1H), 7.43-7.54 (m, 33H), 7.8 (d, 1H, J=6.7 Hz), 7.88 (d, 1H, J=8.5 Hz), 7.98-8.07 (m, 2H), 8.44 (s, 1H), 8.46 (s, 1H).

I-130 mp: 123-124° C. $^1$H-NMR ($CDCl_3$) δ ppm: 1.18-1.34 (m, 2H), 1.40 (s, 9H), 1.62-1.75 (m, 2H), 2.00-2.28 (m, 5H), 3.31 (m, 1H), 3.61 (d, 1H J=9.5 Hz), 5.59 (s, 1H), 7.17 (s, 1H), 7.30-7.37 (m, 6H), 7.41 (d, 1H, J=8.5 Hz), 7.84 (d, 1H, J=2.1 Hz).

I-131 mp: 202-204° C. $^1$H-NMR ($CDCl_3$) δ ppm: 1.27-1.38 (m, 2H), 1.38 (s, 9H), 1.62-1.75 (m, 2H), 1.97-2.04 (m, 2H), 2.18-2.27 (m, 3H), 3.26 (m, 1H), 3.81 (s, 3H), 4.62 (d, 1H, J=7.9 Hz), 7.12 (d, 1H, J=7.8 Hz), 7.40 (t, 1H, J=7.8 Hz), 7.51 (s, 3H), 7.61 (d, 1H, J=7.8 Hz), 7.71 (s, 1H), 8.21 (brs, 1H).

I-132 mp: 236-237° C. $^1$H-NMR ($CDCl_3$) δ ppm: 1.23-1.43 (m, 2H), 1.41 (s, 9H), 1.66-1.80 (m, 2H), 2.08-2.12 (m, 2H), 2.23-2.31 (m, 3H), 3.34 (m, 1H), 3.87 (d, 1H, J=9.5 Hz), 4.02(s, 3H), 7.30 (td, 1H, J=7.3, 1.1 Hz), 7.36 (s, 1H), 7.39 (td, 1H, J=7.3, 1.5 Hz), 7.53 (brd, 1H, J=7.3 Hz), 7.84 (brd, 1H, J=7.3 Hz), 8.05 (s, 1H), 8.73 (s, 1H).

I-133 mp: 198-200° C. $^1$H-NMR ($CDCl_3$) δ ppm: 0.93 (t, 3H, J=7.3 Hz), 0.97 (t, 3H, J=6.7 Hz), 1.18-1.81 (m, 7H), 1.39 (s, 9H), 1.98-2.05 (m, 2H), 2.21-2.24 (m, 3H), 3.29 (m, 1H), 4.00 (dd, 1H, J=10.7, 6.7 Hz), 4.09 (dd, 1H, J=10.7, 6.1 Hz), 4.27 (d, 1H, J=9.8 Hz), 6.37 (d, 1H, J=15.9 Hz), 7.47 (d, 2H, J=8.5 Hz), 7.59 (d, 2H, J=8.5 Hz), 7.62 (d, 1H, J=15.9 Hz), 7.83 (brs, 1H).

I-134 mp: 212-213° C. $^1$H-NMR ($CDCl_3$) δ ppm: 1.21-1.32 (m, 2H), 1.39 (s, 9H), 1.59-1.73 (m, 2H), 1.99-2.04 (m, 2H), 2.10-2.26 (m, 3H), 3.26 (m, 1H), 3.72 (d, 1H, J=9.6 Hz), 6.74 (m, 1H), 7.02 (d, 2H, J=7.4 Hz), 7.11 (t, 1H, J=7.4 Hz), 7.13-7.19 (m, 2H), 7.22-7.26 (m, 2H), 7.34 (t, 2H, J=7.4 Hz).

I-135 mp: 294-296° C. $^1$H-NMR (DMSO-$d_6$) δ ppm: 1.27 (s, 9H), 1.28-1.55 (m, 4H), 1.81-2.05 (m, 4H), 2.26 (m, 1H), 2.98-3.20 (m, 2H), 6.78 (d, 1H, J=9.0 Hz), 7.31 (t, 1H, J=7.5 Hz), 7.54-7.72 (m, 5H), 7.94 (brs, 1H).

I-136 mp: >300° C. $^1$H-NMR (DMSO-$d_6$) δ ppm: 1.28 (s, 9H), 1.29-1.59 (m, 4H), 1.81-2.02 (m, 4H), 2.27 (m, 1H), 3.06 (m, 1H), 6.81 (d, 1H, J=8.7 Hz), 7.38 (t, 1H, J=7.2 Hz), 7.48 (t, 2H, J=7.2 Hz), 7.62-7.81 (m, 10H), 9.93 (brs, 1H).

I-137 mp: 291-292° C. $^1$H-NMR ($CDCl_3$) δ ppm: 1.25-1.39 (m, 2H), 1.41 (s, 9H), 1.61-1.80 (m, 2H), 2.01-2.36 (m, 5H), 3.32 (m, 1H), 3.63 (d, 1H, J=9.3 Hz), 7.20 (brs, 1H), 7.53-7.74 (m, 8H).

I-138 mp: 259-262° C. $^1$H-NMR ($CD_3OD$) δ ppm: 1.40 (s, 9H), 1.40-1.80 (m, 4H), 2.00-2.30 (m, 4H), 2.45 (m, 1H), 3.00 (s, 3H), 3.15-3.30 (m, 2H), 7.90 (d, 1H, J=8.4 Hz), 8.12 (d, 1H, J=9.0 Hz), 8.39 (d, 1H, J=9.0 Hz), 8.72 (s, 1H), 8.92 (d, 1H, J=8.4 Hz), 10.4 (s, 1H).

I-139 mp: 265-268° C. $^1$H-NMR ($CDCl_3$) δ ppm: 1.25-1.40 (m, 2H), 1.40 (s, 9H), 168-1.81 (m, 2H), 2.05-2.10 (m, 2H), 2.23-2.37 (m, 3H), 3.32 (m, 1H), 4.27 (d, 1H, J=9.1 Hz), 7.53 (t, 1H, J=7.9 Hz), 7.63 (td, 1H, J=7.9, 1.4 Hz), 7.77 (d, 1H, J=7.9 Hz), 8.03 (d, 1H, J=7.9 Hz), 8.37 (brs, 1H), 8.85-8.86 (m, 2H).

I-140 mp: 2.58-260° C. $^1$H-NMR ($CDCl_3$) δ ppm: 1.20-1.40 (m, 2H), 1.41 (s, 9H), 1.52-1.85 (m, 2H), 2.03-2.35 (m, 5H), 3.34 (m, 1H), 3.75 (m, 1H), 7.35-7.66 (m, 3H), 8.05 (d, 1H, J=9.0 Hz), 8.11 (d, 1H, J=9.0 Hz), 8.40 (brs, 1H), 8.83 (s, 1H),

I-141 mp: 205-206° C. $^1$H-NMR ($CDCl_3$) δ ppm: 1.20-1.37 (m, 2H), 1.40 (s, 9H), 1.43-1.62 (m, 2H), 1.90-2.01 (m, 2H), 2.02-2.23 (m, 3H), 3.27 (m, 1H), 3.63 (d, 1H, J=9.6 Hz), 3.70 (s, 3H), 6.64 (d, 1H, J=8.8 Hz), 7.28-7.41 (m, 5H), 7.45 (brs, 1H), 8.26 (d, 1H, J=8.8 Hz).

I-142 mp: 277-280° C. $^1$H-NMR ($CDCl_3$) δ ppm: 0.23-0.34 (m, 2H), 1.34 (s, 9H), 1.34-1.55 (m, 5H), 1.76-1.80 (m, 2H), 2.97 (m, 1H), 3.31 (d, 1H, J=9.6 Hz), 7.18 (s, 1H), 7.50-7.59 (m, 4H), 7.77 (dd, 1H, J=7.4, 1.0 Hz), 7.91-7.98 (m, 2H), 8.39 (dd, 1H, J=7.4, 1.9 Hz).

I-143 mp: 202-203° C. $^1$H-NMR ($CDCl_3$) δ ppm: 1.23-1.40 (m, 2H), 1.40 (s, 9H), 1.57-1.71 (m, 2H), 2.05-2.10 (m, 2H), 2.18-2.28 (m, 3H), 3.31 (m, 1H), 3.91 (s, 3H), 3.93 (s, 3H), 4.05 (d, 1H, J=9.5 Hz), 8.15 (s, 1H), 9.56 (s, 1H).

I-144 mp: 177-178° C. $^1$H-NMR ($CDCl_3$) δ ppm: 1.27-1.39 (m, 2H), 1.40 (s, 9H), 1.65-1.79 (m, 2H), 2.04-2.07 (m, 2H), 2.12-2.34 (m, 3H), 3.22 (m, 1H), 3.93 (d, 1H, J=9.1 Hz), 6.90-7.03 (m, 3H), 7.25 (m, 1H), 7.77 (dd, 1H, J=4.9, 1.7 Hz), 7.81 (brs, 1H), 8.72 (dd, 1H, J=7.8, 1.5 Hz).

I-145 mp: >300° C. $^1$H-NMR (DMSO-$d_6$) δ ppm: 1.30 (s, 9H), 1.44-1.70 (m, 4H), 2.05-2.19 (m, 4H), 2.73 (m, 1H), 3.18 (m, 1H), 6.86 (d, 1H, J=8.8 Hz), 7.62 (t, 2H, J=8.5 Hz), 7.86 (t, 2H, J=8.5 Hz), 7.89 (d, 2H, J=8.5 Hz), 8.16 (d, 2H, J=8.5 Hz).

I-146 mp: 240-242° C. $^1$H-NMR (DMSO-$d_6$) δ ppm: 1.26-1.53 (m, 4H), 1.27 (s, 9H), 1.74-1.83 (m, 2H), 1.90-1.97 (m, 2H), 2.26 (m, 1H), 3.04 (m, 1H), 6.59 (brs, 1H), 6.74-6.79 (m, 3H), 7.74 (s, 1H), 10.32 (s, 1H), 12.80 (s, 1H).

I-147 mp: 167-169° C. $^1$H-NMR ($CDCl_3$) δ ppm: 1.05-1.28 (m, 2H), 1.38 (s, 9H), 1.47-1.70 (m, 2H), 1.80-2.00 (m, 3H), 2.13-2.25 (m, 2H), 2.75 (t, 2H, J=6.9 Hz), 3.24 (m, 1H), 3.49 (dt, 2H, J=6.3, 6.9 Hz), 3.58 (d, 1H, J=8.7 Hz), 3.87 (s, 6H), 5.40 (brs, 1H), 6.71 (m, 2H), 6.82 (d, 1H, J=8.7 Hz).

I-148 mp: 171-172° C. $^1$H-NMR($CDCl_3$) δ ppm: 1.16-1.38 (m, 2H), 1.39 (s, 9H), 1.50-1.79 (m, 4H), 1.85-2.02 (m, 3H), 2.15-2.30 (m, 2H), 2.35-2.56 (m, 6H), 3.25 (m, 1H), 3.33 (q, 2H, J=6.0 Hz), 3.63 (d, 1H, J=9.0 Hz), 3.72 (t, 4H, J=4.6 Hz), 6.77 (brs, 1H).

I-149

$^1$H-NMR ($CDCl_3$) δ ppm: 1.20-1.36 (m, 2H), 1.28 (t, 3H, J=7.2 Hz), 1.39 (s, 9H), 1.45-1.70 (m, 2H), 1.85-2.30 (m, 7H), 2,43 (s, 3H), 3.05-3.42 (m, 3H), 3.46-3.80 (m, 3H), 7.31 (d, 1H, J=7.2 Hz), 7.40-7.52 (m, 3H), 8.18 (brs, 1H).

I-150 mp: 203-204° C. $^1$H-NMR ($CDCl_3$) δ ppm: 1.15-1.37 (m, 2H), 1.39 (s, 9H), 1.42-1.70 (m, 2H), 1.85-2.29 (m, 5H), 2.76 (t, 2H, J=6.0 Hz), 3.26 (m, 1H), 3.49 (q, 2H, J=6.0 Hz), 3.61 (m, 1H), 4.03 (s, 2H), 5.88 (brs, 1H), 7.15 (dd, 1H, J=7.0, 8.8 Hz), 7.30-7.35 (m, 2H).

I-151 mp: 181-183° C. $^1$H-NMR ($CDCl_3$) δ ppm: 1.15-1.30 (m, 2H), 1.39 (s, 9H), 1.45-1.64 (m, 2H), 1.88-2.05 (m, 3H), 2.15-2.25 (m, 2H), 2.69 (t, 2H, J=6.0 Hz), 3.28 (m, 1H), 3.47 (q, 2H, J=6.0 Hz), 3.58 (d, 1H, J=9.9 Hz), 3.87 (s, 2H), 5.83 (brs, 1H), 7.00 (m, 1H), 7.20 (m, 2H).

I-152 mp: 222-224° C. $^1$H-NMR ($CDCl_3$) δ ppm: 1.16-1.37 (m, 2H), 1.39 (s, 9H), 1.49-1.70 (m, 2H), 1.90-2.25 (m, 5H), 3.26 (m, 1H), 3.36 (t, 2H, J=6.4 Hz), 3.66 (dt, 3H, J=6.0, 6.4 Hz), 5.87 (t, 1H, J=6.0 Hz), 7.58 (s, 1H), 7.68 (dd, 1H, J=7.0, 8.5 Hz), 7.83 (dd, 1H, J=7.0, 8.5 Hz), 8.19 (t, 2H, J=8.5 Hz).

I-153 mp: 207-209° C. $^1$H-NMR ($CDCl_3$) δ ppm: 1.05-1.25 (m, 2H), 1.38 (s, 9H), 1.40-2.03 (m, 10H), 2.05-2.25 (m, 2H), 2.58 (s, 3H), 2.76 (m, 1H), 3.05-3.35 (m, 2H), 3.97 (d, 1H, J=9.5 Hz), 4.94 (t, 1H, J=4.0 Hz), 8.42 (d, 1H, J=5.5 Hz), 8.97 (d, 1H, J=5.5 Hz).

I-154 mp: 184-185° C. $^1$H-NMR ($CDCl_3$) δ ppm: 1.05-1.25 (m, 2H), 1.37 (s, 9H), 1.50-1.69 (m, 2H), 1.85-2.05 (m, 3H), 2.10-2.21 (m, 2H), 3.24 (m, 1H), 3.64 (m, 1H), 4.87 (s, 1H), 4.88 (s, 1H), 5.67 (brs, 1H), 7.42 (d, 2H, J=5.5 Hz), 7.52 (m, 2H), 7.78 (m, 1H), 7.82 (m, 1H), 7.95 (d, 1H, J=7.0 Hz).

I-155 mp: 208-210° C. $^1$H-NMR (DMSO-$d_6$) δ ppm: 1.26 (s, 9H), 1.27-1.50 (m, 4H), 1.75-2.00 (m, 4H), 2.16 (m, 1H), 2.81 (s, 3H), 3.02 (m, 1H), 6.79 (d, 1H, J=8.5 Hz), 10.00 (s, 1H), 10.66 (s, 1H).

I-156 mp: 256-257° C. $^1$H-NMR ($CDCl_3$) δ ppm: 1.20-1.39 (m, 2H), 1.41 (s, 9H), 1.60-1.81 (m, 2H), 201-2.35 (m, 5H), 2.69 (t, 2H, J=6.0 Hz), 3.11 (t, 2H, J=6.0 Hz), 3.30 (m, 1H), 3.61 (d, 1H, J=9.3 Hz), 7.21 (d, 1H, J=8.0 Hz), 7.31 (s, 1H), 7.70 (d, 1H, J=8.0 Hz), 7.99 (s, 1H).

I-157 mp: 269-271° C. $^1$H-NMR ($CDCl_3$) δ ppm: 1.20-1.45 (m, 2H), 1.41 (s, 9H) 1.70-1.90 (m, 2H), 2.10-2.45 (m, 5H), 3.37 (m, 1H), 3.68 (m, 1H), 7.45 (dd, 1H, J=4.0, 8.0 Hz), 7.53 (brs, 1H), 7.72 (t, 1H, J=8.0 Hz), 7.83 (d, 1H, J=8.0 Hz), 8.02 (d, 1H, J=8.0 Hz), 8.18 (d, 1H, J=8.0 Hz), 8.93 (d, 1H, J=4.0 Hz).

I-158 mp: 253-255° C. $^1$H-NMR ($CDCl_3$) δ ppm: 1.20-1.40 (m, 2H), 1.42 (s, 9H), 1.60-1.90 (m, 2H), 2.06-2.50 (m, 5H), 2.72 (s, 3H), 3.33 (m, 1H), 3.78 (d, 1H, J=9.2 Hz), 7.52 (t, 1H, J=7.0 Hz), 7.62-7.80 (m, 2H), 7.94 (brs, 1H), 8.05 (d, 1H, J=8.5 Hz), 8.20 (s, 1H).

I-159 mp: 253-255° C. $^1$H-NMR ($CDCl_3$) δ ppm: 1.20-1.39 (m, 2H), 1.40 (s, 9H), 1.60-1.80 (m, 2H), 1.98-2.30 (m, 5H), 2.71 (s, 3H), 3.31 (m, 1H), 3.68 (d, 1H, J=9.0 Hz), 7.41 (brs, 1H), 7.61 (d, 2H, J=9.0 Hz), 7.70 (d, 2H, J=9.0 Hz).

I-160 mp: 211-212° C. $^1$H-NMR ($CDCl_3$) δ ppm: 1.20-1.32 (m, 2H), 1.39 (t, 3H, J=7.0 Hz), 1.40 (s, 9H), 1.55-1.79 (m, 2H), 1.98-2.35 (m, 5H), 3.31 (m, 1H), 3.65 (d, 1H, J=9.5 Hz), 4.03 (q, 2H, J=7.0 Hz), 6.64 (d, 1H, J=8.0 Hz), 6.92 (d, 1H, J=8.0 Hz), 7.10 (s, 1H), 7.19 (t, 1H, J=8.0 Hz), 7.30 (brs, 1H).

I-161 mp: 202-203° C. $^1$H-NMR ($CDCl_3$) δ ppm: 0.96 (t, 1H, J=7.3 Hz), 1.29-1.39 (m, 2H), 1.40 (s, 9H), 1.41-1.58 (m, 2H), 1.60-1.80 (m, 4H), 1.98-2.31 (m, 5H), 3.31 (m, 1H), 3.66 (d, 1H, J=8.5 Hz), 3.96 (t, 2H, J=6.4 Hz), 6.64 (d, 1H, J=8.0 Hz), 6.90 (d, 1H, J=8.0 Hz), 7.11 (s, 1H), 7.19 (t, 1H, J=8.0 Hz), 7.31 (brs, 1H).

I-162 mp: 177-180° C. $^1$H-NMR ($CDCl_3$) δ ppm: 1.18-1.38 (m, 2H), 1.39 (s, 9H), 1.59-1.78 (m, 2H), 1.95-2.05 (m, 2H), 2.07-2.25 (m, 3H), 3.26 (m, 1H), 3.46 (s, 3H), 4.17 (d, 1H, J=9.5 Hz), 5.15 (s, 2H), 6.77 (d, 1H, J=8.0 Hz), 7.10-7.23 (m, 2H), 7.34 (s, 1H), 7.58 (s, 1H).

I-163 mp: 175-178° C. $^1$H-NMR (DMSO-$d_6$) δ ppm: 1.27 (s, 9H), 1.28-1.50 (m, 4H), 1.78-2.00 (m, 4H), 2.22 (m, 1H), 2.96-3.15 (m, 2H), 6.67 (m, 1H), 6.79 (d, 1H, J=8.5 Hz), 7.18 (m, 2H), 7.38 (s, 1H), 9.81 (s, 1H).

I-164 mp: 232-233° C. $^1$H-NMR ($CDCl_3$) δ ppm: 0.97 (t, 3H, J=7.3 Hz), 1.22-1.30 (m, 2H), 1.40 (s, 9H), 1.44-1.51 (m, 2H), 1.67-1.77 (m, 4H), 2.02-2.24 (m, 5H), 3.22 (m, 1H), 3.62 (d, 1H, J=9.6 Hz), 4.25 (t, 2H, J=6.8 Hz), 6.71 (d, 1H, J=8.4 Hz), 7.01 (brs, 1H), 7.91 (dd, 1H, J=8.4, 3.3 Hz), 8.08 (d, 1H, J=3.3 Hz).

I-165 mp: 199-200° C. $^1$H-NMR ($CDCl_3$) δ ppm: 0.96 (t, 3H, J=7.4 Hz), 1.24-1.50 (m, 4H), 1.40 (s, 9H), 1.67-1.76 (m, 3H), 2.03-2.08 (m, 2H), 2.24-2.35 (m, 3H), 3.29(m, 1H), 3.76 (d, 1H, J=9.1 Hz), 3.91 (t, 2H, J=6.6 Hz), 6.41 (dd, 1H, J=8.8, 2.5 Hz), 6.55 (d, 1H, J=2.5 Hz), 6.82 (d, 1H, J=8.8 Hz), 7.43 (s, 1H), 8.86 (s, 1H).

I-166 mp: 215-218° C. $^1$H-NMR ($CDCl_3$+$CD_3OD$) δ ppm: 0.97 (t, 3H, J=7.4 Hz), 1.24-1.40 (m, 4H), 1.39 (s, 9H), 1.42-1.50 (m, 2H), 1.54-1.72 (m, 2H), 1.76-1.82 (m, 2H), 1.91-2.00 (m, 2H), 2.06-2.22 (m, 3H), 3.24 (m, 1H), 4.00 (t, 2H, J=6.6 Hz), 6.78 (d, 1H, J=8.8Hz), 6.98 (dd, 1H, J=8.8, 2.5 Hz), 7.09 (d, 1H, J=8.8 Hz).

I-167 mp: 212-213° C. $^1$H-NMR ($CDCl_3$) δ ppm: 0.96 (t, 3H, J=7.5 Hz), 1.26-1.34 (m, 2H), 1.40 (s, 9H), 1.45-1.50 (m, 2H), 1.68-1.77 (m, 4H), 2.03-2.08 (m, 2H), 2.17 (m, 1H), 2.26-2.29 (m, 2H), 3.29 (m, 1H), 3.60 (d, 1H, J=9.0 Hz), 4.25 (t, 2H, J=6.8 Hz), 6.71 (d, 1H, J=8.4 Hz), 7.01 (brs, 1H), 7.91 (dd, 1H, J=8.4, 3.3 Hz), 8.08 (d, 1H, J=3.3 Hz).

I-168 mp: 230-232° C. $^1$H-NMR ($CDCl_3$) δ ppm: 1.22-1.35 (m, 2H), 1.40 (s, 9H), 1.63-1.77 (m, 2H), 2.03-2.08 (m, 2H), 2.15-2.29 (m, 3H), 3.31 (m, 1H), 3.63 (d, 1H, J=9.3 Hz), 6.89 (d, 1H, J=9.4 Hz), 7.10 (brd, 2H, J=7.4 Hz), 7.12 (brs, 1H), 7.18 (t, 1H, J=7.4 Hz), 7.36 (brt, 2H, J=7.4 Hz), 8.09-8.15 (m, 2H).

I-169 mp: 159-160° C. $^1$H-NMR ($CDCl_3$) δ ppm: 0.97 (t, 3H, J=7.3), 1.20-1.35 (m, 2H), 1.40 (s, 9H), 1.37-1.49 (m, 2H), 1.61-1.78 (m, 4H), 2.05-2.08 (m, 2H), 2.23-2.26 (m, 2H), 2.36 (s, 3H), 2.97 (brs, 1H), 3.32 (m, 1H), 3.86 (brs, 1H), 4.30 (t, 2H, J=6.5 Hz), 6.25 (s, 1H), 7.92 (brs, 1H).

I-170 mp: 180-181° C. $^1$H-NMR ($CDCl_3$) δ ppm: 0.88-0.89 (m, 2H), 1.39 (s, 9H), 1.42-1.60 (m, 2H), 1.86-1.90 (m, 2H), 2.04-2.09 (m, 2H), 2.42 (s, 3H), 2.91 (m, 1H), 3.20 (m, 1H), 3.63 (d, 1H, J=9.2 Hz), 6.38 (s, 1H), 7.15 (m, 2H), 7.28 (m, 1H), 7.45 (m, 2H), 7.84 (brs, 1H).

I-171 mp: 173-174° C. $^1$H-NMR ($CDCl_3$) δ ppm: 0.98 (t, 3H, J=7.5 Hz), 1.29-1.40 (m, 2H), 1.40 (s, 9H), 1.55 (m, 2H), 1.62-1.83 (m, 4H), 2.09-2.12 (m, 2H), 2.24-2.32 (m, 3H), 3.32 (m, 1H), 3.63 (d, 1H, J=9.5 Hz), 3.99 (t, 2H, J=6.4 Hz), 7.22 (dd, 1H, J=9.4, 2.7 Hz), 7.66 (d, 1H, J=2.7 Hz), 8.63 (d, 1H, J=9.4 Hz), 10.17 (s, 1H).

I-172 mp: 238-242° C. $^1$H-NMR ($CDCl_3$) δ ppm: 0.96 (t, 3H, J=7.3 Hz), 1.23-1.52 (m, 4H), 1.40 (s, 9H), 1.61-1.78 (m, 4H), 2.05-2.28 (m, 5H), 3.30 (m, 1H), 3.66 (d, 1H, J=9.4 Hz), 3.84 (brs, 2H), 3.90 (t, 2H, J=6.4 Hz), 6.32-6.35 (m, 2H), 6.96 (brs, 1H), 6.97 (d, 1H, J=9.4 Hz).

I-173 mp: 165-166° C. $^1$H-NMR ($CDCl_3$) δ ppm: 1.23-1.26 (m, 2H), 1.40 (s, 9H), 1.67-1.72 (m, 2H), 2.01-2.06 (m, 2H), 2.11-2.28 (m, 3H), 3.31 (m, 1H), 3.60 (s, 2H), 3.69 (s, 3H), 4.02 (brs, 1H), 7.01 (d, 1H, J=8.0 Hz), 7.25 (t, 1H, J=8.0 Hz), 7.43 (d, 1H, J=8.0 Hz), 7.49 (brs, 1H), 7.51 (brs, 1H).

I-174 mp: 264-265° C. $^1$H-NMR ($CDCl_3$+$CD_3OD$) δ ppm: 1.26-1.29 (m, 2H), 1.39 (s, 9H), 1.62-1.69 (m, 2H), 1.96-2.00 (m, 2H), 2.18-2.21 (m, 3H), 3.25 (m, 1H), 3.58 (s, 2H), 7.01 (d, 1H, J=7.5 Hz), 7.26 (t, 1H, J=7.5 Hz), 7.42 (brs, 1H), 7.50 (d, 1H, J=7.5 Hz).

I-175 mp: 90-94° C. $^1$H-NMR ($CDCl_3$) δ ppm: 1.16-1.23 (m, 2H), 1.37 (s, 9H), 1.44-1.56 (m, 2H), 1.73-1.85 (m, 3H), 2.11-2.15 (m, 2H), 3.57 (t, 2H, J=6.4 Hz), 3.21 (m, 1H), 3.58 (m, 2H), 3.84 (d, 1H, J=9.3 Hz), 5.56 (brs, 1H), 7.01 (s, 1.11), 7.11 (t, 1H, J=7.5 Hz), 7.21 (t, 1H, J=7.5 Hz), 7.38 (d, 1H, J=7.5 Hz), 7.59 (d, 1H, J=7.5 Hz), 8.24 (brs, 1H).

I-176 mp: 116-118° C. $^1$H-NMR ($CDCl_3$) δ ppm: 1.18-1.38 (m, 2H), 1.40 (s, 9H), 1.60-1.79 (m, 2H), 1.95-2.30 (m, 5H), 3.30 (m, 1H), 3.69 (m, 1H), 3.80 (s, 3H), 4.64 (s, 2H), 6.67 (d, 1H, J=8.0 Hz), 7.00 (d, 1H, J=8.5 Hz), 7.15-7.24 (m, 2H), 7.32 (brs, 1H).

I-177 mp: 219-220° C. $^1$H-NMR (DMSO-$d_6$) δ ppm: 1.27 (s, 9H), 1.28-1.50 (m, 4H), 1.75-2.01 (m, 4H), 2.18-2.30 (m, 1H), 2.95-3.15 (m, 2H), 4.61 (s, 2H), 6.56 (m, 1H), 6.80 (d, 1H, J=8.5 Hz), 7.16 (m, 2H), 7.28 (brs, 1H), 9.87 (brs, 1H).

I-178 mp: 170-173° C. $^1$H-NMR ($CDCl_3$) δ ppm: 1.18-1.39 (m, 2H), 1.40 (s, 9H), 1.50-1.80 (m, 2H), 1.90-2.33 (m, 5H), 2.36 (s, 6H), 2.75 (t, 2H, J=5.5 Hz), 3.30 (m, 1H), 3.70 (m, 1H), 4.08 (t, 2H, J=5.5 Hz), 6.68 (d, 1H, J=8.0 Hz), 6.94 (d, 1H, J=7.5 Hz), 7.15-7.23 (m, 2H), 7,33 (brs, 1H).

I-179 mp: 191-193° C. $^1$H-NMR ($CDCl_3$) δ ppm: 1.20-1.39 (m, 2H), 1.40 (s, 9H), 1.58-1.80 (m, 2H), 1.98-2.32 (m, 5H), 3.30 (m, 1H), 3.70 (d, 1H, J=9.5 Hz), 4.77 (s, 2H), 6.73 (d, 1H, J=8.0 Hz), 7.04 (d, 1H, J=8.0 Hz), 7.20-7.31 (m, 2H), 7.48 (brs, 1H).

I-180 mp: 174-176° C. $^1$H-NMR ($CDCl_3$) δ ppm: 1.10-1.30 (m, 2H), 1.40 (s, 9H), 1.45-1.65 (m, 2H), 1.81-2.02 (m, 3H), 2.15-2.30 (m, 2H), 2.58 (t, 2H, J=6.5 Hz), 3.25 (m, 1H), 3.37 (dt, 2H, J=5.5, 6.5 Hz), 3.60 (d, 1H, J=9.5 Hz), 3.71 (s, 2H), 5.73 (brs, 1H), 7.20-7.40 (m, 5H).

I-181 mp: 176-178° C. $^1$H-NMR ($CDCl_3$) δ ppm: 1.15-1.30 (m, 2H), 1.39 (s, 9H), 1.45-1.70 (m, 6H), 1.85-2.01 (m, 3H), 2.15-2.28 (m, 2H), 2.63 (t, 2H, J=7.0 Hz), 3.25 (dt, 2H, J=6.0, 7.0 Hz), 3.27 (m, 1H), 3.63 (m, 1H), 5.35 (brs, 1H), 7.17 (m, 3H), 7.29 (m, 2H).

I-182 mp: 152-154° C. $^1$H-NMR ($CDCl_3$) δ ppm: 1.15-1.30 (m, 2H), 1.39 (s, 9H), 1.45-1.65 (m, 2H), 1.85-2.05 (m, 3H), 2.09-2.25 (m, 2H), 3.25 (m, 1H), 3.45 (dt, 2H, J=5.0, 5.0 Hz), 3.55 (t, 2H, J=5.0 Hz), 3.60 (m, 1), 4.51 (s, 2H), 5.81 (brs, 1H), 7.29-7.40 (m, 5H).

I-183 mp: 208-211° C. $^1$H-NMR ($CDCl_3$) δ ppm: 1.20-1.31 (m, 2H), 1.39 (s, 9H), 1.62-1.68 (m, 2H), 1.98-2.25 (m, 5H), 3.30 (m, 1H), 3.57 (d, 1H, J=9.2 Hz), 4.59 (d, 2H, J=5.8 Hz), 5.76(brs, 1H), 7.37 (dd, 1H, J=8.4, 2.0 Hz), 7.46-7.52 (m, 2H), 7.69 (brs, 1H), 7.78-7.83 (m, 3H).

I-184 mp: 180-182° C. $^1$H-NMR ($CDCl_3$) δ ppm: 1.22-1.37 (m, 2H), 1.40 (s, 9H), 1.60-1.69 (m, 2H), 2.05-2.09 (m, 2H), 2.21-2.27 (m, 3H), 3.45 (m, 1H), 3.64 (d, 1H, J=9.6 Hz ), 4.77 (d, 2H, J=4.9 Hz), 7.43 (d, 1H, J=8.6 Hz), 7.46 (brs, 1H), 7.61 (t, 1H, J=7.7 Hz), 7.73 (t, 1H, J=7.7 Hz), 7.87 (t, 1H, J=7.7 Hz), 8.20 (t, 1H, J=7.7 Hz), 8.24 (d, 1H, J=8.6 Hz).

I-185 mp: 260-261° C. $^1$H-NMR ($CDCl_3$) δ ppm: 1.22-1.32 (m, 2H), 1.39 (s, 9H), 1.60-1.70 (m, 2H), 1.97-2.01 (m, 2H), 2.11 (m, 1H), 2.21-2.24 (m, 2H), 3.30 (m, 1H), 3.61 (d, 1H, J=9.3 Hz), 4.95 (d, 2H, J=6.0 Hz), 6.85 (brs, 1H), 7.33 (d, 1H, J=4.8 Hz), 7.62 (dd, 1H, J=8.4, 6.9 Hz), 7.75(dd, 1H, J=8.1, 6.9 Hz), 8.00 (d, 1H, J=8.1 Hz), 8.20 (d, 1H, J=8.4 Hz), 8.42 (d, 1H, J=4.8 Hz).

I-186 mp: 231-233° C. $^1$H-NMR ($CDCl_3$) δ ppm: 1.23-1.40 (m, 2H), 1.40 (s, 9H), 1.62-1.76 (m, 2H), 2.04-2.10 (m, 2H), 2.22-2.32 (m, 3H), 3.30 (m, 1H), 3.95 (d, 1H, J=9.3 Hz), 5.04 (d, 2H, J=4.1 Hz), 7.61 (d, 1H, J=5.8 Hz), 7.63 (brs, 1H), 7.65 (dd, 1H, J=8.2, 6.9 Hz), 7.73 (dd, 1H, J=8.5, 6.9 Hz), 7.86 (d, 1H, J=8.2 Hz), 8.10 (d, 1H, J=8.5 Hz), 8.42 (d, 1H, J=5.8 Hz).

I-187 mp: 184-187° C. $^1$H-NMR ($CDCl_3$) δ ppm: 0.97 (t, 3H, J=7.3 Hz), 1.18-1.30 (m, 2H), 1.39 (s, 9H), 1.42-1.65 (m, 4H), 1.70-1.80 (m, 2H), 1.94-2.08 (m, 3H), 2.18-2.26 (m, 2H), 3.29 (m, 1H), 3.61 (d, 1H, J=9.5 Hz), 3.93 (t, 2H, J=6.4 Hz), 4.39 (d, 2H, J=5.5 Hz), 5.67 (brs, 1H), 6.79-6.83 (m, 3H), 7.23 (t, 1H, J=7.6 Hz).

I-188 mp: 224-226° C. $^1$H-NMR ($CDCl_3$) δ ppm: 16-1.31 (m, 2H), 1.38 (s, 9H), 1.55-1.70 (m, 2H), 1.92-2.07 (m, 3H), 2.17-2.23 (m, 2H), 3.21 (m, 1H), 3.81 (s, 3H), 3.83 (s, 6H), 4.05 (d, 1H, J=9.8 Hz), 4.34 (d, 2H, J=5.8 Hz), 5.96 (brs, 1H), 6.47 (s, 2H).

I-189 mp: 217-218° C. $^1$H-NMR ($CDCl_3$) δ ppm: 1.15-1.30 (m, 2H), 1.37 (s, 9H), 1.52-1.66 (m, 2H), 1.90-2.06 (m, 3H), 2.13-2.20 (m, 2H), 2.93 (s, 6H), 3.24 (m, 1H), 3.94 (d, 1H, J=9.5 Hz), 4.30 (d, 2H, J=5.5 Hz), 5.73 (brs, 1H), 6.69 (d, 2H, J=8.9 Hz), 7.12 (d, 2H, J=8.9 Hz).

I-190 mp: amorphous solid $^1$H-NMR ($CDCl_3$) δ ppm: 1.17-1.32 (m, 2H), 1.39 (s, 9H), 1.54-1.72 (m, 2H), 1.96-2.13 (m, 3H), 2.18-2.27 (m, 2H), 3.30 (m, 1H), 3.63 (d, 1H, J=9.2 Hz), 4.51 (d, 2H, J=5.8 Hz), 5.82 (brs, 1H), 7.40 (d, 2H, J=8.5 Hz), 8.02 (d, 2H, J=8.5 Hz), 8.64 (s, 1H).

I-191 mp: 126-128° C. $^1$H-NMR ($CDCl_3$) δ ppm: 0.97 (t, 3H, J=7.4 Hz), 1.10-1.28 (m, 2H), 1.36 (s, 9H), 1.42-1.86 (m, 9H), 2.06-2.18 (m, 2H), 3.22 (m, 1H), 3.95 (t, 2H, J=4.5 Hz), 4.16 (brs, 1H), 4.85 (s, 2H), 6.82-6.95 (m, 3H), 7.26 (t, 1H, J=7.8 Hz), 8.54 (brs, 1H).

I-192 mp: 178-181° C. $^1$H-NMR ($CDCl_3$) δ ppm: 0.96 (t, 3H, J=7.3 Hz), 1.18-1.52 (m, 4H), 1.39 (s, 9H), 1.58-1.76 (m, 4H), 1.92-2.00 (m, 2H), 2.02-2.29 (m, 3H), 3.28 (m, 1H), 3.78 (d, 1H, J=9.5 Hz), 3.89 (t, 2H, J=6.6 Hz), 6.00 (brs, 1H), 6.78 (s, 4H), 7.35 (brs, 1H).

I-193 mp: 187-188° C. $^1$H-NMR ($CDCl_3$+$CD_3OD$) δ ppm: 1.21-1.40 (m, 2H), 1.38 (s, 9H), 1.52-1.69 (m, 2H), 1.90-2.00 (m, 2H), 2.02-2.20 (m, 3H), 3.22 (m, 1H), 3.75 (s, 3H), 6.79 (s, 4H).

I-194 mp: 251-253° C. $^1$H-NMR (DMSO-$d_6$) δ ppm: 1.27 (s, 9H), 1.24-1.50 (m, 4H), 1.72-1.83(m, 2H), 1.91-1,99 (m, 2H), 2.16 (m, 1H), 3.02 (m, 1H), 3.82 (s, 3H), 6.79 (d, 1H, J=8.2 Hz), 7.01 (d, 2H, J=8.8 Hz), 7.85 (d, 2H, J=8.8 Hz), 9.72 (brs, 1H), 8.64 (brs, 1H).

I-195 mp: 183-185° C. $^1$H-NMR ($CDCl_3$) δ ppm: 1.22-1.37 (m, 2H), 1.40 (s, 9H), 1.58-1.75(m, 2H), 2.05-2.10 (m, 2H), 2.20-2.30 (m, 3H), 3.32 (m, 1H), 3.70 (s, 2H), 3.73 (s, 3H), 6.79 (s, 1H), 8.83 (brs, 1H).

I-196 mp: 185-187° C. $^1$H-NMR ($CDCl_3$) δ ppm: 1.20-1.39 (m, 2H), 1.40 (s, 9H), 1.44 (t, 6H, J=7.0 Hz), 1.60-1.80 (m, 2H), 1.95-2.35 (m, 5H), 3.30 (m, 1H), 3.62 (d, 1H, J=8.9 Hz), 4.06 (q, 2H, J=7.0 Hz), 4.09 (q, 2H, J=7.0 Hz), 6.08 (s, 1H), 7.02 (s, 1H), 7.36 (s, 1H).

I-197 mp: 211-213° C. $^1$H-NMR ($CDCl_3$) δ ppm: 1.20-1.40 (m, 2H), 1.41 (s, 9H), 1.60-1.80 (m, 2H), 2.00-2.36 (m, 5H), 2.61 (s, 3H), 3.32 (m, 1H), 3.64 (d, 1H, J=9.2 Hz), 7.28 (s, 1H), 7.43 (t, 1H, J=7.5 Hz), 7.69 (d, 1H, J=7.5 Hz), 7.85 (d, 1H, J=7.5 Hz), 8.02 (s, 1H).

I-198 mp: 268-269° C. $^1$H-NMR ($CDCl_3$) δ ppm: 1.20-1.39 (m, 2H), 1.40 (s, 9H), 1.42-2.32 (m, 7H), 2.90-3.10 (m, 4H), 3.30 (m, 1H), 3.68 (d, 1H, J=8.8 Hz), 6.59 (s, 1H), 7.18 (d, 1H, J=8.7 Hz), 7.59 (d, 1H, J=8.7 Hz), 7.77 (brs, 1H).

I-199 mp: 221-224° C.

I-200 mp: 237-240° C.

I-201 mp: 87-90° C.

I-202 mp: 222-223° C.

I-203 mp: 255-257° C.

I-204 mp: 234-236° C.

I-205 mp: 208-210° C.

I-206 mp: 217-218° C.

I-207 mp: 275-279° C.

I-208 mp: 248-250° C.

I-209 mp: 256-258° C.

I-210 mp: 270-271° C.

I-211 mp: 219-220° C.

I-212 mp: 260-261° C.

I-213 mp: >300° C.

I-214 mp: 206-207° C.

$^1$H-NMR ($CDCl_3$) δ ppm: 0.93 (t, 3H, J=7.4 Hz), 1.30-1.42 (m, 2H), 1.49 (d, 6H, J=6.9 Hz), 1.53-1.65 (m, 2H), 2.61 (t, 2H, J=7.7 Hz), 4.15 (sept, 1H, J=6.9 Hz), 7.04 (d, 1H, J=8.2 Hz), 7.20 (d, 2H, J=8.2 Hz), 7.51 (d, 2H, J=8.2 Hz), 7.89(d, 1H, J=8.8 Hz), 8.18 (s, 1H), 10.55 (s, 1H).

I-215

$^1$H-NMR ($CDCl_3$) δ ppm: 0.93 (t, 3H, J=7.3 Hz). 1.30-1.41 (m, 2H), 1.52-1.63 (m, 2H), 1.95 (s, 6H), 2.61 (t, 2H, J=7.8 Hz), 6.99 (brs, 1H), 7.20 (d, 2H, J=8.5 Hz), 765 (d, 2H, J=8.5 Hz), 7.93 (dd, 1H, J=8.5, 2.5 Hz), 8.28 (d, 1H, J=8.5 Hz), 8.55 (d, 1H, J=2.5 Hz), 9.76 (brs, 1H).

Ia-1 mp 221-224° C. $^1$H-NMR ($CDCl_3$) δ ppm: 1.19-1.38 (m, 2H), 1.40 (s, 9H), 1.62-1.77 (m, 2H), 2.00-2.31 (m, 5H), 3.18 (t, 4H, J=4.8 Hz), 3.21-3.38 (m, 1H), 3.85 (t, 4H, J=4.8 Hz), 6.64-6.32 (m, 2H), 7.11 (s, 1H), 7.20 (t, 1H, J=7.8 Hz), 7.45 (s, 1H).

Ia-3 mp 87-90° C. $^1$H-NMR ($CDCl_3$) δ ppm: 1.25 (d, 6H, J=6.3 Hz), 1.37 (d, 6H, J=6.9 Hz), 1.59-1.70 (m, 2H), 1.76-1.88 (m, 2H), 2.32-2.42 (m, 4H), 3.11-3.23 (m, 3H), 3.39 (d, 2H, J=10.8 Hz), 3.74-3.86 (m, 2H), 4.34 (t, 1H, J=9.0 Hz), 6.86 (d, 2H, J=9.0 Hz), 7.30 (s, 1H), 7.40 (d, 2H, J=9.0 Hz).

Ia-4 mp 233-234° C. $^1$H-NMR ($CDCl_3$) δ ppm: 1.25 (d, 6H, J=6.3 Hz), 1.40 (s, 9H), 1.26-1.37 (m, 2H), 1.62-1.78 (m, 2H), 2.00-2.22 (m, 5H), 2.42 (t, 2H, J=11.7 Hz), 3.20-3.40

(m, 1H), 3.46 (d, 2H, J=10.5 Hz), 3.67 (d, 1H, J=9.3 Hz), 3.72-3.84 (m, 2H), 6.62-6.76 (m, 2H), 7.10 (s, 1H), 7.18 (t, 1H, J=7.8 Hz), 7.42 (s, 1H).

Ia-5 mp 125-126° C. $^1$H-NMR ($CDCl_3$) δ ppm: 1.25 (d, 6H, J=6.3 Hz), 1.40 (s, 9H), 1.59-1.70 (m, 2H), 1.77-1.84 (m, 2H), 2.30-2.46 (m, 4H), 3.24 (q, 2H, J=6.6 Hz), 3.38 (d, 2H, J=11.7 Hz), 3.74-3.88 (m, 2H), 4.08 (t, 1H, J=5.7 Hz), 6.87 (d, 2H, J=8.7 Hz), 7.30 (s, 1H), 7.41 (d, 2H, J=8.7 Hz).

Ia-6 mp 229-2930° C. $^1$H-NMR ($CDCl_3$) δ ppm: 1.25 (d, 6H, J=6.3 Hz), 1.26-1.34 (m, 2H), 1.39 (d, 6H, J=6.9 Hz), 1.61-1.77 (m, 2H), 1.98-1.26 (m, 5H), 2.32-2.46 (m, 2H), 3.15 (quintet, 1H, J=6.6 Hz), 3.22-3.35 (m, 1H), 3.39 (d, 2H, J=11.4 Hz), 3.74-3.92 (m, 2H), 3.88 (d, 1H, J=8.4 Hz), 6.96-6.71 (m, 2H), 7.05 (brs, 1H), 7.39 (d, 2H, J=9.3 Hz).

Ia-7 mp 253-254° C. $^1$H-NMR (DMSO) δ ppm: 1.24-1.60 (m, 4H), 1.27 (s, 9H), 1.77-2.07 (m, 4H), 2.16-2.34 (m, 1H), 2.97-3.15 (m, 1H), 6.78 (d, 1H, J=7.2 Hz), 7.01 (t, 1H, J=6.0 Hz), 7.27 (t, 2H, J=6.6 Hz), 7.58 (d, 2H, J=7.5 Hz), 9.78 (s, 1H).

Ia-8 mp 257-258° C. $^1$H-NMR (DMSO) δ ppm: 1.22-1.54 (m, 4H), 1.27 (s, 9H), 1.77-1.88 (m, 2H), 1.88-2.00 (m, 2H), 2.16-2.34 (m, 1H), 2.23 (s, 3H), 2.92-3.14 (m, 1H), 6.77 (d, 1H, J=8.4 Hz), 7.07 (d, 2H, J=8.4 Hz), 7.46 (d, 2H, J=8.1 Hz), 9.68 (s, 1H).

Ia-9 mp 231-232° C. $^1$H-NMR ($CDCl_3$) δ ppm: 1.21 (t, 3H, J=7.5 Hz), 1.22-1.38 (m, 2H), 1.40 (s, 9H), 1.62-1.78 (m, 2H), 1.98-2.31 (m, 5H), 2.61 (q, 2H, J=7.5 Hz), 3.24-3.38 (m, 1H), 3.70 (d, 1H, J=9.9 Hz), 7.11 (s, 1H), 7.14 (d, 2H, J=8.7 Hz), 7.40 (d, 2H, J=8.7 Hz).

Ia-10 mp 233-234° C. $^1$H-NMR ($CDCl_3$) δ ppm: 0.96 (t, 3H, J=7.2 Hz), 1.20-1.37 (m, 2H), 1.40 (s, 9H), 1.56-1.78 (m, 4H), 1.98-2.32 (m, 5H), 2.54 (t, 2H, J=7.2 Hz), 3.23-3.39 (m, 1H), 3.66 (d, 1H, J=9.6 Hz), 7.08 (s, 1H), 7.12 (d, 2H, J=8.4 Hz), 7.39 (d, 2H, J=8.4 Hz).

Ia-11 mp 243-244° C. $^1$H-NMR (CDCl3) δ ppm: 1.22 (d, 6H, J=6.9), 1.22-1.77 (m, 4H), 1.40 (s, 9H), 2.01-2.30 (m, 5H), 2.83-2.92 (m, 1H), 3.24-3.40 (m, 1H), 3.66-3.89 (m, 1H), 7.09 (s, 1H), 7.17 (d, 2H, J=8.4 Hz), 7.41 (d, 2H, J=8.1 Hz).

Ia-12 mp 246-247° C. $^1$H-NMR (CDCl3) δ ppm: 0.80 (t, 3H, J=7.5), 1.20 (d, 3H, J=7.2), 1.26-1.77 (m, 6H), 1.40 (s, 9H), 2.01-2.27 (m, 5H), 2.51-2.60 (m, 1H), 3.20-3.38 (m, 1H), 3.64-3.69 (m, 1H), 7.08 (s, 1H), 7.12 (d, 2H, J=8.4 Hz), 7.41 (d, 2H, J=8.4 Hz).

Ia-13 mp 278-279° C. $^1$H-NMR (CDCl3) δ ppm: 1.22-1.52 (m, 4H), 1.29 (s, 9H), 1.40 (s, 9H), 1.61-1.77 (m, 2H), 2.02-2.30 (m, 5H), 3.20-3.38 (m, 1H), 3.66-3.69 (m, 1H), 7.10 (s, 1H), 7.33 (d, 2H, J=9.0 Hz), 7.42 (d, 2H, J=8.7 Hz).

Ia-14 mp 263-264° C. $^1$H-NMR (DMSO) δ ppm: 1.24-1.51 (m, 4H), 1.27 (s, 9H), 1.82-1.99 (m, 4H), 2.19-2.28 (m, 1H), 2.98-3.12 (m, 1H), 6.78 (d, 1H, J=8.7 Hz), 7.33 (d, 2H, J=8.7 Hz), 7.61 (d, 2H, J=9.0 Hz), 9.94 (s, 1H).

Ia-15 mp 209-210° C. $^1$H-NMR ($CDCl_3$) δ ppm: 1.25 (d, 6H, J=6.3 Hz), 1.40 (s, 9H), 1.70-1.98 (m, 8H), 2.19-2.38 (m, 3H), 3.39 (d, 2H, J=11.7 Hz), 3.58-3.92 (m, 3H), 4.12-4.26 (m, 1H), 6.82-6.96 (m, 2H), 7.10 (br, 1H), 7.41 (d, 2H, J=8.1 Hz).

Ia-16 mp 238-240° C. $^1$H-NMR (DMSO) δ ppm: 1.22-1.52 (m, 4H), 1.27 (s, 9H), 1.81-1.84 (m, 2H), 1.93-1.97 (m, 2H), 2.16-2.23 (m, 1H), 2.95-3.12 (m, 1H), 3.70 (s, 3H), 6.77 (d, 1H, J=8.4 Hz), 6.85 (d, 2H, J=9.0 Hz), 7.48 (d, 2H, J=9.3 Hz), 9.64 (s, 1H).

Ia-17 mp 245-246° C. $^1$H-NMR (DMSO) δ ppm: 1.22-1.52 (m, 4H), 1.27 (s, 9H), 1.83-1.87 (m, 2H), 1.94-1.99 (m, 2H), 2.20-2.28 (m, 1H), 2.98-3.12 (m, 1H), 6.78 (d, 1H, J=8.7 Hz), 7.28 (d, 2H, J=8.7 Hz), 7.69 (d, 2H, J=9.0 Hz), 9.64 (s, 1H).

Ia-18 mp 240-241° C. $^1$H-NMR ($CDCl_3$) δ ppm: 1.22-1.78 (m, 4H), 1.40 (s, 9H), 2.05-2.33 (m, 5H), 3.22-3.44 (m, 1H), 3.64-3.67 (m, 1H), 6.61 (s, 1H), 6.69-6.77 (m, 2H).

Ia-19 mp 240-241° C. $^1$H-NMR($CDCl_3$) δ ppm: 1.24-1.77 (m, 4H), 1.40 (s, 9H), 2.05-2.30 (m, 5H), 3.22-3.38 (m, 1H), 3.70-3.74 (m, 1H), 7.00-7.15 (m, 3H), 7.36 (s, 1H), 8.29-8.31 (m, 1H).

Ia-20 mp 239-240° C. $^1$H-NMR ($CDCl_3$) δ ppm: 1.24-1.78 (m, 4H), 1.40 (s, 9H), 2.02-2.30 (m, 5H), 3.22-3.40 (m, 1H), 3.63-3.66 (m, 1H), 6.89-6.84 (m, 1H), 7.10-7.17 (m, 2H), 7.22-7.34 (m, 1H), 7.48-7.51 (m, 1H).

Ia-21 mp 259-260° C. $^1$H-NMR ($CDCl_3$/DMSO) δ ppm: 1.21 (d, 6H, J=6.0 Hz), 1.22-1.44 (m, 2H), 1,40 (s, 9H), 1.60-1.78 (m, 2H), 1.87-2.03 (m, 2H), 2.08-2.29 (m, 3H), 2.39 (t, 2H, J=10.2 Hz), 3.14-3.32 (m, 1H), 3.19 (d, 2H, J=11.4 Hz), 3.77-3.93 (m, 2H), 5.33 (d, 1H, J=9.0 Hz), 6.84 (dd, 1H, JFH, HH=8.1, 8.1 Hz), 7.20 (d, 1H, J=7.8 Hz), 7.49 (d, 1H, JFH=14.7 Hz), 8.86 (s, 1H).

Ia-22 mp 234-235° C. $^1$H-NMR ($CDCl_3$) δ ppm: 1.20 (d, 6H, J=5.7 Hz), 1.22-1.44 (m, 2H), 1.38 (s, 9H), 1.54-1.76 (m, 2H), 1.94-2.32 (m, 5H), 2.27 (s, 3H), 2.39 (t, 2H, J=10.8 Hz), 2.87 (d, 2H, J=1.14 Hz), 3.20-3.40 (m, 1H), 3.76-3.92 (m, 2H), 3.91 (d, 1H, J=9.3 Hz), 6.93 (d, 1H, J=8.1 Hz), 7.21 (brs, 1H), 7.27 (brs, 1H), 7.36 (brs, 1H).

Ia-23 mp 195-196° C. $^1$H-NMR ($CDCl_3$) δ ppm: 1.20-1.44 (m, 4H), 1.41 (s, 9H), 1.59-1.76 (m, 2H), 2.03-2.14 (m, 2H), 2.15-2.33 (m, 3H), 3.20-3.40 (m, 1H), 3.64 (s, 1H, J=9.0 Hz), 7.19-7.24 (m, 1H), 7.44 (brs, 1H), 7.52-7.63 (m, 2H), 8.17 (d, 1H, J=8.7 Hz).

Ia-24 mp 209-210° C. $^1$H-NMR ($CDCl_3$) δ ppm: 1.22-1.39 (m, 2H), 1.56 (s, 9H), 1.61-1.78 (m, 2H), 2.00-2.12 (m, 2H), 2.17-2.33 (m, 3H), 3.24-3.39 (m, 1H), 3.67 (d, 1H, J=9.6 Hz), 6.90-7.01 (m, 1H), 7.21 (s, 1H), 7.95-8.06 (m, 1H).

Ia-25 mp 278-281° C. $^1$H-NMR (DMSO-$d_6$) δ ppm: 1.10 (d, 6H, J=6.3 Hz), 1.27 (s, 9H), 1.28-1.55 (m, 4H), 1.78-2.00 (m, 4H), 2.11-2.26 (m, 1H), 2.31 (t, 2H, J=11.1 Hz), 3.00-3.10 (m, 1H), 3.08 (d, 1H, J=10.8 Hz), 3.67-3.80 (m, 2H), 6.78 (d, 1H, J=8.7 Hz), 7.08 (d, 1H, J=9.0 Hz), 7.41 (dd, 1H, J=2.4, 8.7 Hz), 7.78 (d, 1H, J=8.7 Hz), 9.85 (s, 1H).

Ia-26 mp 253-255° C. $^1$H-NMR (DMSO-$d_6$) δ ppm: 1.13 (d, 6H, J=6.0 Hz), 1.27 (s, 9H), 1.28-1.52 (m, 4H), 1.78-2.00 (m, 4H), 2.21 (t, 2H, J=11.1 Hz), 2.26-2.36 (m, 1H), 2.96-3.10 (m, 1H), 3.56 (d, 1H, J=12.3 Hz), 3.60-3.72 (m, 2H), 6.66-6.84 (m, 4H), 7.47 (t, 1H, J=9.3 Hz), 9.28 (s, 1H).

Ia-27 mp 223-226° C. $^{1}$H-NMR (DMSO-$d_6$) δ ppm: 1.09 (d, 6H, J=6.3 Hz), 1.27 (s, 9H), 1.28-1.54 (m, 4H), 1.77-2.01 (m, 4H), 2.32 (t, 2H, J=11.1 Hz), 2.32-2.42 (m, 1H), 2.90 (d, 1H, J=11.4 Hz), 2.96-3.12 (m, 1H), 3.76-3.92 (m, 2H), 6.78-6.98 (m, 3H), 7.68 (dd, 1H, J=3.3, 8.7 Hz), 8.84 (s, 1H).

Ia-28 mp 237-238° C. $^{1}$H-NMR ($CDCl_3$) δ ppm: 1.22-1.44 (m, 2H), 1,25 (d, 6H, J=6.3 Hz), 1.40 (s, 9H), 1.61-1.79 (m, 2H), 2.05-2.32 (m, 5H), 2.21 (s, 3H), 2.38 (t, 2H, J=10.2 Hz), 3.22-3.42 (m, 1H), 3.40 (d, 2H, J=11.1 Hz), 3.65 (d, 1H, J=9.3 Hz), 3.72-3.90 (m, 2H), 6.70-6.78 (m, 2H), 6.81 (brs, 1H), 7.50 (d, 1H, J=9.6 Hz).

Ia-29 mp 208-209° C. $^{1}$H-NMR ($CDCl_3$) δ ppm: 1.22 (d, 6H, J=6.0 Hz), 1.23-1.40 (m, 2H), 1.40 (s, 9H), 1.60-1.78 (m, 2H), 2.00-2.16 (m, 2H), 2.14-2.33 (m, 3H), 2.45 (t, 2H, J=11.1 Hz), 3.21 (d, 2H, J=10.8 Hz), 3.24-3.38 (m, 1H), 3.63 (d, 1H, J=9.3 Hz), 3.80-3.94 (m, 2H), 5.33 (d, 1H), J=9.0 Hz), 6.66 (dd, 1H, JFH, HH=6.6, 6.6 Hz), 7.16 (brs, 1H), 7.89 (dd, 1H, JFH, HH=9.0, 9.0 Hz).

Ia-30 mp 284-287° C. $^{1}$H-NMR (DMSO-$d_6$) δ ppm: 1.08 (d, 6H, J=6.0 Hz), 1.26 (s, 9H), 1.28-1.53 (m, 4H), 1.82-2.22 (m, 4H), 2.25-2.39 (m, 1H), 2.78 (t, 2H, J=10.5 Hz), 2.97-3.14 (m, 1H), 3.18 (d, 2H, J=11.4 Hz), 3.65-3.76 (m, 2H), 6.79 (d, 1H, J=8.7 Hz), 9.75 (s, 1H).

Ia-31 mp 200-201° C. $^{1}$H-NMR (CDCl3) δ ppm: 1.22-1.40 (m, 2H), 1.40 (s, 9H), 1.62-1.76 (m, 2H), 2.04-2.32 (m, 5H), 3.22-3.40 (m, 1H), 3.62-3.66 (m, 1H), 7.22-7.24 (m, 1H), 7.38-7.38 (m, 1H), 7.60 (s, 1H), 8.33-8.36 (m, 1H).

Ia-32 mp 260-261° C. $^{1}$H-NMR ($CDCl_3$/DMSO) δ ppm: 1.25-1.42 (m, 2H), 1.38 (s, 9H), 1.64 (q, 2H, J=13.5 Hz), 1.95 (d, 2H, J=12.3 Hz), 2.16 (d, 2H, J=10.5 Hz), 2.18-2.32 (m, 1H), 3.14-3.30 (m, 1H), 5.53 (d, 1H, J=9.0 Hz), 7.31 (d, 1H, J=8.7 Hz), 7.46 (dd, 1H, J=2.4, 8.7 Hz), 7.90 (d, 1H, J=2.1 Hz), 9.35 (s, 1H).

Ia-33 mp 227° C. $^{1}$H-NMR (DMSO-$d_6$) δ ppm: 1.27 (s, 9H), 1.30-1.56 (m, 4H), 1.78-2.01 (m, 2H), 2.12-2.36 (m, 2H), 2.96-3.13 (m, 1H), 3.70 (s, 3H), 3.71 (s, 3H), 6.77 (d, 1H, J=8.7 Hz), 6.85 (d, 1H, J=8.7 Hz), 7.06 (dd, 1H, J=2.4, 8.7 Hz), 7.33 (d, 1H, J=2.4 Hz), 9.65 (s, 1H).

Ia-35 mp 214-216° C. $^{1}$H-NMR ($CDCl_3$) δ ppm: 1.23-1.38 (m, 2H), 1.40 (s, 9H), 1.60-1.76 (m, 2H), 2.00-2.12 (m, 2H), 2.20-2.32 (m, 3H), 3.24-3.39 (m, 1H), 3.68 (d, 1H, J=9.0 Hz), 6.77 (d, 1H, J=8.7 Hz), 7.00 (dd, 1H, J=2.4, 8.7 Hz), 7.77 (s, 1H), 8.45 (d, 1H, J=2.4 Hz).

Ia-36 mp 241-242° C. $^{1}$H-NMR ($CDCl_3$/DMSO) δ ppm: 1.25-1.42 (m, 2H), 1.37 (s, 9H), 1.62 (q, 2H, J=11.7 Hz), 1.93 (d, 2H, J=12.0 Hz), 2.12 (d, 2H, J=10.8 Hz), 2.16-2.30 (m, 1H), 3.12-3.28 (m, 1H), 3.84 (s, 3H), 6.07 (d, 1H, J=8.4 Hz), 6.89 (dd, 1H, JFH, HH=9.3, 9.3 Hz), 7.24 (d, 1H, J=8.7 Hz), 7.55 (d, 1H, JFH=13.5 Hz), 9.32 (s, 1H).

Ia-37 mp 248-249° C. $^{1}$H-NMR ($CDCl_3$) δ ppm: 0.60-0.73 (m, 1H), 0.91 (d, 6H, J=6.6), 1.12-1.40 (m, 2H), 1.40 (s, 9H), 1.54-1.88 (m, 5H), 1.98-2.29 (m, 7H), 3.22-3.37 (m, 1H), 3.51-3.54 (m, 2H), 3.72 (d, 1H, J=9.6), 6.88 (d, 1H, J=8.7), 7.06 (s, 1H), 7.35 (d, 1H, J=9.0).

Ia-38 mp 237-238° C. $^{1}$H-NMR ($CDCl_3$) δ ppm: 1.01 (d, 6H, J=6.6), 1.20-1.40 (m, 2H), 1.40 (s, 9H), 1.60-1.74 (m, 4H), 1.99-2.28 (m, 7H), 2.69-2.82 (m, 2H), 3.02-3.14 (m, 2H), 3.20-3.38 (m, 1H), 3.80-3.90 (m, 1H), 6.83-6.86 (m, 2H), 7.14 (s, 1H), 7.34 (d, 1H, J=8.4).

Ia-39 mp 234-235° C. $^{1}$H-NMR ($CDCl_3$) δ ppm: 1.20-1.36 (m, 2H), 1.40 (s, 9H), 1.60-1.77 (m, 2H), 1.90-2.32 (m, 5H), 3.21-3.39 (m, 1H), 3.65 (d, 1H, J=9.6 Hz), 6.87 (d, 1H, J=8.7 Hz), 7.04 (s, 1H), 7.37 (dd, 1H, J=2.7, 8.7 Hz), 7.56 (d, 1H, J=2.7 Hz).

Ia-40 mp 257-258° C. $^{1}$H-NMR (DMSO-$d_6$) δ ppm: 1.14 (d, 6H, J=6.0 Hz), 1.27 (s, 9H), 1.28-1.53 (m, 4H), 1.78-2.00 (m, 4H), 2.13-2.256 (m, 1H), 2.30 (t, 2H, J=11.7 Hz), 2.97-3.12 (m, 1H), 3.53-3.67 (m, 2H), 4.01 (d, 1H, J=12.3 Hz), 6.80 (dd, 1H, J=3.0, 9.0 Hz), 7.79 (d, 1H, J=9.0 Hz), 8.27 (s, 1H), 9.66 (s, 1H).

Ia-41 mp 245-246° C. $^{1}$H-NMR ($CDCl_3$/DMSO) δ ppm: 1.25-1.42 (m, 2H), 1.37 (s, 9H), 1.62 (q, 2H, J=12.6 Hz), 1.94 (d, 2H, J=11.1 Hz), 2.13 (d, 2H, J=11.1 Hz), 2.18-2.35 (m, 1H), 3.11-3.29 (m, 1H), 6.07 (d, 1H, J=8.1 Hz), 6.95-7.06 (m, 1H), 7.14-7.27 (m, 1H), 7.44 (d, 1H, J=7.2 Hz), 7.79 (s, 1H), 9.48 (s, 1H).

Ia-43 mp 294-295° C. $^{1}$H-NMR (DMSO-$d_6$) δ ppm: 1.26 (s, 9H), 1.28-1.53 (m, 4H), 1.76-1.87 (m, 2H), 1.89-2.00 (m, 2H), 2.13-2.25 (m, 1H), 2.96-3.10 (m, 5H), 3.52-3.60 (m, 4H), 6.78 (d, 1H, J=9.0 Hz), 6.88 (d, 2H, J=9.0 Hz), 7.44 (d, 2H, J=9.0 Hz), 9.59 (s, 1H).

Ia-44 mp 250-252° C. $^{1}$H-NMR ($CDCl_3$) δ ppm: 1.13 (d, 6H, J=6.3 Hz), 1.21-1.38 (m, 2H), 1.41 (s, 9H), 1.63-1.80 (m, 2H), 1.93 (t, 2H, J=10.8 Hz), 2.00-2.10 (m, 2H), 2.16-2.32 (m, 3H), 3.24-3.39 (m, 1H), 3.54 (d, 2H, J=10.2 Hz), 3.64-3.78 (m, 3H), 7.47 (s, 1H), 7.69 (d, 2H, J=9.0 Hz), 7.73 (d, 2H, J=9.0 Hz).

Ia-45 mp 193° C. $^{1}$H-NMR (DMSO-$d_6$) δ ppm: 1.10 (t, 6H, J=7.2 Hz), 1.26 (s, 9H), 1.28-1.52 (m, 4H), 1.75-1.86 (m, 2H), 1.89-2.01 (m, 2H), 2.10-2.22 (m, 1H), 2.96-3.10 (m, 1H), 3.30-3.52 (m, 12H), 6.60 (d, 2H, J=9.0 Hz), 6.80 (d, 1H, J=9.0 Hz), 7.33 (d, 2H, J=9.0 Hz), 9.46 (s, 1H).

Ia-46 mp >300° C. $^{1}$H-NMR (DMSO-$d_6$) δ ppm: 1.28 (s, 9H), 1.28-1.58 (m, 4H), 1.83-2.04 (m, 4H), 2.23-2.36 (m, 1H), 2.46 (s, 3H), 3.00-3.14 (m, 1H), 6.79 (d, 1H, J=8.7 Hz), 7.34 (d, 1H, J=8.7 Hz), 7.78 (d, 2H, J=8.7 Hz), 7.89 (d, 1H, J=8.4 Hz), 7.91 (s, 1H), 8.00 (d, 2H, J=8.7 Hz), Ia-47 mp 236-237° C. $^{1}$H-NMR ($CDCl_3$) δ ppm: 0.97 (d, 6H, J=6.6 Hz), 1.01 (d, 6H, J=6.6 Hz), 1.20-1.37 (m, 2H), 1.40 (s, 9H), 1.60-1.84 (m, 3H), 1.97-2.31 (m, 5H), 2.50 (t, 1H, J=10.8 Hz), 2.78 (dt, 1H, J=3.3, 11.4 Hz), 3.25-3.38 (m, 1H), 3.45 (d, 1H, J=11.4 Hz), 3.75 (dt, 1H, J=2.4, 11.4 Hz), 4.02 (dt, 1H, J=2.4, 11.4 Hz), 6.88 (d, 2H, J=9.0 Hz), 7.05 (s, 1H), 7.39 (d, 2H, J=9.0 Hz).

Ia-48 mp 228-229° C. $^{1}$H-NMR ($CDCl_3$) δ ppm: 0.88 (t, 6H, J=7.2 Hz), 1.19-1.45 (m, 4H), 1.40 (s, 9H), 1.45-1.76 (m, 4H), 1.76-1.92 (m, 1H), 1.96-2.30 (m, 5H), 2.66-3.20 (m, 3H), 3.20-3.40 (m, 1H), 3.78 (d, 1H, J=9.3 Hz), 3.82 (s, 1H), 6.62-6.98 (m, 2H), 7.09 (brs, 1H), 7.37 (d, 2H, J=7.8 Hz).

Ia-49 mp 262-263° C. $^{1}$H-NMR ($CDCl_3$/DMSO) δ ppm: 1.21 (d, 6H, J=5.7 Hz), 1.26-1.34 (m, 2H), 1.37 (d, 6H, J=5.4 Hz), 1.52-1.76 (m, 2H), 1.85-2.03 (m, 2H), 2.03-2.30 (m, 3H), 2.30-2.53 (m, 2H), 3.02-3.33 (m, 4H), 3.75-3.98 (m, 2H), 5.70 (brs, 1H), 6.73-6.98 (m, 1H), 7.14-7.25 (m, 1H), 7.52 (d, 1H, JFH=13.5 Hz), 8.86 (brs, 1H).

Ia-50 mp 232-233° C. $^1$H-NMR ($CDCl_3$) δ ppm: 1.21 (d, 6H, J=6.3 Hz), 1.22-1.37 (m, 2H), 1.38 (d, 6H, J=6.9 Hz), 1.68 (q, 2H, J=12.6 Hz), 1.98-2.26 (m, 5H), 2.29 (s, 3H), 2.41 (t, 2H, J=10.2 Hz), 2.88 (d, 2H, J=11.1 Hz), 3.15 (septet, 1H, J=6.6 Hz), 3.21-3.37 (m, 1H), 3.77-3.92 (m, 2H), 3.87 (d, 1H, J=7.8 Hz), 6.88-7.06 (m, 3H), 7.35 (s, 1H).

Ia-51 mp 211-212° C. $^1$H-NMR ($CDCl_3$) δ ppm: 1.20-1.42 (m, 2H), 1.26 (d, 6H, J=6.3 Hz), 1.38 (d, 6H, J=6.9 Hz), 1.62-1.78 (m, 2H), 1.99-2.28 (m, 5H), 2.49 (dd, 2H, J=10.5, 10.5 Hz), 3.17 (quint, 1H, J=6.9 Hz), 3.20-3.38 (m, 1H), 3.66-3.99 (m, 2H), 3.90-4.01 (m, 3H), 6.62 (d, 1H, J=9.0 Hz), 7.06 (s, 1H), 7.90 (dd, 1H, J=2.4, 9.0 Hz), 8.09 (d, 1H, J=2.4 Hz).

Ia-52 mp 247-249° C. $^1$H-NMR ($CDCl_3$) δ ppm: 1.21-1.36 (m, 2H), 1.40 (s, 9H) 1.62-1.7 8 (m, 2H), 1.98-2.32 (m, 5H), 2.55 (t, 4H, J=6.0 Hz), 3.23-3.38 (m, 1H), 3.55 (t, 4H, J=6.0 Hz), 3.72 (d, 1H, J=9.6 Hz), 6.94 (d, 2H, J=9.0 Hz), 7.10 (s, 1H), 7.42 (d, 1H, J=9.0 Hz).

Ia-53 mp 234-235° C. $^1$H-NMR ($CDCl_3$) δ ppm: 1.22-1.38 (m, 2H), 1.41 (s, 9H) 1.64-1.80 (m, 2H), 2.00-2.32 (m, 5H), 3.25-3.40 (m, 1H), 3.73 (d, 1H, J=9.3 Hz), 7.43 (s, 1H), 7.48 (t, 2H, J=7.5 Hz), 7.55-7.66 (m, 3H), 7.68-7.89 (m, 4H).

Ia-54 mp 235-236° C. $^1$H-NMR ($CDCl_3$) δ ppm: 1.24-1.39 (m, 2H), 1.25 (d, 6H, J=6.3 Hz), 1.39 (d, 6H, J=6.9 Hz), 1.60-1.80 (m, 2H), 2.00-2.28 (m, 5H), 2.21 (s, 3H), 2.38 (t, 2H, J=10.8 Hz), 3.15 (septet, 1H, J=6.3 Hz), 3.23-3.38 (m, 1H), 3.40 (d, 2H, J=11.7 Hz), 3.72-3.88 (m, 2H), 3.87 (d, 1H, J=9.3 Hz), 6.78-6.86 (m, 3H), 7.50 (d, 1H, J=9.6 Hz).

Ia-55 mp 185-186° C. $^1$H-NMR ($CDCl_3$) δ ppm: 1.14 (d, 6H, J=6.3 Hz), 1.22-1.38 (m, 2H), 1.41 (s, 9H), 1.62-1.78 (m, 2H), 2.02 (t, 2H, J=10.5 Hz), 2.02-2.10 (m, 2H), 2.16-2.31 (m, 3H), 3.24-3.39 (m, 1H), 3.56 (d, 2H, J=9.3 Hz), 3.63-3.80 (m, 3H), 7.46 (dd, 1H, J=1.5, 8.1 Hz), 7.51 (t, 1H, J=8.1 Hz), 7.63 (s, 1H), 7.81 (t, 1H, J=1.8 Hz), 7.98 (dt, 1H, J=1.8, 8.1 Hz).

Ia-56 mp 229-230° C. $^1$H-NMR (DMSO) δ ppm: 1.27 (s, 9H), 1.28-1.54 (m, 4H), 1.38 (s, 6H), 1.78-1.84 (m, 2H), 1.90-2.00 (m, 2H), 2.15-2.30 (m, 1H), 2.97-3.13 (m, 1H), 4.90 (s, 1H), 6.79 (d, 1H, J=9.0 Hz), 7.34 (d, 2H, J=8.7 Hz), 7.48 (d, 2H, J=8.4 Hz), 9.72 (s, 1H).

Ia-57 mp 211-212° C. $^1$H-NMR ($CDCl_3$/DMSO) δ ppm: 1.24-1.40 (m, 2H), 1.38 (s, 9H), 1.57-1.74 (m, 2H), 1.91 (s, 3H), 1.92-2.01 (m, 2H), 2.12-2.24 (m, 2H), 2.51 (brs, 1H), 3.18-3.33 (m, 1H), 4.96 (d, 1H, J=9.3 Hz), 7.16-7.53 (m, 9H), 7.41 (s, 1H).

Ia-58 mp 298-299° C. $^1$H-NMR (DMSO-$d_6$) δ ppm: 1.24 (s, 9H), 1.27 (s, 9H), 1.28-1.54 (m, 4H), 1.75-2.02 (m, 4H), 2.14-2.28 (m, 1H), 2.97-3.11 (m, 1H), 6.78 (d, 1H, J=8.4 Hz), 7.18 (d, 2H, J=9.0 Hz), 7.48 (d, 2H, J=9.0 Hz), 9.46 (s, 1H), 9.76 (s, 1H).

Ia-59 mp 253-254° C. $^1$H-NMR ($CDCl_3$) δ ppm: 1.22-1.40 (m, 2H), 1.41 (s, 9H), 1.65-1.81 (m, 2H), 2.04-2.16 (m, 2H), 2.22-2.36 (m, 2H), 3.24-3.41 (m, 1H), 3.74 (d, 1H, J=9.6 Hz), 7.40-7.54 (m, 3H), 7.88-8.01 (m, 3H), 8.66 (d, 1H, J=1.5 Hz), 9.57 (d, 1H, J=1.2 Hz).

Ia-60 mp 213-214° C. $^1$H-NMR (DMSO) δ ppm: 1.32-1.50 (m, 2H), 1.35 (s, 9H), 1.52-1.70 (m, 2H), 1.88-2.00 (m, 2H), 2.04-2.16 (m, 2H), 2.22-2.38 (m, 1H), 2.65 (s, 3H), 2.99-3.15 (m, 1H), 6.46 (d, 1H, J=9.3 Hz), 7.28 (d, 1H, J=9.0 Hz), 7.81 (s, 1H), 8.20 (s, 1H), 8.47 (s, 1H), 9.89 (s, 1H).

Ia-61 mp 274-275° C. $^1$H-NMR (DMSO) δ ppm: 1.27 (s, 1H), 1.28-1.58 (m, 4H), 1.84-2.08 (m, 4H), 2.22-2.40 (m, 1H), 2.99-3.15 (m, 1H), 3.01 (s, 3H), 6.81 (d, 1H, J=8.1 Hz), 7.78 (d, 2H, J=7.8 Hz), 7.84 (d, 2H, J=8.4 Hz), 8.18 (s, 1H), 10.43 (s, 1H).

Ia-62 mp 235-236° C. $^1$H-NMR ($CDCl_3$) δ ppm: 1.22-1.39 (m, 2H), 1.41 (s, 3H), 1.66-1.80 (m, 2H), 2.01-2.12 (m, 2H), 2.14-2.22 (m, 1H), 2.23-2.34 (m, 2H), 3.24-3.42 (m, 1H), 3.69 (d, 1H, J=9.5 Hz), 6.44 (d, 1H, J=9.3 Hz), 7.27 (brs, 1H), 7.28 (d, 1H, J=9.3 Hz), 7.37 (dd, 1H, J=2.4, 9.0 Hz), 7.68 (d, 1H, J=9.6 Hz), 8.04 (d, 1H, J=2.4 Hz).

Ia-63 mp 277-279° C. $^1$H-NMR (DMSO-$d_6$) δ ppm: 1.27 (s, 9H), 1.28-1.54 (m, 4H), 1.77-2.02 (m, 4H), 2.15-2.29 (m, 1H), 2.90 (s, 3H), 2.96-3.13 (m, 1H), 6.79 (d, 1H, J=8.7 Hz), 7.12 (d, 2H, J=9.0 Hz), 7.54 (d, 2H, J=9.0 Hz), 9.50 (s, 1H), 9.81 (s, 1H).

Ia-64 mp 259-260° C. $^1$H-NMR (DMSO-$d_6$) δ ppm: 1.26 (s, 9H), 1.26-1.50 (m, 4H), 1.74-1.99 (m, 4H), 2.10-2.25 (m, 1H), 2.95-3.10 (m, 1H), 6.78 (d, 1H, J=8.7 Hz), 6.97 (d, 2H, J=9.0 Hz), 7.42 (d, 2H, J=9.0 Hz), 7.50-7.71 (m, 5H), 9.73 (s, 1H), 10.05 (s, 1H).

Ia-65 mp 292-293° C. $^1$H-NMR (DMSO-$d_6$) δ ppm: 1.27 (s, 9H), 1.28-1.54 (m, 4H), 1.62-1.72 (m, 2H), 1.77-1.87 (m, 2H), 1.91-2.10 (m, 4H), 2.13-2.25 (m, 1H), 2.98-3.12 (m, 1H), 3.41-3.52 (m, 2H), 5.09 (s, 1H), 6.79 (d, 1H, J=9.0 Hz), 6.91 (d, 2H, J=9.0 Hz), 7.37 (d, 2H, J=9.0 Hz), 7.42 (d, 2H, J=9.0 Hz), 7.51 (d, 2H, J=9.0 Hz), 9.56 (s, 1H).

Ia-66 mp >300° C. $^1$H-NMR (DMSO-$d_6$) δ ppm: 1.27 (s, 9H), 1.28-1.58 (m, 4H), 1.85-2.02 (m, 4H), 2.40-2.52 (m, 1H), 3.00-3.16 (m, 1H), 6.81 (d, 1H, J=9.0 Hz), 7.50-7.58 (m, 3H), 7.90-7.97 (m, 2H), 12.58 (s, 1H).

Ia-67 mp 199-200° C. $^1$H-NMR (DMSO-$d_6$) δ ppm: 1.14 (d, 6H, J=6.3 Hz), 1.28 (s, 9H), 1.31-1.48 (m, 4H), 1.76-1.88 (m, 2H), 2.17 (t, 2H, J=11.1 Hz), 2.82 (t, 2H, J=11.7 Hz), 3.46 (d, 2H, J=11.4 Hz), 3.20-3.36 (m, 1H), 3.62-3.74 (m, 2H), 4.02 (d, 2H, J=12.9 Hz), 6.83 (d, 2H, J=9.0 Hz), 6.89 (d, 1H, J=8.7 Hz), 7.28 (d, 2H, J=9.0 Hz), 8.27 (s, 1H).

Ia-68 mp 237-239° C. $^1$H-NMR ($CDCl_3$/DMSO) δ ppm: 1.40 (s, 9H), 1.49-1.65 (m, 2H), 1.99-2.10 (m, 2H), 2.95 (t, 2H, J=11.1 Hz), 3.36-3.52 (m, 1H), 4.17 (d, 1H, J=12.9 Hz), 5.84 (d, 1H, J=8.7 Hz), 6.39 (d, 1H, J=9.6 Hz), 7.21 (d, 1H, J=9.3 Hz), 7.51 (dd, 1H, J=2.4, 9.3 Hz), 7.72 (d, 1H, J=9.9 Hz), 7.85 (d, 1H, J=2.7 Hz), 8.04 (s, 1H).

Ia-69 mp 259-260° C. $^1$H-NMR (DMSO) δ ppm: 1.25-1.55 (m, 4H), 1.27 (s, 9H), 1.82-2.05 (m, 4H), 2.22-2.36 (m, 1H), 2.98-3.17 (m, 1H), 4.16 (s, 3H), 6.80 (d, 1H, J=8.4 Hz), 7.77-7.87 (m, 4H), 10.16 (s, 1H).

Ia-70 mp 259-260° C. $^1$H-NMR (DMSO) δ ppm: 1.28 (s, 9H), 1.36-1.56 (m, 2H), 1.80-1.92 (m, 2H), 2.86-3.02 (m, 2H), 3.36-3.52 (m, 1H), 4.04-4.20 (m, 2H), 6.92 (d, 1H, J=7.5 Hz), 7.38-7.58 (m, 3H), 8.00-8.14 (m, 2H), 8.90 (s, 1H), 9.08 (s, 1H), 9.63 (s, 1H).

Ia-71 mp 228-229° C. $^1$H-NMR ($CDCl_3$/DMSO) δ ppm: 1.27-1.42 (m, 2H), 1.38 (s, 9H), 1.57-1.75 (m, 2H), 1.90-2.02 (m, 2H), 2.12-2.34 (m, 3H), 3.14-3.32 (m, 1H), 5.37 (d, 1H, J=9.3 Hz), 7.38-7.43 (m, 3H), 7.46 (d, 2H, J=8.7 Hz), 7.51-7.60 (m, 2H), 7.68 (d, 2H, J=9.0 Hz), 9.33 (s, 1H).

Ia-75 mp 169-170° C. $^1$H-NMR ($CDCl_3$) δ ppm: 0.58-0.72 (m, 1H), 0.80 (d, 3H, J=6.6 Hz), 0.94 (d, 3H, J=6.0 Hz), 1.14-1.35 (m, 3H), 1.39 (s, 9H), 1.48-1.66 (m, 2H), 1.74-2.06 (m, 5H), 2.06-2.44 (m, 6H), 3.18-3.35 (m, 1H), 3.64-3.74 (m, 1H), 4.46-4.60 (m, 1H), 6.98-7.38 (m, 5H).

Ia-76 mp 236-237° C. $^1$H-NMR ($CDCl_3$/DMSO) δ ppm: 1.27-1.42 (m, 2H), 1.38 (d, 6H, J=6.6 Hz), 1.60-1.78 (m, 2H), 1.94-2.06 (m, 2H), 2.12-2.30 (m, 3H), 3.06-3.34 (m, 2H), 5.10 (brs, 1H), 6.41 (d, 1H, J=9.9 Hz), 7.25 (d, 1H, J=8.4 Hz), 7.48 (dd, 1H, J=2.4, 8.7 Hz), 7.68 (d, 1H, J=9.9 Hz), 8.12 (d, 1H, J=2.4 Hz), 8.88 (brs, 1H).

Ia-77 mp 117-118° C. $^1$H-NMR ($CDCl_3$) δ ppm: 1.38 (d, 6H, J=6.9 Hz), 1.65 (quintet, 2H, J=5.4 Hz), 1.75-1.91 (m, 2H), 2.42 (t, 2H, J=7.4 Hz), 3.10-3.24 (m, 3H), 4.77 (brs, 1H), 6.41 (d, 1H, J=9.6 Hz), 7.18-7.26 (m, 1H), 7.48 (dd, 1H, J=1.8, 8.7 Hz), 7.67 (d, 1H, J=9.9 Hz), 8.01 (s, 1H), 8.23 (brs, 1H).

Ia-78 mp 138-139° C. $^1$H-NMR ($CDCl_3$) δ ppm: 1.41 (s, 9H), 1.64 (quintet, 2H, J=6.6 Hz), 1.84 (quintet, 2H, J=7.3 Hz), 2.42 (t, 2H, J=7.5 Hz), 3.26 (q, 2H, J=6.5 Hz), 4.59 (brs, 1H), 6.41 (d, 1H, J=9.3 Hz), 7.23 (d, 1H, J=8.7 Hz), 7.49 (dd, 1H, J=2.4, 9.0 Hz), 7.67 (d, 1H, J=9.9 Hz), 8.03 (d, 1H, J=2.4 Hz), 8.28 (brs, 1H).

Ia-79 mp 289-290° C. $^1$H-NMR (DMSO) δ ppm: 1.24-1.63 (m, 4H), 1.28 (s, 9H), 1.84-2.08 (m, 4H), 2.24-2.41 (m, 1H), 3.00-3.16 (m, 1H), 6.82 (d, 1H, J=8.1 Hz), 7.36-7.60 (m, 5H), 7.86-7.99 (m, 2H), 8.28 (s, 1H), 10.50 (s, 1H).

Ia-80 mp 239-240° C. $^1$H-NMR (DMSO) δ ppm: 1.22 (d, 1H, J=6.6 Hz), 1.23-1.40 (m, 2H), 1.40-1.59 (m, 2H), 1.83-2.04 (m, 4H), 2.23-2.39 (m, 1H), 2.98-3.23 (m, 2H), 7.00 (d, 1H, J=7.8 Hz), 7.36-7.59 (m, 5H), 7.85-7.97 (m, 2H), 8.29 (s, 1H), 10.50 (s, 1H).

Ia-81 mp 205-206° C. $^1$H-NMR ($CDCl_3$/DMSO) δ ppm: 1.40 (s, 9H), 1.66 (quintet, 2H, J=7.0 Hz), 1.85 (quintet, 2H, J=7.2 Hz), 2.45 (t, 2H, J=7.5 Hz), 3.24 (t, 2H, J=6.5 Hz), 5.17 (brs, 1H), 7.36-7.54 (m, 5H), 7.85 (d, 1H, J=8.4 Hz), 8.07 (dd, 1H, J=1.8, 8.1 Hz), 8.23 (d, 1H, J=1.8 Hz), 9.61 (s, 1H).

Ia-82 mp 216-217° C. $^1$H-NMR (DMSO-$d_6$) δ ppm: 1.14 (d, 6H, J=6.3 Hz), 1.22 (d, 6H, J=6.9 Hz), 1.22-1.53 (m, 4H), 1.76-1.98 (m, 2H), 2.21 (t, 2H, J=10.8 Hz), 2.22-2.36 (m, 1H), 2.96-3.20 (m, 2H), 3.57 (d, 2H, J=12.0 Hz), 3.60-3.74 (m, 1H), 6.66-6.85 (m, 2H), 6.98 (d, 1H, J=7.8 Hz), 7.47 (d, 1H, J=8.7 Hz), 9.30 (s, 1H).

Ia-83 mp 118-119° C. $^1$H-NMR (DMSO-$d_6$) δ ppm: 1.41 (d, 6H, J=6.3 Hz), 1.26 (s, 9H), 1.40-1.67 (m, 4H), 2.17-2.36 (m, 3H), 2.97-3.10 (m, 2H), 3.57 (d, 2H, J=12.0 Hz), 3.61-3.74 (m, 1H), 6.67-6.92 (m, 3H), 7.48 (t, 1H, J=9.0 Hz), 9.37 (s, 1H).

Ia-84 mp 265-267° C. $^1$H-NMR (DMSO-$d_6$) δ ppm: 1.21 (d, 6H, J=6.6 Hz), 1.20-1.67 (m, 4H), 1.60-2.30 (m, 9H), 2.99-3.20 (m, 4H), 3.40-3.52 (m, 2H), 5.09 (s, 1H), 6.91 (d, 2H, J=8.7 Hz), 6.98 (d, 1H, J=7.5 Hz), 7.37 (d, 2H, J=8.7 Hz), 7.42 (d, 2H, J=8.7 Hz), 7.51 (d, 2H, J=8.7 Hz), 9.56 (s, 1H).

Ia-85 mp 185-186° C. $^1$H-NMR (DMSO-$d_6$) δ ppm: 1.26 (s, 9H), 1.42-1.72 (m, 6H), 1.96-2.10 (m, 2H), 2.26 (t, 2H, J=6.9 Hz), 2.96-3.12 (m, 4H), 3.41-3.52 (m, 2H), 5.09 (s, 1H), 6.88 (d, 1H, J=8.7 Hz), 6.92 (d, 2H, J=9.0 Hz), 7.37 (d, 2H, J=8.7 Hz), 7.43 (d, 2H, J=9.0 Hz), 7.52 (d, 2H, J=8.7 Hz), 9.63 (s, 1H).

Ia-86 mp 162-164° C. $^1$H-NMR (DMSO-$d_6$) δ ppm: 1.21 (d, 6H, J=6.6 Hz), 1.41-1.73 (m, 6H), 1.96-2.10 (m, 2H), 2.26 (t, 2H, J=7.2 Hz), 2.91-3.20 (m, 5H), 3.42-3.52 (m, 2H), 5.09 (s, 1H), 6.92 (d, 2H, J=9.3 Hz), 6.99 (t, 1H, J=6.0 Hz), 7.37 (d, 2H, J=8.7 Hz), 7.43 (d, 2H, J=9.3 Hz), 7.52 (d, 2H, J=8.7 Hz), 9.64 (s, 1H).

Ia-87 mp 245-247° C. $^1$H-NMR (DMSO-$d_6$) δ ppm: 1.22 (d, 6H, J=6.6 Hz), 1.22-1.58 (m, 4H), 1.81-2.02 (m, 4H), 2.22-2.36 (m, 1H), 3.00-3.20 (m, 2H), 3.01 (s, 3H), 6.99 (d, 1H, J=8.4 Hz), 7.75-7.88 (m, 2H), 8.19 (d, 1H, J=1.2 Hz), 10.43 (s, 1H).

Ia-88 mp 208-209° C. $^1$H-NMR (DMSO-$d_6$) δ ppm: 1.22 (d, 6H, J=6.9 Hz), 1.22-1.55 (m, 4H), 1.75-1.98 (m, 4H), 2.11-2.24 (m, 1H), 2.98-3.20 (m, 2H), 5.96 (s, 2H), 6.82 (d, 1H, J=8.4 Hz), 6.91-7.03 (m, 2H), 7.30 (d, 1H, J=1.8 Hz), 9.72 (s, 1H).

Ia-89 mp 142-143° C. $^1$H-NMR (DMSO-$d_6$) δ ppm: 1.27 (s, 9H), 1.40-1.66 (m, 4H), 2.26 (t, 2H, J=7.5Hz), 3.02 (q, 2H, J=6.6 Hz), 5.96 (s, 2H), 6.82 (d, 1H, J=8.4 Hz), 6.88 (t, 1H, J=8.4 Hz), 6.94 (dd, 1H, J=1.8, 8.4 Hz), 7.30 (d, 1H, J=1.8 Hz), 9.78 (s, 1H).

Ia-90 mp 100° C. $^1$H-NMR (DMSO-$d_6$) δ ppm: 1.20 (d, 6H, J=6.9 Hz), 1.40-1.66 (m, 4H), 2.26 (t, 2H, J=7.5 Hz), 2.89-2.99 (m, 2H), 3.13 (quint, 1H, J=6.6 Hz), 5.96 (s, 2H), 6.83 (d, 1H, J=8.1 Hz), 6.91-7.02 (m, 2H), 7.30 (d, 1H, J=1.8 Hz), 9.78 (s, 1H).

Ia-91 mp 189-190° C. $^1$H-NMR (DMSO-$d_6$) δ ppm: 1.26 (s, 9H), 1.43-1.71 (m, 4H), 2.40 (t, 2H, J=7.5 Hz), 2.97-3.09 (m, 2H), 3.01 (s, 3H), 6.85-6.93 (m, 1H), 7.76-7.88 (m, 2H), 8.20 (d, 1H, J=1.2 Hz), 10.49 (s, 1H).

Ia-104 mp 238-241° C. $^1$H-NMR (DMSO) δ ppm: 1.27 (s, 9H), 1.3-1.5 (m, 4H), 1.8-2.0 (m, 4H), 2.50 (m, 1H), 3.05 (m, 1H), 6.55 (br s, 1H), 6.79 (d, 1H, J=8.2), 7.15 (t, 1H, J=4.8), 8.64 (d, 2H, J=4.8).

Ia-105 mp 232-234° C. $^1$H-NMR (DMSO) δ ppm: 1.26 (s, 9H), 1.2-1.5 (m, 4H), 1.8-2.0 (m, 4H), 2.55 (m, 1H), 3.05 (m, 1H), 6.77 (d, 1H, J=8.7), 9.92 (s, 2H), 10.93 (s, 1H).

Ia-106 mp 226-228° C. $^1$H-NMR (DMSO) δ ppm: 1.28 (s, 9H), 1.22-1.58 (m, 4H), 1.82-2.04 (m, 4H), 2.29 (m, 1H), 3.07 (m, 1H), 6.79 (d, 1H, J=8.7 Hz), 7.61 (d-d, 1H, J=1.8 Hz, 8.7 Hz), 8.04 (d, 1H, J=8.7 Hz), 8.48 (d, 1H, 2.1 Hz), 9.35 (s, 1H), 10.05 (s, 1H).

Ia-107 mp 282-283° C. $^1$H-NMR (DMSO) δ ppm: 1.22-1.57 (m, 4H), 1.27 (s, 9H), 1.80-2.04 (m, 4H), 2.27 (m, 1H), 3.06 (m, 1H), 6.81 (d, 1H, J=8.7 Hz), 7.32 (m, 1H), 7.44 (t, 2H, J=7.5 Hz), 7.57-7.72 (m, 6H), 9.91 (s, 1H).

Ia-108 mp 191-192° C. $^1$H-NMR (DMSO) δ ppm: 1.24-1.58 (m, 4H), 1.28 (s, 9H), 1.86-2.04 (m, 4H), 2.70 (m, 1H), 3.08 (m, 1H), 6.83 (d, 1H, J=8.7 Hz), 7.63-7.79 (m, 2H), 8.31 (d, 1H, J=7.2 Hz), 10.27 (s, 1H).

Ia-109 mp 283-285° C. $^1$H-NMR (DMSO) δ ppm: 1.24-1.60 (m, 4H), 1.28 (s, 9H), 1.87-2.04 (m, 4H), 2.42 (m, 1H), 3.09 (m, 1H), 3.87 (s, 2H), 6.32 (d, 1H, J=8.7 Hz), 7.28-7.43 (m, 3H), 7.60 (d, 2H, J=7.8 Hz), 7.68 (d, 1H, J=7.2 Hz), 7.89 (d, 1H, J=7.5 Hz), 9.48 (s, 1H).

Ia-110 mp 263-265° C. $^1$H-NMR (DMSO) δ ppm: 1.24-1.54 (m, 4H), 1.27 (s, 9H), 1.76-1.87 (m, 2H), 1.89-2.01 (m, 2H), 2.17 (m, 1H), 3.04 (m, 1H), 4.01 (s, 4H), 6.01 (s, 2H), 6.44 (d, 2H, J=8.7 Hz), 6.77 (d, 1H, J=8.7 Hz), 7.39 (d, 2H, J=9.0 Hz), 9.44 (s, 1H).

Ia-111 mp 239-241° C. $^1$H-NMR (DMSO) δ ppm: 1.24-1.54 (m, 4H), 1.27 (s, 9H), 1.62-1.76 (m, 4H), 1.80-2.02 (m, 4H), 2.30 (m, 1H), 2.47-2.59 (m, 2H), 2.66-2.76 (m, 2H), 6.08 (m, 1H), 6.79 (d, 1H, J=9.0 Hz), 6.88 (d, 1H, J=6.9 Hz), 7.02 (t, 1H, J=7.5 Hz), 7.13 (d, 1H, J=7.5 Hz), 8.98 (s, 1H).

Ia-124 mp 247-249° C. $^1$H-NMR (DMSO) δ ppm: 1.15 (d, 6H, J=6.3 Hz), 1.30 (s, 9H), 2.15-2.26 (m, 2H), 3.48-3.57 (m, 2H), 3.63-3.76 (m, 2H), 6.92 (d, 2H, J=8.7 Hz), 7.59 (d, 2H, J=9.0 Hz), 7.38 (d, 2H, J=9.0 Hz), 7.87 (d, 2H, J=8.7 Hz), 9.92 (brs, 1H), 9.98 (brs, 1H).

Ia-125 mp 228-232° C. $^1$H-NMR (DMSO) δ ppm: 1.30 (s, 9H), 1.95-2.08 (m, 2H), 2.77-2.89 (m, 4H), 7.17 (d, 1H, J=8.4 Hz), 7.39 (d, 2H, J=9.0 Hz), 7.42-7.48 (m, 1H), 7.64 (brs, 1H), 7.87 (d, 2H, J=9.0 Hz), 9.99 (brs, 2H).

Ia-126 mp 244-246° C. $^1$H-NMR (DMSO) δ ppm: 1.31 (s, 9H), 7.42 (d, 2H, J=8.4 Hz), 7.81 (d-d, 1H, J=2.1 Hz, 8.7 Hz), 7.93 (d, 2H, J=9.0 Hz), 8.05 (d, 1H, J=9.0 Hz), 8.66 (d, 1H, J=2.1 Hz), 9.29 (s, 1H), 10.05 (brs, 1H), 10.39 (brs, 1H).

Ia-127 mp 238-239° C. $^1$H-NMR (DMSO) δ ppm: 1.30 (s, 9H), 4.18-4.27 (m, 4H), 6.81 (d, 1H, J=8.4 Hz), 7.16 (d-d, 1H, J=2.7 Hz, 9.0 Hz), 7.34-7.42 (m, 3H), 7.85 (d, 2H, J=8.4 Hz), 9.94 (brs, 1H), 9.99 (brs, 1H).

Ia-128 mp 286-287° C. $^1$H-NMR (DMSO) δ ppm: 1.31 (s, 9H), 7.41 (d, 2H, J=8.7 Hz), 7.71 (d, 2H, J=8.4 Hz), 7.91 (d, 2H, J=8.7 Hz), 7.99 (d, 2H, J=8.7 Hz), 10.05 (brs, 1H), 10.44 (brs, 1H).

Ia-129 mp 232-234° C. $^1$H-NMR (DMSO) δ ppm: 1.27 (s, 9H), 1.3-1.5 (m, 4H), 1.8-2.0 (m, 4H), 2.25 (1H, m), 3.07 (m, 1H), 6.80 (d, 1H, J=9.0), 7.37 (d, 1H, J=8.1), 7.53 (t, 1H, J=8.1), 7.75 (t, 1H, J=8.1), 8.12 (s, 1H), 10.16 (s, 1H).

Ia-130 mp 274-277° C. $^1$H-NMR (DMSO) δ ppm: 1.27 (s, 9H), 1.23-1.58 (m, 4H), 1.81-2.03 (m, 4H), 2.28 (m, 1H), 3.07 (m, 1H), 6.80 (d, 1H, J=8.4 Hz), 7.36 (d-d, 1H, J=0.9 Hz, 5.7 Hz), 7.43 (d-d, 1H, J=2.1 Hz, 8.7 Hz), 7.60 (d, 1H, J=5.4 Hz), 7.78 (d, 1H, J=8.7 Hz), 8.40 (d, 1H, 1.8 Hz), 9.97 (brs, 1H).

Ia-131 mp 259-260° C. $^1$H-NMR (DMSO) δ ppm: 1.31 (s, 9H), 7.40 (d, 1H, J=4.8 Hz), 7.41 (d, 2H, J=8.7 Hz), 7.66 (d, 1H, J=5.1 Hz), 7.67 (d-d, 1H, J=1.8 Hz, 8.7 Hz), 7.84 (d, 1H, J=9.0 Hz), 7.92 (d, 2H, J=8.7 Hz), 8.50 (s, 1H), 10.03 (brs, 1H), 10.27 (brs, 1H).

Ia-132 mp 265-266° C. $^1$H-NMR (DMSO) δ ppm: 1.17 (d, 6H, J=6.6 Hz), 1.31 (s, 9H), 4.10 (m, 1H), 7.35-7.46 (m, 3H), 7.54 (d, 1H, J=7.5 Hz), 7.87-7.97 (m, 3H), 8.15 (brs, 1H), 8.20 (d, 1H, J=7.5 Hz), 10.03 (brs, 1H), 10.25 (brs, 1H).

Ia-133 mp 249-250° C. $^1$H-NMR (DMSO) δ ppm: 1.31 (s, 9H), 7.41 (d, 2H, J=8.7 Hz), 7.45 (d, 1H, J=5.4 Hz), 7.67 (d-d, 1H, J=1.8 Hz, 8.7 Hz), 7.76 (d, 1H, J=5.4 Hz), 7.92 (d, 2H, J=8.7 Hz), 7.95 (d, 1H, J=8.1 Hz), 8.39 (d, 1H, J=1.8 Hz), 10.02 (brs, 1H), 10.23 (brs, 1H).

Ia-134 mp 305-306° C. $^1$H-NMR (DMSO) δ ppm: 1.25 (m, 2H), 1.25 (s, 9H), 1.52 (m, 2H), 1.82 (m, 2H), 1.94 (m, 2H), 2.13 (m, 1H), 3.04 (m, 1H), 6.00 (d, 1H, J=8.1), 6.74 (d, 1H, J=8.4), 7.3-7.5 (m, 6H), 7.85 (d, 2H, J=7.5), 8.31 (d, 1H, J=8.4).

Ia-135 mp 220-222° C. $^1$H-NMR (DMSO) δ ppm: 1.27 (s, 9H), 1.3-1.5 (m, 4H), 1.8-2.0 (m, 4H), 2.37 (m, 1H), 3.03 (m, 1H), 6.80 (d, 1H, J=8.7), 7.04 (m, 1H), 7.29 (m, 1H), 7.79 (m, 1H), 9.60 (s, 1H).

Ia-136 mp 263-264° C. $^1$H-NMR (DMSO) δ ppm: 1.27 (s, 9H), 1.3-1.5 (m, 4H), 1.8-2.0 (m, 4H), 2.20 (m, 1H), 3.03 (m, 1H), 6.80 (d, 1H, J=8.4), 6.87 (m, 1H), 7.31 (m, 2H), 10.21 (s, 1H).

Ia-137 mp 260-262° C. $^1$H-NMR (DMSO) δ ppm: 1.27 (s, 9H), 1.3-1.5 (m, 4H), 1.8-2.0 (m, 4H), 2.30 (m, 1H), 3.05 (m, 1H), 6.80 (d, 1H, J=8.4), 7.13 (t, 2H, J=8.1), 7.31 (m, 1H), 9.52 (s, 1H).

Ia-138 mp 270-273° C. $^1$H-NMR (DMSO) δ ppm: 1.27 (s, 9H), 1.3-1.5 (m, 4H), 1.8-2.0 (m, 4H), 2.12 (m, 1H), 3.05 (m, 1H), 6.79 (d, 1H, J=9.0), 7.31 (m, 2H), 7.80 (m, 1H), 10.05 (s, 1H).

Ia-139 mp 267-270° C. $^1$H-NMR (DMSO) δ ppm: 1.30 (s, 9H), 4.05 (s, 4H), 6.04 (s, 2H), 6.51 (d, 2H, J=8.7 Hz), 7.:34 (d, 2H, J=8.4 Hz), 7.54 (d, 2H, J=8.4 Hz), 7.87 (d, 2H, J=8.4 Hz), 9.82 (brs, 1H), 9.97 (brs, 1H).

Ia-140 mp 227-229° C. $^1$H-NMR (DMSO) δ ppm: 1.22 (d, 6H, J=6.6 Hz), 1.20-1.57 (m, 4H), 1.80-2.01 (m, 4H), 2.27 (m, 1H), 2.95-3.22 (m, 2H), 6.99 (d, 1H, J=7.8 Hz), 7.65 (d, 2H, J=8.7 Hz), 7.80 (d, 2H, J=8.4 Hz), 10.18 (brs, 1H).

Ia-141 mp 205-207° C. $^1$H-NMR (DMSO) δ ppm: 1.22 (d, 6H, J=6.9 Hz), 1.20-1.55 (m, 4H), 1.75-2.05 (m, 6H), 2.21 (m, 1H), 2.72-2.85 (m, 4H), 2.93-3.20 (m, 2H), 6.98 (d, 1H, J=8.1 Hz), 7.10 (d, 1H, J=8.1 Hz), 7.26 (d-d, 1H, J=2.1 Hz, 8.1 Hz), 7.51 (s, 1H), 9.67 (brs, 1H).

Ia-142 mp 295-296° C. $^1$H-NMR (DMSO) δ ppm: 1.15 (d, 6H J=6.6), 1.27 (s, 9H), 1.3-1.5 (m, 4H), 1.8-2.0 (m, 4H), 2.27 (m, 1H), 3.05 (m, 1H), 4.07 (m, 1H), 6.80 (d, 1H, J=8.7), 7.64 (d, 2H, J=8.7), 7.79 (d, 2H, J=8.7), 8.06 (d, 2H, J=7.5), 10.01 (s, 1H).

Ia-143 mp 146-147° C. $^1$H-NMR (DMSO) δ ppm: 1.26 (s, 9H), 1.5-1.7 (m, 4H), 2.36 (t, 2H, J=7.8), 3.03 (q, 2H, J=6.3), 6.89 (t, 1H, J=6.3), 7.66 (d, 2H, J=8.4), 7.80 (d, 2H, J=8.4), 10.25 (s, 1H).

Ia-144 mp 138-140° C. $^1$H-NMR (DMSO) δ ppm: 1.21 (d, 6H, J=6.0), 1.4-1.7 (m, 4H), 2.37 (t, 2H, J=7.5), 2.96 (q, 2H, J=6.3), 3.14 (m, 1H), 6.99 (t, 1H, J=5.4), 7.66 (d, 2H, J=7.8), 7.81 (d, 2H, J=7.8), 10.26 (s, 1H).

Ia-145 mp 134-136° C. $^1$H-NMR (DMSO) δ ppm: 1.26 (s, 9H), 1.39 (m, 2H), 1.4-1.7 (m, 4H), 2.28 (t, 2H, J=7.2), 2.79 (m, 1H), 3.02 (q, 2H, J=7.2), 6.88 (t, 1H, J=6.0), 7.10 (t, 1H, J=6.0), 7.51 (s, 1H), 9.73 (s, 1H).

Ia-146 mp 135-137° C. $^1$H-NMR (DMSO) δ ppm: 1.20 (d, 6H, J=6.6), 1.4-1.7 (m, 4H), 1.99 (m, 2H), 2.28 (t, 2H, J=7.2), 2.79 (m, 4H), 2.94 (q, 2H, J=6.3), 3.13 (m, 1H), 6.98 (t, 1H, J=6.9), 7.10 (d, 2H, J=8.1), 7.26 (d, 2H, J=8.1), 7.51 (s, 1H), 9.73 (s, 1H).

Ia-147 mp 206-207° C. $^1$H-NMR (DMSO) δ ppm: 1.29 (s, 9H), 4.54 (d, 2H, J=5.7 Hz), 7.35 (d, 2H, J=9.0 Hz), 7.52 (d, 2H, J=7.8 Hz), 7.69 (d, 2H, J=8.1 Hz), 7.83 (d, 2H, J=8.7 Hz), 9.02 (t, 1H, J=5.7 Hz), 9.97 (brs, 1H).

Ia-148 mp 250-251° C. $^1$H-NMR (DMSO) δ ppm: 1.30 (s, 9H), 7.18 (t, 2H, J=9.3 Hz), 7.40 (d, 2H, J=8.7 Hz), 7.76 (d-d, 2H, J=5.1 Hz, 9.3 Hz), 7.88 (d, 2H, J=9.0 Hz), 10.02 (brs, 1H), 10.17 (brs, 1H).

Ia-149 mp 220-222° C. $^1$H-NMR (DMSO) δ ppm: 1.30 (s, 9H), 3.74 (s, 3H), 6.92 (d, 2H, J=9.0 Hz), 7.38 (d, 2H, J=9.0 Hz), 7.64 (d, 2H, J=9.0 Hz), 7.87 (d, 2H, J=9.0 Hz), 9.99 (s, 2H).

Ia-150 mp 264-266° C. $^1$H-NMR (DMSO) δ ppm: 1.31 (s, 9H), 1.66-1.76 (m, 4H), 2.57-2.66 (m, 2H), 2.71-2.80 (m, 2H), 6.98 (m, 1H), 7.06-7.16 (m, 2H), 7.38 (d, 2H, J=9.0 Hz), 7.90 (d, 2H, J=8.7 Hz), 9.60 (s, 1H), 9.99 (s, 1H).

Ia-151 mp 235-236° C. $^1$H-NMR (DMSO) δ ppm: 1.03-1.39 (m, 5H), 1.27 (s, 9H), 1.55-1.87 (m, 5H), 3.73 (m, 1H), 7.31 (d, 2H, J=8.7 Hz), 7.76 (d, 2H, J=8.4 Hz), 8.01 (d, 1H, J=7.8 Hz), 9.90 (s, 1H).

Ia-152 mp 244-246° C. $^1$H-NMR (DMSO) δ ppm: 0.50-0.72 (m, 4H), 1.27 (s, 9H), 2.81 (m, 1H), 7.31 (d, 2H, J=8.7 Hz), 7.73 (d, 2H, J=8.7 Hz), 8.30 (d, 1H, J=4.2 Hz), 9.91 (brs, 1H).

Ia-153 mp >300° C. $^1$H-NMR (DMSO) δ ppm: 1.06 (m, 6H), 1.27 (s, 9H), 1.2-1.5 (m, 4H), 1.8-2.0 (m, 4H), 2.25 (m, 1H), 2.7 (m, 1H), 3.05 (m, 1H), 3.51 (m, 4H), 4.30 (m, 1H), 6.80 (d, 1H, J=8.4), 7.34 (d, 2H, J=8.4), 7.65 (d, 2H, J=8.4), 10.01 (s, 1H).

Ia-154 mp 247-249° C. $^1$H-NMR (DMSO) δ ppm: 1.05 (m, 6H), 1.27 (s, 9H), 1.2-1.5 (m, 4H), 1.8-2.0 (m, 4H), 2.23 (m, 1H), 2.77 (m, 1H), 3.05 (m, 1H), 3.52 (m, 4H), 4.33 (m, 1H), 6.80 (d, 1H, J=9.0), 7.03 (d, 1H, J=7.8), 7.35 (t, 1H, J=7.8), 7.59 (d, 1H, J=7.8), 7.68 (s, 1H), 9.96 (s, 1H).

Ia-155 mp 258-259° C. $^1$H-NMR (DMSO) δ ppm: 1.25 (m, 2H), 1.50 (m, 2H), 1.86 (m, 2H), 1.99 (m, 2H), 2.28 (m, 1H), 2.93 (s, 3H), 3.10 (m, 1H), 7.02 (d, 1H, J=7.5), 7.65 (d, 2H, J=8.4), 7.80 (d, 2H, J=8.4), 10.20 (s, 1H).

Ia-156 mp 250-253° C. $^1$H-NMR (DMSO) δ ppm: 1.28 (m, 2H), 1.50 (m, 2H), 1.82 (m, 2H), 2.00 (m, 4H), 2.22 (m, 1H), 2.79 (m, 4H), 2.92 (s, 3H), 3.11 (m, 1H), 7.01 (d, 1H, J=(0.1), 7.26 (d, 1H, J=8.1), 7.51 (s, 1H), 9.68 (s, 1H).

Ia-157 mp 259-262° C. $^1$H-NMR (DMSO) δ ppm: 1.13 (d, 6H, J=6.0), 1.25 (m, 2H), 1.50 (m, 2H), 1.80 (m, 2H), 1.95 (m, 2H), 2.17 (m, 3H), 2.92 (s, 3H), 3.10 (m, 1H), 3.70 (m, 2H), 3.68 (m, 2H), 6.86 (d, 2H J=9.3), 7.00 (d, 1H, J=7.2), 7.43 (d, 2H, J=9.3), 9.58 (s, 1H).

Ia-158 mp 298-300° C. $^1$H-NMR (DMSO) δ ppm: 1.31 (s, 9H), 7.30-7.50 (m, 5H), 7.63-7,71 (m, 4H), 7.87 (d, 2H, J=8.7 Hz), 7.91 (d, 2H, J=9.0 Hz), 10.03 (brs, 1H), 10.22 (brs, 1H).

Ia-159 mp 278-281° C. $^1$H-NMR (DMSO) δ ppm: 0.74-1.87 (m, 20H), 1.29 (s, 9H), 3.76 (m, 1H), 7.32 (d, 2H, J=8.4 Hz), 7.75 (d, 2H, J=8.7 Hz), 7.75 (d, 1H, J=8.7 Hz), 7.90 (brs, 1H).

Ia-160 mp 227-228° C. $^1$H-NMR (DMSO) δ ppm: 1.22-1.55 (m, 4H), 1.27 (s, 9H), 1.80-2.02 (m, 4H), 2.23 (m, 1H), 3.06 (m, 1H), 6.78 (d, 1H, J=8.7 Hz), 7.45 (t, 1H, J=9.9 Hz), 7.82 (m, 1H), 8.12 (d-d, 1H, J=2.4 Hz, 6.3 Hz), 10.17 (brs, 1H).

Ia-161 mp 259-260° C. $^1$H-NMR (DMSO) δ ppm: 1.22-1.54 (m, 4H), 1.27 (s, 9H), 1.78-2.01 (m, 4H), 2.16 (s, 3H), 2.21 (m, 1H), 3.05 (m, 1H), 6.77 (d, 1H, J=8.4 Hz), 7.12-7.21 (m, 2H), 7.53 (m, 1H), 9.90 (brs, 1H).

Ia-162 mp 222-226° C. $^1$H-NMR (DMSO) δ ppm: 1.15 (d, 6H, J=6.3 Hz), 1.26 (d, 6H, J=6.9 Hz), 2.16-2.26 (m, 2H), 3.31 (m, 1H), 3.48-3.58 (m, 2H), 3.63-3.76 (m, 2H), 6.92 (d, 2H, J=9.0H), 7.32 (d, 2H, J=8.7 Hz), 7.59 (d, 2H, 9.0 Hz), 7.89 (d, 2H, J=9.0 Hz), 9.92 (s, 1H), 10.13 (brs, 1H).

Ia-163 mp 197-200° C. $^1$H-NMR (DMSO) δ ppm: 1.26 (d, 6H, J=6.3 Hz), 1.95-2.09 (m, 2H), 2.77-2.90 (m, 4H), 3.32 (m, 1H), 7.17 (d, 1H, J=8.1 Hz), 7.32 (d, 2H, J=8.7 Hz), 7.45 (d-d, 1H, J=1.8 Hz, 8.1 Hz), 7.64 (brs, 1H), 7.90 (d, 2H, J=8.7 Hz), 9.99 (brs, 1H), 10.13 (brs, 1H).

Ia-164 mp 145-247° C. $^1$H-NMR (DMSO) δ ppm: 1.27 (s, 9H), 1.3-2.0 (m, 16H), 2.19 (m, 1H), 3.05 (m, 1H), 4.74 (m, 1H), 6.79 (d, 1H, J=9.0), 6.80 (d, 2H, J=9.0), 7.47 (d, 2H, J=9.0), 9.63 (s, 1H).

Ia-165 mp >300° C. $^1$H-NMR (DMSO) δ ppm: 1.03-2.02 (m, 18H), 1.27 (s, 9H), 2.26 (m, 1H), 3.06 (m, 1H), 3.73 (m, 1H), 6.78 (d, 1H, J=8.7 Hz), 7.6:3 (d, 2H, J=9.0 Hz), 7.78 (d, 2H, J=8.7 Hz), 8.02 (d, 1H, J=8.1 Hz), 10.00 (brs, 1H).

Ia-166 mp 200-201° C. $^1$H-NMR (DMSO) δ ppm: 1.03-2.02 (m, 18H), 1.27 (s, 9H), 2.25 (m, 1H) 3.06 (m, 1H), 3.73 (m, 1H), 6.78 (d, 1H, J=8.7 Hz), 7.33 (t, 1H, J=8.1 Hz), 7.46 (d, 1H, J=8.1 Hz), 7.76 (m, 1H), 7.94 (m, 1H), 8.14 (d, 1H, J=8.1 Hz), 9.92 (brs, 1H).

Ia-167 mp 282-285° C. $^1$H-NMR (DMSO) δ ppm: 1.22-1.57 (m, 4H), 1.27 (s, 9H), 1.87-2.03 (m, 4H), 2.49 (m, 1H), 3.07 (m, 1H), 6.83 (d, 1H, J=8.7 Hz), 13.20 (brs, 1H).

Ia-168 mp 120-124° C. $^1$H-NMR (DMSO) δ ppm: 0.94-1.66 (m, 14H), 1.27 (s, 9H), 1.80-2.04 (m, 4H), 2.25 (m, 1H), 2.92

(m, 1H), 3.06 (m, 1H), 6.78 (d, 1H, J=8.7 Hz), 7.42-7.53 (m, 2H), 7.63 (d, 1H, J=7.2 Hz), 7.73 (m, 1H), 8.17 (m, 1H), 10.11 (brs, 1H).

Ia-169 mp 256-257° C. $^{1}$H-NMR (DMSO) δ ppm: 0.93-1.20 (m, 5H), 1.24-1.64 (m, 9H), 1.27 (s, 9H), 1.80-2.02 (m, 4H), 2.27 (m, 1H), 2.87 (m, 1H), 3.06 (m, 1H), 6.79 (d, 1H, J=9.0 Hz), 7.48 (d, 1H, J=7.2 Hz), 7.68-7.79 (m, 4H), 10.17 (brs, 1H).

Ia-171 mp 242-244° C. $^{1}$H-NMR (DMSO) δ ppm: 1.27 (m, 12H), 1.45 (m, 4H), 1.90 (m, 4H), 2.25 (m, 1H), 3.07 (m, 1H), 3.67 (m, 2H), 6.77 (d, 1H, J=8.7), 6.90 (d, 1H, J=7.8), 7.31 (t, 1H, J=7.5), 7.53 (d, 1H, J=7.8), 7.59 (s, 1H), 9.89 (s, 1H).

Ia-172 mp >310° C. $^{1}$H-NMR (DMSO) δ ppm: 1.27 (m, 12H), 1.38 (m, 4H), 1.84 (m, 2H), 1.97 (m, 2H), 2.25 (m, 1H), 3.07 (m, 1H), 3.36 (m, 2H), 6.81 (d, 1H, J=8.7) 7.20 (d, 2H, J=6.7), 7.61 (d, 2H, J=8.7), 9.94 (s, 1H).

Ia-173 mp 279-281° C. $^{1}$H-NMR (DMSO) δ ppm: 1.27 (s, 9H), 1.3-1.5 (m, 4H), 1.83 (m, 6H), 1.93 (m, 2H), 2.21 (m, 1H), 2.36 (m, 2H), 3.05 (m, 1H), 3.54 (m, 2H), 6.79 (d, 1H, J=8.7), 7.16 (d, 2H, J=9.0), 7.56 (d, 2H, J=9.0), 9.83 (s, 1H).

Ia-174 mp 258-262° C. $^{1}$H-NMR (DMSO) δ ppm: 0.29 (m, 2H), 0.53 (m, 2H), 1.20 (m, 1H), 1.27 (s, 9H), 1.3-1.5 (m, 4H), 1.7-2.0 (m, 4H), 2.20 (m, 1H), 3.05 (m, 1H), 3.75 (d, 2H, J=6.9), 6.79 (d, 1H, J=9.0), 6.83 (d, 2H, J=9.0), 7.46 (d, 2H, J=9.0), 9.64 (s, 1H).

Ia-175 mp 246-248° C. $^{1}$H-NMR (DMSO) δ ppm: 1.27 (s, 9H), 1.3-2.0 (m, 18H), 2.19 (m, 1H), 3.04 (m, 1H), 4.23 (m, 1H), 6.79 (d, 1H, J=8.7), 6.84 (d, 2H, J=9.0), 7.45 (d, 2H, J=9.0), 9.64 (s, 1H).

Ia-176 mp 200-202° C. $^{1}$H-NMR (DMSO) δ ppm: 1.27 (s, 9H), 1.3-2.0 (m, 18H), 2.21 (m, 1H), 3.05 (m, 1H), 4.23 (m, 1H), 6.57 (d, 1H, J=6.9), 6.80 (d, 1H, J=9.0), 7.0-7.2 (m, 2H), 7.28 (s, 1H), 9.74 (s, 1H).

Ia-177 mp 266-268° C. $^{1}$H-NMR (DMSO) δ ppm: 1.22-1.56 (m, 4H), 1.27 (s, 9H), 1.79-2.02 (m, 4H), 2.25 (m, 1H), 3.05 (m, 1H), 6.56 (m, 1H), 6.77-6.84 (m, 2H), 7.58-7.71 (m, 5H), 9.92 (brs, 1H).

Ia-178 mp 223-224° C. $^{1}$H-NMR (DMSO) δ ppm: 1.26-1.54 (m, 4H), 1.27 (s, 9H), 1.81-2.02 (m, 4H), 2.45 (m, 1H), 3.06 (m, 1H), 6.80 (d, 1H, J=8.7 Hz), 8.15 (d-d, 1H, J=2.4 Hz, 9.0 Hz), 8.27 (d, 1H, J=9.0 Hz), 8.70 (m, 1H), 10.85 (hrs, 1H).

Ia-179 mp 224-227° C. $^{1}$H-NMR (DMSO) δ ppm: 1.24-1.56 (m, 4H), 1.27 (s, 9H), 1.80-2.03 (m, 4H), 2.27 (m, 1H), 3.06 (m, 1H), 6.80 (d, 1H, J=8.7 Hz), 6.90 (d, 1H, J=1.8 Hz), 7.72-7.84 (m, 4H), 8.60 (d, 1H, J=1.8 Hz), 10.09 (brs, 1H).

Ia-180 mp 226-227° C. $^{1}$H-NMR (DMSO) δ ppm: 0.92 (d, 6H, J=6.6 Hz), 1.26-1.55 (m, 4H), 1.27 (s, 9H), 1.80-2.03 (m, 4H), 2.27 (m, 1H), 3.05 (m, 1H), 3.20 (m, 1H), 6.80 (d, 1H, J=8.7 Hz), 7.42 (d, 1H, J=7.2 Hz), 7.67-7.79 (m, 4H), 10.19 (brs, 1H).

Ia-181 mp 191-192° C. $^{1}$H-NMR (DMSO) δ ppm: 0.95 (d, 6H, J=6.6 Hz), 1.26-1.55 (m, 4H), 1.27 (s, 9H), 1.80-2.03 (m, 4H), 2.25 (m, 1H), 3.06 (m, 1H), 3.23 (m, 1H), 6.80 (d, 1H, J=8.4 Hz), 7.41-7.53 (m, 2H), 7.58 (d, 1H, J=7.2 Hz), 7.73 (m, 1H), 8.18 (m, 1H), 10.13 (brs, 1H).

Ia-182 mp 192-193° C. $^{1}$H-NMR (DMSO) δ ppm: 0.30 (m, 2H), 0.55 (m, 2H), 1.2-1.5 (m, 5H), 1.27 (s, 1H), 1.8-2.0 (m, 4H), 2.20 (m, 1H), 3.04 (m, 1H), 3.75 (d, 2H, J=6.9), 6.58 (m, 1H), 6.79 (d, 1H, J=8.7), 7.0-7.2 (m, 2H), 7.31 (s, 1H), 9.76 (s, 1H).

Ia-183 mp >310° C. $^{1}$H-NMR (DMSO) δ ppm: 1.27 (s, 9H), 1.3-1.5 (m, 4H), 1.82 (m, 2H), 1.97 (m, 2H), 2.04 (m, 2H), 2.39 (m, 1H), 2.46 (t, 2H, J=7.8), 3.07 (m, 1H), 3.79 (t, 2H, J=7.5), 6.79 (d, 1H, J=8.7), 7.56 (m, 4H), 9.80 (s, 1H).

Ia-184 mp 281-283° C. $^{1}$H-NMR (DMSO) δ ppm: 1.24-1.57 (m, 4H), 1.27 (s, 9H), 1.80-2.04 (m, 4H), 2.27 (m, 1H), 3.06 (m, 1H), 6.80 (d, 1H, J=9.0 Hz), 7.33 (s, 1H), 7.75 (d, 2H, J=9.3 Hz), 7.91 (d, 2H, J=8.7 Hz), 8.16 (s, 1H), 10.09 (brs, 1H).

Ia-185 mp 226-227° C. $^{1}$H-NMR (DMSO) δ ppm: 1.24-1.58 (m, 10H), 1.27 (s, 9H), 1.81-2.02 (m, 4H), 2.28 (m, 1H), 2.78-2.88 (m, 4H), 3.06 (m, 1H), 6.80 (d, 1H, J=8.7 Hz), 7.64 (d, 2H, J=8.7 Hz), 7.82 (d, 2H, J=8.7 Hz), 10.25 (brs, 1H).

Ia-186 mp 148-150° C. $^{1}$H-NMR (DMSO) δ ppm: 1.25-1.60 (m, 10H), 1.27 (s, 9H), 1.82-2.03 (m, 4H), 2.24 (m, 1H), 2.82-2.92 (m, 4H), 3.06 (m, 1H), 6.79 (d, 1H, J=8.4 Hz), 7.36 (m, 1H) 7.55 (t, 1H, J=7.8 Hz), 7.84 (m, 1H), 8.06 (m, 1H), 10.18 (brs, 1H).

Ia-187 mp >310° C. $^{1}$H-NMR (DMSO) δ ppm: 1.27 (s, 9H), 1.36 (s, 9H), 1.43 (m, 4H), 1.85 (m, 2H), 1.93 (m, 2H), 2.27 (m, 1H), 3.06 (m, 1H), 6.80 (d, 1H, J=8.7), 7.58 (s, 1H), 7.62 (d, 2H), 7.75 (d, 2H, J=9.0), 10.00 (s, 1H).

Ia-188 mp 285-292° C. $^{1}$H-NMR (DMSO) δ ppm: 0.85 (t, 3H, J=7.5), 1.11 (d, 3H, J=6.3), 1.26 (s, 9H), 1.3-1.6 (m, 6H), 1.85 (m, 2H), 1.95 (m, 2H), 2.27 (m, 1H), 3.06 (m, 1H), 3.90 (m, 1H), 6.80 (d, 1H, J=8.4), 7.64 (d, 2H, J=8.7), 7.79 (d, 2H, J=8.7), 7.99 (d, 1H, J=8.1), 10.02 (s, 1H).

Ia-189 mp 278-281° C. $^{1}$H-NMR (DMSO) δ ppm: 1.27 (s, 9H), 1.2-2.0 (m, 17H), 2.03 (m, 2H) 3.03 (m, 1H), 6.79 (d, 1H, J=8.4), 7.1-7.3 (m, 3H), 7.94 (s, 1H), 9.78 (m, 2H).

Ia-190 mp >310° C. $^{1}$H-NMR (DMSO) δ ppm: 1.1-2.0 (m, 17H), 1.27 (s, 9H), 2.25 (m, 2H), 3.03 (m, 1H), 6.79 (d, 1H, J=8.7), 7.48 (m, 4H), 9.71 (m, 2H).

Ia-191 mp 275-277° C. $^{1}$H-NMR (DMSO) δ ppm: 1.16 (d, 6H, J=6.6 Hz), 1.31 (s, 9H), 4.09 (m, 1H), 7.41 (d, 2H, J=8.7 Hz), 7.84 (s, 4H), 7.90 (d, 2H, J=9.0 Hz), 8.11 (d, 1H, J=7.5 Hz), 10.04 (brs, 1H), 10.30 (brs, 1H).

Ia-192 mp 204-205° C. $^{1}$H-NMR (DMSO) δ ppm: 1.15 (d, 6H, J=6.6 Hz), 1.20-1.56 (m, 4H), 1.22 (d, 6H, J=6.6 Hz), 1.78-2.00 (m, 4H), 2.25 (m, 1H), 2.98-3.22 (m, 2H), 4.06 (m, 1H), 6.99 (d, 1H, J=8.1 Hz), 7.34 (t, 1H, J=8.1 Hz), 7.46 (d, 1H, J=7.8 Hz), 7.75 (m, 1H), 7.96 (m, 1H), 8.17 (d, 1H, J=8.7 Hz), 9.94 (brs, 1H).

Ia-193 mp 285-286° C. $^{1}$H-NMR (DMSO) δ ppm: 1.15 (d, 6H, J=6.6 Hz), 1.20-1.56 (m, 4H), 1.22 (d, 6H, J=6.9 Hz), 1.79-2.00 (m, 4H), 2.26 (m, 1H), 2.97-3.20 (m, 2H), 4.07 (m, 1H), 6.99 (d, 1H, J=7.8 Hz), 7.64 (d, 2H, J=8.7 Hz), 7.79 (d, 2H, J=8.7 Hz), 8.06 (d, 1H, J=7.5 Hz), 10.02 (brs, 1H).

Ia-194 mp 248-250° C. $^{1}$H-NMR (DMSO) δ ppm: 1.22-1.57 (m, 4H), 1.22 (d, 6H, J=6.6 Hz), 1.78-2.00 (m, 4H), 2.25 (m, 1H), 2.98-3.22 (m, 2H), 6.56 (m, 1H), 6.82 (d, 1H, J=3.3 Hz), 6.99 (d, 1H, J=7.8 Hz), 7.58-7.71 (m, 5H), 9.92 (brs, 1H).

Ia-195 mp 271-275° C. $^{1}$H-NMR (DMSO) δ ppm: 1.27 (s, 9H), 1.28-1.56 (m, 4H), 1.80-2.02 (m, 4H), 2.25 (m, 1H), 3.06 (m, 1H), 6.80 (d, 1H, J=9.0 Hz), 7.57 (s, 1H), 7.62-7.74 (m, 4H), 8.39 (s, 1H), 9.99 (brs, 1H).

Ia-196 mp 226-228° C. $^{1}$H-NMR ($CDCl_3$) δ ppm: 0.30 (m, 2H), 1.23 (d, 6H, J=6.9), 1.2-2.0 (m, 4H), 2.20 (m, 1H), 3.10 (m, 2H), 3.76 (d, 2H, J=6.9), 6.83 (d, 2H, J=8.7), 6.99 (d, 1H, J=8.1), 7.46 (d, 2H, J=8.7), 9.65 (s, 1H).

Ia-197 mp 173-175° C. $^{1}$H-NMR (DMSO) δ ppm: 0.31 (m, 2H), 0.56 (m, 2H), 1.22 (d, 6H, J=6.6), 1.2-1.5 (m, 4H), 1.8-2.0 (m, 4H), 2.22 (m, 1H), 3.10 (m, 1H), 3.76 (d, 1H, J=7.2) 6.58 (d, 1H, J=8.1), 7.0-7.2 (m, 2H), 7.32 (s, 1H), 9.78 (s, 1H).

Ia-198 mp 233-235° C. $^{1}$H-NMR (DMSO) δ ppm: 1.25 (d, 6H, J=6.9), 1.2-2.0 (m, 16H), 2.19 (m, 1H), 3.10 (m, 2H), 4.73 (m, 1H), 6.80 (d, 2H, J=8.7), 6.98 (d, 1H, J=7.8), 7.45 (d, 2H, J=8.7), 9.63 (s, 1H).

Ia-199 mp 185-186° C. $^{1}$H-NMR (DMSO) δ ppm: 1.22 (d, 6H, J=6.9), 1.2-2.0 (m, 16H), 2.22 (m, 1H), 3.10 (m, 2H), 4.73 (m, 1H), 6.54 (m, 1H), 7.0-7.2 (m, 2H), 7.3 (s, 1H), 9.75 (s, 1H).

Ia-200 mp 235-237° C. $^{1}$H-NMR (DMSO) δ ppm: 1.27 (s, 9H), 1.3-1.6 (m, 6H), 1.8-2.0 (m, 6H), 2.20 (m, 1H). 3.05 (m, 1H), 3.45 (m, 2H), 3.82 (m, 2H), 4.47 (m, 1H), 6.79 (d, 1H, J=9.0), 6.89 (d, 2H, J=9.0), 7.47 (d, 2H, J=9.0), 9.66 (s, 1H).

Ia-201 mp 300-301° C. $^{1}$H-NMR (DMSO) δ ppm: 1.15 (d, 6H, J=6.6 Hz), 1.26-1.56 (m, 4H), 1.27 (s, 9H), 1.82-2.03 (m, 4H), 2.23 (s, 3H), 2.37 (m, 1H), 3.06 (m, 1H), 4.07 (m, 1H), 6.81 (d, 1H, J=8.7 Hz), 7.52 (d, 1H, J=8.4 Hz), 7.62 (d, 1H, J=8.4 Hz), 7.68 (s, 1H), 8.09 (d, 1H, J=7.5 Hz), 9.22 (brs, 1H).

Ia-202 mp 269-270° C. $^{1}$H-NMR (DMSO) δ ppm: 1.25-1.26 (m, 4H), 1.27 (s, 9H), 1.80-2.03 (m, 4H), 2.25 (m, 1H), 3.07 (m, 1H), 6.80 (d, 1H, J=8.4 Hz), 7.11 (m, 1H), 7.42 (d, 1H, J=3.6 Hz), 7.48 (m, 1H), 7.58 (d, 2H, J=8.7 Hz), 7.64 (d, 2H, J=8.4 Hz), 9.92 (brs, 1H).

Ia-203 mp 271-273° C. $^{1}$H-NMR (DMSO) δ ppm: 1.14-1.54 (m, 9H), 1.26 (s, 9H), 1.63-1.88 (m, 7H), 1.89-2.01 (m, 2H), 2.21 (m, 1H), 2.42 (m, 1H), 3.04 (m, 1H), 6.79 (d, 1H, J=9.0 Hz), 7.11 (d, 2H, J=8.4 Hz), 7.47 (d, 2H, J=8.1 Hz), 9.70 (brs, 1H).

Ia-204 mp 250-251° C. $^{1}$H-NMR (DMSO) δ ppm: 1.22-1.39 (m, 2H), 1.22 (d, 6H, J=6.6 Hz), 1.40-1.57 (m, 2H), 1.80-2.01 (m, 4H), 2.28 (m, 1H), 2.98-3.21 (m, 2H), 7.00 (d, 1H, J=7.8 Hz), 7.34 (s, 1H), 7.75 (d, 2H, J=9.0 Hz), 7.91 (d, 2H, J=8.7 Hz), 8.17 (s, 1H), 10.10 (brs, 1H).

Ia-205 mp 239-240° C. $^{1}$H-NMR (DMSO) δ ppm: 1.27 (s, 9H), 1.2-1.5 (m, 4H), 1.8-2.0 (m, 5H), 2.08 (m, 2H), 3.05 (m, 1H), 3.80 (m, 4H), 4.95 (m, 1H), 6.79 (d, 1H, J=8.7), 6.83 (d, 2H, J=8.7), 7.48 (d, 2H, J=8.7), 9.66 (s, 1H).

Ia-206 mp 236-238° C. $^{1}$H-NMR (DMSO) δ ppm: 1.27 (s, 9H), 1.2-1.7 (m, 8H), 1.8-2.0 (m, 6H), 2.18 (m, 1H), 3.04 (m, 1H), 3.3-3.6 (m, 2H), 3.85 (m, 3H), 6.80 (d, 1H, J=9.0), 6.84 (d, 2H, J=9.0), 7.47 (d, 2H, J=9.0), 9.65 (s, 1H).

Ia-207 mp 224-226° C. $^{1}$H-NMR (DMSO) δ ppm: 1.27 (s, 9H), 1.2-1.5 (m, 4H), 1.8-2.0 (m, 4H), 2.24(m, 1H), 2.39 (m, 2H), 3.06 (m, 1H), 3.50 (t, 2H, J=7.5), 3.70 (t, 2H, J=6.3), 6.78 (d, 1H, J=6.6), 6.83 (m, 1H), 7.25 (m, 1H), 7.27 (m, 1H), 7.54 (s, 1H), 9.61 (s, 1H).

Ia-208 mp 275-277° C. $^{1}$H-NMR (DMSO) δ ppm: 1.27 (s, 9H), 1.3-1.5 (m, 4H), 1.8-2.0 (m, 4H), 2.22 (m, 1H), 2.38 (m, 2H), 3.07 (m, 1H), 3.47 (t, 2H, J=6.9), 3.69 (t, 2H, J=6.6), 6.80 (d, 1H, J=8.7), 7.14 (d, 2H, J=8.4), 7.58 (d, 2H, J=8.4), 9.83 (s, 1H).

Ia-209 mp 214-215° C. $^{1}$H-NMR (DMSO) δ ppm: 1.26-1.56 (m, 4H), 1.27 (s, 9H), 1.80-2.03 (m, 4H), 2.25 (m, 1H), 3.06 (m, 1H), 6.59 (m, 1H), 6.81 (d, 1H, J=8.4 Hz), 6.86 (d, 1H, J=2.7 Hz), 7.28-7.40 (m, 2H), 7.47 (m, 1H), 7.75 (s, 1H), 8.01 (s, 1H), 9.91 (brs, 1H).

Ia-210 mp 272-275° C. $^{1}$H-NMR (DMSO) δ ppm: 1.31 (s, 9H), 6.59 (m, 1H), 6.87 (d, 1H, J=3.3 Hz), 7.41 (d, 2H, J=8.7 Hz), 7.68 (d, 2H, J=8.7 Hz), 7.72 (m, 1H), 7.83 (d, 2H, J=8.7 Hz), 7.90 (d, 2H, J=8.7 Hz), 10.03 (brs, 1H), 10.22 (brs, 1H).

Ia-211 mp 251-255° C. $^{1}$H-NMR (DMSO) δ ppm: 1.31 (s, 9H), 7.36 (s, 1H), 7.41 (d, 2H, J=8.4 Hz), 7.91 (d, 2H, J=8.4 Hz), 7.92-8.00 (m, 4H), 8.19 (s, 1H), 10.06 (brs, 1H), 10.38 (brs, 1H).

Ia-212 mp 241-244° C. $^{1}$H-NMR (DMSO) δ ppm: 1.30 (s, 9H), 1.50-1.78 (m, 6H), 1.81-1.97 (m, 2H), 4.78 (m, 1H), 6.87 (d, 2H, J=9.0 Hz), 7.38 (d, 2H, J=8.7 Hz), 7.61 (d, 2H, J=9.0 Hz), 7.87 (d, 2H, J=8.7 Hz), 9.97 (brs, 1H), 9.99 (brs, 1H).

Ia-213 mp 283-286° C. $^{1}$H-NMR (DMSO) δ ppm: 1.31 (s, 9H), 7.12 (d-d, 1H, J=3.6 Hz, 5.1 Hz), 7.41 (d, 2H, J=9.0 Hz), 7.46 (m, 1H), 7.50 (d-d, 1H, J=1.2 Hz, 5.1 Hz), 7.64 (d, 2H, J=8.7 Hz), 7.82 (d, 2H, J=8.7 Hz), 7.90 (d, 2H, J=9.3 Hz), 10.03 (brs, 1H), 10.22 (brs, 1H).

Ia-216 mp 224-225° C. $^{1}$H-NMR ($CDCl_3$) δ ppm: 1.22 (d, 6H, J=6.9), 1.2-1.5 (m, 4H), 1.8-2.0 (m, 4H), 2.45 (m, 1H), 3.12 (m, 2H), 6.99 (d, 1H, J=8.1), 8.15 (m, 1H), 8.27 (d, 1H, J=9.0), 8.69 (s, 1H), 10.86 (s, 1H).

Ia-219 mp 270-272° C. $^{1}$H-NMR (DMSO) δ ppm: 1.28 (s, 9H), 1.34-1.51 (m, 2H), 1.80-1.92 (m, 2H), 2.83-2.97 (m, 2H), 3.32 (m, 1H), 3.99-4.12 (m 2H), 6.92 (d, 1H, J=8.7 Hz), 7.57 (d, 2H, J=8.7 Hz), 7.68 (d, 2H, J=9.0 Hz), 8.90 (brs, 1H).

Ia-220 mp 187-189° C. $^{1}$H-NMR (DMSO) δ ppm: 1.28 (s, 9H), 1.31-1.51 (m, 2H), 1.78-1.90 (m, 2H), 2.78-2.93 (m, 2H), 3.30 (m, 1H), 3.97-4.09 (m, 2H), 6.90 (d, 1H, J=8.7 Hz), 7.06 (t, 2H, J=9.0 Hz), 7.44 (d-d, 2H, J=4.8 Hz, 9.0 Hz), 8.53 (brs, 1H)

Ia-221 mp 260-262° C. $^{1}$H-NMR(DMSO) δ ppm: 1.12-1.50 (m, 7H), 1.28 (s, 9H), 1.63-1.90 (m, 7H), 2.40 (m, 1H), 2.76-2.91 (m, 2H), 3.28 (m, 1H) 3.96-4.09 (m, 2H), 6.90 (d, 1H, J=8.7 Hz), 7.06 (d, 2H, J=8.4 Hz), 7.32 (d, 2H, J=8.4 Hz), 8.40 (brs, 1H).

Ia-222 mp 265-267° C. $^{1}$H-NMR (DMSO) δ ppm: 1.23 (d, 6H, J=6.6 Hz), 1.31-1.48 (m, 2H), 1.77-1.90 (m, 2H), 2.84-2.98 (m, 2H), 3.16 (m, 1H), 3.33 (m, 1H), 3.96-4.10 (m, 2H), 7.11 (d, 1H, J=7.8 Hz), 7.57 (d, 2H, J=8.7 Hz), 7.67 (d, 2H, J=8.4 Hz), 8.90 (brs, 1H).

Ia-223 mp 183-186° C. $^{1}$H-NMR (DMSO) δ ppm: 1.23 (d, 6H, J=6.9 Hz), 1.28-1.47 (m, 2H), 1.76-1.88 (m, 2H), 2.80-3.16 (m, 2H), 3.16 (m, 1H), 3.32 (m, 1H), 3.94-4.07 (m, 2H), 7.00-7.14 (m, 3H), 7.44 (d-d, 2H, J=4.8 Hz, 9.0 Hz), 8.53 (brs, 1H).

Ia-224 mp 232-234° C. $^{1}$H-NMR (DMSO) δ ppm: 1.12-1.46 (m, 7H), 1.23 (d, 6H, J=6.6 Hz), 1.63-1.87 (m, 7H), 2.40 (m, 1H), 2.78-2.93 (m, 2H), 3.15 (m, 1H), 3.31 (m, 1H), 3.94-4.07 (m, 2H), 7.06 (d, 2H, J=8.4 Hz), 7.09 (d, 1H, J=8.1 Hz), 7.32 (d, 2H, J=8.4 Hz), 8.39 (brs, 1H).

Ia-225 mp 222-224° C. $^{1}$H-NMR (DMSO) δ ppm: 1.28 (s, 9H), 1.30-1.61 (m, 4H), 1.77-1.98 (m, 4H), 2.66-2.90 (m, 2H), 3.28 (m, 1H), 3.40-3.50 (m, 2H), 3.79-3.88 (m, 2H), 3.96-4.08 (m, 2H), 4.44 (m, 1H), 6.85 (d, 2H, J=9.0 Hz), 6.91 (d, 1H, J=9.0 Hz), 7.31 (d, 2H, J=9.3 Hz), 8.34 (brs, 1H).

Ia-226 mp 194-195° C. $^{1}$H-NMR ($CDCl_3$/DMSO) δ ppm: 1.39 (d, 6H, J=7.2 Hz), 1.66 (quintet, 2H, J=6.8 Hz), 1.87 (quintet, 2H, J=7.7 Hz), 2.47 (t, 2H, J=7.5 Hz), 3.11-3.22 (m, 1H), 3.21 (t, 2H, J=6.2 Hz), 5.00 (brs, 1H), 7.35-7.56 (m, 5H), 7.86 (d, 1H, J=8.4 Hz), 8.05 (dd, 1H, J=1.8, 8.1 Hz), 8.20 (d, 1H, J=1.8 Hz), 9.24 (s, 1H).

Ia-227 mp >300° C. $^{1}$H-NMR (DMSO) δ ppm: 1.22 (d, 6H, J=6.3 Hz), 1.20-1.40 (m, 4H), 1.74-2.10 (m, 4H), 2.20-2.40 (m, 1H), 2.39 (s, 3H), 3.00-3.30 (m, 2H), 6.25 (s, 1H) 6.99 (brs, 1H), 7.43-7.57 (m, 1H), 7.71 (d, 1H, J=8.1 Hz), 7.76 (s, 1H), 10.27 (s, 1H).

Ia-228 mp 168-169° C. $^{1}$H-NMR (DMSO) δ ppm: 1.26 (s, 9H), 1.49 (quintet, 2H, J=7.5 Hz), 1.64 (quintet, 2, J=7.4 Hz), 2.38 (t, 2H, J=7.2 Hz), 2.40 (s, 3H), 3.04 (q, 2H, J=6.5 Hz), 6.25 (s, 1H), 6.89 (t, 1H, J=6.0 Hz), 7.48 (dd, 1H, J=1.8, 8.4 Hz), 7.71 (d, 1H, J=8.4 Hz), 7.77 (d, 1H, J=1.8 Hz), 10.33 (s, 1H).

Ia-229 mp 174-175° C. $^{1}$H-NMR (DMSO) δ ppm: 1.21 (d, 6H, J=6.6 Hz), 1.42-1.56 (m, 2H), 1.56-1.70 (m, 2H), 2.33-2.42 (m, 2H), 2.40 (s, 3H), 2.90-3.02 (m, 2H), 3.14 (septet, 1H, J=6.5 Hz), 6.26 (s, 1H), 6.99 (brs, 1H), 7.48 (d, 1H, J=8.4 Hz), 7.71 (d, 1H, J=8.7 Hz), 7.77 (s, 1H), 10.33 (s, 1H).

Ia-230 mp 194-195° C. $^{1}$H-NMR (DMSO) δ ppm: 0.86 (d, 6H, J=6.9 Hz), 1.25-1.65 (m, 4H), 1.27 (s, 9H), 1.81-2.05 (m, 5H), 2.23-2.35 (m, 1H), 2.99-3.15 (m, 1H), 3.36 (d, 2H, J=7.2 Hz), 6.80 (d, 1H, J=8.4 Hz), 7.80 (d, 1H, J=8.4 Hz), 7.87 (d, 1H, J=8.4 Hz), 8.19 (s, 1H), 10.44 (s, 1H).

Ia-231 mp 221-222° C. $^{1}$H-NMR (DMSO) δ ppm: 0.86 (d, 6H, J=6.9 Hz), 1.22-1.40 (m, 2H), 1.23 (d, 6H, J=6.9 Hz), 1.40-1.58 (m, 2H), 1.82-2.04 (m, 5H), 2.22-2.37 (m, 1H), 3,00-3.16 (m, 1H), 3.15 (septet, 1H, J=6.6 Hz), 3.36 (d, 2H, J=7.5 Hz), 6.99 (d, 1H, J=7.5 Hz), 7.80 (d, 1H, J=8.4 Hz), 7.86 (d, 1H, J=8.4 Hz), 8.19 (s, 1H), 10.45 (s, 1H).

Ia-232 mp 196-197° C. $^{1}$H-NMR ($CDCl_3$) δ ppm: 0.93 (d, 6H, J=6.6 Hz), 1.42 (s, 1H), 1.60-1.70 (m, 2H), 1.88 (quintet, 2H, J=7.4 Hz), 2.02-2.20 (m, 1H), 2.46 (t, 2H, J=7.7 Hz), 3.29 (q, 2H, J=6.1 Hz), 3.48 (d, 2H, J=7.8 Hz), 4.26 (t, 1H, J=6.0 Hz), 7.76 (d, 1H, J=8.1 Hz), 7.90 (dd, 1H, J=1.8, 8.1 Hz), 8.07 (d, 1H, J=1.5 Hz), 8.39 (s, 1H).

Ia-233 p. 151-152° C. $^{1}$H-NMR ($CDCl_3$) δ ppm: 0.93 (d, 6H, J=6.6 Hz), 1.40 (d, 6H, J=6.6 Hz), 1.62-1.69 (m, 2H), 1.88 (quintet, 2H, J=7.3 Hz), 2.03-2.16 (m, 1H), 2.47 (t, 2H, J=7.5 Hz), 3.21 (septet, 1H, J=6.8 Hz), 3.23 (q, 2H, J=6.3 Hz), 3.48 (d, 2H, J=7.5 Hz), 4.43 (t, 1H, J=6.0 Hz), 7.76 (d, 1H, J=8,4 Hz), 7.91 (dd, 1H, J=1.8, 8.4 Hz), 8.06 (d, 1H, J=1.8 Hz), 8.36 (s, 1H).

Ia-234 mp 219-220° C. $^{1}$H-NMR (DMSO-$d_6$) δ ppm: 1.28 (s, 9H), 1.30-1.50 (m, 2H), 1.74-1.88 (m, 2H), 2.83 (t, 2H, J=11.1 Hz), 3.20-3.32 (m, 1H), 3.94-4,07 (m, 2H), 5.94 (s, 2H), 6.77 (d, 1H, J=8.8 Hz), 6.82 (dd, 1H, J=1.8, 8.7 Hz), 6.89 (d, 1H, J=8.7 Hz), 7.11 (d, 1H, J=1.8 Hz), 8.38 (s, 1H).

Ia-235 mp 280-282° C. $^{1}$H-NMR (DMSO-d6) δ ppm: 1.27 (s, 9H), 1.26-1.57 (m, 4H), 1.86-2.03 (m, 4H), 2.38-2.50 (m, 1H), 3.00-3.14 (m, 1H), 6.81 (d, 1H, J=8.4 Hz), 7.29 (t, 1H, J=8.4 Hz), 7.43 (t, 1H, J=7.5 Hz), 7.73 (d, 1H, J=8.4 Hz), 7.96 (d, 1H, J=7.5 Hz), 12.27 (s, 1H).

Ia-237 mp 204-205° C. $^{1}$H-NMR (DMSO) δ ppm: 1.23 (d, 6H, J=6.6 Hz), 1.29-1.61 (m, 4H), 1.75-1.98 (m, 4H), 2.78-2.92 (m, 2H), 3.15 (m, 1H), 3.29 (m, 1H), 3.38-3.51 (m, 2H), 3.78-3.89 (m, 2H), 3.94-4.06 (m, 2H), 4.44 (m, 1H), 6.85 (d, 2H, J=9.0 Hz), 7.10 (d, 1H, J=7.8 Hz), 7.31 (d, 2H, J=9.3 Hz), 8.34 (brs, 1H).

Ia-238 mp 128-130° C. $^{1}$H-NMR (DMSO) δ ppm: 1.26 (s, 9H), 1.41-1.53 (m, 2H), 1.55-1.68 (m, 2H), 2.44 (t, 2H, J=7.2 Hz), 2.98-3.07 (m, 2H), 6.90 (t, 1H, J=6.0 Hz), 8.16 (d-d, 1H, J=2.1 Hz, 8.7 Hz), 8.29 (d, 1H, J=8.7 Hz), 8.70 (m, 1H), 10.91 (brs, 1H).

Ia-239 mp 256-258° C. $^{1}$H-NMR (DMSO) δ ppm: 1.26-1.53 (m, 4H), 1.26 (s, 9H), 1.76-2.00 (m, 4H), 2.23 (s, 3H), 2.39 (m, 1H), 3.04 (m, 1H), 6.80 (d, 1H, J=8.7 Hz), 7.57 (d-d, 1H, J=2.4 Hz, 8.4 Hz), 7.97 (d, 1H, J=8.4 Hz), 8.12 (m, 1H), 10.26 (brs, 1H).

Ia-240 mp 288-290° C. $^{1}$H-NMR (DMSO) δ ppm: 1.26-1.53 (m, 4H), 1.27 (s, 9H), 1.78-1.90 (m, 4H), 2.40 (m, 1H), 3.04 (m, 1H), 6.81 (d, 1H, J=8.7 Hz), 7.07 (m, 1H), 7.75 (m, 1H), 8.07 (d, 1H, J=8.4 Hz), 8.29 (m, 1H), 10.36 (brs, 1H).

Ia-241 mp 249-250° C. $^{1}$H-NMR (DMSO) δ ppm: 1.28 (s, 9H), 1.34-1.50 (m, 2H), 1.79-1.90 (m, 2H), 2.74-2.98 (m, 2H), 3.32 (m, 1H), 4.02-4.14 (m, 2H), 6.91 (d, 1H, J=8.4 Hz), 7.94 (d, 1H, J=9.0 Hz), 8.04 (d-d, 1H, J=2.1 Hz, 9.0 Hz), 8.60 (s, 1H), 9.76 (brs, 1H).

Ia-242 mp 250-252° C. $^{1}$H-NMR (DMSO) δ ppm: 1.24 (s, 9H), 1.27 (s, 9H), 1.24-1.54 (m, 4H), 1.76-1.88 (m, 2H), 1.90-2.01 (m, 2H), 2.21 (m, 1H), 3.05 (m, 1H), 6.79 (d, 1H, J=8.7 Hz), 6.88 (d, 2H, J=9.0 Hz), 7.48 (d, 2H, J=9.0 Hz), 9.72 (brs, 1H).

136-0290 mp 250-252° C. $^{1}$H-NMR (DMSO) δ ppm: 1.15 (d, 6H, J=6.6 Hz), 1.28 (s, 9H), 1.35-1.52 (m, 2H), 1.78-1.92 (m, 2H), 2.20 (s, 3H), 2.81-2.96 (m, 2H), 3.33 (m, 1H), 3.96-4.16 (m, 3H), 6.92 (d, 1H, J=8.7 Hz), 7.27 (d, 1H, J=8.1 Hz), 7.60 (m, 1H), 7.66 (m, 1H), 8.06 (d, 1H, J=7.8 Hz), 8.14 brs, 1H).

Ia-244 mp 211-213° C. $^1$H-NMR (DMSO) δ ppm: 1.29 (s, 9H) 1.35-1.52 (m, 2H), 1.81-1.93 (m, 2H), 2.83-2.97 (m, 2H), 3.32 (m, 1H), 4.03-4.14 (m, 2H), 6.93 (d, 1H, J=8.7 Hz), 7.55 (d-d, 1H, J=2.1 Hz, 9.0 Hz), 7.94 (d, 1H, J=9.0 Hz), 8.29 (d, 1H, J=1.8 Hz), 8.78 (brs, 1H), 9.19 (s, 1H).

Ia-245 mp 196-197° C. $^1$H-NMR (DMSO) δ ppm: 1.27 (s, 9H), 1.2-1.6 (m, 6H), 1.8-2.0 (m, 6H), 2.23 (m, 1H), 3.05 (m, 1H), 3.73 (m, 4h), 4.99 (s, 1H), 6.79 (d, 1H, J=8.7), 7.13 (d, 1H, J=6.8), 7.22 (t, 1H, J=6.8), 7.49 (d, 1H, J=6.8), 7.72 (s, 1H), 9.78 (s, 1H).

Ia-246 mp 242-244° C. $^1$H-NMR (DMSO) δ ppm: 1.27 (s, 9H), 1.2-1.5 (m, 4H), 1.65 (m, 4H), 1.8-2.0 (m, 4H), 2.23 (m, 1H), 2.71 (m, 1H), 3.06 (m, 1H), 3.43 (m, 2H), 3.93 (m, 2H), 6.79 (d, 1H, J=8.7), 6.91 (d, 1H, J=8.7), 7.20 (t, 1H, J=7.5), 7.40 (d, 1H, J=7.5), 7.53 (s, 1H), 9.76 (s, 1H).

Ia-247 mp 242-245° C. $^1$H-NMR (DMSO) δ ppm: 1.27 (s, 9H), 1.2-1.6 (m, 6H), 1.8-2.0 (m, 6H), 2.23 (m, 1H), 3.05 (m, 1H), 3.74 (m, 4H), 4.94 (brs, 1H), 6.79 (d, 1h, J=8.7), 7.38 (d, 1H, J=8.7), 7.52 (d, 1H, J=8.7), 9.76 (s, 1H).

Ia-248 mp 272-274° C. $^1$H-NMR ($CDCl_3$) δ ppm: 1.27 (s, 9H), 1.2-1.5 (m, 4H), 1.62 (m, 4H), 1.8-2.0 (m, 4H), 2.22 (m, 1H), 2.68 (m, 1H), 3.05 (m, 1H), 3.41 (m, 2H), 3.92 (m, 2H), 6.79 (d, 1H, J=9.0), 7.15 (d, 2H, J=8.7), 7.50 (d, 2H, J=8.7), 9.73 (s, 1H).

Ia-249 mp 174-176° C.

Ia-250 mp 255-257° C.

Ia-252 mp 249-251° C.

Ia-253 mp 120-121° C.

Ia-254 mp 236-237° C.

Ia-255 mp 172-174° C.

Ia-256 mp 257-259° C.

Ia-257 mp 179-180° C.

Ia-258 mp 227-229° C.

Ia-259 mp 135-136° C.

Experiment 1 Affinity for NPY Y5 Receptor cDNA sequence encoding a human NPY Y5 receptor (WO096/16542) was cloned in the expression vector pME18S (Takebe et al. Mol. Cell. Biol. 8, 8957). The obtained expression vector was transfected into a host CHO cells by using a Lipofect AMINE reagent (Trademark, Gibco BRL Co., Ltd.) according to an instruction protocol to obtain the cells that stably express NPY Y5 receptor.

The membranes prepared from the above CHO cells expressing NPY Y5 receptor, the compound of the present invention and 30,000 cpm [$^{125}$I] peptide YY (60 pM of final concentration: Amersham) were incubated in the assay buffer (20 mM HEPES-Hanks buffer containing 0.1% bovine serum albumin, pH 7.4) at 25° C. for 2 hours, and then the mixture was filtered with a glassfilter GF/C treated with polyethyleneimine. After the glassfilter was washed with 50 mM Tris-HCl buffer (pH 7.4), the radioactivity on the filter was measured with a gamma counter. The non-specific binding was detected in the presence of 200 nM of peptide YY. The 50% inhibitory concentration of the test compound against the specific peptide YY binding ($IC_{50}$ value) was calculated (Inui, A. et al. Endocrinology 131, 2090-2096 (1992)). The results are shown in Tables 1 and 2.

The compounds of the present invention inhibited the binding of peptide YY (NPY homologue) to NPY Y5 receptors. In other words, the compounds of the present invention showed affinity for the NPY Y5 receptor.

Experiment 2 cAMP production inhibitory activity in CHO cells

After CHO cells expressing human NPY Y5 receptor were incubated in the presence of 2.5 mM isobutylmethylxanthine (SIGMA) at 37° C. for 20 min., the compound of the present invention was added and incubated for 5 min. Then, 50 nM NPY and 10 μM forskolin (SIGMA) were added to the cells and incubated for 30 min. After the reaction was terminated by adding 1N HCl, the amount of cAMP in the supernatant was measured with EIA kit (Amersham LIFE SCIENCE). The inhibitory activity of NPY against forskolin stimulated cAMP was regarded as 100% and the 50% inhibitory concentration ($IC_{50}$ value) of the compound of the present invention against the NPY activity was calculated. The results are shown in Tables 1 to 4.

TABLE 1

| Compound | binding $IC_{50}$(nM) | cAMP $IC_{50}$(nM) |
|---|---|---|
| I-2 | 7.5 | 72 |
| I-7 | 3 | <10 |
| I-11 | 1.3 | 5 |
| I-18 | 4.4 | 29 |
| I-20 | 7 | 21 |
| I-22 | 8.6 | 51 |
| I-24 | 9.6 | 71 |
| I-25 | 0.6 | 2.6 |
| I-41 | 5.3 | 38.2 |
| I-44 | 1.0 | 13.4 |
| I-45 | 1.2 | 27.9 |
| I-46 | 0.8 | 10.5 |
| I-47 | 0.6 | 14.9 |
| I-49 | 0.4 | 8.1 |
| I-50 | 0.3 | 8.4 |
| I-53 | 4.1 | 21 |
| I-55 | 9.0 | 40 |
| I-57 | 4.8 | 47 |
| I-59 | 0.8 | 35 |
| I-60 | 0.69 | 18 |
| I-61 | 0.26 | 5.3 |
| I-62 | 0.58 | 16 |
| I-63 | 1.3 | 50 |
| I-64 | 2.2 | 80 |
| I-65 | 1.8 | 72 |
| I-66 | 1.5 | 30 |
| I-67 | 2 | 17 |
| I-69 | 3.8 | 13 |
| I-72 | 2.3 | 2.1 |
| I-75 | 0.55 | 3.4 |
| I-76 | 0.61 | 5.5 |
| I-77 | 1.8 | 28 |
| I-79 | 0.59 | 25 |
| I-83 | 0.61 | 29 |
| I-84 | 1.3 | 25 |
| I-86 | 3.4 | 100 |
| I-87 | 0.66 | 21 |
| I-90 | 2.8 | 50 |
| I-92 | 7 | 61 |
| I-101 | 3.9 | 38 |
| I-102 | 1.7 | 14 |
| I-106 | 6.4 | 29 |

TABLE 2

| | | |
|---|---|---|
| I-109 | 1.2 | 3.2 |
| I-110 | 4.3 | 13.6 |
| I-111 | 1.8 | 6.1 |
| I-114 | 7 | 30 |
| I-116 | 1.2 | 11 |
| I-120 | 1.4 | 4.8 |
| I-123 | 1.8 | 168 |
| I-126 | 0.6 | 13.2 |
| I-127 | 1.4 | 30.4 |
| I-128 | 1.3 | 10.2 |

TABLE 2-continued

| | | |
|---|---|---|
| I-129 | 2.1 | 174 |
| I-130 | 1.1 | 42.5 |
| I-131 | 1.1 | 34.8 |
| I-132 | 2.2 | 30.4 |
| I-133 | 0.9 | 21.1 |
| I-134 | 0.5 | 10.0 |
| I-135 | 0.7 | 22.0 |
| I-136 | 2.8 | — |
| I-137 | 1.4 | 68.2 |
| I-138 | 1.0 | 18.6 |
| I-139 | 0.41 | 7.6 |
| I-140 | 0.48 | 8.9 |
| I-141 | 0.42 | 7.4 |
| I-142 | 0.49 | 28 |
| I-143 | 3.5 | 44 |
| I-144 | 3.4 | 52 |
| I-146 | 2.3 | 20 |
| I-147 | 7.1 | 63 |
| I-149 | 0.83 | 15 |
| I-150 | 0.17 | 5.2 |
| I-151 | 0.17 | 2.6 |
| I-152 | 0.88 | 46 |
| I-153 | 1.7 | 29 |
| I-154 | 1.1 | 11 |
| I-156 | 0.81 | 17 |
| I-160 | 0.61 | 8.8 |
| I-161 | 0.49 | 3.1 |
| I-162 | 1.7 | 32 |
| I-163 | 2.3 | 83 |
| I-164 | 0.71 | 5.9 |
| I-165 | 0.44 | 47 |
| I-166 | 0.37 | 9.7 |
| I-167 | 0.72 | 39 |
| I-168 | 2.1 | 32 |
| I-171 | 2.4 | 71 |
| I-172 | 0.91 | 36 |
| I-187 | 0.58 | 13 |
| I-191 | 1.1 | 11 |
| I-196 | 1.4 | 6.8 |
| I-197 | 6.7 | 38 |
| I-198 | 7.2 | 33 |
| I-199 | 4.8 | 31 |
| I-202 | 6.7 | 67 |
| I-204 | 1.0 | 6.3 |
| I-205 | 2.9 | 17 |
| I-206 | 5.9 | 54 |
| I-207 | 4.6 | 23 |
| I-210 | 1.1 | 13 |
| I-212 | 0.67 | 7.5 |
| I-213 | 0.44 | 4.0 |
| Ia-1 | 4.8 | 31 |
| Ia-3 | 9.2 | 150 |
| Ia-4 | 1.4 | 15 |
| Ia-5 | 1.6 | 43 |
| Ia-6 | 2.4 | 23 |
| Ia-8 | 2.9 | 34 |
| Ia-9 | 0.94 | 11 |
| Ia-10 | 0.47 | 2.7 |
| Ia-11 | 0.64 | 7.2 |
| Ia-12 | 0.94 | 5.5 |
| Ia-13 | 1.5 | 3.3 |
| Ia-14 | 4.8 | 28 |
| Ia-16 | 0.1 | — |
| Ia-17 | 0.1 | 1.9 |
| Ia-20 | 4.9 | 100 |

TABLE 3

| | | |
|---|---|---|
| Ia-21 | 3.4 | 35 |
| Ia-22 | 3.1 | 38 |
| Ia-24 | 5.2 | 74 |
| Ia-25 | 1.1 | 18 |
| Ia-26 | 1.9 | 27 |
| Ia-28 | 5.2 | 130 |
| Ia-29 | 1 | 7.3 |
| Ia-30 | 2.6 | 25 |

TABLE 3-continued

| | | |
|---|---|---|
| Ia-31 | 3.8 | 11 |
| Ia-32 | 0.52 | 6.7 |
| Ia-33 | 1.8 | 64 |
| Ia-35 | 1.8 | — |
| Ia-36 | 1.6 | 86 |
| Ia-37 | 0.73 | 3.8 |
| Ia-38 | 1 | 2.2 |
| Ia-39 | 1.5 | 3.5 |
| Ia-40 | 2.2 | 9.3 |
| Ia-41 | 2.5 | 9 |
| Ia-42 | 3.6 | 20 |
| Ia-44 | 4.8 | 27 |
| Ia-45 | 4.8 | 42 |
| Ia-46 | 0.87 | 8.3 |
| Ia-47 | 0.82 | 3.8 |
| Ia-48 | 1.2 | 6.1 |
| Ia-49 | 2.6 | 83 |
| Ia-50 | 1.7 | 24 |
| Ia-51 | 1.3 | 3.4 |
| Ia-52 | 1.9 | 22 |
| Ia-53 | 0.22 | 8.1 |
| Ia-54 | 0.44 | 9 |
| Ia-55 | 1.1 | 27 |
| Ia-56 | 2.3 | 96 |
| Ia-57 | 0.93 | 31 |
| Ia-58 | 2.5 | 110 |
| Ia-59 | 0.71 | 16 |
| Ia-60 | 0.95 | 10 |
| Ia-61 | 0.68 | 19 |
| Ia-62 | 1.1 | 29 |
| Ia-63 | 3.9 | 370 |
| Ia-64 | 7.1 | 96 |
| Ia-65 | 1.1 | 11 |
| Ia-66 | 0.59 | 3.2 |
| Ia-67 | 6.3 | 75 |
| Ia-68 | 9.5 | 180 |
| Ia-69 | 2.7 | 33 |
| Ia-70 | 1.5 | 31 |
| Ia-71 | 1.3 | 12 |
| Ia-76 | 2.2 | — |
| Ia-78 | 2 | 150 |
| Ia-79 | 0.82 | — |
| Ia-80 | 0.44 | 3.0 |
| Ia-81 | 2.7 | 4.5 |
| Ia-83 | 1.2 | 53 |
| Ia-84 | 0.25 | 13 |
| Ia-85 | 0.22 | 14 |
| Ia-86 | 0.73 | 11 |
| Ia-87 | 0.49 | 61 |
| Ia-88 | 0.62 | 48 |
| Ia-91 | 4 | 150 |
| Ia-106 | 1.9 | 24 |
| Ia-107 | 0.14 | 1.3 |
| Ia-109 | 0.6 | 3.9 |
| Ia-110 | 0.3 | 1.1 |
| Ia-111 | 5.1 | 28 |
| Ia-124 | 1.1 | 22 |
| Ia-125 | 4.1 | 46 |
| Ia-126 | 2.3 | 58 |
| Ia-127 | 6.1 | 160 |
| Ia-129 | 1.3 | 26 |
| Ia-130 | 0.21 | 3 |
| Ia-131 | 1.3 | 17 |
| Ia-132 | 2.8 | 76 |
| Ia-133 | 1.7 | 8.8 |
| Ia-135 | 8.2 | 49 |
| Ia-136 | 1.6 | 13 |
| Ia-138 | 2.2 | 28 |
| Ia-139 | 1.9 | 25 |
| Ia-140 | 1 | 24 |
| Ia-141 | 1 | 5.7 |
| Ia-142 | 0.67 | 5.5 |

TABLE 4

| | | |
|---|---|---|
| Ia-143 | 7.8 | 39 |
| Ia-144 | 6.1 | 57 |

TABLE 4-continued

| | | |
|---|---|---|
| Ia-145 | 7 | 86 |
| Ia-146 | 9.9 | 79 |
| Ia-158 | 0.71 | 1.7 |
| Ia-160 | 0.76 | 140 |
| Ia-161 | 1.9 | 18 |
| Ia-163 | 7 | 400 |
| Ia-164 | 0.38 | 4.7 |
| Ia-168 | 0.95 | 13 |
| Ia-169 | 1.9 | 88 |
| Ia-173 | 6.9 | 140 |
| Ia-174 | 0.35 | 5.4 |
| Ia-175 | 0.49 | 9.2 |
| Ia-176 | 0.63 | 5.1 |
| Ia-177 | 0.49 | 7.5 |
| Ia-178 | 4.6 | 16 |
| Ia-179 | 0.89 | 19 |
| Ia-180 | 1.9 | 11 |
| Ia-181 | 7.7 | 25 |
| Ia-182 | 0.24 | 2.1 |
| Ia-183 | 1.9 | 7.8 |
| Ia-184 | 0.38 | — |
| Ia-185 | 0.94 | 4.4 |
| Ia-186 | 0.93 | 12 |
| Ia-187 | 1.9 | 60 |
| Ia-188 | 0.75 | 28 |
| Ia-189 | 3.5 | 95 |
| Ia-190 | 0.34 | 1000 |
| Ia-191 | 0.49 | 220 |
| Ia-192 | 5.9 | 200 |
| Ia-193 | 1.4 | 43 |
| Ia-194 | 0.22 | 8.1 |
| Ia-195 | 1.4 | 31 |
| Ia-196 | 0.39 | 1.3 |
| Ia-197 | 0.44 | 2.5 |
| Ia-198 | 0.23 | 2.6 |
| Ia-199 | 0.11 | 1.6 |
| Ia-200 | 1.4 | 18 |
| Ia-201 | 3.1 | 74 |
| Ia-202 | 0.37 | 3.4 |
| Ia-203 | 0.2 | 2.6 |
| Ia-204 | 1 | 6.3 |
| Ia-205 | 2.4 | 99 |
| Ia-206 | 1.9 | 460 |
| Ia-207 | 0.55 | 5.9 |
| Ia-208 | 1.2 | 9.7 |
| Ia-209 | 0.55 | — |
| Ia-210 | 2.8 | 99 |
| Ia-211 | 4.8 | 240 |
| Ia-212 | 0.52 | 2.6 |
| Ia-213 | 0.91 | 28 |
| Ia-219 | 2.5 | 28 |
| Ia-221 | 0.47 | 1.5 |
| Ia-222 | 3.7 | 18 |
| Ia-224 | 0.1 | 1.2 |
| Ia-225 | 3.4 | 20 |
| Ia-226 | 0.37 | 21 |
| Ia-227 | 0.59 | — |
| Ia-228 | 0.96 | — |
| Ia-229 | 1.9 | — |
| Ia-230 | 0.32 | — |
| Ia-231 | 0.29 | — |
| Ia-232 | 0.7 | — |
| Ia-233 | 0.63 | — |
| Ia-235 | 5.5 | — |
| Ia-237 | 1.1 | 15 |
| Ia-241 | 1.9 | — |
| Ia-243 | 1.3 | — |
| Ia-246 | 0.26 | 20 |
| Ia-247 | 0.79 | 31 |
| Ia-248 | 0.27 | 17 |
| Ia-250 | 1.9 | — |
| Ia-252 | 1.2 | — |
| Ia-253 | 0.53 | — |
| Ia-254 | 2.0 | — |
| Ia-255 | 3.2 | — |
| Ia-256 | 5.7 | — |
| Ia-257 | 8.6 | — |
| Ia-258 | 1.8 | — |

As shown in Tables 1 to 4, the compounds of the present invention have an NPY Y5 receptor antagonistic activity.

Experiment 3

Using the membranes prepared from Y1-expression cells (human neuroblastoma, SK-N-MC) and the membranes prepared from Y2-expression cells (human neuroblastoma, SMS-KAN), the experiment was carried out in a similar way as Experiment 1 to determine the affinity for NPY Y1 receptor and NPY Y2 receptor.

Binding $IC_{50}$ values for NPY Y1 and NPY Y2 receptors of I-27, I-32, I-41, I-45, I-46, I-47, I-48, I-49, I-59, I-61, I-63, I-64, I-66, I-69, I-72, I-152, I-154, I-204, I-205, I-212, Ia-3, Ia-5, Ia-6, Ia-12, Ia-16, Ia-17, Ia-20, Ia-21, Ia-22, Ia-26, Ia-28, Ia-29, Ia-30, Ia-31, Ia-32, Ia-33, Ia-37, Ia-39, Ia-40, Ia-50, Ia-51, Ia-54, Ia-62, Ia-67, Ia-124, Ia-126, Ia-139, Ia-140, Ia-142, Ia-178, Ia-199 and Ia-200 were 100,000 nM or higher and each compound had a selectivity for NPY Y5 receptor.

Formulation Example 1

Tablets

| | |
|---|---|
| Compound (I-1) | 15 mg |
| Starch | 15 mg |
| Lactose | 15 mg |
| Crystalline cellulose | 19 mg |
| Polyvinyl alcohol | 3 mg |
| Distilled water | 30 ml |
| Calcium stearate | 3 mg |

After all of the above ingredients except for calcium stearate are uniformly mixed, the mixture is crushed and granulated, and dried to obtain a suitable size of granules. After calcium stearate is added to the granules, tablets are formed by compression molding.

Formulation Example 2

Capsules

| | |
|---|---|
| Compound (I-2) | 10 mg |
| Magnesium stearate | 10 mg |
| Lactose | 80 mg |

After the above ingredients are mixed to prepare powders or granules the obtained are filled in capsules.

Formulation Example 3

Granules

| | |
|---|---|
| Compound (I-3) | 30 g |
| Lactose | 265 g |
| Magnesium Stearate | 5 g |

After the above ingredients are mixed uniformly and formed by compression molding, the obtained are crushed, granulated and sieved to prepare suitable volume of granules.

INDUSTRIAL APPLICABILITY

As shown in the above Experiments, the compounds of the present invention have an NPY Y5 receptor antagonistic activity. Therefore, the compounds of the present invention are useful as an anti-obestic agent and anorectic agent.

The invention claimed is:

1. A pharmaceutical composition comprising a therapeutically effective amount of a compound of the formula (I):

(I)

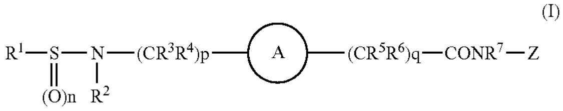

wherein $R^1$ is optionally substituted lower alkyl or optionally substituted cycloalkyl, $R^2$ is hydrogen or lower alkyl, and $R^1$ and $R^2$ taken together may form lower alkylene, n is 1 or 2, $R^3$, $R^4$, $R^5$ and $R^6$ are each independently hydrogen or lower alkyl,

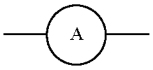

is optionally substituted cycloalkylene or optionally substituted bicycloalkylene, provided that

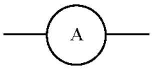

is not

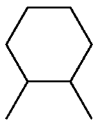

(1, 2-cyclohexylene)

and p and q are each independently 0 or 1, $R^7$ is hydrogen or lower alkyl, and Z is optionally substituted phenyl, optionally substituted phenyl fused with a nonaromatic ring selected from cyclopentane, cyclopentene or cyclohexane; optionally substituted naphthyl, optionally substituted anthryl, optionally substituted biphenyl or a fused heterocyclyl consisting of two rings, selected from the group consisting of indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, tetrahydroquinolyl and tetrahydrobenzothienyl;

or a pharmaceutically acceptable salt thereof.

2. The pharmaceutical composition claimed in claim 1 wherein $R^2$ is hydrogen or lower alkyl.

3. The pharmaceutical composition claimed in claim 1 wherein $R^1$ is optionally substituted lower alkyl or optionally substituted cycloalkyl, and p and q are 0.

4. The pharmaceutical composition claimed in any one of claims 1 to 3 wherein $R^1$ is optionally substituted C3 to C10 alkyl.

5. A method for treating obesity comprising administering to a subject that is obese an effective dose of a compound claimed in any one of claims 1 to 3.

6. A method for suppressing food intake comprising administering to a subject that is obese an effective dose of a compound claimed in any one of claims 1 to 3.

7. A compound of the formula (I):

(I)

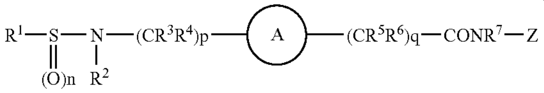

wherein the symbols are the same as defined in claim 1, or a pharmaceutically acceptable salt thereof.

8. The compound described in claim 7 wherein $R^1$ is optionally substituted C3 to C10 alkyl or optionally substituted C5 to C6 cycloalkyl, or a pharmaceutically acceptable salt thereof.

9. The compound described in claim 7 wherein

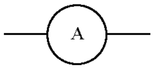

is optionally substituted cyclohexylene and p and q are simultaneously 0, or a pharmaceutically acceptable salt thereof.

10. The compound described in claim 7 or 8 wherein $R^7$ is hydrogen, or a pharmaceutically acceptable salt thereof.

11. The compound of claim 7, in which Z is optionally substituted phenyl, optionally substituted phenyl fused with a nonaromatic ring selected from cyclopentane, cyclopentene or cyclohexane; optionally substituted naphthyl, optionally substituted anthryl or optionally substituted biphenyl.

12. The compound of claim 7, in which Z is fused heterocyclyl consisting of two fused rings selected from the group consisting of indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, tetrahydroquinolyl and tetrahydrobenzothienyl.

13. The compound of claim 11, in which Z selected from the group consisting of indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl.

14. The compound of claim 7, in which Z is optionally substituted phenyl, optionally substituted naphthyl, optionally substituted anthryl or optionally substituted biphenyl.

15. A pharmaceutical composition comprising the compound of claim 7 or 8, or a pharmaceutically acceptable salt thereof and a pharmaceutically acceptable carrier.

16. The pharmaceutical composition of claim 1, in which Z is optionally substituted phenyl, optionally substituted phenyl fused with a nonaromatic ring selected from cyclopentane, cyclopentene or cyclohexane; optionally substituted naphthyl, optionally substituted anthryl or optionally substituted biphenyl.

17. The pharmaceutical composition of claim 1, in which Z is fused heterocyclyl consisting of two fused rings selected from the group consisting of indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, tetrahydroquinolyl and tetrahydrobenzothienyl.

* * * * *